US009743837B2

(12) United States Patent
Ando

(10) Patent No.: US 9,743,837 B2
(45) Date of Patent: *Aug. 29, 2017

(54) MEASURING METHOD OF LIFE ACTIVITY, MEASURING DEVICE OF LIFE ACTIVITY, TRANSMISSION METHOD OF LIFE ACTIVITY DETECTION SIGNAL, OR SERVICE BASED ON LIFE ACTIVITY INFORMATION

(71) Applicant: Hideo Ando, Hino (JP)

(72) Inventor: Hideo Ando, Hino (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,096

(22) Filed: Jan. 7, 2016

(65) Prior Publication Data
US 2016/0113505 A1    Apr. 28, 2016

Related U.S. Application Data

(62) Division of application No. 13/670,814, filed on Nov. 7, 2012, now Pat. No. 9,265,425.

(30) Foreign Application Priority Data

Nov. 11, 2011 (JP) ................................ 2011-248115
Oct. 2, 2012 (JP) ................................ 2012-220305

(51) Int. Cl.
*A61B 6/00* (2006.01)
*A61B 5/00* (2006.01)
(Continued)

(52) U.S. Cl.
CPC .......... *A61B 5/0075* (2013.01); *A61B 5/0013* (2013.01); *A61B 5/0059* (2013.01);
(Continued)

(58) Field of Classification Search
CPC ... A61B 5/0075; A61B 5/0013; A61B 5/4519; A61B 5/486; A61B 5/7246; A61B 5/40;
(Continued)

(56) References Cited

U.S. PATENT DOCUMENTS 5,685,300 A * 11/1997 Kuenstner ............ G01R 33/465
                                                         436/173
6,272,370 B1 *  8/2001 Gillies ............... A61M 25/0105
                                                         324/309
(Continued)

FOREIGN PATENT DOCUMENTS

JP          02-240545          9/1990
JP          09-019408          1/1997
(Continued)

OTHER PUBLICATIONS

Huang, et al, "Raman Spectroscopic Signature of Life in a Living Yeast Cell", Journal of Raman Spectroscopy, J. Raman Spetrosc, 2004; 35: 525-526, 3 Pages. (The applicant believes the materials are relevant to the above-identified application, but not relevant to the patentability).

(Continued)

*Primary Examiner* — Sanjay Cattungal
(74) *Attorney, Agent, or Firm* — Rankin, Hill & Clark LLP

(57) ABSTRACT

According to a measuring method or a control method of life activity, a life object is illuminated with an electromagnetic wave including a wavelength in a designated waveband, and a characteristic in a local area of the life object is detected, or a life activity thereof is controlled. This "local area" is an area constituted by one or more cells. The "designated waveband" is defined based on any one of the following phenomena:

(Continued)

[1] transition energy between a ground state of a vibration mode newly occurring between atoms in a constituent molecule of a cell membrane and a plurality of excited states;

[2] transition energy between vibration modes occurring between specific atoms in a molecule corresponding to the activity of the life object or the change thereof; and

[3] a specific chemical shift value in Nuclear Magnetic Resonance.

24 Claims, 72 Drawing Sheets

(51) Int. Cl.
*G01P 13/00* (2006.01)
*A61B 5/055* (2006.01)

(52) U.S. Cl.
CPC ............ *A61B 5/0068* (2013.01); *A61B 5/055* (2013.01); *A61B 5/40* (2013.01); *A61B 5/4041* (2013.01); *A61B 5/4519* (2013.01); *A61B 5/486* (2013.01); *A61B 5/7228* (2013.01); *A61B 5/7246* (2013.01); *G01P 13/00* (2013.01); *A61B 2562/0242* (2013.01); *A61B 2576/00* (2013.01)

(58) Field of Classification Search
CPC ..... A61B 5/0068; A61B 5/055; A61B 5/4041; A61B 5/7228; A61B 5/0059; A61B 2576/00; A61B 2562/0242; G01P 13/00
USPC .................................................. 600/407–480
See application file for complete search history.

(56) References Cited

U.S. PATENT DOCUMENTS

| | | | |
|---|---|---|---|
| 6,763,261 B2* | 7/2004 | Casscells, III | A61B 5/0077 600/474 |
| 6,919,158 B2* | 7/2005 | Kawamura | H01L 51/0022 430/270.1 |
| 7,398,119 B2* | 7/2008 | Lambert | A61B 5/14532 356/301 |
| 7,983,762 B2 | 7/2011 | Gliner et al. | |
| 7,988,688 B2 | 8/2011 | Webb et al. | |
| 8,025,687 B2 | 9/2011 | Streeter et al. | |
| 8,109,882 B2* | 2/2012 | Baker, Jr. | A61B 5/02416 600/310 |
| 2002/0016533 A1* | 2/2002 | Marchitto | A61B 5/0066 600/310 |
| 2003/0171691 A1* | 9/2003 | Casscells, III | A61B 5/0075 600/549 |
| 2004/0220749 A1* | 11/2004 | Miller | G01N 21/25 702/19 |
| 2004/0242976 A1* | 12/2004 | Abreu | A61B 5/0008 600/315 |
| 2005/0064108 A1* | 3/2005 | Kano | B41M 3/006 427/553 |
| 2005/0216072 A1 | 9/2005 | Mahadevan-Jansen et al. | |
| 2006/0155193 A1* | 7/2006 | Leonardi | A61B 5/0059 600/473 |
| 2006/0193781 A1* | 8/2006 | Frederickson | A61B 5/055 424/9.36 |
| 2006/0280688 A1* | 12/2006 | Kovar | A61K 49/0032 424/9.6 |
| 2007/0135693 A1 | 6/2007 | Melman et al. | |
| 2009/0062685 A1* | 3/2009 | Bergethon | A61B 5/0059 600/554 |
| 2009/0069871 A1 | 3/2009 | Mahadevan-Jansen et al. | |
| 2009/0105605 A1* | 4/2009 | Abreu | A61B 5/0008 600/549 |
| 2009/0216301 A1* | 8/2009 | Streeter | A61N 5/0618 607/89 |
| 2009/0299435 A1* | 12/2009 | Gliner | A61N 1/3606 607/45 |
| 2010/0234837 A1 | 9/2010 | Alfano | |
| 2011/0028827 A1* | 2/2011 | Sitaram | A61B 5/0059 600/410 |
| 2013/0317572 A1 | 11/2013 | Zhu et al. | |

FOREIGN PATENT DOCUMENTS

| | | |
|---|---|---|
| JP | 2003-159239 | 6/2003 |
| JP | 3931638 | 6/2007 |
| JP | 2008-224420 | 9/2008 |
| JP | 2009-222531 | 10/2009 |
| JP | 2010-237139 | 10/2010 |
| WO | 00/22413 | 4/2000 |
| WO | 01/09589 | 2/2001 |
| WO | 2010073769 | 7/2010 |

OTHER PUBLICATIONS

Kawasaki, et al., "Effect of Mid-infrared Free-Electron Laser Irradiation on Refolding of Amyloid-Like Fibrils of Lysozyme into Native Form", Protein J (2012), 31: 710-716, 8 pages. (The applicant believes the materials are relevant to the above-identhed application, but not relevant to the patentability).

Komori, The Japanese Society for the Study of Chronic Pain, vol. 27, No. 1, Nov. 20, 2008 pp. 23-27, 6 pages.

Notification of Transmittal, International Search Report and Written Opinion, mailing date Feb. 12, 2013, 12 pages.

Yukihiro Ozaki/Satoshi Kawata: Kinsekigaibunkouhou (Gakkai Shuppan Center, 1996) Section 4.6, Discussed on pp. 1-2 of specification, English abstract included.

Takashi Tachibana: Nou Wo Kiwameru Noukenkyu Saizensen (Asahi Shimbun Publishing 2001) p. 197, Discussed on p. 2 of specification, English abstract included.

Masahiko Watanabe: Nou Shinkei Kagaku Nyumon Koza Gekan (Yodosha, 2002) p. 188, Discussed on p. 2 of specification, English abstract included.

Carter, R., 2000, "Mapping the Mind", Orion Boods, London, pp. 26-27, 2 pages.

Jobsis, F.F., 1977, "Noninvasive, Infrared Monitoring of Cerebral and Myocardial Oxygen Sufficiency and Circulatory Parameters", Science, 198: 1264-1267, 5 pages.

Binder, et al., 2002, "The Effect of Metal Cations on the Phase Behavior and Hydration Characteristics of Phospholipid Membranes", Chem. Phys. Lipids, 115:39-61, 23 pages.

Binder, et al,m 2001, "Interaction of Zn2+ with Phospholipid Membranes", Biophysical Chem. 90:57-74, 18 pages.

Pandit, et al., 2003, "Molecular Dynamic Simulation of a Dipalmitoylphosphatidylcholine Bilayer with NaCl", Biophysical Journal, 84: 3743-3750, 8 pages.

Mukhopadhyay, P. et al., 2004, "Molecular Dynamics Simulation of a Palmitoyl-Oleoyl Phosphatidylserine Bilayer with Na+—Counterions and NaCl", Biophysical Journal, 86: 1601-1609, 9 pages.

Sachs, et al., 2004, "Changes in Phosphatidylcholine Headgroup Tilt and Water Order Induced by Monovalent Salts: Molecular Dynamics Simulations", Biophysical Journal, 86: 3772-3782, 11 pages.

Lee, et al., 2008, "Molecular Dynamics Simulations of Asymmetric NaCl and Kcl Solutions Separated by Phosphatidylcholine Bilayers: Potential Drops and Structural Changes Induced by Strong Na+—Lipid Interactions and Finite Size Effects", Biophysical Journal, 94: 3565-3576, 12 pages.

Jendrasiak, G.L., 1972, "Halide Interacti Witonh Phospholipids: Proton Magnetic Resonance Studies", Chem. Phys. Lipids., 9: 133-146, 14 pages.

(56) References Cited

OTHER PUBLICATIONS

MacDonald et al., 1988, "Anion Binding to Neutral and Positively Charged Lipid Membranes", Biochemistry, 27: 6769-6775, 7 pages.
Japanese Office Action dated Apr. 26, 2016.
Japanese Office Action dated Mar. 14, 2017.

* cited by examiner

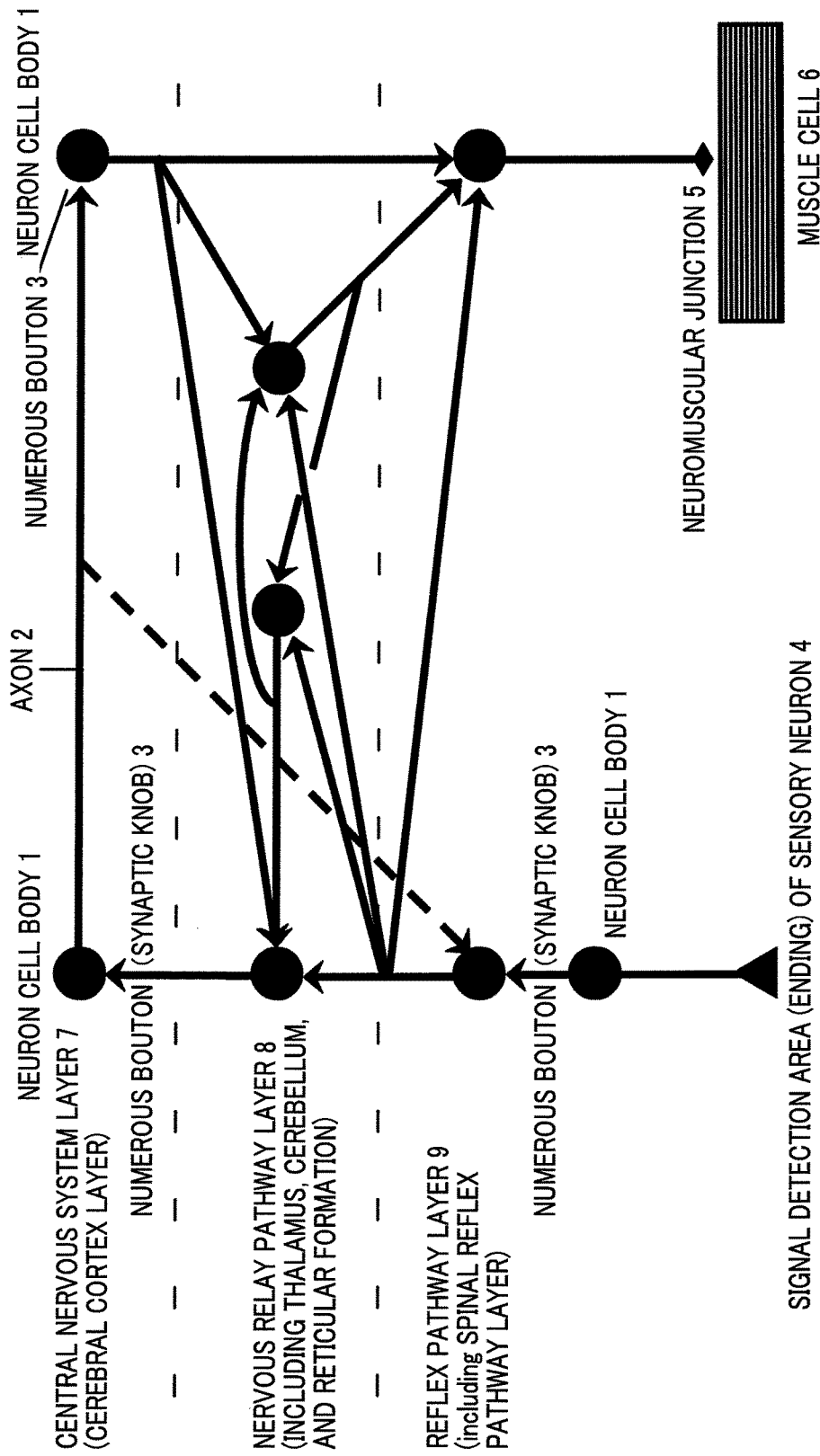
FIG.1 SIGNAL TRANSMISSION PATHWAY IN NERVOUS SYSTEM

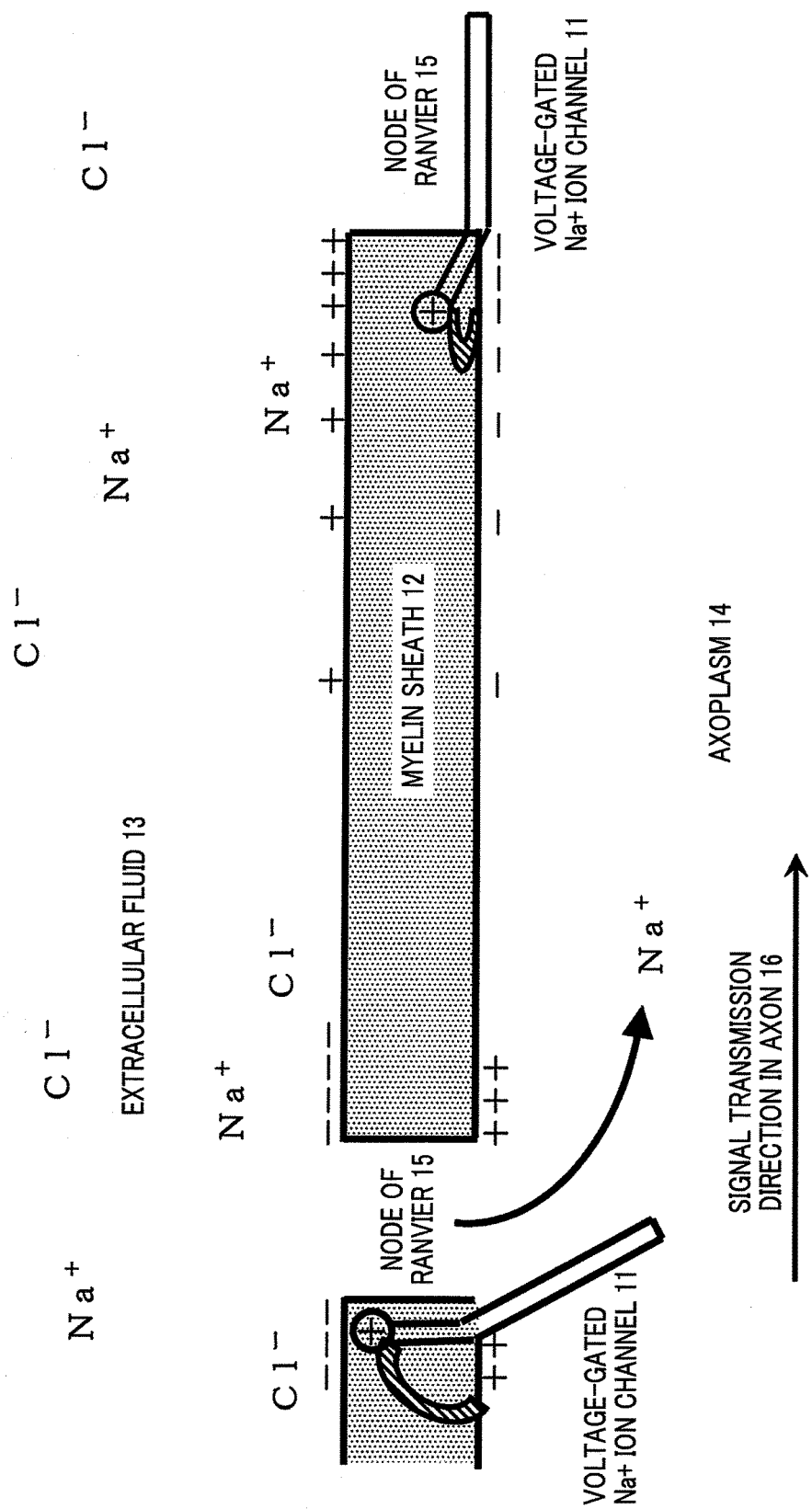
FIG.2 SIGNAL TRANSMISSION IN AXON

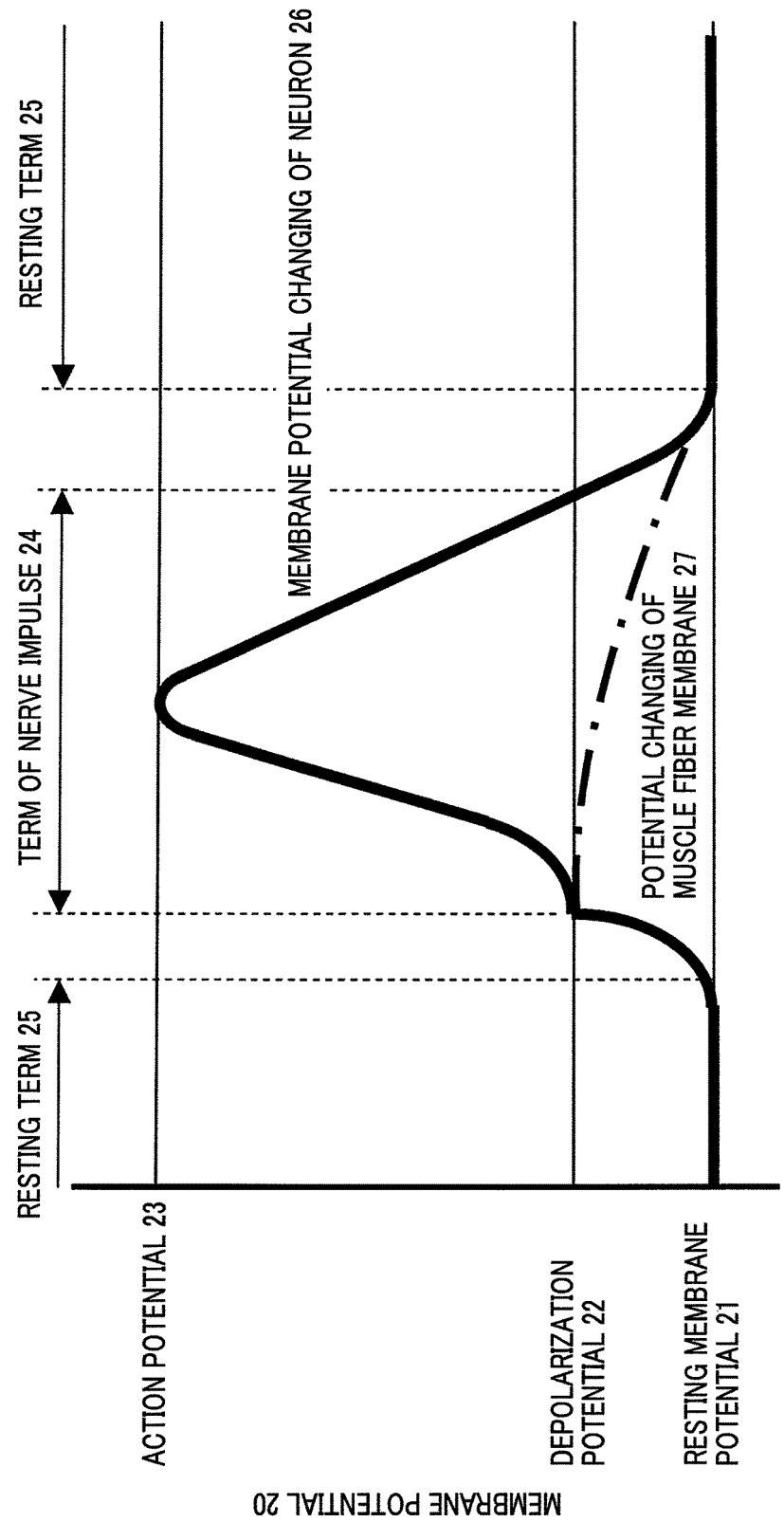
FIG.3 CHANGING STATES OF NEURONAL MEMBRANE VOLTAGE AND MUSCULAR MEMBRANE POTENTIAL IN CASE OF ACTION POTENTIAL

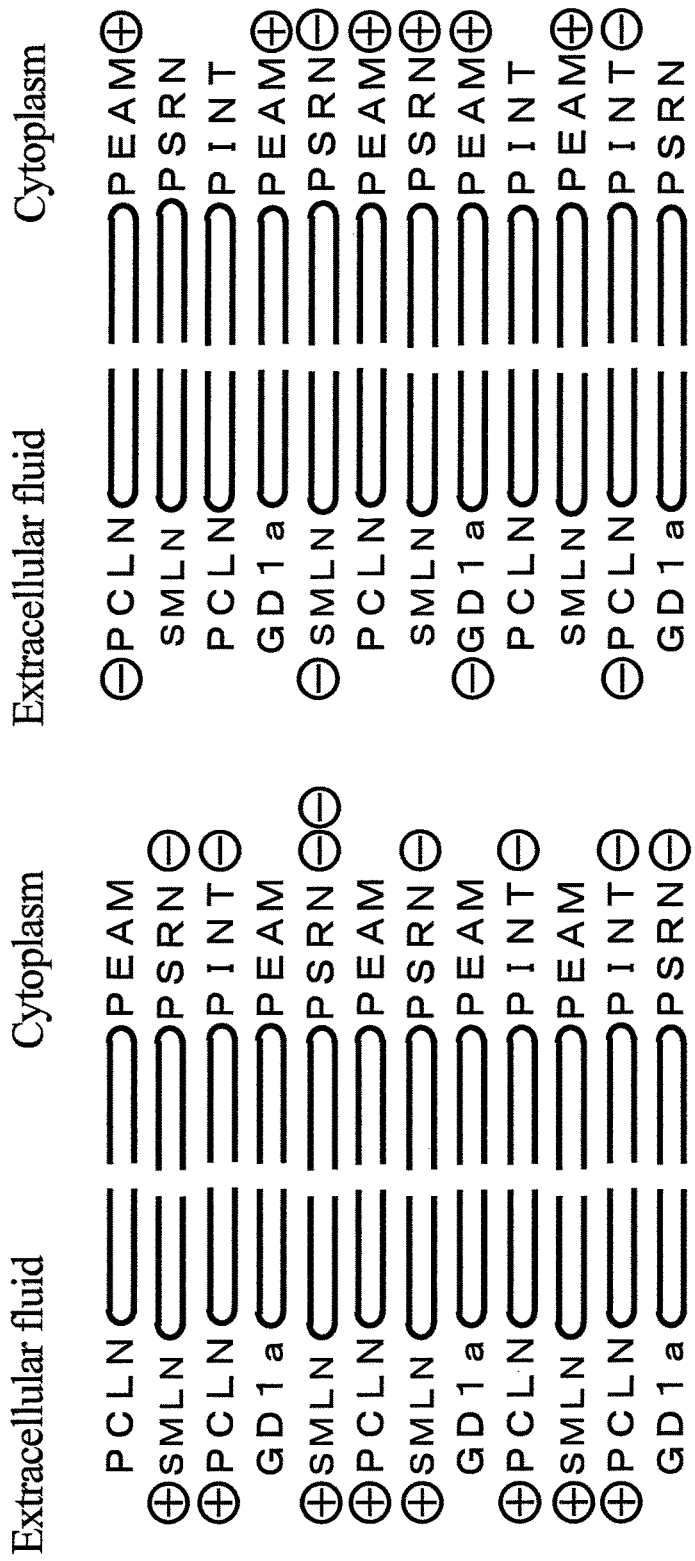
FIG.4 Charging model on both surfaces of neuronal membrane in case of action and resting potentials
PCLN : Phosphatidylcholine, SMLN : Sphingomyelin, GD1a : Ganglioside type D1a,
PSRN : Phosphatidylserine, PEAM : Phosphatidylethanolamine, PINT : Phosphatidylinositol.

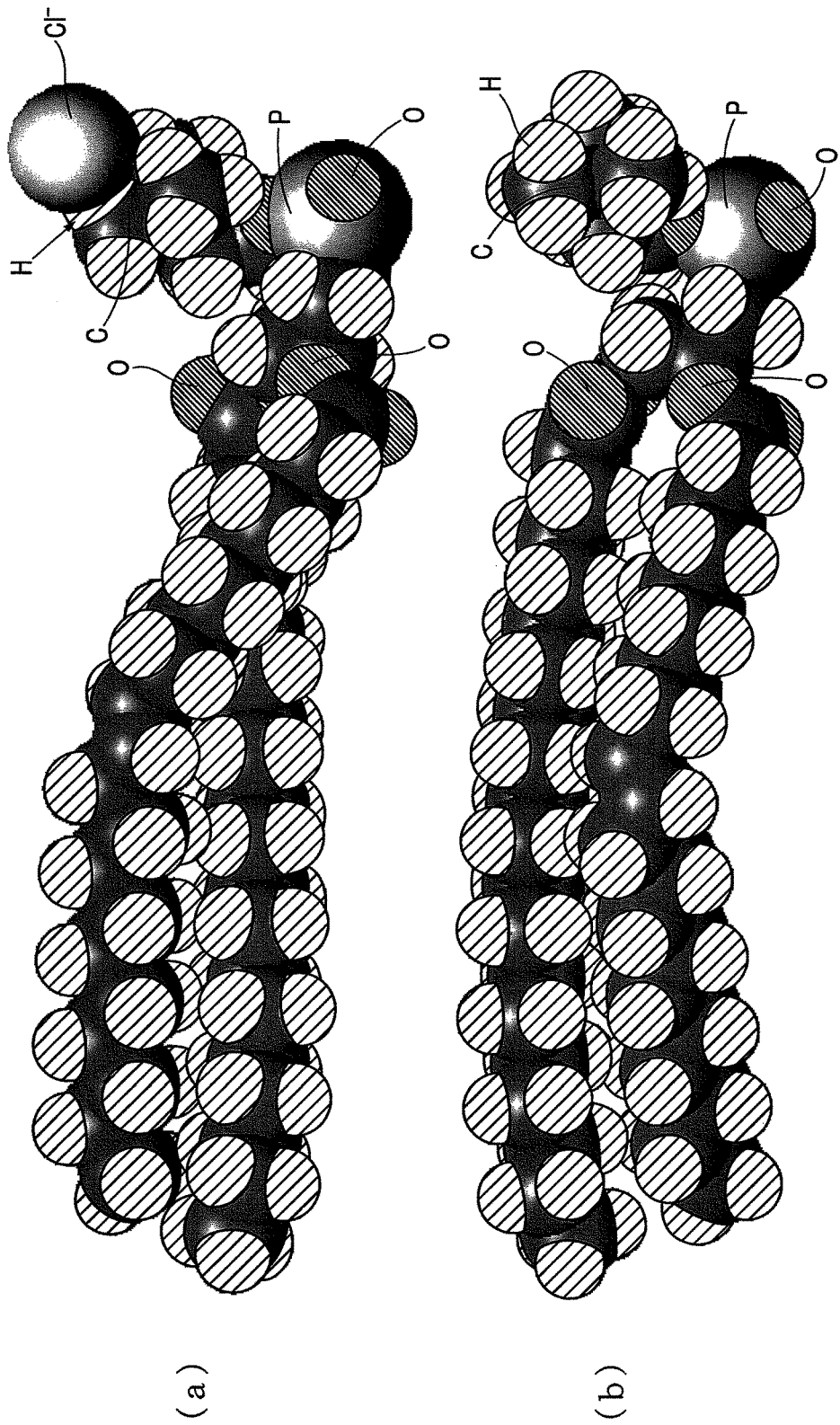
FIG. 5  Estimated molecular structure of PCLN in case of Cl⁻ ion attachment and detachment

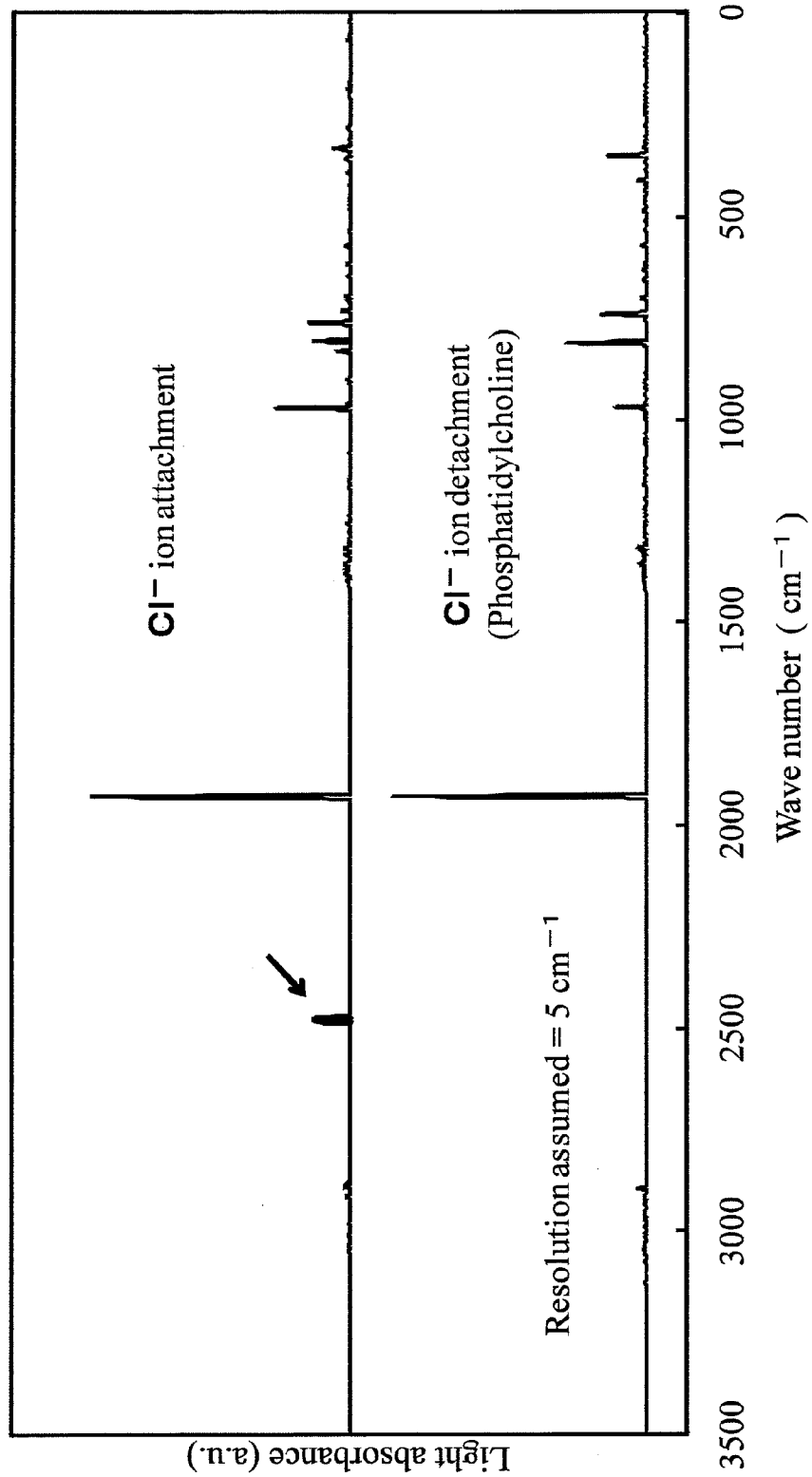
FIG. 6 Infrared spectral characteristics estimation of PCLN in case of Cl− ion attachment and detachment.

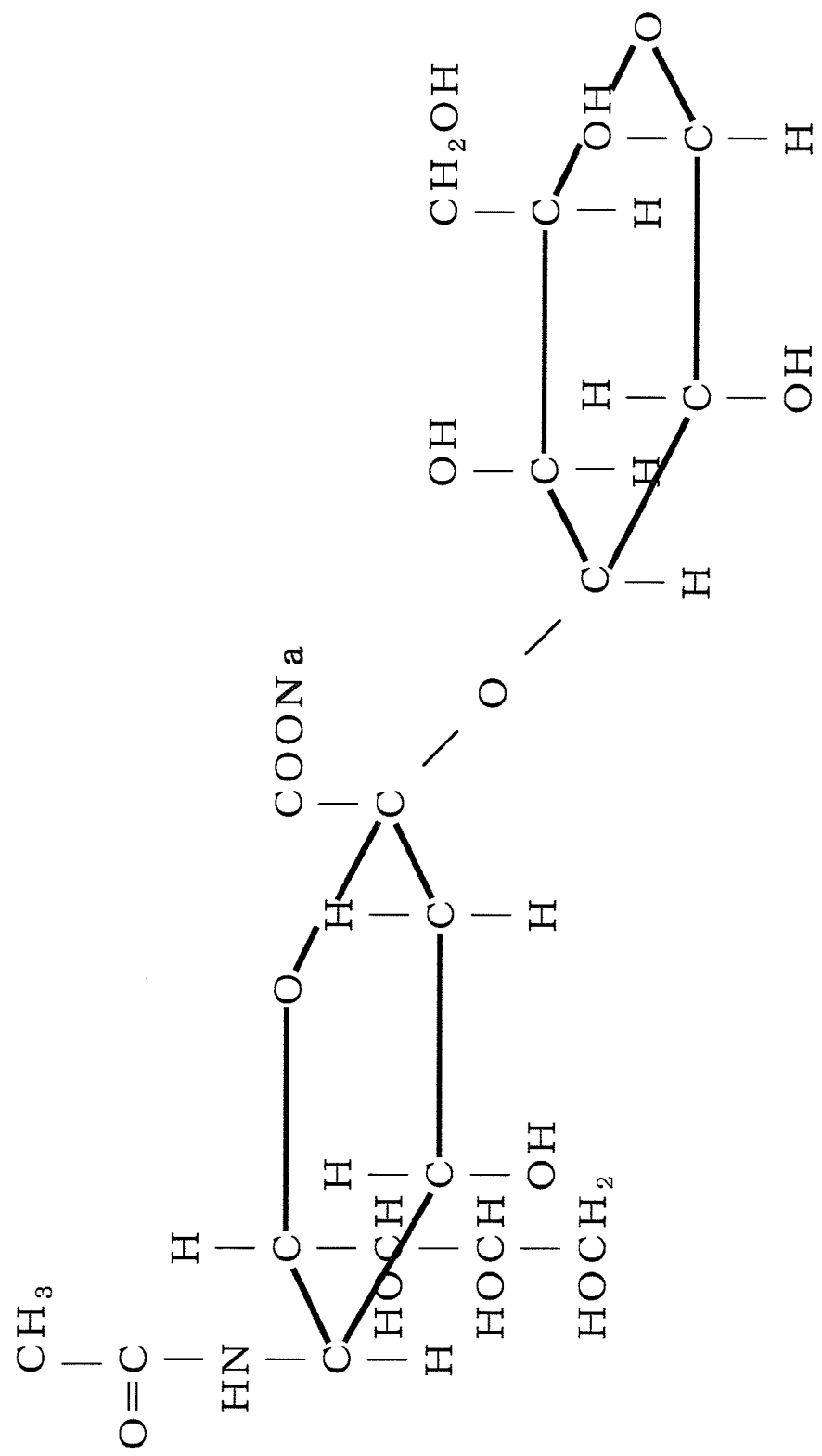
FIG. 7 Part of GD1a structure used for calculating infrared spectral characteristics

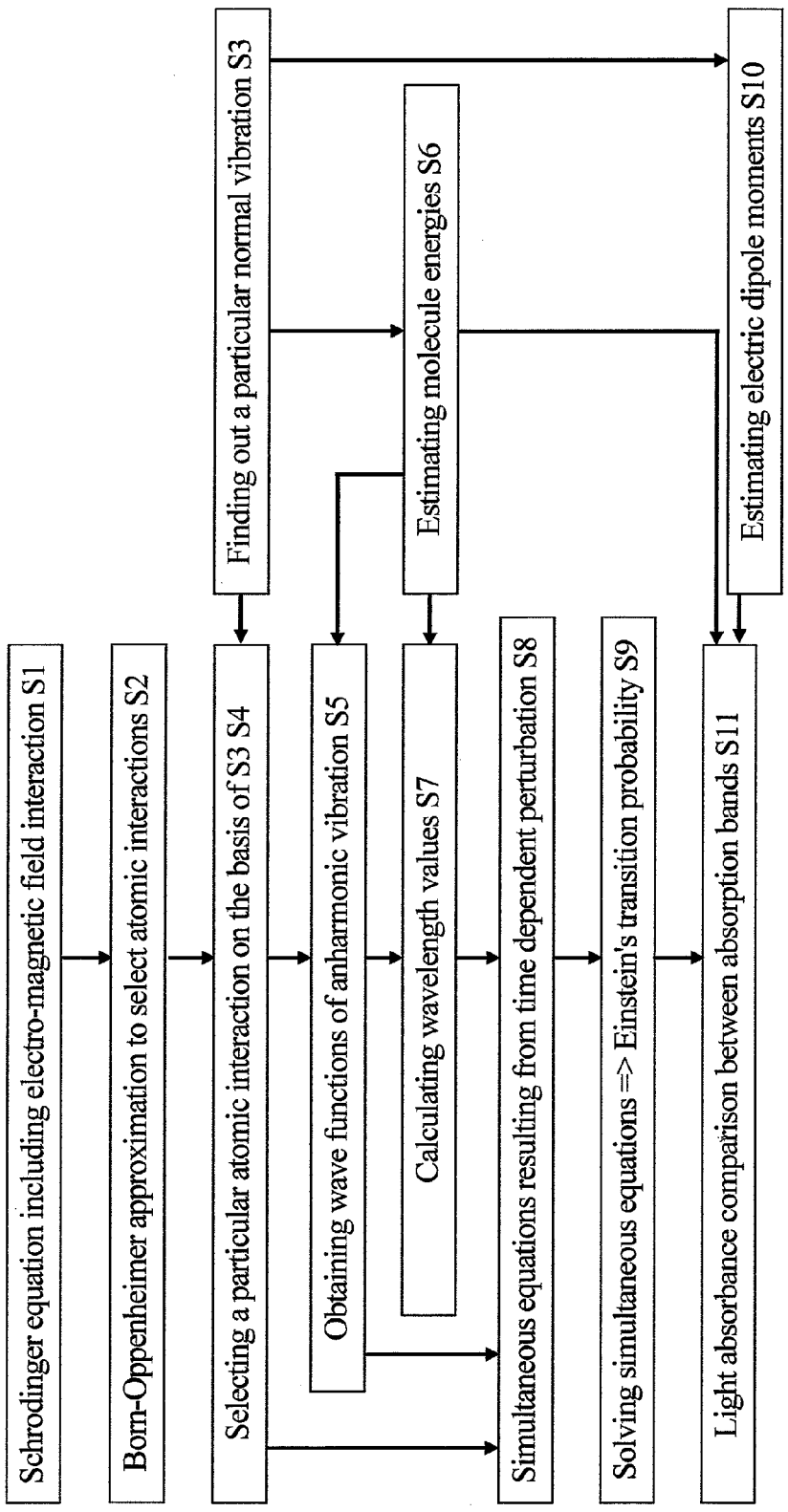
FIG. 8 Flow chart used for originally calculating near infrared spectral characteristics based on anharmonic vibrations

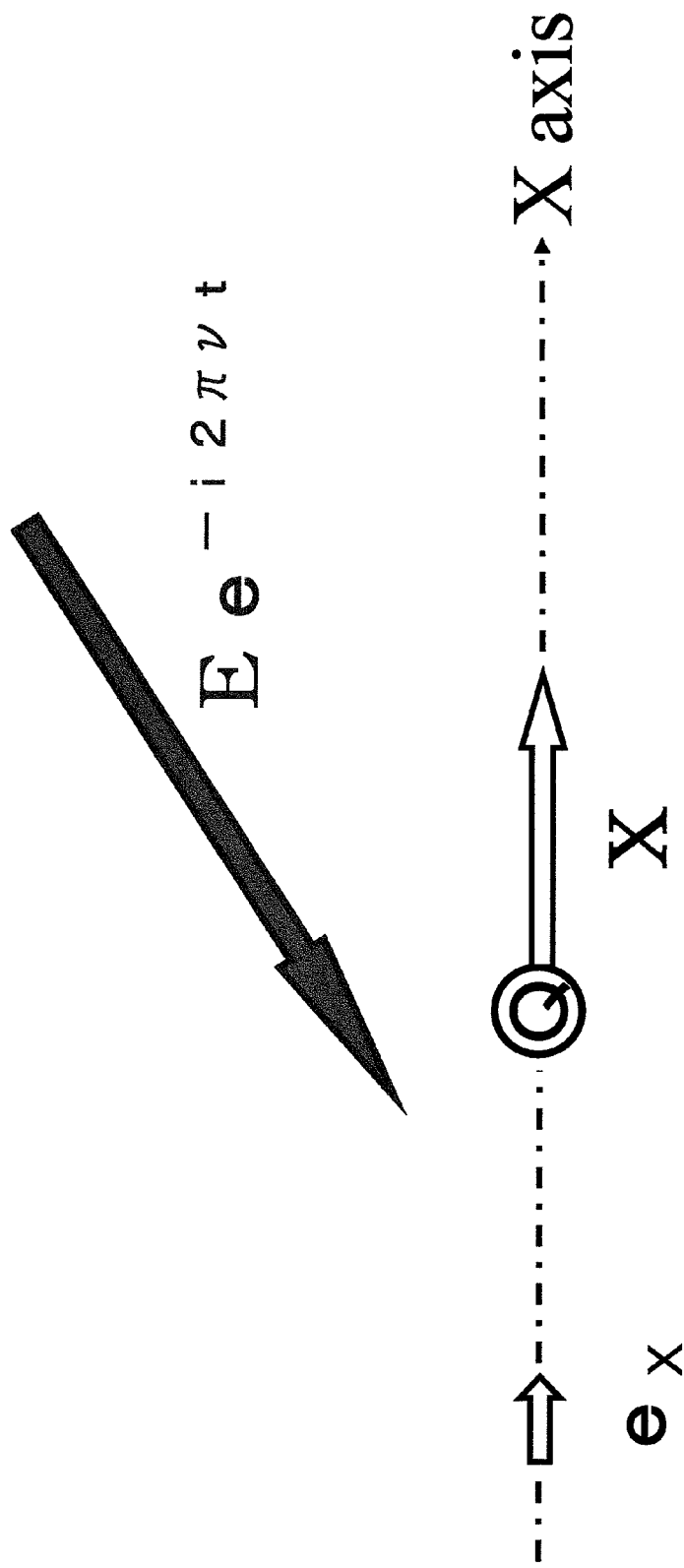
FIG. 9 Charged particle movement in electric field having specific direction

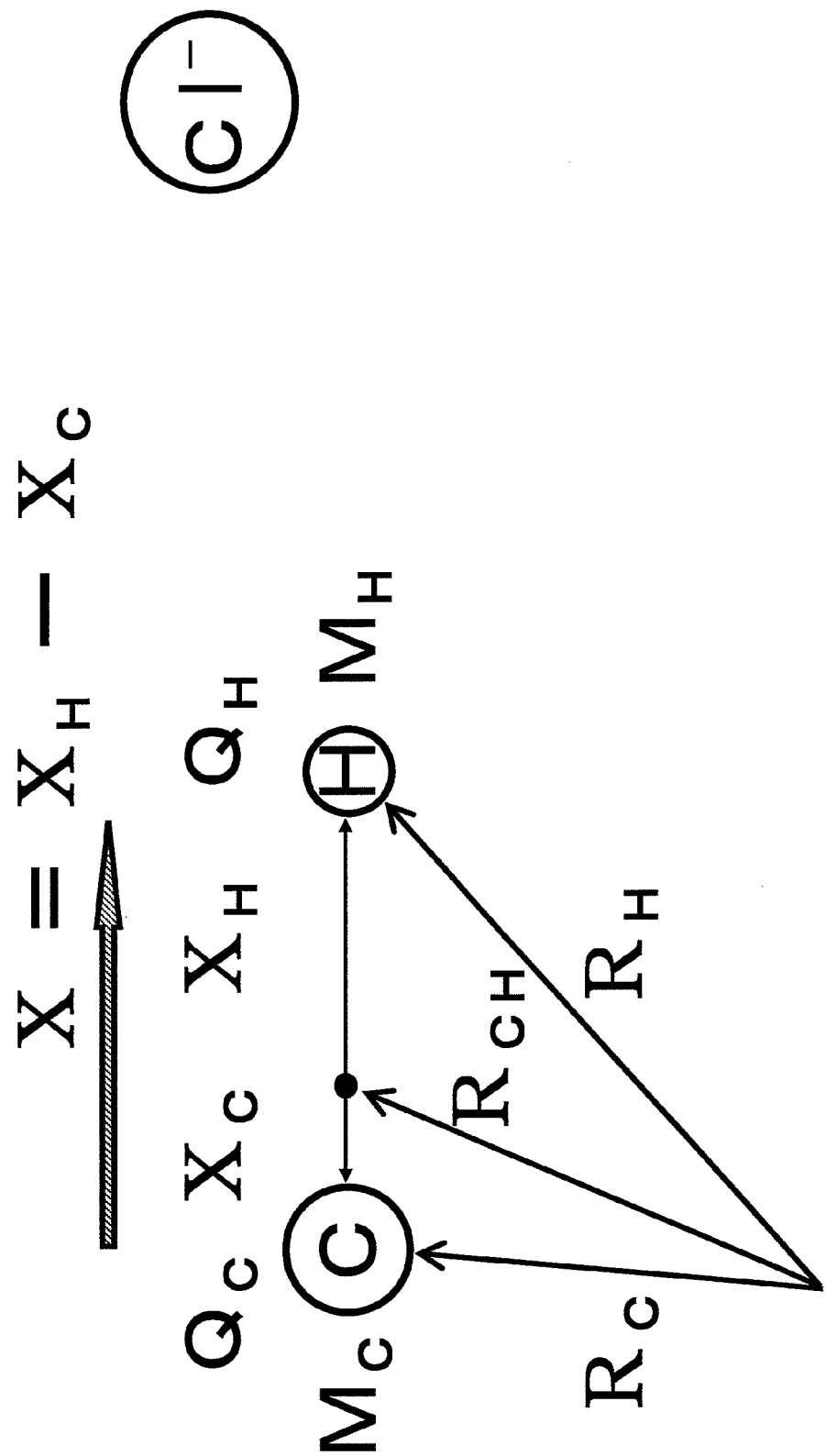
FIG. 10 Position vectors pointing to carbon and hydrogen atomic nucleuses which together make asymmetrical stretching of C-H-Cl⁻

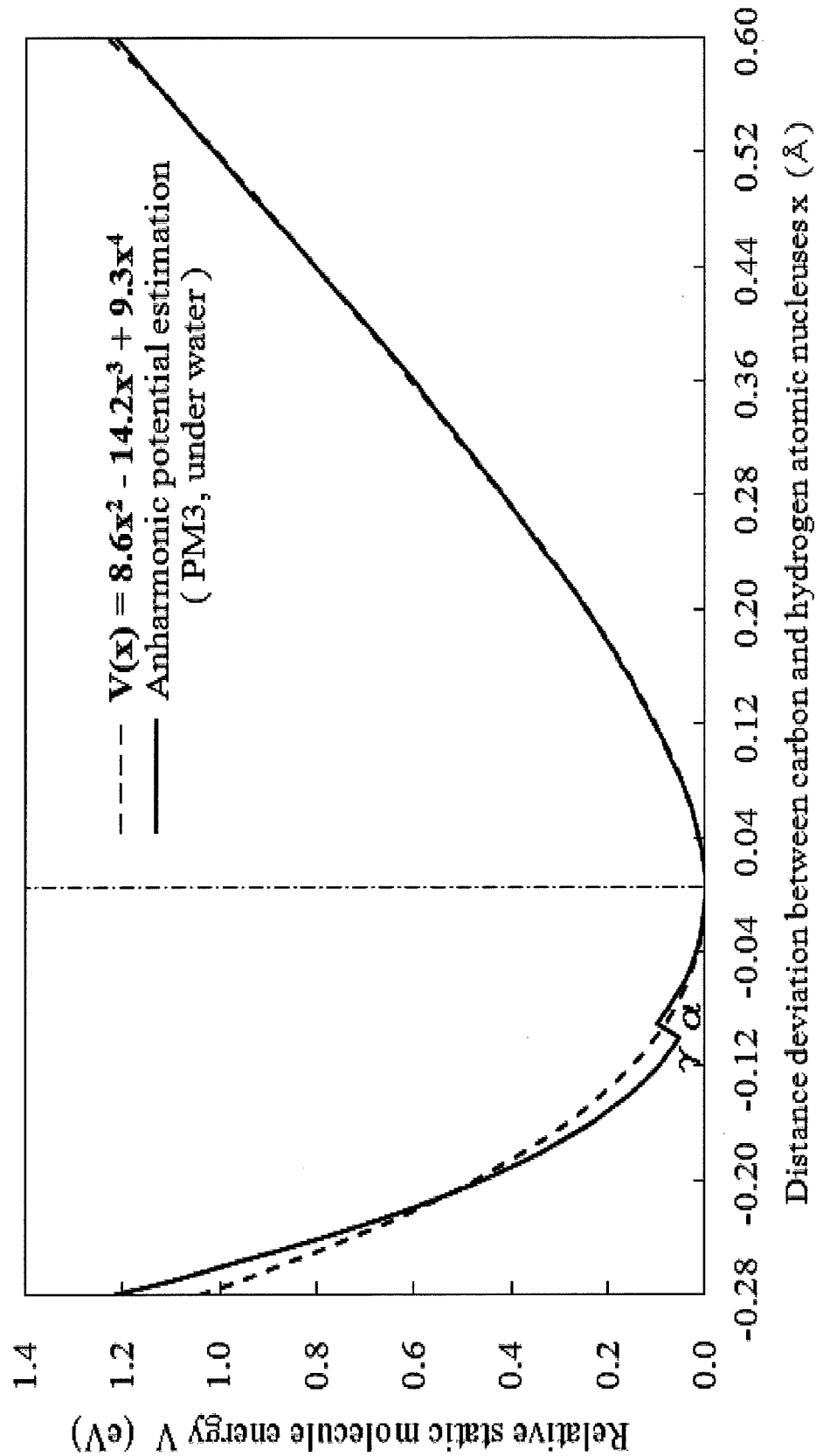
FIG11 Relative static molecule energy vs. distance deviation between carbon and hydrogen atomic nucleuses.

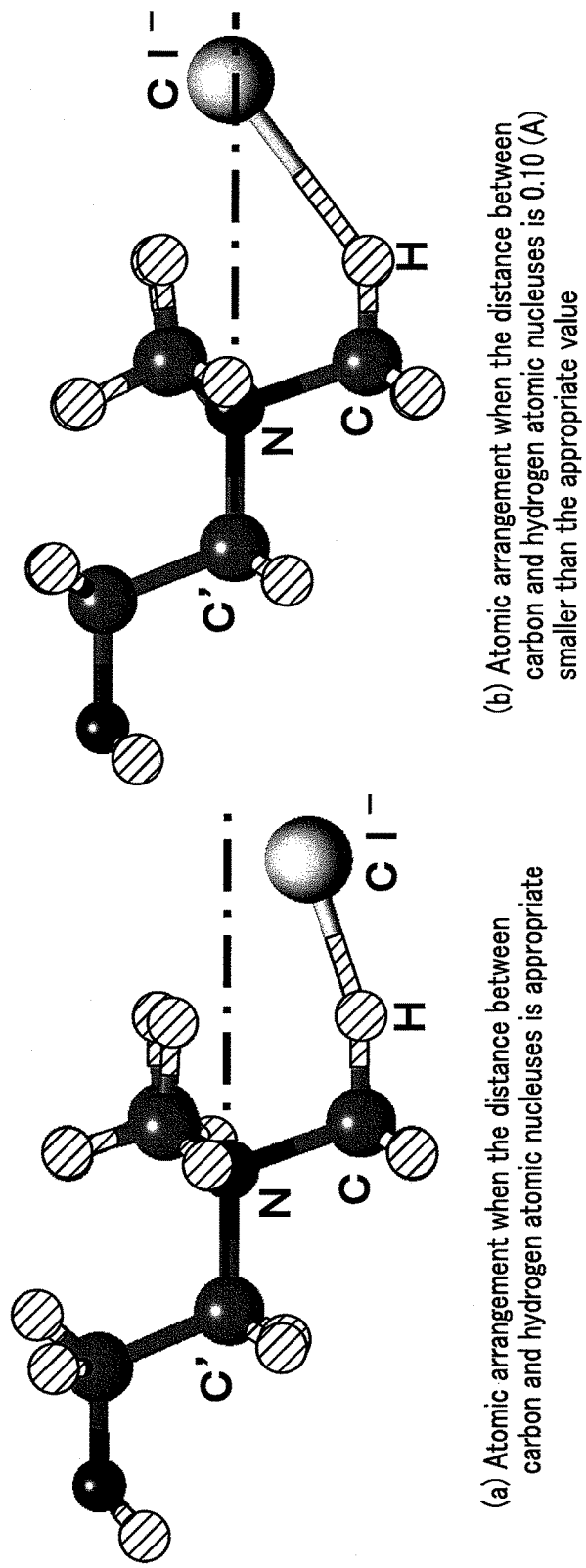
FIG. 12. Cl⁻ potision fluctuation dependent on distance deviation of carbon and hydrogen atomic nucleuses.

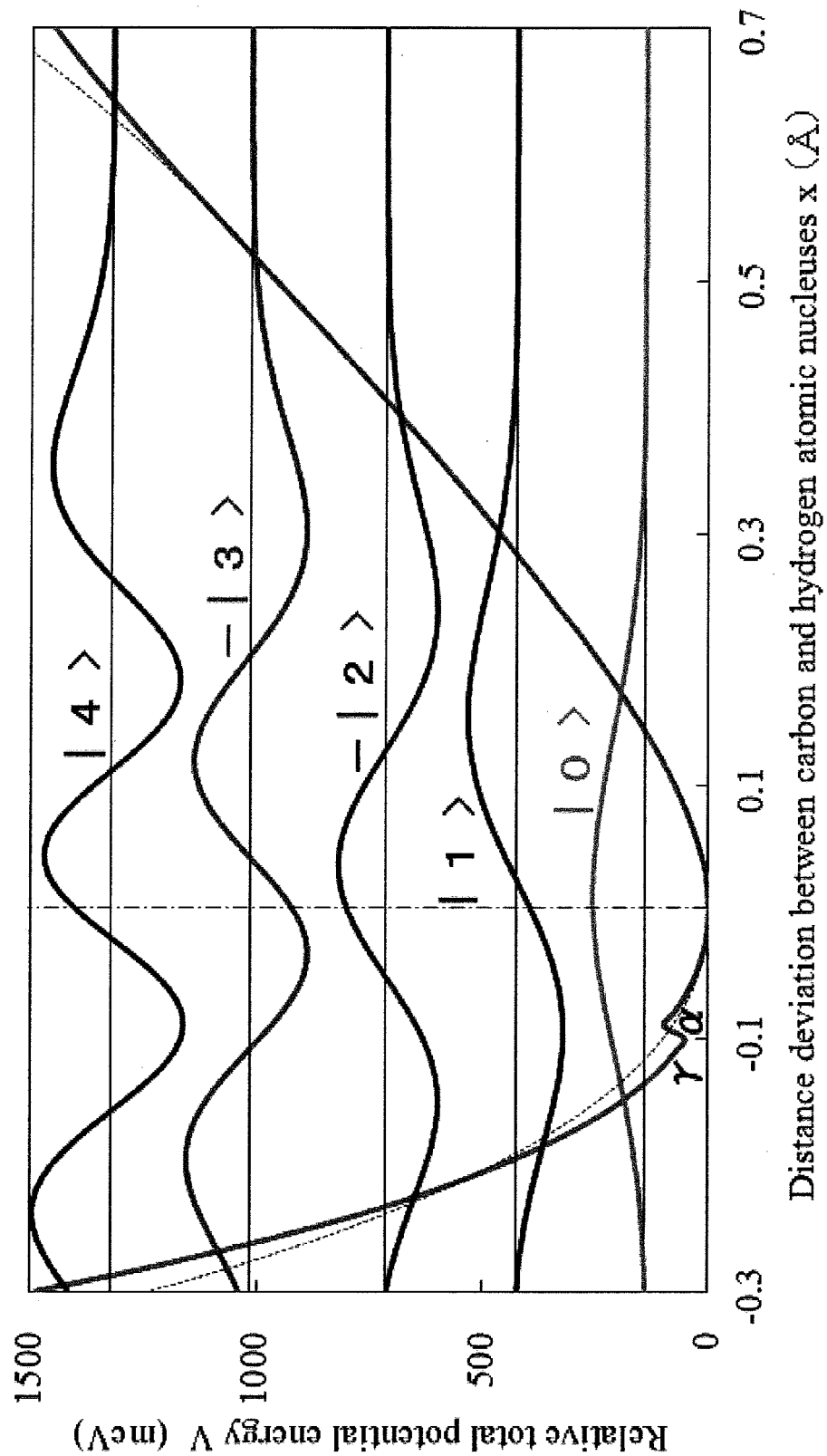
FIG. 13 Amplitude distributions of wave functions $|m\rangle$ regarding anharmonic vibrations.

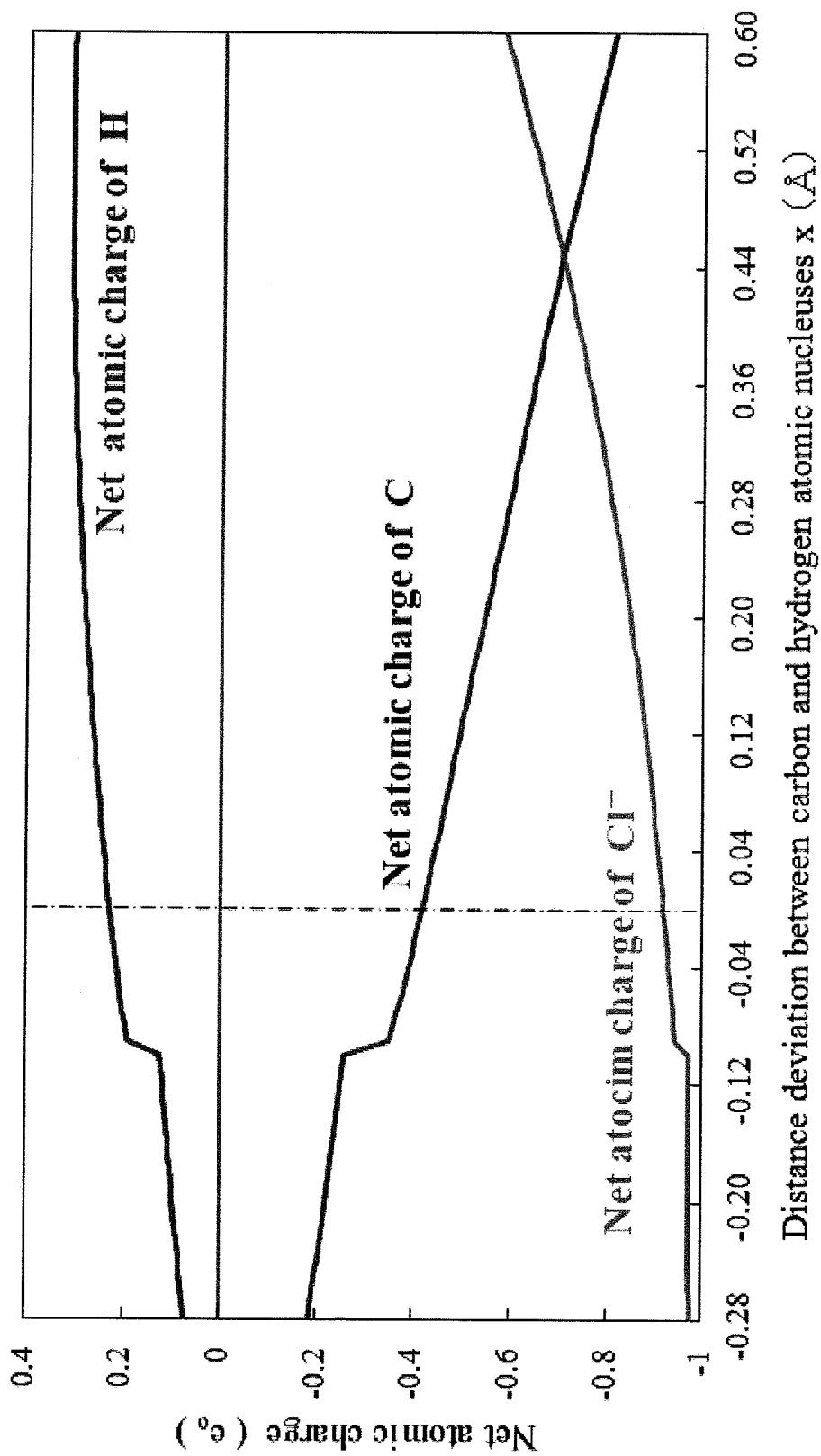
FIG. 14 Net atomic charges vs. distance deviations between carbon and hydrogen atomic nucleuses

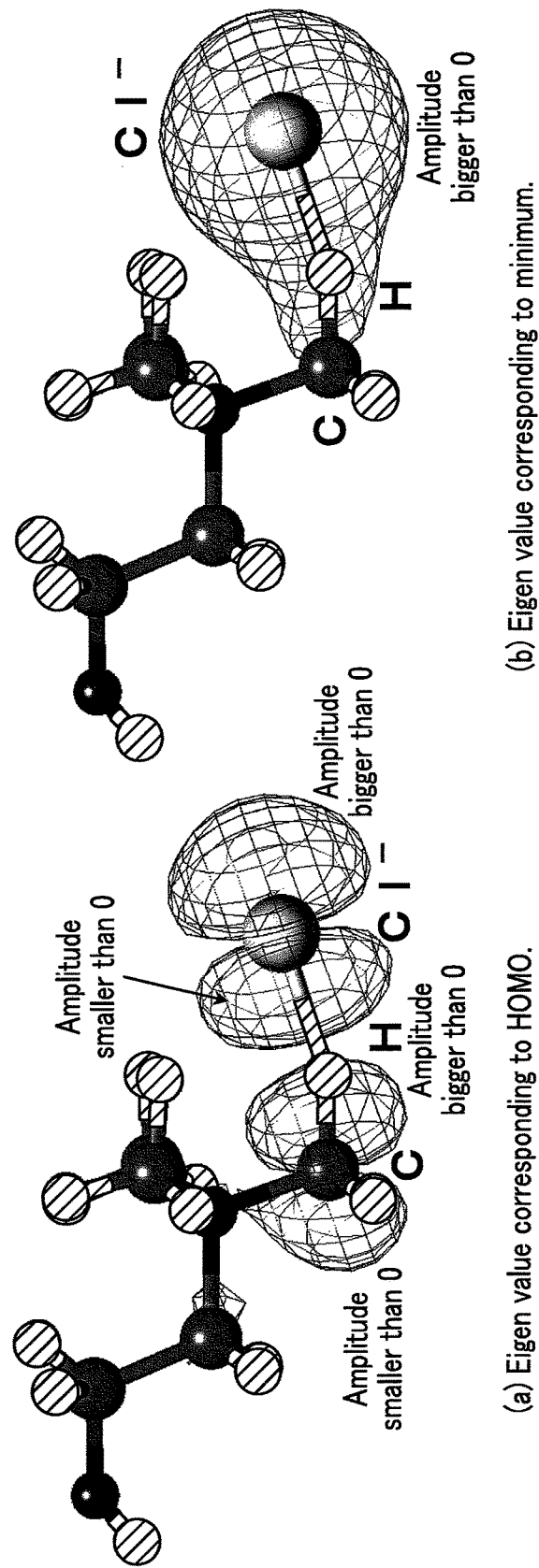
FIG.15 Amplitude distributions of molecular orbitals whose eigen values of energy correspond to HOMO and the minimum

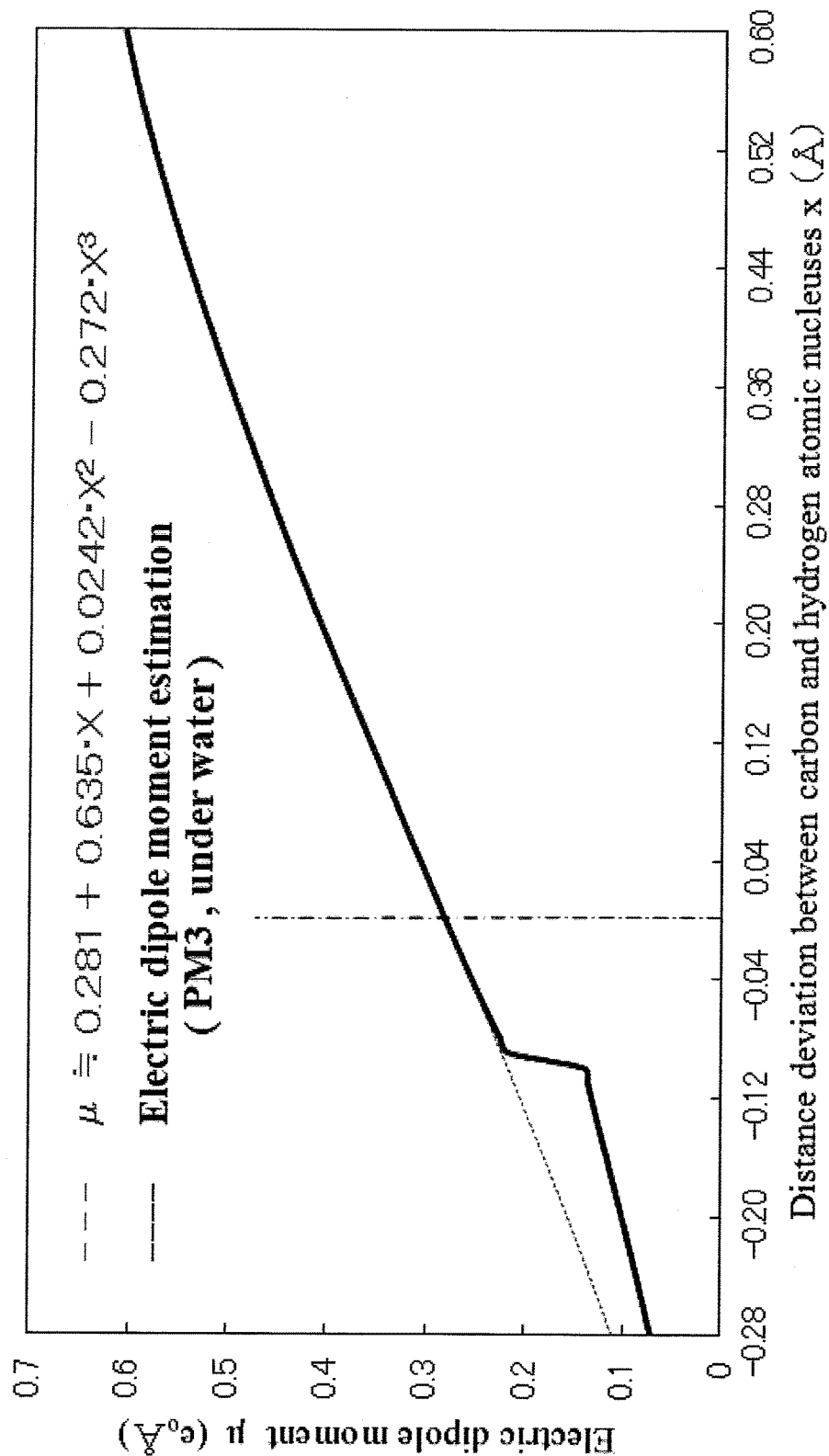
FIG. 16 Electric dipole moments vs. distance deviations between carbon and hydrogen atomic nucleuses

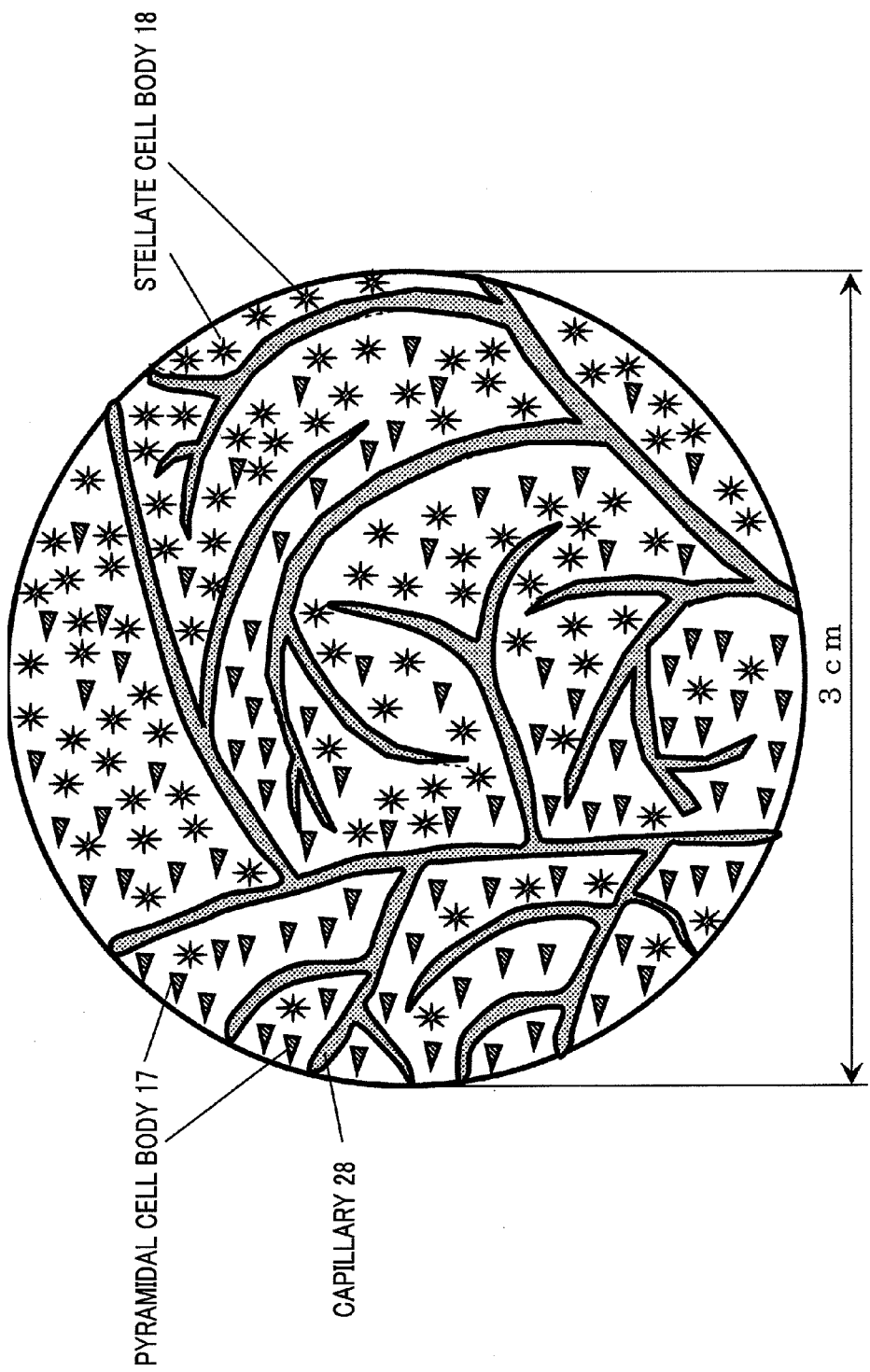
FIG.17  COMPARISON IN SPATIAL RESOLUTION BETWEEN MEMBRANE POTENTIAL CHANGING DETECTION AND OXYGEN CONCENTRATION CHANGE DETECTION IN BLOOD

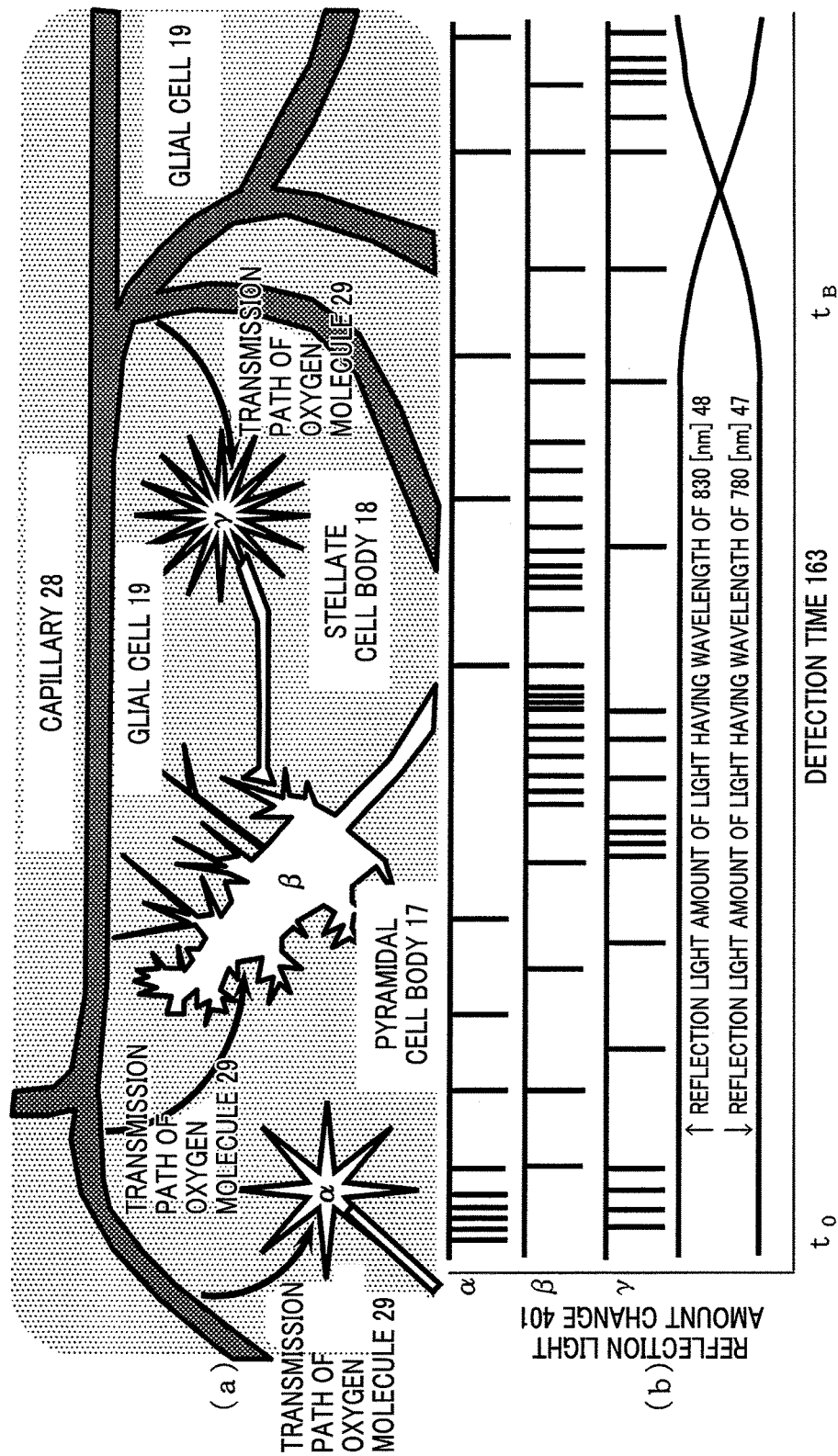
FIG.18 COMPARISON IN TEMPORAL RESOLUTION BETWEEN MEMBRANE POTENTIAL CHANGING DETECTION AND OXYGEN CONCENTRATION CHANGE DETECTION IN BLOOD

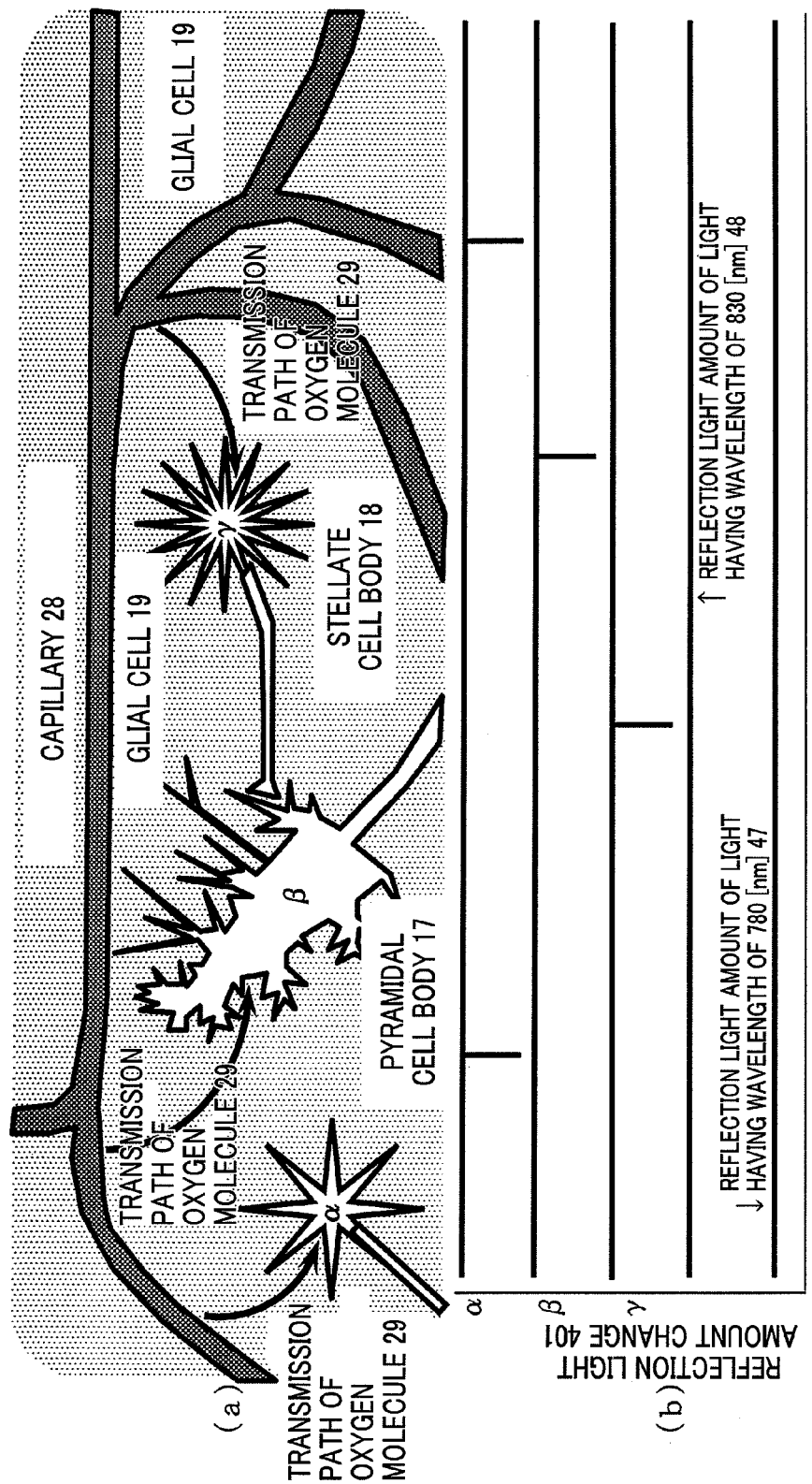
FIG.19 COMPARISON IN DETECTION ACCURACY BETWEEN MEMBRANE POTENTIAL CHANGING DETECTION AND OXYGEN CONCENTRATION CHANGE DETECTION IN BLOOD

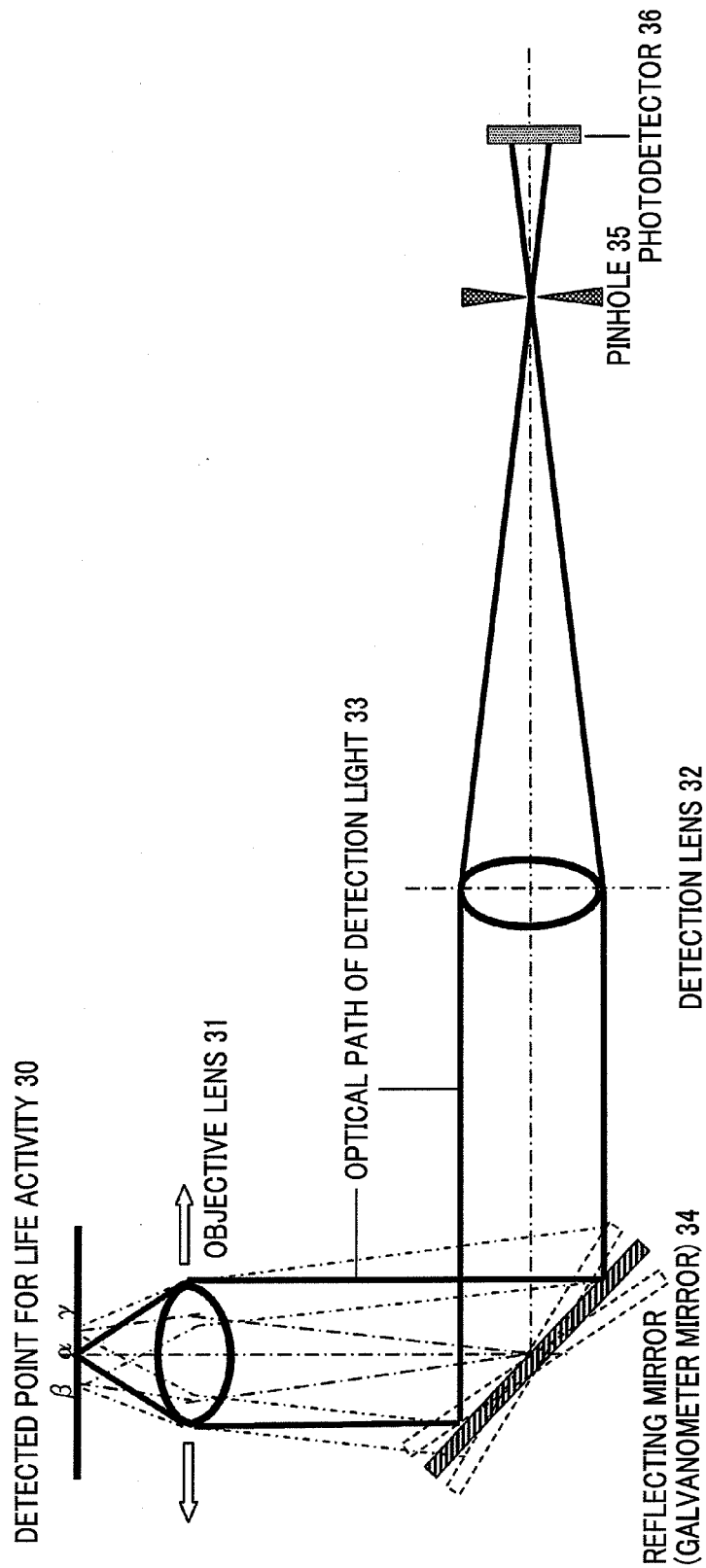
FIG.20 FIRST PRINCIPLE OF MONITORING METHOD OF DETECTED POINT FOR LIFE ACTIVITY

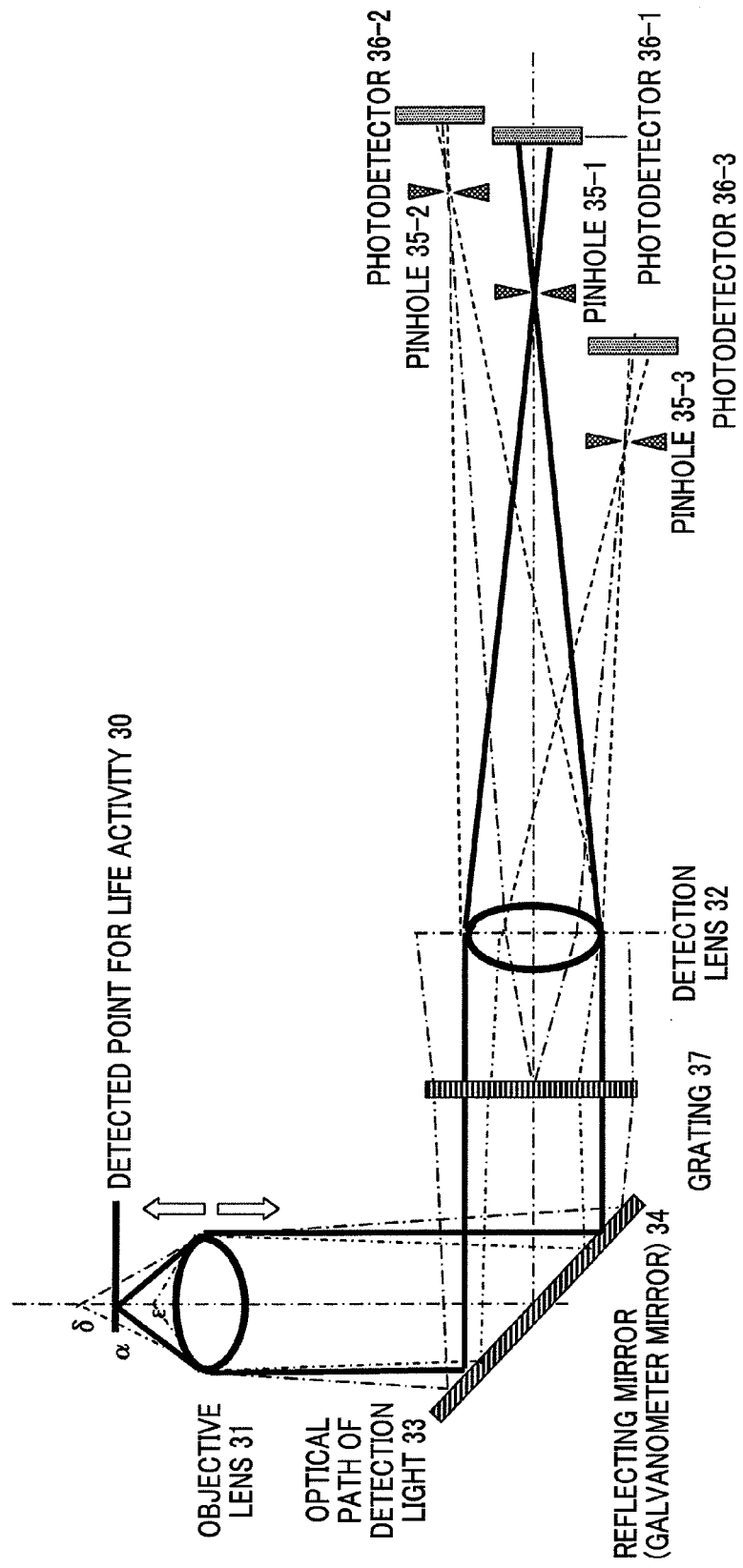
FIG.21 FIRST PRINCIPLE OF MONITORING METHOD OF PATTERN OF DETECTED POINT FOR LIFE ACTIVITY IN DEPTH DIRECTION

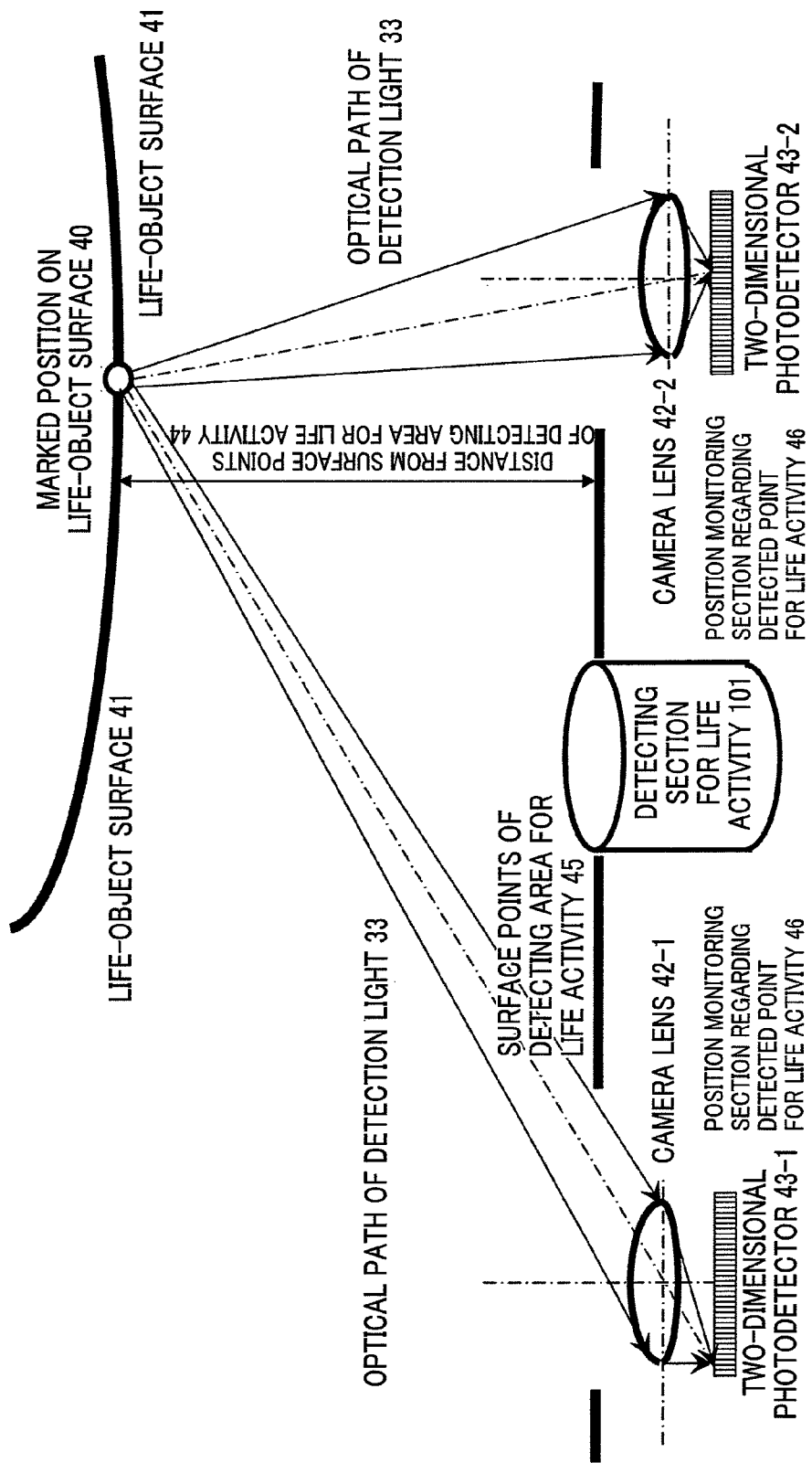
FIG.22 SECOND PRINCIPLE OF MONITORING METHOD OF MARKED POSITION ON LIFE-OBJECT SURFACE

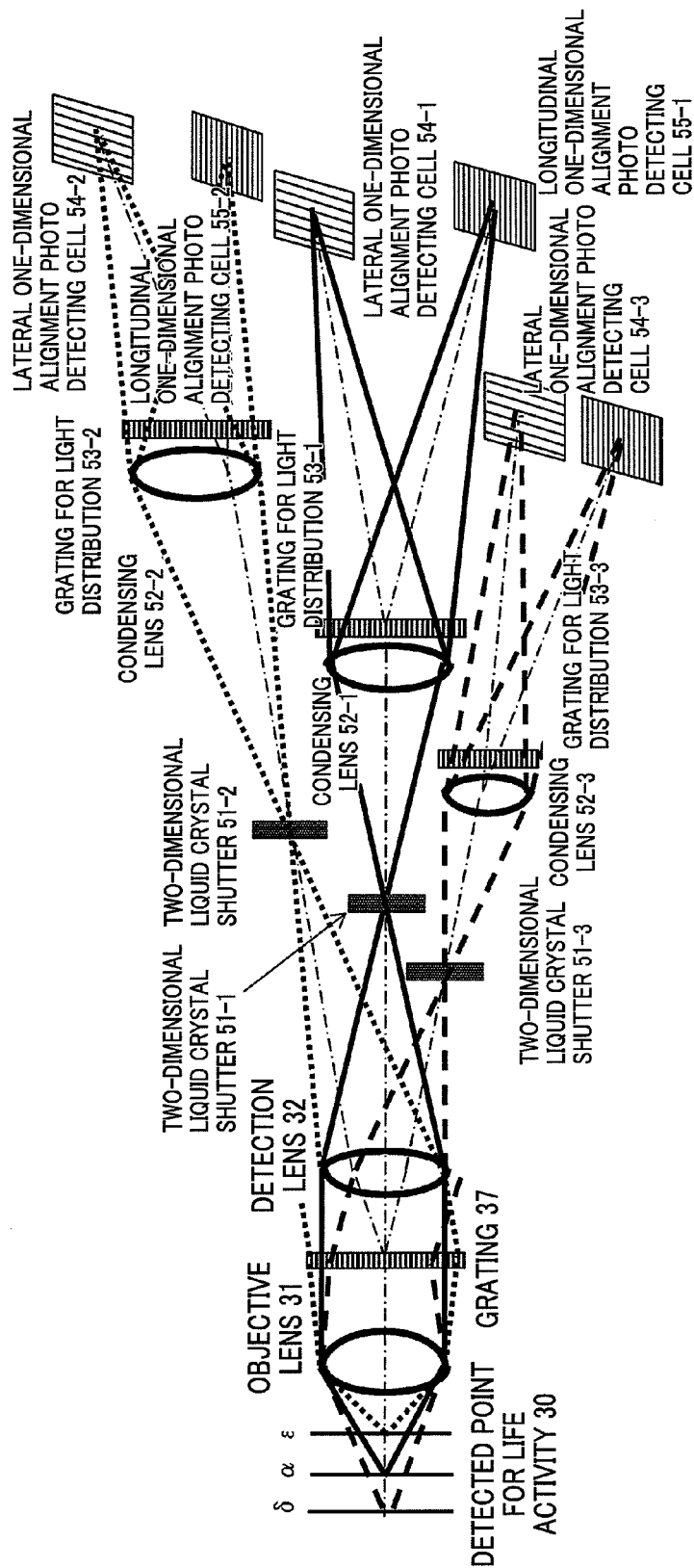
FIG. 23 PRINCIPLE (USING CONFOCAL SYSTEM) OF FIRST EXEMPLARY EMBODIMENT REGARDING OPTICAL SYSTEM FOR LIFE ACTIVITY DETECTION

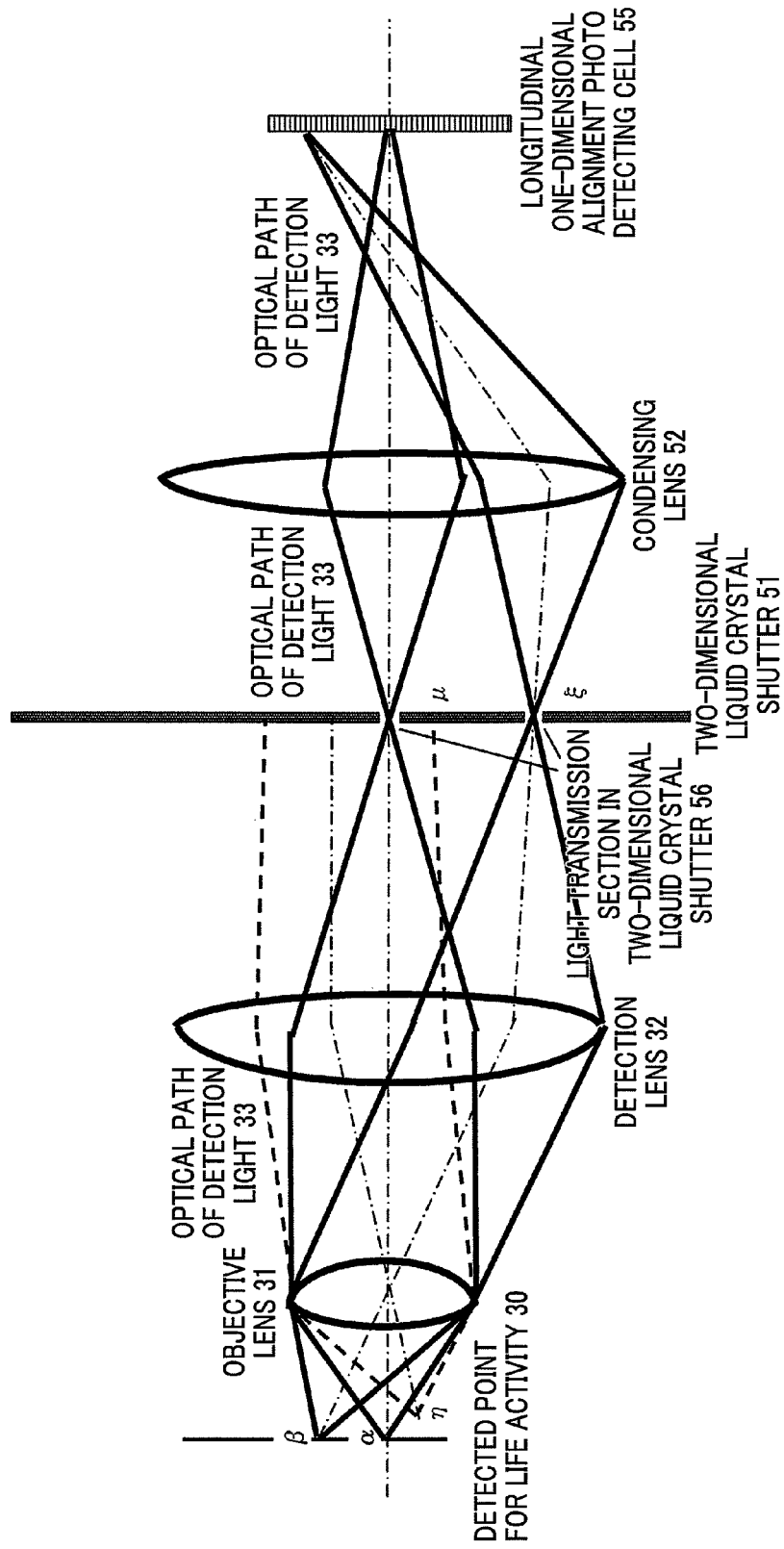
FIG.24  OPERATION PRINCIPLE OF FIRST EXEMPLARY EMBODIMENT REGARDING OPTICAL SYSTEM FOR LIFE ACTIVITY DETECTION

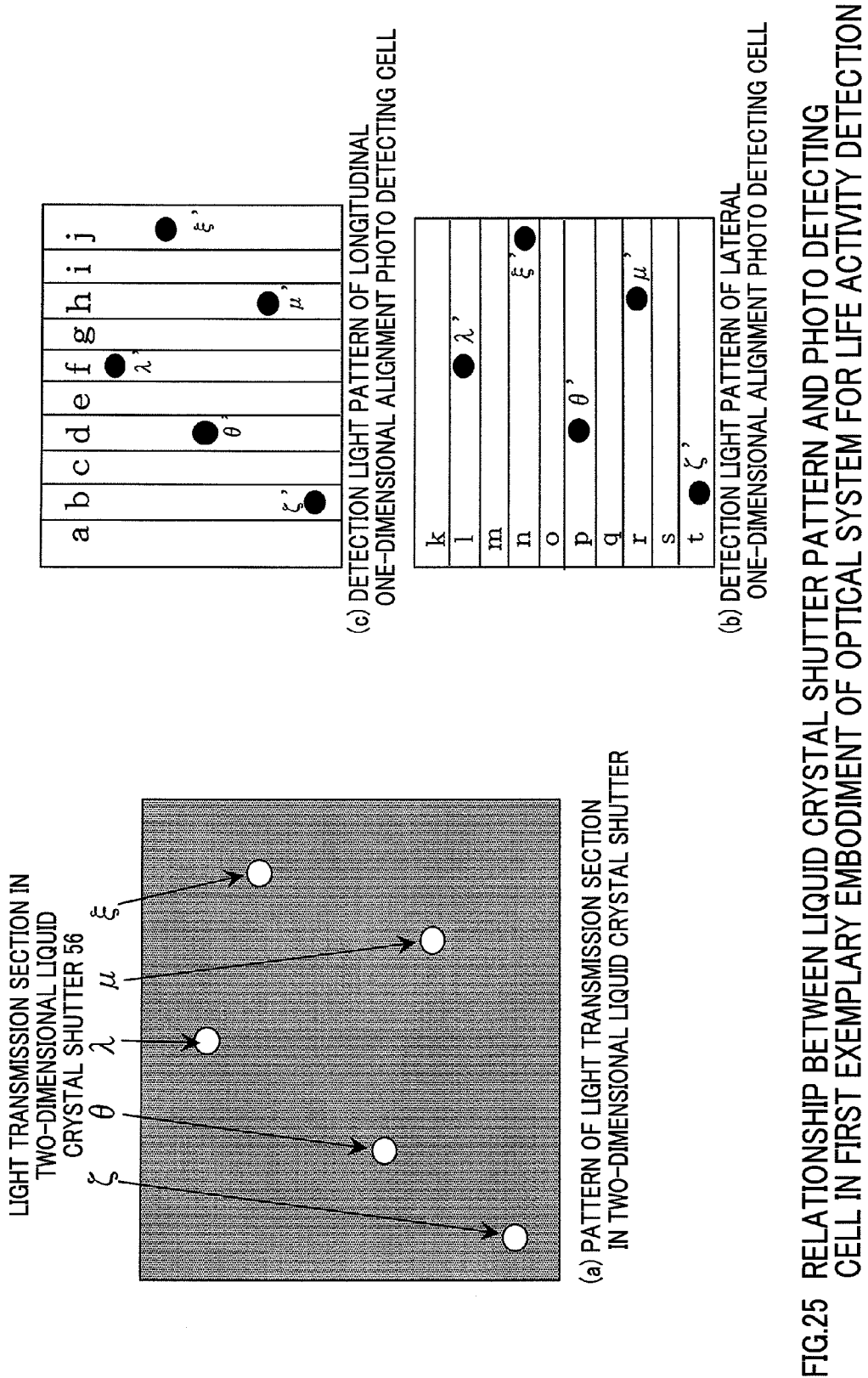
FIG.25 RELATIONSHIP BETWEEN LIQUID CRYSTAL SHUTTER PATTERN AND PHOTO DETECTING CELL IN FIRST EXEMPLARY EMBODIMENT OF OPTICAL SYSTEM FOR LIFE ACTIVITY DETECTION

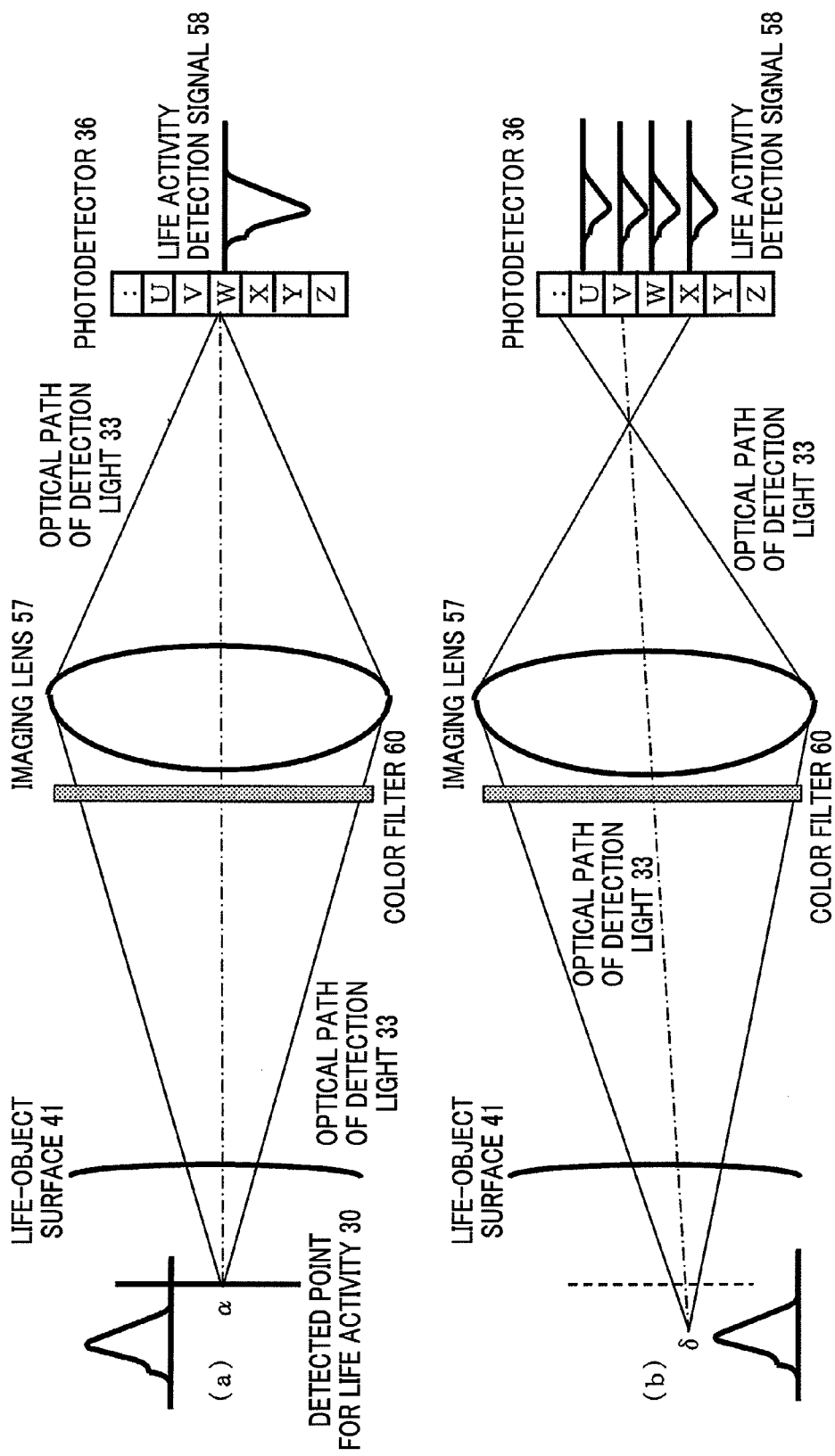
FIG.26 OPERATION PRINCIPLE REGARDING APPLIED EMBODIMENT OF OPTICAL SYSTEM FOR LIFE ACTIVITY DETECTION

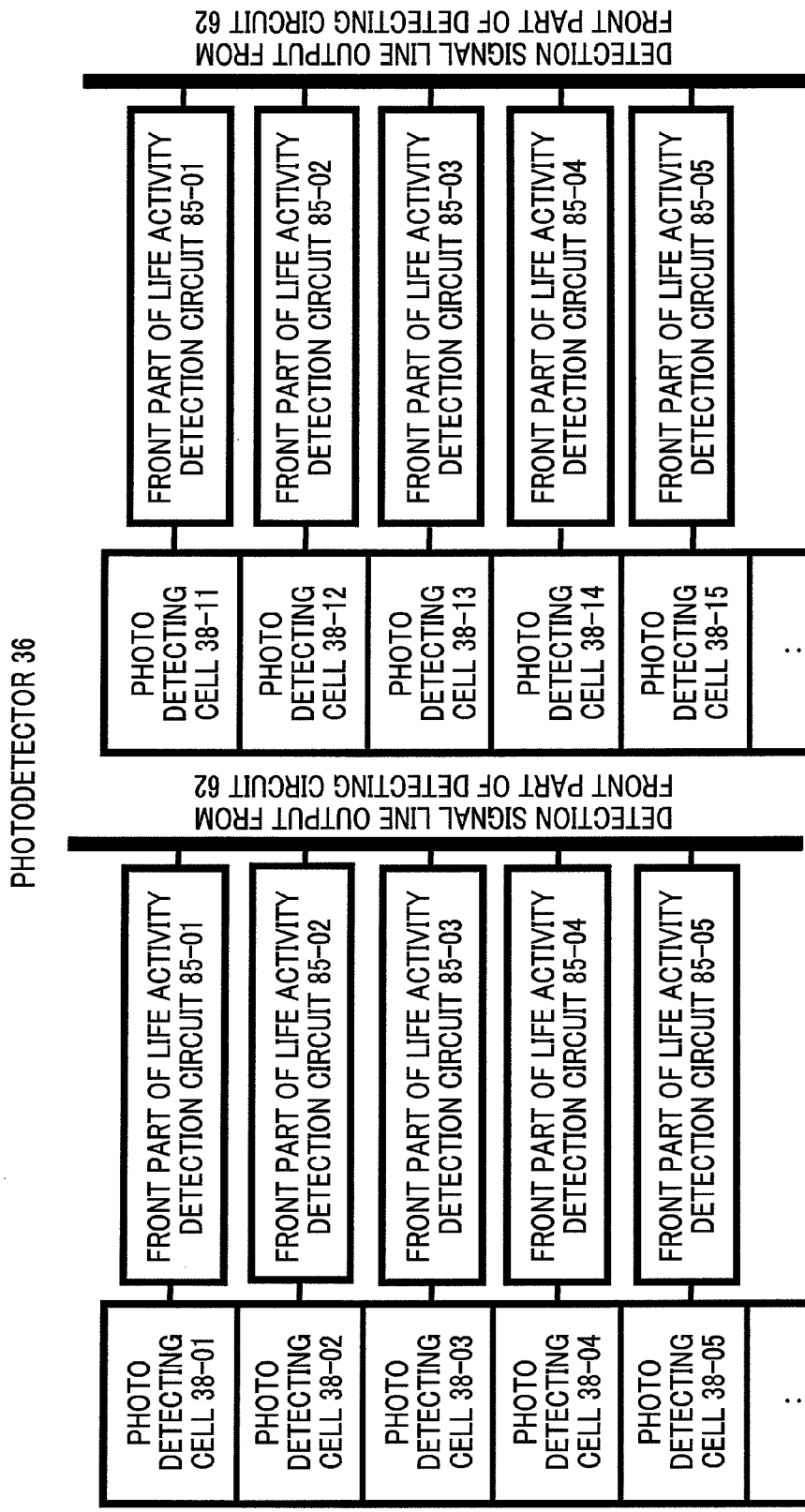
FIG.27 CONFIGURATION OF PHOTODETECTOR IN APPLIED EMBODIMENT OF OPTICAL SYSTEM FOR LIFE ACTIVITY DETECTION

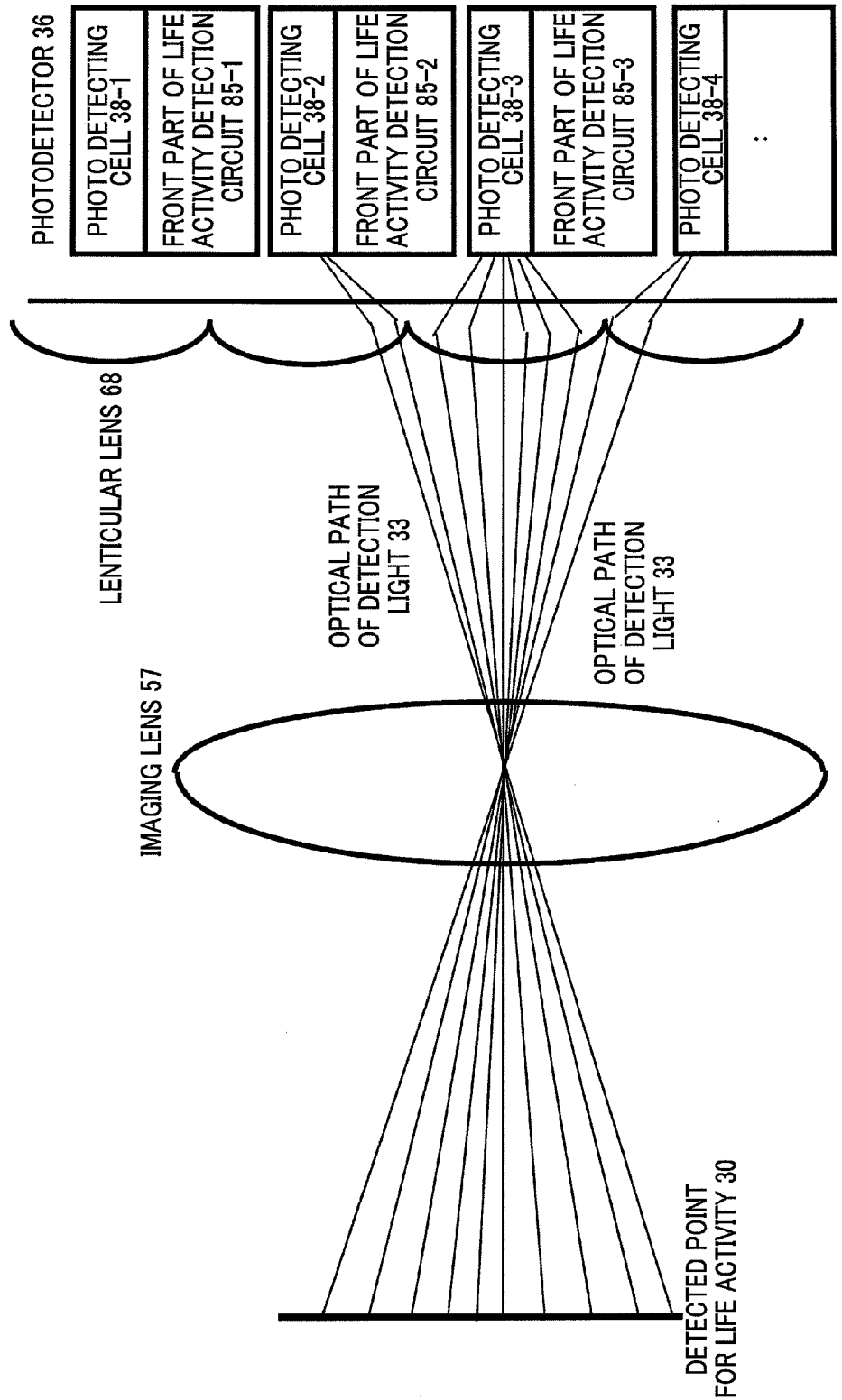
FIG.28 DETAILED OPTICAL ARRANGEMENT REGARDING APPLIED EMBODIMENT OF OPTICAL SYSTEM FOR LIFE ACTIVITY DETECTION

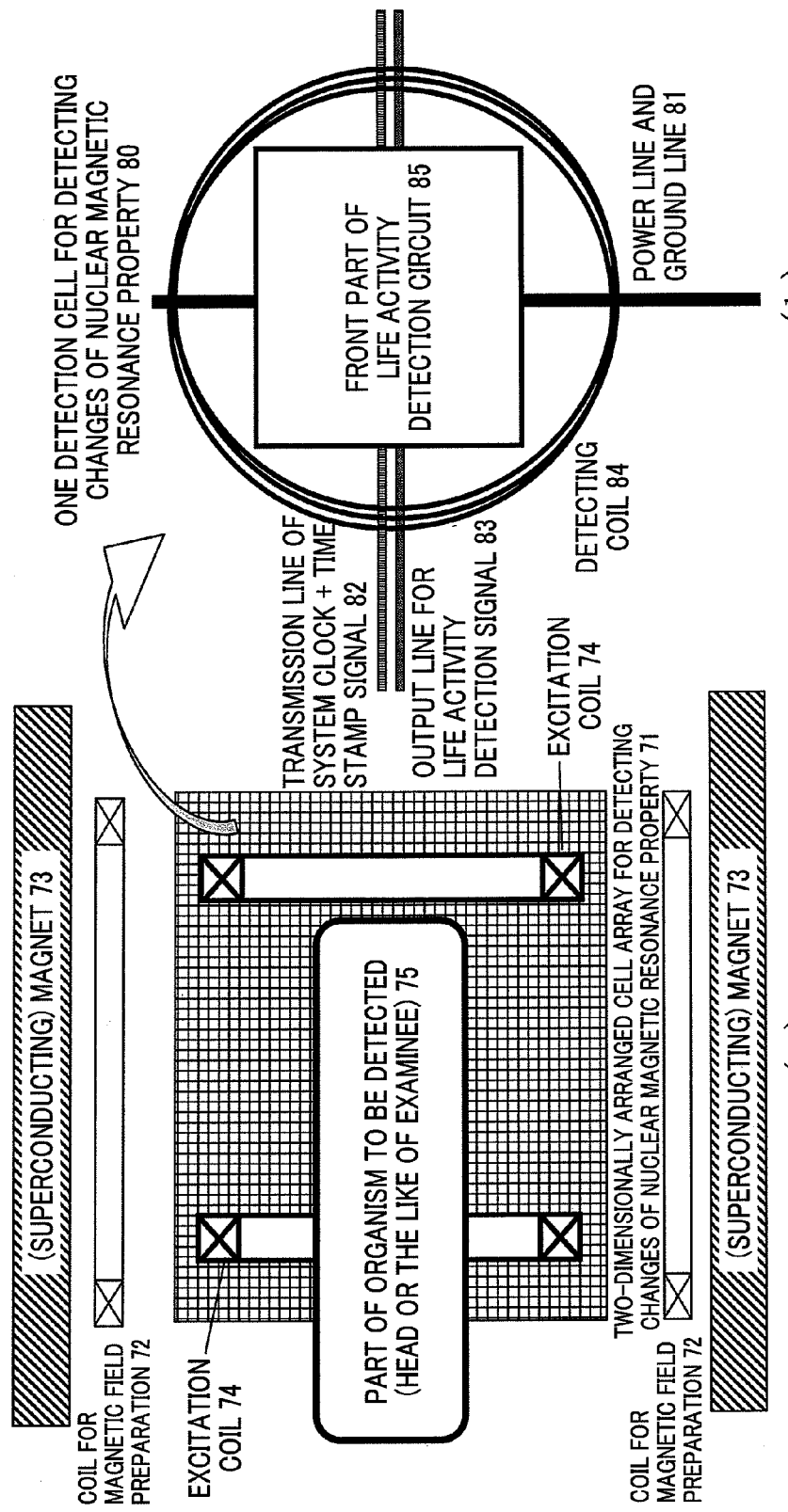
FIG.29  METHOD FOR DETECTING LOCAL CHANGE OF NUCLEAR MAGNETIC RESONANCE PROPERTY IN LIFE OBJECT AT HIGH SPEED

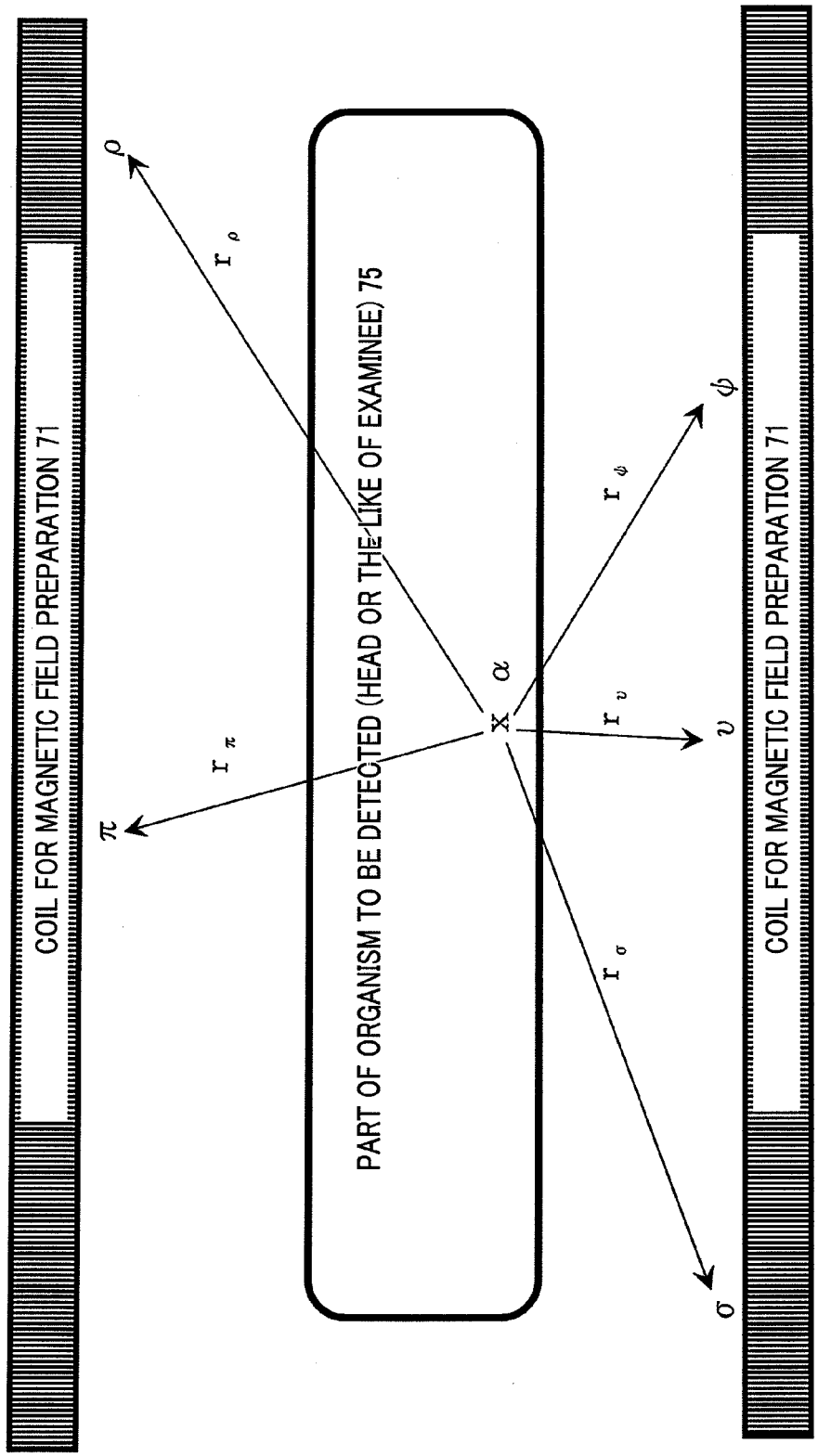
FIG.30 METHOD FOR DETECTING LOCATION WHERE NUCLEAR MAGNETIC RESONANCE PROPERTY CHANGES

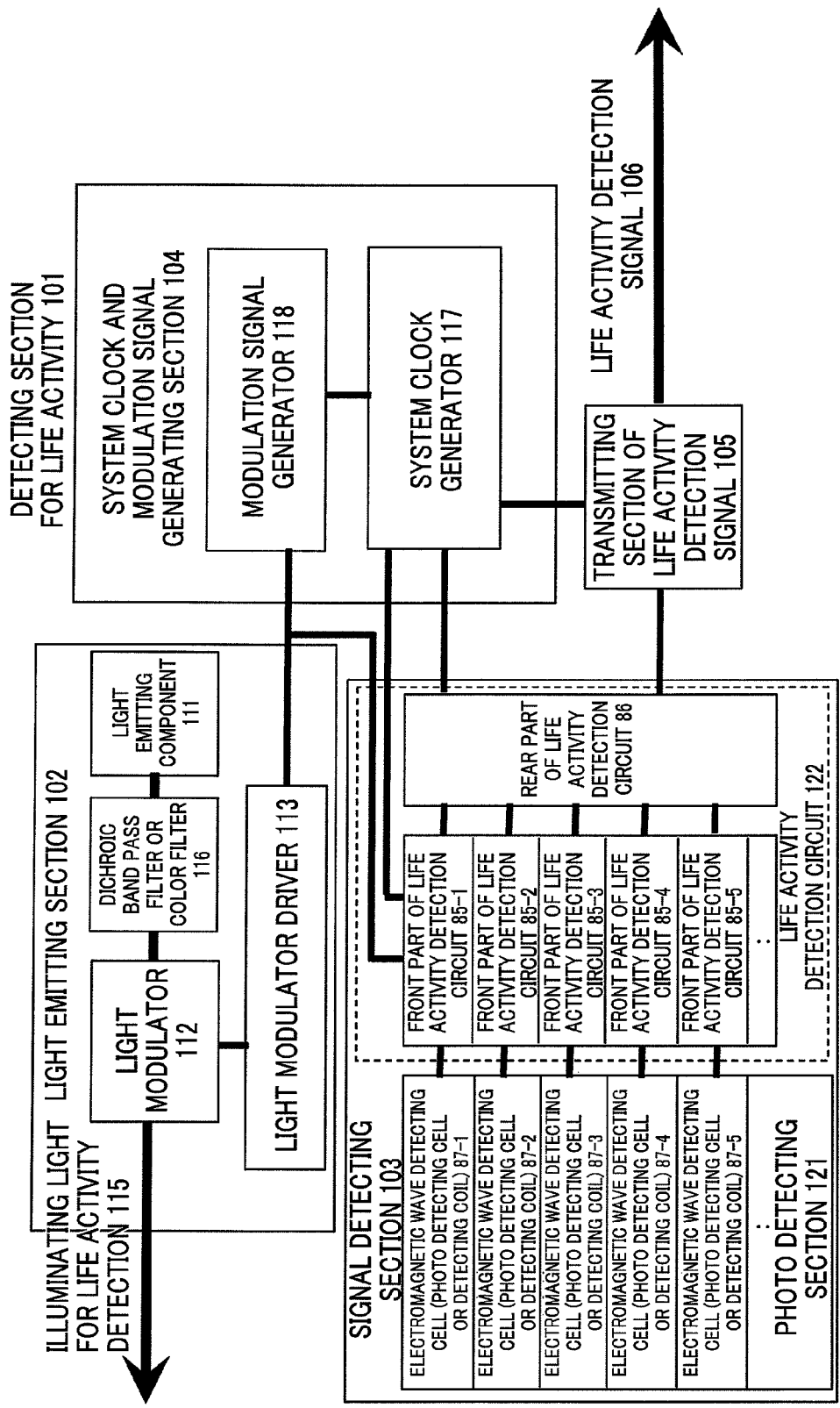
FIG.31  CONFIGURATION OF DETECTING SECTION FOR LIFE ACTIVITY

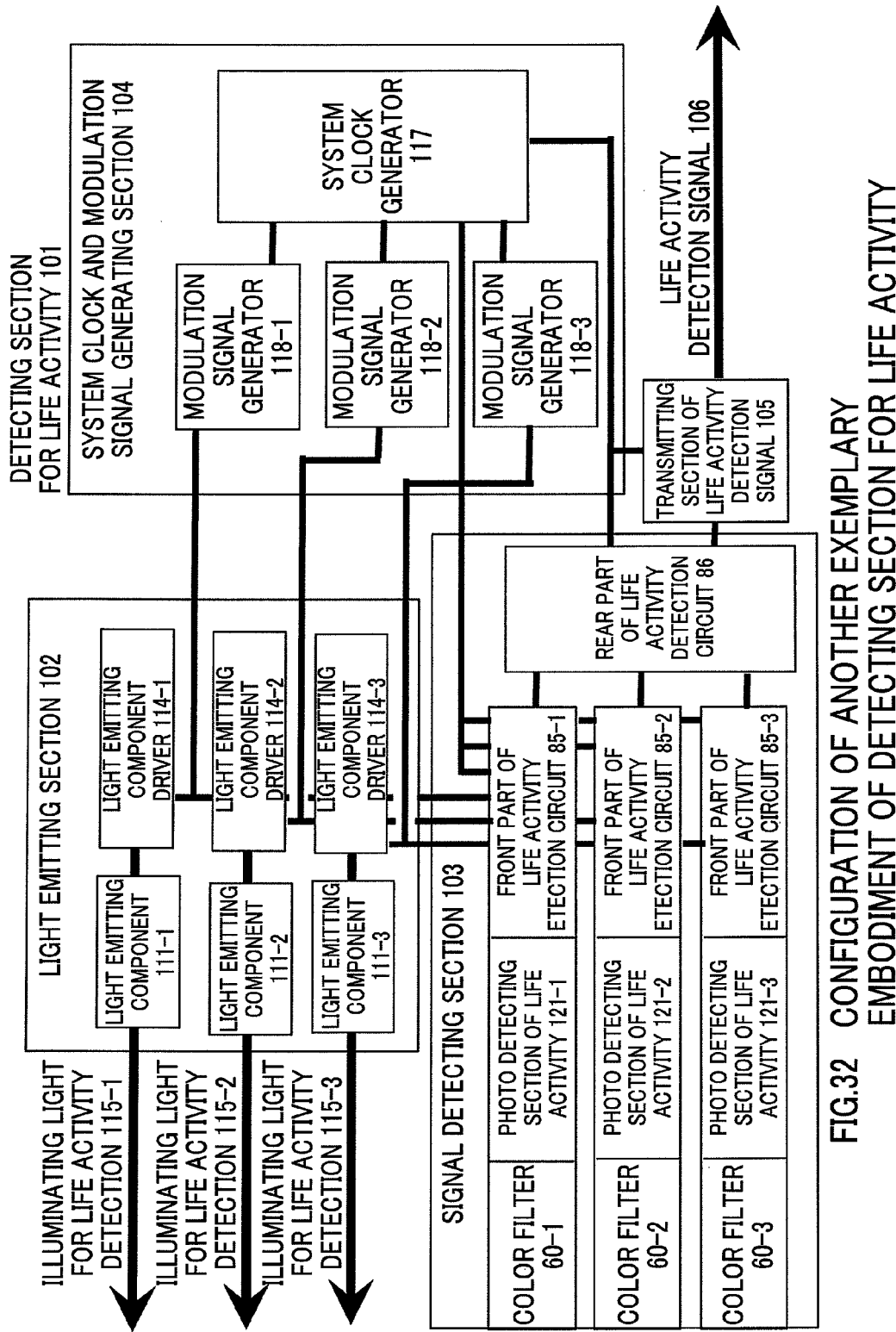
FIG.32 CONFIGURATION OF ANOTHER EXEMPLARY EMBODIMENT OF DETECTING SECTION FOR LIFE ACTIVITY

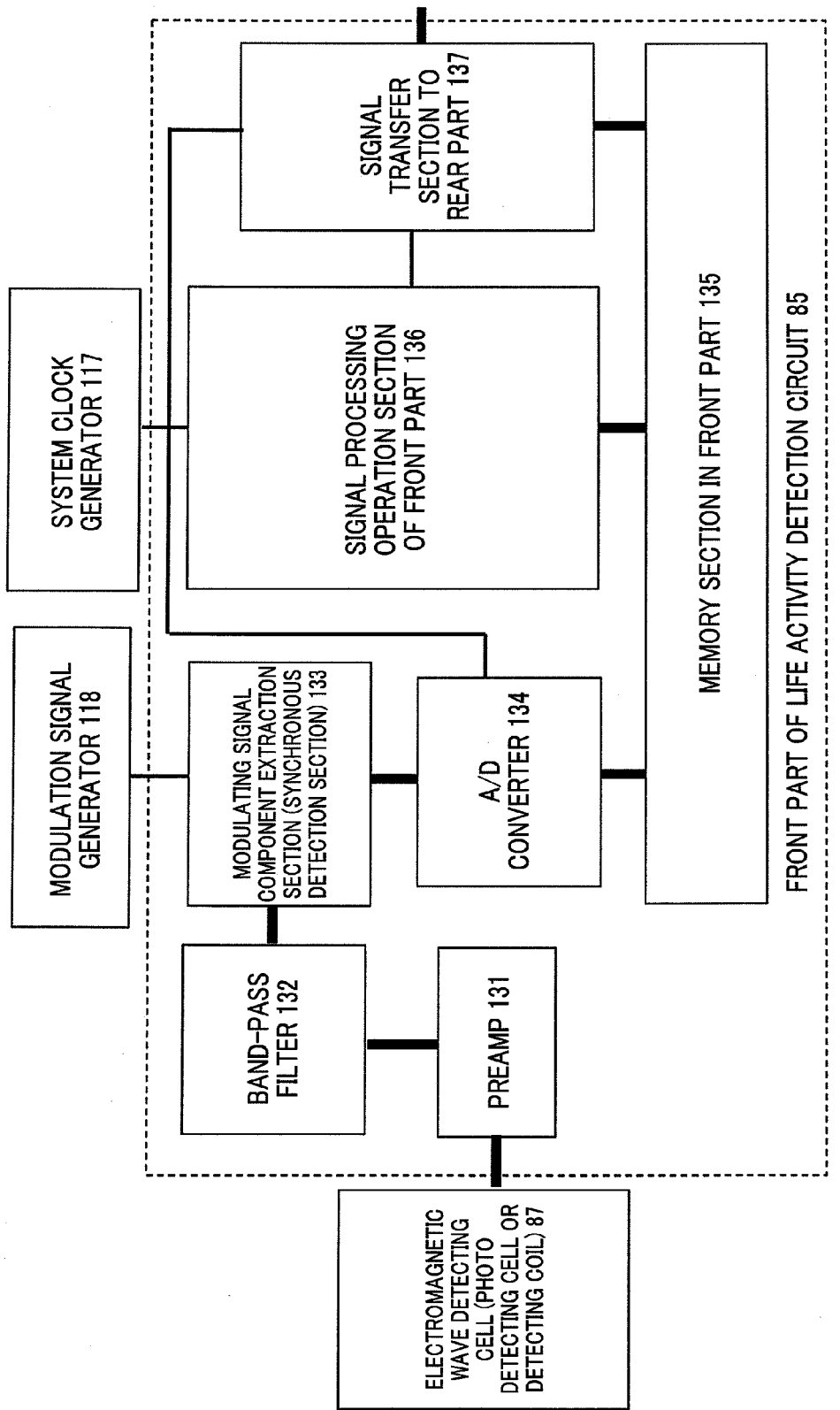
FIG.33 CONFIGURATION OF FRONT PART OF LIFE ACTIVITY DETECTING CIRCUIT

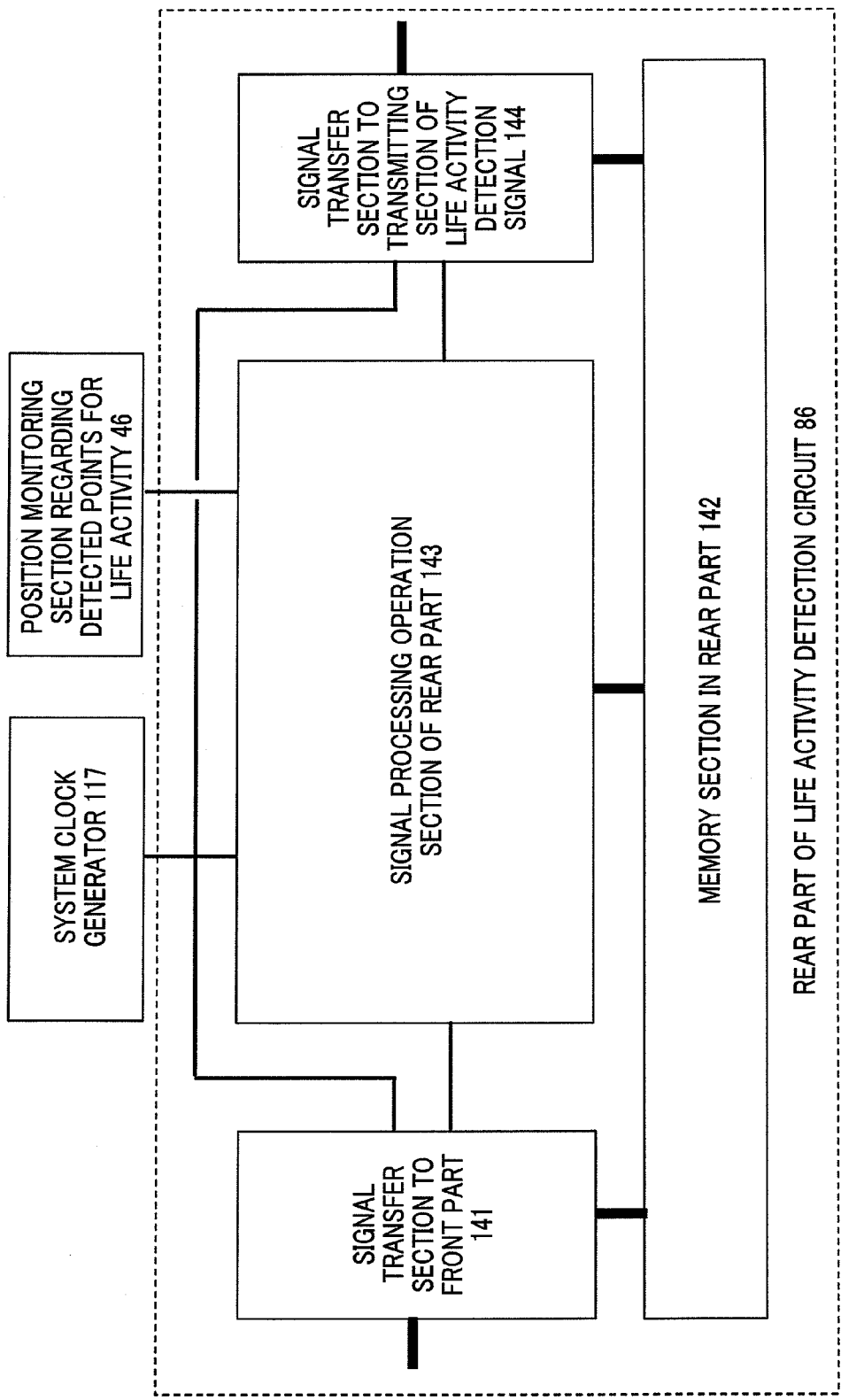
FIG.34 CONFIGURATION OF REAR PART OF LIFE ACTIVITY DETECTING CIRCUIT

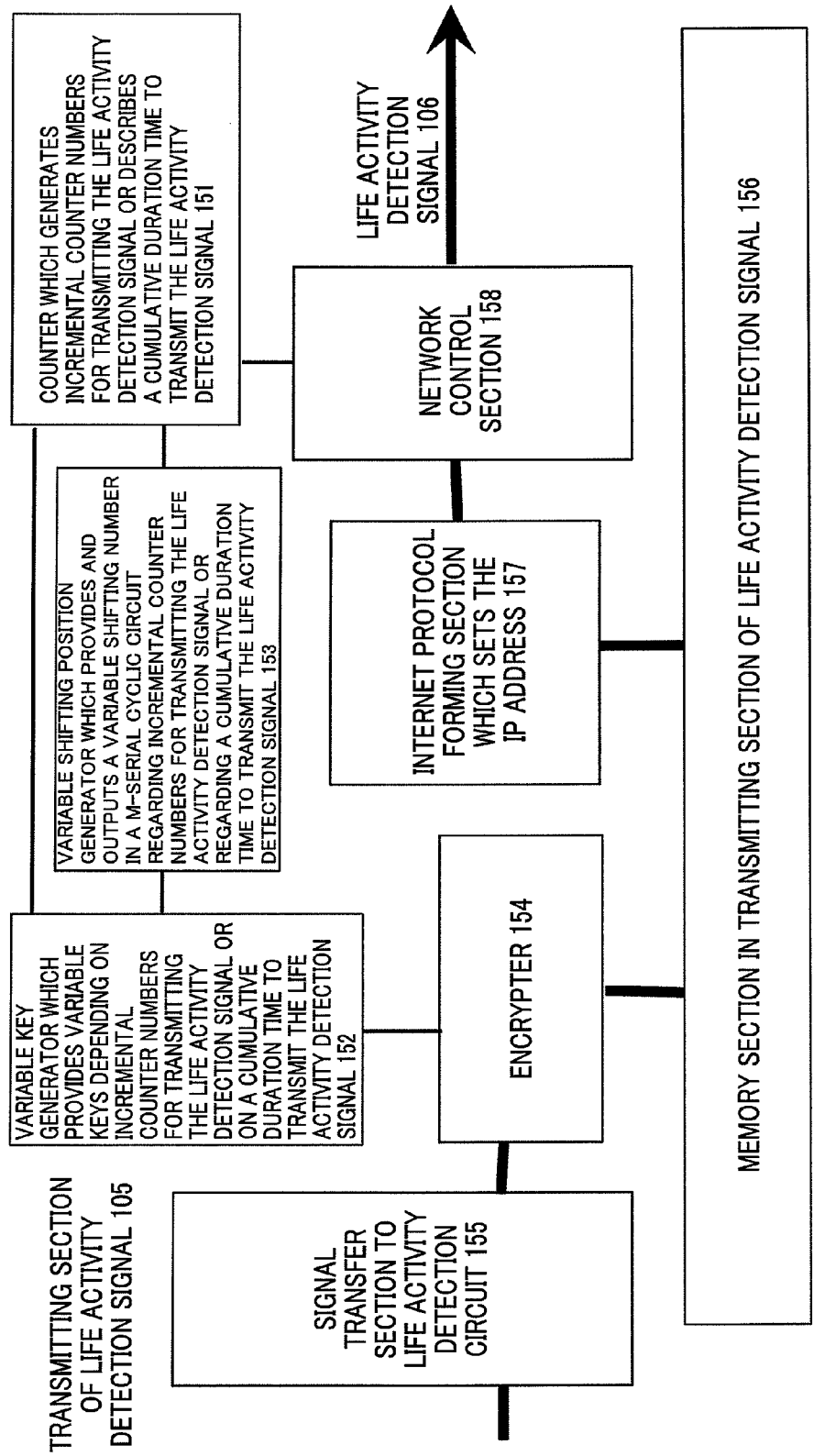
FIG.35 CONFIGURATION OF TRANSMITTING SECTION OF LIFE ACTIVITY DETECTION SIGNAL

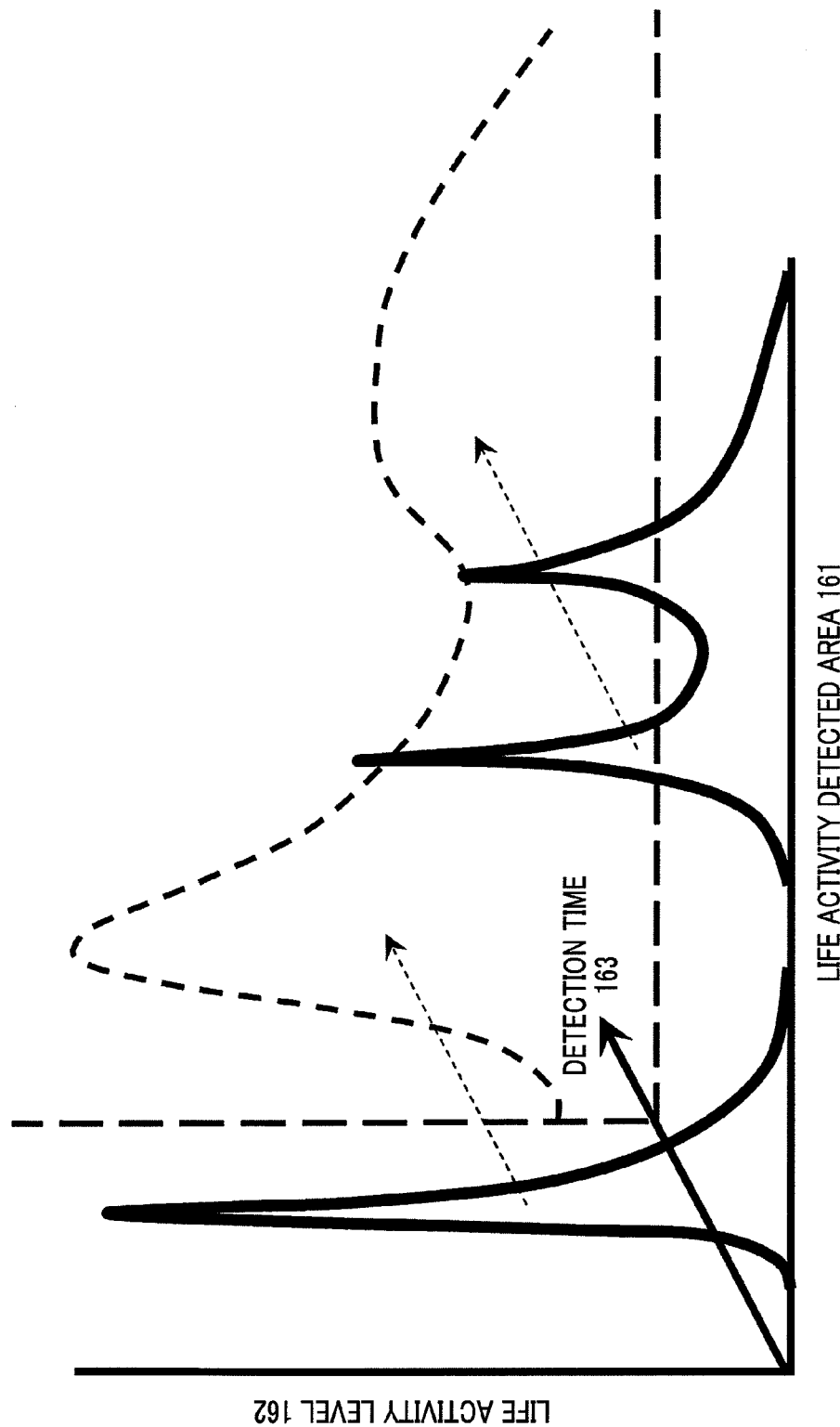
FIG.36 CONTENT OF LIFE ACTIVITY DETECTION SIGNAL

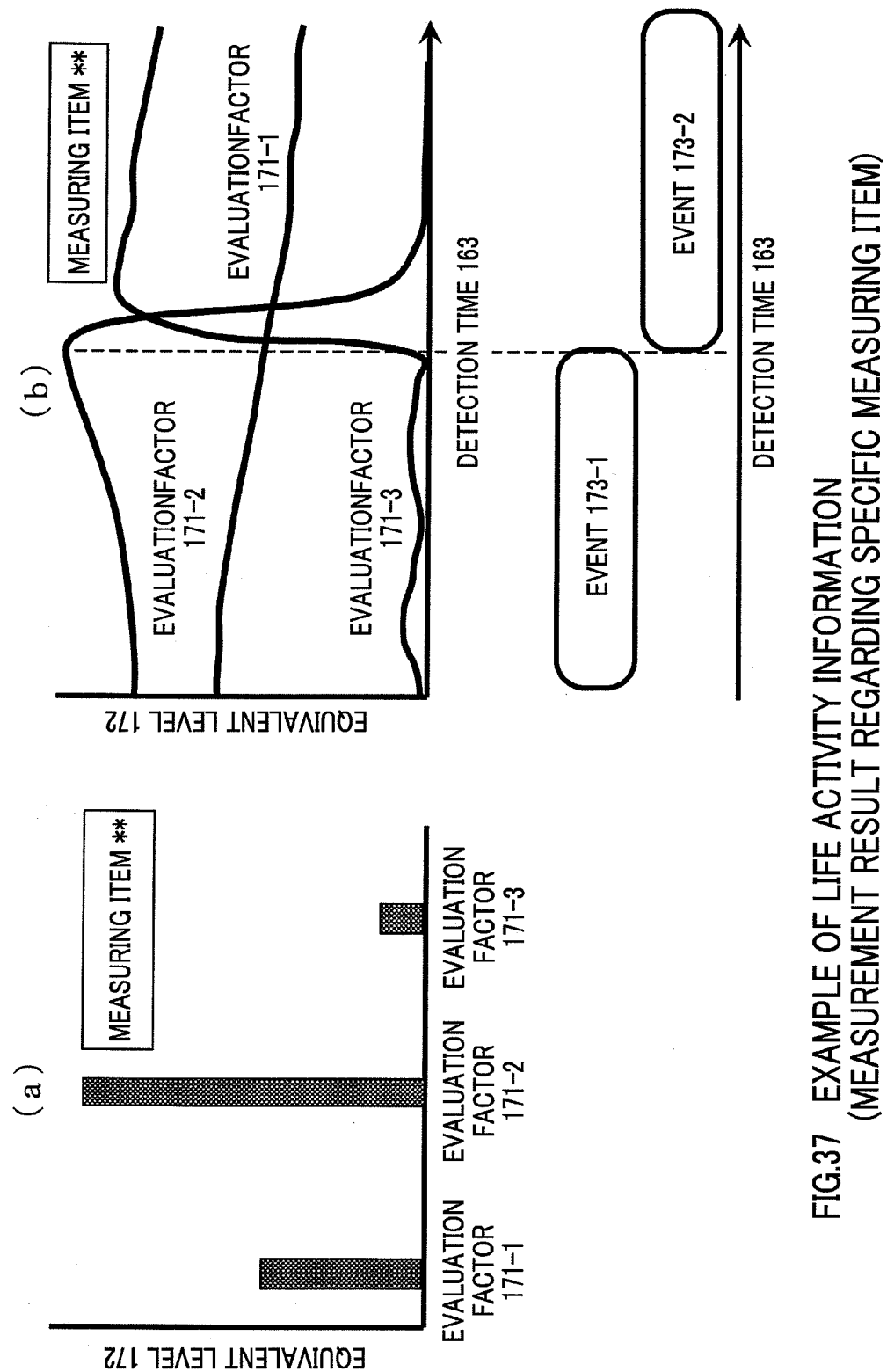
FIG.37 EXAMPLE OF LIFE ACTIVITY INFORMATION
(MEASUREMENT RESULT REGARDING SPECIFIC MEASURING ITEM)

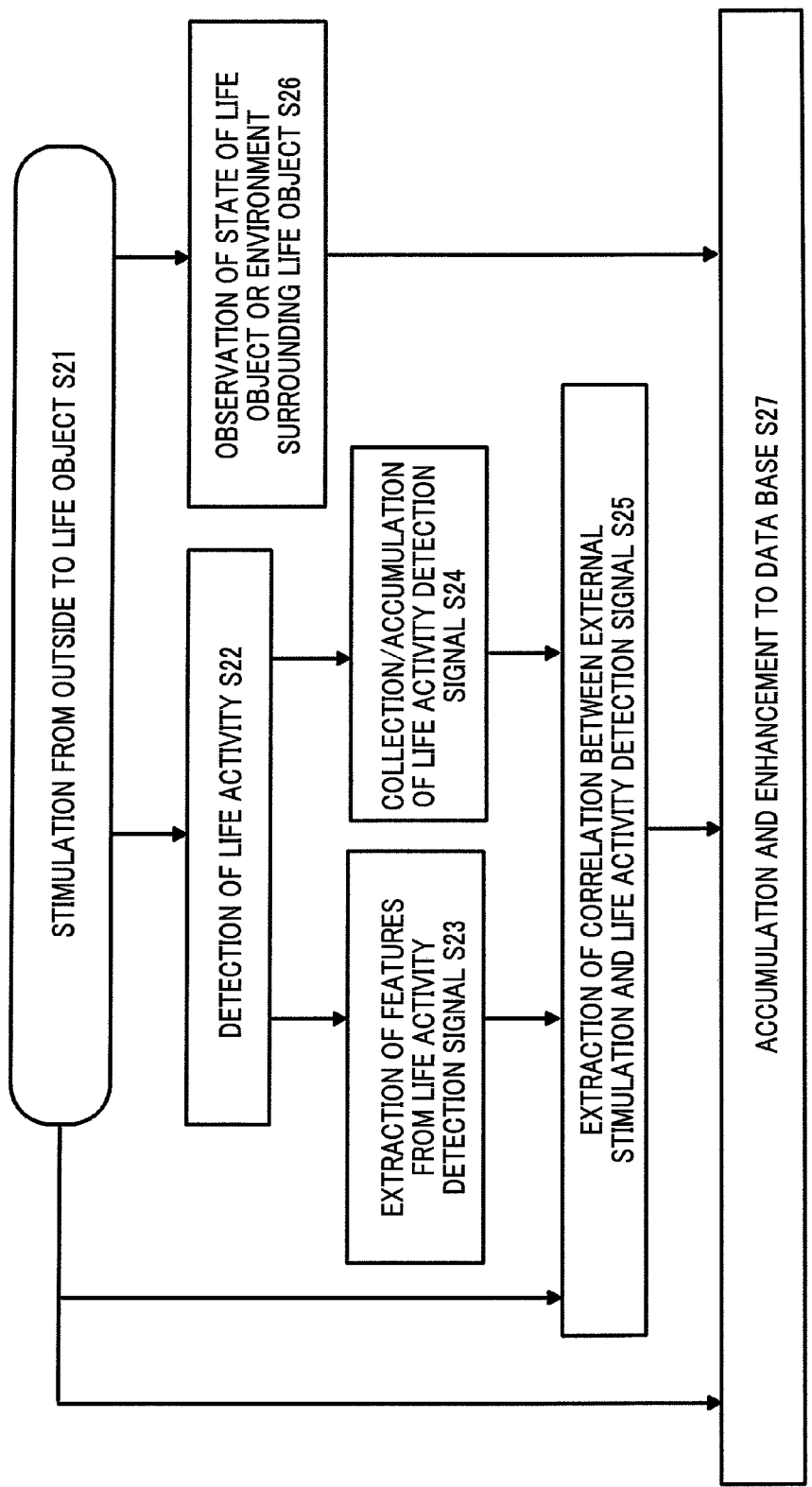
FIG.38 EXAMPLE OF DATA BASE CONSTRUCTION RELATED TO LIFE ACTIVITY INTERPRETATION

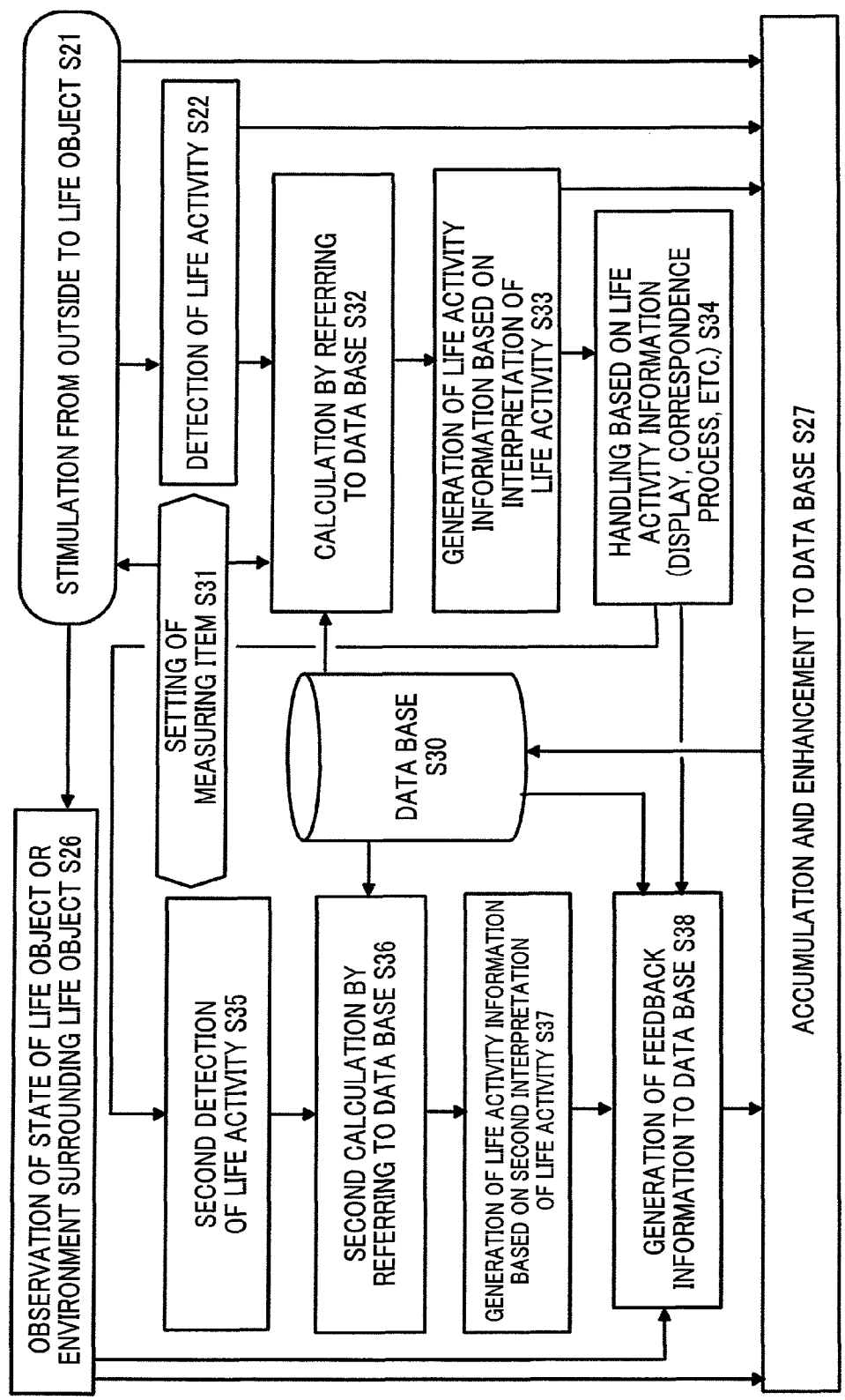
FIG.39 EXAMPLE OF LIFE ACTIVITY INTERPRETATION

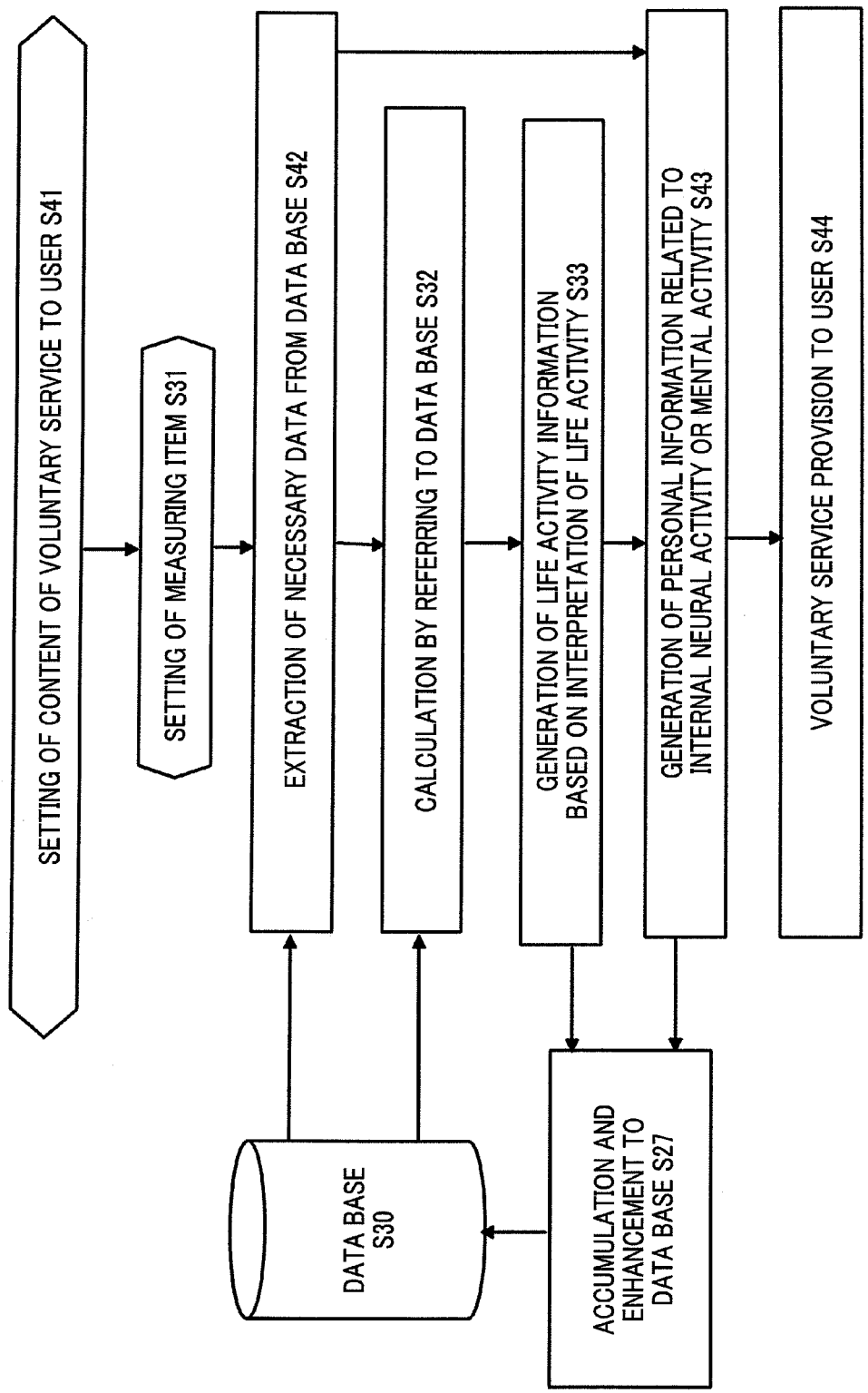
FIG. 40  APPLIED EMBODIMENT OF LIFE ACTIVITY INTERPRETATION

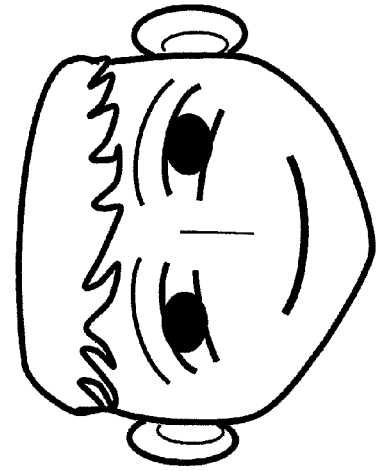
(b) FACIAL EXPRESSION AT THE TIME OF SMILING
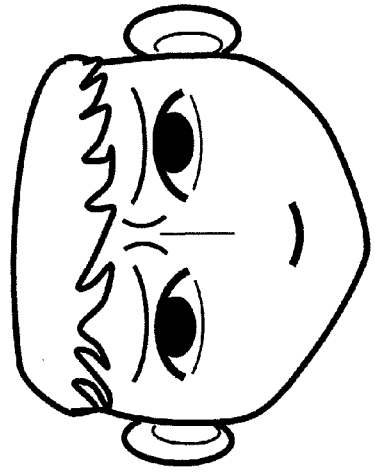
(d) FACIAL EXPRESSION AT A LOSS
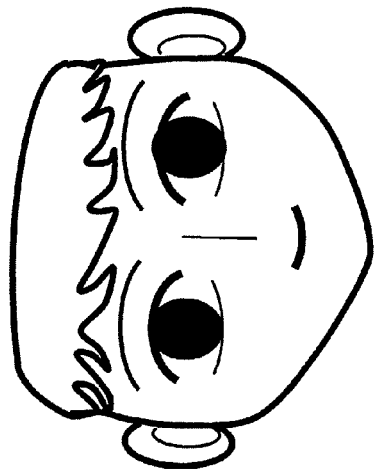
(a) FACIAL EXPRESSION DURING REST
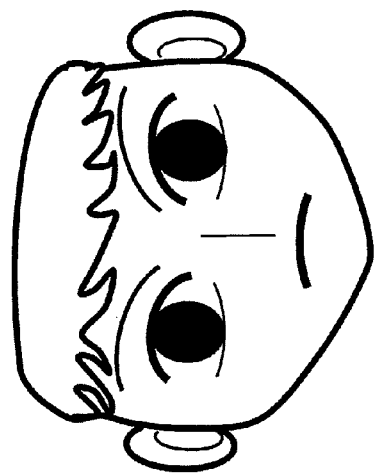
(c) FACIAL EXPRESSION AT THE TIME OF GETTING ANGRY
FIG.41  RELATIONSHIP BETWEEN FACIAL EXPRESSION AND EMOTIONAL REACTION

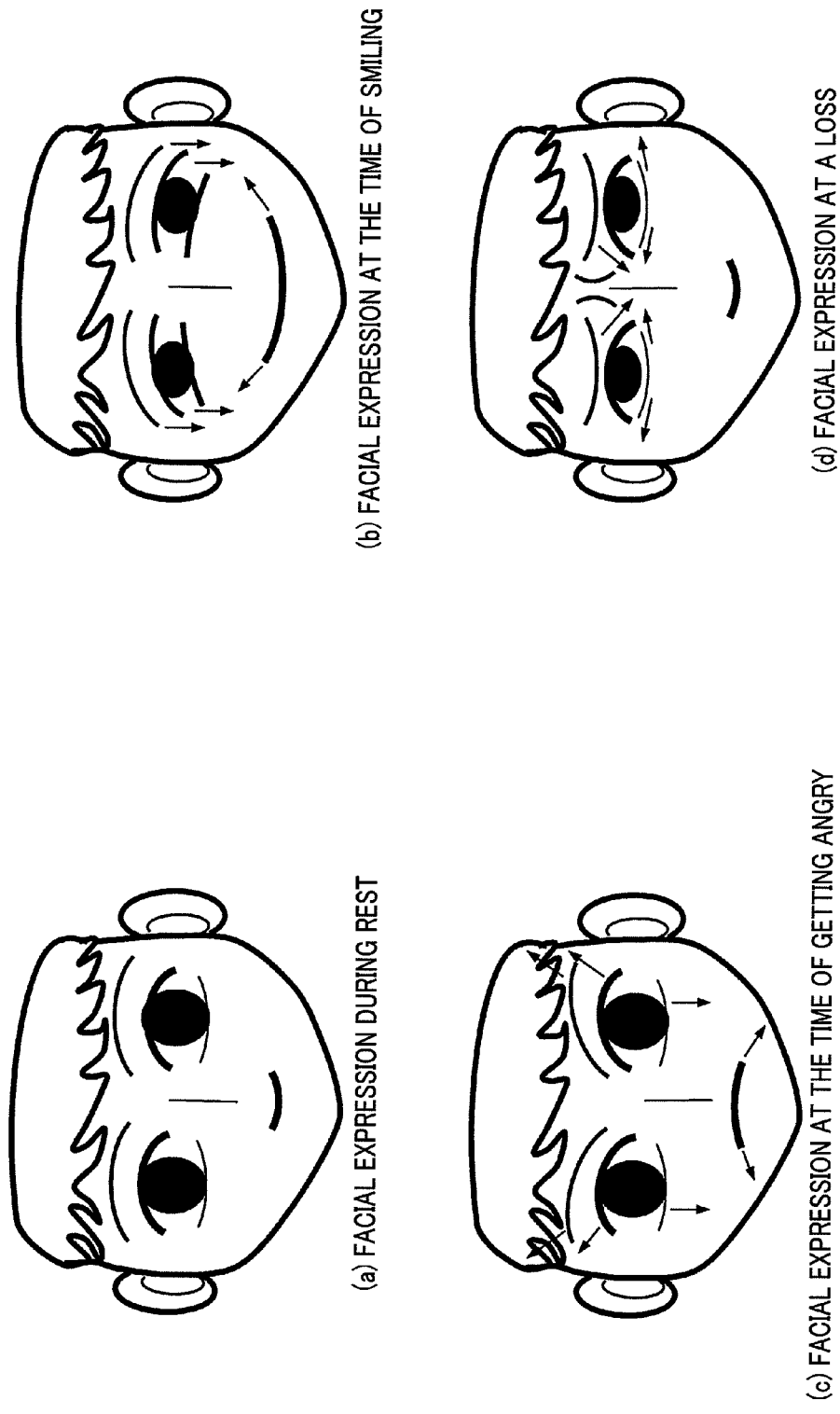
FIG.42 METHOD FOR OBTAINING LIFE ACTIVITY INFORMATION FROM MOVEMENT OF FACIAL MUSCLE

MEASURING ITEM **

| | EVALUATION FACTOR 171-1 | EVALUATION FACTOR 171-2 | EVALUATION FACTOR 171-3 | ...... | EVALUATION FACTOR 171-N |
|---|---|---|---|---|---|
| PROCESS/OPERATION 178-1 | WEIGHTING H11 | WEIGHTING H12 | WEIGHTING H13 | ...... | WEIGHTING H1n |
| PROCESS/OPERATION 178-2 | WEIGHTING H21 | WEIGHTING H22 | WEIGHTING H23 | ...... | WEIGHTING H2n |
| PROCESS/OPERATION 178-3 | WEIGHTING H31 | WEIGHTING H32 | WEIGHTING H33 | ...... | WEIGHTING H3n |
| ...... | ...... | ...... | ...... | ...... | ...... |
| PROCESS/OPERATION 178-M | WEIGHTING Hm1 | WEIGHTING Hm2 | WEIGHTING Hm3 | ...... | WEIGHTING Hmn |

(a) WEIGHTING TABLE OF WEIGHTING TO EACH PROCESS OR OPERATION PER EVALUATION FACTOR 171 IN SPECIFIC MEASURING ITEM **

EQUIVALENT LEVEL 172 OF EVALUATION FACTOR 171-i IN MEASURING ITEM ** ≡ Pi

EVALUATION VALUE OF Jth PROCESS/OPERATION = Σ Hji · Pi (SUM from i = 1 to N)

(b) EXEMPLARY CALCULATION OF EVALUATION VALUE INDICATIVE OF SELECTION BASIS TO PROCESS OR OPERATION BASED ON WEIGHTING TABLE

FIG.43 EXPLANATORY VIEW OF A METHOD FOR SELECTING AN OPTIMUM PROCESS/OPERATION METHOD BASED ON LIFE ACTIVITY INFORMATION

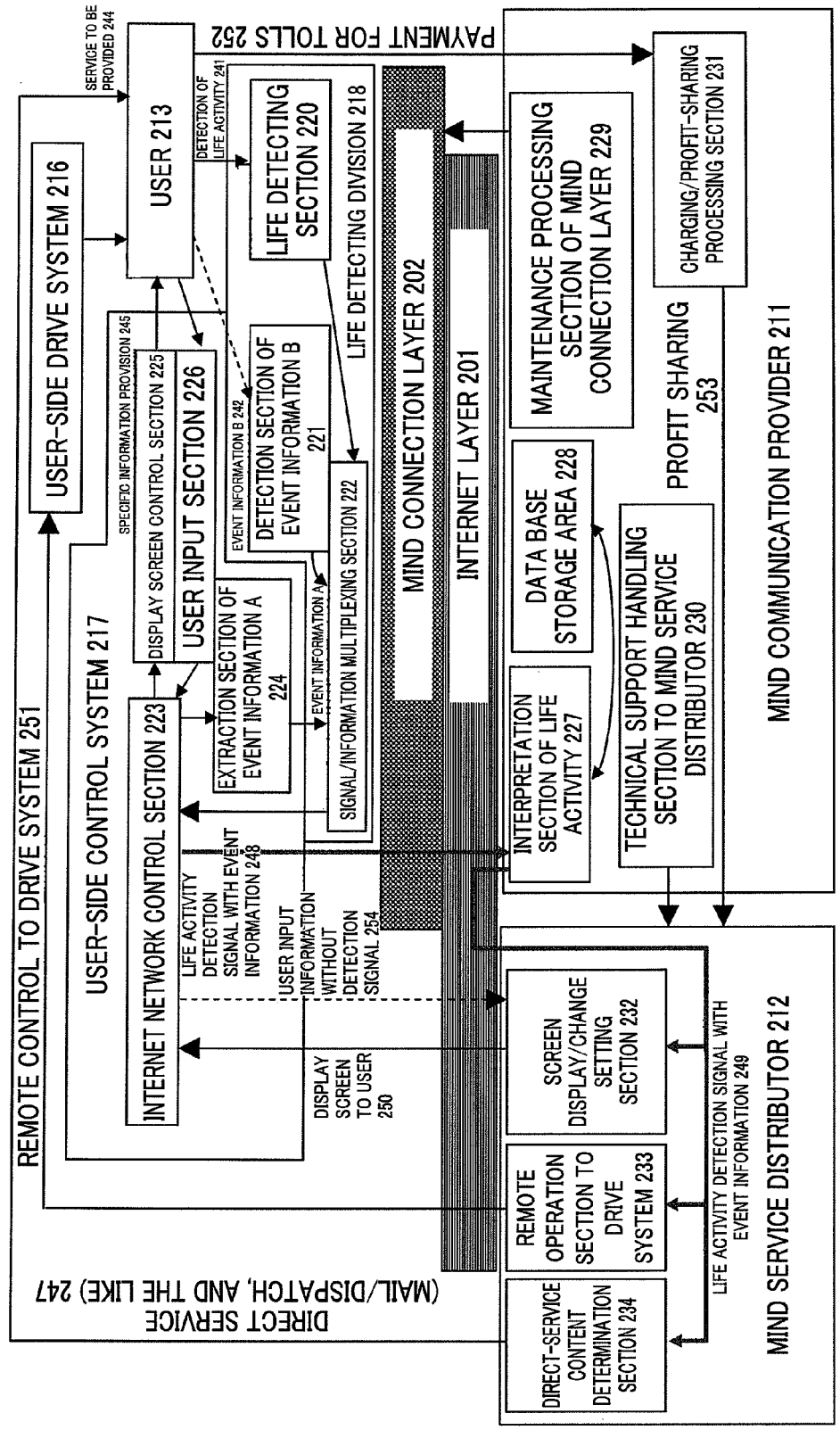
FIG.44 OVERVIEW OF NETWORK SYSTEM USING DETECTING SECTION FOR LIFE ACTIVITY

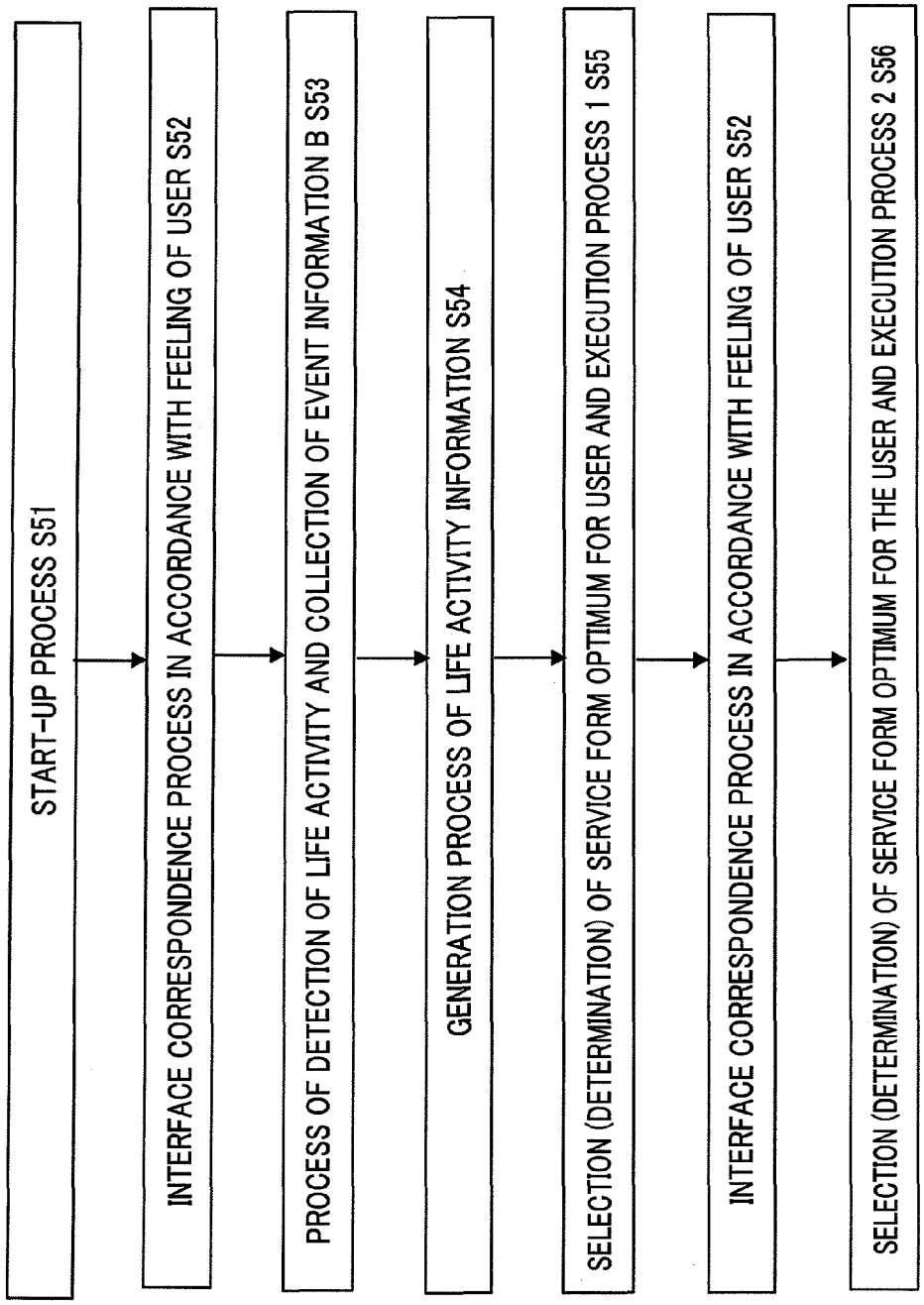
FIG.45 EXAMPLE OF SERVICE BASED ON LIFE ACTIVITY MEASUREMENT

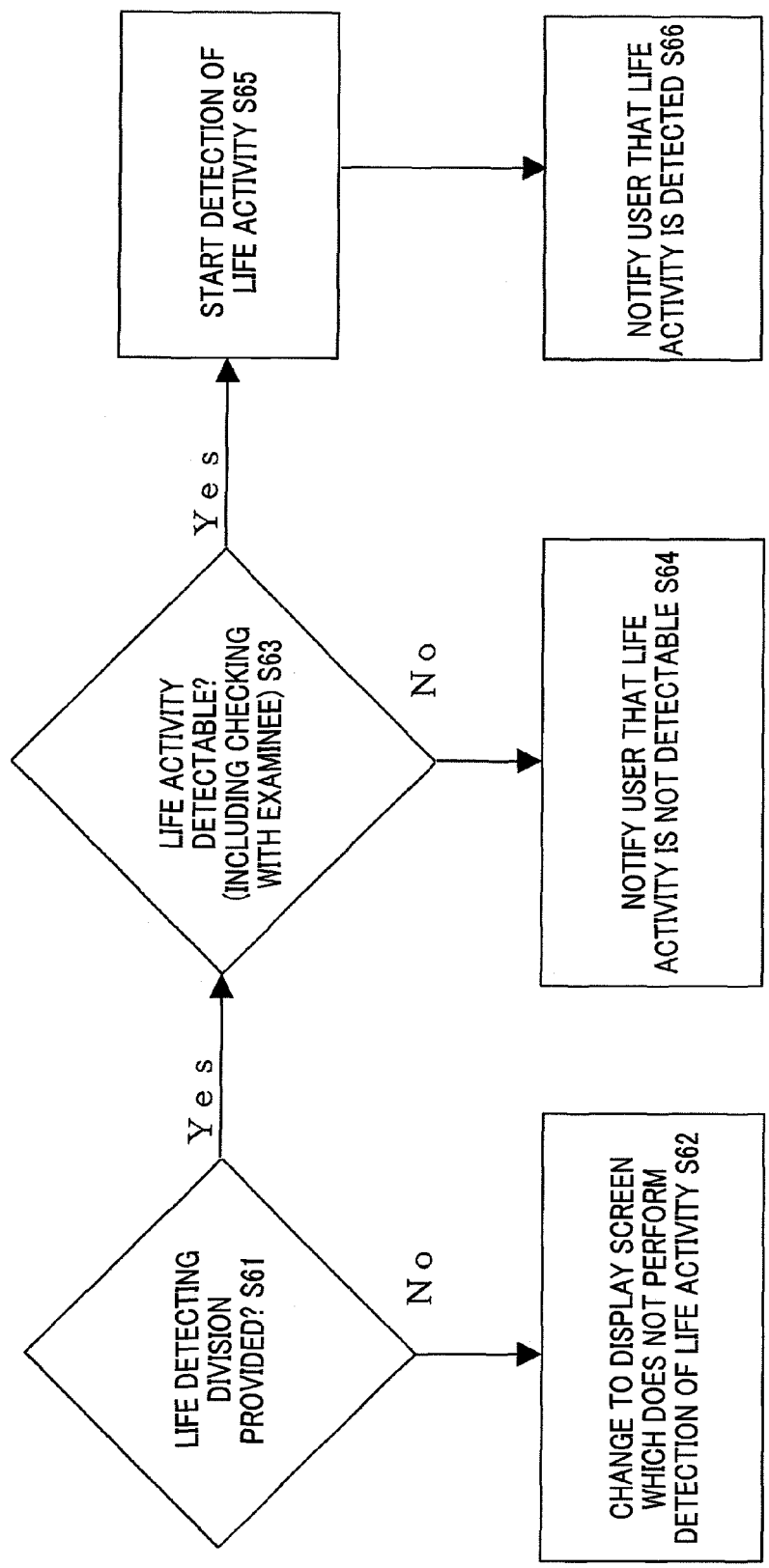
FIG.46 ACTIVATION PROCESS IN SERVICE BASED ON LIFE ACTIVITY MEASUREMENT

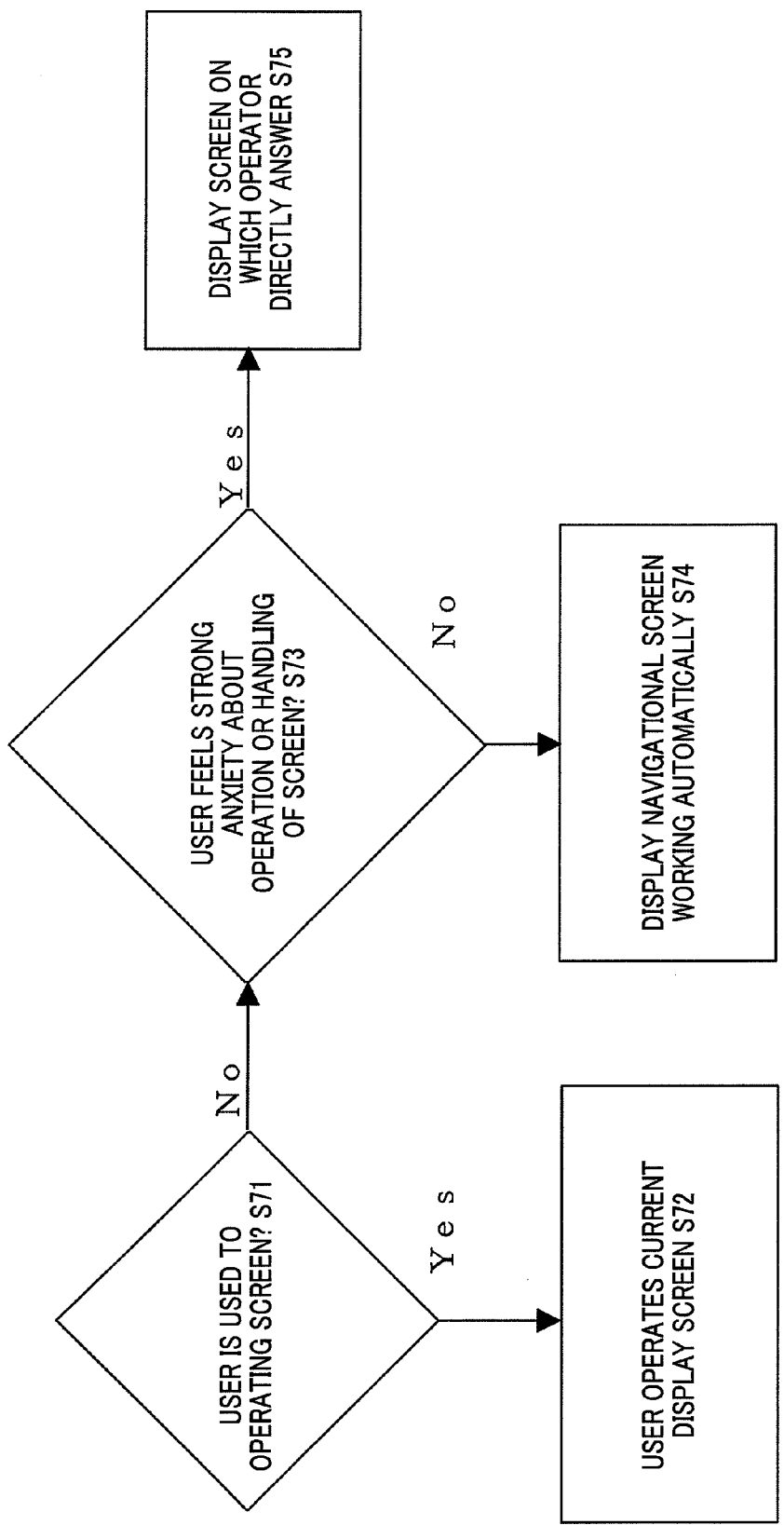
FIG.47 METHOD OF INTERFACE CORRESPONDENCE IN PRESENT EXEMPLARY EMBODIMENT

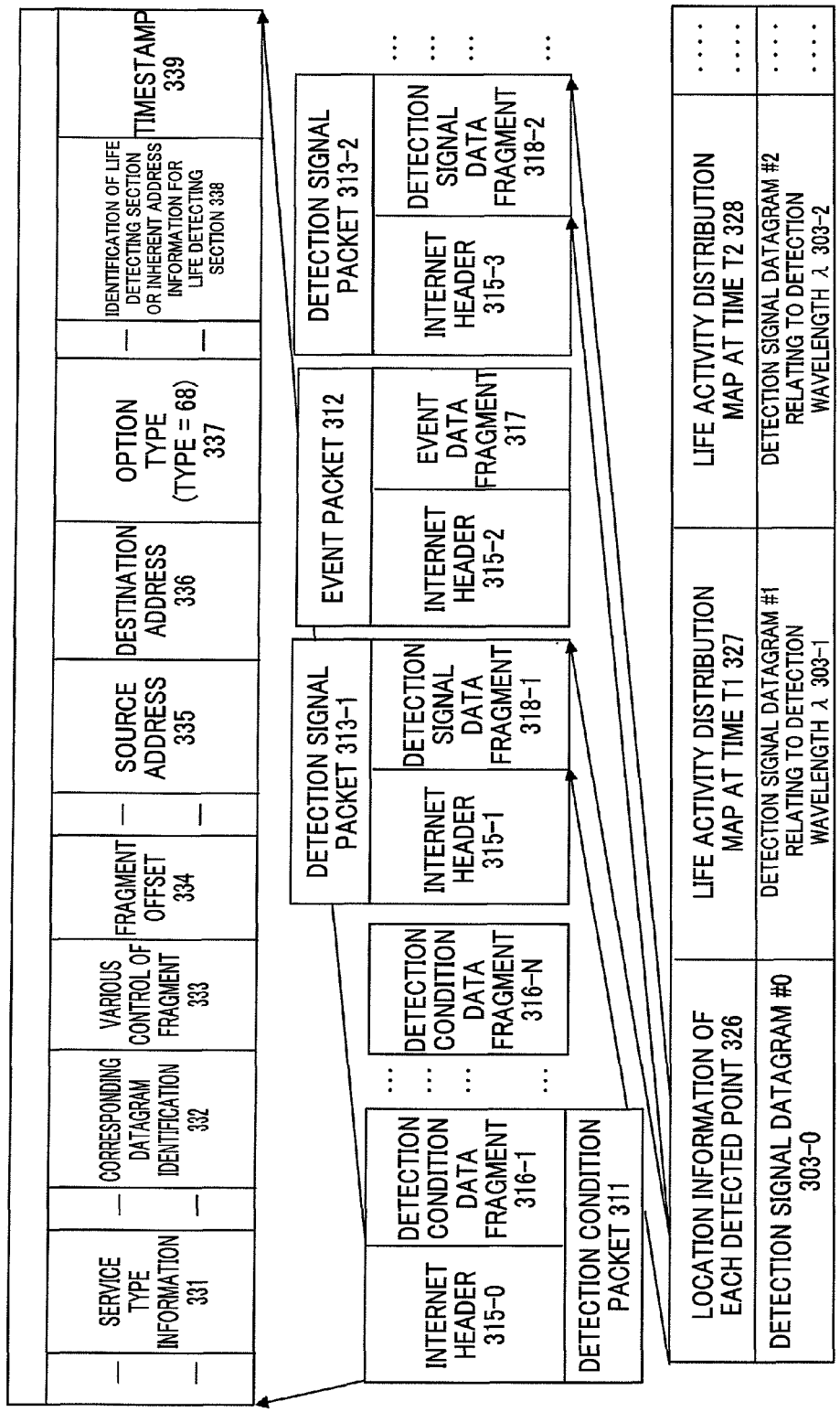
FIG.48 COMMUNICATION PROTOCOL (1) OF LIFE ACTIVITY DETECTION SIGNAL WITH EVENT INFORMATION

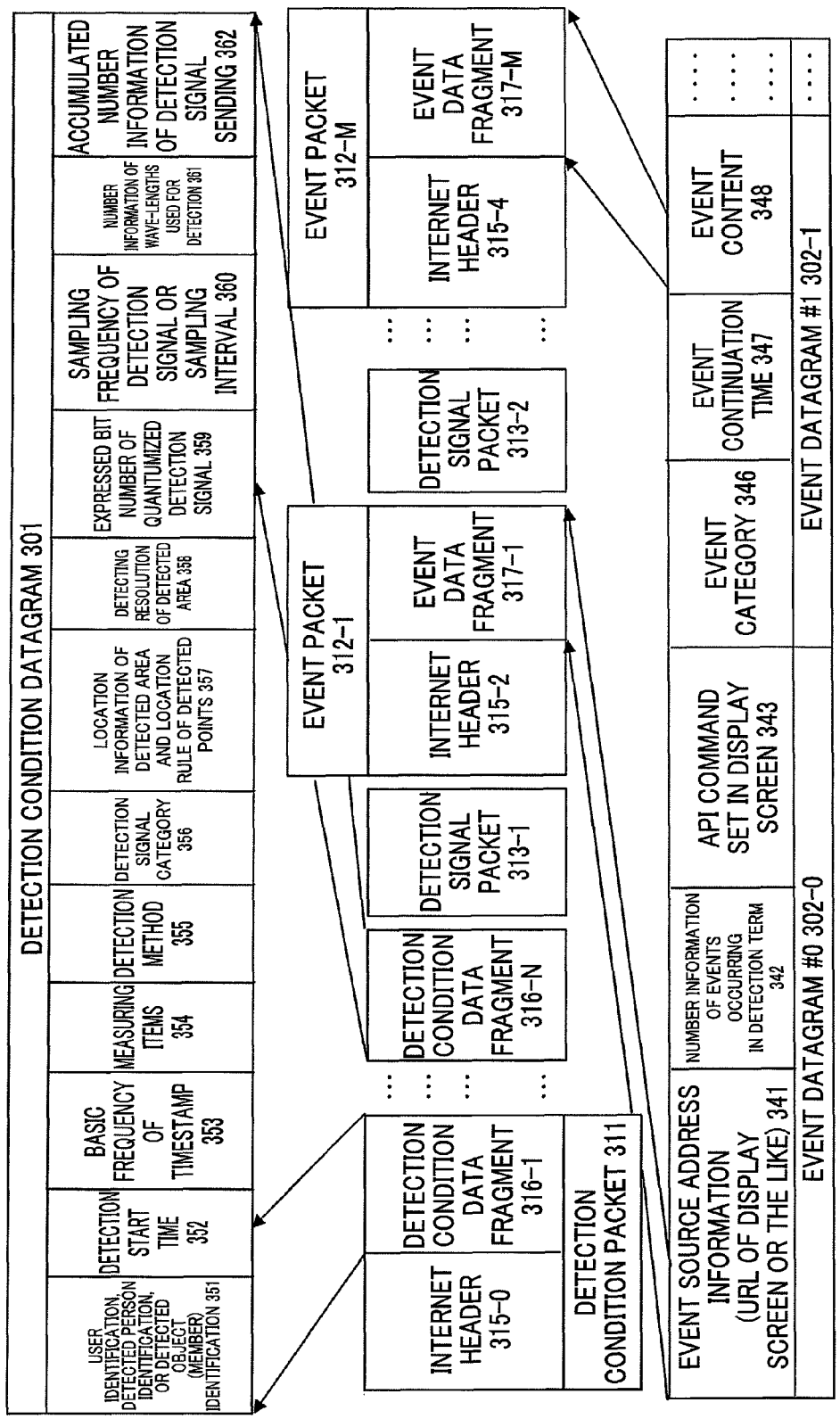
FIG.49 COMMUNICATION PROTOCOL (2) OF LIFE ACTIVITY DETECTION SIGNAL WITH EVENT INFORMATION

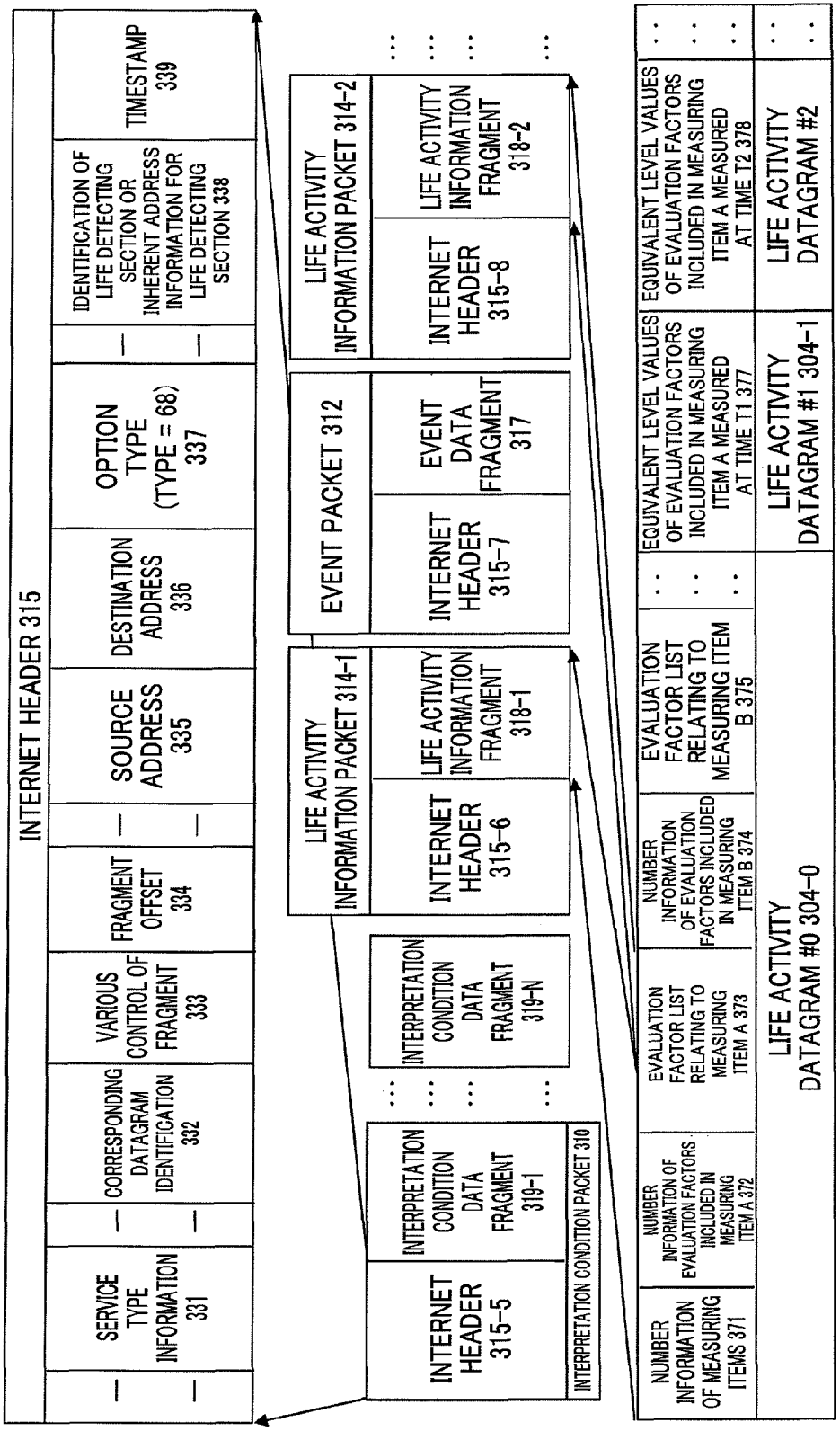
FIG.50 COMMUNICATION PROTOCOL (1) OF LIFE ACTIVITY INFORMATION WITH EVENT INFORMATION

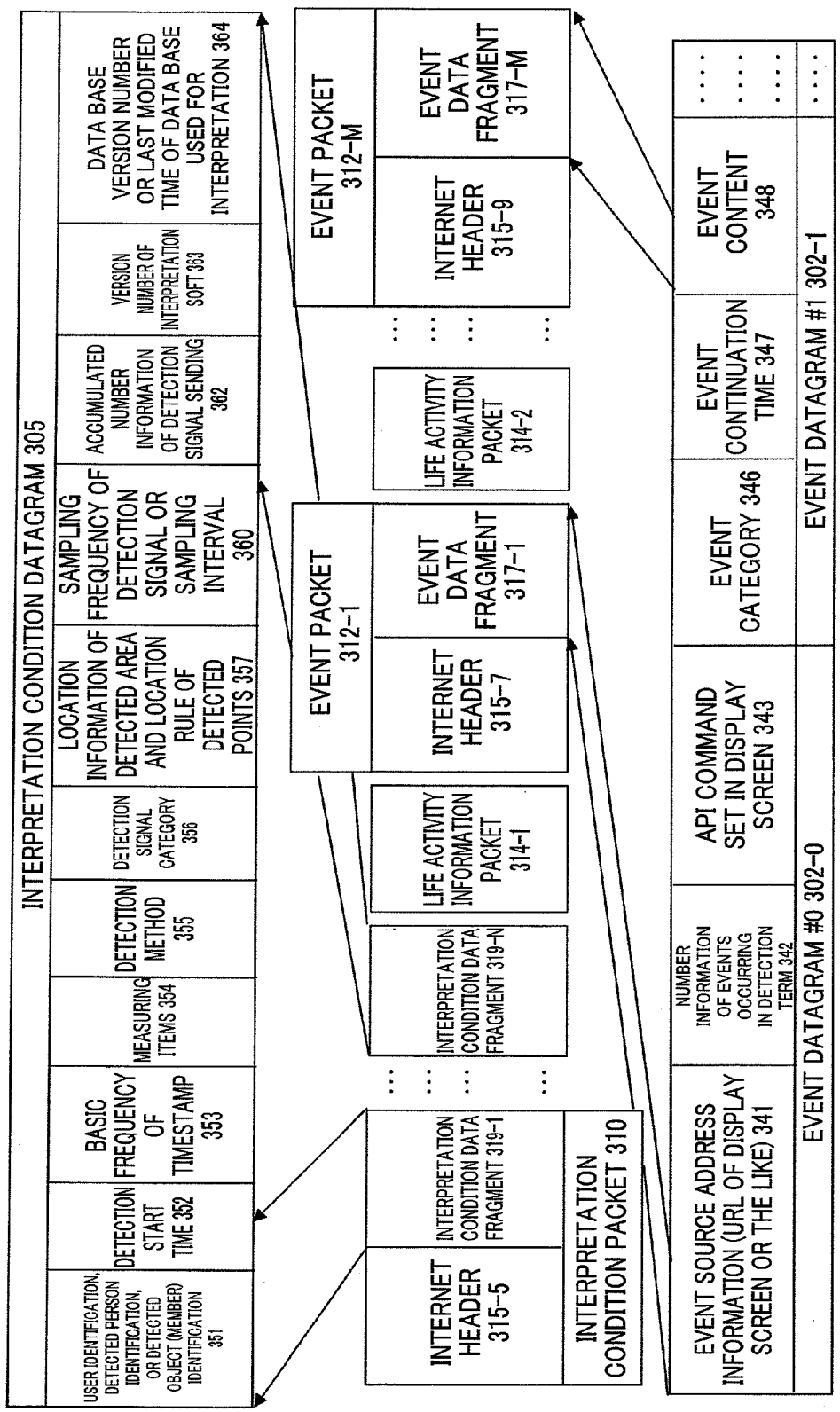
FIG.51 OMMUNICATION PROTOCOL (2) OF LIFE ACTIVITY INFORMATION WITH EVENT INFORMATION

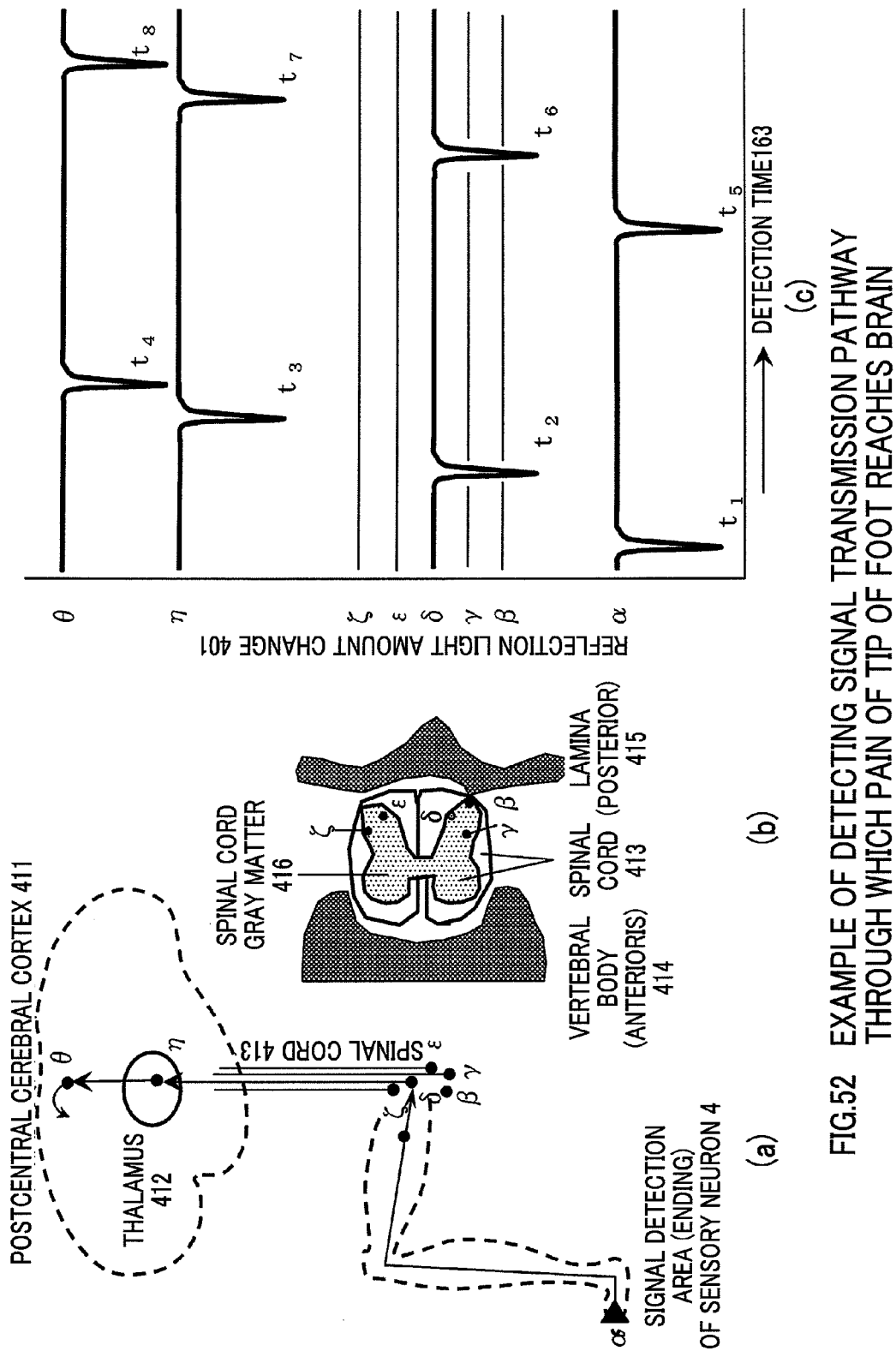
FIG.52   EXAMPLE OF DETECTING SIGNAL TRANSMISSION PATHWAY THROUGH WHICH PAIN OF TIP OF FOOT REACHES BRAIN

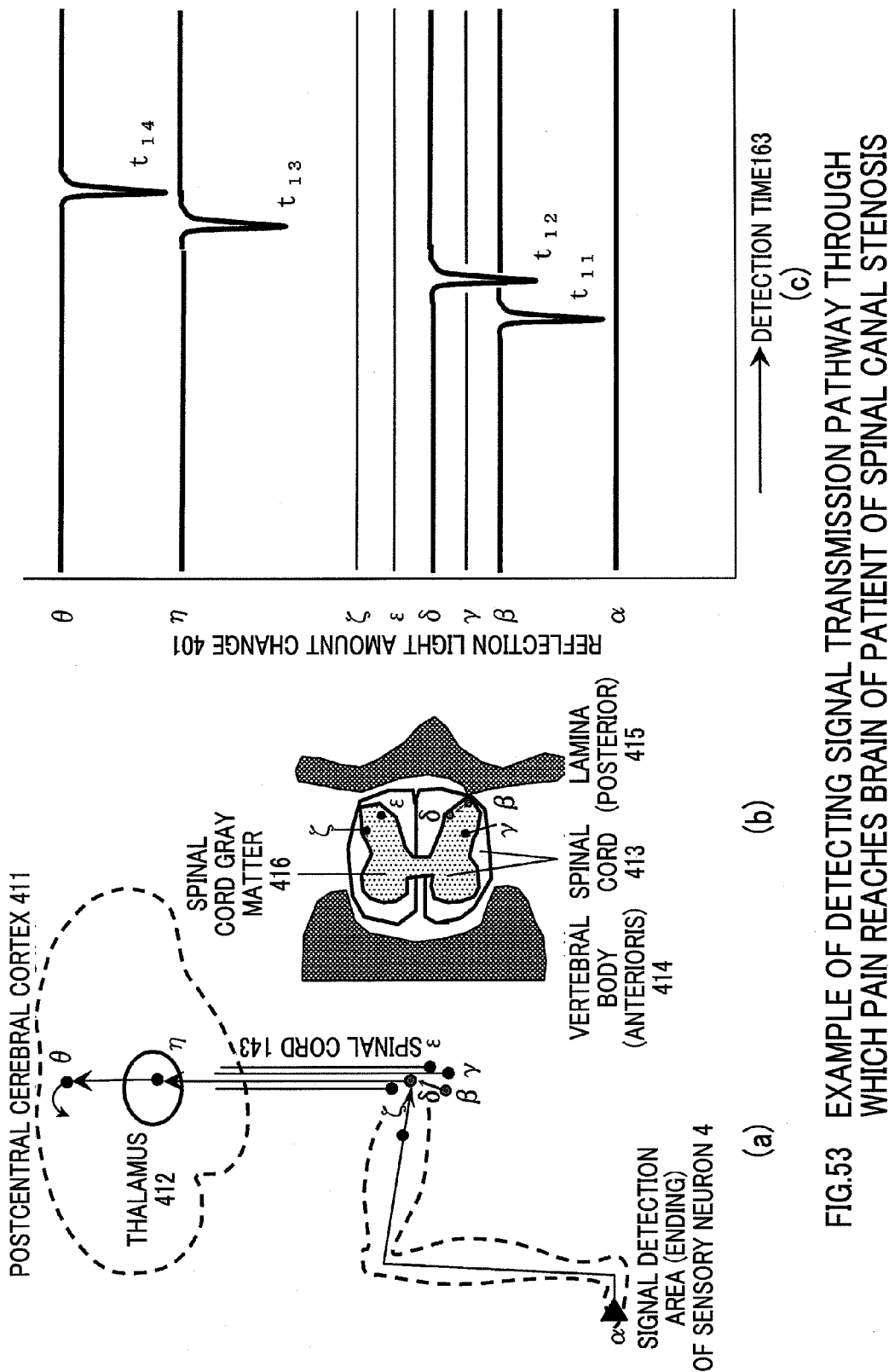
FIG. 53 EXAMPLE OF DETECTING SIGNAL TRANSMISSION PATHWAY THROUGH WHICH PAIN REACHES BRAIN OF PATIENT OF SPINAL CANAL STENOSIS

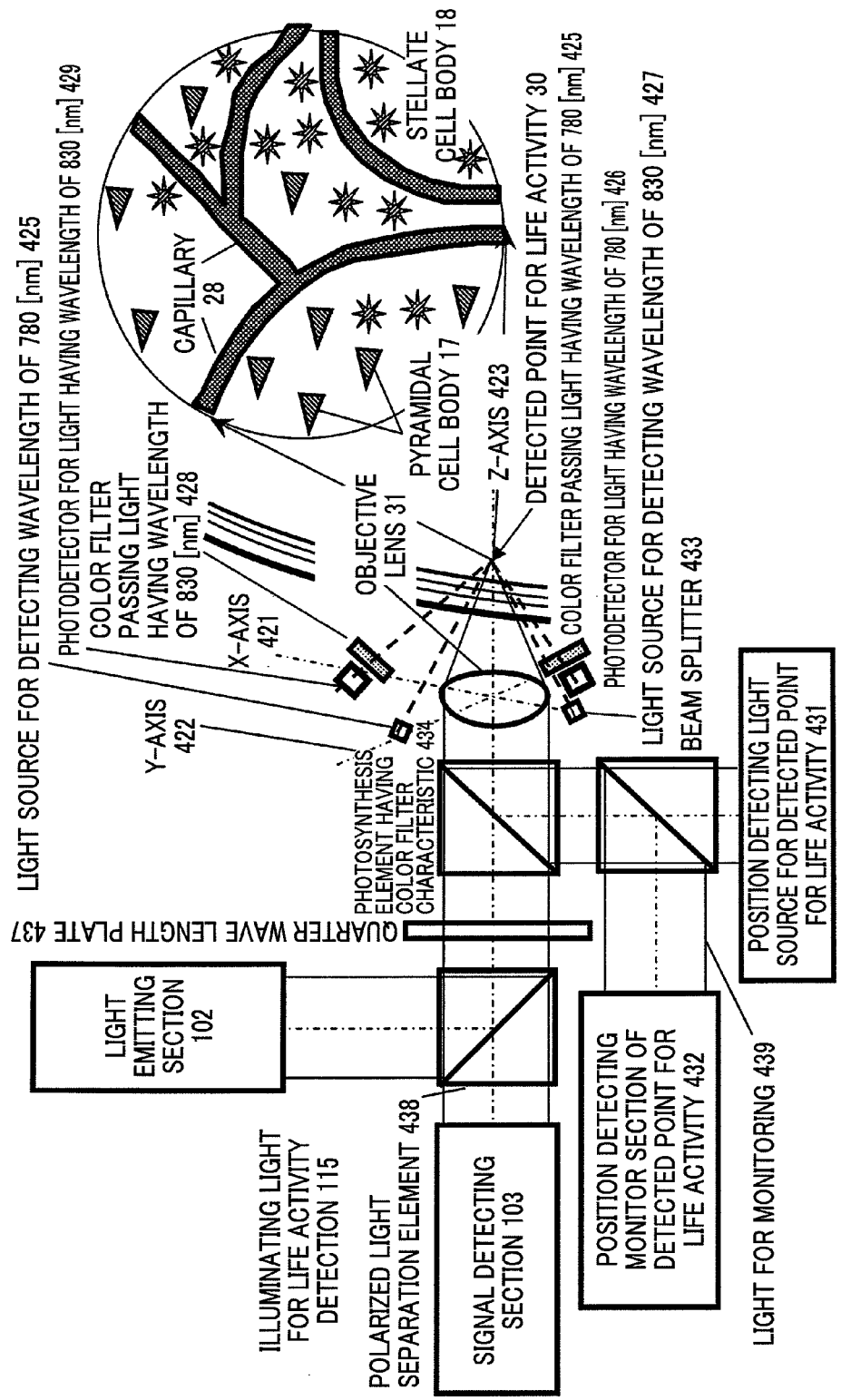
FIG.54 APPLIED EMBODIMENT IN WHICH MEMBRANE POTENTIAL CHANGING AND OXYGEN CONCENTRATION CHANGE IN BLOOD ARE DETECTED AT THE SAME TIME

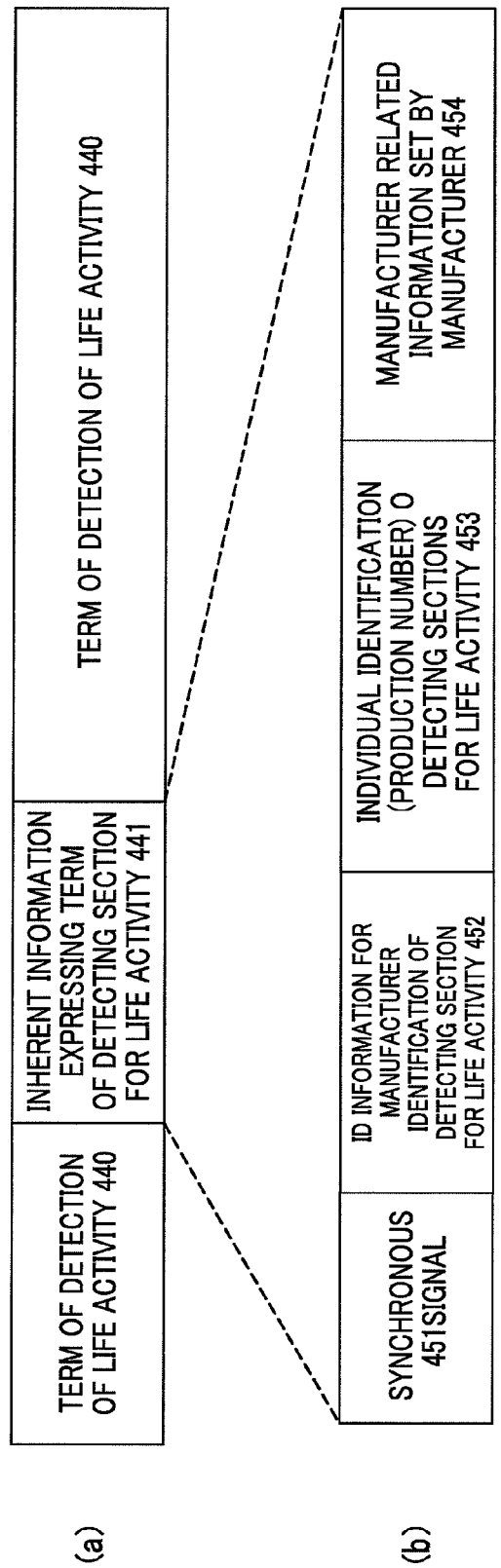
FIG.55 LIGHT EMITTING PATTERN OF ILLUMINATING LIGHT FOR LIFE ACTIVITY DETECTION IN DETECTION OF LIFE ACTIVITY

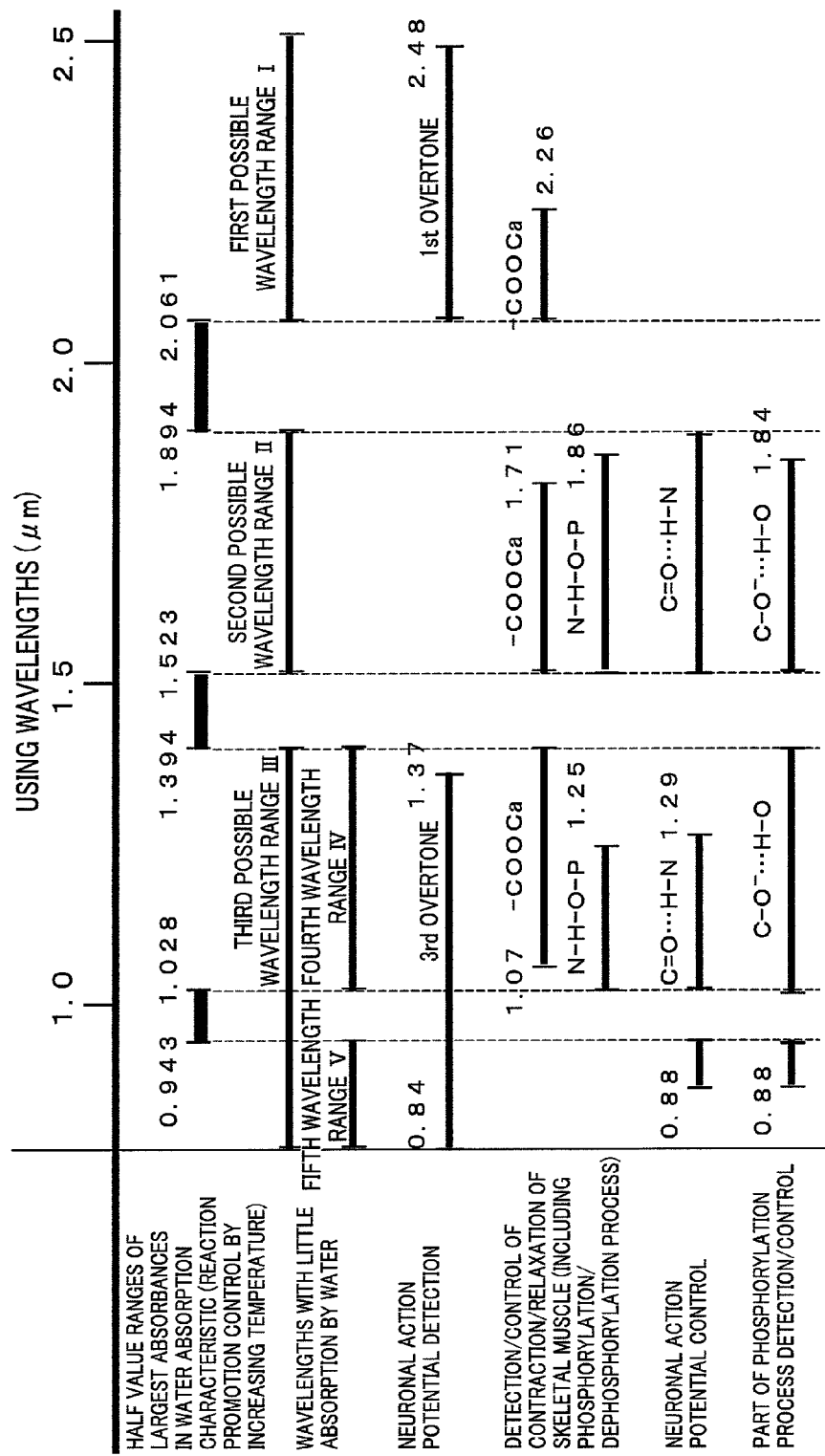
FIG.56 APPROPRIATE WAVELENGTHS FOR DETECTION/CONTROL OF LIFE ACTIVITY IN PRESENT EXEMPLARY EMBODIMENT/APPLIED EMBODIMENT

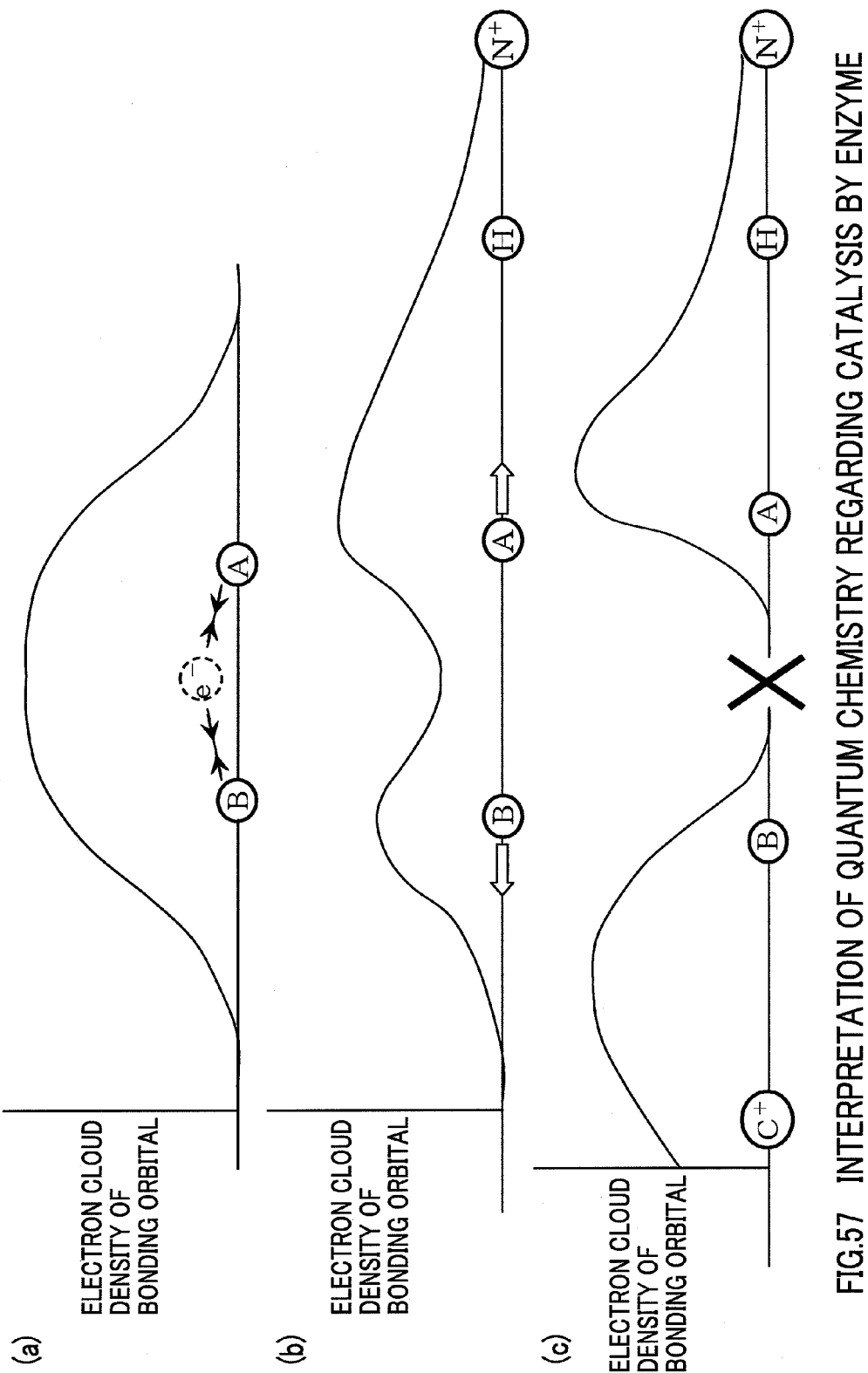
FIG.57 INTERPRETATION OF QUANTUM CHEMISTRY REGARDING CATALYSIS BY ENZYME

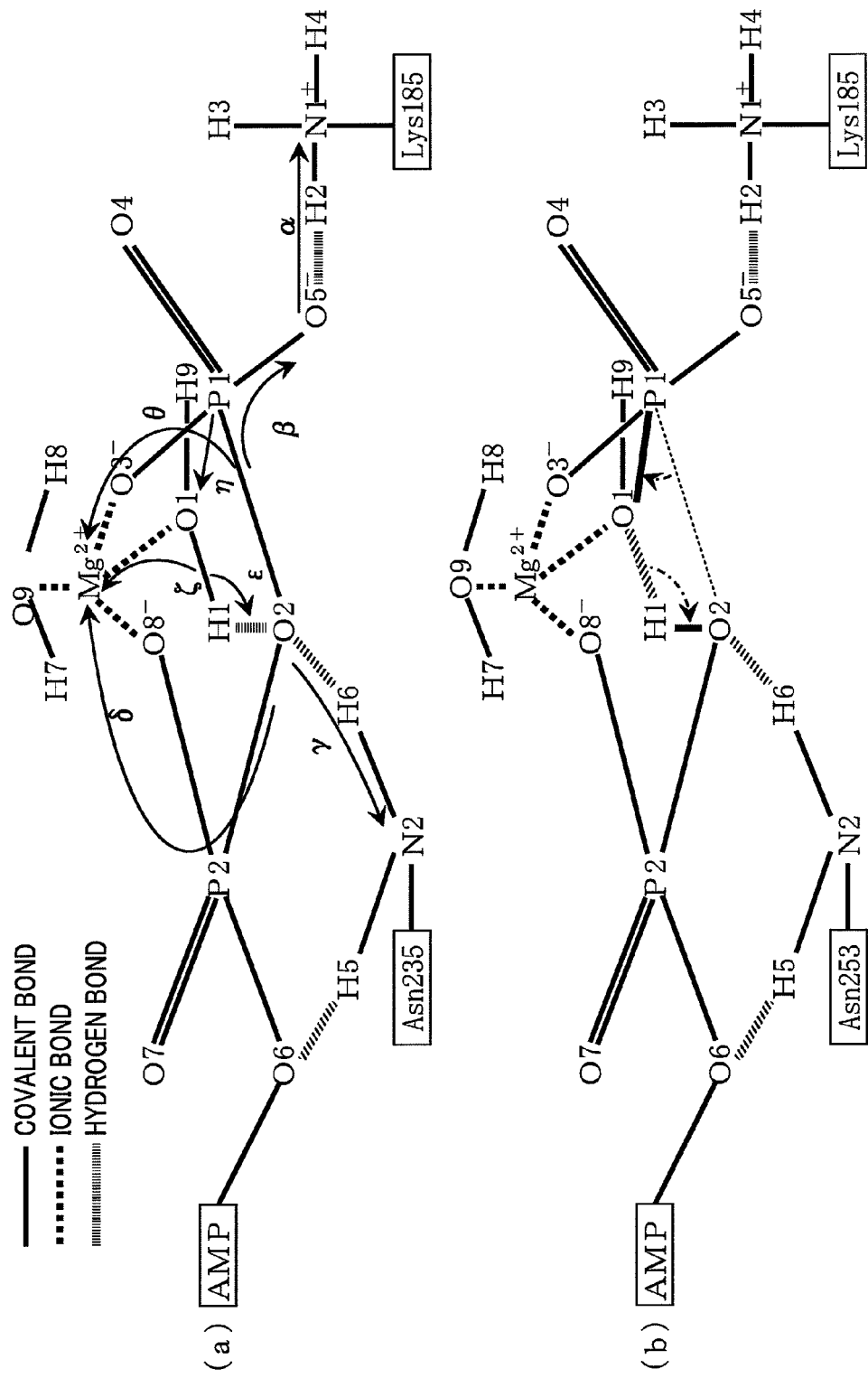
FIG.58  MECHANISM FOR ATP HYDROLYSIS BY MYOSIN ATPASE

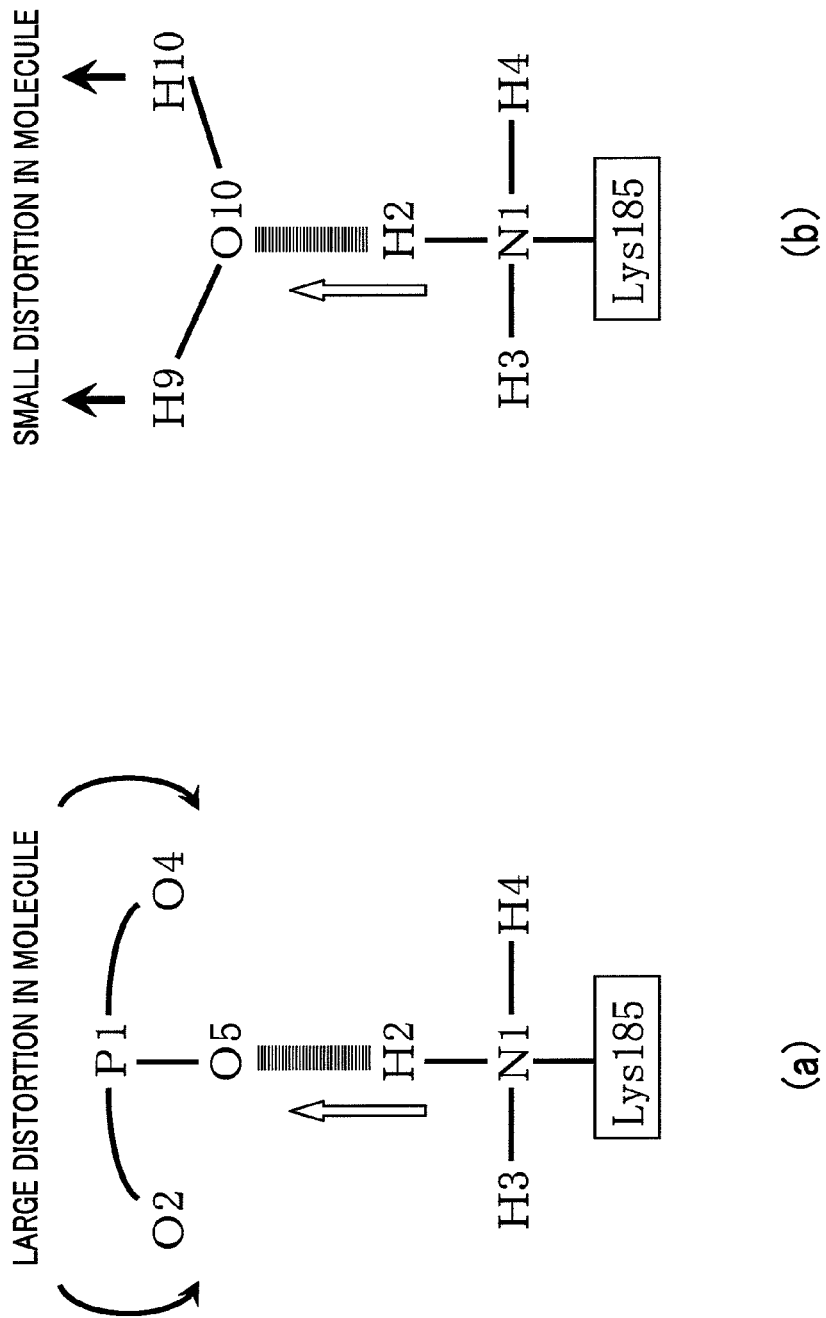
FIG.59 REASON WHY ABSORPTION BAND WAVELENGTH VARIES DEPENDING ON TO WHICH RESIDUE OF LYSINE IS HYDROGEN BONDED

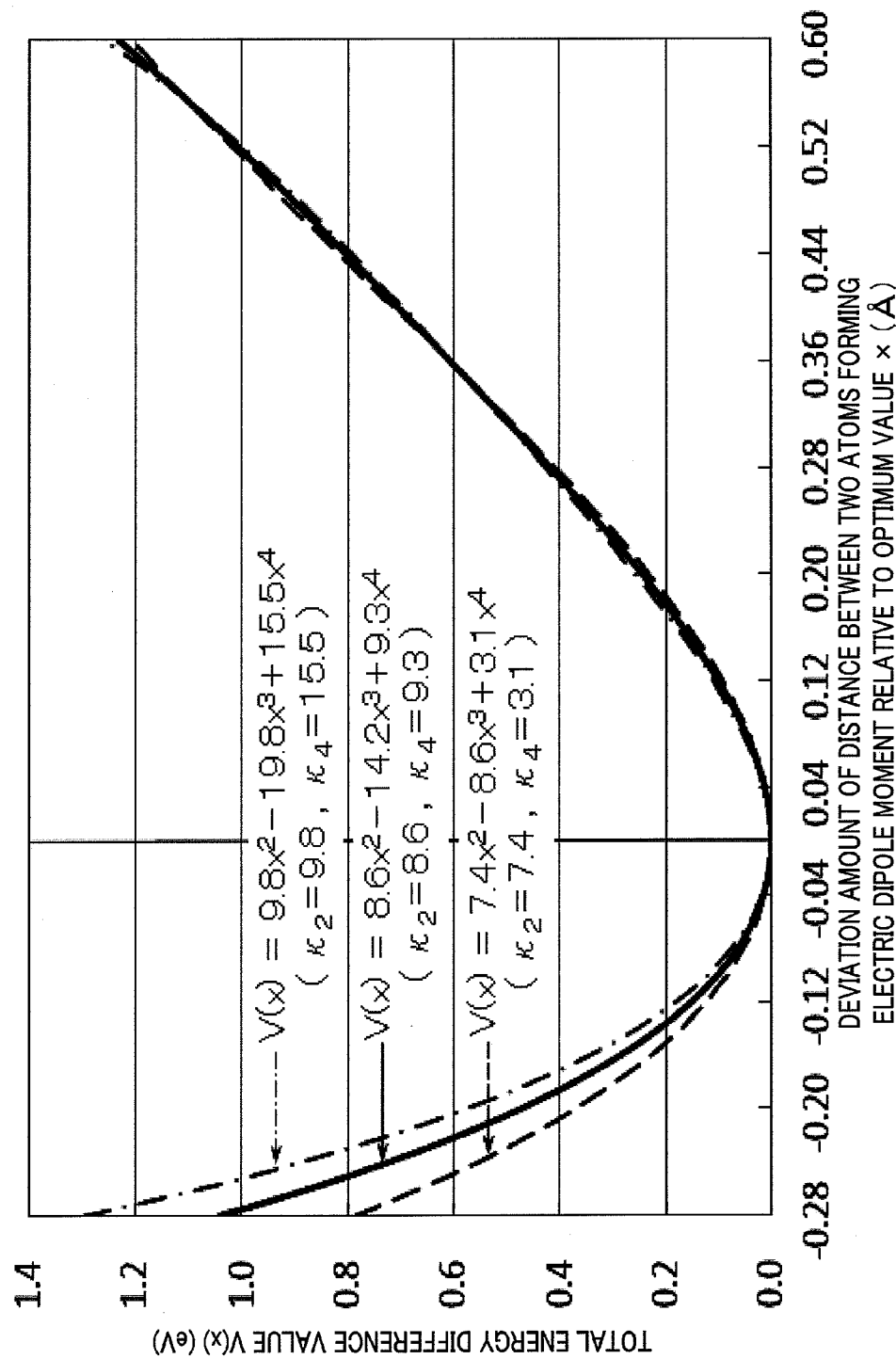
FIG.60 RELATIONSHIP BETWEEN HYDROGEN-BONDING PARTNER AND ANHARMONIC VIBRATION POTENTIAL PROPERTY

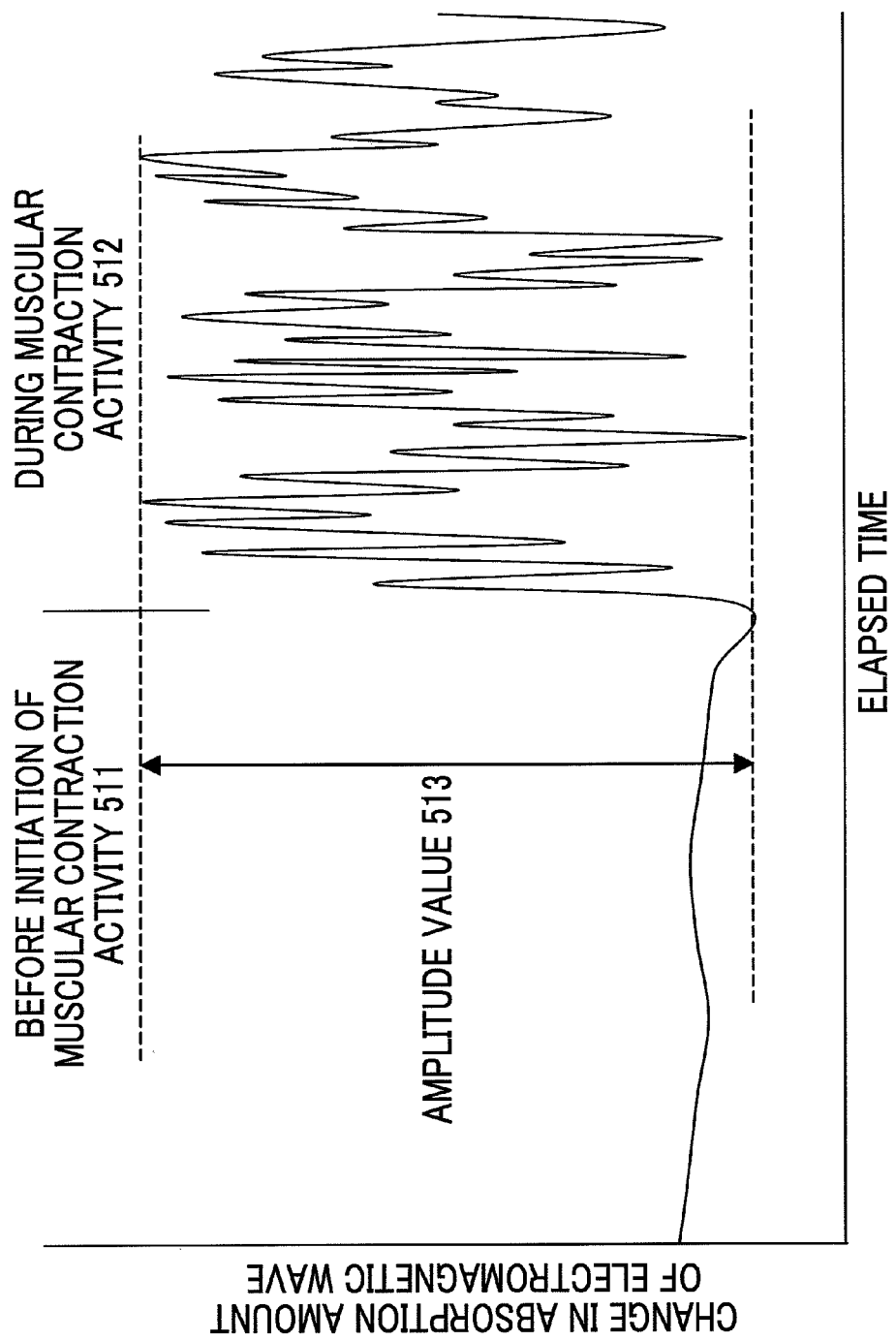
FIG.61  EXEMPLARY DETECTION SIGNAL RELATED TO MOVEMENT OF MIMETIC MUSCLE

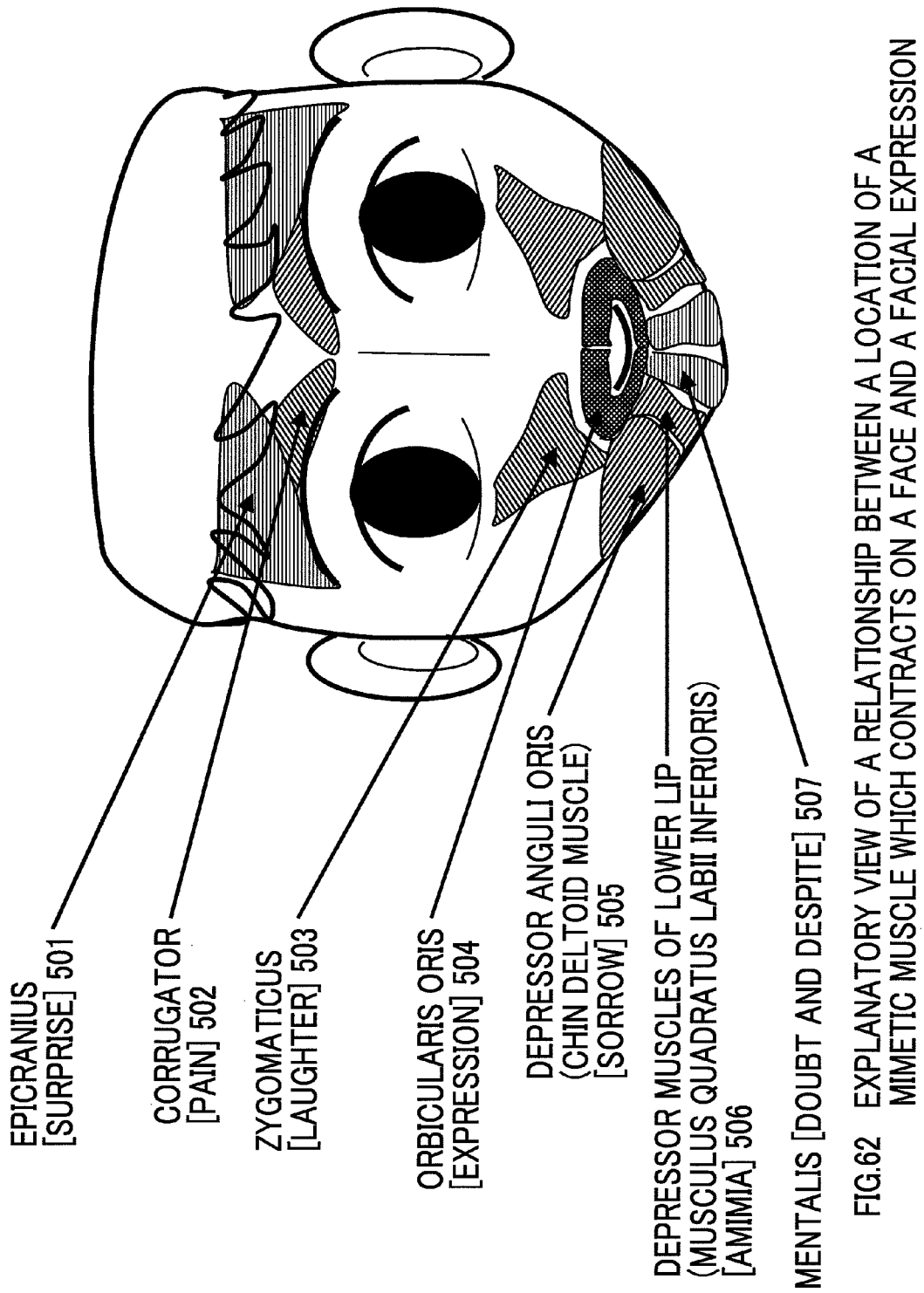

FIG.62  EXPLANATORY VIEW OF A RELATIONSHIP BETWEEN A LOCATION OF A MIMETIC MUSCLE WHICH CONTRACTS ON A FACE AND A FACIAL EXPRESSION

EPICRANIUS [SURPRISE] 501

CORRUGATOR [PAIN] 502

ZYGOMATICUS [LAUGHTER] 503

ORBICULARIS ORIS [EXPRESSION] 504

DEPRESSOR ANGULI ORIS (CHIN DELTOID MUSCLE) [SORROW] 505

DEPRESSOR MUSCLES OF LOWER LIP (MUSCULUS QUADRATUS LABII INFERIORIS) [AMIMIA] 506

MENTALIS [DOUBT AND DESPITE] 507

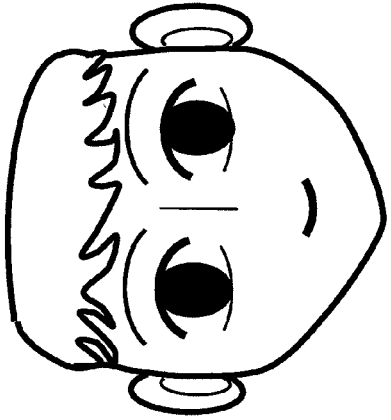
FIG.63 POSITIONAL RELATIONSHIP BETWEEN DETECTABLE RANGE AND DETECTION TARGET BY DETECTING SECTION FOR LIFE ACTIVIT

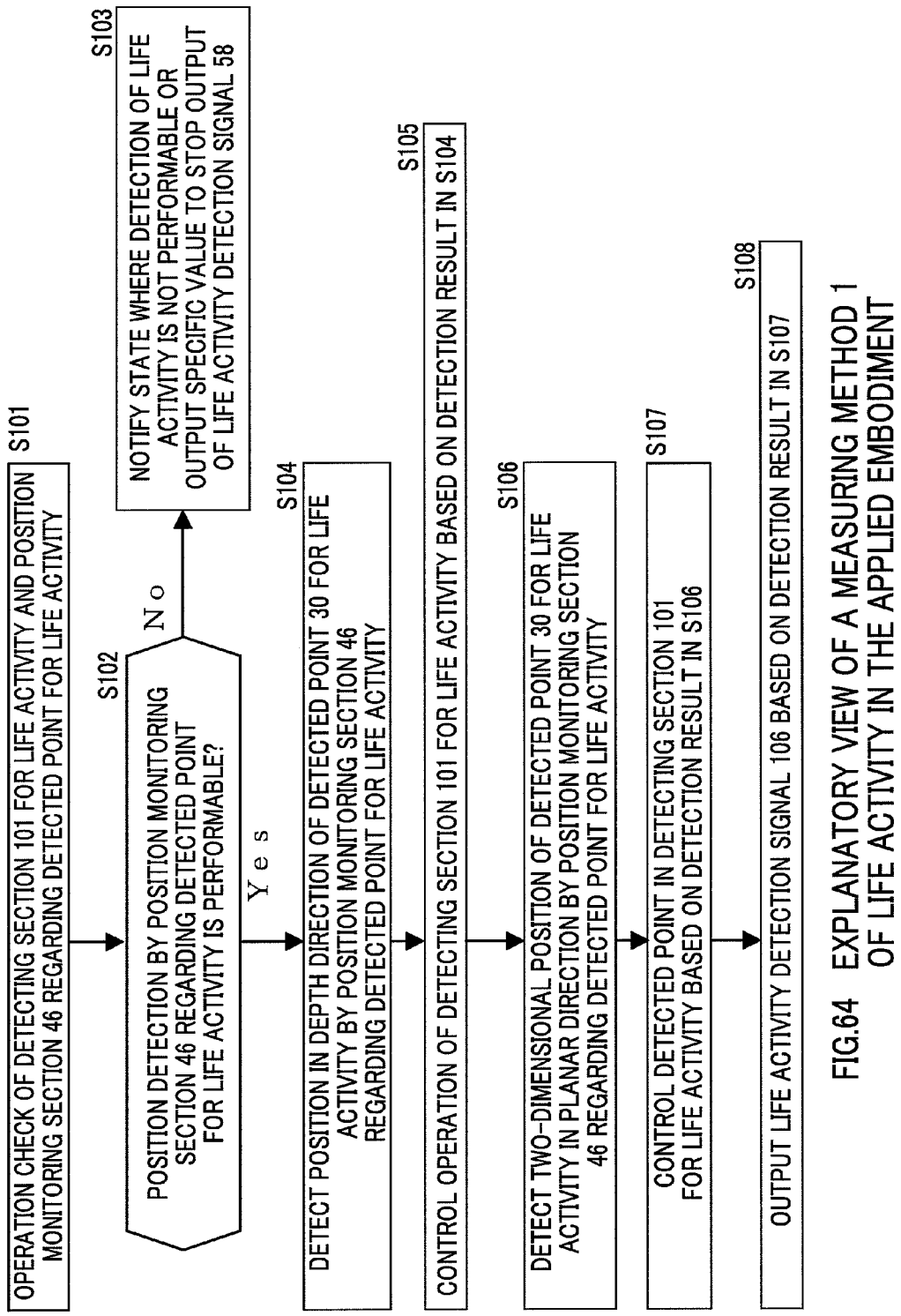
FIG.64 EXPLANATORY VIEW OF A MEASURING METHOD 1 OF LIFE ACTIVITY IN THE APPLIED EMBODIMENT

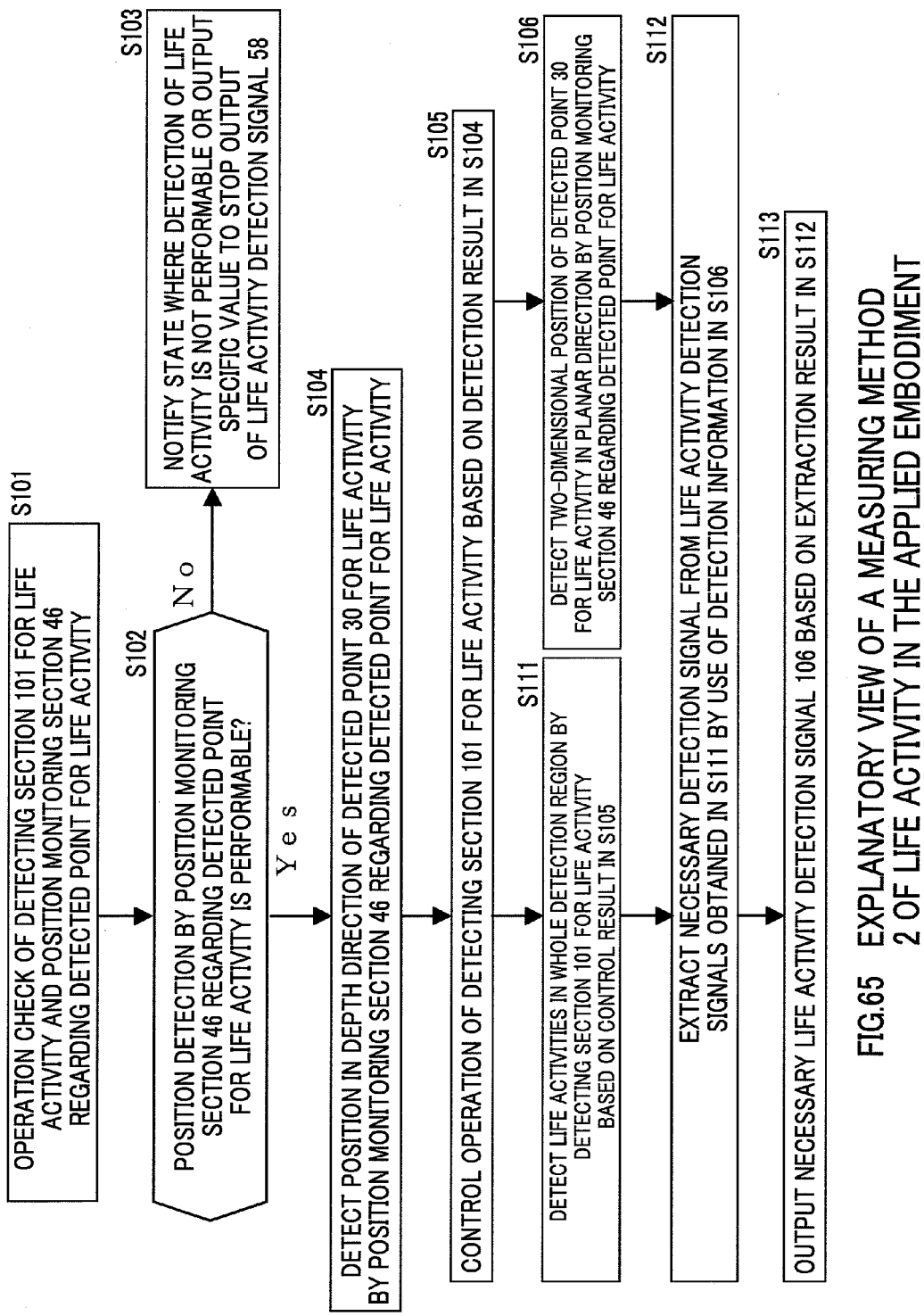
FIG.65 EXPLANATORY VIEW OF A MEASURING METHOD 2 OF LIFE ACTIVITY IN THE APPLIED EMBODIMENT

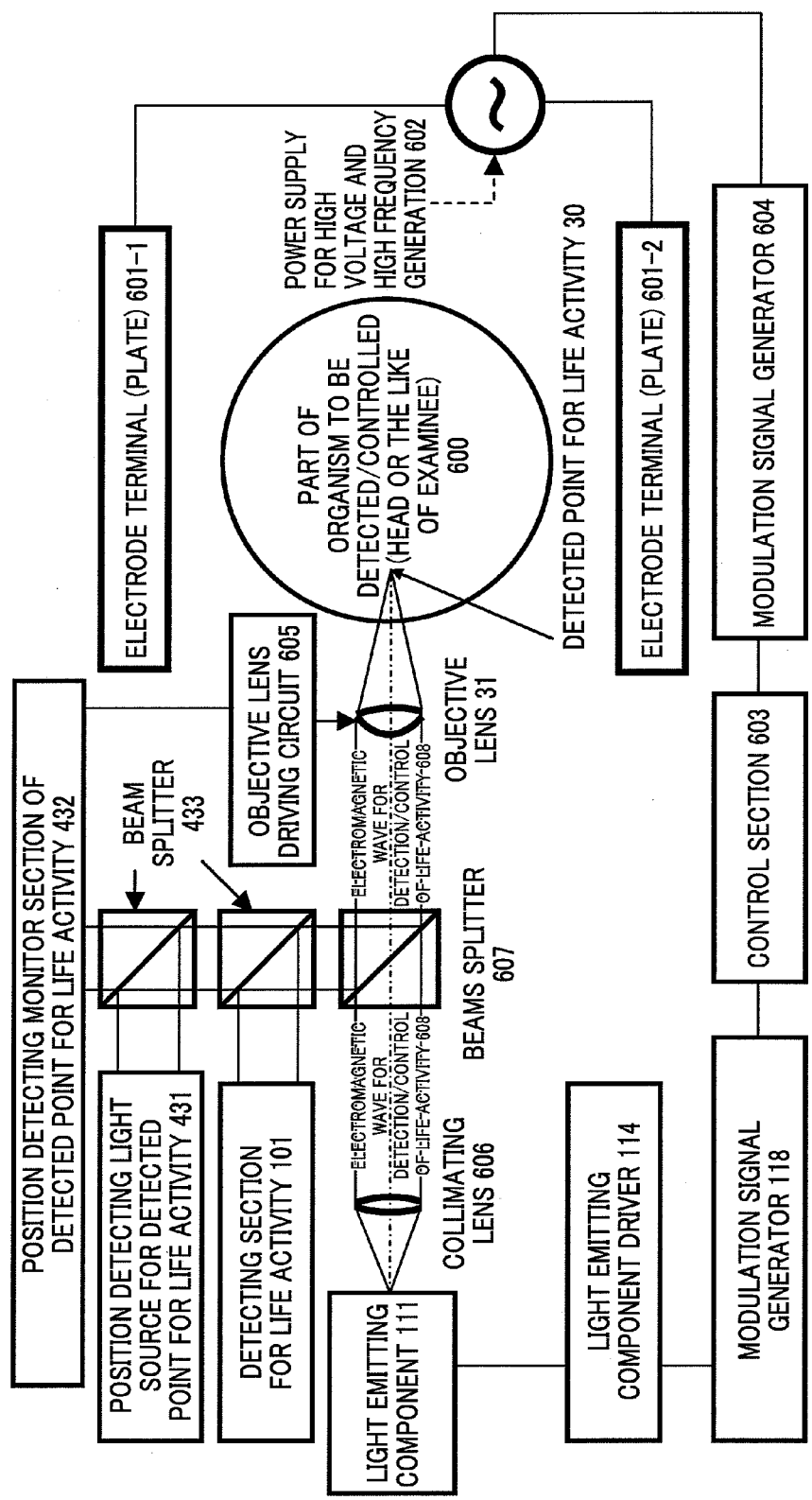
FIG. 66 CONFIGURATION IN LIFE ACTIVITY CONTROL DEVICE IN PRESENT EXEMPLARY EMBODIMENT

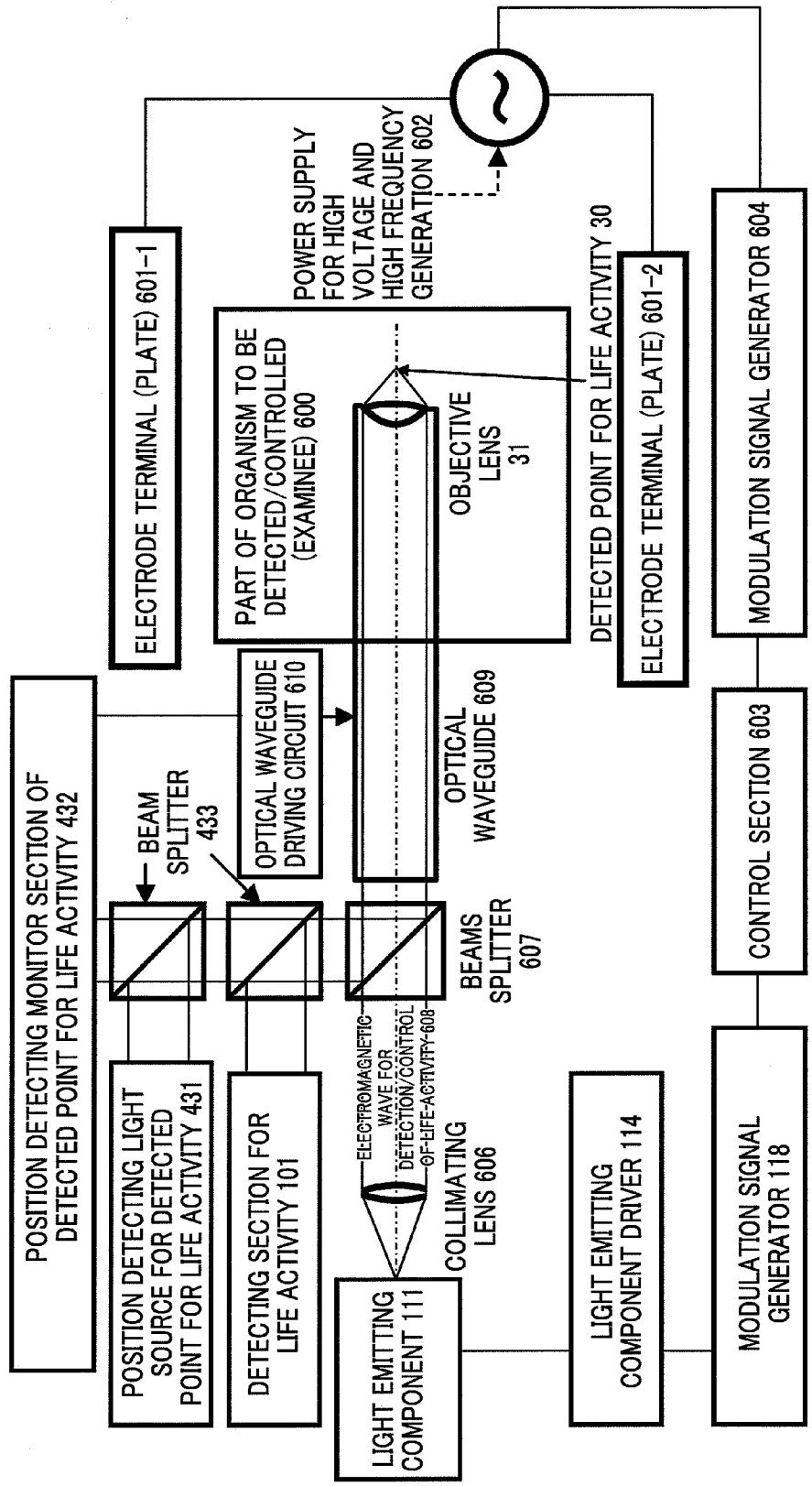
FIG.67 APPLIED EMBODIMENT OF LIFE ACTIVITY CONTROL DEVICE

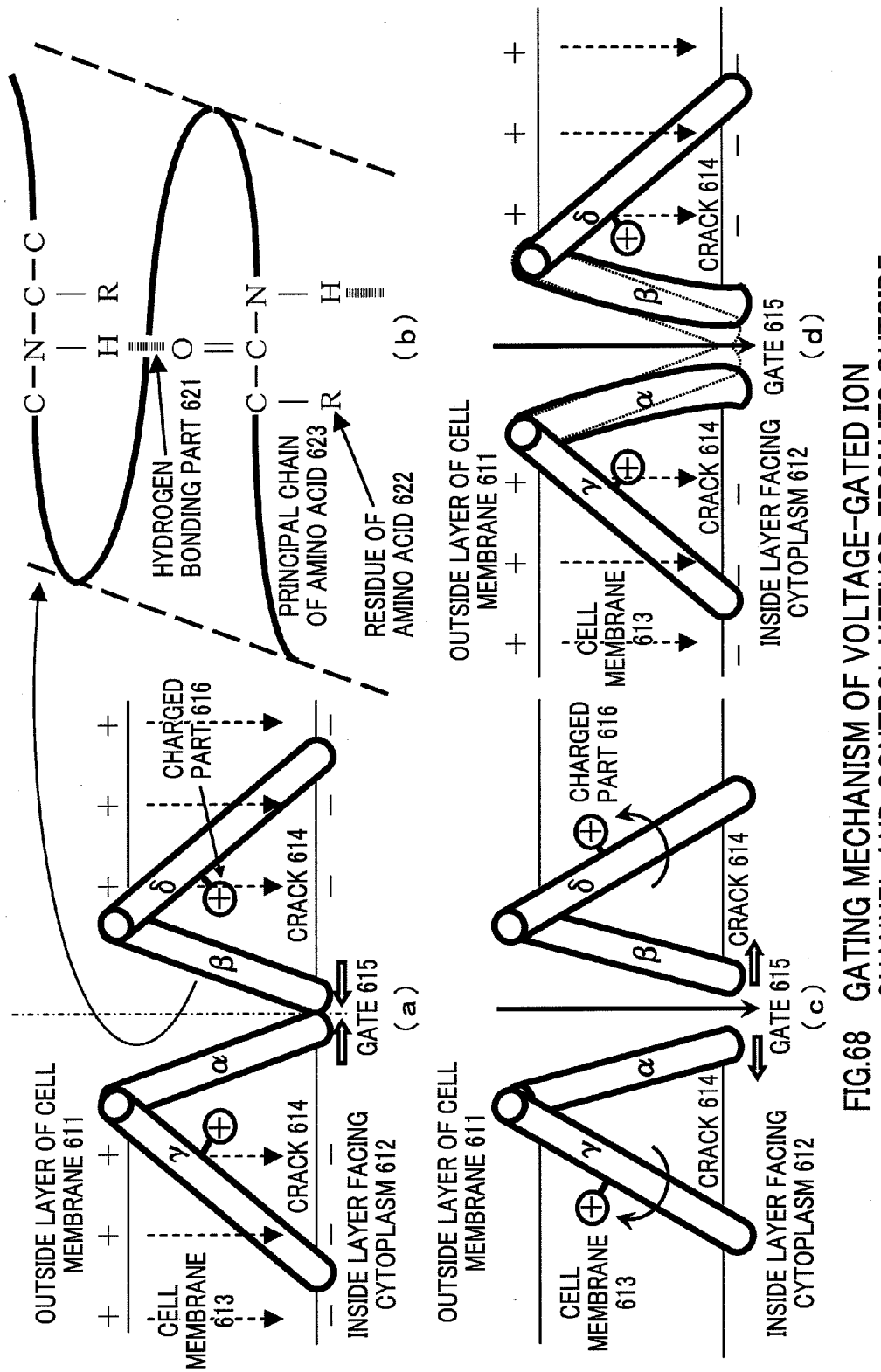
FIG.68 GATING MECHANISM OF VOLTAGE-GATED ION CHANNEL AND CONTROL METHOD FROM ITS OUTSIDE

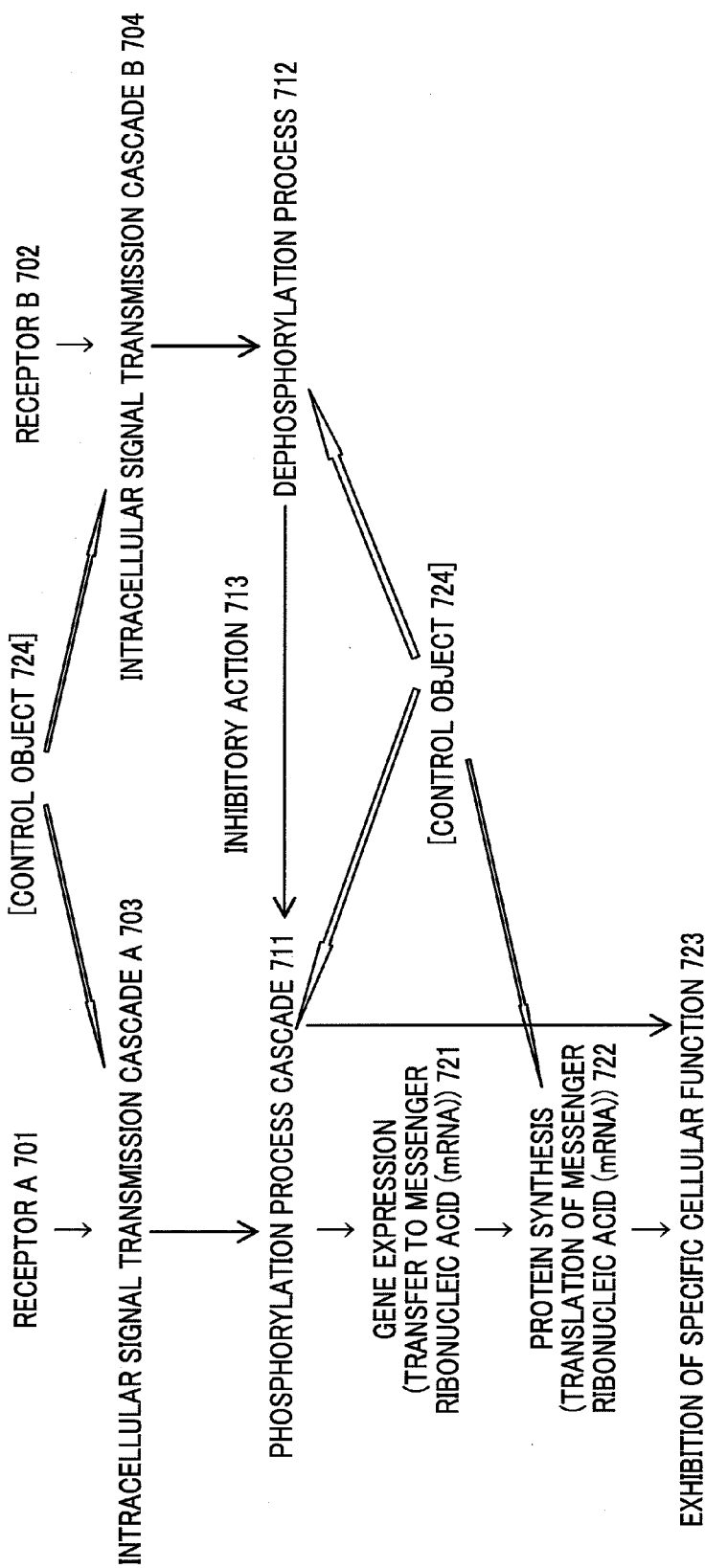
FIG.69  STATE OF INTRACELLULAR LIFE ACTIVITY CHAIN

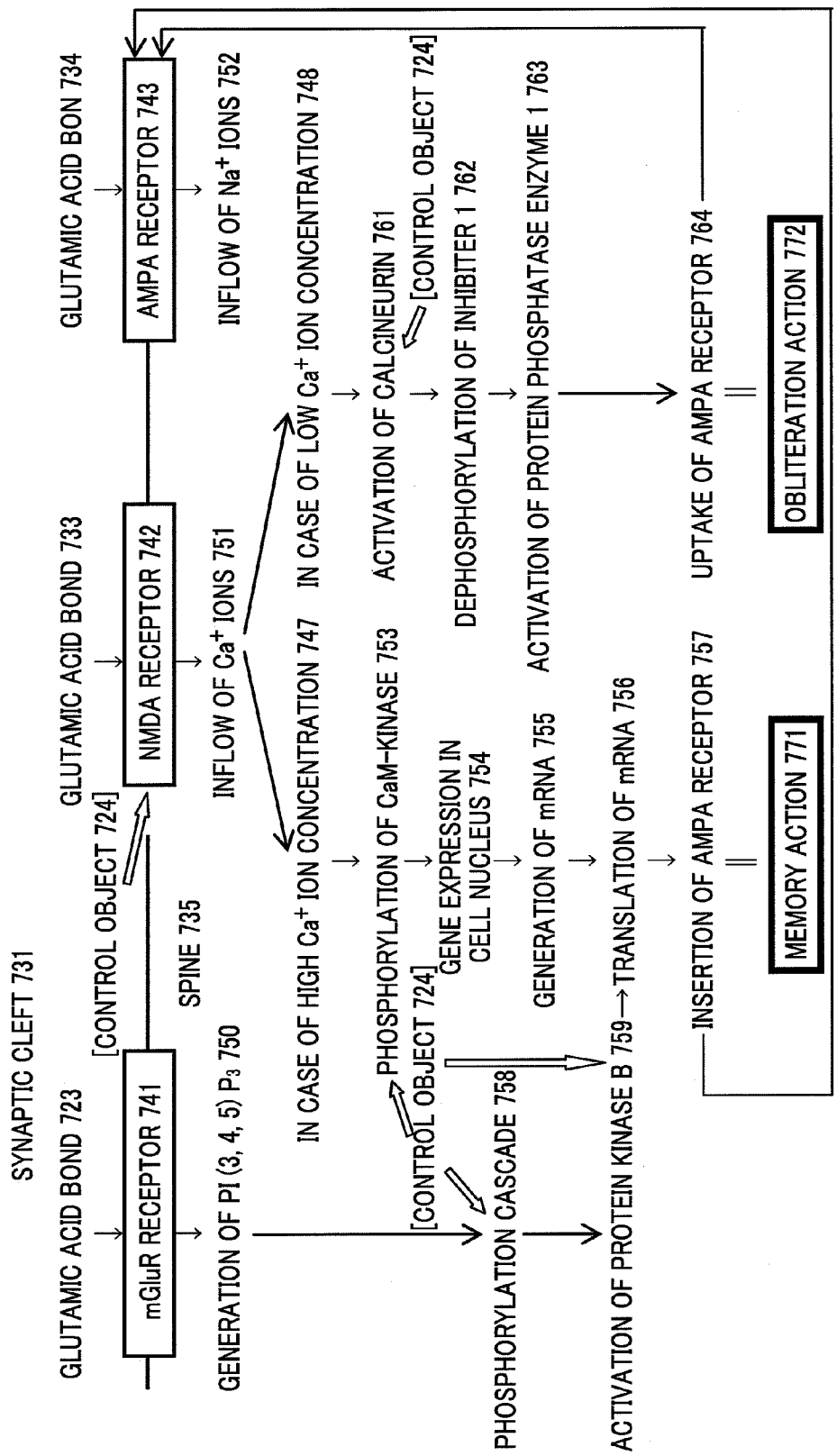
FIG. 70  MECHANISM MODEL IN WHICH MEMORY ACTION AND OBLITERATION ACTION OCCUR IN PYRAMIDAL CELL

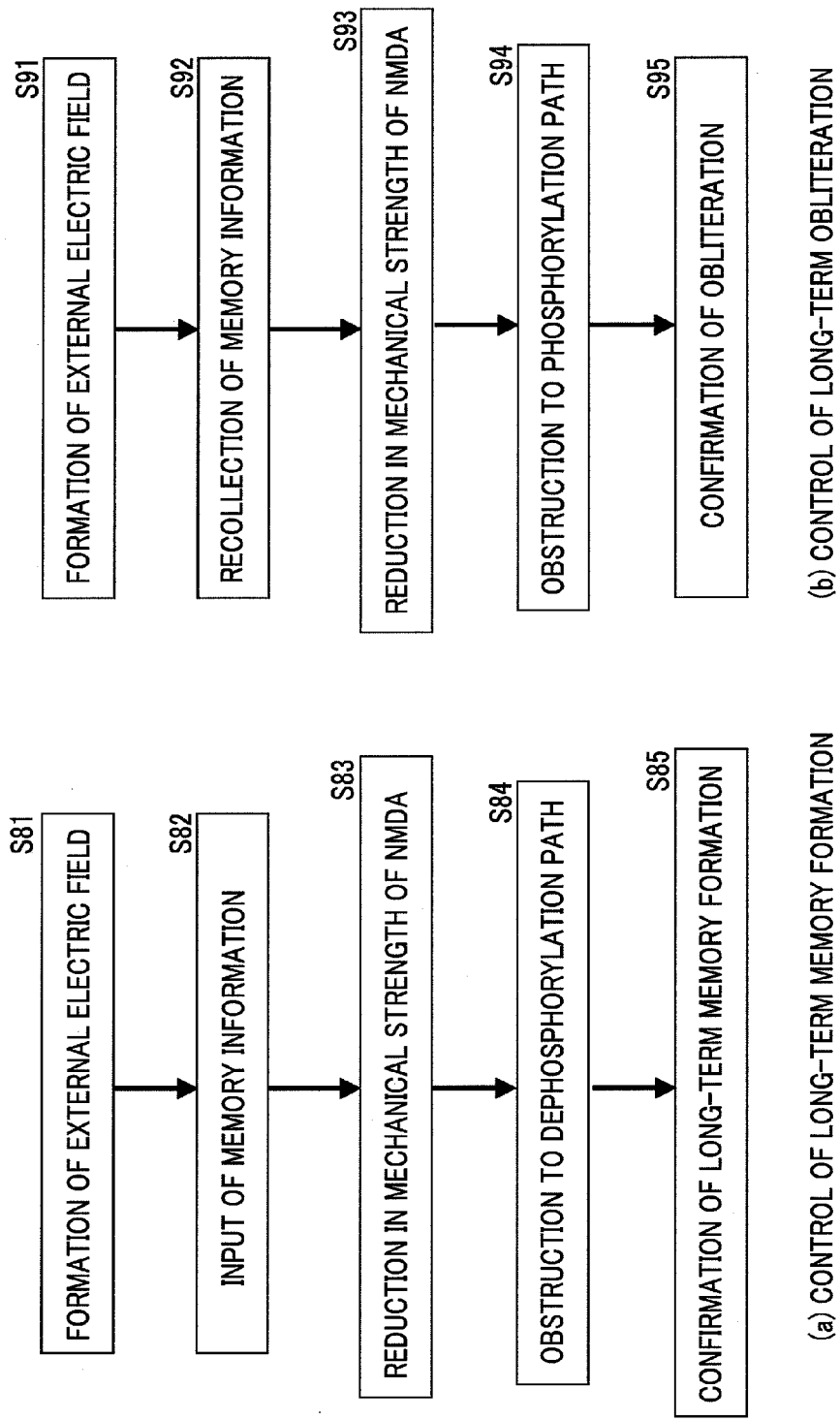
FIG.71 LONG-TERM MEMORY FORMATION AND CONTROL METHOD RELATED TO LONG-TERM OBLITERATION

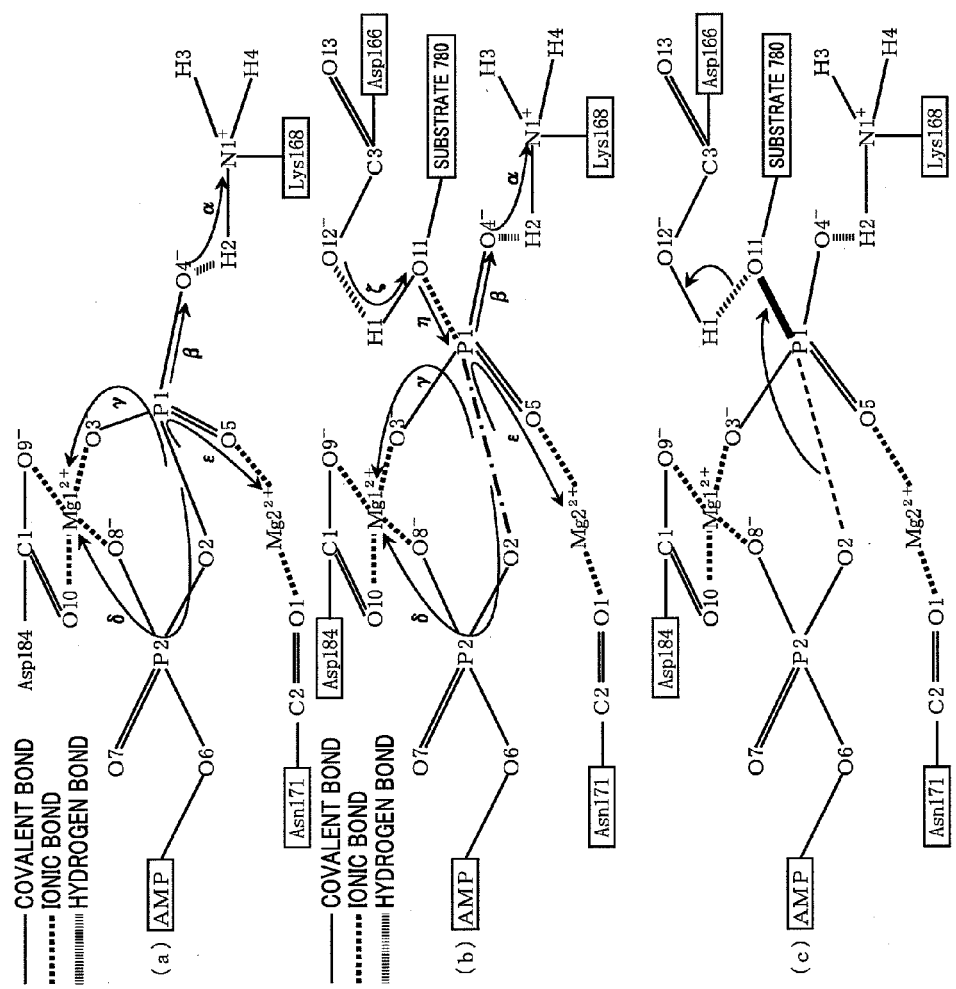
FIG.72 MECHANISM MODEL OF PHOSPHORYLATION PROCESS OCCURRING IN ACTIVE SITE IN PKA

MEASURING METHOD OF LIFE ACTIVITY, MEASURING DEVICE OF LIFE ACTIVITY, TRANSMISSION METHOD OF LIFE ACTIVITY DETECTION SIGNAL, OR SERVICE BASED ON LIFE ACTIVITY INFORMATION

BACKGROUND OF THE INVENTION

1. Field of the Invention

The present invention relates to, a measuring method or a control method for measuring (in vivo measurement) or controlling, in a living state, dynamical life activities changing at high speed in a life object such as an animal including a human or a plant or changes thereof by a non-contact and noninvasive method.

2. Description of the Related Art

An example of dynamical life activities changing at high speed in a life object is activities of the nervous system. Methods for measuring an intracerebral activity include a blood oxygen analyzing of blood with near infrared light (hereinafter referred to as "Conventional Technique 1") and oxygen analyzing of blood with a functional Magnetic Resonance Imaging (fMRI) method (hereinafter referred to as "Conventional Technique 2"), which are representative examples of conventional techniques.

According to Conventional Technique 1, the oxygen concentration in blood is measured by use of a change of a near infrared light absorbing spectrum of oxyhemoglobin and deoxyhemoglobin (see Non Patent Document 1). That is, the oxyhemoglobin which is a particular hemoglobin bonding to an oxygen molecule has a maximum absorption at a wavelength of 930 nm, and the deoxyhemoglobin which is other particular hemoglobin separated from an oxygen molecule has maximum absorption at wavelengths of 760 nm and 905 nm. A head is illuminated with each light of 780 nm, 805 nm, and 830 nm as a light source (a semiconductor laser) for measurement, and changes in intensity of respective beams of transmitted light are measured. Signals relating to cortex areas of the brain at 3 to 4 cm in depth are hereby obtained from a surface of the head.

Except the method using near infrared light, there is a method using Nuclear Magnetic Resonance to perform the measurement of the oxygen concentration in blood. That is, when adsorption of oxygen molecules is switched to release of oxygen molecules, electron orbitals in hemoglobin molecules are changed, which changes magnetic susceptibility and shortens T2 relaxation time of MR.

According to Conventional Technique 2, a location (activation area) where an oxygen consumption rate has increased in the nervous system is estimated by use of this phenomenon (see Non Patent Documents 2 and 3). When this method is used, a measurement result can be obtained by a computer process and the oxygen concentration distribution in blood in the head can be exhibited in a three-dimensional manner.

Meanwhile, as a method for controlling dynamical life activities in a life object, there has been known medical treatment.

CITATION LIST

Non-Patent Documents

Non Patent Document 1: Yukihiro Ozaki/Satoshi Kawata: Kinsekigaibunkouhou (Gakkai Shuppan Center, 1996) Section 4.6

Non Patent Document 2: Takashi Tachibana: Nou Wo Kiwameru Noukenkyu Saizensen (Asahi Shimbun Publishing, 2001) p. 197

Non Patent Document 3: Masahiko Watanabe: Nou Shinkei Kagaku Nyumon Koza Gekan (Yodosha, 2002) p. 188

SUMMARY OF THE INVENTION

Problem to be Solved by the Invention

However, according to Conventional Techniques 1 and 2, a temporal resolution and a spatial resolution for the active state measurement of the neuron are low.

In order to facilitate the understanding of the problem, the following initially explains that the oxygen analyzing of blood is indirect measurement. The measurement of the oxygen concentration in blood is based on a tacit hypothesis that "when a neuron is activated, hemoglobin should be deoxygenated to supply its activity energy."

However, as described in Chapter 4 of the B. Alberts et. al: Essential Cell Biology (Garland Publishing, Inc., 1998), energy caused at the time of hydrolysis from ATP (Adenosine triphosphate) to ADP (Adenosine diphosphate) is used for the activity energy of the neuron.

The ADP is generated in the course of an oxidation process of Acetyl CoA occurring in Mitochondria existing in the neuron. Further, the neuron does not contact with blood vessels directly, and oxygen molecules are transmitted into the neuron via glial cells intervening between the neuron and the blood vessels. The transmission of the oxygen molecules is involved with the activity in the neuron via such a complicated course.

Accordingly, it is considered that a phenomenon that the oxygen concentration in blood is changed (decreased) occurs only around a local area where a large amount of cells are activated in the nervous system at the same time. For this reason, it is difficult, in Conventional Techniques 1 and 2, to observe instant changes of a few cells in the nervous system, such as short-term action potentials from a few neurons. That is, since only a local area where a large amount of cells are activated at the same time can be detected, it is theoretically difficult to raise the spatial resolution. As such, in Conventional Techniques 1 and 2, the activity of the neuron is observed not directly but indirectly, so that the measurement accuracy is poor.

(Regarding Temporal Resolution)

According to the Report of Nikkei Electronics (Nikkei BP), p. 44, Published on May 3, 2010, a hemoglobin level in blood which changes about 5 s after a neuron became active is detected in accordance with Conventional Technique 1. Therefore, in the detection based on Conventional Technique 1, a large delay occurs from initiation of the activity of the neuron.

Further, according to Conventional Technique 2, the use of a BOLD (Blood Oxygenation Level Dependent) effect causes a similar situation to the above. The BOLD effect is as follows: when a neuronal activity increases due to a brain activity, an oxygen consumption increases at first. As a result, a deoxyhemoglobin concentration slightly increases, and several seconds later, a cerebral blood flow in capillaries in vicinal areas increases rapidly, thereby causing a supply of a large amount of oxygen which greatly exceeds the oxygen consumption. This rapidly increases the oxyhemoglobin concentration, and consequently, fMRI signals are enhanced and relaxation time thereof is made longer. That is, even in Conventional Technique 2, the detection of the increase in the oxyhemoglobin concentration requires several seconds after the activity of the neuron has started due to the brain activity, and thus, Conventional Technique 2 also causes a delay of several seconds for the detection, similarly to Conventional Technique 1.

As such, as long as Conventional Techniques 1 and 2 measure the oxygen concentration in blood, there is a delay for the hemoglobin level in blood to change after the initiation of the activity of the neuron. In view of this, the temporal resolution in either of Conventional Techniques 1 and 2 is about 5 s, which is very low.

(Regarding Spatial Resolution)

The spatial resolution of Conventional Technique 1 is determined by a distance between a light source and a photodetector for measuring an intensity change of light passing through the head (See p. 43 of Nikkei Electronics (Nikkei BP) published on May 3, 2010). As the distance between the light source and the photodetector becomes smaller, a penetration depth of a measuring beam into the head becomes shallower.

Accordingly, if the distance between the light source and the photodetector is shortened to raise the spatial resolution, it becomes impossible to measure the nervous system in the head. As described earlier, in a case where measurement is performed on an area inside the head which is at a depth of 3 to 4 cm from a surface of the head, the light source should be placed so as to be distanced from the photodetector by about 3 cm, and thus, the spatial resolution is about 3 cm.

On the other hand, the spatial resolution in the case of Conventional Technique 2 is determined by a wavelength of a detecting transaction magnetic field (an electromagnetic wave) according to a diffraction theory of the electromagnetic wave, and the wavelength of this detecting transaction magnetic field is determined by a DC magnetic field intensity to be applied. Even if the DC magnetic field intensity is raised using a super conductive magnet, there is a theoretical upper limit of the spatial resolution due to a technical limitation. According to p. 42 of Nikkei Electronics (Nikkei BP) published on May 3, 2010, which is mentioned above, the spatial resolution is a few mm at best, even in an fMRI device having the highest spatial resolution.

The following describes a penetration depth into a life object regarding Conventional Technique 1. As apparent from the skin color of a human, visible light is easy to be reflected diffusely on a surface of a life object and is hard to penetrate the life object. In the examples described above, light of 780 nm, light of 805 nm, and light of 830 nm are used as measuring beams. The light of 830 nm, which has the longest wavelength among them, is near infrared light, but is close to a visible light area. Therefore, the penetration depth thereof into the life object is also short. As a result, only a signal relating to the cortex area in the brain located at a depth of 3 to 4 cm from the surface of the head can be measured at best, as previously described.

In view of this, it is an object of the present invention to provide a method and the like which can measure an active state in a life object while attempting to enhance the spatial resolution and the temporal resolution.

Meanwhile, in the medical treatment, which is known as a method for controlling life activities, it is difficult to effectively control only a particular region in a life object. This is because a medicine given by mouth or by injection circulates through the body and spreads over the body. Therefore, even medication for a therapeutic purpose, for example, not only causes a relative decrease in a medicine amount working on a target part to be cured (controlled), but also side effects due to other drug actions to other parts except the target part to be cured (controlled).

In view of this, the present invention is also intended to provide a method and the like for effectively controlling an active state of only a particular region (an area constituted by one cell or a group of a plurality of cells) in a life object.

Means for Solving the Problem

A measuring method of life activity or a control method of life activity according to the first aspect of the present invention is a measuring method of life activity or a control method of life activity for measuring or controlling an active state of a life object including an animal and a plant or a change thereof, including: an illumination step of illuminating the life object with an electromagnetic wave of which a wavelength is included in a designated waveband; and a detection step of detecting a characteristic associated with the electromagnetic wave in a local area constituted by one or more cells in the life object, or a control step of controlling the active state by use of the characteristic associated with the electromagnetic wave, wherein any of the following phenomena is used for detecting or controlling the active state of the life object or a change thereof:

[1] transition energy between a ground state of a vibration mode newly occurring between atoms in a constituent molecule of a cell membrane and a plurality of excited states;

[2] transition energy between vibration modes occurring between specific atoms in a molecule corresponding to the activity of the life object or the change thereof and

[3] a specific chemical shift value in Nuclear Magnetic Resonance, and the designated waveband is determined on the basis of any of the phenomena.

The measuring method of life activity according to one exemplary embodiment of the present invention is such that the designated waveband is determined under such a condition that the potential change of the cell membrane is accompanied with a phenomenon in which a specific ion is attached to or detached from a specific substance in the local area.

The measuring method of life activity according to a first aspect of the present invention is such that the designated waveband is determined under such a condition that the specific substance and the specific ion is at least one of a combination of Phosphatidylcholine or Sphingomyelin and a chlorine ion, a combination of Phosphatidylserine and a sodium ion or a potassium ion, and a combination of Glycolipid and a sodium ion.

The measuring method of life activity according to the first aspect of the present invention is such that: the designated waveband according to attachment or detachment of the chlorine ion with respect to the Phosphatidylcholine is determined on the basis of a wavenumber of 2480 $cm^{-1}$ or a chemical shift value from $\delta2.49$ to $\delta2.87$ ppm or a chemical shift value related to $\delta3.43$ ppm to $\delta3.55$ ppm; the designated waveband according to attachment or detachment of the chlorine ion with respect to the Sphingomyelin is determined on the basis of a wavenumber of 2450 $cm^{-1}$ or a chemical shift value from $\delta2.49$ to $\delta2.87$ ppm or a chemical shift value related to $\delta3.43$ ppm to $\delta3.55$ ppm; the designated waveband according to attachment or detachment of the sodium ion with respect to the Phosphatidylserine is determined on the basis of a wavenumber of 429 cm$^{-1}$; the designated waveband according to attachment or detachment of the potassium ion with respect to the Phosphatidylserine is determined on the basis of a wavenumber of 118 cm$^{-1}$ or 1570 cm$^{-1}$; and the designated waveband according to attachment or detachment of the sodium ion with respect to the Glycolipid is determined on the basis of a wavenumber of 260 to 291 cm$^{-1}$.

The measuring method of life activity according to the first aspect of the present invention is such that the designated waveband is determined so that at least a part of a waveband corresponding to a wavenumber range having a margin of 10 to 20% with respect to a wavenumber to be the basis or a range of a chemical shift value having a margin of 0.45 ppm to 0.49 ppm with respect to a chemical shift value to be the basis is included therein.

The measuring method of life activity according to the first aspect of the present invention is such that the designated waveband is determined such that wavebands of electromagnetic waves absorbed by other substances including at least water constituting the life object are removed.

The measuring method of life activity according to the first aspect of the present invention is such that the designated phenomenon is a phenomenon to occur within a designated response time in a range of 4 to 200 ms after the active state of the life object has changed.

The measuring method of life activity according to the first aspect of the present invention is such that the detection step is a step of detecting an absorption characteristic of the electromagnetic wave in the local area at any cross section in the life object by using a confocal system.

The measuring method of life activity according to the first aspect of the present invention further includes: a step of acquiring, by the illumination step and the detection step, designated information representing a spatial distribution aspect and an aspect of a time dependent variation of the absorption characteristic of the electromagnetic wave in the life object; and a step of specifying life activity information of the life object or environmental information defining an environment surrounding the life object, by referring to a data base in which to store a relationship between the life activity information or the environmental information and the designated information, based on the acquired designated information.

The measuring method of life activity according to the first aspect of the present invention further includes: a step of recognizing the life activity information or environmental information of the life object; and a step of setting or correcting the relationship between them to be stored in the data base, based on the recognized life activity information or environmental information and the acquired designated information.

A measuring method of life activity according to a second aspect of the present invention is such that a dynamical activity of a life object is detected by use of a characteristic in a local area corresponding to an electromagnetic wave having a wavelength of not less than 0.84 μm but not more than 110 μm or a characteristic in a local area corresponding to an electromagnetic wave associated with a chemical shift value in a range of not less than δ1.7 ppm but not more than δ4.5 ppm.

The measuring method of life activity according to one exemplary embodiment of the present invention is such that a time dependent variation of the characteristic in the local area of the life object is measured.

The measuring method of life activity according to the second aspect of the present invention is such that at least a part of the life object is illuminated with a modulated electromagnetic wave having a basic frequency in a range of 0.2 Hz to 500 kHz.

The measuring method of life activity according to the second aspect of the present invention is such that a time dependent variation of the characteristic in one fixed local area in the life object is detected or a set of individual time dependent variations related to the characteristic in a plurality of local areas fixed to different positions in the life object are detected.

The measuring method of life activity according to the second aspect of the present invention at least one of the fixed local areas corresponds to one cell or a part of the cell and is illuminated with a modulated electromagnetic wave having a basic frequency in a range of 0.2 Hz to 500 kHz.

The measuring method of life activity according to the second aspect of the present invention is such that the local area corresponds to one cell or a part of the one cell, and a change of the characteristic to occur according to a potential change of a cell membrane constituting the cell is detected.

The measuring method of life activity according to the second aspect of the present invention is such that the life object is illuminated with electromagnetic waves including electromagnetic waves having a plurality of different wavelengths or electromagnetic waves having a plurality of different frequencies so as to detect characteristics in the local area of the life object corresponding to the electromagnetic waves having the plurality of wavelengths or the electromagnetic waves having the plurality of frequencies.

The measuring method of life activity according to one exemplary embodiment of the present invention includes: a generation step of generating dynamical life activity information from the obtained detection signal.

A measuring device of life activity according to a first aspect of the present invention is a measuring device of life activity for measuring an active state of a life object including an animal and a plant, including: an illuminator for illuminating the life object with an electromagnetic wave of which a wavelength is included in a designated waveband; and a detector for detecting a characteristic associated with the electromagnetic wave in a local area constituted by one or more cells in the life object, wherein: any of the following phenomena is used for detecting or controlling the active state of the life object or a change thereof:

[1] transition energy between a ground state of a vibration mode newly occurring between atoms in a constituent molecule of a cell membrane and a plurality of excited states;

[2] transition energy between vibration modes occurring between specific atoms in a molecule corresponding to the activity of the life object or the change thereof; and

[3] a specific chemical shift value in Nuclear Magnetic Resonance, and the designated waveband is determined on the basis of any of the phenomena.

A measuring device of life activity, according to a second aspect of the present invention, having a detecting section for life activity and performing a predetermined process based on a detection signal related to a life activity obtained from the detecting section for life activity is such that: the detecting section for life activity is constituted by a light emitting section and a signal detecting section; the light emitting section generates electromagnetic waves illuminated to a life object; the electromagnetic waves include an electromagnetic wave having a wavelength of not less than 0.84 μm but not more than 110 μm or an electromagnetic wave associated with a chemical shift value in a range of not less than δ1.7 ppm but not more than δ4.5 ppm; and the signal detecting section detects an electromagnetic wave including the detection signal related to the activity of the life object obtained as a result of the illumination of the electromagnetic waves.

The measuring device of life activity according to the second aspect of the present invention is such that the local area corresponds to one cell or a part of the one cell, and a change of the characteristic to occur according to a potential change of a cell membrane constituting the cell is detected.

The measuring device of life activity according to the second aspect of the present invention is such that the light emitting section generates electromagnetic waves including electromagnetic waves having a plurality of different wavelengths or electromagnetic waves having a plurality of different frequencies.

A transmission method of a life activity detection signal is such that: a life object is illuminated with electromagnetic waves including an electromagnetic wave having a wavelength of not less than 0.84 μm but not more than 110 μm or an electromagnetic wave associated with a chemical shift value in a range of not less than δ1.7 ppm but not more than δ4.5 ppm; a life activity detection signal related to a characteristic in a local area of the life object is detected; and the life activity detection signal is transmitted.

The transmission method of a life activity detection signal according to one exemplary embodiment of the present invention is such that: the local area corresponds to one cell or a part of the one cell; and a change of the characteristic to occur due to a potential change of a cell membrane constituting the cell is detected.

A transmission method of life activity information according to one exemplary embodiment of the present invention is such that a life object is illuminated with an electromagnetic wave having a wavelength of not less than 0.84 μm but not more than 110 μm or an electromagnetic wave associated with a chemical shift value in a range of not less than δ1.7 ppm but not more than δ4.5 ppm, so as to obtain a life activity detection signal related to a local area of the life object, life activity information is generated from the obtained life activity detection signal, and the life activity information is transmitted.

The transmission method of a life activity detection signal according to one exemplary embodiment of the present invention is such that: life activity detection signals related to respective characteristics in a local area of the life object corresponding to electromagnetic waves having a plurality of wavelengths in a range of not less than 0.84 μm but not more than 110 μm or electromagnetic waves associated with a plurality of chemical shift values in a range of not less than δ1.7 ppm but not more than δ4.5 ppm are detected; and the life activity detection signals related to the respective wavelengths or the respective frequencies are transmitted.

A service based on life activity information according to one exemplary embodiment of the present invention is such that: a life object is illuminated with electromagnetic waves including an electromagnetic wave having a wavelength of not less than 0.84 μm but not more than 110 μm or an electromagnetic wave associated with a chemical shift value in a range of not less than δ1.7 ppm but not more than δ4.5 ppm; a life activity detection signal related to a characteristic in a local area of the life object is detected; and based on a result of generating life activity information from the life activity detection signal, a service corresponding to the life activity information is provided, or the life object is illuminated with the electromagnetic wave to provide a service corresponding to control of the life activity.

A service based on life activity information according to one embodiment of the present invention is such that a service is provided based on detection or measurement results, or control of a life activity occurring in the local area constituted by one or more cells.

Effects of the Invention

According to the measuring method of life activity or the control method of life activity of the present invention, a life object is illuminated with an electromagnetic wave of which a wavelength is included in a designated waveband, and a characteristic in a local area of the life object corresponding to the electromagnetic wave or a change thereof is detected or controlled. The "designated waveband" is a waveband determined on the basis of transition energy between vibration modes formed between specific atoms in a local area which can occur associated with an active state of a life object or a change thereof or on the basis of a specific chemical shift value. A "local area" is an area constituted by one or more cells.

Consequently, according to the present invention, characteristics associated with electromagnetic waves and appearing rapidly or in a very short time according to changes of an active state of a life object can be detected. That is, it is possible to measure an active state of a life object while attempting to enhance the temporal resolution. Further, according to one embodiment of the present invention, since only a minute local area is illuminated with the electromagnetic wave by use of convergence properties of the electromagnetic wave, not only the spatial resolution for the detection or measurement of the life activity is improved, but also the life activity is controllable only in a minute local area. Further, if this control method or this detection result is used, the recognition accuracy for an active state of a life object can be improved and an appropriate service can be provided to the life object or a person concerned.

BRIEF DESCRIPTION OF THE DRAWINGS

FIG. 1 is a general explanatory view of a signal transmission pathway in a nervous system.

FIG. 2 is a general explanatory view illustrating signal transmission in an axon.

FIG. 3 is an explanatory view illustrating changing states of a neuronal membrane potential and a muscular membrane potential in case of an action potential.

FIG. 4 illustrates a charging model on both surfaces of a neuronal membrane in case of action and resting potentials.

FIG. 5 is an estimated molecular structure of PCLN in case of Cl$^-$ ion attachment and detachment.

FIG. 6 illustrates infrared spectral characteristics estimation of PCLN in case of Cl$^-$ ion attachment and detachment FIG. 7 is an explanatory view of a part of GD1a structure used for calculating infrared spectral characteristics.

FIG. 8 is a flow chart used for originally calculating near infrared spectral characteristics based on anharmonic vibrations.

FIG. 9 is an explanatory view of a charged particle movement in electric field having specific direction.

FIG. 10 is an explanatory view of position vectors pointing to carbon and hydrogen atomic nucleuses which together make asymmetrical stretching of C—H—Cl$^-$.

FIG. 11 illustrates a relative static molecule energy vs. distance deviation between carbon and hydrogen atomic nucleuses.

FIG. 12 is an explanatory view of Cl⁻ position fluctuation dependent on distance deviation between carbon and hydrogen atomic nucleuses.

FIG. 13 illustrates amplitude distributions of wave functions |m> regarding anharmonic vibrations.

FIG. 14 illustrates net atomic charges vs. distance deviations between carbon and hydrogen atomic nucleuses.

FIG. 15 illustrates amplitude distributions of molecular orbitals whose eigen values of energy correspond to HOMO and the minimum.

FIG. 16 illustrates electric dipole moments vs. distance deviations between carbon and hydrogen atomic nucleuses.

FIG. 17 illustrates a comparison in spatial resolution between membrane potential changing detection and oxygen concentration change detection in blood.

FIG. 18 illustrates a comparison in temporal resolution between membrane potential changing detection and oxygen concentration change detection in blood.

FIG. 19 is an explanatory view of comparison in detection accuracy between membrane potential changing detection and oxygen concentration change detection in blood.

FIG. 20 is an explanatory view of a first principle of a monitoring method of a detected point for life activity.

FIG. 21 is an explanatory view of a first principle of monitoring method of a pattern of a detected point for life activity in a depth direction.

FIG. 22 is an explanatory view of a second principle of a monitoring method of a marked position on a life-object surface.

FIG. 23 is an explanatory view of a principle (using a confocal system) of a first exemplary embodiment regarding an optical system for life activity detection.

FIG. 24 is an explanatory view of an operation principle of the first exemplary embodiment regarding the optical system for life activity detection.

FIG. 25 shows a relationship between a liquid crystal shutter pattern and a photo detecting cell in the first exemplary embodiment of the optical system for life activity detection.

FIG. 26 is an explanatory view of an operation principle regarding an applied embodiment of the optical system for life activity detection.

FIG. 27 is an explanatory view of a configuration of a photodetector in the applied embodiment of the optical system for life activity detection.

FIG. 28 is an explanatory view of a detailed optical arrangement regarding the applied embodiment of the optical system for life activity detection.

FIG. 29 is an explanatory view illustrating a method for detecting a local change of a Nuclear Magnetic Resonance property in a life object at high speed.

FIG. 30 is an explanatory view regarding a method for detecting a location where the Nuclear Magnetic Resonance property changes.

FIG. 31 is an explanatory view of a configuration of a detecting section for life activity.

FIG. 32 is an explanatory view of a configuration of another exemplary embodiment of a detecting section for life activity.

FIG. 33 is an explanatory view of a configuration of a front part of a life activity detecting circuit.

FIG. 34 is an explanatory view of a configuration of a rear part of a life activity detecting circuit.

FIG. 35 is an explanatory view of a configuration of a transmitting section of a life activity detection signal.

FIG. 36 is a general explanatory view illustrating a content of a life activity detection signal.

FIG. 37 is a general explanatory view illustrating an example of life activity information (a measurement result regarding a specific measuring item).

FIG. 38 is an explanatory view illustrating an example of a data base construction related to life activity interpretation.

FIG. 39 is an explanatory view illustrating an example of life activity interpretation.

FIG. 40 is an explanatory view illustrating an applied embodiment of life activity interpretation.

FIG. 41 is an explanatory view illustrating a relationship between facial expression and emotional reaction.

FIG. 42 is an explanatory view of a method for obtaining life activity information from movement of a facial muscle.

FIG. 43 is an explanatory view of a method for selecting an optimum process/operation method based on life activity information.

FIG. 44 is an explanatory view of an overview of a network system using a detecting section for life activity.

FIG. 45 is a whole explanatory view of an example of a service based on life activity measurement.

FIG. 46 is an explanatory view of a content of an activation process in a service based on life activity measurement.

FIG. 47 is a detailed explanatory view of a method of interface correspondence in the present exemplary embodiment.

FIG. 48 is an explanatory view (1) of a communication protocol of a life activity detection signal with event information.

FIG. 49 is an explanatory view (2) of a communication protocol of a life activity detection signal with event information.

FIG. 50 is an explanatory view (1) of a communication protocol of life activity information with event information.

FIG. 51 is an explanatory view (2) of a communication protocol of life activity information with event information.

FIG. 52 is an explanatory view of an example of detecting a signal transmission pathway through which pain of the tip of a foot reaches the brain.

FIG. 53 is an explanatory view of an example of detecting a signal transmission pathway through which pain reaches the brain of a patient of spinal canal stenosis.

FIG. 54 is an explanatory view of an applied embodiment in which membrane potential changing and oxygen concentration change in blood are detected at the same time.

FIG. 55 is an explanatory view of a light emitting pattern of illuminating light for life activity detection in detection of life activity.

FIG. 56 is an explanatory view of an appropriate wavelength range for detection/control of life activity in the present exemplary embodiment/applied embodiment.

FIG. 57 illustrates interpretation of quantum chemistry regarding catalysis by enzyme.

FIG. 58 is an explanatory view of a mechanism for ATP hydrolysis by Myosin ATPase.

FIG. 59 is an explanatory view of a reason why an absorption band wavelength varies depending on to which a residue of Lysine is hydrogen bonded.

FIG. 60 is an explanatory view of a relationship between a hydrogen-bonding partner and an anharmonic vibration potential property.

FIG. 61 is an explanatory view of an exemplary detection signal related to a movement of a mimetic muscle.

FIG. 62 is an explanatory view of a relationship between a location of a mimetic muscle which contracts on a face and a facial expression.

FIG. 63 is an explanatory view of a positional relationship between a detectable range and a detection target by a detecting section for life activity.

FIG. 64 is an explanatory view of a measuring method 1 of life activity in the applied embodiment.

FIG. 65 is an explanatory view of a measuring method 2 of life activity in the applied embodiment.

FIG. 66 is an explanatory view of a configuration in a life activity control device in the present exemplary embodiment.

FIG. 67 is an explanatory view of an applied embodiment of the life activity control device.

FIG. 68 is an explanatory view of a gating mechanism of a voltage-gated ion channel and a control method from its outside.

FIG. 69 is an explanatory view of a state of an intracellular life activity chain.

FIG. 70 is a mechanism model in which a memory action and an obliteration action occur in a pyramidal cell.

FIG. 71 is an explanatory view of long-term memory formation and a control method related to long-term obliteration.

FIG. 72 is an explanatory view of a mechanism model of a phosphorylation process occurring in an active site in PKA.

DESCRIPTION OF THE PREFERRED EMBODIMENTS

A table of contents which provides an outline of the embodiments described below is listed before the embodiment descriptions. In addition, the embodiments described later relate to a measuring method of life activity, a measuring device of life activity, a transmission method of life activity detection signal, or a service based on life action information.

1] Outline of Activity of Nervous System
  1.1) Signal transmission pathway in nervous system of animals
  1.2) Signal transmission in axon
  1.3) Signal occurrence/transmission mechanism in nervous system and membrane potential changing in action potential 2] Action Potential Model regarding Neuron
  2.1) Structural peculiarity of neuronal membrane based on background information
  2.2) Electromagnetical analysis regarding action potential
  2.3) Charging model on both surfaces of neuronal membrane in case of action and resting potentials
  2.4) Ion concentrations in cytoplasm and extracellular fluid which are described in background information
  2.5) Molecular structures of Phospholipids and ion attachment locations in Phospholipids
  2.6) Probability comparison between ion attachment and detachment phenomena in extracellular fluid side regarding action potential 3] Infrared Spectral Characteristics Estimation based on Action Potential Model
  3.1) Calculation method with quantum chemistry simulation program
  3.2) Attachment model of $Cl^-$ ion to $-N^+(CH_3)_3$ group and wave number estimation of corresponding absorption band
  3.3) Detachment model of $Na^+$ ion from Ganglioside type D1a and wave number estimation of corresponding absorption band
  3.4) Attachment model of $Na^+$ ion to Carboxyl group of Phosphatidylserine and wave number estimation of corresponding absorption band
  3.5) Infrared Spectrum changing based on attachment model of $K^+$ ion to Phospholipid
  3.6) Infrared Spectrum changing based on another attachment model of ion to neuronal membrane
  3.7) Overview of infrared spectrum changing based on action potential Model 4] Near Infrared Spectral Characteristics Estimation based on Action Potential Model
  4.1) Requirement for establishing original calculation method regarding Near Infrared Spectral Characteristics
  4.2) Describing outline of original calculation method based on anharmonic vibrations
  4.3) Schrodinger equation indicating particular normal vibration
  4.4) Formulae relating to wave functions of harmonic vibrations
  4.5) Obtaining Einstein's transition probability
  4.6) Substituting estimation results from quantum chemistry simulation program
    4.6.1) Numerical analysis method with quantum chemistry simulation program
    4.6.2) Estimating anharmonic potential
    4.6.3) Estimating dipole moment characteristics
    4.6.4) Light absorption wavelengths and light absorbances of corresponding absorption bands
  4.7) Discussion about detectable range in present exemplary embodiment 5] NMR Spectral Characteristics Estimation based on Action Potential Model
  5.1) NMR Spectral Characteristic changing and estimated chemical shift values regarding action potential
    5.1.1) Prospect for changing NMR Spectral Characteristics regarding action potential
    5.1.2) Calculation method with another quantum chemistry simulation program
    5.1.3) Estimating chemical shift values in NMR Spectral Characteristics
  5.2) Discussion about measurable range in present exemplary embodiment 6] Technical Features of Detection/Control Method of Life Activity and Measuring Method of Life Activity in Present Exemplary Embodiment
  6.1) Content of life activity to be measured and features of detection/control method of life activity
    6.1.1) Life activity in various meanings to be taken as detection target in present exemplary embodiment
    6.1.2) Various detection methods to be applied to detection method of life activity in present exemplary embodiment
    6.1.3) Life activity in life object from surface area to very deep area to be taken as detection/control target
    6.1.4) Generation of life activity information from detection signal
    6.1.5) Complicated activity calculable from relatively simple detection signal using association between life activities
  6.2) Alignment and preservation method of detected/controlled point for life activity
    6.2.1) Method for setting detection position by detecting cross-sectional image including detected/controlled point 6.2.2) Method for estimating and setting position of detected point by detecting specific position on life-object surface 6.3) Photoelectric conversion method for detection of life activity 6.3.1) Utilization of confocal system 6.3.2) Extraction of spatial variations and time dependent variations by imaging optical system 6.3.3) Method for detecting high-speed change of Nuclear Magnetic Resonance property 6.3.4) Method for reducing interference from other adjacent life activity detection systems 6.4) Life activity detection circuit 6.4.1) Configuration of detecting section for life activity.

6.4.2) Configuration of life activity detection circuit 6.4.3) Configuration of transmitting section of life activity detection signal 6.5) Measuring method of life activity 6.5.1) Overview of information obtained from life activity detection signal 6.5.2) Content of life activity information 6.5.3) Interpretation method of life activity 6.5.3.1) Feature of life activity interpretation 6.5.3.2) Exemplary construction of data base related to interpretation of life activity 6.5.3.3) Data content stored in data base 6.5.3.4) Exemplary Embodiment regarding interpretation of life activity and feedback to data base 6.5.3.5) Applied Embodiment of interpretation of life activity using life activity detection signal in data base 6.5.4) Other measuring methods of life activity 7] Device or System with Detecting Section for Life Activity Incorporated therein 7.1) Packaged device with detecting section for life activity incorporated therein 7.1.1) Feature of packaged device with detecting section for life activity incorporated therein 7.1.2) Exemplary Embodiment of packaged device with combination of detecting section for life activity and driving section 7.1.3) Exemplary Embodiment of packaged device with combination of detecting section for life activity and information providing section 7.1.4) Exemplary Embodiment of selection of optimum process or operation method based on life activity information 7.2) Network system and business model using detecting section for life activity.

7.2.1) Outline of whole network system using detecting section for life activity 7.2.2) User-side front end 7.2.2.1) Role of user-side front end 7.2.2.2) Detailed function of user-side front end 7.2.2.3) Exemplary Embodiment of integration of life detecting division and applied embodiment using the same 7.2.3) Mind communication provider 7.2.3.1) Role of mind communication provider 7.2.3.2) Mechanism to prevail Internet service using life activity information 7.2.3.3) Business model of mind communication provider 7.2.4) Mind service distributor 7.2.4.1) Role of mind service distributor 7.2.4.2) Business model of mind service distributor 7.2.4.3) Exemplary service of mind service distributor 8] Communicating Protocols for Life Activity Detection Signal and Life Activity Information 8.1) Feature of common parts of communication protocols for life activity detection signal and life activity information 8.2) Communication protocol for life activity detection signal 8.3) Communication protocol for life activity information 8.4) Exemplary new command used for Web API 9] Applied Embodiment using Detection or Measurement of Biosis Activity 9.1) Feature of Applied Embodiment of biosis activity measurement and new feasible unique function 9.2) Expansion of Applied Embodiment using measurement of biosis activity 9.3) Applied Embodiment of detection of life activity to medical diagnosis 9.3.1) Exemplary search of neural transmission pathway in life object 9.3.2) Exemplary diagnosis with combination of detection of membrane potential changing and detection of oxygen concentration change in blood 10] Abuse Prevention Method using Measurement Technique of Biosis Activity 10.1) Notes for use of objective technique of present exemplary embodiment 10.2) Encryption processing method of transfer signal/information 10.3) Other abuse prevention methods 11] Other Applied Embodiments regarding Detection/Control of Life Activity 11.1) Other life activity phenomena of which contracted and relaxed states of skeletal muscle are to be detected/controlled 11.2) Basic thought regarding biocatalyst action by enzyme 11.3) Movement mechanism of Myosin ATPase 11.4) Characteristics of detection/control of life activity 11.5) Features of detection method of life activity 12] Control Method of Life Activity 12.1) Outline of basic control method of life activity 12.2) Outline of basic principle used for control of life activity 12.3) Molecular structure of ion channel and gating control method 12.4) Characteristic of control of life activity 12.5) Suppression control of neuronal action potential 13] Detection and Control of Intracellular Life Activity 13.1) General view of intracellular life activity 13.2) Thought of control method for contradicting life activities 13.3) Memory and obliteration mechanism models in pyramidal cell 13.4) Reaction process of Phosphoenzyme (kinase)

13.5) Reaction process of Calcineurin 13.6) Characteristics of detection and control of intracellular life activity 1] Overview of Activity of Nervous System 1.1) Signal Transmission Pathway in Nervous System of Animals Initially explained is an overview of a signal transmission pathway in a nervous system of an animal with reference to FIG. 1. FIG. 1 is based on the content of F. H. Netter: The Netter Collection of Medical Illustrations Vol. 1 Nervous System, Part 1, Anatomy and Physiology (Elsevier, Inc., 2003) Section 8.

In general, a neuron is constituted by neuron cell bodies 1 (see black circles), axons 2 (see bold lines), and numerous boutons (synaptic knobs) 3, and a signal is transmitted via the axon 2 in the neuron.

As an input section of information from an outside thereof, FIG. 1 shows only a signal detection area (ending) 4 of a sensory neuron, but this area may be replaced with another detection area, such as a visual sense, an auditory sense, a gustatory sense, or a sense of smell. Further, the nervous system leads to contraction of a muscle cell 6 via a neuromuscular junction 5, conclusively.

The nervous system has a large characteristic in that "a signal transmission pathway constitutes a parallel circuit."

A reflex pathway layer 9 is formed in a lower layer of this parallel circuit, so as to perform a process of the most primitive reflection reaction such as a spinal reflex. In an upper layer thereof, a nervous relay pathway layer 8 including a thalamus, a cerebellum or a reticular formation is formed. This nervous relay pathway layer 8 not only relays signal transmission between a cerebral cortex and the input section (the signal detection area (ending) 4 of the sensory neuron and the like) of information from the outside or the muscle cell 6, but also performs simple information processing inside the nervous relay pathway layer 8. Advanced information processing is performed by a central nervous system layer (cerebral cortex layer) 7.

As such, the signal transmission pathway constitutes a parallel circuit, thereby resulting in that relatively easy information processing can be performed without intention while the central nervous system layer (cerebral cortex layer) 7 does not "realize" it. In addition, if activities in the reflex pathway layer 9 including the neuromuscular junction 5 are observed, it is possible to estimate activities of the upper nervous relay pathway layer 8 and the central nervous system layer 7 to some extent.

1.2) Signal Transmission in Axon

The following describes a mechanism of how a signal is transmitted in the axon, with reference to FIG. 2.

The axon 2 is surrounded by a myelin sheath 12, so that an axoplasm 14 in the axon 2 is isolated from an outside extracellular fluid 13. $Na^+$ ions and $Cl^-$ ions are abundantly distributed over the extracellular fluid 13. Further, nodes 15 of Ranvier where the thickness of the myelin sheath 12 becomes thin are formed partially along a direction where the axon 2 extends, and voltage-gated $Na^+$ ion channels 11 are placed at the nodes 15 of Ranvier.

During a normal resting term (when no signal is transmitted in the axon 2), as shown on the right side of FIG. 2, a cover (gate) of a voltage-gated $Na^+$ ion channel 11 is closed, so that inflow of $Na^+$ ions into the axoplasm 14 from the extracellular fluid 13 is prevented. At this time, positive electric charges gather on an outside layer (facing the extracellular fluid 13) of the myelin sheath 12, while negative electric charges gather on an inside layer (facing the axoplasm 14) of the myelin sheath 12. As a result, the axoplasm 14 has a "negative potential."

Due to an electrostatic force of such positive and negative charges gathering on the surfaces of the myelin sheath 12, a positive electric charge section of the voltage-gated $Na^+$ ion channel 11 (a part corresponding to a circled "+" mark in FIG. 2) is pushed toward the axoplasm 14 during the resting term. In the meantime, it is considered that a very weak force toward a direction of the extracellular fluid 13 works at this positive electric charge section.

When the potential in the axoplasm 14 rises to a positive potential on the left side of FIG. 2 during signal transmission in the axon 2 and thereby amounts of positive and negative charges gathering on the surfaces of the myelin sheath 12 are decreased, the above weak force works and moves the positive electric charge section of the voltage-gated $Na^+$ ion channel 11 toward a direction of the extracellular fluid 13. This accordingly causes the cover (gate) to be opened, thereby initiating the inflow of $Na^+$ ions into the axoplasm 14 from the extracellular fluid 13. As a result, the negative electric charges gather on the outside layer (facing the extracellular fluid 13) of the myelin sheath 12 and the positive electric charges gather on the inside layer (facing the axoplasm 14) of the myelin sheath 12, thereby temporarily changing the axoplasm 14 into the "positive potential." As such, an area to become a positive potential temporarily in the axoplasm 14 moves along a signal transmission direction 16 in the axon, thereby transmitting the signal through the axon.

1.3) Signal Occurrence/Transmission Mechanism in Nervous System and Membrane Potential Changing in Action Potential Section 1.3 explains about a signal generation mechanism in the nervous system illustrated in FIG. 1 and a signal transmission mechanism between neurons. Further, as a part of the explanation, a changing state of a neuronal membrane voltage during an action potential is explained.

The signal detection area (ending) 4 of the sensory neuron in FIG. 1 detects pain, temperature, mediating tactile, pressure, kinesthetic sensation or the like. As illustrated in FIG. 3, a membrane potential 20 of the ending 4 of the sensory neuron during a resting term 25 before detecting such a variety of sensations is a resting membrane potential 21, which is a negative potential. According to Masahiko Watanabe: Nou Shinkei Kagaku Nyumon Koza Gekan (Yodosha, 2002), p. 112, pH decreases when an inflammation or ischemia to cause pain occurs, and at least either one of $Na^+$ ions and $Ca^+$ ions flow into the cytoplasm due to an action of a proton-activated cation channel.

At this time, "depolarization" occurs in the ending 4 of the sensory neuron, so that the membrane potential 20 rises to a depolarization potential 22. This causes the cover (gate) of the voltage-gated $Na^+$ ion channel 11 (see FIG. 2) distributed in a cell membrane of the signal detection area (ending) 4 of the sensory neuron to be opened, and a large amount of $Na^+$ ions existing in the extracellular fluid 13 flow into the cytoplasm. As a result, the membrane potential 20 rises to an action potential 23, which is a positive potential, as shown by membrane potential changing 26 of a neuron.

The action potential 23 occurring in the signal detection area (ending) 4 of the sensory neuron is transmitted as a signal through the axon 2 according to the mechanism as described in section 1.2.

When this signal is transmitted to the numerous bouton (synaptic knob) 3, a transmitter substance is released to a synaptic cleft between this numerous bouton (synaptic knob) 3 and a neuron cell body 1 at a rear side of the numerous bouton 3 or a dendrite (not shown). Then, this transmitter substance bonds to the neuron cell body 1 or a ligand-gated $Na^+$ ion channel distributed over a surface of the dendrite.

A neuronal membrane potential 20 of a neuron on the surface of this rear-side neuron cell body 1 is a resting membrane potential 21 during a resting term 25 as shown in FIG. 3. This resting membrane potential 21 is generally kept at about −60 mV to −80 mV. When the transmitter substance bonds to the neuron cell body 1 or a ligand-gated $Na^+$ ion channel, a gate of the ligand-gated $Na^+$ ion channel is opened, so that $Na^+$ ions in the extracellular fluid 13 flow into neuronal cytoplasm. This results in that the membrane potential 20 rises to the depolarization potential 22, which is about −40 mV.

When the membrane potential 20 rises to the depolarization potential 22 as such, a cover (gate) of a voltage-gated $Na^+$ ion channel 11 is opened according to the mechanism as described in section 1.2 and a large amount of $Na^+$ ions flow into the axoplasm 14, thereby causing an action potential phenomenon. The membrane potential 20 during the action potential rises to an action potential 23 in a range from about +20 mV to +40 mVas shown in the membrane potential changing 26 of a neuron.

When the membrane potential 20 reaches the action potential 23 at once, the cover (gate) of the voltage-gated $Na^+$ ion channel 11 is closed, and the membrane potential 20 falls to the resting membrane potential 21.

A term 24 of this nerve impulse continues from about 0.5 ms to 2 ms in most cases. Although the term 24 of nerve impulse varies to some extent depending on neuron types, the term 24 of nerve impulse is 4 ms or less in most cases. Accordingly, it may be said that the term 24 of nerve impulse in neurons is generally in a range of 0.5 to 4 ms.

A detection signal occurring in the signal detection area (ending) 4 of the sensory neuron reaches a neuromuscular junction 5 via the complicated pathways as shown in FIG. 1 in most cases. It is said that a resting membrane potential 21 indicating a membrane potential 20 of a muscle cell 6 during the resting term 25 is nearly −80 mV. When the neuromuscular junction 5 is activated, Acetylcholine is often released as a transmitter substance between this neuromuscular junction 5 and the muscle cell 6.

In view of this, when this Acetylcholine bonds to the ligand-gated $Na^+$ ion channel and a ligand-gated $K^+$ ion channel distributed over surfaces of a muscular membrane of the muscle cell 6, their gates are opened, thereby improving muscular membrane transmitting properties for $Na^+$ ions and the $K^+$ ions. As a result, the membrane potential 20 rises to the depolarization potential 22 as illustrated by a curve of a potential changing 27 of a muscle fiber membrane. It is said that the depolarization potential 22 at this time is nearly −15 mV. When the potential changing 27 of a muscle fiber membrane is close to the depolarization potential 22 as such, $Ca^{2+}$ ions in a sarcoplasmic reticulum inside the muscle cell 6 are released, thereby causing muscle contraction.

2] Action Potential Model regarding Neuron

First of all, sections 2.1 and 2.4 describe well-known information regarding the structure of a neuronal membrane and environmental conditions thereof. Subsequently, section 2.2 describes an electromagnetical analysis regarding a widely known part of action potential phenomenon. Then sections 2.3 and 2.5 describe a neuronal action potential model which is originally proposed.

This neuronal action potential model is based on a concept of charging model proposed in section 2.3.

2.1) Structural Peculiarity of Neuronal Membrane Based on Background Information First of all, structural peculiarities of a neuronal membrane which are well-known are described. The neuron has a common membrane which can be included in another kind of cell except the neuron, and the common membrane comprises: Phospholipids; Glycolipids; Cholesterol; and Membrane proteins including ion channels.

Lipid bilayer, which comprises the Phospholipids, the Glycolipids, and the Cholesterol, is configured to be split into an outside layer facing an extracellular fluid and an inside layer facing a cytoplasm. The outside layer includes particular molecules which belong to the Phospholipids, and the particular molecules are rarely included in the inside layer. FIG. 4 (a) shows what kind of molecules belonging to the Phospholipids or the Glycolipids are located in the outside and inside layers. The outside layer principally comprises Phosphatidylcholine PCLN, Sphingomyelin SMLN, and the Glycolipids, and the inside layer principally comprises Phosphatidylserine PSRN, Phosphatidylethanolamine PEAM, and Phosphatidylinositol PINT (a content by percentage of PINT is relatively small). According to FIG. 4, the double lines indicate Fatty acid parts which are packed into the Lipid bilayer.

Ganglioside belongs to the Glycolipids and particularly has a negative electric charge, and a content of it is biggest in any kinds of molecules belonging to the Glycolipids. It is said that total weight of Gangliosides in the neuronal membrane is 5% to 10% of total weight of Lipids. Therefore, the Ganglioside can be seemed to represent the Glycolipids in this embodiment. Moreover, it is reported that a content by percentage of Ganglioside type D1a (GD1a) is biggest in the neuronal membrane of Mammalia (H. Rahmann et. al.: Trends in Glycoscience and Glycotechnology Vol. 10, No. 56(1998) p. 423), so that GD1a can represent all kinds of Gangliosides in this explanation. And another kind of molecule belonging to Glycolipids can fit into descriptions mentioned later.

2.2) Electromagnetical Analysis Regarding Action Potential

A voltage in cytoplasm is kept to be negative in case of a resting membrane potential, and the voltage changes to be positive in case of an action potential. It is known that a plurality of positive electric charges gather on a surface of the inside layer facing the cytoplasm when the action potential occurs (B. Alberts et. al.: Molecular Biology of the Cell 4th edition (Garland Science, 2002) Chapter 10).

Lipid bilayer can be presumed to function as an electrostatic capacity in case of action and resting potentials because an electrical resistance value of Lipid bilayer is very big and is bigger than 100 giga-ohms, and the electrostatic capacity value is approximately 1.0 micro-farad $cm^2$ (M. Sugawara: Bionics vol. 3, No. 7 (2006) p. 38-p. 39 [in Japanese]).

Electrostatic Capacity Theory of Electromagnetics teaches us that a plurality of negative electric charges must gather on a surface of the outside layer facing the extracellular fluid in case of an action potential when a plurality of positive electric charges gather on a surface of the inside layer facing the cytoplasm, and an absolute value of the negative electric charges must be equal to the positive electric charge value.

TABLE 1

Functional groups of Phospholipids relating to ion attachment or detachment in case of action potential.

| | Outside layer of membrane | | Inside layer of membrane | |
|---|---|---|---|---|
| | Negative ion attachment possibility | Positive ion detachment possibility | Positive ion attachment possibility | Negative ion detachment possibility |
| Phosphatidylcholine (PCLN) | $-N^+(CH_3)_3$ | $>PO_2^-$ | | |
| Sphingomyelin (SMLN) | $-N^+(CH_3)_3$ | $>PO_2^-$ | | |
| Ganglioside type D1a (GD1a) | 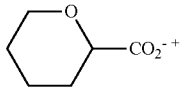 | | | |
| Phosphatidylserine (PSRN) | | | $-NH_3^+$ <br> $-C-CO_2^-$ <br> $>PO_2^-$ | |
| Phosphatidylethanolamine (PEAM) | | | $>PO_2^-$ | $-NH_3^+$ |
| Phosphatidylinositol (PINT) | | | $>PO_2^-$ | |

2.3) Charging Model on Both Surfaces of Neuronal Membrane in Case of Action and Resting Potentials Section 2.3 describes an originally proposed charging model on both surfaces of the neuronal membrane in case of action and resting potentials, and this charging model was thought out by applying the electromagnetical analysis mentioned in section 2.2 to the membrane structure explained in section 2.1.

Table 1 lists functional groups of Phospholipids which a plurality of ions can be attached to or detached from when the action potential occurs, and Table 1 shows that the outside layer principally comprises PCLN, SMLN, and GD1a and the inside layer principally comprises PSRN, PEAM, and PINT, as described in section 2.1.

PSRN under water tends to have "−1" charges because PSRN comprises two functional groups $>PO_2^-$ & $-CO_2^-$ which respectively tend to have negative electric charges and one functional group $-NH_3^+$ which tends to have a positive electric charge.

PINT under water also tends to have "−1" charges because PINT comprises only one functional group $>PO_2^-$ which tends to have a negative electric charge. According to FIG. 4 (a), the "−1" charges generate a negative charge domain on the surface of the neuronal membrane, and "Minus mark" represents this negative charge domain.

Electrostatic attraction makes positive electric charges gather on the outside layer of Lipid bilayer when the negative charge domains are generated on the inside layer in case of a resting membrane potential. Therefore, positive charge domains, which are represented by "Plus marks" in FIG. 4(a), may be generated on hydrophilic head parts of PCLNs and SMLNs.

In case of an action potential, a plurality of negative charge domains may be generated on not only the hydrophilic head parts of PCLNs and SMLNs but also GD1a, when positive electric charges gather on the inside layer and a plurality of positive charge domains are generated on hydrophilic head parts of PEAMs and PSRNs (FIG. 4 (b)).

In conclusion of this section, it is presumed that a reversible formation of positive and negative charge domains on both surfaces of membrane changes the neuronal membrane voltage.

2.4) Ion Concentrations in Cytoplasm and Extracellular Fluid which are Described in Background Information

TABLE 2

Ion concentrations in cytoplasm and extracellular fluid.

| Ion symbol | Extracellular fluid (milli-mol/l) | Cytoplasm (milli-mol/l) |
|---|---|---|
| $Na^+$ | 145 | 5-15 |
| $K^+$ | 5 | 140 |
| $H^+$ | $4 \times 10^{-5}$ (pH 7.4) | $7 \times 10^{-5}$ (pH 7.2) |
| $Cl^-$ | 110 | 5~15 |

This section discusses concrete carriers which generate the reversible formation of positive and negative charge domains.

As shown in Table 2, Alberts teaches the ion concentrations in a cytoplasm and an extracellular fluid of a general Mammalia (B. Alberts et. al.: Molecular Biology of the Cell 4th edition (Garland Science, 2002) Chapter 11, Table 11-1). The majority ions are $Na^+$ and $Cl^-$ in the extracellular fluid and K+ in the cytoplasm. And it is known that $Na^+$ ions flow from the extracellular portion into the cytoplasm when the action potential occurs. Therefore, it can be presumed that the majority carriers which generate the reversible formation of positive and negative charge domains are $Na^+$ or $Cl^-$ ion attachments or detachments on the outside layer and $K^+$ or $Na^+$ ion attachments or detachments on the inside layer.

According to Table 2, it seems that $H^+$ ion (Hydronium ion) and $OH^-$ ion have less influence on the action potential because concentrations of these ions are relatively small.

2.5) Molecular Structures of Phospholipids and Ion Attachment Locations in Phospholipids This section discusses detailed structures and locations of the positive and negative charge domains on both surfaces of the neuronal membrane by combining the charging model considered in section 2.3 with the carrier model described in section 2.4.

When the resting membrane potential continues and the negative charge domains are generated on the inside layer facing the cytoplasm, $Na^+$ ion may be attracted to the surface of outside layer and ionically bonds to $>PO_2^-$ groups to locally form a neutral salt $>PO_2^-Na^+$ in PCLN or SMLN. According to Table 1, both PCLN and SMLN under water comprise functional groups of $>PO_2^-$ and $—N^+(CH_3)_3$. Therefore, when PCLN or SMLN has the neutral part $>PO_2^-Na^+$, the remaining positive group $—N^+(CH_3)_3$ can generate a positive charge domain in PCLN or SMLN.

Table 1 also shows that GD1a under water hardly forms a positive charge domain because it comprises no positive group. GD1 as comprise only functional groups $—CO_2^-$ which usually have negative electric charges. It is considered that a plurality of GD1 as include neutral salts $—CO_2^-Na^+$ and generate no charge domain when the resting membrane potential continues.

According to this originally proposed charging model, it is presumed that the $Na^+$ or $K^+$ ion may ionically bond to the $>PO_2^-$ group of one of PEAM, PSRN, and PINT or to $—CO_2^-$ group of PSRN in case of an action potential. Furthermore, when the $Na^+$ or $K^+$ ion newly forms a neutral salt, the remaining functional group $—NH_3^+$, which usually has "+1" charge under water, generates a positive charge domain on a hydrophilic head part of PEAM or PSRN.

When the positive charge domains are generated on the inside layer facing the cytoplasm, an electrostatic repulsion may make $Na^+$ ions be detached from neutral salts $>PO_2^-Na^+$ of PCLNs and SMLNs and $-CO_2^-Na^+$ of GD1 as on the outside layer. This $Na^+$ ion detachment may newly generates a negative charge domain on GD1a because the $—CO_2^-$ group which has "-1" charges remains in GD1a.

Moreover, an electrostatic attraction of the positive charge domains on the inside layer attracts $Cl^-$ ions to the surface of the outside layer, and these $Cl^-$ ions may be combined with $—N^+(CH_3)_3$ groups of PCLNs or SMLNs to form hydrogen (or ionic) bonds. These newly created neutral salts $—N^+(CH_3)_3Cl^-$ may generate negative charge domains on hydrophilic head parts of PCLNs or SMLNs in case of an action potential when PCLNs or SMLNs have both the neutral salts $—N^+(CH_3)_3Cl^-$ and the negative groups $>PO_2^-$ from which $Na^+$ ions were detached.

This charging model can be applied not only to the action potential of neuron mentioned above but also to a signal transmission through axon 5 of neuron and a somatic neuromuscular transmission passing through a neuromuscular junction 5, as shown FIG. 1.

FIG. 2 shows that the axon 5 is covered with a myelin sheath 12 which is extremely thicker than the neuronal membrane. Electrostatic Capacity Theory of Electromagnetics teaches us that an electrostatic capacity value is inversely proportional to the thickness of the myelin sheath 12, so that the density of the charged domains on a surface of myelin sheath 12 falls down. Therefore, a life activity detecting method should be devised when the signal transmission through the axon 5 of a neuron is detected. This life activity detecting method will be explained later.

Netter (F. H. Netter: The Netter Collection of Medical Illustrations Vol. 1 Nervous System Part 1 Anatomy and Physiology (Elsevier, Inc., 1983) p. 162) teaches us that the membrane potential of a muscular membrane changes when a somatic neuromuscular signal passes through the neuromuscular junction 5, so that the muscular membrane potential can be detected with this embodiment.

2.6) Probability Comparison Between Ion Attachment and Detachment Phenomena in Extracellular Fluid Side Regarding Action Potential The discussion result mentioned in section 2.5 indicates that the following phenomena may occur on the surface of the outside layer in case of an action potential:

A] $Na^+$ ion detachment from $—CO_2^-Na^+$ of GD1a;
B] $Cl^-$ ion attachment to $—N^+(CH^3)^3$ of PCLN or SMLN to form $—N^+(CH_3)_3Cl^-$.

It is considered that a probability of $Cl^-$ ion attachment is relatively bigger than a probability of $Na^+$ ion detachment because of the following reasons;

1. $Na^+$ ion detachment from $—CO_2^-Na^+$ hardly have enough response speed, and it is hardly adapted to a rapid voltage transition at a start timing of an action potential;

The bonding strength of an ionic bond forming the salt $—CO_2^-Na^+$ is bigger than the bonding strength of a hydrogen bond forming $—N^+(CH_3)_3Cl^-$. Therefore, it is predicted that $Na^+$ ion detachment does not quickly occur relatively.

2. A probability of $Na^+$ ion detachment substantially decreases because $Na^+$ ion concentration is high in an extracellular fluid;

3. Cage effect under water reduces an influence of $Na^+$ ion detachment;

Cage effect under water (W. J. Moore: Physical Chemistry 4th Edition (Prentice-Hall, Inc., 1972) Chapter 9, Section 38) may make the $Na^+$ ion stay near the $—CO_2^-$ group for a long time after the detachment (from $>PO_2^-Na^+$ of PCLN or SMLN). And because this $Na^+$ ion staying corresponds to be electrically neutral and substantially generates no negative charge domain, this $Na^+$ ion staying makes the $Cl^-$ ion be attracted to the surface of outside layer. Therefore, $Cl^-$ ion attachment tends to occur before the $Na^+$ ion detached goes away from the outside layer.

4. The $Cl^-$ ion is easily attached to the $—N^+(CH_3)_3$ group because there are plenty of $—N^+(CH_3)_3$ groups in case of a resting membrane potential;

In case of resting membrane potential, the surface of outside layer must have plenty of positive charge domains corresponding to $—N^+(CH_3)_3$ groups of PCLNs or SMLNs (Table 1) which will make $Cl^+$ ion attachment in case of an action potential.

5. The $—N^+(CH_3)_3$ group increases a probability of $Cl^-$ ion attachment because 9 hydrogen atoms of the $—N^+(CH_3)_3$ group can similarly bond to the $Cl^-$ ion;

6. A high density of the $Cl^-$ ion in extracellular fluid (Table 2) increases a probability of $Cl^-$ ion attachment.

3] Infrared Spectral Characteristics Estimation Based on Action Potential Model

Chapter 3 describes Infrared Spectral Characteristics based on the Action Potential Model proposed in Chapter 2, and the Infrared Spectral Characteristics result from computer simulations of quantum chemistry simulation program.

3.1) Calculation Method with Quantum Chemistry Simulation Program

In Chapters 3 and 4, an author used "SCIGRESS MO Compact Version 1 Pro" for a quantum chemistry simulation program. This quantum chemistry simulation program is sold by Fujitsu Corporation, and "SCIGRESS" is a registered trademark. This quantum chemistry simulation program uses a semiempirical molecular orbital method.

This calculation method comprises two calculation steps to keep high calculation accuracy. A first calculation step is to optimize a molecular structure, and a second calculation step is to analyze vibration modes.

Some keywords of optimization are "PM3 EF PRECISE EPS=78.4 GNORM=0.00001 LET DDMIN=0.00001 PULAY SAFE SHIFT=1.00", wherein "PM3 EPS=78.4" means the optimization under water, "PM3" means an approximation method of Hamiltonian, and other keywords mean a setting calculation accuracy or convergent conditions of calculation. Furthermore, some keywords of vibration analysis are "FORCE ISOTOPE EPS=78.4 PM3", wherein "FORCE ISOTOPE" means the vibration analysis.

Table 3 shows the calculation results, and each calculation result is fully described after this section.

TABLE 3

Calculation results regarding Infrared Spectral Characteristics

| Neutral salt part of functional group | Phospholipid/ Glycolipids including functional groups | Wave number (cm$^{-1}$) | Relative light absorbance (a.u.) |
|---|---|---|---|
| —N$^+$(CH$_3$)$_3$Cl$^-$ | Phosphatidylcholine Sphingomyelin | 2480 | 41.0 |
| [cyclic structure with O and —CO$_2^-$Na$^+$] | Ganglioside type D1a | 276 | 5.24 |
| —C—CO$_2^-$Na$^+$ | Phosphatidylserine | 429 | 20.3 |
| —C—CO$_2^-$K$^+$ | Phosphatidylserine | 118 | 2.89 |

3.2) Attachment model of ion to —N$^+$(CH$_3$)$_3$ group and wave number estimation of corresponding absorption band This section describes a newly generated absorption band estimated by the computer simulation when a Cl$^-$ ion is attached to the —N$^+$(CH$_3$)$_3$ group of PCLN. A molecular structure represented by Chemical formula 1 is used for this computer simulation.

Chemical Formula 1

A molecular structure used for computer simulation when the Cl$^-$ ion is attached to the —N$^+$(CH$_3$)$_3$ group of PCLN

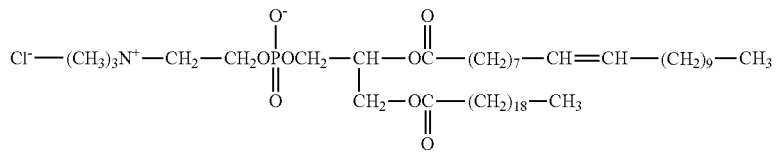

FIG. 5 shows structures optimized by computer simulation. FIG. 5 (a) illustrates a Cl$^-$ ion attachment state, and FIG. 5 (b) illustrates a Cl$^-$ ion detachment state. As shown in FIG. 5 (a), A Cl$^-$ ion is attached to a hydrogen atom located at the most far position from a phosphorus atom, and the Cl$^-$ ion and the hydrogen atom form a hydrogen (or ionic) bond. Of course, the Cl$^-$ ion can be attached to one of 8 hydrogen atoms not located at the most far position from the phosphorus atom.

FIG. 6 shows absorption spectrums estimated by the computer simulation, and resolution is set to 5 cm$^{-1}$. The upper part of FIG. 6 shows a Cl$^-$ ion attachment state, and the lower part of FIG. 6 showing a Cl$^-$ ion detachment state illustrates an absorption spectrum of a single PCLN. A particular absorption band marked with an arrow appears in the upper part of FIG. 6, but it does not appear in the lower part. Moreover, the particular absorption band results from an asymmetrical stretching of C—H—Cl$^-$. According to Table 3, a wave number value of this particular absorption band is 2480 cm$^{-1}$, and a relative light absorbance value of it is 41.0.

Another absorption spectrum is estimated when a Cl$^-$ ion is attached to the —N$^+$(CH$_3$)$_3$ group of SMLN. A result of the another estimation shows that a wave number value of a similar absorption band is 2450 cm$^{-1}$ and that a relative light absorbance value of the similar absorption band is 41.0. Therefore, it is confirmed that the Cl$^-$ ion attachment states of both PCLN and SMLN similarly generate the particular absorption bands.

As shown in the upper part of FIG. 6, the particular absorption band marked with the arrow has a big light absorbance. A reason of this phenomenon should be considered.

Table 4 shows net atomic charges calculated with Mulliken's population analysis (Y. Harada: *Ryoushi kagaku* (Quantum Chemistry) vol. 2 (Shyoukabou, 2007) Chapter 18, Section 18.6, p. 163 [in Japanese]) in case of Cl$^-$ ion attachment and detachment, and each position of the carbon atom C, the hydrogen atom H, and the chlorine ion Cl$^-$ is shown in FIG. 5 (a). And these carbon and hydrogen atoms, and this chlorine ion together contribute to an asymmetrical stretching of C—H—Cl$^-$.

TABLE 4

Net atomic charges in case of Cl$^-$ ion attachment and detachment

| | Carbon atom C | Hydrogen atom H | Chlorine ion Cl$^-$ |
|---|---|---|---|
| Cl$^-$ ion attachment state | −0.434 | 0.230 | −0.920 |
| Cl$^-$ ion detachment state | −0.251 | 0.109 | −1.00 |

Table 4 shows that the net charge of a carbon atom C dynamically decreases and the net charge of a hydrogen atom H obviously increases when the Cl$^-$ ion attaches to the —N$^+$(CH$_3$)$_3$ group. It is considered that molecular orbitals flow to the carbon atom C and are repelled from the hydrogen atom H in case of Cl$^-$ ion attachment, and a reason of these phenomena will be fully described in section 4.6.3. And the variation of net atomic charges makes an electric dipole moment μ increase to raise the light absorbance.

3.3) Detachment Model of Na$^+$ Ion from Ganglioside Type D1a and Wave Number Estimation of Corresponding Absorption Band This section describes a newly generated absorption band estimated by the computer simulation when a Na$^+$ ion is attached to the —CO$_2$ group of GD1a in case of the resting membrane potential.

As shown in FIG. 7, a "part" of GD1a structure is used for the computer simulation because a full molecular structure of GD1a is too complex to be used for the computer simulation.

Some skeletal vibrations of $-CO_2{}^-Na^+$ generate some absorption bands whose wave number values are 260 $cm^{-1}$-291 $cm^{-1}$ and relative light absorbance values are 3.50-7.62. Moreover, Table 3 shows the mean values: the wave number value is 276 $cm^{-1}$ and the relative light absorbance value is 5.24. It is anticipated that another kind of Glycolipid which has a similar structure can newly generate similar absorption bands when a $Na^+$ ion is attached to the $-CO_2$ group in case of the resting membrane potential.

3.4) Attachment Model of $Na^+$ Ion to Carboxyl Group of Phosphatidylserine and Wave Number Estimation of Corresponding Absorption Band This section describes a newly generated absorption band estimated by the computer simulation when a $Na^+$ ion is attached to the $-CO_2{}^-$ group of PSRN in case of the action potential.

Table 3 shows that a skeletal vibration of $-C-CO_2{}^-Na^+$ generates a new absorption band whose wave number value is 429 $cm^{-1}$ and relative light absorbance value is 20.3.

This section describes different values regarding the absorption band from those described in section 3.3 even though $Na^+$ ion attached PSRN and GD1a have the same structure of $-CO_2{}^-Na^+$, because a part of molecular structure directly bonding to $-CO_2{}^-$ group of PSRN is different from a corresponding structure directly bonding to $-CO_2{}^-$ group of GD1a.

According to the computer simulation, an optimized molecular structure of $Na^+$ ion attached PSRN provides a specific $Na^+$ ion position indicating that an interatomic distance between $Na^+$ ion and an oxygen atom of the $-CO_2{}^-$ group is similar to an interatomic distance between the $Na^+$ ion and another oxygen atom of the $-CO_2{}^-$ group.

3.5) Infrared Spectrum Changing Based on Attachment Model of $K^+$ Ion to Phospholipid This section describes generated and suppressed absorption bands estimated by the computer simulation when a $K^+$ ion is attached to the $-CO_2{}^-$ group of PSRN in case of the action potential. A molecular structure represented by Chemical formula 2 is used for this computer simulation.

Chemical Formula 2

A molecular structure used for computer simulation when the $K^+$ ion is attached to $-CO_2{}^-$ group of PSRN

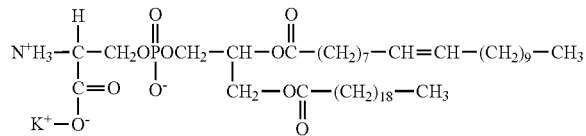

According to the computer simulation, an optimized molecular structure of $K^+$ ion attached PSRN indicates that the $K^+$ ion is located near only one oxygen atom of the $-CO_2{}^-$ group, and this location is different from a location described in section 3.4. It seems that this difference of the ionic location results from the $K^+$ ionic radius which is bigger than the $Na^+$ ionic radius.

Table 3 shows that a skeletal vibration of $-C-CO_2{}^-K^+$ generates a new absorption band whose wave number value is 118 $cm^{-1}$ and a relative light absorbance value is 2.89 which is very smaller than the corresponding value regarding $Na^+$ ion 20.3. It seems that this small value 2.89 results from the $K^+$ ionic radius which is bigger than the $Na^+$ ionic radius. Moreover, a computer simulation generates no new absorption band when the $K^+$ ion is attached to the $>PO_2{}^-$ group of PSRN shown in Table 1.

According to the computer simulation, $K^+$ ion attachment to the $-CO_2{}^-$ group has a distinguishing characteristic of absorption spectrum which suppresses a symmetrical stretching of Carboxyl group and drastically reduces a corresponding relative light absorbance value from 98.0 to 15.2, and a wave number value of the symmetrical stretching is 1570 $cm^{-1}$. It is considered that the $K^+$ ion located near one oxygen atom of the $-CO_2{}^-$ group may strongly obstruct the symmetrical stretching of the Carboxyl group.

3.6) Infrared Spectrum Changing Based on Another Attachment Model of Ion to Neuronal Membrane Table 1 and section 2.5 indicate that the $Na^+$ ion may be attached to the $>PO_2{}^-$ group on the inside layer when the action potential occurs. But all result of computer simulation does not provide any obvious absorption band when the $Na^+$ ion is attached to the $>PO_2{}^-$ group of all kind of Phospholipid.

Moreover, the $Na^+$ ion attachment to the $>PO_2{}^-$ group on the inside layer and the $Na^+$ ion detachment from the $>PO_2{}^-Na^+$ on the outside layer may simultaneously occur in case of an action potential, and opposite phenomena may occur in case of a resting membrane potential. Therefore, even if the $Na^+$ ion attachment to the $>PO_2{}^-$ group generates an obvious absorption band, a light absorbance value of this absorption band hardly vary to be used for detecting the action potential.

3.7) Overview of Infrared Spectrum Changing Based on Action Potential Model

According to Table 3 and section 3.5, it is predicted that the action potential newly generates absorption bands whose wave numbers are 2480 $cm^{-1}$, 429 $cm^{-1}$, and 118 $cm^{-1}$, and it is also predicted that the action potential reduces light absorbances of absorption bands whose wave numbers are 1570 $cm^{-1}$ and 276 $cm^{-1}$.

4] Near Infrared Spectral Characteristics Estimation Based on Action Potential Model 4.1) Requirement for Establishing Original Calculation Method Regarding Near Infrared Spectral Characteristics Infrared Spectral Characteristics can be easily estimated with a quantum chemistry simulation program using a molecular orbital calculation method, because each absorption band in Infrared Spectrum corresponds to each normal vibration which is generated by atomic nucleuses composing one molecule.

Near Infrared light has a wavelength of 800 nm-2500 nm. At the present time, Near Infrared Spectral Characteristics are hardly estimated with the general quantum chemistry simulation program, because absorption bands in Near Infrared Spectrum complicatedly relate to overtones and combinations. As known by an author, only an "Anharmonic command" belonging to vibrational analysis of "Gaussian 09" can estimate wavelength values regarding a first overtone and combinations. But it does not give us information on each light absorbance of each absorption band, and a user has to calculate particular conversions if he wants to know wavelength values regarding second or more overtones.

In the meantime, the Near Infrared light easily passes through life bodies, and it is called "Window of Life". Thereby, dynamical life activities can be detected with no contact and no encroachment by a cheap and simple apparatus which uses the Near Infrared light.

Therefore, a newly proposed original calculation method which can estimate Infrared Spectral Characteristics is required. This calculation method might theoretically predict influences of Infrared Spectral Characteristic based on life activities, and it can be used for quantitatively estimating a detecting sensitivity required to directly detect life activities.

4.2) Describing Outline of Original Calculation Method Based on Anharmonic Vibrations This newly proposed original calculation method regarding Infrared Spectral Characteristics has the following peculiarities:

1. Using a perturbation theory of quantum mechanics, relational formulae for the n-th overtone wavelength and Einstein's transition probability are obtained from Schrodinger equation;
2. Using a quantum chemistry simulation program, an anharmonic potential property and an electric dipole moment property are calculated to substitute these properties for the relational formulae mentioned in 1;
3. Combining the properties with the relational formulae, wavelength values of the n-th overtone and corresponding light absorbances are estimated.

According to FIG. 8, an outline of the calculation method is described below.

Using a quantum chemistry simulation program, a vibrational analysis for a specific macromolecule is executed to find out a particular normal vibration corresponding to a harmonic vibration (S3). In the meantime, The Schrodinger equation including an electro-magnetic field interaction within the specific macromolecule is set (S1). Then, using Born-Oppenheimer approximation, an atomic interaction part is extracted from the Schrodinger equation (S2). After Step 2 and Step 3 executions, a particular atomic interaction regarding the particular normal vibration is selected on the basis of S3 (S4). In this Step 4, all influence of other atomic interactions which were not selected is substituted for the anharmonic potential property.

Total static molecule energy values can be numerically calculated by using the quantum chemistry simulation program (S6). In this Step 6, the molecular structure is repetitively optimized to estimate one of the total static molecule energy values whenever a distance deviation between two atomic nucleuses is set to every incremental value, and the two atomic nucleuses relate to the particular atomic interaction selected in Step 4. In Steps 5-7, a substitution of the total static molecule energy values based on the quantum chemistry simulation program for the anharmonic potential property based on Quantum Mechanics combines the numerical analysis of computer simulations with the relational formulae based on the Quantum Mechanics. After Step 6, the electric dipole moment property is estimated by using the quantum chemistry simulation program (S10), and this electric dipole moment property is used for Step 11 execution.

An equation obtained in Step 4 includes the anharmonic potential property which contains the 4th-order coefficient $\kappa_4$ and 3rd-order coefficient $\kappa_3$ (anharmonic terms), and 2nd-order coefficient $\kappa_2$ (harmonic term). At first, a specific equation in which both $\kappa_4$ and $\kappa_3$ of the equation are set to "0" is solved to obtain wave functions of harmonic vibration, and these wave functions of harmonic vibration correspond to a series of basic functions. Further, using the basic functions and a time independent perturbation theory, the equation including $\kappa_4$ and $\kappa_3$ is solved to obtain wave functions of anharmonic vibration (S5).

In Step 7, wavelength values of absorption band belonging to Near Infrared light are calculated with subtracting a wave function's eigen value of energy from another wave function's eigen value of energy.

Using a time dependent perturbation theory and the wave functions of anharmonic vibration, simultaneous equations regarding a time dependent amplitude variation of each anharmonic vibration mode are formulated (S8). And then the simultaneous equations are solved to obtain relational formulae of Einstein's transition probability (S9), and a light absorbance comparison between absorption bands can be achieved from the Einstein's transition probabilities (S11).

This embodiment shows an estimation method regarding a series of wavelength values and corresponding light absorbances of n-th overtones, and the n-th overtones relate to an anharmonically asymmetrical stretching of covalent and hydrogen bonds C—H—Cl⁻. This estimation method can be extended to estimate deformations or some kinds of combinations between deformations and asymmetrical stretchings if new wave functions are obtained to multiply wave functions indicating asymmetrical stretching by wave functions indicating deformation.

4.3) Schrödinger Equation Indicating Particular Normal Vibration

According to Step 1 of FIG. 8, this section 4.3, at first, describes the Schrodinger equation of a macromolecule which interacts with an electro-magnetic field.

FIG. 9 shows that a charged particle which has an atomic charge value Q is located on the X axis, and $e_x$ represents a unit vector of X axis. When the charged particle moves with a distance of X along the X axis whose direction is against an external electric field $Ee^{-i2\pi vt}$, a generated work is:

Formula 1

$$U = -\int_0^X Q(E \cdot e_x) \exp(-i2\pi vt) dr = -Q(E \cdot X) \exp(-i2\pi vt) \quad (A \cdot 1)$$

In eq. (A•1), (E·X) represents an inner product of E vector and X vector. Moore teaches us that eq. (A•1) represents a perturbation term when the macromolecule interacts with the external electric field (W. J. Moore: Physical Chemistry 4th Edition (Prentice-Hall, Inc., 1972) Chapter 17, Section 4). And eq. (A•1) is allowed not to include the external magnetic field because Harada says that an interaction with external magnetic field is extremely smaller than the external electric field and it is negligible (Y. Harada: *Ryoushi Kagaku* (Quantum Chemistry) vol. 1 (Syoukabou, 2007) Chapter 9, Section 9-9, p. 190 [in Japanese]).

Using eq. (A•1), the following Schrodinger equations are obtained when a macromolecule corresponding to Cl⁻ attached PCLN or SMLN interacts with the external electric field:

Formula 2

$$i\hbar \frac{\partial}{\partial t} \Psi(\ldots, ri, \ldots, \sigma i, \ldots, Ra, \ldots, t) = \{H_{nucl} + H_{el}\} \Psi(\ldots, ri, \ldots, \sigma i, \ldots, Ra, \ldots, t); \quad (A \cdot 2)$$

Formula 3

$$H_{nucl} \equiv -\sum_{a=1}^{N} \frac{\hbar^2}{2Ma} \Delta a + \frac{e_0^2}{4\pi\varepsilon_0} \sum_{a>b}^{N} \frac{Za \cdot Zb}{|Ra - Rb|} - \sum_{a=1}^{N} Qa(E \cdot Ra) \exp(-i2\pi vt); \quad (A \cdot 3)$$

-continued

Formula 4

$$H_{el} \equiv -\sum_{i=1}^{n} \frac{\hbar^2}{2me}\Delta i - \frac{e_0^2}{4\pi\varepsilon_0}\sum_{i,=1}^{n}\sum_{a=1}^{N}\frac{Za}{|ri-Ra|} + H_{eladd}; \text{ and} \quad (A \cdot 4)$$

Formula 5

$$H_{eladd} \equiv \frac{e_0^2}{4\pi\varepsilon_0}\sum_{i>j}^{n}\frac{1}{|ri-rj|} + \sum_{i=1}^{n}e_0(E\cdot ri)\exp(-i2\pi vt). \quad (A \cdot 5)$$

In above formulae, $\hbar$ is [Planck's constant]/$2\pi$, $e_0$ is the quantum of electricity, me is the mass of an electron, N is the total number of atomic nucleuses composing the macromolecule, n is the total number of electrons composing the macromolecule, t is time, Ma is the mass of an a-th atomic nucleus, Ra is the position vector of the a-th atomic nucleus, Qa is a net atomic charge regarding an a-th atomic nucleus which is based on Mulliken's population analysis (Y. Harada: *Ryoushi kagaku* (Quantum Chemistry) vol. 2 (Shyoukabou, 2007) Chapter 18, Section 18-6, p. 163 [in Japanese]), ri is the position vector of an i-th electron, and σi is the spin coordinate of the i-th electron.

And then the Born-Oppenheimer approximation described in Step 2 of FIG. 8 selects atomic interaction factors from eqs. (A•2)-(A•5). The Born-Oppenheimer approximation (Y. Harada: *Ryoushi kagaku* (Quantum Chemistry) vol. 2 (Shyoukabou, 2007) Chapter 16, Section 16-1, p. 33 [in Japanese]) presumes Formula 6

$$\Psi \cong \Psi_{nucl}(R_1, \ldots, Ra, \ldots, R_N, t) \cdot \Psi_{el}(\ldots, ri, \ldots, \sigma i, \ldots, Ra, \ldots, t) \quad (A \cdot 6)$$

Using eq. (A•6), eq. (A•2) can be transformed to

Formula 7

$$\frac{\left\{i\hbar\frac{\partial}{\partial t} - H_{nucl}\right\}\Psi_{nucl}}{\Psi_{nucl}} = -\frac{\left\{i\hbar\frac{\partial}{\partial t} - H_{el}\right\}\Psi_{el}}{\Psi_{el}} = W(R_1, \ldots, R_N, t) \text{ and} \quad (A \cdot 7)$$

Formula 8

$$i\hbar\frac{\partial}{\partial t}\Psi_{nucl}(R_1, \ldots, R_N, t) = \{H_{nucl} + W\}\Psi_{nucl}(R_1, \ldots, R_N, t). \quad (A \cdot 8)$$

Here, $W(R_1, ---, R_N, t)$ includes all influence of optimized molecular orbitals.

As has been described in section 3.2, a Cl⁻ ion and the nearest hydrogen atom form a hydrogen (or ionic) bond when the Cl⁻ ion is attached to the —N⁺(CH$_3$)$_3$ group of PCLN or SMLN in case of an action potential. Further, a combination of C—H—Cl⁻ makes an asymmetrical stretching corresponding to the particular normal vibration in Step 3 of FIG. 8. Relating to Step 3 of FIG. 8, some analytical results of computer simulation taught that this asymmetrical stretching has the following special characteristics regarding a vibration of classical mechanics:

A] The Cl⁻ ion hardly moves and is almost fixed because the Cl⁻ ion is relatively heavy;

B] Movement directions of both carbon and hydrogen atomic nucleuses are substantially parallel to a covalent bond direction between carbon and hydrogen atoms;

C] The hydrogen atomic nucleus widely moves than the carbon atomic nucleus because the hydrogen atomic nucleus is the lightest.

Using the above-mentioned special characteristics, Step 4 of FIG. 8 selects a particular atomic interaction, as described below.

FIG. 10 shows locations of the carbon atomic nucleus, hydrogen atomic nucleus, and Cl⁻ ion which relate to the asymmetrical stretching. $R_C$ is the position vector of the carbon atomic nucleus based on the center position of gravity of PCLN or SMLN, and $R_H$ is the position vector of the hydrogen atomic nucleus based on the center position of gravity, $R_{CH}$ is the position vector of the center of gravity of carbon and hydrogen atomic nucleuses, $M_C$ is the mass of the carbon atomic nucleus, and $M_H$ is the mass of the hydrogen atomic nucleus. And a formula of $R_{CH}$ is Formula 9

$$R_{CH} = \frac{M_H R_H + M_C R_C}{M_H + M_C}. \quad (A \cdot 9)$$

This section defines X as:

Formula 10

$$X \equiv R_H - R_C, \quad (A \cdot 10)$$

Using eqs. (A•9) and (A•10), the following equations are obtained:

Formula 11

$$X_H \equiv R_H - R_{CH} = \frac{M_C}{M_H + M_C}X; \text{ and} \quad (A \cdot 11)$$

Formula 12

$$X_C \equiv R_C - R_{CH} = \frac{M_H}{M_H + M_C}X. \quad (A \cdot 12)$$

When $Q_C$ and $Q_H$ represent net atomic charges of carbon and hydrogen atoms based on Mulliken's population analysis, an electric dipole moment comprising a pair of the carbon and hydrogen atomic nucleuses is Formula 13

$$\mu = Q_H X_H + Q_C X_C. \quad (A \cdot 13)$$

Further, using eq. (A•13), the 3rd-term in the right-hand side of eq. (A•.3) is transformed to Formula 14

$$\{Q_H(E\cdot R_H) + Q_C(E\cdot R_C)\}\exp(-i2\pi vt) = (E\cdot\mu)\exp(-i2\pi vt) + \{Q_H + Q_C\}(E\cdot R_{CH})\exp(-i2\pi vt). \quad (A \cdot 14)$$

Classical mechanics says that the total kinetic energy of the carbon and hydrogen atomic nucleuses is Formula 15

$$T = \frac{M_H}{2}\left[\frac{dR_H}{dt}\right]^2 + \frac{M_C}{2}\left[\frac{dR_C}{dt}\right]^2 = \frac{M_H + M_C}{2}\left[\frac{dR_{CH}}{dt}\right]^2 + \frac{M_X}{2}\left[\frac{dX}{dt}\right]^2, \quad (A \cdot 15)$$

-continued wherein

Formula 16

$$M_X \equiv \frac{M_H M_C}{M_H + M_C}. \quad (A\cdot 16)$$

$M_X$ is a reduced mass regarding a relative motion between the carbon and hydrogen atomic nucleuses in eq. (A•16). And according to Harada's method (Y. Harada: *Ryoushi kagaku* (Quantum Chemistry) vol. 2 (Shyoukabou, 2007) Appendix 2, Section A2-3, p. 405 [in Japanese]) and eqs. (A•15) and (A•16), a part of the 1st-term in the right-hand side of eq. (A•3) regarding the carbon and hydrogen atomic nucleuses is transformed to Formula 17

$$-\frac{\hbar^2}{2M_H}\Delta_{RH} - \frac{\hbar^2}{2M_C}\Delta_{RC} = \quad (A\cdot 17)$$
$$-\frac{\hbar^2}{2(M_H + M_C)}\Delta_{RCH} - \frac{\hbar^2}{2M_X}\left\{\frac{\partial^2}{\partial X^2} + \frac{\partial^2}{\partial Y^2} + \frac{\partial^2}{\partial Z^2}\right\}.$$

Here, the X axis is parallel to the covalent bond direction between the carbon and hydrogen atoms, and the Y and Z axes are perpendicular to the covalent bond direction in eq. (A•17). If it is presumed that a potential factor $W_X(X)$ regarding the asymmetrical stretching of C—H—Cl$^-$ can be selected from $W(R_1, ---, R_N, t)$ described in eq. (A8), $W(R_1, ---, R_N, t)$ can be approximated to:

$$W(R_1, \ldots, R_N, t) \cong W_X(X) + W_{OTHER}(R_1, \ldots R_{N-2}, R_{CH}, X, Y, Z, t). \quad (A\cdot 18)$$

Therefore, the Hamiltonian shown in the right-hand side of eq. (A•8) can be changed to the following formulae when eqs. (A•14), (A•17), and (A•18) are substituted for eq. (A•8):

Formula 19

$$H_{nucl} + W(R_1, \ldots, R_N, t) \cong H_X + H_{OTHER}; \quad (A\cdot 19)$$

Formula 20

$$H_X = -\frac{\hbar^2}{2M_X}\frac{\partial^2}{\partial X^2} + \frac{e_0^2 Z_H Z_C}{4\pi\varepsilon_0 X} + W_X(X) - (E\cdot\mu)\exp(-i2\pi\nu t); \text{ and} \quad (A\cdot 20)$$

Formula 21

$$H_{OTHER} = -\sum_{a=1}^{N-2}\frac{\hbar^2}{2M_a}\Delta a + \quad (A\cdot 21)$$
$$\frac{e_0^2}{4\pi\varepsilon_0 X}\sum_{Ra-Rb\neq X}^{N-1}\frac{Za\cdot Zb}{|Ra-Rb|} - \sum_{a=1}^{N-2}Qa(E\cdot Ra)\exp(-i2\pi\nu t) -$$
$$\frac{\hbar^2}{2(M_H + M_C)}\Delta_{RCH} - \frac{\hbar^2}{2M_X}\left[\frac{\partial^2}{\partial Y^2} + \frac{\partial^2}{\partial Z^2}\right] +$$
$$W_{OTHER} - (Q_H + Q_C)(E\cdot R_{CH})\exp(-i2\pi\nu t).$$

Because the special characteristic [B] mentioned above indicates that the X axis corresponds to a normal coordinate of the particular normal vibration described in Step 3 of FIG. 8, $\Psi$nucl shown in eq. (A•8) can be approximated to Formula 22

$$\Psi_{nucl}(R_1, \ldots, R_N, t) \cong \phi_X(X, t)\cdot\phi_{OTHER}(R_1, \ldots, R_{N-2}, R_{CH}, Z, t). \quad (A\cdot 22)$$

When eqs. (A•19)-(A•22) are substituted for eq. (A8),

Formula 23

$$\frac{\left(i\hbar\frac{\partial}{\partial t} - H_X\right)\phi_X(X,t)}{\phi_X(X,t)} = \quad (A\cdot 23)$$
$$-\frac{\left\{i\hbar\frac{\partial}{\partial t} - H_{OTHER}\right\}\phi_{OTHER}}{\phi_{OTHER}} = W^*(X)$$

can be obtained.

Relating to eqs. (A•20) and (A•23), this section defines V(X) as

Formula 24

$$V(X) \equiv \frac{e_0^2 Z_H Z_C}{4\pi\varepsilon_0 X} + W_X(X) + W^*(X), \quad (A\cdot 24)$$

and presumes that V(X) has the minimum value $V(X_0)=0$ when $X=X_0$. With the Taylor expansion method near $X=X_0$, V(X) is approximated to Formula 25

$$V(X) \cong \kappa_2(X-X_0)^2 \kappa_3(X-X_0)^3 + \kappa_4(X-X_0)^4. \quad (A\cdot 25)$$

And this section defines x as

Formula 26

$$x \equiv X - X_0. \quad (A\cdot 26)$$

Substituting eqs. (A•20) and (A•24)-(A•26) for eq. (A•23), the following equation can be obtained:

Formula 27

$$i\hbar\frac{\partial}{\partial t}\phi_X = \quad (A\cdot 27)$$
$$\left\{-\frac{\hbar^2}{2M_X}\frac{\partial^2}{\partial x^2} + \kappa_2 x^2 + \kappa_3 x^3 + \kappa_4 x^4 - (E\cdot\mu)\exp(-i2\pi\nu t)\right\}\phi_X.$$

Equation (A•27) shows an interaction between an external electromagnetic wave and an anharmonic oscillator based on the reduced mass.

4.4) Formulae Relating to Wave Functions of Harmonic Vibrations

It is presumed that, in case of $\kappa_2=\kappa_3=0$, wave functions $\phi x(x,t)$ of eq. (A•27) are Formula 28

$$\phi_X(x,t)=\exp(-i\varepsilon_m t/\hbar)|m\rangle \quad (A\cdot 28)$$

And eq. (A•27) satisfies the following equation when $\kappa_2=\kappa_3=E=0$:

Formula 29

$$\left\{-\frac{\hbar^2}{2M_\chi}\frac{\partial^2}{\partial x^2} + \kappa_2 x^2\right\}|m\rangle = \varepsilon_m|m\rangle. \quad (A\cdot 29)$$

Harada (Y. Harada: *Ryoushi kagaku* (Quantum Chemistry) vol. 1 (Shyoukabou, 2007) Chapter 3, Section 3-6, p. 60 [in Japanese]) teaches us that a series of solutions of eq. (A•29)|m> are Formula 30

$$|m\rangle = \left(\frac{\beta}{\pi}\right)^{1/4}\sqrt{(2\beta)^m m!}\exp\left[-\frac{\beta}{2}x^2\right]\sum_{0\leq 2J\leq m}\left[-\frac{1}{4\beta}\right]^J\frac{x^{m-2J}}{J!(m-2J)!}, \quad (A\cdot 30)$$

Formula 31

$$\varepsilon_m = \left(\frac{2\kappa_2}{\beta}\right)\left(m + \frac{1}{2}\right), \text{ and} \quad (A\cdot 31)$$

Formula 32

$$\beta \equiv \sqrt{2M_\chi \kappa_2}/\hbar. \quad (A\cdot 32)$$

And a series of solutions |m> satisfies the following normalized orthogonal system:

Formula 33

$$\langle l|m\rangle = \delta_{lm} \quad (A\cdot 33)$$

Meanwhile, when "m" is an integer value, the formula (A•30) can be transformed to Formula 34

$$|m\rangle = \sqrt{(2\beta)^m m!}\,|0\rangle\sum_{0\leq 2J\leq m}\left[-\frac{1}{4\beta}\right]^J\frac{x^{m-2J}}{J!(m-2J)!}, \quad (A\cdot 34)$$

Formula 35

$$x^m|0\rangle = \frac{m!}{(2\beta)^{m/2}}\sum_{0\leq 2J\leq m}\frac{|m-2J\rangle}{2^J \cdot J!\sqrt{(m-2J)!}}, \quad (A\cdot 35)$$

Formula 36

$$\langle 0|x^{2m+1}|0\rangle = 0, \text{ or} \quad (A\cdot 36)$$

Formula 37

$$\langle 0|x^{2m}|0\rangle = \frac{(2m)!}{(4\beta)^m m!}. \quad (A\cdot 37)$$

4.5) Obtaining Einstein's Transition Probability

According to Step 5 of FIG. 8, this section solves eq. (A•27) to obtain wave functions of anharmonic vibration when E=0. Here, Step 5 of FIG. 8 utilizes time independent perturbation theory (Y. Harada: *Ryoushi kagaku* (Quantum Chemistry) vol. 1 (Shyoukabou, 2007) Chapter 9, Section 9-1, p. 161 [in Japanese]) which regards the 3rd and 4th terms $\kappa_3 x^3 + \kappa_4 x^4$ in the right-hand side of eq. (A•27) as perturbed terms and obtains approximate solutions based on formulae (A•30). Therefore, referring to formulae (A•31), (A•34), (A•36), (A•37), and Koide's formula (S. Koide: *Ryoushi rikigaku* (Quantum Mechanics) vol. 1 (Shyoukabou, 1969) Chapter 7, Section 7-3, p. 174 [in Japanese]), eigen values of energy $\varepsilon_m$ for anharmonic vibration are Formula 38

$$\varepsilon_m \cong \underline{\varepsilon_m} + \langle \underline{m}|\kappa_3 x^3 + \kappa_4 x^4|\underline{m}\rangle = \\ \frac{2\kappa_2}{\beta}\left(m + \frac{1}{2}\right) + \frac{3\kappa_4}{4\beta^2}(2m^2 + 2m + 1) \quad (A\cdot 38)$$

Formula (A•38) shows that eigen values of energy $\varepsilon_m$ for anharmonic vibration depend on $\kappa_4 x^4$ term described in eq. (A•27) and are independent of $\kappa_3 x^3$ term approximately.

And the time independent perturbation theory teaches us that wave functions |m> of anharmonic vibration are Formula 39

$$|m\rangle \cong \sum_u g_{mu}|u\rangle, \quad (A\cdot 39)$$

wherein

Formula 40

$$g_{mu} = \frac{\langle \underline{u}|\kappa_3 x^3 + \kappa_4 x^4|\underline{m}\rangle}{\varepsilon_m - \varepsilon_u}, (u \neq m) \text{ and} \quad (A\cdot 40)$$

Formula 41

$$g_{mm} = 1. \quad (A\cdot 41)$$

Therefore, substituting formulae (A•31) and (A•33)-(A•35) for (A•40), formula (A•39) can be transformed to Formula 42

$$|m\rangle \cong |\underline{m}\rangle - \frac{\kappa_3}{\kappa_2\sqrt{\beta}}G_{m3} - \frac{\kappa_4}{\kappa_2}G_{m4}, \quad (A\cdot 42)$$

and

Formula 43

$$G_{03} = \frac{\sqrt{3}}{12}\left|\underline{3}\right\rangle + \frac{3\sqrt{2}}{8}\left|\underline{1}\right\rangle, \quad (A\cdot 43)$$

$$G_{04} = \frac{\sqrt{6}}{16}\left|\underline{4}\right\rangle + \frac{3\sqrt{2}}{8}\left|\underline{2}\right\rangle,$$

$$G_{13} = \frac{\sqrt{3}}{6}\left|\underline{4}\right\rangle + \frac{3}{2}\left|\underline{2}\right\rangle - \frac{3\sqrt{2}}{8}\left|\underline{0}\right\rangle,$$

$$G_{14} = \frac{\sqrt{30}}{16}\left|\underline{5}\right\rangle + \frac{5\sqrt{6}}{8}\left|\underline{3}\right\rangle,$$

$$G_{23} = \frac{\sqrt{30}}{12}\left|\underline{5}\right\rangle + \frac{9\sqrt{6}}{8}\left|\underline{3}\right\rangle - \frac{3}{2}\left|\underline{1}\right\rangle,$$

$$G_{24} = \frac{3\sqrt{10}}{16}\left|\underline{6}\right\rangle + \frac{7\sqrt{3}}{4}\left|\underline{4}\right\rangle - \frac{3\sqrt{2}}{8}\left|\underline{0}\right\rangle,$$

$$G_{33} = \frac{\sqrt{15}}{6}\left|\underline{6}\right\rangle + 3\sqrt{2}\left|\underline{4}\right\rangle - \frac{9\sqrt{6}}{8}\left|\underline{2}\right\rangle - \frac{\sqrt{3}}{12}\left|\underline{0}\right\rangle,$$

$$G_{34} = \frac{\sqrt{210}}{16}\left|\underline{7}\right\rangle + \frac{9\sqrt{5}}{4}\left|\underline{5}\right\rangle - \frac{5\sqrt{6}}{8}\left|\underline{1}\right\rangle,$$

$$G_{43} = \frac{\sqrt{105}}{12}\left|\underline{7}\right\rangle + \frac{15\sqrt{10}}{8}\left|\underline{5}\right\rangle - 3\sqrt{2}\left|\underline{3}\right\rangle - \frac{\sqrt{3}}{6}\left|\underline{1}\right\rangle,$$

$$G_{44} = \frac{\sqrt{105}}{8}\left|\underline{8}\right\rangle + \frac{11\sqrt{30}}{8}\left|\underline{6}\right\rangle - \frac{7\sqrt{3}}{4}\left|\underline{4}\right\rangle - \frac{\sqrt{6}}{16}\left|\underline{0}\right\rangle.$$

When an external electromagnetic wave of wavelength $\lambda_m$ excites a wave function having an eigen value of energy co to a wave function having $\epsilon_m$, the following relational equation is satisfied:

Formula 44

$$\varepsilon_m - \varepsilon_0 = \frac{hc}{\lambda_m}. \qquad (A\cdot 44)$$

Here, $\lambda_m$ is the wavelength, "c" is the light speed, and "h" is the Planck's constant.

And then according to Steps 8 and 9 of FIG. 8, this section generates a formula representing Einstein's transition probability on the basis of time dependent perturbation theory (Y. Harada: *Ryoushi kagaku* (Quantum Chemistry) vol. 1 (Shyoukabou, 2007) Chapter 9, Section 9-8, p. 188 [in Japanese]). Using eqs. (A•28) and (A•39), a solution of eq. (A•27) is Formula 45

$$\phi_X(x,t) \cong \sum_m \eta_m(t) \exp\left(\frac{-i\varepsilon_m t}{\hbar}\right)\bigg| m>. \qquad (A\cdot 45)$$

And the following equation can be obtained when the formula (A•45) is substituted for eq. (A•27):

Formula 46

$$i\hbar \sum_m \frac{\partial \eta_m(t)}{\partial t} \exp\left(\frac{-i\varepsilon_m t}{\hbar}\right)\bigg| m> \cong -\sum_m \eta_m(t)\exp\left(-i2\pi\left(v+\frac{\varepsilon_m}{h}\right)t\right)(E\cdot\mu)\bigg| m>. \qquad (A\cdot 46)$$

If the formula (A•45) satisfies $\phi x(x,0)=|0>$ which indicates an initial state, $\eta_m(t)$ described in eq. (A•46) can be approximated to Formula 47

$$\eta_0(t) \cong 1, (\text{when } t \cong 0) \text{ and}$$

$$\eta_m(t) \cong 0 \text{ (when } m \ne 0, t \cong 0). \qquad (A\cdot 47)$$

Moreover, this section presumes the following condition when "m" is more than and equal to 5:

Formula 48

$$\frac{\partial \eta_m(t)}{\partial t} \cong 0 (m \ge 5). \qquad (A\cdot 48)$$

Using formulae (A47) and (A48), eq. (A•46) is transformed to

Formula 49

$$i\hbar \sum_{0 \le m \le 4} \frac{\partial \eta_m(t)}{\partial t}\exp\left(\frac{-i\varepsilon_m t}{\hbar}\right)\bigg| m> \cong -\exp\left(-i2\pi\left(v+\frac{\varepsilon_0}{h}\right)t\right)(E\cdot\mu)\big| 0>. \qquad (A\cdot 49)$$

Here, this section approximates an electric dipole moment $\mu$ described in formula (A•13) to Formula 50

$$|\mu| \cong \mu_0 + \mu_1 x + \mu_2 x^2 + \mu_3 x^3, \qquad (A\cdot 50)$$

and FIG. 10 shows that the direction of an electric dipole moment vector $\mu$ is parallel to the X axis. When Ex represents the X component of an external electric field vector, a part of the right-hand side of eq. (A•49) is transformed to Formula 51

$$(E\cdot\mu)\big| 0> \cong E_X(\mu_0 + \mu_1 x + \mu_2 x^2 + \mu_3 x^3)\big| 0> \equiv E_X \sum_u L_u \big| u >. \qquad (A\cdot 51)$$

By using formulae (A•34), (A•35), (A•42), and (A•43), the relational expressions of $L_u$ of eq. (A•51) are represented by Formula 52

$$L_0 = \mu_0 + \frac{\mu_2}{2\beta} - \frac{3}{8\beta}\left\{\frac{\kappa_3}{\kappa_2}\left(\mu_1 + \frac{11\mu_3}{6\beta}\right) + \frac{\kappa_4 \mu_2}{\kappa_2 \beta}\right\}, \qquad (A\cdot 52)$$

$$L_1 = \frac{1}{\sqrt{2\beta}}\left\{\mu_1 + \frac{3\mu_3}{2\beta} - \frac{\kappa_3}{\kappa_2}\left(\frac{3}{4}\mu_0 + \frac{11\mu_2}{8\beta}\right) - \frac{\kappa_4}{\kappa_2}\left(\frac{3\mu_1}{4\beta} + \frac{21\mu_3}{8\beta^2}\right)\right\},$$

$$L_2 = \frac{1}{\sqrt{2}\beta}\left\{\mu_2 - \frac{\kappa_3}{\kappa_2}\left(\mu_1 + \frac{27\mu_3}{8\beta}\right) - \frac{\kappa_4}{\kappa_2}\left(\frac{3\mu_0}{4} + \frac{9\mu_2}{4\beta}\right)\right\},$$

$$L_3 = \frac{\sqrt{3}}{2\beta^{3/2}}\left\{\mu_3 - \frac{\kappa_3}{\kappa_2}\left(\frac{\beta}{6}\mu_0 + \frac{4\mu_2}{3}\right) - \frac{\kappa_4}{\kappa_2}\left(\mu_1 + \frac{39\mu_3}{8\beta}\right)\right\},$$

and $$L_4 = -\frac{\sqrt{6}}{4\beta}\left\{\frac{\kappa_3}{\kappa_2}\left(\frac{1}{3}\mu_1 + \frac{7\mu_3}{2\beta}\right) + \frac{\kappa_4}{\kappa_2}\left(\frac{1}{4}\mu_0 + \frac{21\mu_2}{8\beta}\right)\right\}.$$

Subsequently, eqs. (A•39) and (A•51) are substituted for eq. (A49), the substituted result is multiplied by $<u|$ from a left side and is integrated, and eq. (A•33) is applied to the integrated result to obtain the simultaneous equations:

Formula 53

$$i\hbar \sum_{0 \le m \le q} g_{mu} \frac{\partial \eta_m(t)}{\partial t}\exp\left(i2\pi\left(v - \frac{\varepsilon_m - \varepsilon_0}{h}\right)t\right) \cong -E_X \cdot L_u, (0 \le u \le 4). \qquad (A\cdot 53)$$

The simultaneous equations (A•53) is described in Step 8 of FIG. 8.

Step 9 of FIG. 8 solves the simultaneous equations (A•53), and the solutions represent Formula 54

$$i\hbar \frac{\partial \eta_m(t)}{\partial t} \exp\left(i2\pi\left(v - \frac{\varepsilon_m - \varepsilon_0}{h}\right)t\right) = -E_X \cdot P_m. \quad (A\cdot 54)$$

When both right-hand and left-hand sides of eq. (A•54) are integrated with "t" and $hv \ne \varepsilon_m - \varepsilon_0$, $\eta_m(t)=0$ because different phase factors in the left-hand side of eq. (A•54) each other cancel in case of the integration.

Meanwhile, the following formula can be obtained when both right-hand and left-hand sides of eq. (A•54) are integrated with "t" and $hv = \varepsilon_m - \varepsilon_0$ corresponding to eq. (A•44):

Formula 55

$$\eta_m(t) = \frac{i}{\hbar} E_X P_m t. \quad (A\cdot 55)$$

Furthermore, Moore (W. J. Moore: Physical Chemistry 4th Edition (Prentice-Hall, Inc., 1972) Chapter 17, Section 5) teaches us that Einstein's transition probability is Formula 56

$$B_{0m} = \frac{8\pi^3}{3h^2} P_m^2 \quad (A\cdot 56)$$

Therefore, using (simultaneous) equations (A•42)-(A•43) and (A•52)-(A•54), Einstein's transition probability is calculated.

4.6) Substituting Estimation Results from Quantum Chemistry Simulation Program

According to FIG. 8, section 4.6 substitutes a few results of numerical analysis with computer simulations for relational formulae based on Quantum Mechanics, so that it obtains wavelength values of absorption bands and corresponding light absorbance comparison. Further, section 4.6 also describes the numerical analysis method in detail.

4.6.1) Numerical Analysis Method with Quantum Chemistry Simulation Program

This section describes the numerical analysis method with computer simulations.

A molecular structure model used for this numerical analysis is $Cl^-(CH_3)_3N^+CH_2CH_2OH$ under water which results from the $Cl^-$ attachment to Choline $(CH_3)_3N^+CH_2CH_2OH$ corresponding to an ingredient of PCLN or SMLN.

Whenever a distance deviation between carbon and hydrogen atomic nucleuses composing the asymmetrical stretching of $Cl^-$—H—C is set to every incremental value, each molecular structure is repetitively optimized to estimate one of total static molecule energies and net atomic charges calculated with Mulliken's population analysis.

Some keywords of optimization are "PM3 EF PRECISE EPS=78.4 GNORM=0.00001 LET DDMIN=0.00001 ALL-VEC". And this numerical analysis keeps a high accuracy because a molecular structure of distance deviation "0" is confirmed to have no negative wave number value regarding a vibration analysis.

4.6.2) Estimating Anharmonic Potential

Relating to Step 6 of FIG. 8, FIG. 11 shows relative static molecule energy vs. distance deviation between carbon and hydrogen atomic nucleuses composing the asymmetrical stretching of $C^-$—H—C, and the relative static molecule energy means a shifted value of the total static molecule energy to adjust a minimum value of the relative static molecule energy to "0". Based on FIG. 11, parameters in eq. (A•27) are associated as follows:

Formula 57

$$\kappa_2 \approx 8.6, \kappa_3 \approx -14.2, \kappa_4 \approx 9.3 [eV/Å^2]. \quad (A\cdot 57)$$

Substituting formulae (A•57) for formula (A•32) obtains

Formula 58

$$\beta \approx 62.1 [Å^{-2}]. \quad (A\cdot 58)$$

FIG. 11 has a seemingly discontinuous point of anharmonic potential property which occurs between α-point and β-point, and this section will describe the cause of seemingly discontinuous point.

As shown in FIG. 12 (*a*), the quantum chemistry simulation program "SCIGRESS MO Compact Version 1 Pro" provides the optimized molecular structure of $Cl^-(CH_3)_3N^+CH_2CH_2OH$ when the value of distance deviation between carbon and hydrogen atomic nucleuses is "0". FIG. 12 (*a*) shows that $Cl^-$ ion, Hydrogen atomic nucleus H, and Carbon atomic nucleus C are approximately arranged on a straight line, so that the $Cl^-$ ion seems to be located below an extrapolation (an alternate long and short dash line) of bonding of Nitrogen atomic nucleus N and Carbon atomic nucleus C' located on the left side of N. This arrangement continues when the distance between carbon and hydrogen atomic nucleuses increases. On the contrary, when the distance deviation exceeds −0.1 angstrom, the $Cl^-$ ion seems to be moved to a specific position which is located on the extrapolation (an alternate long and short dash line) of bonding of N and C', as shown in FIG. 12 (*b*). This seeming $Cl^-$ ion movement causes the seemingly discontinuous point.

FIGS. 11 and 12 are obtained on the basis of a semi-classical mechanics model which presumes that all atomic nucleus position is fixed in detail. According to a perfect quantum mechanics, all atomic nucleus position is not fixed in detail and is represented by each of the wave functions, and the seemingly discontinuous point substantially goes out.

FIG. 13 indicates a proof of above-mentioned explanation. FIG. 13 shows the wave functions |m> which are obtained by substituting formula (A•57) for formula (A•42), and it shows that the ground state |0> has an enough existence probability on the seemingly discontinuous point. This phenomenon suggests that the position of $Cl^-$ ion has probabilities of both FIGS. 12 (*a*) and 12(*b*) in case of the ground state |0>.

4.6.3) Estimating Dipole Moment Characteristics

FIG. 14 shows net atomic charges vs. distance deviation between carbon and hydrogen atomic nucleuses composing the asymmetrical stretching of $Cl^-$—H—C, and a unit of the net atomic charge is a quantum of electricity $e_0$.

According to a viewpoint of classical mechanics regarding atomic nucleus movements composing the asymmetrical stretching of $Cl^-$—H—C, as shown in [A] and [C] of section 4.3, the $Cl^-$ ion hardly moves and the Hydrogen atomic nucleus H widely moves. Therefore, when the distance between the carbon and hydrogen atomic nucleuses decreases (the left side area in FIG. 14), the distance between the $Cl^-$ ion and hydrogen atomic nucleus H increases, and the net atomic charge value of the $Cl^-$ ion approaches to "−1" and the net atomic charge values of carbon and hydrogen approach to original values when the Cl⁻ ion detaches.

On the contrary, when the distance between the carbon and hydrogen atomic nucleuses increases (the right side area in FIG. 14), the distance between the Cl⁻ ion and hydrogen atomic nucleus decreases, and the net atomic charge value of carbon monotonously reduces but the net atomic charge value of the hydrogen approaches to a saturation value.

Using results of molecular orbital analysis, reasons of net atomic charge properties shown in FIG. 14 can be described below. FIGS. 15 (a) and 15(b) show Highest and Lowest Occupied Molecular Orbitals.

The Highest Occupied Molecular Orbital (HOMO) shown in FIG. 15 (a) mainly comprises Atomic Orbitals 3Px of Cl⁻ ion and 2Px of carbon atom, and the red-lined and blue-lined orbitals represent negative and positive amplitudes. Further, FIG. 15 (a) shows that a boundary position between negative and positive amplitudes, where an existence probability of HOMO electron is "0", is located on the right side of the hydrogen atomic nucleus. Therefore, a surrounding existence probability of HOMO electron decreases and a net atomic charge value of hydrogen increases when the location of the hydrogen atomic nucleus is moved toward the right side in FIG. 15 (a) and the distance between the carbon and hydrogen atomic nucleuses increases. Moreover, the net atomic charge value of hydrogen approaches to a saturation value when the location of the hydrogen atomic nucleus substantially arrives at the boundary position.

The Lowest Occupied Molecular Orbital shown in FIG. 15 (b) mainly comprises Atomic Orbitals 3S of Cl⁻ ion and 1S of hydrogen atom, and this Molecular Orbital especially extends to the position of the carbon atomic nucleus. Moreover, the existence probabilities of molecular orbitals around the Cl⁻ ion which relate to not only the Lowest Occupied Molecular Orbital but also different molecular orbitals tend to flow toward the carbon atom when the location of the hydrogen atomic nucleus is moved toward the right side in FIG. 15 (b). Therefore, the net atomic charge value of carbon decreases when the distance between carbon and hydrogen atomic nucleuses increases, as shown in FIG. 14.

FIG. 16 shows electric dipole moments μvs. distance deviations between carbon and hydrogen atomic nucleuses, and the electric dipole moment μ is obtained by substituting net atomic charges of carbon and hydrogen for formula (A•13). According to FIG. 16, each parameter of formula (A•50) is as follows:

Formula 59

$$\mu_0 \approx 0.281, \mu_1 \approx 0.635, \mu_2 \approx 0.0242, \mu_3 \approx -0.272 [e_0 \cdot Å] \quad (A \cdot 59)$$

4.6.4) Light Absorption Wavelengths and Light Absorbances of Corresponding Absorption Bands Table 5 shows wave numbers, wavelengths, and transition probability ratios regarding asymmetrical stretching of Cl⁻—H—C, and the transition probability ratio corresponds to the relative light absorbance value. Using eq. (A•44), the wave numbers and the wavelengths can be calculated, and each $\epsilon_m$ is obtained by substituting values (A•57) and (A•58) for formula (A•38). In addition, each $B_{0m}$ can be calculated by solving the simultaneous eq. (A•53) and substituting eqs. (A•54) and (A•55) for formula (A•56).

TABLE 5

Wave numbers, wavelengths, and transition probability ratios regarding asymmetrical stretching of Cl⁻—H—C.

| m | 1 | 2 | 3 | 4 |
|---|---|---|---|---|
| Transition mode | Fundamental | 1st overtone | 2nd overtone | 3rd overtone |
| Wave number (cm⁻¹) | 2283 | 4635 | 7040 | 9487 |
| Wavelength λm (μm) | 4.38 | 2.16 | 1.42 | 1.05 |
| Transition probability ratio $B_{0m}/B_{01}$ | 1 | 1/176 | 1/3480 | 1/3030 |

Table 5 shows the fundamental wave number is 2283 cm⁻¹, and Table 3 shows the corresponding value is 2480 cm⁻¹. It is considered that the slight difference between 2283 cm⁻¹ and 2480 cm⁻¹ occurs because Table 3 is obtained with a harmonic vibration approximation and Table 5 is obtained with taking account of anharmonic vibration terms.

Table 5 shows that the relative light absorbance value of a 1st overtone (transition probability ratio $B_{02}/B_{01}$) is very small and the relative light absorbance values of 2nd and 3rd overtones are smaller.

If a measuring device of life activity has a particular contrivance to detect a small signal, as described later, it can sufficiently detect absorption bands regarding the 2nd and 3rd overtones.

Table 5 relates to specific transitions from a ground state |0⟩ to one of excited states |m⟩(m≠0). This embodiment, however, may detect another absorption band regarding another transition between excited states |m⟩(m≠0).

4.7) Discussion about Detectable Range in Present Exemplary Embodiment

There occur large reading errors when the value obtained in formula (A 57) is read from FIG. 11 and when the value obtained in formula (A 59) is read from FIG. 16. In view of this, some differences are expected between theoretically estimated values as shown in Table 5 and actual values. The differences in such a case are generally said to be about ±20% (±10% at best). Accordingly, a lower limit of the near infrared light wavelength adopted in the present exemplary embodiment is estimated to be 1.05×(1−0.1)=0.945 μm, or 1.05×(1−0.2)=0.840 μm with a larger estimated error.

However, when light of the 3rd overtone shown in Table 5 is not used for measurement and only light of the 2nd overtone or less is used for measurement, the lower limit of the near infrared light wavelength adopted in the present exemplary embodiment is estimated to be 1.42×(1−0.1)=1.278 μm, or 1.42×(1−0.2)=1.136 μm with a larger estimated error.

Further, when light of the 2nd overtone or more shown in Table 5 is not used for measurement and only light of the 1st overtone is used for measurement, the lower limit of the near infrared light wavelength adopted in the present exemplary embodiment is estimated to be 2.16×(1−0.1)=1.944 μm or 2.16×(1+0.1)=2.376 μm, or 2.16×(1−0.2)=1.728 μm or 2.16×(1+0.2)=2.592 μm with a larger estimated error.

An upper limit of the infrared radiation wavelength to be used in measurement method as shown in the present exemplary embodiment will be described as follows.

As for a relationship between a wavelength (wavenumber) of an absorption band measured by infrared light and an intramolecular vibration, the following vibrations are caused in order from a shorter absorption wavelength (in order from a larger wavenumber value): a local vibration of functional groups, a principal chain vibration of molecule, a vibration of whole molecule, and a rotation of whole molecule.

Accordingly, a high-speed change along with the aforementioned "local state change in a molecule" corresponds to measurement of the "local vibration" or the "principal chain vibration of molecule" among them.

In the meantime, the analysis result of a vibration mode occurring when a sodium ion is attached to a carboxyl group to form an ion bond are as follows: [A] according to section 3.3, the wavenumber values (wavelengths) of the absorption band corresponding to the skeletal vibration of $>C$—$CO_2^-$ $Na^+$ are 260 to 291 $cm^{-1}$ (34.4 to 38.5 μm); and [B] according to section 3.4, the wavenumber value (wavelength) of the absorption band corresponding to the skeletal vibration of $N^+$—C—$CO_2^-Na^+$ is 429 $cm^{-1}$ (23.3 μm).

Further, the analysis result of a vibration mode occurring when a potassium ion is attached to a carboxyl group to form an ion bond is as follows: according to section 3.3, [C] the wavenumber value (wavelength) of the absorption band corresponding to the skeletal vibration of C—$CO_2^-K^+$ is 118 $cm^{-1}$ (84.7 μm); and [D] the symmetrically telescopic vibration of the carboxyl group —$CO_2^-$ at a wavenumber (wavelength) of 1570 $cm^{-1}$ (6.37 μm) is largely restricted due to potassium ion attachment.

Accordingly, it is necessary to consider the above values as a part of the application range (detectable range) of the present exemplary embodiment. However, in advance of this consideration, [E] according to section 3.2, the wavenumber value (wavelength) of the absorption band corresponding to the skeletal vibration of —$N^+(CH_3)_3Cl^-$ is 2465 $cm^{-1}$ (4.06 μm) (an average of 2480 $cm^{-1}$ for PCLN and 2450 $cm^{-1}$ for SMLN), whereas the waveband value is 2283 $cm^{-1}$ in section 4.6.4. In view of this, it is necessary to take into consideration such a slight difference. As have been described in section 4.6.4, the reason of this slight difference is because "the vibrational analysis result in section 3.1 is obtained based on a harmonic vibration approximation," whereas "section 4.6.4 takes account of anharmonic vibration terms."

Accordingly, it may be said that the measurement wavelengths L listed in [A] to [D] can be changed up to (2465/2283)×L depending on a computation model. Further, the values exhibited in [A] to [E] are merely theoretically estimated values, and some difference up to about ±20% with respect to the actual values is expected, as described earlier. Thus, the lower limit of the experimental value based on [A] to [E] is estimated as L×(1−0.2) and the upper limit thereof is estimated as (2465/2283)×L×(1+0.2).

In view of this, the application ranges (detectable ranges) of the present exemplary embodiment to detect each of the phenomena [A] to [E] in consideration of the above relational formulae will be as follows:

[A] The skeletal vibration of $>C$—$CO_2^-Na^+$ (section 3.3)⇒ 27.5 to 49.9 μm (34.4×0.8≈27.5, (2465/2283)×38.5× 1.2≈49.9);

[B] The skeletal vibration of $N^+$—C—$CO_2^-Na^+$ (section 3.4)⇒ 18.6 to 30.2 μm;

[C] The skeletal vibration of C—$CO_2^-K^+$ (section 3.3)⇒ 67.8 to 110 μm;

[D] The symmetrically telescopic vibration of —$CO_2^-$ (section 3.3)⇒ 5.10 to 8.25 μm; and

[E] The skeletal vibration of —$N^+(CH_3)_3Cl^-$ (section 3.2)⇒ 3.25 to 5.26 μm.

From the overall view of the above, the infrared radiation wavelength to be used in the measurement method of the present exemplary embodiment is desirably at least 110 μm or less (a wavenumber value of 91.1 $cm^{-1}$ or more), in view of the upper limit of [C].

Accordingly, to summarize the discussion as above is that a wavelength range of the light to be used in the present exemplary embodiment are "from 0.840 μm to 110 μm" as the maximum range and "from 2.592 μm to 110 μm" as the minimum range.

Subsequently, an influence of absorption wavelengths of water is added to the summary of the discussion. Most part of a life object is constituted by water molecules. Therefore, when electromagnetic waves are illuminated to measure or detect dynamical life activities in the life object, absorption of the electromagnetic waves by the water molecules will be a large problem. Accordingly, the present exemplary embodiment devises to use a wavelength region where the absorption by the water molecules is relatively small. According to B. Alberts et. al.: Essential Cell Biology (Garland Publishing, Inc. 1998), p. 68, FIGS. 2 to 24, the composition of a chemical compound constituting an animal cell (including inorganic ions) is occupied by water molecules by 70% by weight. Further, 15% out of the remaining 30% of the composition is occupied by proteins, followed by 6% by RNA, 4% by ions/small molecules, 2% by Polysaccharides, and 2% by Phospholipids. Meanwhile, the light absorption characteristic of the proteins varies depending on a tertiary structure in a cell, and therefore, it is difficult to specify an absorption wavelength region of an absorption band by general proteins. In view of this, in the present exemplary embodiment, "the light absorption characteristic of the water molecule" is focused on because [1] the water molecules are included in an animal cell overwhelmingly abundantly, and [2] the light absorption characteristic thereof is determined due to its stable molecular structure, and a wavelength region with relatively small light absorption by the water molecule is used for detection of dynamical life activities in a life object. This allows relatively stable and accurate measurement or detection while preventing detection light for life activity from being absorbed by water molecules along the way. Yukihiro Ozaki/Satoshi Kawata: Kinsekigai bunkouhou (Gakkai Shuppan Center, 1996), p. 12, p. 120, p. 122 or p. 180 describes the maximum absorption wavelength of the water molecule, and the present exemplary embodiment will provide an explanation using the values described herein.

Respective center wavelengths of absorption bands of the water molecule corresponding to a symmetrically telescopic vibration and an anti-symmetrically telescopic vibration are 2.73 μm and 2.66 μm. Further, in a wavelength region having wavelengths longer than the above wavelengths, light absorption by a rotation of a hydrogen molecule occurs. Accordingly, in the present exemplary embodiment, in order to measure dynamical activities in a life object, 2.50 μm, which is a wavelength slightly shorter than 2.66 μm, is taken as a boundary, and the measurement is performed using electromagnetic waves in a wavelength region having a wavelength shorter than the boundary value (more specifically, in a range from 0.840 μm to 2.50 μm in consideration of the discussion as above).

On the other hand, in the near-infrared region, an absorption band corresponding to combinations between the anti-symmetrically telescopic vibration and deformation vibration of the water molecule is at a center wavelength of 1.91 μm. In view of this, other embodiments can use, for measurement, electromagnetic waves in a wavelength region except for this absorption band. More specifically, light of the 1st overtone (having a wavelength of 2.16 μm) as shown in Table 5 is used for measurement. However, as having been mentioned above, a reading error of about ±10% to ±20% occurs when a value is read from FIG. 11 or FIG. 1.

In consideration of this reading error, electromagnetic waves of not less than 2.16×(1−0.05)=2.05 μm but not more than 2.16×(1+0.15)=2.48 μm are used in another exemplary embodiment.

Further, an absorption band corresponding to combinations between the symmetrically telescopic vibration and the anti-symmetrically telescopic vibration of the water molecule is at a center wavelength of 1.43 μm. In view of this, for another applied embodiment, light in a wavelength region between the above wavelength and 1.9 μm (more specifically, light of not less than 1.5 μm but not more than 1.9 μm to avoid a center wavelength of the absorption band of the water molecule) may be used, or light in a wavelength region having a wavelength shorter than 1.43 μm may be used. As an electromagnetic wave for measurement corresponding to the latter, light of the 3rd overtone (having a wavelength of 1.05 μm) as shown in Table 5 is used for measurement. In consideration of the above reading error, a specific wavelength to be used in this case is in a range of:

1.05×(1−0.2)=0.840 μm or more but 1.05×(1+0.3)=1.37 μm or less.

In the meantime, other wavelength ranges may be set as an applied embodiment, as well as the wavelengths mentioned above. That is, as described below, the wavelength ranges may be set so as to avoid a wavelength region absorbed by an "oxygen concentration indicator" existing in a living tissue. For example, when a palm or a finger is illuminated with near-infrared light, a pattern of blood vessels can be observed around a surface thereof. This is because hemoglobin included in the blood vessels absorbs the near-infrared light. That is, in a case where a life activity in an area on a backside of the blood vessels (behind the blood vessels) placed in vicinity of the surface of the life object is detected, there is such a risk that detection light may be absorbed by the blood vessels in the middle of a detection light path and an S/N ratio of a detection signal may decrease. Besides the hemoglobin, myoglobin and cytochrome oxidase also have absorption bands in the near-infrared region, and the absorption spectrum of the near-infrared region varies between an oxygenation state and a deoxygenating state. For this reason, these substances are called an oxygen concentration indicator. Further, according to F. F. Jobsis: Science vol. 198 (1977), p. 1264-p. 1267, it is said that the cytochrome oxidase and hemoglobin have a weak absorption band over wavelengths of 0.780 μm to 0.870 μm. Accordingly, in consideration of a general range of measurement errors of ±0.005 μm, if the detection light to be used in the present exemplary embodiment or the applied embodiment has a wavelength of 0.875 μm or more, a detection signal of a life activity is stably obtained without having any influence (light absorption) by the oxygen concentration indicators. From this viewpoint, the aforementioned wavelength ranges "from 0.840 μm to 110 μm," "from 0.840 μm to 2.50 μm," or "of not less than 0.840 μm but not more than 1.37 μm" will be assumed as, respectively, "from 0.875 μm to 110 μm," "from 0.875 μm to 2.50 μm," or "of not less than 0.875 μm but not more than 1.37 μm." In a case where the using wavelengths of detection light or control light for life activity are determined as such, even if an oxygen concentration indicator exists in the middle of a detection light path or a control light path, the detection light or the control light is not absorbed, so that the S/N ratio of a life activity detection signal can be secured and stable life activity control can be performed.

FIGS. 17, 18, and 19 are images showing qualitative performance comparisons between membrane potential changing detection and oxygen concentration change detection in blood from respective viewpoints of spatial resolution, temporal resolution, and detection accuracy.

As described above, the spatial resolution in Conventional Technique 1 is of the order of 3 cm (see FIG. 17), and it is said that the spatial resolution in the case of magnetic detection using an fMRI device is a few mm order. In this case, as shown in FIG. 17, a mean value of oxygen concentrations in blood flowing in a plurality of capillaries 28 in this area is detected. In comparison with that, in a case where membrane potential changing is detected, the spatial resolution is of the order of a wavelength of the detection light described above.

However, in a case where an action potential of one neuron is detected as an example of the potential changing detection of a cell membrane, an average distance between adjacent neurons corresponds to a substantial spatial resolution. It is said that an average distance between adjacent neurons in a cerebral cortex of a human is of the order of 20 μm.

Thus, there is a difference of 100 times in terms of the order between these spatial resolutions. An image of the difference is shown in FIG. 17 in a simulated manner. That is, in a case where the oxygen concentration change in blood is detected by use of near infrared light like Conventional Technique 1, a mean value within an area having a diameter of 3 cm is detected. In contrast, in this exemplary embodiment, an action potential of each single pyramidal cell body 17 or stellate cell body 18 in the area can be detected individually.

On the other hand, as will be described below in section 6.3.1 or section 9.3.2, in the present exemplary embodiment in which the membrane potential changing is detected, a size (aperture size) of a light transmission section 56 in a two-dimensional liquid crystal shutter 51 as shown in FIG. 24 or 25 can be made adequate so as to detect activities of a group unit of a plurality of neurons such as a column unit (a total firing rate of a set of the plurality of neurons, such as a column). Since the column has a cylindrical shape (or rectangular solid) with about 0.5 to 1.0 mm in diameter and almost 2 mm in height, the spatial resolution can be advantageously changed freely into to the above values (or below those values) to detect the activities per column unit.

(Regarding Size Range of Detection Unit)

As described above, the detection unit in the present exemplary embodiment can be widely set from one neuron unit (or a particular region in an axon) or one muscle cell unit (or neuromuscular junction unit), to a group unit of a plurality of neurons (or muscle cells). That is, in a detected point for life activity, a local area constituted by one or more cells is set to a single unit for detection and a characteristic per detection unit (in the local area) corresponding to an electromagnetic wave is detected so as to detect a life activity.

Further, this electromagnetic wave is near infrared light or infrared light having a wavelength in a range to be described herein (section 4.7), or alternatively an electromagnetic wave with which a detected point for life activity is illuminated to detect a life activity by use of Nuclear Magnetic Resonance, which will be explain later in chapter 5. Further, when the life activity is detected by use of Nuclear Magnetic Resonance, either continuous wave CW (Continuous wave) spectroscopy or pulse FT (Fourier Transformation) spectroscopy may be used.

A size of the detection unit (a local area) in the present exemplary embodiment is desirably in a range of 1 cm from the wavelength of an electromagnetic wave used for detection, and further desirably not less than 10 μm but not more than 3 mm, for the following reason. If the size is expressed in terms of a cell number included in this detection unit (the local area), the cell number is desirably not less than 1 but not more than 100 million, and particularly desirably not less than 1 but not more than 2 million.

The following describes the size range of the detection unit (the local area). An electromagnetic wave is narrowed down to its wavelength size (diffraction limited) according to a diffraction theory. Further, it is known that voltage-gated $Na^+$ ion channels, which greatly relate to a neuronal action potential, are largely distributed over an axonal root site in a cell body. In view of this, in a case where an action potential of only one neuron is detected, detection efficiency is more improved by condensing light around this axonal root rather by widely illuminating the whole cell body with detection light. Consequently, it is desirable that the size of the detection unit (the local area) in the present exemplary embodiment be larger than the wavelength of the electromagnetic wave to be used for detection.

Next will be described an upper limit of the size of the detection unit (the local area) in the present exemplary embodiment. As will be described below in section 6.5.4 with reference to FIG. 41 or 42, life activity information is obtained from movement of a facial muscle in an applied embodiment. In this case, sufficient detection accuracy cannot be obtained by the spatial resolution (about 3 cm in diameter: see FIG. 17) as described in Conventional Technique 1. Since the width of an eyelid or a lip of a human is about 1 cm, it is necessary for the upper limit of the size of the detection unit (the local area) to be set to 1 cm so as to obtain detection accuracy to some extent or more. Further, an average distance between neurons is about 20 μm, and when a deep part of the brain is measured with a cube 1 cm on a side as a detection unit, $(10 \div 0.02) \times (10 \div 0.02) \times (10 \div 0.02) \approx 100$ million neurons will be included within this detection unit (the local area).

The following assumes a case where the detection unit (the local area) is set to a unit of integral multiple of the aforementioned column. As described above, since the height of one column (a thickness of a spinal cord gray matter in a cerebral cortex) is 2 mm, $2 \div 0.02 = 100$ neurons will be aligned in the detection unit on the average. When the life activity is detected in broad perspective, activities of around 10 columns within one detection unit (local area) may be detected at the same time. In this case, one side of the length of the detection unit (local area) is $10^{1/2} \times 1 \approx 3$ mm. In view of this, $(3 \div 0.02) \times (3 \div 0.02) \times 100 \approx 2$ million neurons will be included in this detection unit (local area). Further, when one side (or a diameter) of the detection unit (local area) is set to 0.5 mm or 1.0 mm, a life activity of one column can be detected as the detection unit (the local area) (from the viewpoint of the aforementioned column size). At this time, the number of neurons included in the detection unit (the local area) will be $(0.5 \div 0.02) \times (0.5 \div 0.02) \times 100 \approx 60,000$ or $(1 \div 0.02) \times (1 \div 0.02) \approx 300,000$. Accordingly, in a case where the life activity of one neuron to the life activity of a column unit are detected, a local area constituted by not less than 1 but not more than 60,000 to 300,000 cells is set as a detection unit, and a characteristic thereof corresponding to an electromagnetic wave is detected so as to detect the life activity.

(Regarding Temporal Resolution)

The detection of an oxygen concentration change in blood by use of near infrared light or fMRI is compared with the detection of potential changing of a cell membrane by optical or magnetic means described in the present exemplary embodiment in terms of the temporal resolution.

Like Conventional Technique 1, as long as the oxygen concentration change in blood is detected, a delay of about 5 s is caused, so that the temporal resolution is restricted essentially. In comparison with that, as described in section 1.3, in a case of detecting membrane potential changing, there is a temporal resolution which allows faithful reproduction of an action potential pulse waveform of about 0.5 to 4 ms occurring during the term 24 of nerve impulse as shown in FIG. 3.

The difference between them is shown by an image of FIG. 18(*b*). When stellate cell bodies 18 at a position α and a position γ or a pyramidal cell body 17 at a position β fires an action potential and a potential of a cell membrane is changed, unique vibration modes occur due to ion adsorption (or ion release), as has been described in chapter 3 or 4 (the present chapter). Accordingly, when the cell body is illuminated with light having a wavelength in the aforementioned range, this light is absorbed and causes transition between the unique vibration modes.

As a result, as shown in FIG. 18(*b*), a reflection light amount change 401 occurs due to a temporal decrease in the amount of reflection light. In the example of FIG. 18(*b*), the stellate cell body 18 at the position α starts firing an action potential at $t_0$ in a detection time 163, which causes the stellate cell body 18 at the position γ to start firing an action potential, followed by causing an action potential of the pyramidal cell body 17 in the position β with a little delay. Here, one "whisker" in FIG. 18 (*b*) indicates "one action potential." Since the temporal resolution is very high in the present exemplary embodiment in which the membrane potential changing is detected as such, each action potential state can be detected per different neuron.

Then, at $t_B$, which is 5 s after $t_0$ at which the action potential started in the detection time 163, a reflection light amount 48 of light having a wavelength of 830 nm and a reflection light amount 47 of light having a wavelength of 780 nm start to change slowly.

It is found that after the neuron fires an action potential, the oxygen concentration change in blood will not occur if any of the following phenomena does not continue: (1) lack of ATP in the cell bodies 17 and 18; (2) lack of oxygen molecules in the cell bodies 17 and 18; and (3) lack of oxyhemoglobin in the capillary 28. That is, only when action potentials are fired frequently as shown in FIG. 18(*b*), the above phenomena from (1) to (3) occur continuously.

Therefore, when action potentials are rarely fired as shown FIG. 19(*b*), the oxygen concentration in blood does not change because the phenomena (1) to (3) do not occur. Hence, it is considered that the method for detecting the oxygen concentration change in blood has relatively low detection accuracy of the life activity. In contrast, since the present exemplary embodiment in which the membrane potential changing is detected can detect only one action potential as shown in FIG. 19(*b*), it is advantageously possible to improve detection accuracy drastically in either of the optical means (near infrared light) and the magnetic means (fMRI).

(Regarding Detection of Weak Signal)

As can be seen from a value of $B_{0m}/B_{01}$, which is a transition probability ratio in the reference tone of the transition probability in the overtone levels described in Table 5, a very weak changing signal is detected in the present exemplary embodiment. Therefore, an electromagnetic wave (near infrared light) to be projected on a life object is modulated in advance in the present exemplary embodiment as described later.

Thus, an S/N ratio of a detection signal can be increased by extracting only a signal component synchronized with a modulation signal from detection light returning from the life object. If a modulation cycle thereof is longer than a time interval at which a measurement subject changes, it is difficult to detect time dependent variations of the measurement subject. Accordingly, in order to measure time dependent variations of the measurement subject stably, it is necessary to set a basic cycle of the modulating signal to be equal to or less than ⅕ the time interval at which the measurement subject changes.

In view of this, one exemplary embodiment has a feature in that a basic frequency of a modulation signal is set as follows: 1 Hz or more (at least 0.2 Hz or more) for an object changing at an interval shorter than 5 s; 25 Hz or more (at least 5 Hz or more) for an object changing at an interval shorter than 200 ms; and 1.25 kHz or more (at least 250 Hz or more) for an object changing at an interval shorter than 4 ms.

Next will be described an upper limit of the basic frequency of the modulation and an interval of time dependent variations in one exemplary embodiment. Generally, it is known that analog signals having a signal bandwidth of several hundred kHz work easily and stably without oscillating a detecting circuit. Further, at such a signal bandwidth, implementation including how to connect grounds in a printed circuit or the like is stable even without careful attention. On the other hand, when the bandwidth of an operating range exceeds 20 MHz, the detecting circuit is easy to be oscillated, and considerable technique is necessary for the implementation in the printed circuit. In a case where an action potential of about 0.5 to 2 ms is measured in one example of the present exemplary embodiment, such high-speed signal detection is not required. Therefore, a detecting signal bandwidth is restrained to a minimum, so as to stabilize the circuit and reduce costs.

For the aforementioned reasons, the basic frequency of the modulation is restrained to 500 kHz or less specifically, in one example of the present exemplary embodiment, and the interval of time dependent variations of the measurement subject is set to not less than 10 ns (at least 2 ns or more).

5] NMR Spectral Characteristics Estimation Based on Action Potential Model 5.1) NMR Spectral Characteristic Changing and Estimated Chemical Shift Values Regarding the Action Potential 5.1.1) Prospect for Changing NMR Spectral Characteristics Regarding Action Potential Section 4.7 said that this embodiment shows a new measuring method of life activity which exposes a life object to an electromagnetic wave of 0.85 µm-50 µm (or 0.84 µm-2.5 µm) wavelength, and this new measuring method can detect time dependent variations of the electromagnetic wave indicating a life activity. And according to the new measuring method, a local property of life object can be measured in detail, and dynamical life action information can be obtained by converting the measurement results.

This chapter 5 proposes another embodiment which detects time dependent variations of Nuclear Magnetic Resonance property in a local area of a life object and converts the detection results to dynamical life action information.

According to section 3.2, a net charge value regarding a hydrogen atomic nucleus varies when the $Cl^-$ ion attaches to the hydrogen atom of $—N^+(CH_3)_3$ belonging to PCLN or SMLN and forms a hydrogen (or ionic) bond with the hydrogen atom. This net charge variation means a change of molecular orbitals located around the hydrogen atomic nucleus. Therefore, it is predicted that Nuclear Magnetic Resonance property and a corresponding chemical shift value change when the molecular orbitals located around hydrogen atomic nucleus change, because the change of molecular orbitals may make a magnetic shielding effect for hydrogen atomic nucleus vary.

This chapter proposes another embodiment which detects time dependent variations of Nuclear Magnetic Resonance property or a corresponding chemical shift and converts the detection results to dynamical life action information.

5.1.2) Calculation Method with Another Quantum Chemistry Simulation Program

In this chapter 5, Gaussian 09 is used for a quantum chemistry simulation program, and "Gaussian" belongs to a registered trademark (Gaussian 09, Revision A. 1, M. J. Frisch, G W. Trucks, H. B. Schlegel, G E. Scuseria, M. A. Robb, J. R. Cheeseman, G Scalmani, V. Barone, B. Mennucci, G A. Petersson, H. Nakatsuji, M. Caricato, X. Li, H. P. Hratchian, A. F. Izmaylov, J. Bloino, G Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G Zakrzewski, G A. Voth, P. Salvador, J. J. Dannenberg, S. Dapprich, A. D. Daniels, O. Farkas, J. B. Foresman, J. V Ortiz, J. Cioslowski, and D. J. Fox, Gaussian, Inc. Wallingford Conn., 2009).

A molecular structure $Cl^-(CH_3)_3N^+CH_2CH_2OH$ is used for this computer simulation to obtain a short time and simple estimation. And this calculation method also comprises two calculation steps to keep high calculation accuracy. The first calculation step is to optimize a molecular structure and to confirm whether the optimization is fully finished or not, and the second calculation step is to analyze Nuclear Magnetic Resonance property.

Some keywords of optimization are "#P RHF/6-31G(d) Opt Freq SCRF=(Solvent=Water,PCM)". Here, "RHF/6-31G(d)" means an approximation method and basic functions used for a series of calculations, "Opt SCRF=(Solvent=Water,PCM)" means the optimization under water, and "Freq" is used to confirm the optimized structure.

And some keywords of Nuclear Magnetic Resonance analysis are "#P RHF/6-31G(d) NMR SCRF=(Solvent=Water,PCM)". Here, "NMR" means the Nuclear Magnetic Resonance analysis for calculating a corresponding chemical shift value. This chemical shift value is based on "δ scale" which represents a subtraction value between a corresponding output data and a basic chemical shift of Tetramethylsilane (TMS) which was previously calculated (R. M. Silverstein and F. X. Webster: Spectrometric Identification of Organic Compounds 6th Edition (John Wiley & Sons, 1998) Chapter 4, Section 4.7).

5.1.3) Estimating Chemical Shift Values in NMR Spectral Characteristics

At first, Gaussian 09 calculated a chemical shift value regarding a hydrogen atomic nucleus belonging a methyl group which is included in a single choline $(CH_3)_3N^+CH_2CH_2OH$ without $Cl^-$ ion attachment. And the first calculation results were between δ2.49 ppm and δ2.87 ppm.

Then it calculated a chemical shift value regarding a hydrogen atomic nucleus which forms a hydrogen (or ionic)

bond with Cl⁻ ion in a molecule Cl⁻(CH₃)₃N⁺CH₂CH₂OH, and the next calculation results are between δ3.43 ppm and δ3.55 ppm.

Therefore, these calculation results show an obvious transition of a chemical shift between Cl⁻ ion attachment and detachment.

5.2) Discussion about Measurable Range in Present Exemplary Embodiment

If a chlorine ion Cl⁻ is attached to PCLN or SMLN on an outside layer of a cell membrane at the time when a neuron fires an action potential, an NMI spectrum reaches its peak in a range from δ3.43 ppm to δ3.55 ppm temporarily (during the action potential), and a peak area in a range from δ2.49 ppm to δ2.87 ppm must be decreased by an amount corresponding to the peak area in the range from δ3.43 ppm to δ3.55 ppm.

Accordingly, in another applied embodiment of the present exemplary embodiment, a temporary increment of the peak in the range from δ3.43 ppm to δ3.55 ppm on the NMI spectrum or a temporary decrement of the peak in the range from δ2.49 ppm to δ2.87 ppm on the NMI spectrum is measured so as to measure an action potential phenomenon.

A value calculated according to a computer simulation often has some difference to an actual result of measurement. The difference is estimated to be about 0.45 to 0.49 ppm. In view of this, an applied embodiment of the present exemplary embodiment measures a time dependent variation (a temporary increase and decrease) of the peak area (or a peak height) in the range from δ2.0 ppm (2.49−0.49) to δ4.0 ppm (3.55+0.45) on the NMI spectrum.

However, the applied embodiment of the present exemplary embodiment is not limited to the measurement of a neuronal action potential, but the present exemplary embodiment is applicable to measurement of rapid dynamical life activity changing in a life object by detecting a temporary increase or decrease (a time dependent variation) of a peak in a particular region on the NMI spectrum.

The reason is as follows: judging from the explanation in section 4.7, a phenomenon that a dynamical life activity in a life object changes in a short time (a reaction velocity is fast) often causes a change of a magnetic screening effect due to molecular orbitals located around the proton change.

Further, this another applied embodiment has a large feature in that a change of molecular state in water is detected to measure life activities. This another applied embodiment has a technical device to detect a particular change of molecular state under water, and this technical device is based on detecting spectrum peaks which are different from specific peaks corresponding to one or more water molecules in the NMR spectrum.

It is said that a chemical shift value of a hydrogen nucleus constituting a single water molecule is in a range from δ0.4 ppm to δ1.55 ppm, and a chemical shift value due to a hydrogen bond between water molecules is δ4.7 ppm (R. M. Silvestein & F. M. Webster: Spectrometric Identification of Organic Compounds, 6th edition (John Wiley & Sons, Inc., 1998) see Chapter 4).

An electronegativity of an oxygen atom related to the hydrogen bond between water molecules is large, which follows fluorine, according to the calculation result of Pauling. Thus, a chemical shift value at the time when a hydrogen bond to an atom except for an oxygen atom (for example, the aforementioned chlorine ion) is formed is smaller than δ4.7 ppm as mentioned above, and will be δ4.5 ppm or less in consideration of a margin of 0.2 ppm.

On the other hand, an upper limit of the chemical shift value of the hydrogen nucleus constituting a single water molecule is δ1.55 ppm, but should be set to δ1.7 ppm or more, to which a margin of 0.15 ppm is added, so as to avoid the peak of the water molecule. In view of the above consideration, this another applied embodiment measures a dynamical life activity in a life object by detecting a time dependent variation of the peak area (or the peak height) in a range of the chemical shift value of not less than δ1.7 ppm but not more than δ4.5 ppm on the NMR spectrum.

In this another applied embodiment, an interval of time dependent variations to be detected in a case of detecting dependent variations of the peak area (or the peak height) on the NMR spectrum is not less than 10 ns (at least 2 ns or more) but not more than 5 s as has been described in section 4.7. Alternatively, depending on a measurement subject, the interval may be not less than 10 ns (at least 2 ns or more) but not more than 200 ms, or not less than 10 ns (at least 2 ns or more) but not more than 4 ms.

6] Technical Features of Detection/Control Method of Life Activity and Measuring Method of Life Activity in Present Exemplary Embodiment Chapter 6 explains about basic principles and technical features of a detection method of life activity and a measuring method of life activity in the present exemplary embodiment. Further, this chapter deals with an exemplary embodiment to be commonly used even in a control method of life activity.

More specific operation using the basic principles to be explained herein will be described in or after chapter 7.

6.1) Content of Life Activity to be Measured and Features of Detection/Control Method of Life Activity Table 6 shows a list of exemplary life activities to be measured in the present exemplary embodiment. The exemplary life activities are listed in Table 6 in order from a surface area in a life object to an area deeper inside the life object. Further, Table 6 also shows a detection signal category to be measured per life activity, and a physical phenomenon generating a detection signal and a detection method thereof

TABLE 6

| Depth | Signal Complexity | Life activity | Category of detection signal to be measured | Signal generative physical phenomenon and detection method |
|---|---|---|---|---|
| Shallowest ↑ \| \| \| \| \| \| | Simple ↑ \| \| \| \| \| | Sense on skin surface | Detection signal at ending of sensory neuron (pain, temperature, mediating tactile, pressure) | Membrane potential changing in nervous system |
| | | Expansion and contraction of sweat gland | Indication signal transmission of expansion and contraction to sweat gland by autonomic nervous system | Membrane potential changing in nervous system |
| | | | Surface temperature change on surface corresponding to expansion and contraction of sweat gland | Temperature change by thermography |

TABLE 6-continued

| Depth | Signal Complexity | Life activity | Category of detection signal to be measured | Signal generative physical phenomenon and detection method |
|---|---|---|---|---|
| | | Expansion and contraction of capillary | Indication signal transmission of expansion and contraction to capillary by autonomic nervous system | Membrane potential changing in nervous system |
| | | | Bloodstream change in blood flowing through capillary | Detection of oxygen concentration change in blood |
| | | | Local time dependent variation of capillary width | Absorption amount change of near infrared light in blood |
| | | | Surface temperature change on surface corresponding to expansion and contraction of capillary | Temperature change by thermography |
| | | Contraction and relaxation of skeletal muscle | Indication signal of contraction or relaxation to muscle cell | Membrane potential changing in nervous system |
| | | | Transmission signal to neuromuscular junction | Membrane potential changing in nervous system |
| | | | Oxygen or nutrition supply state along with activity of skeletal muscle | Detection of oxygen concentration change in blood in surrounding areas |
| | | | Pyretic action along with contractile activity of skeletal muscle | Temperature change by thermography |
| | | Sense in muscle and articulation | Detection signal at ending of sensory neuron (pain, moving amount perception) | Membrane potential changing in nervous system |
| | Most complicated ↑ | Active state of visceral organ | Indication signal transmission of expansion and contraction to visceral organ by autonomic nervous system | Membrane potential changing in nervous system |
| | | Activity in cerebral cortex | Distribution state of activation area in cerebral cortex | Detection of oxygen concentration change in blood in surrounding areas |
| | | | | Detection of oxygen concentration change by fMRI |
| | | | Signal transmission or information processing activity between neurons existing in cerebral cortex | Membrane potential changing in nervous system |
| | | | | Activation neuron distribution by fMRI |
| | | | Signal transmission (signal transmission pathway) transmitted through axon in cerebral cortex | Membrane potential changing in same axon |
| | | Intraspinal signal relay transmission in spine | Internuncial signal transmission (action potential state) in spinal cord | Membrane potential changing in nervous system |
| | | | Signal transmission (signal transmission pathway) transmitted through axon in spinal cord | Membrane potential changing in same axon |
| | | Activity in basal ganglia or limbic system | Signal transmission or activation state between neurons existing in basal ganglia | Activation neuron distribution by fMRI |
| ↓ | ↓ | | Signal transmission or activation state between neurons existing in limbic system | Detection of oxygen concentration change by fMRI |
| Deepest | Complex | Activity in brainstem area | Signal transmission or activation state between neurons existing in brainstem | Activation neuron distribution by fMRI |

As can be seen from Table 6, life activities to be measure in the present exemplary embodiment have characteristics as will be shown in sections 6.1.1 and 6.1.3. Further, in association with that, features of the measuring method of life activity in the present exemplary embodiment will be described in sections 6.1.3 to 6.1.5.

6.1.1) Life Activity in Various Meanings to be Taken as Detection Target in Present Exemplary Embodiment The sense on a skin surface indicates pain, temperature, mediating tactile, pressure, kinesthetic sensation or the like detected by the signal detection area (ending) 4 of the sensory neuron in FIG. 1. As has been described in section 1.3, the membrane potential 20 of the ending 4 of the sensory neuron rises to the action potential 23 temporarily.

Further, indication signal transmission from the autonomic nervous system causes expansion and contraction of at least one of a sweat gland and capillary. A signal transmission mechanism at this time is basically the same as the signal transmission from the neuromuscular junction 5 to the muscle cell 6 as described in section 1.3 and FIG. 1. At the time of transmitting an indication signal for expansion or contraction, the membrane potential 20 changes to the depolarization potential 22 (see FIG. 3).

This accordingly allows detection of the membrane potential changing can be detected at the time of expansion or contraction of each of the sweat gland and the capillary. On the other hand, a body temperature increases locally when the bloodstream in blood flowing through the capillary increases. The temperature increasing around the capillary reaches the skin surface, thereby allowing indirect measurement by a thermography. In addition to that, when the bloodstream in the capillary changes, an absorption amount of near infrared light in blood changes or an amount of oxyhemoglobin or deoxyhemoglobin per unit volume changes, so that the change can be detected by the near infrared light.

In the meantime, the thermography herein refers to a method or a measuring device for measuring an infrared ray emitted from a skin surface by use of an infrared camera. Here, according to a principle of black-body radiation, a center wavelength of the infrared ray emitted from the skin surface varies depending on the temperature of the skin surface (the center wavelength deviates toward a shorter-wavelength side as the temperature is higher). Thus, the temperature of the skin surface can be expected from this center wavelength of the infrared ray. Then, by use of the thermography, a two-dimensional distribution of the temperature of a measurement subject can be measured.

As shown in Table 6, skeletal muscles are distributed relatively near the life-object surface. Particularly, facial muscles exist right under skin. When these skeletal muscles contract, membrane potential changing occurs (section 1.3). An electrocardiogram measures potential changing occurring at the time of contraction and relaxation of a striated muscle in the heart. Here, the electrocardiogram measures the potential changing in such a manner that electrodes are directly attached to a skin surface, whereas the present exemplary embodiment measures the potential changing in a "non-contact" manner. Further, the use of the after-mentioned measuring method in the present exemplary embodiment allows non-contact measurement of the electrocardiogram (with clothing), which largely reduces a burden on an examinee.

Further, when such a skeletal muscle is active, a pyretic action occurs at the same time. This heat is transmitted to the skin of the life-object surface, so that the activity of the skeletal muscle can be indirectly measured even by using the thermography. Further, supply of oxygen and nutrition (energy source) is necessary for the activity of the skeletal muscle. As a result, the oxygen concentration change in blood (within the capillary) around the skeletal muscle also occurs.

In an area slightly deeper than the position of the skeletal muscle, pain or a moving amount in a muscle or an articulation is sensed, which is also detected by the ending 4 of the sensory neuron in FIG. 1 and causes local potential changing.

Furthermore, in a further deeper area, activity control of visceral organs by indication signal transmission from the autonomous nerve is performed. This is also performed by signal transmission in the form of membrane potential changing, similarly to the expansion/contraction control of the sweat gland or capillary. Here, it is premised that the measurement is performed by using insertion of an endoscope or a catheter, so that the visceral organs are described near the surface in Table 6.

In a signal transmission pathway from a spinal cord to a cerebral cortex via a brainstem, a limbic system, a basal ganglia as shown in FIG. 1, a signal transmission state can be measured by detecting a local change of a membrane potential. Particularly, as has been described in section 2.5, if a signal path of a signal transmitted in the axon is traced, a detailed signal transmission pathway and its function in the body become clear as well as inside the brain.

6.1.2) Various Detection Methods to be Applied to Detection Method of Life Activity in Present Exemplary Embodiment The method for detecting the change of the membrane potential 20 (FIG. 3) by use of electromagnetic waves (near infrared light or infrared light) having the wavelengths described in chapters 3 and 4 based on the action potential or the signal transmission mechanism model as described in chapter 2 corresponds to "Membrane potential change in nervous system" as shown in the column of "Signal generative physical phenomenon and detection method" in Table 6.

Furthermore, the method for detecting the spectrum changing by Nuclear Magnetic Resonance corresponding to a chemical shift value in the range described in chapter 5 based on the action potential or the signal transmission mechanism model as described in chapter 2 corresponds to the measurement of "Activation neuron distribution by fMRI" in Table 6.

The present exemplary embodiment may use other existing detection methods as well as the detection methods initially proposed in the explanation of the present exemplary embodiment. That is, Conventional Technique 1 corresponds to the detection of "the oxygen concentration change in blood" in Table 6.

Furthermore, the detection of "Oxygen concentration change by fMRI" in Table 6 corresponds to Conventional Technique 2.

Further, "Temperature change by thermography" in Table 6 corresponds to "infrared imaging (including an infrared camera)" and "Absorption amount change of near infrared light in blood" in Table 6 corresponds to "near infrared imaging (applications to authentication using a pattern of blood vessel)."

The detection methods shown in Table 6 has a tendency as follows: in a case of detecting life activities at relatively shallow areas from the surface at least either of the infrared light and the near infrared light is used, whereas for detection of life activities at relatively deep areas from the surface, Nuclear Magnetic Resonance (fMRI) is used. In the meantime, Conventional Technique 2 has a relatively low spatial resolution. In view of this, for advanced measurements such as signal transmission between neurons and information processing activities in deep areas, the activation neuron distribution by fMRI is suitable in view of its high temporal resolution and spatial resolution.

6.1.3) Life Activity in Life Object from Surface Area to Very Deep Area to be Taken as Detection/Control Target As shown in Table 6, the present exemplary embodiment assumes life activities in a life object from a surface area to very deep positions as detection/control targets. This requires an extraction technique of a life activity detection signal from a specific location in a three-dimensional space in the life object or a selective life activity control technique with respect to a specific location.

At a first stage of the present exemplary embodiment to realize that, in order to perform "alignment of a detected/controlled point for life activity and preservation thereof" in the life object, the following operations are performed: (1) interpretation of an internal configuration in three dimensions (arrangement of all parts constituting the life object); and (2) calculation of a position of a measurement subject in three dimensions and control of the position based on the interpretation in (1).

At a second stage, (3) "extraction of a life activity detection signal" or "control of a local life activity" at the position specified in (2) is performed. The first stage and the second stage may be performed in series through time, or may be performed at the same time.

Hereinafter, "position detection of a detected/controlled point for life activity" performed in the operations (1) and (2) is referred to as a "first detection." In the present exemplary embodiment, an electromagnetic wave (or light) having a wavelength described below is used for this first detection (which will be described in section 6.2, more specifically).

Furthermore, the operation (3) is hereinafter referred to as a "second detection." For this second detection, electromagnetic waves including an electromagnetic wave having a specific wavelength or an electromagnetic wave corresponding to a specific chemical shift value are used (which will be described in section 6.3, more specifically).

In other words, "in the present exemplary embodiment, detection or control of a life activity in a life object includes 'the first detection of detecting an electromagnetic wave,' and 'the second detection of detecting electromagnetic waves including an electromagnetic wave having a specific wavelength or an electromagnetic wave corresponding to a specific chemical shift value' or 'control using electromagnetic waves including an electromagnetic wave of a specific wavelength,'" and the second detection or control will be performed based on a result of the first detection. A specific procedure thereof is performed such that a position of a measuring/control object in three dimensions is calculated by the first detection, and a detection signal related to a life activity is obtained by the second detection from the internal position thus calculated, or alternatively, the life activity is controlled locally by illuminating an area at the position thus calculated with electromagnetic waves including a specific wavelength. However, the present exemplary embodiment is not limited to the above, and may be performed such that:

[1] a position of a measuring/control object in three dimensions is calculated by the first detection;

[2] a detection signal related to a life activity is obtained by the second detection from the internal position thus calculated; and

[3] the life activity is controlled locally based on the detection signal (by changing the intensity of the electromagnetic wave for illumination).

Thus, the first detection to perform position detection and position control of a detected/controlled point for life activity is combined with the second detection to perform actual detection of the life activity.

In the present exemplary embodiment, since the first detection to perform the position detection and position control of a detected point for life activity is performed separately from the second detection to perform detection or control of life activity, a measurement section for performing the second detection (the after-mentioned detecting section for life activity) can be fixed to a location away from a user without directly attachment to the body of the user. Therefore, the use can move around without being conscious of the detection of life activity. This largely reduces a burden on the user and greatly improves convenience.

Here, the "electromagnetic wave having a specific wavelength" indicates the "light having a wavelength in the range from 0.840 μm to 50 μm" for detection of the "membrane potential changing in nervous system" shown in Table 6, while indicating the "light having a wavelength in the range from 780 nm to 805 nm or 830 nm" for detection of "oxygen concentration change in blood in surrounding areas" in Table 6. Further, the "electromagnetic wave having a specific wavelength" indicates "infrared light having a wavelength of around 8.7 μm" for detection of "temperature change by thermography" in Table 6. The reason why the wavelength should be 8.7 μm is described below. The thermography detects black-body radiation released from a life-object surface, but a largest-intensity wavelength of this black-body radiation depends on a released surface temperature of the life object. When the largest-intensity wavelength corresponding to a human body temperature is calculated, a result thereof is 8.7 μm, and therefore this value is used herein.

On the other hand, the "electromagnetic wave corresponding to a specific chemical shift value" indicates the "electromagnetic wave corresponding to a chemical shift value in the range of not less than δ1.7 ppm but not more than δ4.5 ppm" as described in section 5.2 for detection of "activation neuron distribution by fMRI" shown in Table 6, while indicating the "electromagnetic wave corresponding to a chemical shift value corresponding to the change of the magnetic susceptibility" for detection of "oxygen concentration change by fMRI" shown in Table 6.

In the meantime, in the present exemplary embodiment, the electromagnetic wave having a specific wavelength may be detected from electromagnetic waves released naturally from a life object. However, since the electromagnetic waves thus naturally released have a low intensity, it is difficult to have a large S/N ratio for a detection signal. In order to handle this, in the present exemplary embodiment, a life object is illuminated with the electromagnetic waves including the electromagnetic wave having a specific wavelength or the electromagnetic wave corresponding to a specific chemical shift value, and the illuminating light obtained from the life object is detected, so as to perform the second detection. This can improve detection accuracy of a detection signal. Further, as has been described in section 4.7, the electromagnetic waves for illumination to the life object may be modulated by a basic frequency in a range of not less than 0.2 Hz but not more than 500 kHz so as to further improve the accuracy of the detection signal.

Meanwhile, a wavelength of the electromagnetic wave used for the first detection to set a detected point or controlled point for life activity in the life object so as to obtain a life activity detection signal by the second detection may be harmonized with a wavelength of the electromagnetic wave used in the second detection. However, in the present exemplary embodiment, the wavelength range of both electromagnetic waves are set to different values (that is, the largest-intensity wavelength of the electromagnetic wave in the frequency distribution used for the first detection is set to be different from the specific wavelength or the specific chemical shift value included in the electromagnetic waves for the second detection), so as to remove interference between the electromagnetic wave used for the first detection and the electromagnetic waves used for the second detection or the control. In this case, color filters for blocking light of specific wavelengths are disposed at first and second detection openings (an entry port of the signal detecting section), so as to prevent the electromagnetic wave used for the first detection from entering into to the second detection side and vice versa.

A specific method in the present exemplary embodiment in which the electromagnetic waves for the first detection and the second detection or control are set to have different wavelengths is such that: a position of a measurement subject in three dimensions is detected by use of a camera having sensitivity for visible light; by use of the aforementioned infrared radiation or near infrared light, a water concentration distribution in a life object subjected to life activity detection is measured by MRI, or the position of the measurement subject is determined by use of a CT scan; the water concentration distribution in the life object for which a detection signal related to a life activity at the position is detected by fMRI is measured by MRI or the position of the measurement subject is determined by use of a CT scan; and by use of infrared light or near infrared light, the detection or control of a detection signal related to the life activity at the position is performed.

Here, the terms to be used for future explanations of the exemplary embodiments are defined as below. The same terms will be used according to the following definitions hereinafter. Initially, an operation of obtaining information (e.g., intensity, change in intensity, phase amount, phase shift, frequency value or frequency change) related to a certain electromagnetic wave is defined as "detection." In the explanation, as described earlier, this "detection" has two definitions, "the first detection" and "the second detection." Further, this second detection is referred to as "detection of life activity" in a narrow sense. However, in some cases, the first detection and the second detection may be generally referred to as "detection of life activity." An obtained signal as a result of detection is referred to as a "detection signal" and a signal obtained as a result of detection of life activity is referred to as a "life activity detection signal" in the present specification.

Accordingly, a signal directly obtained from a physical phenomenon shown in the column of "signal generative physical phenomenon and detection method" in Table 6 corresponds to "a detection signal obtained as a result of the second detection," but if there occurs no confusion for the interpretation of the terms hereinafter, that signal may be generally referred to as a "detection signal."

As described above, among all biosis activities, a biosis activity of which a state can change over time along with a particularly physicochemical phenomenon is included in the "life activity." Table 6 gives an explanation focusing on the activity of the nervous system as an example of the life activity, but the present exemplary embodiment is not limited to that, as described above, and all detection of activities corresponding to the aforementioned life activities will be included in the scope of the present exemplary embodiment. Alternatively, in the present exemplary embodiment, "a state or a change of the state (a time dependent variation or a spatial variation) of a life object which is detectable by an electromagnetic wave in a non-contact manner" may be defined as the life activity.

In the meantime, examples of the life activity focusing on the activity of the nervous system as shown in Table 6 encompass "signal transmission (a transmission path or a transmission state) in the nervous system," "reflection reaction," "unconscious activity," "cognitive reaction," "recognition/discrimination reaction," "emotional reaction," "information processing," "thought/contemplation process," and the like. These certain types of "controlled life activities of a higher degree" are defined as "life activity information" (the symptom of a schizophrenia patient is partially controlled to some extent, and therefore included in the controlled life activity of higher degree).

Alternatively, "interpretable or distinguishable information about a composite action which causes an activity (for example, between cells)" can be also defined as the "life activity information." Even if plant or microbial activities include some sort of controlled composite action, the activities are also included in the life activity information. In order to obtain this life activity information, it is necessary to interpret a life activity detection signal including a signal of a dynamical life activity in the life object and to generate life activity information. A process to generate the life activity information from this life activity detection signal is referred to as "interpretation of life activity." Further, a process ranging from the acquisition of a life activity detection signal to the generation of life activity information may be referred to as "biosis activity measurement."

Furthermore, a part which receives light including light having a specific wavelength with a signal associated with a life activity or electromagnetic waves including an electromagnetic wave corresponding to a specific chemical shift value with a signal associated with a life activity and detects a life activity detection signal therefrom is referred to as a "signal detecting section." Moreover, a part in the signal detection section which receives the light or the electromagnetic waves and converts it into an electric signal is referred to as a "photo detecting section of life activity" in a wide sense, and a method for receiving the light or the electromagnetic waves and converting it into an electric signal is referred to as a "photo detecting method of life activity." Further, an electric detecting section including amplification to signal processing of an electric signal obtained by the photo detecting section in the signal detecting section is referred to as a "life activity detection circuit."

In the photo detecting section of life activity having a configuration as shown in section 6.3.3 section as one exemplary embodiment, a detecting coil 84 detects an electromagnetic wave corresponding to a specific chemical shift value (the detecting coil 84 converts it into an electric signal). On the other hand, in another exemplary embodiment, the photo detecting section of life activity having a configuration as shown in section 6.3.1 or section 6.3.2 photoelectrically converts light having a specific wavelength (near infrared light or infrared light). In the exemplary embodiments of the photo detecting section of life activity, an optical system used for photoelectric conversion of light including the aforementioned light having a specific wavelength (and placed as a front part of the photoelectric conversion) is referred to as an "optical system for life activity detection."

Meanwhile, since the life activity detection signal has a large S/N ratio in the present exemplary embodiment, there may be used such a method in which an electromagnetic wave having a specific wavelength (or corresponding to a specific chemical shift value) is modulated by a predetermined basic frequency so that a life object as a measurement subject (or a detection target) is illuminated with the modulated electromagnetic wave. A section which generates at least the electromagnetic wave (or light) having the specific wavelength (or corresponding to a specific chemical shift value) in this case is referred to as a "light emitting section." A whole section constituted by the signal detecting section and the light emitting section is referred to as a "detecting section for life activity." Here, in exemplary embodiments which do not have the light emitting section, the detecting section for life activity corresponds to the signal detecting section. The relationship between these terms described so far is illustrated in FIG. 31. Specific operations and functions of each section in the detecting section for life activity will be described later in section 6.4.1.

On the other hand, a section which aligns a detected point for life activity and performs the first detection to preserve the position therein as described above is referred to as a "position monitoring section regarding a detected point for life activity" or just referred to as a "position monitoring section." A whole section constituted by the "detecting section for life activity" and the "position monitoring section regarding a detected point for life activity" is referred to as a "life detecting section." A signal is transmitted between the position monitoring section regarding a detected point for life activity and the detecting section for life activity in this life detecting section. That is, as has been described in the beginning of this section, detection of life activity is performed by the detecting section for life activity based on a result of position detection by the position monitoring section.

6.1.4) Generation of Life Activity Information from Detection Signal

A detection signal of a dynamical life activity is obtained by the method described in section 6.1.3. However, in order to obtain life activity information from the detection signal, an interpretation process of the detection signal is required. The detection signal is compared with an accumulated data base, and life activity information is generated accordingly.

6.1.5) Complicated Activity Calculable from Relatively Simple Detection Signal Using Association Between Life Activities The complexity of a detection signal of each life activity as a measurement subject is shown in Table 6. A life activity at a position closer to a surface of the life object corresponds to a relatively simple detection signal, and it is presumed that life activity information can be generated relatively easily from the detection signal. In contrast, a detection signal obtained from an area such as the limbic system, the basal ganglia, and the cerebral cortex, which detection signal is transmitted from the spinal cord via the brainstem, is complicated, and generation of life activity information is accompanied with technical difficulty. Meanwhile, a life activity at a shallow position is associated with a life activity in a deep position as shown in FIG. 1. In the present exemplary embodiment, this association is used to estimate life activity information at a deep position from a detection signal related to a life activity in a relatively shallow position.

As a specific example, there is a method for estimating life activity information of a central nervous system layer 7 (FIG. 1) from detection signals indicative of activities of the capillary and the muscle (particularly facial muscle) shown in Table 6 (which will be described later in section 6.5.4).

6.2) Alignment and Preservation Method of Detected/Controlled Point for Life Activity By use of the first detection method as described in section 6.1.3, the following describes a method in which a spatial arrangement in three dimensions in (1) is grasped, and based on the result, a detected point for life activity or a controlled point for life activity (a position of a measurement subject) is calculated in three dimensions and position control is performed in (2).

6.2.1) Method for Setting Detection Position by Detecting Cross-Sectional Image Including Detected/Controlled Point The following describes a basic principle to detect a cross-sectional image including a detected point, which is used in the position monitoring section regarding a detected point for life activity in the present exemplary embodiment, with reference to FIG. 20. Note that detected points 30 for life activity described in FIGS. 20, 21, 23, 24, 26, and 28 correspond to a target area for life activity control to be locally affected in a life object in the present exemplary embodiment. Light (or electromagnetic waves) is projected via an objective lens 31 toward a wide area around a detected point 30 for life activity, like a reflection-type light microscope, which is omitted in FIG. 20. Then, the light (or the electromagnetic waves) thus projected is reflected diffusely on the detected point 30 for life activity constituted by a two-dimensional plane including respective points α, β, and γ, and its peripheral area. By use of this phenomenon, the diffused reflection light on the two-dimensional plane (the detected point 30 for life activity) including the respective points α, β, and γ is used as detection light with respect to the detected point for life activity.

In the meantime, in order to find (detect) a point from which a life activity detection signal in the life object is obtained or a point where the life activity is controlled (i.e., the detected point 30 for life activity), it is necessary to interpret an internal structure on the two-dimensional plane including the respective points α, β, and γ (interpretation of each part constituting the life object and grasp of an arrangement thereof) in regard to (1) in section 6.1.3. Similarly to detection of an intensity change of light reflected diffusely on a surface when a surface structure is grasped by a conventional light microscope, an intensity change of the diffused reflection light at each point on the two-dimensional plane is measured.

However, in the present exemplary embodiment, it is necessary to detect an image (a detection signal pattern) in a specific cross section in the life object, which is different from the conventional light microscope. Therefore, the present exemplary embodiment uses a feature of a confocal system to detect the cross section in the life object.

That is, a pinhole 35 is disposed at a rear focus position of a detection lens 32, so that only detection light passing through this pinhole is detected by the photodetector 36. The light reflected diffusely on points except for the detected point 30 for life activity and passing through the objective lens 31 becomes non-parallel beams in the middle of an optical path 33 of the detection light and forms a very wide spot cross section (a very large spot diameter) at the pinhole 35, so that most of the light cannot pass through the pinhole 35.

Accordingly, since the photodetector 36 can detect only parallel detection light in the optical path 33 for the detection light between the objective lens 31 and the detection lens 32, only detection light emitted from a position of an anterior focal plane of the objective lens 31 can be detected. Thus, by synchronizing the detected point 30 for life activity with the position of the anterior focal plane of the objective lens 31, a detection signal obtained only from the detected point 30 for life activity can be detected by the photodetector 36.

Here, a reflecting mirror (a galvanometer mirror) 34 which can be inclined in two axial directions is disposed between the objective lens 31 and the detection lens 32. Before the reflecting mirror (galvanometer mirror) 34 is inclined, only detection light emitted from the position α on the detected point 30 for life activity can be detected by the photodetector 36. Further, when the reflecting mirror (galvanometer mirror) 34 is inclined to the right side, only detection light emitted from the position γ can be detected, and when the reflecting mirror 34 is inclined to the left side, only detection light emitted from the position β can be detected.

FIG. 20 shows a case where the reflection mirror 34 is inclined in a crosswise direction, but the present exemplary embodiment is not limited to this, and when the reflecting mirror 34 is inclined in a front-back direction, detection light emitted from a position deviated in a direction perpendicular to the page space can be detected. As such, when the reflecting mirror (galvanometer mirror) 34 performs scanning in the biaxial directions and a light amount detected by the photodetector 36 is monitored through time in sync with the inclination, a two-dimensional detection signal pattern can be obtained from the light reflected diffusely on the detected point 30 for life activity.

In regard to (2) of section 6.1.3, the following describes a detection method and a correction method (an alignment method) of a displacement direction and a displacement amount of a current detection position for the detected point 30 for life activity in a two-dimensional direction at right angles to an optical axis of the objective lens 31. Although not illustrated in the optical system described in FIG. 20, a member having elasticity such as a leaf spring or a wire is disposed between the objective lens 31 and a fixing member so that the objective lens 31 can move in triaxial directions. Further, three voice coils are connected with the objective lens, and the three voice coils are partially disposed in a DC magnetic field generated by a fixed magnet (not illustrated).

Accordingly, when a current flows in each of the voice coils, the objective lens can move in an individual direction of corresponding one of the three axes due to an effect of an electromagnetic force.

In the present exemplary embodiment, the detected point 30 for life activity to become a target for extraction of a life activity detection signal ((3) as described in section 6.1.3) is predetermined, and a detection signal pattern obtained therefrom is stored in advance. This detection signal pattern indicates two-dimensional image information which is obtained as a detection signal from the photodetector 36 synchronized with the scanning in biaxial directions of the reflecting mirror (galvanometer mirror) 34 and which is indicative of a distribution of diffused reflection light amount at the detected point 30 for life activity. The objective lens 31 is disposed at a suitable location close to the detected point 30 for life activity, and a two-dimensional signal detection pattern (a monitoring signal) obtained from the photodetector 36 synchronized with a biaxial-direction inclination of the reflecting mirror (galvanometer mirror) 34 obtained at this time is compared with the aforementioned detection signal pattern stored in advance.

At this time, by use of a pattern matching method, a displacement direction and a displacement amount of a detection position between two-dimensional image information indicated by the currently obtained detection signal pattern and an ideal position in a direction at right angles to the optical axis of the objective lens 31 (a center position of an image in the two-dimensional image information indicated by the detection signal pattern stored in advance) are calculated.

When the displacement direction and the displacement amount in the direction at right angles to the optical axis of the objective lens 31 are obtained as such, a current is flowed into the voice coils integrated with the objective lens 31, so as to align the detected point 30 for life activity by moving the objective lens 31 in the biaxial directions at right angles to the its optical axis. Such electric feedback is performed continually during a detection period, and the objective lens is held at a predetermined position (where the detected point 30 for life activity can be measured).

Next will be described a monitor detection method of a detected point for life activity in a direction along the optical axis of the objective lens 31 (operations of (1) and (2) in section 6.1.3). A basic principle is such that: cross-sectional images in a plurality of areas having different depths in a life object are extracted by use of the feature of the confocal (imaging) system; a pattern equivalent level with respect to cross-sectional image information stored in advance is calculated, and a current position in a direction along the optical axis of the objective lens 31 is detected. A detailed explanation thereof is given below.

First discussed is a case where light emitted from the position α in the detected point 30 for life activity is condensed at the pinhole 35-1 as shown in FIG. 21. Light emitted from a position δ which is deeper than the position α is condensed at a pinhole 35-3 placed ahead of the pinhole 35-1, and detected by a photodetector 36-3. Similarly, light emitted from a position δ which is shallower than the position α is condensed at a pinhole 35-2 placed behind the pinhole 35-1, and detected by a photodetector 36-2. A grating 37 is disposed in the detection system in FIG. 21 to incline the optical axis so that the placement position can be changed from the pinhole 35-1 to the pinhole 35-3 in a direction at right angles to the optical axis. In such an optical arrangement, when the reflecting mirror (galvanometer mirror) performs scanning in the biaxial directions, a detection signal pattern on a plane at right angles to the optical axis of the objective lens 31 and including the position δ is obtained from the photodetector 36-3. Similarly, a detection signal pattern on a plane at right angles to the optical axis of the objective lens 31 and including the position δ is obtained from the photodetector 36-2.

Meanwhile, detection signal patterns obtained from the detected point 30 for life activity and areas at a shallower side and a deeper side of the detected point 30 for life activity are stored in advance. At this time, not only the detection signal patterns on the plane including the position δ and the position ε obtained when the objective lens is placed at an ideal position (where the detected point 30 for life activity can be measured), but also detection signal patterns obtained from positions greatly displaced toward the shallower side or the deeper side of the detected point 30 for life activity are stored at this time.

Then, these detection signal patterns stored in advance are compared with detection signal patterns obtained from the photodetectors 36-1 to 36-3 (pattern matching in consideration of a displacement amount in the two-dimensional direction at right angles to the optical axis of the objective lens 31), it is possible to judge whether the objective lens 31 is currently positioned at the shallower side or the deeper side of a designated position in the optical axial direction.

In this pattern matching process, equivalent levels of the respective detection signal patterns currently obtained from the photodetectors 36-3, 36-1, and 36-2 with respect to detection signal patterns at corresponding positions stored in advance are calculated, and it is estimated that the objective lens 31 is located at a place where the equivalent level is the highest.

For example, assume a case where as a result of calculating the equivalent levels with detection signal patterns stored in advance, a detection signal pattern corresponding to a two-dimensional surface currently obtained from the photodetector 36-2 in synch with the biaxial-direction scanning of the reflecting mirror (galvanometer mirror) 34 has the highest equivalent level with respect to a detection signal pattern obtained from the detected point 30 for life activity stored in advance.

In that case, it is found from FIG. 21 that a current location of the objective lens 31 is too near to the detected point 30 for life activity. In the detection result as such, a current is flowed into the voice coils integrated with the objective lens 31, so as to move the objective lens backward along the optical axis. When the objective lens 31 is set at a position most suitable for the measurement of the detected point 30 for life activity, a detection signal pattern obtained from the photodetector 36-1 in synch with the biaxial-direction scanning of the reflecting mirror (galvanometer mirror) 34 is matched with the detection signal pattern obtained from the detected point 30 for life activity stored in advance.

Even in a case where the objective lens 31 is largely displaced from a measurement location of the detected point 30 for life activity, if signal patterns of the objective lens 31 in case of large displacement are stored as described above, then it is possible to estimate a displacement direction and a displacement amount of the objective lens 31 by performing the pattern matching with a current signal pattern (calculating an equivalent level between the patterns).

6.2.2) Method for Estimating and Setting Position of Detected Point by Detecting Specific Position on Life-Object Surface In the method described in section 6.2.1, a cross-sectional pattern including the detected point 30 for life activity is directly detected to find a position of the detected point. Another embodiment proposes a method in which when a depth from a life-object surface to the detected point is found in advance, a position of the life-object surface in three dimensions is detected and the position of the detected point is automatically estimated.

With reference to FIG. 22, the following will explain a method for detecting a relative position of a marked position 40 on a life-object surface from the detecting section for life activity, which is newly proposed as another exemplary embodiment (a second principle) related to the position monitoring section 46 regarding a detected point for life activity. It is assumed that a life-object surface is illuminated by an illumination lamp for general household use and light reflected diffusely on the life-object surface 41 is used for detection. However, another present exemplary embodiment is not limited to this, and may include a specific light source to illuminate the life-object surface 41.

The second principle to detect a position of a detected point, which is shown in this exemplary embodiment, uses a principle of the "trigonometry." That is, in the another exemplary embodiment shown in FIG. 22, the detecting section for life activity is provided with a plurality of camera lenses 42, and a plurality of two-dimensional photodetectors 43 (CCD sensors) disposed behind the plurality of camera lenses 42 and which can detect a two-dimensional image. Light emitted from the marked position 40 on the life-object surface (reflected diffusely from the marked position 40 of the life-object surface) is condensed at one point on a two-dimensional photodetector 43-1 due to the action of a camera lens 42-1. Similarly, light is condensed at one point on a two-dimensional photodetector 43-2 by the action of a camera lens 42-2. Accordingly, based on projected locations of the marked position 40 on the life-object surface, which are on the two-dimensional photodetectors 43-1 and 43-2 and on which images are formed, a distance 44 from surface points of an area where the detecting section for life activity is disposed to the life-object surface 41 and positions of the marked position 40 on the life-object surface in a lateral direction and a depth direction are calculated by use of the trigonometry.

Further, an exemplary embodiment shown in FIG. 22 has a feature in that the position monitoring section 46 regarding a detected point for life activity and the detecting section 101 for life activity are provided in an integrated manner. As a result of such an integrated provision, if the depth of the detected point 30 for life activity from the life-object surface is found in advance, a distance from the surface points 45 of an area where the detecting section for life activity is disposed to the detected point 30 for life activity can be estimated.

6.3) Photoelectric Conversion Method for Detection of Life Activity

The following describes a basic principle of the method (the second detection method) in (3) for extracting a life activity detection signal from a specified position in a life object by use of the second detection method described in section 6.1.3.

6.3.1) Utilization of Confocal System

As a first exemplary embodiment, a method using the confocal system as well as the technical device described in section 6.2.1 is described. A basic principle of this exemplary embodiment has a feature in that an optical principle that 'light emitted from one point in a life object to every direction is condensed again on one point at a confocal position or an image forming position' is applied and 'only the light condensed on the one point at the confocal position or the image forming position is extracted so as to detect light emitted from a corresponding point in the life object.'

One exemplary embodiment of an optical system for life activity detection in a signal detecting section configured to detect a life activity detection signal from a specific position in a life object based on this basic principle is shown in FIG. 23. Further, a theory of the optical system for life activity detection of FIG. 23 is shown in FIGS. 24 and 25.

The exemplary embodiment in FIG. 23 shows an optical system which can simultaneously measure life activities on three planar regions ($\delta$, $\alpha$, $\epsilon$) having different depths in a life object. That is, in an optical system constituted by an objective lens 31 and a detection lens 32, a two-dimensional liquid crystal shutter 51-1 is disposed at a position of an image forming surface corresponding to a planar region including a detected point $30\alpha$ for life activity in the life object. In the two-dimensional liquid crystal shutter 51-1, a pinhole-shaped light transmission section 56 can be set partially as shown in FIG. 25(a).

Accordingly, among light beams passing through the two-dimensional liquid crystal shutter 51-1, only a light beam passing through this light transmission section 56 is transmittable. As a result, only light emitted (reflected diffusely) from one point at the detected point $30\alpha$ for life activity in a confocal relationship (image-forming relationship) with this light transmission section 56 can reach a lateral one-dimensional alignment photo detecting cell 54-1 and a longitudinal one-dimensional alignment photo detecting cell 55-2.

Accordingly, a life activity detection signal detected from the detected point $30\alpha$ for life activity constituted by a two-dimensional plane including a point $\alpha$ is directly detected by the lateral one-dimensional alignment photo detecting cell 54-1 and the longitudinal one-dimensional alignment photo detecting cell 55-2 (the details thereof will be described later). On the other hand, a two-dimensional liquid crystal shutter 51-3 is disposed on an image forming surface corresponding to a detected point $30\delta$ for life activity which is located deeper than the detected point $30\alpha$ for life activity and which is constituted by a planar region including a point $\delta$. Hereby, a life activity detection signal in two dimensions detected from the detected point $30\delta$ is detected by a lateral one-dimensional alignment photo detecting cell 54-3 and a longitudinal one-dimensional alignment photo detecting cell 55-3.

Further, a two-dimensional liquid crystal shutter 51-2 is disposed on an image forming surface corresponding to a detected point $30\epsilon$ for life activity which is located shallower than the detected point $30\alpha$ for life activity and which is constituted by a planar region including a point $\epsilon$. Hereby, a life activity detection signal in two dimensions detected from the detected point $30\epsilon$ is detected by a lateral one-dimensional alignment photo detecting cell 54-2 and a longitudinal one-dimensional alignment photo detecting cell 55-2.

In FIG. 23, the two-dimensional liquid crystal shutter 51 capable of automatically opening and shutting a particular region is used for extraction of light (or an electromagnetic wave) obtained from the detected point 30 for life activity. However, the present exemplary embodiment is not limited to that, and a two-dimensional modulation element using EO (Electrical Optics) or AO (Acoustic Optics) may be used as the optical component capable of automatically opening and shutting a particular region. Still further, a fixed-type mechanical pinhole or slit incapable of automatically opening and shutting a particular region, or a very small refractor or diffraction element may be also usable.

In the meantime, as the detection and position control methods of a location to obtain a life activity detection signal in a life object (the operations (1) and (2) described in section 6.1.3), which methods are used together with the detecting section for life activity (see section 6.1.3 for the definition of the term) including an optical system for life activity detection shown in FIG. 23, a method for "detecting a cross-sectional image in an life object" shown in FIG. 20 and FIG. 21 and described in section 6.2.1 is adopted.

If a two-dimensional changing pattern of diffused reflection light amount is detected from a specific cross section in this life object, then it is possible to find not only positions of a neuron cell body 1 and an axon 2 in a neuron and a position of a neuromuscular junction 5 (see FIG. 1) on the specific cross section, but also an arrangement of a muscle cell 6 and a glial cell (Astrocyte).

In view of this, light (or an electromagnetic wave) emitted (reflected diffusely) from a location where a life activity is desired to be detected on a specific cross section as a measurement subject (e.g., a specific position in a neuron cell body or an axon) is condensed by the objective lens 31 and the detection lens 32, and the light is extracted at a condensed position (an image forming position or a confocal position for the detected point 30 for life activity).

A principle to detect a life activity detection signal from a specific position in the life object by use of the optical system for life activity detection as illustrated in FIG. 23 will be described here with reference to FIG. 24 in detail. In FIG. 24, light emitted (reflected diffusely) from the detected point 30α for life activity is condensed (imaged) at a spot μ on the two-dimensional liquid crystal shutter 51. Therefore, the liquid crystal shutter is locally opened only at this spot so as to form a light transmission section 54μ in the two-dimensional liquid crystal shutter. Similarly, a spot ζ on which light emitted (reflected diffusely) from the detected point 30β for life activity is condensed (imaged) is taken as a light transmission section 56ζ in the two-dimensional liquid crystal shutter.

In the meantime, light emitted (reflected diffusely) from a position η different from the above spots (see the optical paths 33 of detection light shown in a "wavy line" in FIG. 24) spreads out greatly over the two-dimensional liquid crystal shutter 51, and therefore, most of the light is blocked by the two-dimensional liquid crystal shutter 51. Thus, only a very slight amount of the light passes through the light transmission section 56μ in the two-dimensional liquid crystal shutter, but the amount of the light passing therethrough is very small. As a result, the light is buried among noise components on the longitudinal one-dimensional alignment photo detecting cell 55.

As described above, by "selectively extracting light or an electromagnetic wave passing through a particular region" in an image forming surface or at a confocal position corresponding to a particular cross section in a life object, it is possible to selectively extract a life activity detection signal from a particular position in the life object. In view of this, by changing the arrangement of an optical element for selectively extracting light or an electromagnetic wave via the particular region, it is possible to simultaneously detect life activities in a plurality of regions at different positions along a depth direction in a life object.

In that case, the light or electromagnetic wave obtained from the life object is split into a plurality of light beams or electromagnetic waves by light amount, and optical elements for selectively extracting light or an electromagnetic wave passing through a particular region are placed on respective image forming surfaces (confocal positions) of the plurality of light beams (electromagnetic waves) thus split.

In FIG. 23, the two-dimensional liquid crystal shutter 51-1 is disposed on an image forming surface corresponding to the detected point 30α for life activity and the two-dimensional liquid crystal shutters 51-3 and 51-2 are disposed on respective image forming surfaces corresponding to the detected points 30δ and 30ε for life activity.

In the meantime, in FIG. 23, the light or electromagnetic wave obtained from the life object is split by a grating 37 into light beams (electromagnetic waves) traveling in three directions, but this is not limited in particular. The light or electromagnetic wave obtained from the life object can be split into light beams (electromagnetic waves) traveling in five directions or light beams (electromagnetic waves) traveling in seven directions by changing the design of the grating 37. Further, as light amount splitting means for splitting the light or electromagnetic wave obtained from the life object, a half mirror, a half prism, or a polarizing mirror or prism may be used.

The following describes a method for directly obtaining a life activity detection signal. As shown in FIG. 24, after only the light or electromagnetic wave obtained from a particular detected point 30 for life activity in the life object is extracted by use of the two-dimensional liquid crystal shutter 51, a photodetector is disposed on a condensed plane (a re-imaging surface) constituted by a condensing lens 52, and a life activity detection signal is obtained by use of photoelectric conversion. Alternatively, a two-dimensional light detecting element (light sensing array) such as a CCD sensor may be disposed here.

However, in a case of attempting to detect a dynamical life activity rapidly changing in the life object (e.g., "to simultaneously trace respective action potential changes in a plurality of neurons through time") as the detection of membrane potential changing in a nervous system as shown in Table 6, for example, the CCD sensor cannot achieve a sufficient response speed.

In contrast, in exemplary embodiments shown in FIGS. 23 to 25, one-dimensional alignment photo detecting cells 54 and 55 capable of tracing high-speed changes through time are combined in a matrix manner so that the high-speed changes on a two-dimensional surface can be detected at the same time and in real time. More specifically, light or an electromagnetic wave passing through the condensing lens 52 is split into pieces by light amount, and respective beams (electromagnetic waves) are directed toward the lateral one-dimensional alignment photo detecting cell 54 and toward the longitudinal one-dimensional alignment photo detecting cell 55. In FIG. 23, for splitting, by light amount, of the light passing through the condensing lens 52, a grating 53 for light distribution in which a 0th-order light transmittance is approximately 0% and a ratio of a +1st-order light transmittance to −1st-order light transmittance is approximately 1:1 is used. However, the present exemplary embodiment is not limited to this, and a half mirror, a half prism, or a polarizing mirror or prism may be used as the light amount splitting means.

The following explains about a method for obtaining a life activity detection signal by combining a lateral one-dimensional alignment photo detecting cell 54 and longitudinal one-dimensional alignment photo detecting cell 55 having alignment directions inclined to each other, with reference to FIG. 25.

Photo detecting cells a to j are arranged in a one-dimensional direction (lateral direction), and respective signal of the photo detection cells a to j can be detected independently at the same time. Although not illustrated here, respective preamps and signal processing circuits are connected to the photo detecting cells a to j independently, so that respective high-speed changes of detection light amounts of the photo detecting cells a to j can be monitored in parallel through time. Since the changes of the detection light amounts of the respective photo detecting cells a to j can be detected in parallel, it is possible to detect a very rapid and slight change occurring at only one place without overlooking.

Further, in the lateral one-dimensional alignment photo detecting cells shown in FIG. 25(b), the parallel changes of the detection light amounts in the one-dimensional direction can be detected through time. Still further, a change of a detection light amount at one point in a two-dimensional plane can be extracted in combination with pieces of information on changes of detection light amounts obtained from longitudinal one-dimensional alignment photo detecting cells k to t, which are aligned in an alignment direction inclined toward that of the lateral one-dimensional alignment photo detecting cells (in a non-parallel relationship).

That is, "a plurality of photo detecting cell groups capable of independently detecting signals at the same time (the lateral one-dimensional alignment photo detecting cell 54 and the longitudinal one-dimensional alignment photo detecting cell 55) are disposed so that respective alignment directions of the photo detecting cells are inclined to each other (not in parallel), and a plurality of detection signals obtained from the respective photo detecting cell groups (detection signals obtained from the photo detecting cells a to j and the photo detecting cells k to t in the respective groups) are combined in a matrix manner." Accordingly, a high-speed change of a detection signal obtained only from a specific spot within the detected point 30 for life activity configured in two dimensions can be detected independently and continuously through time. This is a feature of the present exemplary embodiment shown in FIG. 25.

In the meantime, the alignment directions of the photo detecting cells in the respective photo detecting cell groups are set at right angles to each other in (b) and (c) of FIG. 25, but the present exemplary embodiment is not limited to this, and an angle of inclination between the alignment directions of the photo detecting cells may largely differ from 90 degree, as long as the arrangement directions of the photo detecting cells are not in parallel.

The following describes this more specifically, with reference to FIG. 25. At first, it is assumed that five neuron cell bodies are found in a detected point 30 for life activity as a result of analysis of an internal structure as described in (1) of section 6.1.3 performed with the use of the optical system (see section 6.2.1 illustrated in FIGS. 20 and 21. Then, the position control described in (2) of section 6.1.3 is performed, and even if a life object (e.g., an examinee) for measurement moves to some extent, the objective lens 31 is also moved in conjunction with the movement of the life object so that a location subjected to the detection of life activity is fixed relatively.

Subsequently, as the extract operation of a life activity signal shown in (3) of section 6.1.3, shutters are opened locally at image forming positions on the two-dimensional liquid crystal shutter 51 corresponding to the locations of the five neuron cell bodies in the detected point 30 for life activity, so as to form light transmission sections 56ζ, θ, λ, μ and ξ in the two-dimensional liquid crystal shutter.

Then, due to the operation of the condensing lens 52, respective light beams passing through the light transmission sections 56ζ, θ, λ, μ and ξ in the two-dimensional liquid crystal shutter are condensed at a point ζ' in the photo detecting cell b, a point θ' in the photo detecting cell d, a point λ' in the photo detecting cell f, a point μ' in the photo detecting cell h, and a point in the photo detecting cell j on the lateral one-dimensional alignment photo detecting cell 54. Similarly, respective light beams passing through the light transmission sections 56λ, ξ, θ, μ, and ζ in the two-dimensional liquid crystal shutter are condensed at a point λ' in the photo detecting cell l, a point ξ' in the photo detecting cell n, a point θ' in the photo detecting cell p, a point μ' in the photo detecting cell r, and a point ζ' in the photo detecting cell t on the longitudinal one-dimensional alignment photo detecting cell 55.

For example, when a neuron having an image-forming relationship with the light transmission section 56μ in the two-dimensional liquid crystal shutter fires an action potential, intensity of convergence light at the position μ' changes instantly in response to the action potential. As a result, detection signals having a waveform similar to that in FIG. 3 is obtained from the photo detecting cells h and r. As such, by knowing from which photo detecting cells in the lateral one-dimensional alignment photo detecting cell 54 and in the longitudinal one-dimensional alignment photo detecting cell 55, detection signals having a waveform similar to that in FIG. 3 can be obtained, it is found which neuron in the detected point 30 for life activity fires an action potential.

Then, as will be described later, pulse counting is performed in the life activity detection circuit and the number of action potentials in a specific time per neuron is calculated to detect an activation state.

The above explanation deals with the action potential of the neuron (corresponding to the "membrane potential changing in nervous system" in Table 6) as an example of the detection of life activity. However, the present exemplary embodiment is not limited to this, and if a path of the axon 2, the neuromuscular junction 5, or the muscle cell 6 is set so as to correspond to an image forming position on the light transmission section 56 in two-dimensional liquid crystal shutter, a signal transmission state in the axon 2 or a signal transmission state to the muscle can be measured.

In the exemplary embodiment described above, respective sizes (aperture sizes) of the light transmission sections 56ζ, θ, λ, μ and ξ in the two-dimensional liquid crystal shutter are set relatively small, and a life activity per small region on the detected point 30 for life activity such as one neuron cell body 1 in the neuron or one muscle cell 8, axon 2 or neuromuscular junction 5 is detected. Other applied embodiments of this exemplary embodiment are as follows: (1) in FIG. 23, all two-dimensional liquid crystal shutters 51-1, 51-2, 51-3 may be disposed only at confocal positions or image forming positions corresponding to locations having the same depth (e.g., at the detected point 30α for life activity), so as to detect life activities in a two-dimensional direction corresponding to fixed locations having a specific depth; and (2) in FIG. 25, respective sizes (aperture sizes) of the light transmission sections 56ζ, θ, λ, μ and ξ in the two-dimensional liquid crystal shutter may be made larger, so that life activities in a relatively large range on the detected point 30α for life activity are detected. In this case, every one of the condensed spots ζ', θ', λ', μ', and ξ' in FIGS. 25 (b) and (c) includes activity signals related to a plurality of neurons in the detected point 30α for life activity. Therefore, even if a pulsed signal corresponding to one action potential is detected at one of the condensed spots, a single neuron firing the action potential cannot be specified. However, by detecting the occurrence frequency of the pulsed signal corresponding to the action potential in the condensed spot, an activation state in a particular region constituted by a plurality of neurons in the detected point 30α for life activity can be detected.

This applied embodiment makes it possible to grasp life activities slightly in broad perspective (as compared with an activity per neuron). An example of a specific purpose of this detection method is activity detection per column in the cerebral cortex.

When the respective sizes (aperture sizes) of the light transmission sections 56$\zeta$, $\theta$, $\lambda$, $\mu$ and $\xi$ in the two-dimensional liquid crystal shutter are made larger, action potential signals from neurons at positions having different depths leak easily. Here, a thickness of the cerebral cortex in a human is slightly smaller than 2 mm, so that there is a low possibility that an action potential signal is obtained from a position at a shallower side or a deeper side than the cerebral cortex in a depth direction. Accordingly, if activities of neurons within 2 mm, which is a thickness of the cerebral cortex, are detected in a mass in this applied embodiment, the problem that action potential signals leak out from the positions having different depths beyond the range will be solved (because no action potential signal occur at the shallower side or the deeper side than that).

Further, the cerebral cortex is constituted by columns of about 0.5 to 1.0 mm in width, and it is said that there is relatively a little signal transmission between adjacent columns. Accordingly, when the respective sizes (aperture sizes) of the light transmission sections 56$\zeta$, $\theta$, $\lambda$, $\mu$ and $\xi$ in the two-dimensional liquid crystal shutter are set according to one column size (about 0.5 to 1.0 mm), an activation state per column (e.g., an action-potential detection-frequency characteristic per column unit) can be detected.

On the other hand, in the cerebral cortex, there are many parts in which information processing is performed per column unit. In view of this, the present exemplary embodiment can effectively solve how the information processing is performed per column unit and find its details for the first time. In addition to the detection method as described above, the present exemplary embodiment has such a technical device that: (3) one two-dimensional liquid crystal shutter 51 blocks light at an image forming position of a column adjacent to a target column located at a light transmission section 56 in the two-dimensional liquid crystal shutter, so as to prevent detection of an action potential signal from the adjacent column, and "another light transmission section 56 in another two-dimensional liquid crystal shutter 51" is disposed at the image forming position of the adjacent column, so that an action potential signal from the adjacent column is detected by another photo detecting cells 54 and 55; and (4) by use of action potential signals obtained from columns adjacent to each other by different photo detecting cells 54 and 55 in (3), cross talk (leak of a detection signal) from the adjacent column is removed by computing process of the signal. This yields an effect of improving signal detection accuracy per column unit by removing cross talk from an adjacent column.

The above explanation deals with the detection method in which a detection range of a measurement subject is about 10 to 1000 μm, which is relatively narrow area, at a corresponding image forming position of the light transmission section 56 in the two-dimensional liquid crystal shutter. In contrast, in a case where the oxygen concentration change in blood in surrounding areas in Table 6 is detected by use of the optical system for life activity detection as illustrated in FIG. 23, it is necessary to set the detection range more widely. In addition, it is necessary to further broaden the respective sizes (aperture sizes) of the light transmission sections 56$\zeta$, $\theta$, $\lambda$, $\mu$ and $\xi$ in the two-dimensional liquid crystal shutter in conformity with the detection area thus set widely. In this case, although not illustrated in FIG. 23, a plurality of optical systems for life activity detection shown in FIG. 23 are provided, and color filters for selectively transmitting light having wavelengths of 780 nm, 805 nm, and 830 nm, respectively, are also disposed in the middle of the optical paths 33 of the detection light. Then, light beams having respective wavelengths of 780 nm, 805 nm, and 830 nm are detected separately, and a ratio between them in terms of detection light amount is calculated. A detection method of life activity in this case is performed (1) according to a time dependent variation of the ratio in terms of detection light amount between the detection light beams having respective wavelengths of 780 nm, 805 nm, and 830 nm, or (2) by comparing values obtained during the detection with preliminary measured values (reference values) of the ratio in detection light amount between the detection light beams having respective wavelengths of 780 nm, 805 nm, and 830 nm.

6.3.2) Extraction of Spatial Variations and Time Dependent Variations by Imaging Optical System As another applied embodiment with respect to the method described in section 6.3.1, the following describes an optical system for life activity detection which does not require such a high spatial resolution and which is suitable for a case of easily (generally) detecting a life activity at a low cost by use of a simplified optical system for life activity detection.

In the applied embodiment of the optical system for life activity detection described below, a photodetector 36 is disposed at an image forming position corresponding to a detected point 30 for life activity in a life object (at a location where a photo detecting cell corresponding to a detecting section thereof is placed), as shown in FIG. 26. An imaging lens 57 is automatically moved in an optical axial direction in accordance with movement of the life object (an examinee) so that the photodetector 36 always comes at the image forming position corresponding to the detected point 30 for life activity even if the life object (the examinee) moves.

More specifically, when the life object (the examinee) moves and the photodetector 36 comes off from the image forming position, a direction and a moving amount of the life object (the examinee) are estimated (the alignment operation corresponding to (1) and (2), partially) by use of the method described in section 6.2.2 and FIG. 22. If a necessary correction amount is found as a result of that, the imaging lens 57 is moved in the optical axial direction automatically to be corrected, as position control corresponding to the remaining operation of (2) in section 6.1.3.

In an exemplary embodiment shown in FIG. 26, the imaging lens 57 works in conjunction with a forwarding motor (not illustrated in the figure), and the imaging lens 57 moves along the optical axial direction in accordance with the drive operation of the forwarding motor.

Here, the position detection of a measurement subject as described in FIG. 22 uses general visible light. On the other hand, the optical system for life activity detection uses near infrared light (or infrared light). In view of this, a color filter 60 is disposed in the middle of the optical paths 33 of the detection light so that the visible light used for the position detection of the measurement subject is not mixed into the optical system for life activity detection as noise components.

Here, assume a case where a neuron fires an action potential at the detected point 30α for life activity. When the neuron fires an action potential to change the membrane potential 20 as shown in FIG. 3, light absorption in the wavelengths of near infrared light (or infrared light) described in section 4.7 occurs for a short time. As a result, diffused reflection intensity (or transmitted light intensity) of light having the corresponding wavelength at the position α decreases. As shown in FIG. 26(*a*), when the photodetector 36 is disposed at an image forming position corresponding to the detected point 30 for life activity, a life activity detection signal 58 corresponding to the detected point 30 appears only at a photo detecting cell W located at the confocal (imaging forming) position corresponding to the position α in the photodetector 36.

If a neuron fires an action potential at a position δ away from the detected point 30 for life activity (e.g., a location deeper than the detected point 30 for life activity viewed from the life-object surface 41), the optical paths 33 of the detection light reflected diffusely at the position δ (or passing through the position δ) is once condensed at a position ahead of the photodetector 36, and then large-sized detection light having a cross-sectional spot size is projected over a wide area on the photodetector 36. As a result, not only life activity detection signals 58 are detected in a large range from photo detecting cells U to X in the photodetector 36, but also the detection signal amplitude of a life activity detection signal 58 detected from one photo detecting cell is largely reduced in comparison with FIG. 26(*a*).

In view of this, only when a large life activity detection signal 58 having a large detection signal amplitude is obtained only from one photo detecting cell, it is judged that a life activity on the detected point 30 for life activity is detected, and the life activity detection signal 58 is extracted.

On the other hand, if action potentials are fired at non-image forming positions like FIG. 26(*b*), the life activity detection signals 58 detected in the respective photo detecting cells U to X have a very small detection signal amplitude in most cases, so that they cannot be detected and are buried among noise components.

The above explanation deals with a case where the membrane potential changing in the nervous system in Table 6 is detected as the life activity detection signal 58. The present exemplary embodiment is not limited to this, and in a case where the oxygen concentration change in blood in surrounding areas in Table 6 is detected, it is necessary that a plurality of optical systems for life activity detection shown in FIG. 26 be disposed, and color filters 60 for selectively transmitting light having wavelengths of 780 nm, 805 nm, and 830 nm, respectively, be disposed in the middle of the optical paths 33 of the detection light. Then, light beams having respective wavelengths of 780 nm, 805 nm, and 830 nm are detected separately, and a ratio between them in detection light amount is calculated per photo detecting cell.

When a life activity detection signal 58 is obtained from the detected point 30 for life activity located at an image forming position corresponding to the photodetector 36 as shown in FIG. 26(*a*), a ratio of a detection light amount from a specific photo detecting cell changes prominently. Therefore, only a detection signal having a prominent ratio in detection light amount, in comparison with the other photo detecting cells, is extracted as a life activity detection signal 58. Adversely, when respective ratios in detection light amount are not so different between adjacent photo detecting cells U, V, and W, they may be in the state of FIG. 26 (*b*). In view of this, signals of these cells are not extracted as the life activity detection signal 58.

Thus, (A) when detection light amounts obtained from neighboring photo detecting cells are compared with each other and a value (or a ratio) of a specific photo detecting cell is largely changed (has a high spatial resolution in the photodetector 36), only a signal component of the specific photo detecting cell is extracted as the life activity detection signal 58. Alternatively, the life activity detection signal 58 may be extracted (B) according to a time-dependent variation, in each photo detecting cell, of a ratio in detection light amount between the detection light beams having respective wavelengths of 780 nm, 805 nm, and 830 nm, or (C) by comparing values obtained during detection with preliminarily measured values (reference values) of the ratio in detection light amount of the detection light beams having respective wavelengths of 780 nm, 805 nm, and 830 nm.

Further, in addition to that, the optical system for life activity detection as illustrated in FIG. 26 may be applied to the temperature change measurement by the thermography in Table 6. In this case, the optical system for position detection as illustrated in FIG. 22 may be also used together for alignment. That is, as shown in FIG. 26, when that part inside the life object which is deeper than the life-object surface 41 is activated, the bloodstream increases and the temperature of the life-object surface 41 increases locally. A temperature distribution of the life-object surface 41 at this time is measured, and an activation state at the detected point 30 for life activity is measured indirectly. In this case, the temperature distribution of the life-object surface 41 is extracted as a life activity detection signal 58.

In a case where at least one of the "membrane potential changing in the nervous system" and the "oxygen concentration change in blood in surrounding areas" is detected, a CCD sensor can be generally used as the photodetector 36 of FIG. 26. In a case where a local high-speed change in the detected point 30 for life activity is detected continuously (through time), a response speed of the CCD sensor is not enough for the detection. In this exemplary embodiment, preamps are provided for respective photo detecting cells 38-01 to 38-15 disposed in a two-dimensional manner, so that detection light amounts of the photo detecting cells 38-01 to 38-15 are detected in parallel at the same time and a local high-speed change in the detected point 30 for life activity is detected continuously (through time).

A configuration on the photodetector 36 in such a case is shown in FIG. 27. A photo detecting cell group constituted by photo detecting cells 38-01 to photo detecting cells 38-05 is a one-dimensional alignment photo detecting cell, similarly to FIGS. 25(*b*) and (*c*). The photo detecting cells 38-01 to 38-05 are individually and directly connected to respective front parts 85 of the life activity detection circuit.

The photo detecting cell 38 and its corresponding front part 85 of the life activity detection circuit are formed in a monolithic manner on a semiconductor chip of the photodetector 36 (by patterning together on the same semiconductor chip). Alternatively, the photo detecting cell 38 and its corresponding front part 85 of the life activity detection circuit may be formed in a hybrid manner in which they are constituted by separate semiconductor chips and disposed side by side on a surface of the photodetector 36.

The front part 85 of the life activity detection circuit corresponding to the photo detecting cell 38 includes a preamp and a simple signal processing circuit (a pulse counting circuit described in section 6.4) incorporated therein, and its output is connected to a detection signal line 62 output from a front part and a rear part of the detecting circuit. Since the photo detecting cells 38 are connected to their corresponding front parts 85 of the life activity detection circuit in the photodetector 36, a life activity detection signal can be extracted stably and accurately without receiving any influence of disturbance noise even if the signal is very weak.

Adjacent to the photo detecting cell group constituted by the photo detecting cells 38-01 to the photo detecting cells 38-05, a photo detecting cell group constituted by photo detecting cells 38-11 to photo detecting cells 38-15 is disposed with some space, and each of the photo detecting cells 38 is connected to its corresponding front part 85 of the life activity detection circuit. With the use of the photo detecting cells 38-01 to the photo detecting cell 38-15 thus disposed in a two-dimensional manner, each life activity occurring in two dimensions of the detected point 30 for life activity can be detected independently at high speed and continuously.

On the photodetector 36 shown in FIG. 27, the front parts 85 of the life activity detection circuit corresponding to the photo detecting cells 38 are disposed in a large area. As a technical device to prevent detection light from the detected point 30 for life activity from being project on this area, as shown in FIG. 28, a lenticular lens 68 is disposed in the middles of the optical paths 33 of the detection light (between the imaging lens 57 and the photodetector 36). The lenticular lens 68 has a shape in which a plurality of cylindrical lens (in each of which a lens surface partially has a column shape) are provided in line, and has a function to locally change the optical paths 33 of the detection light.

Here, in order to simplify the explanation, FIG. 28 illustrates only optical paths of light rays passing through a center of the imaging lens 57 among the optical paths 33 of detection light rays emitted (reflected diffusely or transmitted) from respective spots on the detected point 30 for life activity. By use of optical refraction by the lenticular lens 68 in FIG. 28, the detection light rays emitted from the respective spots on the detected point 30 for life activity reach the photo detecting cells 38-2 to 38-4. However, the front parts 85 of the life activity detection circuit corresponding to the photo detecting cells 38 are configured not to be illuminated with these detection light rays.

In the meantime, the exemplary embodiment illustrated in FIG. 28 employs the lenticular lens 68, so that light (or an electromagnetic wave) from the detected point 30 for life activity is projected not on a region where the front parts 85 of the life activity detection circuit corresponding to the photo detecting cells 38 in the photodetector 36 are provided, but only on a region where the photo detecting cells 38 are provided.

However, the present exemplary embodiment is not limited to this, and other polarizing elements or partial light-blocking elements for projecting light only on a particular region in the photodetector 36 may be disposed on the way of the optical paths 33 of the detection light to the photodetector 36. As an example of the other polarizing elements mentioned above, a blazed diffraction element (having an inclination in a specific region) (e.g., a diffraction grating having a characteristic that the transmittances of 0th-order light and −1st-order light are almost 0%, and the transmittance of +1st-order light is almost 100%) can be used.

6.3.3) Method for Detecting High-Speed Change of Nuclear Magnetic Resonance Property As another applied embodiment of this exemplary embodiment, a method for detecting a high-speed change of a Nuclear Magnetic Resonance property is described below with reference to FIG. 29 and FIG. 30.

When one neuron fires an action potential, its membrane potential changes temporarily, which causes absorption of electromagnetic waves in the range of chemical shift values described in section 5.2 due to Nuclear Magnetic Resonance (excitation by magnetic resonance in a hydrogen nucleus) and emission of an electromagnetic wave based on excitation relaxation occurring just after that.

On the other hand, when a specific region (a relatively wide region constituted by a plurality of neurons) in the nervous system is activated, the plurality of neurons in the specific region repeats firing of their action potentials in a short time. In view of this, an activation state in the specific area in the nervous system can be detected as a life activity detection signal by using MRI or fMRI not as a single action potential in one neuron, but as a signal averaged in a specific time range in a specific spatial region. Accordingly, in an alternative exemplary embodiment of the embodiment described in section 6.3.1 or 6.3.2, a local change of the Nuclear Magnetic Resonance property in the range of chemical shift values described in section 5.2 is detected by use of MRI (Magnetic Resonance Imaging) or fMRI (functional MRI) and thereby a life activity detection signal corresponding to the membrane potential changing of the neuron is detected.

However, in this alternative exemplary embodiment, a temporal resolution of the life activity detection signal which can be detected has only a level equal to that of the current MRI or fMRI. In this regard, since the temporal resolution and the spatial resolution are low in Conventional Technique 2, a single action potential of one neuron cannot be detected.

FIG. 29 shows another applied embodiment which can solve this problem and detect an internal high-speed change of the Nuclear Magnetic Resonance property. In FIG. 29(*a*), a plane where a (superconducting) magnet 73 and a coil 72 for magnetic field preparation are provided, a plane where an excitation coil 74 is provided, and a plane on which a two-dimensionally arranged cell array 71 for detecting a change of the Nuclear Magnetic Resonance property are arranged at right angles to each other. Herein, similarly to the conventional MRI or fMRI, the (superconducting) magnet 73 is used for application of a DC magnetic flux density from the outside. Furthermore, a coil 72 for magnetic field preparation is disposed for spatial distribution correction of the magnetic flux density to form a uniform magnetic flux density in a part 75 of an organism to be detected (the head of an examinee) and for fine adjustment of a value of the DC magnetic flux density in accordance with the chemical shift values described in section 5.2. This coil 72 for magnetic field preparation may be used in the conventional MRI device or fMRI device in some cases.

Here, the head of a human body is mainly assumed a target for the detection of life activity as a target organism for the measurement in the applied embodiment shown in FIG. 29. However, the applied embodiment is not limited to this, and the detection of life activity may be performed on visceral organs such as the heart in the human body or an inside of limbs. Further, the organism is not limited to mammals such as dogs or cats, and any organisms including microorganisms may be set at the part 75 of the organism to be detected.

Further, this applied embodiment has a feature that "the part 75 of an organism to be detected (the head of an examinee) can be taken in or out through the excitation coil 74." Accordingly, by increasing the excitation coil 74 in size, the detection of life activity can be performed on an inside of a large organism like a human. This also yields such an advantage that a surface to detect a high-speed change of the Nuclear Magnetic Resonance property (a plane where the two-dimensionally arranged cell array 71 for detecting the change of the Nuclear Magnetic Resonance property is disposed) can be used freely. The following describes this situation more specifically. In order to detect the life activity, it is necessary to put a part 75 of the organism to be detected in or out of a region where respective DC magnetic flux densities formed by the (superconducting) magnet 73 and the coil 72 for magnetic field preparation are distributed over, and the following conditions are required: a) a space to provide the part 75 of the organism to be detected is secured in the area where the DC magnetic flux densities are distributed over; and b) a space where the part 75 of the organism to be detected can be put in and out is secured.

These conditions are also required even in the conventional MRI device or fMRI device. However, in these conventional devices, the space where the part 75 of the organism to be detected can be put in and out is often provided at a detecting-coil side (not illustrated in FIG. 29), which is provided for detection of a change of the Nuclear Magnetic Resonance property.

In the meantime, as shown in the applied embodiment of FIG. 29, there is no space where the part 75 of the organism to be detected can be put in and out, on a plane on a side of the (superconducting) magnet 73 for generating a DC magnetic flux density. If the space where the part 75 of the organism to be detected is put in and out is set at a side of a plane to detect a change of the Nuclear Magnetic Resonance property (the plane where the two-dimensionally arranged cell array 71 for detecting a change of the Nuclear Magnetic Resonance property is disposed) like in the conventional MRI device or fMRI device, the physical arrangement on this plane is largely restricted, thereby largely impairing the degree of freedom of the detection method of a change of the Nuclear Magnetic Resonance property. In contrast, the arrangement in FIG. 29 largely improves the degree of freedom of the detection method of a change of the Nuclear Magnetic Resonance property.

However, since a length (circumference) around the excitation coil 74 is longer in the arrangement of FIG. 29, a resistance value in the excitation coil 74 rises, thereby causing a problem that a frequency characteristic of the excitation coil 74 easily decreases. This applied embodiment has such a technical device that the cross section of a wire rod constituting the excitation coil 74 is widened so as to decrease the resistance value, thereby solving the above problem.

The applied embodiment illustrated in FIG. 29 has the following features: a plurality of detection cells 80 for detecting a change of the Nuclear Magnetic Resonance property, each including a detecting coil 84 for detection of life activity having a circumference shorter than that of the excitation coil 74, are disposed two-dimensionally in an array form (see FIG. 29(*a*)); and one detection cell 80 for detecting a change of the Nuclear Magnetic Resonance property is configured to include a front part 85 of the life activity detection circuit, so as to have an amplification function (a preamp function) of a detection signal obtained from the detecting coil 84 and a signal processing function equivalent to a front-part level (see FIG. 29(*b*)).

Here, when a single circumference of the detecting coil 84 is set to be shorter than the excitation coil 74, the resistance value in the detecting coil 84 is reduced and a frequency characteristic of the signal detection by the detecting coil 84 is improved. This makes it possible to detect a life activity detection signal changing at high speed more accurately.

In the meantime, since a preamp is provided outside a detecting coil (not illustrated in FIG. 29) in the conventional MRI device or fMRI device, disturbance noises are mixed in through a cable between the detecting coil and the preamp. On the other hand, in this applied embodiment, one detection cell 80 for detecting a change of the Nuclear Magnetic Resonance property is configured to have the preamp function to a detection signal obtained from each detecting coil 84 and the signal processing function equivalent to the front-part level, so that the mixture of disturbance noises is reduced and a life activity detection signal can be obtained stably and accurately.

This feature is described below, more specifically. As shown in FIG. 29(*a*), two-dimensionally arranged cell arrays 71 for detecting a change of the Nuclear Magnetic Resonance property, which is one type of a life activity detection signal, are disposed at both of a shallower side (not illustrated) and a deeper side of a part 75 of an organism to be detected (the head of an examinee), on the page space. In each of the two-dimensionally arranged cell arrays 71 for detecting a change of the Nuclear Magnetic Resonance property, detection cells 80 for detecting a change of the Nuclear Magnetic Resonance property, each having a configuration as illustrated in FIG. 29(*b*), are arranged two-dimensionally so as to form an array configuration.

Here, as shown in FIG. 29(*b*), a power line and ground line 81 to be provided in a front part 85 of the life activity detection circuit and a transmission line 82 for system clock+time stamp signal are disposed so as to be at right angles to the detecting coil 84. The reason is as follows: such an arrangement prevents not only transmission signals (a system clock and a time stamp signal) flowing through the transmission line 82 for system clock+time stamp signal from leaking to the detecting coil 84, but also the power line and ground line 81 from affecting the detecting coil 84 adversely. On the other hand, in this applied embodiment, a timing of detection of a change of the Nuclear Magnetic Resonance property (detection of life activity) is switched into an output timing of a life activity detection signal output from the front part 85 of the life activity detection circuit and vice versa, thereby improving detection accuracy of the detection of a change of the Nuclear Magnetic Resonance property (detection of life activity). Alternatively, as shown in FIG. 29(*b*), if the output line 83 for a life activity detection signal is disposed at right angles to the detecting coil 84, it is possible to prevent an output signal from the output line 83 for a life activity detection signal from leaking to the detecting coil 84. This makes it possible to simultaneously perform the detection of a change of the Nuclear Magnetic Resonance property (detection of life activity) and the output of a life activity detection signal, so that the detection of a change of the Nuclear Magnetic Resonance property (detection of life activity) can be performs over a long period of time.

When one neuron fires an action potential, its membrane potential changes temporarily, which causes absorption and emission of an electromagnetic wave corresponding to the chemical shift value described in section 5.2. An absorption/emission characteristic of the electromagnetic wave changes in accordance with the action potential pattern of FIG. 3, and its change signal appears in the detecting coil 84.

Although omitted in FIG. 29(*b*), an end part of this detection coil 84 is directly connected to a preamp in the front part 85 of the life activity detection circuit. Accordingly, when a life activity detection signal corresponding to the action potential pattern occurring in one neuron appears in the detecting coil 84, the life activity detection signal is amplified by the preamp. The signal thus amplified passes through a band-pass filter (or a detector circuit) tuned up with electromagnetic wave frequencies supplied from an excitation coil 74 in the front part 85 of the life activity detection circuit so that only an electromagnetic wave component corresponding to the chemical shift value is taken out, and the signal is converted into a digital signal by an A/D converter (Analog to Digital Converter) and temporarily stored in a memory section. The S/N ratio of the detection signal is largely improved due to the operation of the band-pass filter (or the detector circuit) as such. However, this detection signal is very weak, and therefore is subjected to signal processing (front-part processing) to increase the detection accuracy more in the front part 85 of the life activity detection circuit.

That is, since an action potential pattern to occur in a neuron is determined in advance as shown in FIG. 3, the action potential pattern corresponding to that is stored in the front part 85 of the life activity detection circuit. Then, a pattern matching calculation is performed between this detection pattern corresponding to the action potential stored in advance and a detection signal temporarily stored in the memory section (note that standardization processing of an amplitude value is performed at this time) at different checking timings. When a calculation result of the pattern matching is larger than a specific value, it is considered that an action potential of the neuron has occurred, and a "detection time" and a "detection amplitude value" are temporarily stored in the memory.

As has been described in section 1.3, the term 24 of nerve impulse in FIG. 3 is about 0.5 to 4 ms. Accordingly, in order to perform the signal processing on this change accurately and efficiently during the term, it is desirable that a system clock frequency transmitted in the transmission line 82 for system clock+time stamp signal in FIG. 29(*b*) be in a range from 10 kHz to 1 MHz. A time stamp signal is given as a counter value incremented by 1 per each clock along this system clock frequency ("1" is added per each system clock). Further, this time stamp signal (this binary counter value is synchronized with the timing of the system clock and transferred along NRZI (Non Return to Zero Inverting)) and the system clock repeated specific number of times are arranged alternately through time and transferred. A time when a top bit of this time stamp signal has arrived at the front part 85 of the life activity detection circuit is taken as a "time indicated by the time stamp signal" and all the detection cells 80 for detecting a change of the Nuclear Magnetic Resonance property are synchronized with this time.

Initially, in the front part 85 of the life activity detection circuit, the "detection time" and the "detection amplitude value" of the action potential of the neuron are temporarily stored in the memory in response to a transmission signal from the transmission line 82 for system clock+time stamp signal. The information thus stored in the memory for a specific period of time is output to the output line 83 for a life activity detection signal at a timing designated from the outside.

Here, in the output line 83 for a life activity detection signal, an output timing is assigned to each detection cell 80 for detecting a change of the Nuclear Magnetic Resonance property, and the signal temporarily stored in the memory is transmitted over the output line 83 for a life activity detection signal at the timing thus designated in advance.

As such, signals from all the detection cells 80 for detecting a change of the Nuclear Magnetic Resonance property collected in the output line 83 for a life activity detection signal are used for: (a) achievement of high accuracy and high reliability of a detection signal based on a statistic process; and (b) calculation of an action-potential firing (or activated) area in a life object. The above (a) and (b) are performed in a rear part (not illustrated in the figure) of the life activity detection circuit.

The following describes the former process at first. Every signal from all the detection cells 80 for detecting a change of the Nuclear Magnetic Resonance property includes a "detection time" of an action potential. Accordingly, when an action potential can be detected precisely, a detection signal of the action potential is obtained from a neighboring detection cell 80 for detecting a change of the Nuclear Magnetic Resonance property at the same timing.

Therefore, if no detection signal of the action potential is obtained from the neighboring detection cell 80 for detecting a change of the Nuclear Magnetic Resonance property at this timing, it is considered that there occurs "false detection" in a specific front part 85 of the life activity detection circuit, which is then removed from detection targets. By performing a comparison process on signals (detection times of action potentials) obtained from such a plurality of detection cells 80 for detecting a change of the Nuclear Magnetic Resonance property, higher accuracy and higher reliability of the detection signal can be achieved.

With reference to FIG. 30, the following describes a calculation method of an action-potential firing (or activated) area in a life object, which calculation method is performed by a rear part of the life activity detection circuit. When an action potential is fired by a neuron at a position α in a part 75 of an organism to be detected (the head of an examinee), a detection signal can be obtained from each spot within a two-dimensionally arranged cell array 71 for detecting a change of the Nuclear Magnetic Resonance property. According to the electromagnetics, a detected amplitude value of the detection signal obtained from each spot within the two-dimensionally arranged cell array 71 for detecting a change of the Nuclear Magnetic Resonance property can correspond to an intensity distribution of a magnetic field formed by a dipole moment (point magnetic charge) at the position α.

That is, the detected amplitude value of the signal obtained from each spot ($\pi$, $\rho$, $\sigma$, $\nu$, $\psi$) within the two-dimensionally arranged cell array 71 for detecting a change of the Nuclear Magnetic Resonance property is inversely proportional to a square of a distance ($r_\pi$, $r_\rho$, $r_\sigma$, $r_\nu$, $r_\psi$) from each spot to the position α. In view of this, after smoothing "detected amplitude values" at the same "detection time" obtained from respective detection cells 80 for detecting a change of the Nuclear Magnetic Resonance property so as to remove spike noise components, the relationship illustrated in FIG. 30 is used. As a result, it is possible to estimate an activated area in the part 75 of the organism to be detected (the head or the like of the examinee).

The estimation of an activated area corresponds to the extraction of a life activity detection signal in (3) of section 6.1.3. Accordingly, it is necessary to align an extraction location of a life activity detection signal or to identify the extraction location as described in (1) and (2) of section 6.1.3. For this operation, it is necessary to measure, in advance, an internal water concentration distribution pattern or an internal fat concentration distribution pattern according to the conventional MRI detection method by use of the signal detecting section described in FIG. 29 or the conventional MRI device. Subsequently, an image pattern obtained by the conventional MRI detection method and an extraction result of the life activity detection signal are combined, and alignment (identification of a location) of an activated area (or a region where action potentials are fired frequently) is performed.

Then, from the rear part of the life activity detection circuit provided in the signal detecting section (see section 6.1.3 about the definitions of the terms), "a signal of an internal activated area (a signal of a location and a range of an activated region)," "a signal of action-potential numbers per area during each setting term," "an internal signal transmission pathway based on a firing rate in an activated area," or the like is output as a life activity detection signal.

6.3.4) Method for Reducing Interference from Other Adjacent Life Activity Detection Systems In the measuring method of life activity in the present exemplary embodiment, an amount of a life activity detection signal is very small, and in addition, it is necessary to illuminate a measurement subject with illuminating light 115 for life activity detection (see FIG. 31 or FIG. 32). Therefore, in a case where a plurality of different detecting sections 101 for life activity are disposed at positions in proximity to each other, there is such a risk that a detecting section 101 for life activity may be affected (interfered) by illuminating light 115 for life activity detection from another detecting section 101 for life activity. In order to reduce this interference, in this exemplary embodiment, each illuminating light 115 for life activity detection has identification information, so that a degree of influence from other illuminating light 115 for life activity detection is measurable quantitatively. This makes it possible to offset interference by a computing process at a detection side (in the signal processing operation section 143 of the rear part in FIG. 34), thereby yielding an effect that high accuracy for the detection of life activity can be secured even if there are some physical interference to each other.

The following describes the method in which each illuminating light 115 for life activity detection is configured to have identification information. As has been described in the explanation in section 4.7 (about the detection of a weak signal) and in section 6.4.1 with reference to FIG. 31 or 32, intensity modulation is performed on the illuminating light 115 for life activity detection with the use of the modulation signal generator 113 or 118 in advance. The present exemplary embodiment employs, as the modulation method, a modulation method called MSK (Maximum Shift Keying) using a (time-serial) combination of only two types of frequencies, i.e., a basic frequency and a frequency of 1.5 times the basic frequency. FIG. 55(a) shows the method in which each illuminating light 115 for life activity detection is configured to have identification information by use of MSK. An illuminating time of the illuminating light 115 for life activity detection is divided into a term 440 of detection of life activity and an inherent information expressing term 441 of a detecting section for life activity. Here, during the term 440 of detection of life activity, the illuminating light 115 for life activity detection 115 is subjected to intensity modulation with a single frequency of only a basic frequency and with constant amplitude, and life activities are detected during this term. Further, in a case where a life activity is controlled, a measurement subject is illuminated with strong and continuous illuminating light 115 for life activity detection (linear illuminating light without intensity modulation) only for a specific period within in this term 440 of detection of life activity. On the other hand, during the inherent information expressing term 441 of a detecting section for life activity, the illuminating light 115 for life activity detection is modulated based on MSK. Even in a case where a life activity is controlled, the intensity and the modulation method of the illuminating light 115 for life activity detection are maintained to be the same as during the term of detection. Hereby, the illuminating light 115 for life activity detection can be stably detected during the inherent information expressing term 441 of detecting section for life activity. Thus, the identification information of each illuminating light 115 for life activity detection can be recognized regardless of the detection term or the control term of life activity.

A modulation state of the illuminating light 115 for life activity detection during the inherent information expressing term 441 of a detecting section for life activity is shown in FIG. 55(b). An intensity modulation period at a frequency of 1.5 times the basic frequency continues during a period of a synchronous signal 451. Accordingly, a start timing of the inherent information expressing term 441 of a detecting section for life activity can be easily found by detecting this synchronous signal 451. After that, illuminating light 115 for life activity detection is generated based on an originally combinatorial pattern of: the basic frequency, which is based on the MSK frequency and corresponds to ID information 452 for manufacturer identification of the detecting section for life activity; and a frequency of 1.5 times the basic frequency. By identifying the ID information 452 for manufacturer identification of the detecting section for life activity, the detecting section 101 for life activity can identify a manufacturer which manufactured a detecting section for life activity disposed at an adjacent position. Subsequently, an original combinational pattern of a basic frequency indicative of identification information 453 of a corresponding detecting section for life activity and a frequency of 1.5 times the basic frequency appears. In this exemplary embodiment, a production number of a corresponding detecting section for life activity is shown as the identification information 453, but alternatively, if all detecting sections for life activity have different patterns (information), the identification information 453 may have other information except the production number. Original information 454 related to a manufacture, which can be set by the manufacturer subsequently to the identification information 453, can be shown by the MSK modulation.

Next will be explained a method to remove influence in terms of signal processing in case where interference occurs between different detecting sections for life activity. Light emissions are not synchronized between the different detecting sections for life activity, and therefore inherent information expressing terms 441 of the detecting sections for life activity come at different timings. In a term 440 of detection of life activity during which one detecting section for life activity emits light, an inherent information expressing term 441 of another detecting section for life activity in another device may also occur at the same time. In this case, during the term 440 of detection of life activity during which the one detecting section for life activity emits light, modulated light with a frequency of 1.5 times the basic frequency leaks therein, so that interference of the light can be found immediately. Further, during a period of a synchronous signal 451, intensity modulation is continued with the frequency of 1.5 times the basic frequency, so that a leakage level (interference level) can be detected accurately by comparing amplitude values at respective frequencies after the spectrum analysis. A computing process is performed in a signal processing operation section 143 at a rear part as illustrated in FIG. 34 based on the detection result, thereby largely removing the influence from other detecting sections 101 for life activity. Thus, when each illuminating light 115 for life activity detection is configured to have identification information as illustrated in FIG. 55, the life activity can be detected stably and highly accurately even if interference occurs from other detecting sections 101 for life activity.

6.4) Detection Circuit of Life Activity 6.4.1) Configuration of Detecting Section for Life Activity.

Initially explained is a configuration of the detecting section for life activity (see section 6.1.3 for the definition of the term) in the present exemplary embodiment, with reference to FIG. 31. This detecting section 101 for life activity includes a signal detecting section 103 as has been already described in section 6.1.3. Further, depending on exemplary embodiments, the detecting section 101 for life activity may also include a light emitting section 102 producing illuminating light 115 for life activity detection to be projected into a life object so as to obtain a life activity detection signal. Alternatively, a system clock and modulation signal generating section 104 and a transmitting section 105 of a life activity detection signal may be also included in this detecting section 101 for life activity.

Further, the signal detecting section 103 is constituted by a photo detecting section 121 of life activity and a life activity detection circuit 122. Further, the photo detecting section 121 of life activity includes a plurality of electromagnetic wave detecting cells (photo detecting cells or detecting coils) 87-1 to 87-5. The life activity detection circuit 122 is segmented into a front part 85 of the life activity detection circuit and a rear part 86 of the life activity detection circuit.

Further, respective electric signals obtained by photoelectric conversion by the electromagnetic wave detecting cells (photo detecting cells or detecting coils) 87-1 to 87-5 are input into respective front parts 85-1 to 85-5 of the life activity detection circuit. Subsequently, output signals from the respective front parts 85-1 to 85-5 of the life activity detection circuit are subjected to a unifying process in the rear part 86 of the life activity detection circuit.

Here, in a case where a life activity detection signal is obtained based on a local change of the Nuclear Magnetic Resonance property in a life object, the signal detecting section 103 has a configuration as described in section 6.3.3 and FIG. 29. Further, in this case, one electromagnetic wave detecting cell (photo detecting cell or detecting coil) 87 in FIG. 31 corresponds to the detecting coil 84 in one detection cell 80 for detecting a change of the Nuclear Magnetic Resonance property in FIG. 29(b). In FIG. 31, one front part 85 of the life activity detection circuit is connected to an output section of one electromagnetic wave detecting cell (photo detecting cell or detecting coil) 87, which corresponds to the front part 85 of the life activity detection circuit in the FIG. 29(b).

In the meantime, in a case where light having a specific wavelength (near infrared light or infrared light) is photoelectrically converted by the photo detecting section of life activity, this photo detecting section of life activity includes the optical system for life activity detection described in section 6.3.1 or 6.3.2 (as has been described in section 6.1.3). In this case, one electromagnetic wave detecting cell (photo detecting cell or detecting coil) 87 in FIG. 31 corresponds to the photo detecting cell 38 illustrated in FIGS. 27 to 28 or the lateral one-dimensional alignment photo detecting cell 54 and the longitudinal one-dimensional alignment photo detecting cell 55 illustrated in FIGS. 23 to 25. Further, one front part 85 of the life activity detection circuit in FIG. 31 has the same requirements as in the front part 85 of the life activity detection circuit illustrated in FIGS. 27 to 28.

As for a signal connection method between output signals of the respective front parts 85-1 to 85-5 of the life activity detection circuit and inputs to the rear part 86 of the life activity detection circuit, parallel signal lines may be input into the rear part 86 of the life activity detection circuit as shown in FIG. 31. Alternatively, as has been described in section 6.3.3, such a method may be adopted that each output signal is output at a different timing, assigned in advance to each of the front parts 85-1 to 85-5 of the life activity detection circuit on the same bus line in advance, through time (output signals of the front parts 85-1 to 85-5 of the life activity detection circuit are multiplexed in a time-serial manner on the same bus line).

The system clock and modulation signal generating section 104 is constituted by a system clock generator 117 and a modulation signal generator 118. A system clock generated by this system clock generator 117 has a frequency desirably in a range from 10 kHz to 1 MHz as has been described in section 6.3.3, but the system clock frequency may be set in a range wider than the above. Then, based on the system clock generated here, a modulation signal is generated by the modulation signal generator 118. The system clock and the modulation signal generated by this system clock and modulation signal generating section 104 are input to the front part 85 of the life activity detection circuit and used for extraction of a life activity detection signal.

Next will be explained the light emitting section 102. In a case where a halogen lamp bulb or a xenon lamp is used, for example, for a light emitting component 111, light having a broad waveband is emitted from the light emitting component 111. Accordingly, in order to obtain a life activity detection signal efficiently, a specific wavelength light beam is extracted selectively so as to be used for the illuminating light 115 for life activity detection. In view of this, the specific wavelength light beam included in the range described in section 4.7 is extracted from the light emitted from the light emitting component 111 by use of a dichroic band pass filter 116. This dichroic band pass filter 116 to be used here may be an optical color filter or an optical band-pass filter (using thin-film multiple beam interference) to which the specific wavelength light beam to be extracted is fixed, or alternatively, a spectrometer which can change the specific wavelength light beam to be extracted (e.g., wavelength separation having a changed incident angle to a diffraction grating, wavelength separation using an acoustic optical grating, or the like).

Light passing through the dichroic band pass filter 116 is optically modulated by the light modulator 112, and the light thus optically modulated is projected inside a life object as a detection target, as the illuminating light 115 for life activity detection. Here, an EO modulator (Electro-Optical Modulator) or an AO modulator (Acousto-Optical Modulator) can be used as this light modulator 112. Further, a modulation signal obtained from the modulation signal generator 118 is input into a light modulator driver for driving this light modulator 112. When the illuminating light 115 for life activity detection is optically modulated as such, only a detection signal synchronized with this modulation signal can be taken out within the front part 85 of the life activity detection circuit. This largely improves detection accuracy and reliability of the life activity detection signal 106.

Further, the output signal from the rear part 86 of the life activity detection circuit is converted into a predetermined format in the transmitting section 105 of a life activity detection signal, and is then output as a life activity detection signal 106 from the detecting section 101 for life activity to the outside.

FIG. 32 shows another exemplary embodiment of the detecting section for life activity. This another exemplary embodiment is suitable particularly for the detection of oxygen concentration change in blood in surrounding areas in Table 6. As described above, in this case, a difference in intensity variations between transmitted beams in a life object, which correspond to light beams of 780 nm, 805 nm, and 830 nm, is detected. Accordingly, beams of illuminating light 115-1 to 115-3 for life activity detection having different wavelengths of 780 nm, 805 nm, and 830 nm are projected inside a life object at the same time. Here, semiconductor laser elements are used as light emitting components 111-1 to 111-3 for emitting light beams of 780 nm, 805 nm, and 830 nm.

Further, modulation signals based on respective modulation rules are input into light emitting component drivers 114-1 to 114-3 for controlling light beams from the light emitting component 111-1 to 111-3. In view of this, the system clock and modulation signal generating section 104 includes modulation signal generators 118-1 to 118-3 each for outputting such a modulation signal based on a different modulation rule.

By using different modulation signals to the respective beams of illuminating light 115-1 to 115-3 for life activity detection as such, influence (cross talk) from different-wavelength light beams is removed electrically, thereby largely improving detection accuracy and reliability of the life activity detection signal 106 in the signal detecting section 103.

In order to detect three different-wavelength light beams in the signal detecting section 103 separately, three photo detecting sections 121-1 to 121-3 of life activity are disposed. Here, similarly to FIG. 31, each of the photo detecting sections 121-1 to 121-3 of life activity includes a plurality of electromagnetic wave detecting cells 87, which are not illustrated herein to simplify the explanatory view.

Further, in order not to detect illuminating light 115 for life activity detection having different wavelength in each of the photo detecting sections 121-1 to 121-3 of life activity by mistake, color filters 60-1 to 60-3 for only transmitting corresponding wavelength light therethrough are disposed on a light incidence plane. Further, respective front parts 85-1 to 85-3 of the life activity detection circuit are individually connected to the photo detecting sections 121-1 to 121-3 of life activity.

Next will be explained another applied embodiment using the detecting section 101 for life activity illustrated in FIG. 32. Herein, several types of near infrared light beams having different wavelengths are used at the same time so as to detect the membrane potential changing in the nervous system accurately. That is, a detected point 30 for life activity is illuminated with a plurality of wavelength light beams at the same time so as to individually detect the plurality of wavelength light beams obtained therefrom, and the reliability of individual detection results is evaluated by comparing the individual detection results with each other.

As shown in Table 4, when a neuron fires an action potential, a near infrared light beam having a wavelength of about 1.05 μm, which corresponds to the 3rd overtone, and a near infrared light beam having a wavelength of about 2.16 μm, which corresponds to the 1st overtone, are absorbed. Accordingly, in response to that, two wavelength light beams of a near infrared light beam in the range from 0.840 μm to 1.37 μm and a near infrared light beam in the range from 2.05 μm to 2.48 μm (see section 4.7) are projected toward the detected point 30 for life activity at the same time.

Subsequently, the near infrared light beam in the range from 0.840 μm to 1.37 μm obtained from the detected point 30 for life activity, for example, is photoelectrically converted by the photo detecting section 121-1 of life activity so as to generate an electric signal, and the near infrared light beam in the range from 2.05 μm to 2.48 μm is photoelectrically converted by the photo detecting section 121-2 of life activity. Theoretically, when the neuron fires an action potential, pulse counting is performed in the front part 85-1 and 85-2 of the life activity detection circuit at the same time.

The concurrence of this pulse counting is monitored by the rear part 86 of the life activity detection circuit. If the pulse counting is not performed at the same time in the front part 85-1 and 85-2 of the life activity detection circuit, it is estimated that false detection or omission of detection occurs in either of the front parts 85. Thus, the monitoring of the concurrence of the pulse counting in the front part 85-1 and 85-2 of the life activity detection circuit largely improves detection accuracy and detection reliability of the detection of life activity (detection of action potentials in neurons).

In the above applied embodiment, near infrared light beams having a plurality of wavelengths are illuminated at the same time, and the plurality of wavelength light beams are detected individually to monitor the concurrence detection. Alternatively, in the present exemplary embodiment, panchromatic near infrared light including many wavelength light beams may be projected toward the detected point 30 for life activity at the same time. In this case, a near infrared light beam in the range from 0.840 μm to 1.37 μm and a near infrared light beam in the range from 2.05 μm to 2.48 μm are detected individually.

The above applied embodiment is not limited to that, and a plurality of internal phenomena may be detected by use of a plurality of wavelength light beams. For example, as further another applied embodiment, the detected point 30 for life activity is illuminated with light beams (near infrared light beams) having different wavelengths, and light beams obtained therefrom are separately detected according to respective wavelengths. This allows detection of a transmitter substance released at the time of signal transmission between neurons as well as action potentials of neurons, or allows estimation of a neural circuit related to the transmitter substance.

For example, a midbrainlimbic DA pathway to transfer a signal to nucleus accumbens from the tegmentum of midbrain is called a reward system circuit, and causes an emotional reaction of pleasant. At this time, dopamine is used for the signal transmission (Hideho Arita: Nounai busshitsu no sisutemu shinkei seirigaku-seishin seiki no nyurosaiensu-(Chugai-igakusha, 2006) p. 104).

Further, from the same reason as the explanations of sections 3.2 and 4.6.4, when the dopamine bonds to a receptor in a synaptic cleft, an original vibration mode occurs, thereby causing an original absorption band at a specific wavelength. Meanwhile, the transmitter substances include mono-amines which the dopamine belongs to, glutamic acid called an excitatory transmitter substance, and Acetylcholine concerning motor control or an autonomic nervous system. They have different molecular structures, so that wavelengths of absorption bands corresponding to vibration modes occurring at the time of bonding to the receptor are different.

Accordingly, if the action potential of the neuron is detected by use of a specific wavelength light beam among a plurality of wavelength light beams for detection, and a wavelength of a light beam which is largely absorbed at the same time as the action potential or just before or after the action potential is detected, then it is possible to estimate the detection of a transmitter substance used for the signal transmission and the neural circuit thereof.

In accordance with the explanation in section 5.1.1, the detection is enabled even by use of Nuclear Magnetic Resonance. That is, when a transmitter substance bonds to a receptor in a synaptic cleft, a maximum absorption appears at a chemical shift value corresponding to the bonding. Accordingly, from the chemical shift value of the maximum absorption newly appearing due to the bonding between the transmitter substance and the receptor, the transmitter substance related to the signal transmission and the neural circuit thereof can be detected.

In this case, in order to increase the detection accuracy, the detected point 30 for life activity may be illuminated, at the same time, with an electromagnetic wave having a frequency corresponding to the chemical shift value of the action potential of the neuron and an electromagnetic wave having a frequency corresponding to the chemical shift value at the time of bonding between the specific transmitter substance and the receptor.

Next will be explained further another applied embodiment. The above explanations mainly deals with the detection of life activity to increase a life activity level 162 (see FIG. 36) of a neuronal action potential according to transmission of an excitatory transmitter substance. As further another applied embodiment, the following describes a detection method for detecting an activity to decrease this life activity level 162.

According to B. Alberts et. al.: Essential Cell Biology (Garland Publishing, Inc. 1998), Chapter 12, when an inhibitory transmitter substance such as Glycine or γ-aminobutyric acid (GABA) is transmitted, chlorine ions Cl⁻ flow into the inside layer facing the cytoplasm in the neuron from outside. In the meantime, as shown in FIG. 3, since the membrane potential 20 is the negative resting membrane potential 21 during the resting term 25, no electrostatic force works in a direction where chlorine ions Cl⁻ flow into the cell body. However, as shown in Table 1, since a difference in the concentration of chlorine ions Cl⁻ is large between the inside and outside of the neuron, chlorine ions Cl⁻ are flowed into the inside layer facing the cytoplasm by an osmotic pressure corresponding to this concentration difference. Then, a state of hyperpolarization to decrease the membrane potential 20 to be lower than the resting membrane potential 21 in FIG. 3 is caused.

As shown in FIG. 4 and Table 2, PSRN and PEAM including an amino group ($-NH_3^+$) are distributed abundantly over the inside layer facing the cytoplasm in the neuronal membrane. Accordingly, from the same reason as the speculation in section 2.5, it is considered that the chlorine ion Cl⁻ flowing into the inside layer facing the cytoplasm at the time of the depolarization is ion-bonded or hydrogen-bonded to the amino group in PSRN or PEAM to form a state of $-NH_3^+Cl^-$. As a result of this, as has been described in chapter 4, a new absorption band based on the anti-symmetrically telescopic vibration between the N—H—Cl⁻ occurs, and as has been described in chapter 5, a new maximum absorption (corresponding to the specific chemical shift value) according to the Nuclear Magnetic Resonance property based on a change of an orbital located around a hydrogen nucleus in N—H—Cl⁻ occurs.

Accordingly, an action state and a hyperpolarization state of the inhibitory transmitter substance can be detected by use of the absorbing phenomenon of an electromagnetic wave having a wavelength corresponding to the transition between the 1st/2nd/3rd overtones of the anti-symmetrically telescopic vibration between N—H—Cl⁻ or a frequency corresponding to the maximum absorption (a chemical shift value) of Nuclear Magnetic Resonance in the hydrogen nucleus in N—H—Cl⁻, instead of detecting the action potential of the neuron using the absorbing phenomenon of an electromagnetic wave having a frequency corresponding to the wavelength or the chemical shift value explained in chapters 3 to 5.

In view of this, by changing a setting value of the wavelength or the frequency (corresponding to the chemical shift value) of the electromagnetic wave for a detection target (or projected for detection), the hyperpolarization state and the transmission state of the inhibitory transmitter substance can be detected instead of the action potential state of the neuron.

The detection of the hyperpolarization state can be performed by the detection of only an electromagnetic wave of one specific wavelength or one specific frequency. When an electromagnetic wave having a wavelength of an absorption band corresponding to a vibration mode occurring at the time when Glycine or GABA bonds to a receptor or a frequency corresponding to a chemical shift value at that time is measured as well as the electromagnetic wave having the wavelength/frequency, the hyperpolarization state and the transmission state of the inhibitory transmitter substance can be measured at the same time. As a result, the activity mechanism of a very complicated neuron system can be known more in detail.

In addition to that, a combination of a plurality of wavelengths or frequencies to be used for detection (or a combination of a plurality of wavelengths or frequencies included in an electromagnetic wave projected to the detected point 30 for life activity for detection) makes it possible to know, for example, a relationship between the action potential and the generation of the hyperpolarization state by transmission of the inhibitory transmitter substance more in detail, which can largely contribute to solution of the signal transmission mechanism in the neural circuit.

6.4.2) Configuration of Detection Circuit of Life Activity

With reference to FIG. 33, the following describes a configuration of the front part 85 of the life activity detecting circuit. An electric signal obtained by photoelectric conversion by one electromagnetic wave detecting cell (photo detecting cell or detecting coil) 87 in the photo detecting section 121 of life activity is subjected to current-voltage conversion by a preamp 131 in the front part 85 of the life activity detection circuit.

Then, after unnecessary noise components are removed by a band-pass filter 132 (or a lower-band block filter), the signal is subjected to synchronous detection in a modulating signal component extraction section (synchronous detection section) 133. Herein, the synchronous detection is performed in sync with a modulation signal obtained from the modulation signal generator 118 in the system clock and modulation signal generating section 104, and only a signal component synchronized with the modulation signal is extracted. After the signal is converted into a digital signal by the A/D converter 134, the signal is synchronized with a system clock obtained from the system clock generator 117, and signal data is accumulated within a memory section 135 in the front part, sequentially.

The signal data thus accumulated within the memory section 135 in the front part is subjected to signal processing (described later) in the signal processing operation section 136 of the front part, and then stored within the memory section 135 in the front part, again. A signal transfer section 137 to the rear part reads the signal data subjected to the signal processing from the memory section 135 in the front part in response to an instruction from the signal processing operation section 136 of the front part, and transfers the signal data to the rear part 86 of the life activity detection circuit. In the meantime, the signal transfer section 137 to the rear part also has a function to transfer necessary signal data from the rear part 86 of the life activity detection circuit to the signal processing operation section 136 of the front part.

With reference to FIG. 34, the following describes a configuration of the rear part 86 of the life activity detecting circuit. The signal data output from the signal transfer section 137 to the rear part is temporarily stored within a memory section 142 in the rear part via a signal transfer section 141 to the front part. Although not illustrated in FIG. 34, the memory section 142 in the rear part collectively stores signal data sent from the front parts 85-1 to 85-5 of the life activity detection circuit (see FIGS. 31 and 32). In the meantime, the signal transfer section 141 to the rear part also has a function to transfer necessary signal data from a signal processing operation section 143 of the rear part to the front part 85 of the life activity detection circuit.

Then, the signal processing operation section 143 of the rear part reads necessary signal data from the memory section 142 in the rear part, and stores again the signal data which has been subjected to further signal processing in the memory section 142 in the rear part. One of the further signal processing to be performed herein is a computing process by use of location information (information obtained due to the first detection) of the detected point 30 for life activity, which is obtained from the position monitoring section 46 regarding a detected point for life activity.

Further, the signal transfer section 144 to a transmitting section of a life activity detection signal reads the signal data subjected to the further signal processing from the memory section 142 in the rear part, in response to an instruction from the signal processing operation section 143 of the rear part, and then transfers the signal date to a transmitting section 105 of a life activity detection signal.

Here, a series of these processes are performed in accordance with timings of system clocks generated from the system clock generator 117.

In both of FIGS. 33 and 34, a transfer path of signal data is shown in a "bold full line," while a transfer path of a system clock or a command is shown in a "narrow full line."

As the signal processing performed in the signal processing operation section 136 of the front part and the signal processing operation section 143 of the rear part, different computing processes are performed according to types of life activities to be a detection target. Along with the contents shown in the column of "signal generative physical phenomenon and detection method" in Table 6, the following gives an outline of the computing processes to be performed in each of the signal processing operation sections 136 and 143.

Detection of <Membrane Potential Changing in Nervous System>

In this case, a life activity detection signal corresponding to a change of the membrane potential 20 illustrated in FIG. 3 is obtained. In view of this, for the life activity detection signal, "a pulse counting number indicative of how many times the membrane potential 20 changes in a specific unit time" is important. A life activity detection signal pattern corresponding to the change of the membrane potential 20 illustrated in FIG. 3 is stored beforehand in the signal processing operation section 136 of the front part (or the memory section 135 in the front part), and a computing process of "pattern matching" (sequential calculation of a pattern equivalent level) is performed on a signal data stream stored in the memory section 135 in the front part.

When a pattern equivalent level exceeds a specific value, it is considered that "one action potential occurred," and a pulse counting number is incremented by 1. Here, there are some cases where action potentials from a plurality of different neurons may be detected on one electromagnetic wave detecting cell (photo detecting cell) 87 at the same time. Accordingly, when it is presumed that "one action potential occurred," a subtraction process is performed on a life activity detection signal pattern component detected in response to one action potential from the signal data stream stored in the memory section 135 in the front part, and then, the pattern matching computing is performed again. By this process, simultaneous action potentials from a plurality of different neurons can be detected.

Subsequently, the signal processing operation section 143 of the rear part can add up a "pulse counting value" per specific unit time obtained from each electromagnetic wave detecting cell (photo detecting cell) 87, and output a total sum directly from the signal transfer section 144 to the transmitting section of a life activity detection signal. Alternatively, a result of statistical analysis of a distribution of pulse counting values may be output. Still further, an area having more pulse counting values is considered as an "activation area" in the nervous system, so that location information of the activation area or a time dependent variation in the activation area (a signal transmission pathway in the nervous system) may be output.

Next will be explained a processing method in the signal processing operation section 143 of the rear part in which the signal detecting section 103 shown in FIG. 32 is used for detection of the membrane potential changing in the nervous system and which uses two wavelength light beams, i.e., a near infrared light beam in the range from 0.840 µm to 1.37 µm and a near infrared light beam in the range from 2.05 µm to 2.48 µm. When an action potential occurs in a neuron, respective pulse counting values are incremented by 1 in both the front parts 85-1 and 85-2 of the life activity detection circuit at the same time.

On the other hand, this exemplary embodiment also has such a risk that because of weak detection signals, only one of the front parts 85-1 and 85-2 of the life activity detection circuit may be misdetected as an action potential under the influence of disturbance noises (a pulse counting value is incremented). Thus, in a case where only one of the front parts 85-1 and 85-2 of the life activity detection circuit is (mis)detected as an action potential (a pulse counting value is incremented), the signal processing operation section 143 of the rear part determines it as false detection and performs a process of preventing a corresponding signal from being output from the rear part 86 of the life activity detection circuit to the outside (the corresponding signal is deleted from the life activity detection signal 106). By detecting multiple action potentials of neurons as such, detection accuracy and reliability of the life activity detection signal 106 are largely improved.

Detection of <Oxygen Concentration Change in Blood in Surrounding Areas>

In this case, a spatial variation amount or a time dependent variation amount of signal data is important, the following processes are performed: (1) calculation of a difference value between pieces of signal data detected from electromagnetic wave detecting cells (photo detecting cells) 87 corresponding to adjacent locations (or peripheral locations) on the detected point 30 for life activity; (2) extraction of a time dependent variation for signal data in the same single electromagnetic wave detecting cell (photo detecting cell) 87; (3) calculation of a difference value to signal data stored in advance in the electromagnetic wave detecting cell (photo detecting cell) 87; (4) calculation of a value obtained in combination of (1) to (3); and (5) a computing process of comparison/calculation between pieces of signal data from the photo detecting sections 121-1 to 121-3 of life activity corresponding to different wavelength light beams including signals related to life activities.

In the calculation (1), the signal processing operation section 143 of the rear part once receives signal data detected from each electromagnetic wave detecting cell (photo detecting cell) 87 and notifies a result thereof to the signal processing operation section 136 of the front part.

Further, in the computing process (2), previous signal data stored within the memory section 135 in the front part is read out and a difference between the previous signal data and the current signal data is computed.

On the other hand, in the computing process (3), signal data detected in advance from each position on the detected point 30 for life activity, is stored in the memory section 142 in the rear part. At the time of detection of life activity, the data is transferred to a signal processing operation section 136 of the front part corresponding to each position on the detected point 30 for life activity, and a difference value between the data and the current signal data is calculated. Further, as shown in (4), a value (an additional value, a subtracted value, a product value, or a quotient value) in combination of results obtained by the computing processes in (1) to (3) is calculated if necessary.

Thus, data of the "difference value" is collected in the signal processing operation section 143 of the rear part. Next will be explained the computing process shown in (5) as above. In a case where oxygen concentration changes in blood in surrounding areas are measured using near infrared light, respective pieces of signal data are separately obtained from three different wavelength light beams as shown in FIG. 32, in particular.

As has been described above in regard to the BOLD effect, when a neuron is activated, an oxyhemoglobin concentration increases in capillaries around the neuron several seconds later. Further, the oxyhemoglobin which is a particular hemoglobin bonding to oxygen molecule has a maximum absorption at a wavelength of 930 nm and the deoxyhemoglobin which is other particular hemoglobin separated from oxygen molecule has a maximum absorption at wavelengths of 760 nm and 905 nm.

Accordingly, several seconds after a neuron is activated, respective detection light amounts of wavelength light beams of 780 nm, 805 nm, and 830 nm change (e.g., a detection light amount at 780 nm increases and a detection light amount at 830 nm decreases). In the signal processing operation section 143 of the rear part, a subtraction process or a division process is performed as comparison/calculation between pieces of signal data output from respective front parts 85-1 to 85-3 of the life activity detection circuit, respectively corresponding to three different wavelength light beams.

Although FIG. 32 is simplified, each of the photo detecting sections 121-1 to 121-3 of life activity includes a plurality of electromagnetic wave detecting cells (photo detecting cells or detecting coils) 87-1 to 87-5, and the electromagnetic wave detecting cells (photo detecting cells or detecting coils) 87-1 to 87-5 are connected respectively to the front parts 85 of the life activity detection circuit (see FIG. 31). In view of this, the subtraction process or the division process for the three different wavelength light beams in the signal processing operation section 143 is performed between pieces of signal data obtained from those corresponding ones of the electromagnetic wave detecting cells (photo detecting cells or detecting coils) 87-1 to 87-5 which are disposed at the same position (or positions related to each other) with respect to the three different wavelength light beams.

When the computing process is performed on pieces of signal data from these photo detecting sections 121-1 to 121-3 of life activity corresponding to respective wavelength light beams, an S/N ratio of the signal data is improved, thereby improving reliability of the life activity detection signal 106. The reason is as follows. There is such a case where movement of a life object (an examinee or the like) as a detection target may change a position of the detected point 30 for life activity relative to the detecting section 101 for life activity, thereby changing detection light amounts of the above three wavelength light beams at the same time.

The changes of these detection light amounts appear as noise components in pieces of signal data output from the front parts 85-1 to 85-3 of the life activity detection circuit. However, when the subtract process or the division process is performed in the signal processing operation section 143 of the rear part, the influence by these noise components is largely reduced, thereby improving the S/N ratio of the signal data.

Further, another exemplary embodiment about the comparison/calculation on pieces of signal data from respective photo detecting sections 121-1 to 121-3 of life activity shown in (5) is explained. Here, respective pieces of signal data are compared with each other, so that detection accuracy of the life activity detection signal 106 is improved. More specifically, the authenticity of a detection signal is judged from directional symmetry or directional asymmetry in changes of detection light amounts occurring in respective pieces of signal data at the same time. More specifically, as has been mentioned above, when the oxyhemoglobin concentration increases in a capillariy, the detection light amount at 780 nm may increase and the detection light amount at 830 nm may decrease in some cases.

Accordingly, in this case, signal data output from a front part 85 of the life activity detection circuit for detection of light of 780 nm (strictly speaking, a front part 85 of the life activity detection circuit for processing an electric signal obtained by photoelectrical conversion by an electromagnetic wave detecting cell (photo detecting cell or detecting coil) 87 disposed at an image forming position corresponding to a capillary portion where the oxyhemoglobin concentration increases) should show information indicative of an increase in the detection light amount.

Meanwhile, signal data output from a front part 85 of the life activity detection circuit for detection of light of 830 nm should show information indicative of a decrease in the detection light amount. The signal processing operation section 143 of the rear part grasps this simultaneous increase/decrease relationship, and when either one of the changes does not occur or when the changes occur toward the same direction, the signal processing operation section 143 of the rear part judges that "the front part 85 of the life activity detection circuit misdetected" and performs a process of deleting this change state from the life activity detection signal 106. On the other hand, when the increase/decrease relationship occurs at the same time, the signal processing operation section 143 of the rear part regards "the life activity detection signal 106 as reliable" and adds this change state to signal data output from the rear part 86 of the life activity detection circuit.

Detection of <Temperature Change by Thermography>

In this case, the same computing process as in the case of <oxygen concentration changes in blood in surrounding areas> is performed. Note that it is not necessary to perform the division process or the subtraction process on pieces of signal data from three different wavelength light beams.

Detection of <Oxygen Concentration Change by fMRI>

In this case, in the signal processing operation section 143 of the rear part, estimation computing (detection of an area where a change of the Nuclear Magnetic Resonance property occurs) in an activated area is performed using the method described in FIG. 30 and section 6.3.3.

In either of the cases, this exemplary embodiment performs "a standardization process of a life activity detected area" (describes later) after performing the computing process in the signal processing operation section 143 of the rear part.

The following describes a case using the optical system for life activity detection shown in FIG. 26. At the time of detection of life activity, if the detected point 30 for life activity moves, the imaging lens 57 automatically moves in an optical axial direction according to a result of the "first detection" (position detection and position control of a detected point for life activity) as described above. This results in that an imaging pattern relative to the detected point 30 for life activity always appears on the photodetector 36.

When the detected point 30 for life activity moves in the optical axial direction of the imaging lens 57, such an optical phenomenon occurs that a size of the imaging pattern on the photodetector 36 changes. Further, when the detected point 30 for life activity moves in a direction perpendicular to the optical axial direction of the imaging lens 57, the position of the imaging pattern on the photodetector 36 goes out of alignment. In the present exemplary embodiment, in order to facilitate the process of the biosis activity measurement (the process of generating life activity information from a life activity detection signal) in case of such phenomena, even if the detected point 30 for life activity moves, the life activity detection signal 106 is output in the form that the center position and the size of the imaging pattern on the photodetector 36 are fixed to the detected point 30 for life activity.

For example, in a case where the "first detection" is performed using the optical system shown in FIG. 22 as a position monitoring section regarding a detected point for life activity, not only a distance 44 surface points of an area where the detecting section for life activity is disposed (at a position of the detected point 30 for life activity in a direction along the optical axis of the imaging lens 57 in FIG. 26) but also a marked position 40 on a life-object surface along a direction at right angles to the optical axis of the imaging lens 57 can be found from imaging pattern positions on two-dimensional photodetectors 43-1 and 43-2 relative to the marked position 40 on the life-object surface.

When this information is received from the position monitoring section 46 regarding a detected point for life activity, [A] changing of an imaging pattern size (standardization of the size) and [B] a displacement process of a center position of the imaging pattern are performed by the signal processing operation section 143 of the rear part in FIG. 34.

That is, as the operation of [A], in a case where the detected point 30 for life activity is close to the imaging lens 57 as compared with a standard position, a "downsampling process" of signal data read from the memory section 142 of the rear part is performed to reduce the imaging pattern in size, and a result thereof is stored in the memory section 142 of the rear part again. On the other hand, in a case where the detected point 30 for life activity is away from the imaging lens 57 as compared with the standard position, an "interpolation process" of signal data read from the memory section 142 of the rear part is performed to enlarge the imaging pattern, and a result thereof is stored in the memory section 142 of the rear part again. As described in section 6.5.4, as one example thereof, there is a method in which an imaging pattern size is standardized to a face size of an examinee (user).

Subsequently, the operation of [B] is performed according to the following procedure. When location information of a center of the imaging pattern is received from the position monitoring section 46 regarding a detected point for life activity, the location information of the center is stored in the memory section 142 of the rear part. Then, based on the information, only signal data with respect to a standardized area (of the imaging pattern) is output from the signal transfer section 144 to the transmitting section of a life activity detection signal.

6.4.3) Configuration of Transmitting Section of Life Activity Detection Signal

With reference to FIG. 35, the following describes a configuration of the transmitting section of life activity detection signal. Similarly to the above, in FIG. 35, a transfer path of signal data is shown in a "bold full line", while a transfer path of a system clock or a command is shown in a "narrow full line."

The present exemplary embodiment has such a feature that from the viewpoint of protection of personal data, the life activity detection signal 106 output from the detecting section 101 for life activity is encrypted.

In the transmitting section 105 of a life activity detection signal, the life activity detection signal 106 is transmitted to the outside via the network control section 158. At this time, the number of times the life activity detection signal 106 is transmitted via the network control section 158 (a cumulative duration time in which the life activity detection signal 106 is transmitted to the outside) is counted by a counter 151 which generates incremental counter numbers for transmitting the life activity detection signal or describes a cumulative duration time to transmit the life activity detection signal.

The transmitting section 105 of a life activity detection signal includes two types of control circuits related to encryption keys, i.e., a variable key generator 152 and a variable shifting position generator 153 in an M-serial cyclic circuit. Here, the variable key generator 152 and the variable shifting position generator 153 in an M-serial cyclic circuit are both constituted by an M-serial random number generator. The variable shifting position generator 153 in an M-serial cyclic circuit is simpler and its number of output bits and the number of cycles (an M value) are largely smaller than the variable key generator 152. Initial values of the variable key generator 152 and the variable shifting position generator 153 in an M-serial cyclic circuit are set at the time of manufacturing of the detecting section 101 for life activity. Although not illustrated here, values of the variable key generator 152, the variable shifting position generator 153 in a M-serial cyclic circuit, and a counter 151 which generates incremental counter numbers for transmitting the life activity detection signal or describes a cumulative duration time to transmit the life activity detection signal (hereinafter just referred to as the "counter 151), can be turned back to respective initial values by a hidden command.

When an output value of the variable shifting position generator 153 (which provides and outputs a variable shifting number in a M-serial cyclic circuit regarding incremental counter numbers for transmitting the life activity detection signal or regarding a cumulative duration time to transmit the life activity detection signal: (hereinafter just referred to as the "variable shifting position generator 153 in a M-serial cyclic circuit")) does not change, an output value (random number) of the variable key generator 152 (which provides variable keys depending on incremental counter numbers for transmitting the life activity detection signal or on a cumulative duration time to transmit the life activity detection signal (hereinafter just referred to as the "variable shifting key generator 152")) changes every time the counter 151 increments the counter number by 1 (or every time the cumulative duration time during which the life activity detection signal 106 is supplied (output) to the outside via the network control section 158 elapses a predetermined period).

The output value of the variable shifting position generator 153 in a M-serial cyclic circuit changes every time the counter number of the counter 151 increases by a specific number (for example, 10 or 100) (that is, every specific number of times the life activity detection signal 106 is transmitted to the outside or every time the cumulative duration time in which the life activity detection signal 106 is output to the outside via the network control section 158 elapses a specific period).

At this time, if the output value of the variable shifting position generator 153 changes at this time, the output value (random number) of the variable key generator 152 also changes. Thus, the output value (random number) of the variable key generator 152 changes depending on a combination of the output value of the counter 151 and the output value of the variable shifting position generator 153 in a M-serial cyclic circuit. The output value of the variable key generator 152 is used as an encryption key for encryption performed in an encrypter 154.

Here, the following describes the output value from the variable key generator 152, more specifically.

The M-serial random number generator constituting the variable key generator 152 is a circuit for outputting a random number varying depending on an input step number "i" and can generate M pieces of random numbers at the maximum. That is, in steps from "0" to "M−1," different random numbers (which do not overlap with numbers which have been already output) are output. However, when the input step number exceeds "M" (after one cycle), the random numbers which have been output before are repeatedly output in the output order.

In this exemplary embodiment, a timing when the output value of the counter 151 changes corresponds to a timing when the input step number "i" changes. That is, every time the incremental counter number for transmitting the life activity detection signal 106 from the network control section 158 changes (or every time the cumulative duration time in which the life activity detection signal 106 is output to the outside via the network control section 158 passes a specific period), the input step number changes from "i" to "i+1" and the random number output from the variable key generator 152 changes.

In the meantime, every time the counter 151 increments the incremental counter number by a specific number of times (that is, every specific number of times the life activity detection signal 106 is transmitted to the outside or every time the cumulative duration time in which the life activity detection signal 106 is output to the outside via the network control section 158 passes a specific period), the output value of the variable shifting position generator 153 in a M-serial cyclic circuit changes. The output value at this time is assumed "j."

At this time, the input step number of the variable key generator 152 varies from "i" to "i+j+1," and a random number according to the input step number "i+j+1" is output from the variable key generator 152. That is, only when the output value of the variable shifting position generator 153 in an M-serial cyclic circuit has changed, the output value of the variable key generator 152 is changed by just the output value "j" in an M-serial continuous change.

As such, when the encryption key is generated by the combination of the variable shifting position generator 153 in an M-serial cyclic circuit and the variable key generator 152, unauthorized decryption of the encryption key is prevented, thereby ensuring high security at the time of transferring the life activity detection signal 106 to the outside.

Signal data transmitted from the life activity detection circuit 122 via a signal transfer section 155 from the life activity detection circuit is subjected to an encryption process in the encrypter 154, and temporarily stored in the memory section 156 in the transmitting section of life activity detection signal. Here, the present exemplary embodiment has a feature in that the life activity detection signal 106 is not only encrypted as described above, but also stored in a communication format in accordance with IP (Internet Protocol).

This improves easy transmission of the life activity detection signal 106 over the Internet. In order to enable this, an internet protocol forming section which sets the IP address and in which to store IP address information in advance reads encrypted signal data from the memory section 156 in the transmitting section of life activity detection signal, and changes it into the communication format in accordance with IP (Internet Protocol). The life activity detection signal 106 generated in a final format by the internet protocol forming section which sets the IP address is transferred to the outside via the network control section 158.

6.5) Measuring Method of Life Activity

As has been described in section 6.3.1, in the present exemplary embodiment, interpretation of life activity is performed based on the life activity detection signal obtained from the detecting section for life activity to obtain life activity information. A series of these operations are generally referred to as life activity measurement. This chapter deals with a measuring method of life activity mainly focusing on the interpretation of life activity.

6.5.1) Overview of Information Obtained from Life Activity Detection Signal

FIG. 36 shows information obtained when the encryption of the life activity detection signal 106 is decrypted in accordance with the methods described in sections 6.3 and 6.4. A life activity detected area 161 shown in FIG. 36 indicates a location of a single neuron firing an action potential or a location of a particular region constituted by a plurality of neurons firing action potentials. Alternatively, the life activity detected area 161 may indicate a location on a neural transmission pathway in a whole body or a location of a particular region in a life object which performs life activities beyond the activities of the nervous system.

Further, a life activity level 162 described in FIG. 36 indicates an activated degree of a life activity in each detected area 161 in the life object. Depending on a detection target, this life activity level 162 corresponds to a total number of action potentials (a pulse counting number) in a neuron, an oxyhemoglobin concentration (or a deoxyhemoglobin concentration) in a capillary, a distribution of surface temperature (variation) measured by a thermography, or the like. A distribution characteristic of the life activity level 162 (a pattern of a characteristic distribution) illustrated in FIG. 36 changes through a detection time 163.

In the meantime, when a transmission state or a hyperpolarization state of an inhibitory transmitter substance is detected as has been described in section 6.4.1 instead of detecting a neuronal action potential by use of near infrared light or a change of the Nuclear Magnetic Resonance property, a value of the life activity level 162 is decreased in a local area absorbing an electromagnetic wave having a specific wavelength or a frequency corresponding to a specific chemical shift value. Accordingly, it is necessary to pay attention to changes in a direction of the life activity level 162 according to a phenomenon of a detection target.

Accordingly, the "interpretation of life activity," which will be described later, is performed by using or extracting the following matters from the life activity detection signal illustrated in FIG. 36: (1) an activated area (a location where the value of the life activity level 162 in the life activity detected area 161 exceeds a designated value); (2) a value of the life activity level 162 (intensity of activation) in a specific activated area; (3) a connection pattern of the activated area (an activation distribution characteristic=the activation characteristic distribution shown in FIG. 36); (4) a time dependent connection of the activated area (a signal transmission pathway in a nerve, and the like); and (5) a characteristic of a time dependent variation in the activation distribution (a feature that the activation distribution changes through a detection time 163), and the like.

6.5.2) Content of Life Activity Information

In the present exemplary embodiment, an active state in a life object which can change over time is a target of the life activity information. Particularly, "information of an active state in a particular person or a plurality of life objects at the time of measurement, which information is indicated (expressed or described) in an interpretable manner (in a judgeable or distinguishable form) by a human or a machine" is referred to as "life activity information."

This life activity information includes information indicative of (explaining) internal neural activity or mind activity or a mental status. Further, this mind activity or mental status may indicate information peculiar to a particular individual (an examinee or a user), or may indicate a characteristics of a group (collective entity) constituted by a plurality of members (a plurality of examinees or users) as well.

FIG. 37 is a conception diagram of life activity information obtained by interpretation of life activity in the present exemplary embodiment.

In this exemplary embodiment, respective pieces of life activity information corresponding to a plurality of "measuring items" can be extracted from the aforementioned life activity detection signal. Further, one or more "evaluation factors 171" are defined for each of the measuring items. As a result of interpretation of life activity, an equivalent level 172 per each of evaluation factors 171-1 to 171-3 in a specific measuring item can be expressed along each detection time 163 during which detection of life activity is performed, as illustrated in FIG. 37(*a*). In consideration of simple explanation herein, results of the interpretation of life activity are shown in a form of graph in FIG. 37.

Alternatively, the equivalent level 172 of each of the evaluation factors 171-1 to 171-3 may be expressed in a form of values or some sort of animation.

Since the life activity changes from moment to moment, the equivalent level 172 of each of the evaluation factors 171-1 to 171-3 also changes through the detection time 163. The changing state is shown in FIG. 37(*b*).

An "event 173" shown in FIG. 37(*b*) is information related to life activity measurement, and a detection time of the event 173 is also mapped on a timeline (a coordinate axis indicative of the detection time 163) in sync with the detection time 163 of the detection of life activity.

The event 173 herein mainly includes: (1) an external state of a life object as a target for biosis activity measurement or an environment of the life object; (2) an internal state of the life object; and (3) information such as stimulation given to the life object from the outside. However, the even 173 is not limited to the above, and all information which affects the life activity is included in the event 173.

The "external state of a life object as a target for biosis activity measurement or an environment of the life object" corresponds to "observation of a state of the life object or an environment of the life object," which will be described later with reference to FIGS. 38 and 39. Here, the method described in section 6.2.2 with reference to FIG. 22 as one example of the "position monitoring section regarding a detected point for life activity" uses a camera lens 42 and a two-dimensional photodetector 43 such as a CCD sensor disposed behind the camera lens 42.

In this case, at the time when the position of the detected point is detected by use of the camera lens 42 and the two-dimensional photodetector 43 (the first detection to align and hold the detected point for life activity), the external state of the life object as a target for biosis activity measurement or the environment of the life object is measured simultaneously. Concrete examples of the information on the external state of the life object or the environment of the life object include information on "whether the life object is alone during the detection of life activity or the life object is in company with other people" or "whether the life object (examinee, or the like) as a target for biosis activity measurement stays in a small place or in a large place." Further, in a case where the detecting section 101 for life activity includes a temperature sensor or a humidity sensor, temperature/humidity information during the detection of life activity is also taken as information of the "environment of the life object."

The information on the "state in the life object" includes information such as "regional pain due to a change state of posture or disease." The change state of posture among them can be simultaneously measured in the "position monitoring section regarding a detected point for life activity." On the other hand, the information such as the regional pain due to disease is input by an examinee (a user) as a life object to be a target of biosis activity measurement by other means.

The "stimulation given from the outside to the life object," which is listed last, corresponds to "giving a stimulation from the outside to the life object (S21)," which will be described later with reference to FIGS. 38 and 39.

Concrete examples thereof may be as follows: causing pain to a limited part of the life object by use of a needle; causing the life object (examinee) to have a specific emotion forcibly by displaying a pleasant (or terrible/sad) image on a display screen; and the like.

Along such concrete examples, the following explains a relationship between the event 173 and each of the evaluation factors 171-1 to 171-3 as shown in FIG. 37(b). When a pleasant image is displayed for the life object (examinee) as the event 173-1 only for a specific period on the timeline, the equivalent level 172 of the evaluation factor 171-2 as "pleasant" increases, whereas the equivalent level 172 of the evaluation factor 171-3 as "scared" is maintained low. After that, when a terrible image is displayed as the event 173-2, the equivalent level 172 of the evaluation factor 171-2 as "pleasant" and the equivalent level 172 of the evaluation factor 171-3 as "scared" are reversed. Further, the equivalent level 172 of the evaluation factor 171-1 as "relieved" decreases through the detection time 163.

Measuring items and evaluation factors corresponding to the respective measuring items to be set in the present exemplary embodiment are shown as follows. Here, the evaluation factors are set in consideration of convenience for applications to the present exemplary embodiment. Further, an explanation before the mark " . . . " indicates a "measuring item," and an explanation after " . . . " indicates an "evaluation factor 171."

Somesthetic system . . . . A part in the body which feels pain. Each part in the body corresponds to each evaluation factor 171.

Motor component . . . . A part which gives an instruction of which part of the body is moved or a part to be moved corresponds to each evaluation factor 171.

Control intention (Intention of mechanical operation of TV games or the like) . . . . Movement to up/down/left/right, aggressive shot, change of color, selection of a specific button Autonomic nervous system . . . . Sympathetic system per each inner organ or vessel/sweat gland, and parasympathetic system per each inner organ or vessel/sweat gland Awakening/turgescence . . . . Emergency recognition, turgescence, awakening, relaxed state, drowsiness, REM sleep, non-REM sleep Attraction . . . . Possession desire, attracted, good feeling, subject of interest, insensitivity, repulsion, elusive subject Emotional reaction . . . . Joy, anger, sympathy (sadness), comfort, love, loneliness, fear, anxiety, relief, etc.

Involuntary decision (unconscious state) . . . . Good feeling, repulsion, conciliation, escape, aggression, inhibitory activity region Recognition . . . . Visual sense, auditory sense, gustatory sense, olfaction, mediating tactile Visual recognition/identification . . . . Various shapes, color tones, area identification, various individual discriminations Audible recognition/identification . . . . Pitch, rhythm, various words, phrases Recollection (content intended to be expressed or occurring image) . . . . Various words, various shapes, collaboration between words Malfunction detection (of physical condition or mind activity) . . . . Abnormal active site (location), algogenesia site (location), site (location) where active duration is too long The present exemplary embodiment has a feature in that the "involuntary decision (unconscious state)" or "malfunction detection (of physical condition or mind activity)," which is caused in an examinee without any consciousness, can be measured in the present exemplary embodiment, and further, the "control intention (a machine such as a TV game is operated by just thinking)" and the like can be measured. These items could not be measured in the conventional techniques.

In the meantime, in consideration of applications of the present exemplary embodiment to a "marketing research," the item of "attraction" is added to the measuring items. Further, the measurement items "attraction" and "involuntary decision (unconscious state)" both include the same evaluation elements "good feeling" and "repulsion." However, they are different in that the examinee has such feelings under consciousness in the former item, whereas the examinee has such feelings without any consciousness in the latter item.

6.5.3) Interpretation Method of Life Activity 6.5.3.1) Feature of Life Activity Interpretation As has been described in section 6.1.3, the present exemplary embodiment requires interpretation of life activity in order to obtain life activity information from a life activity detection signal obtained by the detecting section for life activity. The interpretation of life activity as shown in the present exemplary embodiment has the following three features. These features can be performed separately or may be performed in combination at the same time.

[A] A specific "stimulation" is given to a life object as a measurement subject from the outside to detect a life activity detection signal. The "stimulation" as used herein includes not only "physical irritation," which is, for example, pain to be given by partially pricking a life-object surface with a "needle" or by giving "electrical stimulation," but also "psychological stimulation" to be given to the examinee by "showing a pleasant image or a terrible image." In this exemplary embodiment, the action to "calm a heart" by letting the examinee listen to quiet music is considered as part of the "psychological stimulation."

[B] The interpretation based on a life activity detection signal is performed by referring to a data base.

(1) Existing information such as well-known documents or Web information or (2) accumulation of previous life activity detection signals can be utilized as the data base. The data base in the present exemplary embodiment is not fixed, and the "data base contents are kept expanded and improved" based on a "learning function."

In order to enhance the data base, the present exemplary embodiment includes such a mechanism that: (a) a storage location of the data base is accessible via the network, thereby securing easiness in changing the content thereof; and (b) an interpretation result of a life activity obtained with reference to the data base is fed back. As a reference method of the data base, "equivalent levels 172" (or pattern matching levels) for the items each listed with a mark "-" in section 6.5.1 are calculated. The calculation results can be expressed as in FIG. 37.

However, the reference method is not limited to the above, and other reference methods of the data base which may be used herein are as follows: calculation of a correlation coefficient by use of a technique of pattern recognition or a statistical analysis technique used in multivariate analysis; multiple regression analysis, primary component regression analysis, or partial least squares regression analysis used in chemometrics; and the like.

[C] Data which is suitable for a use purpose is extracted from data accumulated in the data base and new life activity information is generated from the extracted data. In the present exemplary embodiment, the interpretation of life activity can be performed at a different timing from the detection of life activity. In this case, the interpretation is performed by use of data of life activity detection signals accumulated in the data base.

More specifically, by using event information stored in the data base, a life activity detection signal suitable for a specific use purpose and a "measuring item" associated with the purpose are extracted, and life activity information is generated by use of the extracted signal.

The interpretation method of life activity will be explained more specifically in the following sections by taking as examples the following cases particularly:

a case where a "stimulation" is given to the life object from the outside to interpret a life activity;

a case where life activity detection signals are accumulated to enhance the content of the data base which is referred to for interpretation of life activity;

a case where interpretation of life activity is performed based on life activity detection signals by referring to the database;

a case where a feedback is given to the content of the data base by using a result of the interpretation of life activity;

a case where an appropriate life activity detection signal is extracted from the data base by use of event information; and a case where interpretation of life activity is performed based on a life activity detection signal extracted from the database.

The following explanations will be given with reference to a flowchart of interpretation of life activity.

6.5.3.2) Exemplary Construction of Data Base Related to Interpretation of Life Activity FIG. 38 shows a procedure of interpretation of life activity in the following cases as described in section 6.5.3.1:

a case where a "stimulation" is given to the life object from the outside to interpret a life activity; and a case where life activity detection signals are accumulated to enhance the content of the data base which referred to for interpretation of life activity.

Initially explained is a method to perform "search of an internal signal transmission pathway" by interpretation of life activity as an example, more specifically. Since the signal transmission pathway in the nervous system has complicated paths in parallel as shown in FIG. 1, it was very difficult to search for a detailed signal transmission pathway in a state where a life object is alive, in the conventional techniques.

However, at the time of transmitting a signal, neuron cell bodies 1 except a sensory neuron on the signal transmission pathway fire action potentials by all means. The present exemplary embodiment uses this feature to search for the signal transmission pathway by finding locations of the neuron cell bodies 1 which sequentially fire action potentials. More specifically, when pain is caused by pricking a part of skin of the life object with a "needle," the signal detection area (ending) 4 of the sensory neuron illustrated in FIG. 1 is activated (an action potential occurs). Subsequently, a signal is transmitted through a signal transmission pathway. (A specific method of searching for this internal signal transmission pathway will be described later in section 9.3.1 with reference to FIGS. 52 and 53.)

This operation to cause pain by pricking a part of skin of the life object with a needle corresponds to a step (S21) of giving a stimulation from the outside to the life object as in FIG. 38. Then, an operation of detection of life activity (S22) is performed by the method described in sections 6.2 to 6.4. Further, at the same time, observation of a state of the life object or observation of an environment surrounding the life object as the measurement subject (S26) is performed.

Subsequently, extraction (S23) of a feature portion corresponding to a life activity detection signal obtained therefrom and collection/accumulation (S24) of the life activity detection signal are performed. Here, in the case of this "search of a signal transmission pathway," a life activity level 162 increases for a short time only in a "place where a neuron cell body on the signal transmission pathway is located" within the life activity detected area 161 in FIG. 36. Through the detection time 163, the place where the life activity level 162 increases for a short time moves along the signal transmission pathway.

In this case, information indicative of a value (total sum) to which a value of the life activity level 162 related to the "place where a neuron cell body on the signal transmission pathway is located" within the life activity detected area 161 is added (accumulated) is collected/accumulated as shown in S24. Meanwhile, as shown in FIG. 36, the content of the life activity detection signal changes through the detection time 163. At this time, a process of obtaining information to which a content of a life activity detection signal is added (accumulated) through the detection time 163 or a process of sequentially accumulating a content of a life activity detection signal at each point in the detection time 163 corresponds to a process (S24) of collection/accumulation of life activity detection signals. On the other hand, a feature emerging when the place where the life activity level 162 increases for a short time moves is extracted as extraction of a feature portion as shown in S23.

Then, in a subsequent extraction step (S25) of extracting a correlation between an external stimulation and a life activity detection signal, stimulated-part information obtained in S21, and a collection/accumulation result of life activity detection signals and a feature extraction result respectively obtained in the steps of S23 and S24 are combined. As a result, "correlation information between a stimulated part of the life object and an internal signal transmission pathway" is obtained (or extracted).

Then, the information thus obtained (or extracted) is accumulated sequentially in the data base to enhance the data base (S27). Further, as this step (S27) of accumulation and enhancement to the data base, the stimulation content performed on the life object in step S21 and the observation result of the state of the life object and the observation result of the environment surrounding the life object obtained in step S26 are also stored in the data base as event information. In the above example, pain is caused by use of a "needle," but the present exemplary embodiment is not limited to this, and a signal transmission pathway related to pressure, itch, temperature, visual sense, auditory sense, gustatory sense, olfaction, and the like can be found in detail in the same manner.

The above explanation deals with a data base construction method mainly based on the "somesthetic system" among the measuring items shown by the mark "-" in section 6.5.2, but alternatively, the method in FIG. 38 may be used for construction of the data base corresponding to the other measuring items or a specific evaluation factor 171 in them, shown in section 6.5.2. In this case, a stimulation suitable for the specific evaluation factor 171 is given from the outside (S21) to perform detection of life activity (S22), and then the collection/accumulation (S24) of the result or the feature extraction (S23) is performed.

As another exemplary embodiment using the method in FIG. 38, the following explains about a data base construction method for one evaluation factor in the emotional reaction or for emergency recognition, which is one of evaluation factors in the awakening/turgescence. In this case, the aforementioned "psychological stimulation" will be given as the stimulation from the outside (S21) shown in FIG. 38. More specifically, detection of life activity (S22) is performed while an examinee as a life object is watching a "video just before encountering an accident" or a "video to make the examinee pleased or sad" on a TV screen. After that, interpretation of life activity is performed in the same manner as described above.

6.5.3.3) Data Content Stored in Data Base

FIG. 38 shows an exemplary data base construction. In the present exemplary embodiment, three types of data as below are stored in the data base. A content of each type of data and its purpose are explained below.

α) Representative life activity detection signal (indicative of a feature) for each evaluation factor 171 in each measuring item and features thereof . . . . This corresponds to "data obtained as a result of giving a stimulation suitable for a specific evaluation factor 171 from the outside (S21) to perform the detection of life activity (S22), and then performing the collection/accumulation of the result (S24) or the feature extraction (S23)" as described in section 6.5.3.2 with reference to FIG. 38. As will be explained in section 6.5.3.4 with reference to FIG. 39, the information is used as reference data to generate life activity information by interpreting various life activity detection signals obtained for respective purposes.

β) Life activity detection signal to which event information is added . . . . All life activity signals obtained by the detection of life activity are sequentially stored in the data base after event information is added thereto. At this time, all event information described in section 6.5.2 are stored in the data base together with the life activity detection signals so that the process contents in step S21 and step S26 in FIG. 38 lead to the accumulation and enhancement step to the data base (S27).

As will be explained in section 6.5.3.4 with reference to FIG. 40, the data stored in the data base is mainly used for "interpretation of life activity for another purpose by use of life activity detection signals accumulated in the past."

γ) Life activity information obtained as a result of interpretation of life activity . . . . The life activity information obtained as a result of the interpretation of life activity is also stored in the data base sequentially. This information is used when the content in (α) as above is modified for generation of feedback information to the data base (S38) in FIG. 39, for example.

δ) Personal information related to internal neural activity or mind activity per specific user . . . . This is personal information obtained as a result of the interpretation of life activity as will be described in section 6.5.3.5 with reference to FIG. 40, and is stored in the data base in an encrypted state for protection of personal data. Specific examples thereof include detailed connection in a brain/neural circuit or a place which is easy to be sick in an internal organ of each specific user or inclination of a character or a subject of interest of each specific user.

6.5.3.4) Exemplary Embodiment Regarding Interpretation of Life Activity and Feedback to Data Base FIG. 39 shows a procedure of interpretation of life activity in a case where the following cases among the description in section 6.5.3.1 are performed at the same time:

the case where interpretation of life activity is performed based on life activity detection signals by referring to the database; and the case where a feedback is given to the content of the data base by using a result of the interpretation of life activity.

A flow of a right half of FIG. 39 mainly shows the procedure of:

the case where interpretation of life activity is performed based on life activity detection signals by referring to the database;

and the flow of a left half of FIG. 39 mainly shows the procedure of:

the case where a feedback is given to the content of the data base by using a result of the interpretation of life activity.

In the example of the interpretation of life activity shown in FIG. 39, setting (S31) of a measuring item in accordance with application using life activity information is performed at first. The setting (S31) of a measuring item as used herein indicates an operation of selecting one (or more) measuring item(s) from the measuring items listed with the mark "-" in section 6.5.2.

Subsequently, as an applied embodiment using the life activity information shown in the present exemplary embodiment, in a case where a real-time correspondence process to a client including researches, such as a questionnaire survey or a marketing research or a customer service, is required, the process (S21) of giving a stimulation from the outside to the life object (or the examinee) is performed subsequent to the setting (S31) of a measuring item. Here, a content of the stimulation (S21) given to the life object (or examinee) is associated with (related to) the measuring item set in S31. This stimulation (S21) is a "psychological stimulation" in most cases, and corresponds, more specifically, to a process of showing a product as a subject of search to a user who is an examinee or to displaying a screen for questionnaire, or a process of asking a question to a user (as a customer service) At the same time, the operation (S22) of detection of life activity to the user (examinee) is performed.

On the other hand, in a case where "measurement of life activity in a present situation" is performed (e.g., finding a reason why an infant cries or extraction of information which a person who cannot express his/her will wants to tell), the step of giving a stimulation from the outside to the life object as shown in S21 is omitted, and the step (S22) of detection of life activity is performed immediately after the setting (S31) of a measuring item.

A life activity detection signal in the form as shown, for example, in FIG. 36 which is obtained as a result of the above step is then subjected to a calculation process with reference to a data base S30. At this time, reference data in accordance with the measuring item set in S31 is taken from the data base S30. Further, this data base S30 is built on a network server, so that reading or update (writing to the data base S30) of modified data can be performed via the network. Then, the calculation process performed in S32 is performed to calculate an equivalent level per evaluation factor from the viewpoints shown with the marks "-" in section 6.5.2. Alternatively, the calculation process may be performed using the method explained in [B] of section 6.5.3.1. After that, a handling process (S34) is performed based on life activity information obtained therefrom, so as to exhibit the life activity information to the user or provide an appropriate service for the user.

Here, the present exemplary embodiment has a feature in that at the time of providing a service to the user in S34, an operation (S35) of the second detection of life activity, a second calculation process (S37) referring to the data base based on a result of the second detection, and generation (S37) of life activity information are performed. As the measuring item set at this time, the "emotional reaction" or the "involuntary decision (unconscious state)" is automatically selected from the measuring items described in section 6.5.2.

A purpose of the processes from step S34 to S37 is to check on whether the handling process (provision of a service to the user) performed in S34 fits to the desire of the user (examinee). If the handling process (S34) results in dissatisfaction of the user (examinee), generation (S38) of feedback information to the data base is performed and then the accumulation and enhancement (S26) of the data base is performed.

At the time of the generation (S38) of feedback information to the data base, not only a reaction of the user to the handling process (S34) based on the life activity information (a generation result of second life activity information shown in S38), but also a state of the life object at the time when the stimulation is given (S21) or a result of the observation (S26) of the environment around the life object performed using the position monitoring section regarding a detected point for life activity (see in section 6.5.2) are referred to. Furthermore, past life activity information (see (γ) described in section 6.5.3.3) stored in the data base S30 is reviewed so as to generate a modified content with respect to the information described in (α) in section 6.5.3.3. As a result of this, further accumulation and enhancement (S27) to the data base are performed, thereby improving accuracy or reliability of the interpretation of life activity.

Further, the life activity detection signals obtained by the first and second detection of life activity (S22, S35) and the pieces of life activity information obtained by the first and second interpretation of life activity (S33, S37) are accumulated/added (S27) in the data base S30 as well as event information such as results of the stimulation (21) given to the life object or the observation (S26) of the state of the life object or the environment around the life object.

6.5.3.5) Applied Embodiment of Interpretation of Life Activity Using Life Activity Detection Signal in Data Base The following describes a procedure of the interpretation of life activity in each of the following cases among those described in section 6.5.3.1: the case where an appropriate life activity detection signal is extracted from the data base by use of event information; and the case where interpretation of life activity is performed based on a life activity detection signal extracted from the database.

When the interpretation of life activity shown in FIG. 38 or FIG. 39 is repeated, data such as the life activity detection signals or life activity information of a specific user (an individual examinee) are accumulated in the data base S30. Thereby, necessary information to estimate, by calculation, a subject of interest of the specific user (a favorite product which the specific user wants to buy or a hobby of the specific user), an inclination of a character of the specific user, or an internal place which is weak (an internal place easy to be sick). Accordingly, the interpretation of life activity is performed originally regarding the specific user by use of the life activity detection signals or life activity information are accumulated in the data base S30, and personal information related to neural activity or mental activity, such as the subject of interest or inclination of the character of the specific user or an internal site easy to be sick, is calculated, so that an appropriate service can be proposed to the individual user based on a result thereof voluntarily (without any request from the user). FIG. 40 shows an interpretation method of life activity to provide such a voluntary service to a user.

At first, it is necessary to set a content of the voluntary service to be performed on the user (S41). Based on of the service content thus set, a measuring item on life activity information is set (S31).

As has described in section 6.5.3.2 or 6.5.3.4, past life activity detection signals or life activity information are stored in the data base S30 together with event information. In view of this, event information adequate to the service content (S41) or the measuring item (S31) thus set as above is searched, a life activity detection signal or life activity information accompanied by the adequate event information is selected and acquired, and extraction (S42) of necessary data is performed.

Then, a calculation process (S32) based on the measuring item set in step S31 is performed, and generation (S33) of life activity information is performed. At the same time, generation (S43) of personal information related to internal neural activity or mental activity of the specific user to be a target is performed with reference to the past life activity information extracted from the data base S30, and voluntary provision of a service to the user is performed (S44) using the personal information thus generated. Further, in parallel with that, the life activity information newly obtained in step 33 or the personal information obtained in step S43 is stored in the data base S30, and accumulation and enhancement (S27) of the data base is performed. At this time, the personal information is encrypted from the viewpoint of protection of the personal information, and then stored in the data base S30.

Exemplary relations between the personal information related to internal neural activity or mind activity of the specific user obtained in step S43 and the content of the service (S44) provided to the user in accordance with the personal information are shown below.

In a case where the subject of interest of the user is found, a product which the user wants is introduced via the Internet and arrangements of purchase are made according to a user request.

In a case where an internal site which is easy to be sick is found, the user is notified of the site and advised of how to improve living habit or eating habit.

In a case where the inclination of the character of the user is found, the user is notified of a result of tendency analysis according to the inclination of the character and advised of how to behave in the feature.

Further, an alternative service of the above may be as follows:

In a case where the inclination of the character of the user is found, a boyfriend/girlfriend fitting to the character of the user may be introduced.

Further, a concrete method of providing a service to the user performed in step S44 is as follows:
1) the user is asked about necessity of a service like the above; and
2) a service like the above is performed in response to a user request.

Thus, in this exemplary embodiment, since an appropriate service is provided in accordance with individual characteristics of a specific user, a user satisfaction level is improved by providing a meticulous service to each user.

Further, according to the present exemplary embodiment, not only the character inclination of the user can be found, but also early treatment for the user can be attained by automatically determining an early symptom of depression, an internal disease at an early stage related to the autonomous nerve, or the like.

However, since estimation of negative sides such as psychopath or inclination to commit a crime is also performable, the personal information thus obtained as a result of the above exemplary embodiment should be handled with sufficient care.

6.5.4) Other Measuring Methods of Life Activity

As shown in FIG. 1, the nervous system of a mammalian animal including a human has a hierarchical structure. In a central nervous system layer 7 such as the cerebral cortex layer, very complicated neural circuits are formed, and therefore, it is very difficult to generate personal information or even life activity information from a life activity detection signal detected therefrom.

However, as shown in FIG. 1, the neural circuits between layers are connected with each other, so that activities are performed in cooperation with the respective layers.

In view of this, another exemplary embodiment has a feature in that "life activity information is generated from a life activity detection signal of a lower layer and thereby life activity information of a higher layer is estimated" as measures to the difficulty in acquiring life activity information related to the central nervous system layer 7 including the cerebral cortex layer or the limbic system.

It is said that an amygdala takes a central role in regard to the emotional reaction in the brain of a human or an animal, and the emotional reaction is expressed in a central amygdaloid nucleus (Hideho Arita: Nounai busshitsu no sisutemu shinkei seirigaku (Chugai-igakusha, 2006) p. 105). An output signal from the central amygdaloid nucleus is directly input into a facial motor nucleus (Masahiko Watanabe: Nou Shinkei Kagaku Nyumon Koza (Ge) (Yodosha, 2002), p. 222).

Here, this facial motor nucleus works on a facial muscle to control a facial expression. Accordingly, the emotional reaction expressed in the central amygdaloid nucleus appears on the facial expression directly.

On the other hand, a neural circuit directly output from the central amygdaloid nucleus to the cerebral cortex does not exist remarkably, and an output signal from this central amygdaloid nucleus reaches a prefrontal area via a medial nucleus in the amygdala, for example. In addition to that, this medial nucleus receives signal inputs from other areas in the amygdala, the thalamus, or the hypothalamus (Masahiko Watanabe: Nou Shinkei Kagaku Nyumon Koza Gekan (Yodosha, 2002), p. 221).

When an output signal from the central amygdaloid nucleus reaches the prefrontal area with some change affected by these signals, a feeling recognized in the prefrontal area becomes slightly different from the emotion under subconsciousness occurring in the central amygdaloid nucleus. This indicates such a possibility that "a facial expression exhibits an emotion more accurately than a person is aware of"

In view of this, another embodiment explained herein has a feature in that instead of obtaining a life activity detection signal from the central nervous system layer 7 including the cerebral cortex layer, movement of a facial muscle formed by an action from the facial motor nucleus is detected, and life activity information is generated from the detection signal. Accordingly, without a need to obtain life activity information from the central nervous system layer 7 (including the cerebral cortex layer or the limbic system) for which interpretation of life activity is very complicated and difficult, information about the emotional reaction related to the limbic system or the cerebral cortex can be obtained accurately from a result of "interpretation of the movement of the facial muscle" for which the interpretation is relatively easy.

In this case, the marked position 40 on the life-object surface as shown in FIG. 22 corresponds to a facial position of the examinee (or user). In the meantime, there have been digital cameras with a function to automatically detect a facial position of a subject by use of an image recognition technique in these days. In view of this, in this another embodiment explained herein, the position monitoring section regarding a detected point for life activity (a section for performing the first detection) is configured to have the image recognition technique, and a detection signal from the facial position of the examinee (or user) is assumed as a life activity detection signal.

Further, in a case where the another exemplary embodiment described herein is performed, an imaging pattern size is standardized to a size to show a whole face of the examinee (or user) and stored in the memory section 142 of the rear part, at a stage of the process of "A] changing of an imaging pattern size (standardization of the size)" explained in section 6.4.2. If the face size of the examinee is standardized to a predetermined size as such regardless of how small/large the face of the examinee is or how far a distance between the examinee and the signal detecting section 103 is, easiness and accuracy of position detection of eyes or a mouth in the face are improved, thereby making it easy to generate the life activity information from the life activity detection signal.

FIG. 41 shows relationships between a facial expression and an emotional reaction. FIG. 41(a) shows a facial expression during rest, FIG. 41(b) shows a facial expression at the time of smiling, FIG. 41(c) shows a facial expression at the time of getting angry, and FIG. 41(d) shows a facial expression at a loss (they may be difficult to be distinguished from each other due to poor drawings, but intend to show the respective facial expressions). An expression shows a feeling of the examinee (or user). Muscular movements on the face at this time are shown with arrows in FIG. 42. At the time of smiling as in FIG. 41(b), outside muscles of eyebrows and eyes contract downward. Further, outside muscles of a mouth contract upward and outward. At the time of getting angry as in FIG. 41(c), outside muscles of eyebrows and upper eyelids contract upward, and muscles of lower eyelids contract downward. At the same time, outside muscles of a mouth contract downward and outward. On the other hand, at the time of being at a loss as shown in FIG. 41(d), inside muscles under eyebrows contract toward the inside. Further, at the same time, muscles around lower eyelids contract to raise lower eyelids upward. As such, the detection result of contraction and relaxation states of facial muscles is correlated with life activity information corresponding to the emotional reaction or the like.

As has been described in section 1.3 with reference to FIG. 1, when the facial muscle contracts, activation of the neuromuscular junction 5 (a change of a membrane potential) and subsequent potential changing 27 of a muscle fiber membrane occur. Accordingly, the change of the membrane potentials can be detected by use of the near infrared light/infrared light as shown in section 4.7 sections or the Nuclear Magnetic Resonance as shown in section 5.2.

Further, when the facial muscle contracts, an oxygen concentration change occurs in capillaries around the facial muscle, so that the "detection of oxygen concentration change in blood in surrounding areas" is enabled by use of near infrared light, as shown in Table 6.

Moreover, when the facial muscle contracts or repeats contraction and relaxation, heat generated from the inside of the muscle reaches a surface of the face, thereby locally increasing the temperature on the skin surface of the face.

Accordingly, even if the distribution of temperature on the skin surface of the face is measured using a thermography, the detection of life activity can be performed in regard to activities of the facial muscle.

7] Device or System with Detecting Section for Life Activity Incorporated Therein 7.1) Packaged Device with Detecting Section for Life Activity Incorporated Therein 7.1.1) Feature of Packaged Device with Detecting Section for Life Activity Incorporated Therein Initially explained are features of exemplary embodiments of a packaged device with a detecting section 101 for life activity shown in FIG. 31 or 32 incorporated therein. Common features in the exemplary embodiments are as follows:

A detecting section for life activity is incorporated in a packaged device;

A section for performing position detection (the first detection in section 6.1.3) of a detected point for life activity is included . . . . An exemplary arrangement relationship between the section for performing position detection (the first detection in section 6.1.3) and the detecting section for life activity is shown in FIG. 22. As a position detecting principle for a detected point for life activity, the method described in FIGS. 20 to 22 and section 6.2 is used.

A result of position detection of the detected point for life activity is fed back to the detecting section for life activity . . . . More specifically, as has been described in section 6.3, the objective lens 31 or the imaging lens 57 is moved based on the result of position detection of the detected point for life activity. The feedback to the detecting section for life activity is not limited to this and may use other feedback methods.

A section for interpretation of life activity based on a life activity detection signal obtained from the detecting section for life activity is included . . . . Specific interpretation of life activity is performed by the methods shown in FIGS. 38 to 40, for example. Here, in most cases, the interpretation of life activity is performed in combination with a memory section and a CPU (central processing unit).

Based on life activity information obtained as a result of the interpretation of life activity, a specific process or operation is performed . . . . A plurality of options corresponding to the specific process or operation are prepared in advance, and an optimum option is selected in accordance with the life activity information (details thereof will be described in section 7.1.4).

Thus, interpretation of life activity is performed in the packaged device with a detecting section for life activity incorporated therein, and an optimum process or operation to the user is performed based on life activity information obtained therefrom. However, in parallel with a series of processes as above, a life activity detection signal or life activity information obtained in the packaged device and a content of the process or operation performed on the user may be stored in the data base S30 (see FIGS. 38 to 40) in a server via networks.

As has been described in section 6.5, abundant data accumulation in the data base S30 is necessary to increase accuracy of the interpretation of life activity. For this purpose, the packaged device may be connected to the network appropriately to download software of life activity interpretation (or a part corresponding to the data base S30 in the software) based on the updated data base S30. In this case, the present exemplary embodiment also includes such a business model that a maintenance contract is made with the user at the time of purchase of the packaged device, so that charge for the download of the latest software of life activity interpretation (or a part corresponding to the data base S30 in the software) is collected from the user. Further, as a download method of the software of life activity interpretation, a medium such as CD-ROM (DVD-ROM or BD-ROM) or a USB memory may be used instead of using the network.

Further, as the specific process or operation, the present exemplary embodiment performs:

an operation of the driving section or supply of specific information.

Alternatively, other processes or operations may be performed based on the life activity information.

As a method for the supply of the specific information to the user, this exemplary embodiment performs any of the following methods:

screen display, audio output, printout (a printing process) and data storage.

However, the method is not limited to them, and other method for the supply of information may be used.

7.1.2) Exemplary Embodiment of Packaged Device with Combination of Detecting Section for Life Activity and Driving Section The following describes an exemplary embodiment in which the packaged device with a detecting section for life activity incorporated therein performs the operation of the driving section as the specific process or operation as described in section 7.1.1.

Exemplary Embodiment 1 of Packaged Device with Combination of Detecting Section for Life Activity and Driving Section This exemplary embodiment has a feature in that the detecting section for life activity is attached to a driving seat in a vehicle such as an automobile, a train, and an aircraft, and a risk aversion process is started in a short time at the time of sensing danger. This consequently improves the safety of the vehicle by the prevention of danger largely.

For example, during driving of a car, it will take about 0.1 to 0.4 s for a driver to push a brake pedal after the driver senses danger. A car movement during this time delay increases the danger of car crash. Accordingly, if a risk aversion process can be started without causing this time delay of about 0.1 to 0.4 s, the safety will be increased. When the driver senses danger and feels tense, it is estimated that a front part of the cingulate gyms is suddenly activated (see Rita Carter: Mapping the Mind (Phoenix, 1998) p. 312). In view of this, such a sudden activation of this cingulate gyms is detected by the detecting section for life activity. A "measuring item" at the time of interpreting a life activity detection signal output from the detecting section for life activity corresponds to the "awakening/turgescence" in the explanation in section 6.5.2, and an equivalent level 172 for the "emergency recognition" will be evaluated as an evaluation factor 171 in the measuring item. A result of this interpretation of life activity is output to an engine and a control circuit of brakes. Just after the sensing of danger (at the time when the equivalent level 172 for the "emergency recognition" as the evaluation factor 171 exceeds a specific value), a start of a brake operation and braking of driving by activation of engine braking are performed automatically. Here, this driving brake operation corresponds to the concrete example of the "specific process or operation" described in section 7.1.1.

As an alternative to the above exemplary embodiment, all transportation means may include the detecting section for life activity as an applied embodiment of the packaged device.

Exemplary Embodiment 2 of Packaged Device with Combination of Detecting Section for Life Activity and Driving Section In this exemplary embodiment, the packaged device may be applied to the field of nursing or assistance or the field of movement support, thereby yielding an effect that the convenience of the user is improved by taking advantage of the feature of "the detection of life activity by a non-contact method."

For example, a conventional HAL has such a problem that a burden of attaching measuring sections (18 electrodes in total) to the body of the user is large. In order to solve the problem, the detecting section for life activity of the present exemplary embodiment which can detect life activity in a non-contact manner is used in substitution for the electrodes.

This detection of life activity is performed such that activation of the neuromuscular junction 5 relative to muscles of legs (the changing of the membrane potential) or a potential changing 27 of the muscle fiber membrane (FIGS. 1 and 3) which occurs subsequent to the activation is detected using near infrared light/infrared light. The "measuring item" set at the time of interpretation of life activity herein corresponds to the "motor component" in the explanation in section 6.5.2. A result of this interpretation is input into the driving section directly. When the life activity detection signal is processed as such, the following series of operations are performed: "when a user strains the muscles of legs, a signal thereof is detected by the detecting section for life activity and the driving section is controlled to move the foot." This operation of moving a foot by controlling the driving section corresponds to another concrete example of the "specific process or operation" described in section 7.1.1.

In this exemplary embodiment, this detecting section for life activity is embedded in a part such as pants for covering up the legs. Further, instead of fixing reinforcement metal fittings (supporting metal fittings) to the leg with a belt like the conventional HAL, the user sits on a part (a stool part) corresponding to a saddle of a bicycle, so that easiness of attachment and detachment is enhanced.

As an alternative to the above exemplary embodiment, the detecting section for life activity may be provided in any apparatuses used in the field of nursing or assistance or the field of movement support as an applied embodiment.

Further, it is not necessary to limit to the fields as described in the exemplary embodiments 1 and 2 as above, and the packaged device can be applied such that the detecting section for life activity is provided in any apparatuses having a drive system.

7.1.3) Exemplary Embodiment of Packaged Device with Combination of Detecting Section for Life Activity and Information Providing Section The following describes an exemplary embodiment in which the packaged device with a detecting section for life activity incorporated therein performs the operation of the driving section as the specific process or operation as described in section 7.1.1.

Exemplary Embodiment 1 of Packaged Device with Combination of Detecting Section for Life Activity and Information Providing Section If it is possible to provide any communication method for communicating with a person who has a problem with the throat or a person who cannot speak because of decreased strength due to serious illness, that will be a great help to not only the person himself/herself but also people around him/her. In the exemplary embodiment explained herein, "an image or language occurring to a user" is generated from a life activity detection signal obtained from the detecting section for life activity, and a result thereof is exhibited to the user or people around the user by an information providing section. This can provide an unconventional and new communication method, thereby attaining close communication between the user and people around the user.

It is said that a human has a visual area in the occipital lobe (see F. H. Netter: The Netter Collection of Medical Illustrations Vol. 1 Nervous System, Part 1, Anatomy and Physiology (Elsevier, Inc., 2003)Section 8), and a sentence to speak is assembled in a broca's area in the left brain (see Rita Carter: Mapping the Mind (Phoenix, 1998) p. 250). In view of this, an action potential state (an action potential distribution or a time dependent variation thereof) of a neuron in this visual area or the broca's area is detected. As a "measuring item" at this time, the "recollection (content intended to be expressed or occurring image)" is selected among the explanation in section 6.5.2.

Further, an evaluation factor 171 in the measuring item corresponds to a "specific word" occurring to the user, "collaboration between words (corresponding to a sentence obtained by joining words), or a "specific shape (image)." Particularly, as a feature of this exemplary embodiment, it is necessary to generate two types of life activity information through time as a group of the evaluation factors 171, i.e., (1) a content of "an image or language (including a sentence) occurring to the user" and (2) "determination of right/wrong" ("yes" for confirmation of correctness or "no" for pointing out an error).

A specific interpretation method of a life activity detection signal corresponds to the explanation in section 6.5.3.4 with reference to FIG. 39. Here, the generation of life activity information performed in step 33 in FIG. 39 corresponds to generation of (1) a content of "an image or language (including a sentence) occurring to the user." Further, the "handling process based on life activity information" shown in step 34 corresponds to "provision of specific information (=life activity information) to the user" as shown in section 7.1.1. A concrete method of this is to exhibit, on a display placed at a location where the user can see, the content of "an image or language (including a sentence) occurring to the user" in (1) obtained as a result of interpretation of life activity. Just after that, the user thinks of whether the exhibited content is right or not ("yes" or "no") in head. At that time, the content that the user thinks of in head is detected again (corresponding to the operation (S35) of the second detection of life activity in FIG. 39).

Accordingly, the life activity information generated in step 37 in FIG. 39 indicates a "determination result of right/wrong" in (2) as above. Here, if the content exhibited on the display is wrong, the above step is repeated. On the other hand, if the content exhibited on the display is right, the content exhibited on this display is then provided to people around the user by use of an information providing section. The method of providing information to the people around the user is not limited to the screen display, but may be an audio output, a printout (a printing process), or data storage, as shown in section 7.1.1.

Exemplary Embodiment 2 of Packaged Device with Combination of Detecting Section for Life Activity and Information Providing Section This exemplary embodiment is an applied embodiment of <Exemplary Embodiment 1 of packaged device with combination of detecting section for life activity and information providing section> as described above. This exemplary embodiment is the same as the above steps to the generation of the content of "an image or language (including a sentence) occurring to the user" in (1) by interpreting a life activity detection signal. This exemplary embodiment (applied embodiment) has a feature in that the life activity information thus obtained is considered as a "user request," and a service (correspondence process/operation) in accordance with the user request is provided to the user. Exemplary alternatives of this process/operation corresponding to the service to be provided to the user include, for example, "drink or food service" in a case where the life activity information includes "thirst or hunger of the user,"

"assist to the restroom" in a case where the life activity information includes "excretion desire of the user," and the like.

Further, in this another exemplary embodiment, "a service content to be provided to the user" is shown on information providing means "a display placed so that the user can see)" and the user is asked about "whether he/she requests the service or not." When the user requests the service, in case of a packaged device which does not include a driving section, the "request content is exhibited" to people around the user by use of the information providing section, and in case of a packaged device including a driving section, the packaged device "provides the service" requested by the user.

Note that it is not necessary to limit the present exemplary embodiment to the above exemplary embodiments 1 and 2, and such an applied embodiment is included that the detecting section for life activity is provided in any apparatus having the information providing means.

7.1.4) Exemplary Embodiment of Selection of Optimum Process or Operation Method Based on Life Activity Information With reference to FIG. 43 explained is one method for selecting an optimum process/operation in a case where there are a plurality of alternatives of the process/operation corresponding to the service to be provided to the user, as shown in <Exemplary Embodiment 2 of packaged device with combination of detecting section for life activity and information providing section> described above.

As has been already explained in section 6.5.2 with reference to FIG. 37, a plurality of evaluation factors 171-1 to 171-N are set in advance for each "measuring item **," and a value PI indicative of an equivalent level 172 with respect to each evaluation factor 171-I is included in life activity information. In the meantime, assume a case where a plurality of processes/operations 178-1 to 178-M are predetermined as candidates of a service to be provided to the user. A weighting value HjI for each evaluation factor 171-I per process/operation 178-$j$ is set in advance with respect to this condition at a device side (FIG. 43($a$)).

Then, $\Sigma Hji \cdot Pi$ (a value obtained by adding results of multiplying HiI by PI from i=1 to N) is calculated for each process/operation 178-$j$ in regard to input life activity information, and a resultant value is assumed a determination value of the process/operation 178-$j$ (FIG. 43($b$)). Then, a process/operation 178-$j$ indicating a largest determination value is extracted as an optimum alternative.

Note that the present exemplary embodiment is not limited to the method shown in FIG. 43, and an optimum process/operation 178 may be selected from life activity information by use of other methods.

7.2) Network System and Business Model Using Detecting Section for Life Activity.

Section 7.1 has described mainly exemplary embodiments of the packaged device including a detecting section for life activity. This section will explain a network system using a detecting section for life activity and a business model to which the network system is applied, as another exemplary embodiment.

The present exemplary embodiment explained herein (section 7.2) has a large feature in that: with regard to a service activity performed in accordance with a result of biosis activity measurement (see section 6.1.3 for the definition of the term), the following layers are separated completely on the network:

[A] a layer to detect a life activity to generate a life activity detection signal;

[B] a layer to analyze the life activity detection signal to generate life activity information; and

[C] a layer to generate an appropriate service based on the life activity information, and further,

[D] interfacing information between respective layers is transmittable (in an encrypted state in consideration of prevention of personal data leak) via the network (the Internet). As a result of this, it becomes easy for anyone to newly enter into only a specific layer without a need to know processing methods in the other layers. As such, a barrier to entry into each layer is low, and therefore anyone (any company) can easily obtain a business opportunity on the Internet. Accordingly, if many people (or suppliers) participate in these layers, very inexpensive services can be provided to users.

7.2.1) Outline of Whole Network System Using Detecting Section for Life Activity The outline of a whole network system using a detecting section 101 for life activity in the present exemplary embodiment is explained with reference to FIG. 44.

Here, "[A] a layer to detect a life activity to generate a life activity detection signal" as mentioned above corresponds to a "user-side front end." This user-side front end is constituted by a life detecting division 218 including a life detecting section 220, a user-side control system 217, and a user-side drive system 216. Further, the life detecting section 220 includes a detecting section 101 for life activity (see section 6.1.3). However, the present exemplary embodiment is not limited to the above, and collecting means of every information related to the user as well as detection of life activity or every service executing means for executing a provided service 244 to the user based on life activity information, and control means related to them may be included in the user-side front end as constituents.

The process in "[B] a layer to interpret the life activity detection signal to generate life activity information" is performed by a "mind communication provider 211," and a process in "[C] a layer to generate an appropriate service based on the life activity information" is performed by a "mind service distributor 212."

Further, the present exemplary embodiment has a feature in that an original mind connection layer 202 is structured on a conventional internet layer 201. This mind connection layer 202 indicates a network environment on software which just uses a conventional Internet environment on hardware and in which a life activity detection signal 248 with event information or its related information is transferred. That is, this can be interpreted as kind of a community related to biosis activity measurement formed on the internet layer 201 (an Internet environment), and this layer can be built in a specific domain in the network environment. Alternatively, a software network environment in which the life activity detection signal 248 with event information or its related information is set to be automatically transferred to an address designated by a mind communication provider 211 may be called a "mind connection layer 202 in a narrow sense."

In order to build this "mind connection layer 202 in a narrow sense" more specifically, there is a method in which to embed, in a display screen 250 to a user to form a home page on the Web that anyone can see, a command (for example, a Send Detection Signal command described in section 8.3) to:
(1) judge whether a life activity is detected in the user environment; and
(2) when the life activity is detectable, transfer a life activity detection signal 248 with event information to the address designated by the mind communication provider 211. In order to embed the command in the home page on the Web, Web API (Application Interface) described by JavaScript is usable, for example.

Accordingly, a method for building the mind connection layer 202 on the internet layer 201 includes the following processes:
α) participation members in the mind connection layer 202 are gathered . . . the participation members will be mind service distributors 212 including mind communication providers 211 and users 213 who consent to measurement of biosis activity (to receive a specific service 244 to be provided);
β) various controls are embedded into a home page (a display screen 250 to a user) on the Internet that a mind service distributor 212 provides, which controls include:
moving the life detecting section 220 so as to perform detection 24 of life activity to a user 213,
transferring a life activity detection signal 248 with event information to an address designated by the mind communication provider 211, and
transmitting life activity information 249 with event information to an address designated by the mind service distributor 212;
γ) the user 213 owns a life detecting division 218 . . . paid provision from the mind communication provider 211 to the user 213 based on the contract; and
δ) the mind service distributor 212 prepares for an environment which can provide an optimum service to the user 213 based on the life activity information 249 with event information.

The following describes a flow of signal information in the network system, with reference to FIG. 44.

The life detecting division 218 in the user-side front end includes a life detecting section 220, in which the detecting section 101 for life activity is provided (see section 6.1.3). The detecting section 101 for life activity, which has been explained in sections 6.2 to 6.4, performs detection 241 of life activity on the user 213. A life activity detection signal 248 with event information is automatically transferred to an address designated in the command.

Then, from the life activity detection signal 248 with event information transferred via the mind connection layer 202 and the internet layer 201, life activity information 249 with event information is generated in an interpretation section 277 of life activity according to the method as described in section 6.5. In this exemplary embodiment, the life activity information with event information is transferred to the mind service distributor 212 not via the mind connection layer 202, but only via the internet layer 201 (a network line used for the normal Internet). Thus, transfer to the mind service distributor 212 is performed not via the mind connection layer 202, but only via the internet layer 201, so that a transfer speed of the life activity information 249 with event information is increased and the convenience of the mind service distributor 212 is improved. Then, based on the life activity information 249 with event information decrypted in the mind service distributor 212, the user 213 receives an optimum service 244 selected by the method explained in section 7.1.4, for example.

When the user 213 receives the service 244, the user 213 makes all payment 252 for the toll, which is a counter value, to the mind communication provider 211. After that, by an operation in a charging/profit-sharing processing section 231, profit sharing 253 is automatically made from the mind communication provider 211 to the mind service distributor 212.

FIG. 44 describes only one user 213 for the whole network system using the detecting section for life activity. However, the present exemplary embodiment is not limited to that, and a community such as chat or a TV conference system may be formed between a plurality of users 213 located in distinct places via the mind service distributor 212, for example. In this case, life activity information 249 of a counterpart is displayed on a part of the screen, and so that the users can have communication while understanding an occasional feeling of the counterpart. In a conventional email environment using texts mainly or a TV conference, since only a few amount of information is transmitted to people located at a distant place, misinterpretation or misunderstanding of feelings have occurred frequently. In contrast, in the present exemplary embodiment, since the "occasional feeling information of a counterpart" is sent with an intensity level of the feeling, the user can immediately know "how much angry the counterpart is," or the like, so that a smooth human relationship can be easily established.

Further, the present exemplary embodiment is not limited to FIG. 44, and includes any system in which information (e.g., the life activity detection signal 248 or the life activity information 249) related to biosis activity measurement is transmitted via the network or any device which enables the system. In this case, the provision of the service 244 to the user 213 is not essential, and the present exemplary embodiment may be a system to transmit information related to biosis activity measurement without providing the service 244 to the user 213 or a device enabling the system.

7.2.2) User-Side Front End
7.2.2.1) Role of User-Side Front End

A role of the user-side front end is such that "in accordance with Web API preset on the display screen 250 to the user which is formed by the mind service distributor, detection 241 of life activity is performed on the user 213 so as to collect event information B242 related to an environment surrounding the user 213, and a result thereof is transferred as a life activity detection signal 248 with event information to the mind communication provider 211."

Then, based on the life activity information 249 with event information, the mind service distributor 212 provides various services to the user 213. In the meantime, an "execution of a service to be performed directly on the user" in accordance with a content of the service 244 to be provided which is transferred from the mind service distributor 212 via the network (via the internet layer 201) is also a large role of the user-side front end.

As a specific content of this execution of a service to be performed directly on the user, this exemplary embodiment performs:

(1) specific information provision 245 to the user 213 by screen display (or audio output) via a display screen control section 225;

(2) provision of a service 244 to the user 213 by an operation of a user-side drive system 216 subjected to a remote control 251 via the internet layer 201 (via network communications); or the like.

Alternatively, in the present exemplary embodiment, this user-side front end may perform any other service provisions based on the life activity information obtained from the user.

7.2.2.2) Detailed Function of User-Side Front End

The user-side front end has a configuration shown in FIG. 44 to perform the roles as described in section 7.2.2.1. However, the present exemplary embodiment is not limited to the configuration shown in FIG. 44, but may have any configuration which can perform some part of the roles explained in section 7.2.2.1.

Concrete examples of a user-side control system 217 in the user-side front end include a personal computer, a portable terminal, a mobile phone, and a display (television) having a communication function. Alternatively, any apparatus including some of the requirements shown in FIG. 44 may be considered as the user-side control system 217.

The user-side control system 217 is provided with an internet network control section 223, so that homepage information on the Internet (Web) can be collected via the network (the internet layer 201). This collected homepage screen can be exhibited to the user 213 by the display screen control section 225. A user input section 226 is provided with a keyboard, a touch panel, or a microphone, so that the user 213 can perform input such as key-in, a handwriting input, or a voice input.

In this exemplary embodiment, the homepage screen exhibited to the user includes a display screen 250 provided to the user by the mind service distributor 212. As described in section 6.5.3.4 with reference to FIG. 39, event information A243 corresponding to the stimulation (S21) from the outside to perform the detection (S22) of life activity is often included in this display screen 250 to the user. Accordingly, the user-side control system 217 includes an extraction section 224 of event information A. The extraction section 224 interprets (decodes) a content of the display screen 250 to the user, which is received by the internet network control section 223, and extracts a content of the event information A243 therefrom and transfers the content to the life detecting division 218.

In the meantime, the life detecting section 220 of the user-side front end as shown in FIG. 44 is provided with the detecting section 101 for life activity (see section 6.1.3 for the name of each section and the functional relationship), but the display screen 250 to the user from the mind service distributor 212 can be transmitted to a user environment which is not provided with the life detecting section 220. Therefore, as has been described in (1) in section 7.2.1, a command to "judge whether a life activity can be detected in the user environment" (a Check Mind Detection command, which will be described later in section 8.3, for example) is set in Web API in the display screen 250 to the user, in advance.

Accordingly, the user-side control system 217 checks on whether the life detecting section 220 is provided in a user-side front end, in response to the command instruction. In a case where the life detecting section 220 is not provided, a different corresponding screen is displayed according to a setting command (for example, a Change Mindless Display command, which will be described in section 8.3) within the display screen 250 to the user. In this case, since only information input by the user 213 via the user input section 226 is transmitted to the mind service distributor 212, only user input information 254 without a detection signal will be transmitted to the mind service distributor 212 from the internet network control section 223.

On the other hand, in a case where the user-side front end is provided with the life detecting section 220, a life activity detection signal 248 with event information output from a signal/information multiplexing section 222 in the life detecting division 218 is transmitted to the mind service distributor 212 via the internet network control section 223.

The life detecting division 218 can have various configurations such as: an externally-attachable configuration connectable with the user-side control system 217 via a connection terminal such as a USB terminal; and a configuration incorporated into the user-side control system 217. In addition to the above, the life detecting division 218 also can have other various configurations, which will be explained in section 7.2.2.3.

A role of the life detecting division 218 is such that "detection 241 of life activity is performed on the user 213, a state of the user or its environment is observed, and a result thereof is output to the internet network control section 223 as a life activity detection signal 248 with event information."

Here, a result of the observation of the state of a life object or the environment of the life object, performed in step 26 in FIG. 39, corresponds to the event information B242 described in FIG. 44. Further, as has been described in section 6.5.2, in a case where the event information B242 is collected using a part of the position monitoring section regarding a detected point for life activity (the camera lens 42 and the two-dimensional photodetector 43 shown in FIG. 22), a part of the detection section 221 of event information B also serves as the position monitoring section regarding a detected point for life activity in the life detecting section 220. Other concrete examples of the detection section 221 of event information B include a temperature sensor and a humidity sensor, as has been described in section 6.5.2. On the other hand, the "information related to an internal state, directly input by the user 213" as described in section 6.5.2 is categorized into event information A243 here.

The signal/information multiplexing section 222 multiplexes (information synthesis) a life activity detection signal output (encrypted) by the life detecting section 220, event information B242 output from the detection section 221 of event information B, and event information A243 output from the extraction section 224 of event information A, so as to generate a life activity detection signal 248 with event information, and transmits it to the internet network control section 223. Here, from the viewpoint of protection of personal data, the event information A243 and the event information B242 are also encrypted in the life activity detection signal 248 with event information. In the meantime, in the present exemplary embodiment, the event information A243, the event information B242, and the life activity detection signal thus encrypted are divided into a plurality of packets along the standard of the Internet Protocol. Accordingly, in the signal/information multiplexing section 222, the signal and the information are mixed (synthesized) by multiplexing per packet unit.

The user-side drive system indicates "means for providing a service 244 'by use of a drive system'" to the user 213 (a counterpart intended by the user 213) which service 244 is performed in accordance with life activity information 249." Particularly, a "device including a driving section which allows remote control 251 via the internet layer 201 (the Internet)" corresponds to the user-side drive system 216. Here, concrete examples of the user-side drive system 216 include: a simple drive system which allows remote control 251 such as "on/off of a light switch in a room which the user uses;" a device having an advanced driving mechanism as a drive system, such as an "assistance device including a driving section for an electric wheelchair or a motorized bed" and a "housekeeping device including a driving section, such as a cleaning robot;" and a "printer" to tell an intention of the user 213 to the third person. Alternatively, the user-side drive system 216 includes any means for providing a service 244 to the user 213 or a counterpart intended by the user by use of a drive system.

7.2.2.3) Exemplary Embodiment of Integration of Life Detecting Division and Applied Embodiment Using the Same This section deals with supplemental explanation about the life detecting division 218 shown in FIG. 44, various configurations including the life detecting division, and applied embodiments using the same.

Although not illustrated herein, the life detecting section 220 included in the life detecting division 218 is constituted by, as has been described in section 6.5.2, the detecting section 101 for life activity shown in, for example, FIGS. 31 and 32, the position monitoring section regarding a detected point for life activity shown in, for example, FIGS. 20 to 22, and a connection/control section for connecting them to perform control in a disciplined manner.

Further, only one life detecting division 218 is described in FIG. 44, but the present exemplary embodiment is not limited to this, and a plurality of life detecting divisions 218 having different configurations can be provided in the user-side front end, as described later.

Next will be explained an exemplary product configuration in which the life detecting division 218 is incorporated and an applied embodiment using the configuration.

<The Life Detecting Division 218 Having a Configuration of an Externally-Attaching Device and Connected to the User-Side Control System 217 Via a Connection Terminal>

An optical system for life activity detection in the detecting section 101 for life activity incorporated in the life detecting section 220 and a photodetector used therein employ the configurations as illustrated in FIGS. 26 to 28, and detect movement of face muscles of the user as explained in section 6.5.4, so as to measure an emotional reaction of the user. At this time, the position monitoring section regarding a detected point for life activity uses the principle illustrated in FIG. 22. The marked position 40 on the life-object surface illustrated in FIG. 22 corresponds to a face position of the user. Accordingly, when the user 213 operates the user-side control system 217 (e.g., a personal computer or a portable terminal), it is necessary to provide the life detecting division 218 so that the face of the user 213 can be detected with the two-dimensional photodetector 43.

A measuring item set at the time of interpreting the life activity detection signal 248 is any of the "emotional reaction," the "involuntary decision (unconscious state)," and the "attraction," in many cases (see section 6.5.2).

In a case where the "attraction" is set as the measuring item under the conditions as above, the present exemplary embodiment can be used for "mail order" or "marketing research." For example, a mail order program is broadcasted on the display screen 250 provided to the user by the mind service distributor 212 and the "attraction" is judged every time a new product is introduced, so that an efficient marketing research can be performed. Further, a "seriousness level of the user" can be found when the user 213 makes an inquiry to a specific product, so that efficient correspondence can be achieved.

On the other hand, in a case where the "emotional reaction" or the "involuntary decision (unconscious state)" is set as the measuring item under the conditions as above, an appropriate correspondence process according to an occasional feeling of the user 213, such as guidance or consultation/advice, can be performed. For example, if it is found that the user 213 is upset or at a loss because the user 213 does not know how to operate a homepage which the user 213 sees for the first time, the screen can be automatically changed into a guidance screen to the user 213. This will largely improve the convenience to the user 213.

<Baby Crib with the Life Detecting Division 218 Incorporated Therein>

Parents having a newborn baby for the first time often have difficulty dealing with the baby when he/she is crying. At that time, if the parents know a state of the baby and how to deal with the baby in real time (immediately), that would be a great help to the parents, and the parents will have great brief in the mind service distributor 212. In this exemplary embodiment, when a newborn baby is laid on a crib with the life detecting division 218 incorporated therein and measurement is requested, the measurement of biosis activity is performed automatically. As a result of this, the state of the baby can be estimated, thereby allowing a service 244 of informing the user of the state of the baby and of advising the user of how to deal with the baby in such a state.

Even in this case, the optical system for life activity detection in the detecting section 101 for life activity incorporated in the life detecting section 220 and the photodetector used herein employ the configurations as illustrated in FIGS. 26 to 28. Further, at this time, the position monitoring section regarding a detected point for life activity uses the principle illustrated in FIG. 22. The marked position 40 on the life-object surface illustrated in FIG. 22 corresponds to the head of the newborn baby. Therefore, it is necessary to provide the life detecting division 218 so that the head of the newborn baby can be detected with the two-dimensional photodetector 43 when the baby is laid on the baby crib.

Meanwhile, a presumable reason why the newborn cries is as follows: A) a regional pain due to disease, B) a notification of excretion, C) a request (dependence) of love (embrace) to a parent, D) a complaint of hunger or thirst, or the like. Here, when an internal regional pain or discomfort in the excretion occurs, a somatosensory area is activated locally (see F. H. Netter: The Netter Collection of Medical Illustrations Vol. 1 Nervous System, Part 1, Anatomy and Physiology (Elsevier, Inc., 2003) P. 166). Accordingly, if correlation data between an activated pattern in the somatosensory area and a place where pain or discomfort occurs are accumulated in advance by the method explained in section 6.5.3.2 with reference to FIG. 38, (A) a place of the pain or (B) an excretion state can be estimated from the activated pattern in the somesthetic system. As a measuring item in this case, the "somesthetic system" is set (see section 6.5.2).

On the other hand, when the emotional reaction of the newborn baby is measured by the detection movement of face muscles of a user, as has been explained in section 6.5.4, the request of love (embrace) to a parent from a feeling of dependence in (C) can be estimated. Further, as a measuring item in this case, the "emotional reaction" is set (see section 6.5.2).

If any of (A) to (C) is not applied, it can be estimated that the reason for the baby crying is the complaint of hunger or thirst in (D), as a result of elimination of the other options.

<Pillow or Head Part of Bed in Bedroom with the Life Detecting Division 218 Incorporated Therein>

There is a difference in a brain wave between awakening and sleeping of a human. A sleep state of a user is measured using the detection method of the present exemplary embodiment which can be performed in a non-contact manner in substitution for the electroencephalography, so that a service 244 such as "automatic turning off of a light and music in the room when the user 213 falls asleep" and "automatic turning on of a light in the room when the user 213 wakes up."

Even in this case, the optical system for life activity detection in the detecting section 101 for life activity incorporated in the life detecting section 220 and the photodetector used herein employ the configurations as illustrated in FIGS. 26 to 28. Further, at this time, the position monitoring section regarding a detected point for life activity uses the principle illustrated in FIG. 22. The marked position 40 on the life-object surface illustrated in FIG. 22 corresponds to the head of the user 213. Accordingly, it is necessary to provide the life detecting division 218 so that the head of the user 213 can be detected with the two-dimensional photodetector 43.

Further, as a measuring item in this case, the "awakening/turgescence" is set (see section 6.5.2).

Judgment on whether a light and music in the room are turned on or off based on a result of measurement of biosis activity is performed by the method explained in section 7.1.4 with the use of FIG. 43.

<Entrance Door or Wall or Window of Entrance Hall with the Life Detecting Division 218 Incorporated Therein>

The present exemplary embodiment is usable for security. In this case, it is necessary to provide the life detecting division 218 so that the face of a person standing at the entrance or the door of the entrance can be detected with the two-dimensional photodetector 43. The detection of movement of face muscles of a user, as described in section 6.5.4, is performed so as to measure an emotional reaction of the user (the "emotional reaction" is set as a measuring item). Thereby, it can be estimated whether or not the person standing at the entrance or the door of the entrance "has malice" or "is going to harm to people in the house." This will be useful in terms of security.

<Street Surveillance Camera with the Life Detecting Division 218 Incorporated Therein>

The above exemplary embodiment is useful for security measures in a private house. As an applied embodiment of the above exemplary embodiment, the life detecting division 218 is incorporated in a surveillance camera provided at a place such as an intersection where people gather, so that the life detecting division 218 can be used for crime prevention in the public place. That is, people having malice aforethought or malice such as pickpocket/shoplifting are found among people walking on streets and kept chased with cameras. This makes it possible to prevent accidents or to record occurrences of accidents. As a result, the peace and order in the public place are improved.

<Desk or Chair with the Life Detecting Division 218 Incorporated Therein>

The above exemplary embodiment is usable for a teacher to know a degree of learning eagerness of students in school (whether students listen to what the teacher says), for a boss to evaluate performance of a subordinate in the company, or the like.

In this case, it is necessary to provide the life detecting division 218 so that the face or head of a person sitting in front of a desk or sitting on a chair can be detected with the two-dimensional photodetector 43. Further, the optical system for life activity detection in the detecting section 101 for life activity incorporated in the life detecting section 220 and the photodetector used herein employ the configurations as illustrated in FIGS. 26 to 28. Further, at this time, the position monitoring section regarding a detected point for life activity uses the principle illustrated in FIG. 22. As a measuring item, the "emotional reaction" or the "awakening/turgescence" is set (see section 6.5.2). In a case of measuring the "emotional reaction," the detection of movement of face muscles of a user is performed as described in section 6.5.4. On the other hand, in a case of measuring the "awakening/turgescence," the activation level in the cingulate gyms is measured as has been explained in <Exemplary Embodiment 1> of section 7.1.2.

As shown in the above exemplary embodiments, new applied embodiments can be provided by incorporating the life detecting division 218 into various devices (or products). However, the configuration is not limited to the product configurations shown in the above exemplary embodiments, and the life detecting division 218 can be provided in "any configuration which can be provided (also movable) at a place where people or animals can approach or make contact with so as to measure biosis activity."

7.2.3) Mind Communication Provider 7.2.3.1) Role of Mind Communication Provider

The following shows roles of the mind communication provider 211. The largest role is:

[A] Interpretation of a life activity detection signal 248 with event information transmitted via the mind connection layer 202 and the internet layer 201, and transmission of life activity information 249 with event information obtained as a result of the interpretation to the mind service distributor 212 via the internet layer 201.

Other roles except for the above are as follows:

[B] Reception of a payment 252 for the toll from the user 213 and profit-sharing 253 of a reasonable amount of the payment 252 to the mind service distributor 212;

[C] Technical support for the mind service distributor 212 to perform the following processes on the display screen 250 to the user:

a method for performing detection 241 of life activity on the user 213 and collection of event information B242 by moving the life detecting section 220 or the detection section 221 of event information B at the user-side front end;

a method for transmitting the life activity detection signal 248 with event information to an address designated by the mind communication provider 211; and a method for forming/providing a display screen 250 to a next user to whom specific information provision 245 can be performed based on the life activity information 249 with event information obtained from the mind communication provider 211, so as to perform an optimum service 244 to the user 213;

[D] Translation, into other language, of the display screen 250 to the user provided by the mind service distributor 212 . . . . When the display screen 250 to the user translated into other languages is posted on the Internet, people around the world can receive the service 244 from the mind service distributor 212;

[E] Technical guidance or technical support to the mind service distributor 212 as to how to perform remote control 251 on a drive system to move the user-side drive system 216; and

[F] Maintenance of the mind connection layer.

The role [A] is executed by the interpretation section 227 of life activity in the mind communication provider 211 and processed by the method explained in section 6.5, as shown in FIG. 44. At this time, the data base stored in the database storage area 228 is utilized.

The role [B] is handled by a charging/profit-sharing processing section 231.

Further, the roles [C] to [E] are handled by a technical support processing section 230 with respect to the mind service distributor. In this case, expenses for the technical support corresponding to [C] to [E] are collected from the mind service distributor 212 in a route different from a route of "the payment 252 for the toll from the user 213→the profit-sharing" as described in [B].

On the other hand, the role [F] is handled by a maintenance processing section 229 of the mind connection layer.

7.2.3.2) Mechanism to Prevail Internet Service Using Life Activity Information

As has been described in the beginning of section 7.2 before the explanation of section 7.2.1, it is important to "reduce a technical burden at the time when the mind service distributor 212 participates in the mind connection layer 202" so as to prevail the Internet service using life activity information. Therefore, the mind communication provider 211 performs the interpretation of a life activity detection signal, which is accompanied with technical difficulty, on behalf of the mind service distributor 212.

Further, a full-scale technical support corresponding to [C] to [E] in section 7.2.3.1 and complicated charging duties corresponding to [B] are also handled by the mind communication provider 211.

As a result, anyone (including corporations) in the world can participates as the mind service distributor 212 to propose an original service 244 which users 213 jump at. Further, by setting a business area on the internet layer 201 which does not require shipping charges or personnel expenses, it is possible to restrain service costs very much.

Further, a user 213 to receive the service 244 (to participate in the mind connection layer 202) only requires "a contract with the mind communication provider 211 (including the setting of a charging method and a purchase contract of the life detecting division 218)," which can be made on the Internet. This can largely reduce a burden on the user 213.

As a result, if the service 244 that the user 213 expects truly can be provided at a bargain price, the Internet service using life activity information can be made widely available, thereby enhancing the mind connection layer.

7.2.3.3) Business Model of Mind Communication Provider

A business model in the present exemplary embodiment has such a feature that "based on life activity information 249 obtained as a result of measurement of biosis activity about a user 213 (a plurality of users 213), a payment 252 of the toll is made in compensation for the service 244 to be provided to the user 213." Further, "the mind communication provider 211 receives the payment 252 of the toll collectively, and then the mind communication provider 211 provides profit sharing 253 to the mind service distributor 212."

When this business model is adopted, the mind service distributor 212 is released from the complicated duties of "collecting payments for the toll from individual users 213," which allows a large reduction in service charges to the users 213.

The following explains how a general user 213 participates in the mind connection layer 202. First of all, a general user 213 makes a contract with the mind communication provider 211 and determines a charging way (how to make a payment 252) or a service content related to the mind connection layer 202 (what kind of service the user 213 wants to receive from the mind service distributor 212). At this time, the user 213 determines contents of the life detecting division 218 and the user-side drive system 216 purchased from the mind communication provider 211.

The contract made between the user 213 and the mind communication provider 211 or the determination of a life detecting division 218 and a user-side drive system 216 to purchase from the mind communication provider 211 is basically performed on the Internet (using the internet layer 202), but alternatively, a franchise of the mind communication provider 211 or a general merchandising store of electric appliance may be used. Further, a charging contract on the Internet (using the internet layer 202) is made by a notification of an account number and a password from the user 213, but alternatively, the user 213 may sign on automatic debt transfer.

In the meantime, if a personal computer or a portable terminal which the user 213 has already is used as the user-side control system 217, the user 213 purchases only an external life detecting division 218, connects it to the user-side control system 217 via a connection terminal such as a USB, and installs necessary software in the personal computer or the portable terminal. Further, if the user 213 wants to purchase a user-side control system 217, the user 213 purchases a set of a user-side control system 217 equipped with a life detecting division 218 and a user-side drive system 216, which are connected with each other.

When the user 213 receives the life detecting division 218 (or the user-side drive system 216) which the user 213 purchased and necessary settings are completed, the user can use the mind connection layer 202.

The payment 252 from the user 213 to the mind communication provider 211 is made by withdrawal from a debit account number or automatic withdrawal from an account monthly or every time the user 213 uses the service, based on the charging contract.

7.2.4) Mind Service Distributor 7.2.4.1) Role of Mind Service Distributor

Roles of the mind service distributor 212 are as follows:
to determine an optimum service 244 based on life activity information 249 with event information and to provide the service 244 to the user 213; and
to receive a service request from the user 213 on the Internet.

In order to receive a service request from the user 213, a display screen 250 to a user, which is a homepage screen of the mind service distributor 212 to be posted on the Internet (the internet layer 201), is formed. This screen is formed on the premise of the detection 24 of life activity with respect to the user 213. Accordingly, when the screen display/change setting section 232 receives information 254 with no detection signal from a user 213 who does not have a life detecting division 218, the screen display/change setting section 232 changes the screen to a display screen 250 corresponding to the user. In this case, the screen display/change setting section 232 refuses life activity information 249 with event information from the mind communication provider 211, changes the screen to the display screen 250 to the user corresponding to user input information 254 with no detection signal input via a user input section 226, and performs specific information provision 245 as a service 244 to the user 213.

On the other hand, if the user 213 owns a life detecting division 218, a method for providing an optimum service 244 is selected according to the method explained in section 7.1.4 with reference to FIG. 43, based on life activity information 249 with event information. There are three types of methods for providing the service 244 from the mind service distributor 212.

A first method is such that the screen display/change setting section 232 changes the display screen 250 to the user, and performs specific information provision 245 to the user 213.

A second method is such that the remote control 251 to a drive system is performed on a user-side drive system 216 by a function of the remote operation section 233 of the drive system and provides a service 244 to the user 213.

A last method is such that the direct-service content determination section 234 operates to perform a direct service 247 by means of mail or dispatch as the service 244 to be provided to the user 213. This corresponds to, for example, product delivery in a case where the user 213 ordered a specific product on a mail-order video played on the display screen 250 to the user. Alternatively, this direct service 247 corresponds to a case where lesion of a user 213 is found by life activity information 249 with event information and a doctor or a helper is sent to the user 213.

In this exemplary embodiment, a biosis activity of the user 213 is measured appropriately, and therefore, even if a physical condition of the user 213 changes, the change can be found immediately, so that the user 213 can escape death. As such, this exemplary embodiment can provide a large contribution to life support. Accordingly, the present exemplary embodiment will be a great help to health management or security for elderly people who are living alone.

7.2.4.2) Business Model of Mind Service Distributor

A business model of the mind service distributor 212 is "provision of a service 244 by use of measurement of biosis activity (life activity information 249) and collection of counter value thereof." Particularly, the mind service distributor 212 can receive a technical support based on the contract with the mind communication provider 211, so that the mind service distributor 212 does not need any knowledge about a measuring technique for biosis activity or Web API, and can conduct business by just "drafting of a service 244 to make a user 213 happy."

Further, since the mind communication provider 211 takes charge of a charging contract with individual users 213, the mind service distributor 212 can provide a service 244 without being conscious of individual users 213.

However, such easiness that anyone can participate in the mind connection layer 202 as the mind service distributor 212 has a risk adversely. That is, it is also easy to participate in this mind connection layer 202 to brew up some mischief. The following shows an example thereof. Life activity information 249 with event information is transmitted to the internet layer 201 in an encrypted state, but is decrypted in the mind service distributor 212. Accordingly, there is such a risk that a heartless mind service distributor 212 releases personal information of users 213 on the internet layer 201.

In order to prevent such a risk, it is necessary that even third party organizations other than the mind communication provider 211 monitor a utilization state of a life activity detection signal 248 with event information or life activity information 249 with event information so as to prevent abuses.

7.2.4.3) Exemplary Service of Mind Service Distributor

With reference to FIG. 45, the following explains an exemplary embodiment of the service 244 to be provided to the user 213 from the mind service distributor 212 including an operation of the life detecting section 220 working behind the scenes or the mind communication provider 211.

At the time when the user 213 opens a display screen 250 to a user formed by the mind service distributor 212 on the Web, or at the time when the user 213 performs some sort of operation on the screen 250, a start-up process (S51) is initiated. Just after that, the life detecting section 220 starts its operation to initiate detection 214 of life activity 241 with respect to the user 213. Then, based on life activity information 249 with event information obtained as a result thereof, an interface correspondence process (S52) in accordance with a feeling of the user is initiated. After that, a process of detection of life activity and collection of event information B (S53) is performed in response to a request from the user 213. A specific method of detection 241 of life activity here and a principle thereof are based on the explanation in sections 6.1 to 6.4. Subsequently, a generation process (S54) of life activity information is performed in the interpretation section 227 of life activity of the mind communication provider 211. Here, a generation method of life activity information and a collection method of event information B are based on the explanation in section 6.5. Subsequently, as a result thereof, selection (determination) of a service form which is optimum for a user and its execution process 1 (S55) are performed in the mind service distributor 212. Then, at a stage where a service 244 to be provided to the user 213 is performed, the detection 241 of life activity is performed with respect to a reaction of the user 213 similarly to FIG. 39 (the operation of the second detection of life activity (S35)), and an interface correspondence process (S52) in accordance with a feeling of the user is performed as needed. Then, a second selection (determination) of a service form which is optimum for the user and its execution process 2 are performed (S56) if necessary as a result of S52.

Next will be explained a detailed content about the exemplary embodiment of FIG. 45 with regard to a specific applied embodiment in combination of <Baby crib with the life detecting division 218 incorporated therein> and <The life detecting division 218 having a configuration of an externally-attaching device and connected to the user-side control system 217 via a connection terminal> as described in section 7.2.2.3.

As has been described in section 7.2.2.3, assume a case where a parent having a newborn baby for the first time feels awkward when the baby cries. This parent has two sets of life detecting divisions 218 at home, and one of the sets is attached in a baby crib. The other one of the sets is an externally-attaching device connected to a personal computer corresponding to the user-side control system 217 via a connection terminal (a USB terminal), and is provided so as to be able to detect movement of face muscles of a user 213 sitting down in front of this personal computer.

Here, assume a case where the parent opens a homepage established by a mind service distributor 212, for the first time, to know "why the baby cries."

It is supposed herein that a Check Mind Detection command is set in a display screen 250 to a user on Web API, and when the detection of life activity cannot be performed, a Change Mindless Display command is executed, so that respective commands of Display Mind Searching, Start Mind Searching, Send Detection Signal, and Send Mind Information are executed in succession when the detection of life activity cannot be performed (see section 8.3).

A specific content of the start-up process (S51) in FIG. 45 is shown in FIG. 46. Initially, in accordance with the Check Mind Detection command, the user-side control system 217 checks on whether there is a life detecting division in the user-side front end (S61). If there is no life detecting division 218 in the user-side front end, the user-side control system 217 sends information 254 without a detection signal to the mind service distributor 212 via the internet network control section 223, and changes a screen to a display screen which does not perform detection of life activity, in accordance with the Change Mindless Display command (S62). The screen thus changed is obtained such that the display screen 250 to a user changes only in response to user input information 254 without a detection signal.

On the other hand, even in a case where there is a life detecting division 218 in the user-side front end, the user-side control system 217 notifies, via the internet network control section 223, the mind service distributor 212 that there is a detection signal. Then, in accordance with the Check Mind Detection command, it is determined whether detection of life activity is performable using the life detecting division 218 (S63). This indicates determination on whether there is a measuring subject (user or the like) within a range detectable by the life detecting section 220 and determination on whether a detection permission is received from an examinee. As described above, the life detecting division 218 at the side of the externally-attaching device is provided so as to be able to detect movement of face muscles of the user 213 sitting down in front of the user-side control system 217 (personal computer), and the other life detecting division 218 is provided so that the head of the baby can be detected with a two-dimensional photodetector 43 when the baby is laid on the baby crib. However, when the user 213 does not sit down in front of the user-side control system 217 and the baby is not laid in the baby crib, life activities cannot be detected. In this exemplary embodiment, in a case where either one of the life detecting divisions 218 can operate on the user-side front end, the process of detection 241 of life activity is initiated. However, if the detection 241 of life activity cannot be performed in both of the life detecting divisions 218, the mind service distributor 212 is notified of information about that via the internet network control section 223. Thereafter, the user is notified of the state where the detection of life activity cannot be performed (S64). A notification method at this time is comment representation or audio representation on the display screen 250 to the user exhibited by the mind service distributor 212. Alternatively, the user may be notified by a representation function of the life detecting division 218.

When it is confirmed that the user 213 sits down in front of the user-side control system 217, the examinee (the user 213 in this case) is inquired about whether detection of life activity can be initiated or not. An inquiry method at this time also uses comment representation or audio representation in the display screen 250 to the user exhibited by the mind service distributor 212. When a permission for detection of life activity is obtained from the user 213 as an examinee of the detection of life activity via a user input section 226, the detection of life activity is initiated using the life detecting division 218 at the externally-attaching device side in accordance with the Start Mind Searching command (S65), and the user is notified of the detection of the life activity in accordance with the Display Mind Searching command (S66). A specific method to notify the user (S66) is such that a screen like "Mind Searching by " is displayed in a part of the homepage screen (the display screen 250 to the user) which the user 213 watches or an audio guidance is performed. Alternatively, the user may be notified by a representation function of the life detecting division 218 (e.g., a lamp representation of a specific color). Like the exemplary embodiment explained herein, in a case where the user-side front end is provided with a plurality of life detecting divisions 218, the use 213 can be notified of "which life detecting division 218 is used for the detection of life activity" by use of an expression of "" in "Mind Searching by ." Meanwhile, the process (S66) of notifying the user of this detection of life activity is very important from the viewpoint of protection of personal data or invasion of privacy. This is because a measurement result of biosis activity (life activity information 249) is very highly confidential personal information and breach of privacy. Accordingly, by notifying the user (S66) of this, such an effect is yielded that the user 213 can have options such as avoidance of biosis activity measurement by moving away (rejection of collection of personal information of the user 213**).

FIG. 47 shows a specific content of the interface correspondence process (S52) in accordance with the feeling of the user in FIG. 45. In this exemplary embodiment, a feeling of the user 213 which varies every second can be found by biosis activity measurement appropriately (in real time). Accordingly, the present exemplary embodiment has a feature in that a user interface matched with the feeling of the user 213 can be provided by making use of the above. The following deals with "changing of a display screen" as an example of this user interface, but any method which makes a user interface method adequate (change a user interface method) by use of a measurement result of biosis activity (life activity information 249), such as "adequacy of music for a user," "adequacy of an expression method with audio or text," or "adequacy (changing of sex or age) of people appearing," are also included in the range of the present exemplary embodiment.

When the user 213 uses a new machine for the first time or when the user 213 browses a homepage which the user 213 has never seen before on the Internet, the user 213 may be puzzled over how to operate. At that time, there will be no problem if the user 213 learns how to operate while making trial and error. However, if the user 213 does not know how to operate at all and gets stuck, some advice will be required. As for how to give an advice, some cases require just automatic display of a navigation screen showing a guidance by use of an animation, but some other cases require a detailed guidance to the user 213 by a technical operator. As an example of a method for providing a user interface in accordance with a feeling of the user 213, the following explains the adequacy of a screen to explain how to operate (changing to an appropriate screen) with reference to FIG. 47.

As described in <The life detecting division 218 having a configuration of an externally-attaching device and connected to the user-side control system 217 via a connection terminal> in section 7.2.2.3, if movement of face muscles of the user is detected and an emotional reaction of the user is measured, the feeling of the user 213 which varies every second can be understood. It is determined whether or not the user is used to operating the screen (S71), regarding the current display screen 250 to the user (a homepage that the user 213 is currently browsing) provided by the mind service distributor 212. The determination is performed by use of life activity information 249 with event information related to the emotional reaction, which is transmitted from the mind communication provider 211. More specifically, the "emotional reaction" is set as a measuring item as has been explained in section 6.5.2, and among evaluation factors included in the measuring item thus set, whether or not a value of an equivalent level 172 about "anxiety" is equal to or less than a determination value and whether or not a value of an equivalent level 172 about "relief" is equal to or more than a determination value are checked. If the user is used to the operation of the current screen, the user is allowed to operate the current display screen (S72). On the other hand, if the user is not used to the operation of the screen, it is determined whether or not the user feels anxiety about the operation or handling of the screen (S73). A specific method thereof is such that the value of the equivalent level 172 about the evaluation factor, "anxiety," is checked in detail, similarly to the above. When the equivalent level 172 about "anxiety" is lower than a standard value, it is considered that the user does not feel anxiety so much, and a navigational screen which works automatically is displayed to the user 213 (S74) so as to explain to the user 213 about how to operate, by giving a guidance using an animation. The changing to this navigation screen which works automatically (S74) is executed by an operation of the screen display/change setting section 232 in the mind service distributor 212. On the other hand, when the equivalent level 172 of "anxiety" is higher than the standard value, it is considered that the user 213 feels strong anxiety, and a screen on which an operator directly gives a guidance on the Web is displayed (S75), so that the user 213 can understand how to operate or handle by directly communicating with the operator at ease. As such, by providing an interface in accordance with a feeling of the user 213 (by changing a content or a method of the interface), the user 213 can feel at ease and use the interface comfortably.

At the stage where the user 213 understands how to use, the user 213 lays his/her baby in the baby crib. The life detecting division 218 on a baby-crib side accordingly detects a presence of the baby automatically, which initiates detection of life activity in accordance with the Display Mind Searching command. After that, the user is notified of the detection of life activity using the life detecting division 218 on the baby-crib side in accordance with the Display Mind Searching command.

In a case of finding a reason why the baby cries, the "somesthetic system" and the "emotional reaction" are set as measuring items as mentioned above. As will be described later in section 8.3, information of these measuring items is designated as a parameter in the Send Mind Information command. Here, on the display screen 250 (homepage on the Web) to the user formed by the mind service distributor 212, a Send Mind Information command is set as Web API. When the internet network control section 223 receives this information, the event information extraction section 224 extracts the Send Mind Information command as a part of event information A243 therefrom. Then, the Send Mind Information command is multiplexed by the signal/information multiplexing section 222, and a life activity detection signal detected from the baby and this Send Mind Information command (or parameter information inside the command) are transmitted to the mind communication provider 211 as a life activity detection signal 248 with event information (corresponding to the collection process (S53) of detection of life activity and event information B of FIG. 45).

In the generation process of life activity information (S54) of FIG. 45, the mind communication provider 211 performs interpretation of the life activity detection signal based on the measuring items specified in the Send Mind Information command (or parameter information therein) included in the life activity detection signal 248 with event information thus transmitted.

Subsequently, in the selection (determination) of an optimum service form for the user and its execution process 1 (S55) in FIG. 45, the mind service distributor estimates that the reason why the baby cries is any of the following reasons as described in <Baby crib with the life detecting division 218 incorporated therein> in section 7.2.2.3: A) a regional pain due to disease; B) a notification of excretion; C) a request (dependence) of love (embrace) to a parent; and D) a complaint of hunger or thirst. A result of the estimation is displayed on the display screen 250 to the user, so as to notify the user 213 of the reason in a form of provision of specific information 245.

In a case where the reason why the baby cries is any of the reasons (B) to (D), the service 244 is completed just by notifying the user 213 of the reason. On the other hand, in a case where the reason why the newborn cries is (A), it is necessary to notify the user 213 of the situation as well as to advise the user of how to deal with the situation, for example, consultation to a doctor. In this case, an optimum way to deal with that is selected according to the method explained in section 7.1.4 with reference to FIG. 43, and the user 213 is notified of a result thereof.

If there is a possibility that the baby is sick, the parent (the user 213) will be upset. As the interface correspondence process (S52) in accordance with a feeling of the user and the selection (determination) of an optimum service form for the user and its execution process 2 (S56) in FIG. 45, the optimum way to deal with the situation is displayed on the screen first. At the same time, the way to deal with the situation is made adequate in accordance with the feeling of the parent (the user 213) as has been described in FIG. 47. As an option, the way to deal with the situation may be set to direct consultation with a pediatrician on the Internet (the internet layer 201) if the user wants. As such, since the way to deal with the situation is made adequate in accordance with the feeling of the user 213, not only early detection of illness is enabled, but also the user can have a large relief 8] Communicating Protocols for Life Activity Detection Signal and Life Activity Information As has been described in chapter 7 with reference to FIG. 44, a life activity detection signal 248 with event information and life activity information 249 with event information are transferred via the network. This chapter explains communication protocols to be used in this networking.

Further, as has been described in chapter 7, in the present exemplary embodiment, an API command is set on the display screen 250 (a homepage screen on the Internet) to a user. Further, this chapter also deals with a content of an API command to be used in the present exemplary embodiment for the first time.

8.1) Feature of Common Parts of Communication Protocols for Life Activity Detection Signal and Life Activity Information First of all, features and effects (described after " . . . ") of common parts of the communication protocols for the life activity detection signal 248 with event information and the life activity information 249 with event information are described below:

(1) The communication protocols for the life activity detection signal and the life activity information partially have a common structure to be shared . . . . A part of the communication protocol included in the life activity detection signal can be diverted as a part of the life activity information, so that the life activity information can be generated easily;

(2) The life activity detection signal and the life activity information are made compatible with an Internet Protocol IP . . . . As has been described in section 7.2.1 with reference to FIG. 44, both the life activity detection signal 248 and the life activity information 249 are subjected to communication processing on the internet layer 201 according to the Internet Protocol IP. Thus, since both of them are configured to have a structure (a communication protocol) compatible with the Internet Protocol IP in advance, a burden to the internet network control section 223 in FIG. 44 can be reduced;

(3) A plurality of datagrams per common content are defined and multiplexed to be sent .... By employing a method for fragmentation (multiplexing) of datagrams defined in the Internet Protocol IP, a plurality of different contents can be communicated in a mixed form in the life activity detection signal and the life activity information;

(4) A plurality of datagrams collected per common content are defined so that it is possible to identify which packet corresponds to which datagram by a corresponding datagram identification 332 in an Internet header 315 .... This allows high-speed determination on which datagram each fragment is included per packet, thereby making it easy to restructure a datagram from fragments;

(5) An Internet header 315 in each packet is configured to have a timestamp 339 so that packets can be synchronized with each other .... Different datagrams can be synchronized with each other very easily; and (6) The life activity detection signal and the life activity information are configured to have a common structure of an event datagram 302 .... Information of the event datagram 302 included in the life activity detection signal can be just diverted as a part of the life activity information, so that the life activity information can be generated easily.

Next will be explained common parts of the communication protocols for the life activity detection signal and the life activity information, more specifically.

As shown in FIGS. 48 and 49, in a life activity detection signal, a detection condition datagram 301, one or more detection signal datagrams 303, and one or more event datagrams 302 are defined. Further, as shown in FIGS. 50 and 51, in life activity information, an interpretation condition datagram 305, one or more life activity datagrams 304, and one or more event datagrams 302 are defined.

As shown in FIGS. 48 to 51, each datagram is divided into small fragments 316, 317, 318, and 319, and stored in packets 310, 311, 312, and 313.

An internet header 315 is placed in a headmost part in each of the packets 310, 311, 312, and 313. As shown in FIGS. 48 and 50, the internet header 315 has a structure common in the life activity detection signal and in the life activity information. Service type information 331 in the internet header 315 indicates a type required for packet transmission, for example, whether a packet included in this internet header 315 "is required to be transmitted at a high through put (transmission rate)," "is required to be transmitted with high reliability (with low error occurrences after the transmission)," "is transmitted with a short allowable delay time (is not allowed to be transmitted with a large delay)," or the like. Further, a corresponding datagram identification 332 is expressed by 16 bits and indicates in which datagram a data fragment in a corresponding packet is included. More specifically, upper 3 bits indicate any of a detection condition datagram 301, an interpretation condition datagram 305, a detection signal datagram 303, a life activity datagram 304, and an event datagram 302. In the detection signal packet 313, subsequent 2 bits indicate a type of a detection wavelength λ (in the present exemplary embodiment, concurrent measurements can be performed with the use of four types of detection wavelength light beams having different wavelengths). Further, remaining lower 11 bits indicate to be included in a detection signal datagram 303 corresponding to the same detection time. Here, an actual detection time is synchronized with the timestamp 339, so that if it takes a longer time for detection and all detection times cannot be shown by 11 bits (i.e., overflows), the 11 bits can be repeatedly used in a cyclic manner.

On the other hand, in the life activity information packet 314, subsequent 2 bits indicate identification information of a measuring item (in the present exemplary embodiment, pieces of life activity information about 4 different measuring items can be extracted at the same time). Then, remaining lower 11 bits indicate to be included in a life activity datagram 303 corresponding to the same detection time. Here, an actual measurement time is synchronized with the timestamp 339, so that if it takes a longer time for measurement and all measurement times cannot be shown by 11 bits (i.e., overflows), the 11 bits can be repeatedly used in a cyclic manner.

A various control 333 of fragment and a fragment offset 334 indicate where data fragments 315, 316, 317, 318, 319 placed just after their corresponding internet header 315 are located in a single datagram 301, 302, 303, 304, 305. More specifically, the various control 333 of fragment is constituted by 3 bits, and a first bit is set to "0." When a subsequent bit is "0," which indicates that fragmentation is performed, a plurality of data fragments 315, 316, 317, 318, 319 are included in a single datagram 301, 302, 303, 304, 305. When this bit is "1," the bit indicates that fragmentation is not performed. Another subsequent bit has location information in the single datagram 301, 302, 303, 304, 305. That is, when this bit is "0," this bit indicates a last fragment in the single datagram 301, 302, 303, 304, 305. On the other hand, when this bit is "1," the bit indicates other occasions except the above. The fragment offset 334 indicates to which fragment in the single datagram 301, 302, 303, 304, 305, the data fragment 315, 316, 317, 318, 319, which is placed just after a corresponding internet header 315, corresponds. More specifically, in a case of a first data fragment 315, 316, 317, 318, 319 in the single datagram 301, 302, 303, 304, 305, a value of a corresponding fragment offset 334 is set to "0." In a case of a subsequent data fragment 315, 316, 317, 318, 319, a value of a corresponding fragment offset 334 is set to "1." Thus, the value in the fragment offset 334 is increased sequentially.

Further, a source address 335 and a destination address 336 indicate IP (Internet protocol) addresses of a source and a destination in a case of communication via the internet layer 201 (see FIG. 44). Further, the internet header 315 has identification information of a life detection section or peculiar address information 338 of the life detecting section. The life detecting section 220 shown in FIG. 44 is configured to have unique identification information or peculiar address information for each model. This information may correspond to a production number per model. This information is stored within the internet header 315, and is used in common in the life activity detection signal 248 with event information and the life activity information 249 with event information (in a case where detection is performed in the same model and measurement is performed based on a result thereof). This allows long-term history management of the life activity detection signals 248 with event information and the life activity information 249 with event information.

In the present exemplary embodiment, the internet header 315 is configured to have a timestamp 339. This makes it possible to synchronize respective datagrams 301, 302, 303, 304, 305 (to have the same timing). This timestamp 339 is constituted by 32 bits, and indicated by a counting number of a system clock which assumes 1 clock interval as 1 ms. When the counting number overflows, a counting value starts from "0" again. As such, the counting value is cyclic, but an absolute time can be calculated by combining this time stamp 339 with detection start time information 352 shown in in the detection condition datagram 301 in FIG. 49 or the interpretation condition datagram 305 in FIG. 51. As information indicating that this timestamp 339 is included in the internet header 315, a value of option-type information 337 is set to "68."

As shown in FIG. 49 or 51, an event datagram 302-1 which varies depending on even information is stored. One event datagram 302 is divided into pieces, each of which is placed dispersedly within an event data fragment 317 in an event packet 312. Further, a content of each event is placed within a corresponding event datagram 302 as an event content 348. In a single event datagram 302, an event continuation time 347 is stored just before the event content 348. Here, an event start time per event is prescribed by the timestamp 339 described above, and an ending time of the event is calculated by a combination of this timestamp 339 and information of the event continuation time 347. Further, just before this event continuation time 347, an event category 346 is stored. Examples of the event in the present exemplary embodiment encompass:

(A) event information A243 which is a content of the display screen 250 (a content of a homepage on the Web) to a user shown in FIG. 44 and extracted by the extraction section 224 of event information A;

(B) event information 242 extracted by the extraction section 221 of event information B shown in FIG. 44 . . . . An environment surrounding a user 213 (an examinee) at the time of detection of life activity based on temperature/humidity conditions during detection (e.g., whether the user stays alone or with other people); and the like.

This event category 346 indicates which category the event content 348 belongs to. Thus, since the event category 346 is included in the event datagram 302, there will be an effect that selection and extraction of the event content 348 per event category can be performed easily afterwards.

Further, as shown in FIG. 49 or 51, common information between different events is included in an event datagram #0 302-0 and is placed at a headmost part of event datagrams #1 302-1 . . . each including an event content 348. This event datagram #0 includes number information 342 of events occurring in detection term, event source address information 341, and the like. Here, in the event source address information 341, a URL of a display screen and the like are stored. Still further, in a case where an API command is set on a display screen (a homepage screen on the Web) designated by the URL, this information is stored in an API command 343 set in the display screen.

8.2) Communication Protocol for Life Activity Detection Signal

Features of the communication protocol for the life activity detection signal 248 with event information are explained with reference to FIGS. 48 and 49.

A source address 335 in the internet header 315 corresponds to an IP address of the user-side control system 217 (a personal computer, a portable terminal, a mobile phone, or the like) in FIG. 44. On the other hand, a destination address 336 is an IP address designated by the mind communication provider 211 in FIG. 44 and is determined in advance. In most cases, an IP address of a place where the interpretation section 227 of life activity is placed is set as the destination address 336.

In the communication protocol for the life activity detection signal 248 with event information, a detection condition datagram 301 and a detection signal datagram 303 are defined. Here, a life activity detection signal detected by the life detecting section 220 of FIG. 44 is stored in the aforementioned one or more detection signal datagrams 303 and then transferred. This detection signal datagram 303 is divided into pieces, which are dispersedly placed in corresponding detection signal data fragments 318 in respective detection signal packets 313. On the other hand, the detection condition datagram 301 is divided into pieces, which are dispersedly placed in corresponding detection condition data fragments 316 in the detection condition packet 311.

In the detection of life activity in the present exemplary embodiment, locations of individual detected points are different depending on detection types of life activity (detection targets), e.g., an intracerebral neuronal arrangement, an arrangement of face muscles, or the like. In view of this, location information 326 of each detected point is defined in a detection signal datagram #0 303-0 placed at a headmost part in a plurality of detection signal datagrams 303. More specifically, three-dimensional location information of a first detected point is described first, and three-dimensional location information of a second detected point is described next, for example. Thus, three-dimensional location information for all detected points is predefined.

In subsequent detection signal datagrams 303, a value of a detection signal of each detected point for which a three-dimensional location is defined (e.g., a value of a pulse counting number of an action potential, a reflection light amount of light of 780 nm/830 nm, a surface temperature measured by a thermography, or a peak area (or a peak height) by Nuclear Magnetic Resonance) is stored as a life activity distribution map 327, 328 per detected point.

In this exemplary embodiment, a detection signal datagram 303 relating to a different detection wave length λ is defined per wavelength of light to be used for detection and per measured time T1, T2.

As shown in FIG. 49, the detection condition datagram 301 is configured to include identification information 351 of a user (an examinee). This makes it possible to individually manage detection signals of different users (examinees). The usage of the detection start time information 352 has been already explained in section 8.1. This detection start time information 352 includes time information in a form of year/month/day/time/second/subsecond (a unit of 0.1 sec). Further, a system clock cycle of the timestamp 339 is 1 ms as described in section 8.1. Alternatively, a basic frequency of a timestamp can be reset in a column for a basic frequency 353 of a timestamp in the detection condition datagram 301. Hereby, in a case where the detection signal changes at high speed, the basic frequency is raised so as to increase detection accuracy, and in a case where the detection signal changes very slowly, the basic frequency is lowered so as to facilitate long-term measurement. Thus, flexible setting in accordance with characteristics (a time dependent variation) of the detection signal is attainable. A subsequent measuring item 354 corresponds to a measuring item described in section 6.5.2. When this measuring item 354 is included in the detection condition datagram 301, the convenience in interpretation by the interpretation section 227 of life activity (FIG. 44) in the mind communication provider 211 is improved. Further, the detection method 355 indicates the detection method shown in Table 6. Further, a detection signal category 356 indicates which part in a life object is detected and what detection method is used for the detection specifically. A subsequent location information of detected area and location rule of detected points 357 indicates what kind of method is employed as a position monitoring method of a detected point 30 for life activity, more specifically (e.g., whether the method described in section 6.2.1 is used, the method described in section 6.2.2 is used, and the like). On the other hand, a detecting resolution 358 of detected area, an expressed bit number 359 of quantized detection signal, and a sampling frequency or sampling interval 360 of detection signal indicates detection accuracy of the detection signal. Further, the number of detection signal datagrams 303 relating to the detection wave length λ can be estimated from number information 361 of wavelengths used for detection. This improves the convenience in interpretation by the interpretation section 227 of life activity (FIG. 44) in the mind communication provider 211. Furthermore, as will be describe in section 10.2, the mind communication provider 211 can be notified of a timing for purchasing new key information with respect to an encryption key generator by use of accumulated number information 362 of detection signal sending. Accordingly, when this accumulated number information 362 of detection signal sending is included in the detection condition datagram 301, the mind communication provider 211 can acquire key information at an appropriate timing, so that even if life activity detection signals 248 with event information are transferred a number of times, the interpretation section 227 of life activity can stably perform interpretation (see FIG. 44).

8.3) Communication Protocol for Life Activity Information

As shown in FIG. 44, the source address 335 in the internet header 315 in the communication protocol for the life activity information indicates an IP address of the interpretation section 227 of life activity in the mind communication provider 211. On the other hand, the destination address 336 is an IP address of the mind service distributor 212.

In the communication protocol for the life activity information, an interpretation condition datagram 305 and one or more life activity datagrams 304 are defined. A result of interpretation by the interpretation section 227 of life activity in FIG. 44 is divided into pieces, which are respectively stored in the one or more life activity datagrams 304. Further, as shown in FIG. 50, one life activity datagram 304 is divided into pieces, which are dispersedly placed in respective life activity information fragments 318 in life activity information packets 314.

On the other hand, common information at the time of interpretation performed in the interpretation section 227 of life activity is stored in the interpretation condition datagram 305. As shown in FIG. 51, the interpretation condition datagram 305 is divided into pieces, which are dispersedly placed in respective interpretation condition data fragments 319 in the interpretation condition packet 310.

As shown in FIG. 50, a different life activity datagram 304 is set per measuring item as described in section 6.5.2, and different life activity datagrams 304 are respectively set for times T1 and T2. In a single life activity datagram 304, an equivalent level indicative of an interpretation result for each evaluation factor (see section 6.5.2) at the same time is recorded as equivalent level values 377, 378 of evaluation factors included in a measuring item A measured at time T*. Further, a life activity datagram #0 304-0 placed before those single life activity datagrams 304 includes information about interpretation of a life activity detection signal, which is common to the equivalent level values 377 and 378 of evaluation factors. That is, number information 371 of measuring items is specified first, and then information related to measuring items A, B, . . . are sequentially described in accordance with the number information 371. More specifically, number information 372, 374 of evaluation factors included in each measuring item and an evaluation factor list 373, 375 based on the number information are described. Here, in a case where a measuring item A is the "awakening/turgescence" as described in section 6.5.2, for example, the evaluation factor list 373 relating to the measuring item A indicates "emergency recognition, turgescence, awakening, relaxed state, drowsiness, REM sleep, non-REM sleep."

Specific contents and effects from user identification, detected person identification, or detected object (member) identification 351 to accumulated number information 362 of detection signal sending, which are included within the interpretation condition datagram 305, are the same as the contents in the detection condition datagram 301 which has been already explained. In the meantime, interpretation software or a data base used for interpretation of a life activity detection signal to obtain life activity information is kept improved (upgraded) every day. In view of this, if the interpretation condition datagram 305 further includes a version number 363 of interpretation soft and a data base version number or last modified time 364 of a data base used for interpretation, it is found with which grade the interpretation is performed. If the interpretation is performed with a very low grade, it is possible to perform interpretation with the use of the latest interpretation software or data base again and to update the data base. Accordingly, with the use of this version number 363 of interpretation soft or the data base version number or last modified time 364 of a data base used for interpretation, the life activity information in the data base can be kept updated to a maximum level.

8.4) Exemplary New Command Used for Web API

The following explains examples of a new command to be used for Web API in the present exemplary embodiment.

Check Mind Detection . . . . Regarding the detection of life activity, it is determined (1) whether or not a life detecting division 218 is provided at a use side, and (2) whether there is a measuring subject (user or the like) within a range detectable by the life detecting section 220, and results thereof are transmitted to an address designated by a parameter in this command.

Change Mindless Display . . . . A display screen is automatically changed to a display screen which does not require measurement of biosis activity. A URL of a corresponding screen is designated by a parameter in this command.

Start Mind Searching . . . . Detection of the life activity is started.

Display Mind Searching . . . . A message indicative of detection of life activity is displayed to the user. A display size or a display range is designated by a parameter in this command.

Send Detection Signal . . . . A life activity detection signal is transferred to an address designated by a parameter in this command.

Send Mind Information . . . . Life activity information after interpretation is transferred to an address designated by a parameter in this command. Further, a "measuring item" for the interpretation is designated by a parameter in this command.

Display Mind Information . . . . Life activity information after the interpretation is displayed to the user. Further, a "measuring item" for the interpretation, a display form of the life activity information to a user, or a display area/display size is also designated by a parameter in this command.

Start Navigation Display . . . . A screen on which a navigator (an animation) gives a guidance is displayed.

Start Human Interface . . . . An interpersonal correspondence screen is displayed, and a direct face to face correspondence by a technical operator is started.

Start Mind Connection . . . . A connection to other people (TV telephone) is established, and life activity information of a counterpart is displayed thereon.

Further, a "measuring item" for the interpretation, a display form of the life activity information to a user, or a display area/display size is also designated by a parameter in this command.

9] Applied Embodiment Using Detection or Measurement of Biosis Activity

Chapter 9 explains an applied embodiment using detection or measurement of biosis activity explained from chapters 2 to 6. First of all, an outline of the fields to which the present invention can be applied is given, and then, exemplary embodiments in which biosis activity detection is used in diagnosis as application to the medical field, which is one of the fields of application, are explained.

9.1) Feature of Applied Embodiment of Biosis Activity Measurement and New Feasible Unique Function A field of application in which a computer, consumer electronics, or a robot is operated using information obtained from brain measurement by electroencephalographs or the like is generally called BMI (Brain machine interface), conventionally (See p. 33 of Nikkei Electronics (Nikkei BP) published on May 3, 2010). In the measuring method of life activity in the present exemplary embodiment, not only an activity (action potential or contraction) of one neuron or one muscle cell can be detected, but also a mutual network connection therebetween can be detected. Accordingly, detection accuracy is drastically improved in comparison with the electroencephalograph as mentioned above. In view of this, this field of application using the detection method of life activity is referred to as NEI (Neuron electronics interface), including the meaning that features or functions different from the BMI can be provided. Further, the detection method of life activity to be used in NEI is not limited to the detection of membrane potential changing, and other detection methods shown in Table 6 may be used as well.

The example of <Baby crib with the life detecting division 218 incorporated therein> in section 7.2.2.3 and the service example in section 7.2.4.3 have explained the method to understand the feeling of a "newborn baby who is crying." Further, in <Exemplary Embodiment 1 of packaged device with combination of detecting section for life activity and information providing section>, the provision of the communication method with "a person who has a problem the throat or a person who cannot speak because of decreased strength due to serious illness" has been explained. Further, in the service examples in sections 6.5.4 and 7.2.4.3, the method to understand the feeling (emotion) of people from movement of facial muscles has been explained. As such, the NEI (the field of application in which the present applied embodiment is included) has a large feature that "new communication environments" which have been unrealizable in the past can be provided.

The achievement of "information sharing in a group for problem solving by use of a communication method" is considered to greatly contribute to "development of humankind" on earth. The communication method in the history of humankind was developed in order of occurrence of words, invention of letters, invention of printing techniques, and then construction of Internet infrastructure. Further, tradition of the art including painting or music, which has occurred in parallel with a series of development progresses, is also considered as one of the communication methods. Culture or civilization has changed in accordance with the development of new communication methods. Here, the NEI is positioned on an extension line of the development of the communication methods.

More specifically, the inventor of the present invention eagerly hopes that the society would get rid of conventional "deep attachment to products (possession) at hand" or "mammonism" and would shift to a society which "is interested in the heart of people" by spread of the NEI. The development of the Internet has caused the whole world to shift to a global society, thereby making it possible to easily contact with people around the world. In the meantime, it is extremely difficult to "estimate feelings of a counterpart" between people who grew up in totally different environments. Therefore, they are prone to insist what they want or express their ego to each other, which tends to decrease harmony. In contrast, if they can receive an interpretation result of the feeling (emotion) of a counterpart based on movement of facial muscles at once (during conversation) by the NEI, then they can make adequate how to deal with the counterpart by referring to the interpretation result. This may result in that the NEI can contribute to harmonization or correction of differences in the whole society.

Further, as section 6.5.4 has described that "a facial expression could exhibit an emotion more accurately than a person is aware of," the person can know what you are under his/her subconsciousness which he/she is not aware of. As a result, the NEI can be used as an assistant to "understand oneself deeply."

However, if the interpretation result about the feelings of other people thus obtained is relied on too much, there may be such a possibility that "an opportunity to improve characters by distress or mature consideration to understand the feelings of people" would be lost. Accordingly, "the NEI should be used as an assistant."

The following describes original functions to be demonstrated only in accordance with this applied embodiment (NEI) of the biosis activity measurement (i.e., the functions unrealizable in the past).

New communication methods . . . . See the above explanation. This will allow the user to understand feelings of dementia elderly people or to communicate with animals.

Securing of safety by risk aversion in case of emergency . . . . As described in <Exemplary Embodiment 1 of packaged device with combination of detecting section for life activity and driving section> in section 7.1.2, at the moment when a brain senses risk (before moving hands and feet), the user can shift to a risk aversion operation automatically. This will be advantageous in a case where "speed is important" to avoid risk.

Clarification of high-speed neural activity of a human [the examinee can check] . . . . Since the will or thought of a measurement subject could not be checked in conventional animal experiments using needle electrodes, validation of analysis of experimental findings were poor. Further, the temporal resolution is low in the detection method of oxygen concentration changes in blood (see section 4.7). In view of this, in this applied embodiment using the detection of membrane potential changing as in the example of section 9.3, high-speed neural activities can be detected and the validation can be performed in the communication with the examinee, so that measurement accuracy is improved.

Completely non-contact interface which reduces a burden on the user . . . . Since it is not necessary to attach electrodes like the electroencephalograph, the burden on the user is largely reduced. As another applied embodiment, this interface may be used for detection of cardiac muscular movement so as to measure the electrocardiogram in a non-contact manner. Since keyboard operation, pen-based input, or voice input is unnecessary for input, movement of limbs or a vocal band is not regulated at the time of the input to a device. Accordingly, the operation can be performed while "talking" or "moving a hand."

Expansion/development facilitating function for new applied development or new service development . . . . As has been described in section 7.2 with reference to FIG. 44, a domain (mind connection layer 202) can be established on an open world of the internet layer 201. Accordingly, in this case, new applied development or new service development can be made thereon very easily, and thus, this feature is excellent in extensibility or expandability.

9.2) Expansion of Applied Embodiment Using Measurement of Biosis Activity

The fields of application (a range of the NEI) using the life activity measurement, which have been explained in the present exemplary embodiment, are summarized as follows:

Basic research of medical science . . . . Mechanism analysis of image recognition, language process, thought, emotion, or memory. Explication of internal information network path (see section 9.3.1). Particularly, this is suitable for studies which make use of a feature (section 9.1) that "high-speed neural activities can be detected while checking to an examinee." Concrete examples encompass studies at a neuron network level of human language processing. Since hominoidea (apes) does not have a language that people have (Atsushi Iriki: Gengo to shiko wo umu nou-Shirizu nokagaku (3)-(University of Tokyo Press, 2008) P. 170), the human language processing can be researched only by a non-contact and noninvasive method to human. Further, since the temporal resolution is low in the detection of oxygen concentration changes in blood, a high-speed process such as the language process cannot be traced in detail. Accordingly, a study using the detection of membrane potential changing in the above field will make a significant contribution.

In addition to that, the life activity measurement can be applied to tracing of time dependent variations in human recognition or thinking/recollection process.

Determination of Life and Death

Medical diagnosis (including action for disease prevention) . . . . See examples of section 9.3. In this applied embodiment, an abnormality of the autonomic nervous system is easy to be found at an early stage.

Medical treatment . . . . See examples in section 9.3.2.

Care support or aiding support, mobile suit . . . . See the explanation in <Exemplary Embodiment 2 of packaged device with combination of detecting section for life activity and driving section> in section 7.1.2.

Communication method . . . . Corresponding to the explanation in section 9.1.

Management/supervision . . . . See the explanation in <Desk or chair with the life detecting division 218 incorporated therein> in section 7.2.2.3.

The detecting section 101 for life activity shown in FIG. 31 is attached to a driving seat of a car, so that a process of waking up a driver or the like process may be performed by sensing that the driver feels sleepy.

Security or authorization process . . . . See the explanation in <Street surveillance camera with the life detecting division 218 incorporated therein> or <Entrance door or wall or window of entrance hall where with the life detecting division 218 incorporated therein> in section 7.2.2.3. Further, the life activity measurement is usable as validation information of a "lie detector."

High-speed input process . . . . As described in <Exemplary Embodiment 1 of packaged device with combination of detecting section for life activity and information providing section> in section 7.1.3, documentation or drawing input may be performed at high speed without performing voice inputting or key-in.

Entertainment game . . . . As described in <Exemplary Embodiment 1 of packaged device with combination of detecting section for life activity and driving section> in section 7.1.2, a high-speed response can be achieved without moving hands and feet. Thus, the life activity measurement is suitable for a competition game or an operation simulation game of a high-speed mobile object (a car or an airplane).

Further, a service of character judgment or affinity diagnosis may be provided.

Vicarious operation . . . . See the explanation of <Exemplary Embodiment 2 of packaged device with combination of detecting section for life activity and information providing section> in section 7.1.3, and <Pillow or head part of bed in bedroom with the life detecting division 218 incorporated therein> in section 7.2.2.3.

9.3) Applied Embodiment of Detection of Life Activity to Medical Diagnosis

The detection method of life activity of the present exemplary embodiment to detect membrane potential changing in a non-contact and noninvasive manner using the principle explained from chapters 2 to 5 can yield a very high temporal resolution and spatial resolution. In view of this, when an action potential state of a neuron or contractile activity of a muscle cell is detected, for example, by use of the detection of life activity, abnormality (malfunction) can be found highly precisely per single cellular unit.

Accordingly, if the detection method of life activity or the measuring method of life activity of the present exemplary embodiment is applied to the medical field, it is possible to progress the advanced study greatly and to make a highly accurate diagnosis.

The following describes two examples in which this detection method of life activity is applied to medical diagnosis.

9.3.1) Exemplary Search of Neural Transmission Pathway in Life Object

Section 6.5.3.2 has already described a method in which a part of skin of a life object is pricked with a "needle" to cause pain so that a signal detection area (ending) of a sensory neuron is activated (an action potential occurs), and a path through which the signal is transmitted is searched to be used for a data base construction for interpretation of life activity. A diagnosis method of a medical treatment using this internal neural transmission pathway search is explained below by taking, as an example, "diagnosis of spinal canal stenosis."

In most vertebrates, signal transmission is performed between a brain and a somatic end via a spinal cord. This spinal cord is placed in a space referred to as a vertebral canal in a backbone. A patient suffering from spinal canal stenosis feels pain in lower limbs because a part of a narrowed vertebral canal presses a part of the spinal cord. However, a diseased part is located inside the vertebral canal, and the lower limbs where the patient feels pain are actually not a diseased part.

In conventional techniques, it is possible to find a narrowed area in the vertebral canal by MRI (Magnetic Resonance Imaging) or CT scanning (Computer Tomography Scanning), but it is impossible to specify neurons involved with the actual pain occurrence. This applied embodiment makes it possible to specify a single neuron which causes the pain, thereby yielding an effect that diagnosis accuracy is improved drastically. Further, since a diseased part can be specified in more detail, medical treatment can be performed more easily in comparison with the conventional techniques. Further, even if surgery is necessary for the treatment, since the diseased part can be specified beforehand in detail (a single neuron unit), a physical burden on the patient during surgery can be reduced at the minimum.

With reference to FIGS. 52 and 53, the following describes the diagnosis method of this applied embodiment. Here, in FIGS. 52 and 53, (a) shows a path through which a signal of pain is transmitted in the body, and (b) shows a cross-sectional view around the spinal cord in the lumbar part. Further, (c) shows an example of a life activity detection signal detected according to this applied embodiment.

Initially, examples of a factor and symptom of the spinal canal stenosis are shown in FIG. 52(b) and FIG. 53(b). That is, a part of the lamina placed in the rear of the backbone comes in contact with the spinal cord at a position β, and a neuron β in a spinal cord gray matter 416 is pressed, thereby causing a false signal of pain. The following takes, as an example, a case where this false signal causes a patient to feel pain in the tip of a foot.

There is such a feature of the patient of the spinal canal stenosis that a pain level in the lower limbs changes depending on a posture. Here, in most cases, when the patient "straightens himself/herself," the pain level increases, whereas when the patient "bends down (slouches forward)," the pain tends to be relaxed. This phenomenon is caused presumably because when the patient "straightens himself/herself," the spinal cord 413 comes toward the lamina 415 so that the pressure at the position β is increased, and when the patient "bends down (slouches forward)", the spinal cord 413 is distanced from the lamina 415. This feature is used for diagnosis.

That is, as a first step of diagnosis is to let a patient of spinal canal stenosis "bend down (slouch forward)," so as to cause a state in which the pain of the lower limbs (the patient thinks) is relaxed. While keeping this state, an intraneural transmission path of a pain signal at the time when the patient really feels pain in the tip of a foot is searched. At the beginning of this search, a part where the patient feels pain (a position α in the tip of a foot, in this example) is stimulated with a "needle." As shown in FIG. 52(a), there is a signal detection area (ending) 4 of a sensory neuron on a surface part (the position α in the tip of a foot) thus stimulated with the needle, and a pain signal is generated here. The pain signal generated here is transmitted to a neuron θ in a postcentral cerebral cortex 411 via a neuron δ in a spinal cord gray matter 416 and a neuron η in a thalamus 412 (see FIG. 52(a)(b)).

At this time, respective spots α, δ, η, and θ are illuminated with light having a wavelength in the range specified in section 4.7 so as to detect reflection light amount changes 401 along a detection time 163. Results thereof are shown in FIG. 52(c).

As has been already described in section 1.3, when a stimulation is given locally with a needle, pH decreases due to an inflammation or ischemia to cause pain, and $Na^+$ ions or $Ca^{2+}$ ions flow into a cytoplasm due to an action of a proton-activated cation channel. As a result, "depolarization" occurs in the ending 4 of the sensory neuron, and a membrane potential rises to a depolarization potential. According to the speculation in section 2.2, it is considered that a negative charge domain is formed outside the cell membrane constituting the signal detection area (ending) 4 of the sensory neuron during this depolarization.

From the reason explained in chapters 3 and 4, a reflection light amount from the negative charge domain thus formed outside the cell membrane decreases locally. In this applied embodiment, this reflection light amount change 401 is detected as a pain signal (=a life activity detection signal) to be transmitted in the body. The pain signal generated in the signal detection area (ending) 4 of the sensory neuron is not generated continuously, but is an intermittent pulse-like signal as shown in FIG. 52(c). In the example of FIG. 52(c), pulse-like pain signals generated in the signal detection area (ending) 4 of the sensory neuron at the position α occur at times $t_1$ and $t_5$ along the detection time 163.

In the spinal cord gray matter 416 including a neuronal cell body δ which relays a pain signal generated in the signal detection area (ending) 4 of the sensory neuron, many other neuronal cell bodies are also concentrated therein. In view of this, since the detection technique using a conventional non-contact method or noninvasive method has a low spatial resolution, it was very difficult to specify a location of one neuron which relays a pain signal. In contrast, the detection of life activity in this applied embodiment has a high spatial resolution, so that a location of one neuron which relays a pain signal can be specified for the first time.

This applied embodiment uses a phenomenon that "a neuron fires an action potential when it relays a pain signal." When the neuron fires an action potential, the reflection light amount decreases locally (at a place where a neuron cell body relaying a pain signal is located), from the same principle as above. In view of this, by searching a place where the reflection light amount change 401 occurs when the pain signal is transmitted, a neuron (a location of cytoplasm) δ relaying a pain signal can be detected.

Here, for detection of a place where an action potential occurs, the method explained in section 6.3.1 with reference to FIGS. 23 to 25 is employed. Further, at the same time, a detected point 30 for life activity is monitored by the method explained in section 6.2.1 with reference to FIGS. 20 and 21. Then, the position of the objective lens 31 is automatically corrected based on a result thereof (a servo for misalignment correction is applied), thereby resulting in that the detection of life activity can be continued even if the examinee moves to some extent during the detection and the detected point 30 for life activity is displaced.

More specifically, as shown in FIGS. 52(a) and (b), for example, γ, δ, ε, and ζ are temporarily set as candidates of a neuron (a position where its cytoplasm is located) relaying pain signals, and reflection light amount changes 401 are detected at respective positions along the detection time 163.

As a result, as shown in FIG. 52 (c), decreases of the reflection light amount can be detected at the position δ at times $t_2$ and $t_6$ slightly delayed from times $t_1$ and $t_5$ at which pain signals are generated in the signal detection area (ending) 4 of the sensory neuron 4 located at the position α. In contrast, no reflection light amount is detected at respective positions γ, ε, and ζ, as shown in FIG. 52(c), it can be estimated that the neuron (the position of the cytoplasm) relaying pain signals is located at the position δ.

When a neuron δ fires an action potential, a pain signal thereof is transmitted through the spinal cord 413 and relayed in the thalamus 412. Then, a neuron η in the thalamus 412 fires action potentials at times $t_3$ and $t_7$, which are delayed from times $t_2$ and $t_6$, and then a neuron θ in the postcentral cerebral cortex 411 fires action potentials at times $t_4$ and $t_8$, which are a little delayed further. Respective timings of the action potentials are detected as the reflection light amount changes 401 as shown in FIG. 52(*c*).

In this way, an intraneural transmission path of a pain signal at the time when the patient really feels pain in the tip of a foot is searched. The applied embodiment shown in FIG. 52 detects a position of "a neuron cell body by use of an action potential phenomenon." Alternatively, this applied embodiment is applicable to other methods to detect the membrane potential changing by a non-contact method or a noninvasive method, and "an axonal path at the time when a signal is transmitted" may be detected, for example. That is, when a signal is transmitted through an axon in a neuron cell body, a membrane potential in the axon changes locally, so that the change can be detected as the reflection light change amount 401.

Subsequently, a second step of diagnosis is to let the patient of spinal canal stenosis "straighten himself/herself" so as to increase the pain of the lower limbs (the patient thinks). At this time, assume a case where a neuron (cell body) β in the spinal cord gray matter 416 is pressed by a part of the lamina 415 (FIG. 53(*b*)), so as to generate a false signal (fire an action potential) at a time $t_{11}$ (FIG. 53(*c*)). It is assumed herein that no pain signal is detected in the signal detection area (ending) 4 of the sensory neuron at the position α at this time, but a reflection light amount temporarily decreases in the neuron (a position of cytoplasm) β, which is detected in the first step, at a time $t_{12}$ which is right after the time $t_{11}$ along the detection time 163, and the patient expresses pain (FIG. 53(*c*)). From an obtained detection signal of the reflection light amount change 401 in FIG. 53(*c*), such a correct diagnosis can be made that a false signal generated in the neuron β due to the pressure from a part of the lamina 415 is transmitted to the neuron δ, and the signal is transmitted to the brain, thereby causing the patient to misunderstand that he/she "feels pain in the tip of a foot" (see FIG. 53(*a*)(*b*)).

If a location of a diseased part can be found precisely (with the accuracy of one cell unit) as such, the most appropriate treatment including surgery can be performed on the patient.

This section has dealt with the "diagnosis of the spinal canal stenosis" as one of the applied embodiments of the present exemplary embodiment. Alternatively, the search of an internal neural transmission pathway using the detection of life activity may be applied to other medical studies or medical diagnosis or treatment.

9.3.2) Exemplary Diagnosis with Combination of Detection of Membrane Potential Changing and Detection of Oxygen Concentration Change in Blood When a plurality of "signal generative physical phenomena and detection methods" used in the detection of life activity in the present exemplary embodiment as described in sections 6.1.1 to 6.1.2 with reference to Table 6 are combined, more advanced and more accurate diagnosis can be performed. Section 9.3.2 deals with, as one of the applied embodiments of the combination, a method in which "detection and diagnosis of early-stage dementia" is performed with a "combination of detection of membrane potential changing and detection of an oxygen concentration change in blood." Alternatively, a plurality of "signal generative physical phenomena and detection methods" described in Table 6 may be combined in other methods to perform detection of life activity, so as to be used for other diagnoses or studies in the medical field or the field of brain science.

It is said that a main factor for an elderly to suffer from dementia is:

[A] extinction of neurons (Alzheimer type); or
[B] reduction in intracerebral bloodstream.

As for [A], in particular, it is considered that either of the following phenomena promotes the extinction of neurons:

a phenomenon that amyloid β proteins are attached to an outside layer of a neuron; and a phenomenon that tau proteins are attached to an inside layer of a neuron.

For current diagnoses of dementia, the factors [A] and [B] are checked by different measurement methods.

That is, for the diagnosis of the factor [A], an occupied capacity of neurons in the head is examined by use of MRI (Magnetic Resonance Imaging) or CT scanning (Computer Tomography Scanning). If it is found that atrophy of the brain occurs as a result of the examination, it is judged that the dementia of the Alzheimer type progresses. However, this method can obtain a diagnosis only after atrophy of the brain has really occurred, and therefore it is difficult to detect the disease at an early stage.

On the other hand, for the diagnosis of the factor [B], a contrast agent is mixed into blood in the body by injection, and a radiological distribution emitted from the contrast agent is visualized so as to examine the intracerebral bloodstream. In this method, the patient feels pain at the time of injection to introduce the contrast agent in a blood vessel, so that the burden on the patient is large at the time of diagnosis.

Further, since these two types of inspection are necessary for diagnosis, the burden on the patient becomes large.

In order to solve these problems, in this applied embodiment, membrane potential changing of a neuron and an oxygen concentration change in blood are detected at the same time by a device shown in FIG. 54, so as to perform the diagnoses about the factors [A] and [B] at the same time.

First of all, the following explains a configuration of the device shown in FIG. 54 and a detection principle to be adopted herein.

In FIG. 54, when an optical axis of an objective lens 31 used for detection of the membrane potential changing (an action potential phenomenon or a firing rate) of a neuron is assumed a Z-axis 423, a light source 424 for detecting a wavelength of 780 nm, a color filter 425 passing light having a wavelength of 780 nm, and a photodetector 426 for light having a wavelength of 780 nm are provided on a Y-axis 422 orthogonal to the Z-axis 423. Further, a light source 427 for detecting a wavelength of 830 nm, a color filter 428 passing light having a wavelength of 830 nm, and a photodetector 429 for light having a wavelength of 830 nm are provided on an X-axis 421. Accordingly, a single detected point 30 for life activity in the brain is illuminated with light having a wavelength of 780 nm and light having a wavelength of 830 nm emitted from a light emitting section 102 at the same time, and respective light beams obtained from the single detected point 30 for life activity can be detected individually.

That is, the light having a wavelength of 780 nm emitted from the light source 424 for detecting a wavelength of 780 nm, provided on the Y-axis 422, is reflected in a capillary 28 in the detected point 30 for life activity, and its light amount is detected by the photodetector 426 for light having a wavelength of 780 nm, similarly provided on the Y-axis 422. Thus, a relative light absorption amount of the light having a wavelength of 780 nm by blood flowing through the capillary 28 is hereby found. In the meantime, in order not to detect other wavelength light beams by the photodetector 426 for light having a wavelength of 780 nm, the color filter 425 passing only light having a wavelength of 780 nm by blocking other wavelength light beams is provided just before the photodetector 426. Similarly, with a combination of the light source 427 for detecting a wavelength of 830 nm and the photodetector 429 for light having a wavelength of 830 nm provided on the X-axis 421, a reflection light amount in the capillary 28 in the detected point 30 for life activity (and a relative light absorption amount of the light having a wavelength of 830 nm to be absorbed by blood flowing through the capillary 28, based on the reflection light amount) is detected. In the meantime, in order not to detect other wavelength light beams by the photodetector 429 for light having a wavelength of 830 nm, the color filter 428 passing only light having a wavelength of 830 nm by blocking other wavelength light beams is provided just before the photodetector 429.

Then, detection signals from the photodetector 426 for light having a wavelength of 780 nm and the photodetector 429 for light having a wavelength of 830 nm are compared with each other so as to detect an oxygen concentration in blood flowing through the capillary 28. In this applied embodiment, in order to increase detection accuracy by removing external noise components, light amounts of the light emitted by the light source 424 for detecting a wavelength of 780 nm and the light emitted by the light source 427 for detecting a wavelength of 830 nm are modulated by different methods. Then, the detection signals obtained from the photodetector 426 for light having a wavelength of 780 nm and the photodetector 429 for light having a wavelength of 830 nm are passed through a circuit such as the modulating signal component extraction section (synchronous detection section) 133 in FIG. 33 so that synchronous detection or extraction of only a modulation signal component is performed.

In the range shown in FIG. 54, a detection system except the detection system for detecting an oxygen concentration in blood as described above is used for the detection of the membrane potential changing of a neuron (an action potential phenomenon or a firing rate in the neuron).

The illuminating light 115 for life activity detection which has a wavelength in the range explained in section 4.7 is emitted from the light emitting section 102. This light emitting section 102 has a configuration shown in FIG. 31, and the illuminating light 115 for life activity detection is optically modulated by the light modulator 112. In the applied embodiment shown in FIG. 54, this illuminating light 115 for life activity detection is linearly polarized light having a polarized light component to be "S-wave" with respect to a polarized light separation element 438.

The illuminating light 115 for life activity detection is reflected in the polarized light separation element 438, and then becomes circularly polarized light after passing through the quarter wave length plate 437. Here, the photosynthesis element 434 having color filter characteristics has optical properties to cause the wavelength of the illuminating light 115 for life activity detection to travel straight. Thereafter, the illuminating light 115 for life activity detection is condensed around the detected point 30 for life activity by the objective lens 31. Although not illustrated in FIG. 54, this illuminating light 115 for life activity detection is condensed at a position slightly deeper than the detected point 30 for life activity.

This light-condensed location is set so as to correspond to a surface of the capillary 28 or a surface of a glial cell, which is a relatively flat boundary surface where the light is easy to be reflected diffusely in broad perspective. This allows the illuminating light 115 for life activity detection which is reflected diffusely on this boundary surface to pass through the detected point 30 for life activity from its backside, mainly.

Accordingly, from the detected point 30 for life activity which is circled on the right side in FIG. 54, a transmitted light component of the illuminating light 115 for life activity detection projected from the backside is detected like a transmission-type light microscope.

Further, as described above, instead of condensing the illuminating light 115 for life activity detection at a position slightly deeper than the detected point 30 for life activity so as to be a small spot size, such another illumination method may be used that a random phase shifter (having a characteristic to change phases at different positions in a beam cross section in the illuminating light 115 for life activity detection) may be disposed within the light emitting section 102 so as to form a converging ray of a large spot size at the detected point 30 for life activity. In this case, a relatively wide area in the detected point 30 for life activity is illuminated with the illuminating light 115 for life activity detection, so that reflection light components can be detected in various positions in the detected point 30 for life activity.

The reflection light thus obtained from the detected point 30 for life activity passes through the objective lens 31 and the photosynthesis element 434 having color filter characteristics, and then passes through the quarter wave length plate 437 again so as to be converted into linearly polarized light having a polarized light component to be "P-wave" with respect to the polarized light separation element 438. As a result, the reflection light travels straight in the polarized light separation element 438, and enters the signal detecting section 103.

The signal detecting section 103 in this applied embodiment has a configuration shown in FIG. 31. Further, as a detection principle at this time, the method explained in section 6.3.1 with reference to FIGS. 23 to 25 is employed. This makes it possible to individually detect respective action potential states of pyramidal cell bodies 17 or stellate cell bodies 18 in the detected point 30 for life activity, which is circled on the right side of FIG. 54. Alternatively, as has been described in section 6.3.1, a size (aperture size) of the light transmission section 56 in the two-dimensional liquid crystal shutter 51 may be made adequate so as to detect activities of a group unit of a plurality of neurons such as a column unit (a total firing rate of a set of the plurality of neurons, such as a column).

Further, in the present exemplary embodiment, the objective lens 31 is configured to move automatically for collection so that the detected point 30 for life activity does not change even if the examinee (patient) moves to some extent. A relative moving amount and a relative direction of the movement of the examinee (patient) at this time are detected by the position detecting monitor section 432 of the detected point for life activity. A wavelength of light 439 for monitoring used for this detection is set to a value different from the wavelength of the illuminating light 115 for life activity detection, 780 nm, or 830 nm described above, so that interference (cross talk) between different detection light beams are prevented by use of color filters. After the light 439 for monitoring is emitted from the position detecting light source 431 of the detected point for life activity and passes through a beam splitter 433, the light 439 for monitoring is reflected by the photosynthesis element 434 having color filter characteristics, and condensed by the objective lens 31 around the detected point 30 for life activity.

The light 439 for monitoring thus reflected here passes through the objective lens 31 and then is reflected by the photosynthesis element 434 having color filter characteristics again. After the light 439 for monitoring is reflected by the beam splitter 433, the relative moving amount and the relative direction of the movement of the examinee (patient) are detected by the position detecting monitor section 432 of the detected point for life activity. In the meantime, this position detecting monitor section 432 of the detected point for life activity adopts the configuration explained in section 6.2.1 with reference to FIGS. 20 and 21. The photosynthesis element 434 having color filter characteristics in FIG. 54 doubles as the reflecting mirror (galvanometer mirror) 34 explained in section 6.2.1. That is, the photosynthesis element 434 having color filter characteristics has a configuration in which the photosynthesis element 434 can be inclined in the biaxial directions. As such, one photosynthesis element 434 having color filter characteristics is configured to perform:

(1) two-dimensional direction scanning of the light 439 for monitoring condensed at the detected point 30 for life activity; and (2) synthetic operation and separation operation between the light 439 for monitoring and the illuminating light 115 for life activity detection.

This accordingly attains downsizing and simplification of the optical system shown in FIG. 54 and achieves cost reduction by reduction in the number of optical components.

Next will be explained the dementia diagnosis method using the device of FIG. 54 explained as above.

First explained is a case where a physically unimpaired person is examined by use of the device of FIG. 54. An examinee (a physically unimpaired person in this case) is asked questions first, so as to promote a cerebral activation. In the present diagnosis of dementia, the following method has been known. That is, the examinee is asked 30 questions at first. Examples of the questions are as follows:

"Please tell a name of a prefecture where you live (even in the case of Tokyo, the term "prefecture" is used on purpose);"

"What is obtained by subtracting 7 from 100?;"

"What is obtained by subtracting 7 from the number obtained above?," and the like.

Then, it is judged whether the examinee is dementia or not based on the number of correct answers (if the examinee answered correctly more than 20 questions, the examinee is considered to be a physically unimpaired person). The use of these questions is effective to make diagnosis of the dementia from various perspectives. Alternatively, the cerebrum may be stimulated by other methods to promote the activation thereof.

When the cerebrum is activated, action potentials occur in the pyramidal cell body 17 or stellate cell body 18 in the detected point 30 for life activity frequently. This action potential phenomenon is detected by the signal detecting section 103 in FIG. 54. Here, this signal detecting section 103 detects action potentials of the neurons one by one. Alternatively, as described above, the size (aperture size) of the light transmission section 56 in the two-dimensional liquid crystal shutter may be broadened, so as to detect an activated state (a total firing rate) per set of a plurality of neurons, such as a column unit.

As such, the oxygen concentration in blood flowing through the capillary 28 changes about 5 s after the neuron is activated (see the explanation in section 4.7 with reference to FIG. 17). This oxygen concentration change in blood is detected by the photodetector 426 for light having a wavelength of 780 nm and the photodetector 429 for light having a wavelength of 830 nm.

Next will be explained a case where the above method is used for the diagnosis of dementia. While questions are given to the examinee to promote a cerebral activation as described above, the activity in the detected point 30 for life activity is detected.

If the oxygen concentration in blood flowing through the capillary 28 does not change even after 5 or more s have passed since action potentials occur in the pyramidal cell body 17 or stellate cell body 18 by answering the questions, there is a possibility that the aforementioned "B] reduction in intracerebral bloodstream" may occur. In a case where the number of correct answers out of the 30 questions used for the diagnosis of dementia is far below 20, the examinee is suspicious of "B] development of dementia based on the reduction in intracerebral bloodstream."

In a case where no action potential of a specific pyramidal cell 17 or stellate cell 18 is observed even though the change of the oxygen concentration in blood occurs while the examinee is considering answers (or in a case where a firing rate as the whole of a plurality of neurons included in a particular region including the specific column is extremely low), there is a possibility of "A] deterioration of a specific neuron." In a case where the number of correct answers out of the 30 questions is far below 20, the examinee is suspicious of "A] development of Alzheimer type dementia."

Especially in a case where a specific neuron does not fire an action potential at all even though the oxygen concentration in blood has changed and the number of the correct answers to the questions has exceeded 20 (or in a case where a firing rate as the whole of a plurality of neurons included in a particular region such as a specific column is extremely low), the examinee is suspicious of such a state that "a specific neuron (or a plurality of neurons included in the particular region) may be deteriorated and dementia may be developed in the future." In this case, "disease prevention measures" can be performed, for example, an improvement of a life environment or cerebral training not to develop dementia in the future, or medication in accordance with necessity.

Further, in a case where the number of correct answers to the questions is far below 20, all neurons in the detected point 30 for life activity do not fire action potentials and the oxygen concentration in blood in the capillary 28 does not change, the examinee is suspicious of "A] development of Alzheimer type dementia." The reason is because the oxygen concentration change in blood does not occur until neighboring neurons are activated, and therefore, an inactive state of the neurons is suspicious as a factor at first.

As has been described above, when the combination of the detection of a firing rate of a neuron based on membrane potential changing and the detection of an oxygen concentration change in blood is used for the diagnosis of dementia, such a great effect can be yielded that early diagnosis before dementia is developed can be made, thereby attaining disease prevention measures at an early stage. Further, in comparison with the conventional techniques in which it is necessary to inject a contrast agent into a blood vessel so as to check the "B] reduction in intracerebral bloodstream," the present exemplary embodiment is a non-contact and noninvasive method, thereby yielding such an effect that a patient is easy to have a medical examination because the patient does not feel pain in diagnosis. Further, since measurements are performed on the same location at the same time, not only a diseased part can be specified more specifically and accurately, but also the mental strain of the patient is decreased by large reduction in diagnosis time.

This applied embodiment is not limited to the configuration of the detection device as shown in FIG. 54 as long as the membrane potential change and the oxygen concentration change in blood are detected at the same time, and may be configured as a detection device employing other configurations or principles.

10] Abuse Prevention Method Using Measurement Technique of Biosis Activity 10.1) Notes for Use of Objective Technique of Present Exemplary Embodiment The application (NEI) of life activity measurement performed in a "non-contact" manner by use of the detection method described in Table 6 brings "a new value (a new function or an original effect)" as has been described in chapter 9, and has a wide applicable range. However, the NEI also has a risk of invasion of privacy and a threat of lack of privacy protection. Further, as shown in section 9.1, excessive dependence on this would lead to obstruction of character enhancement. Accordingly, it is desirable that this applied embodiment (NEI) is used to aim at "a common profit for users, humankind, and the earth."

10.2) Encryption Processing Method of Transfer Signal/Information

A most effective method which prevents invasion of privacy and protects personal information is to encrypt a life activity detection signal 248 with event information and life activity information 249 with event information in FIG. 44.

A third party, which is different from the mind communication provider 211 and the mind service distributor 212, serves as an encryption key generator (not shown in FIG. 44) and manages an encryption key.

Here, the present exemplary embodiment has a feature that the encryption key is constituted by two types of keys, i.e., "a key to be supplied first" and "a key to be required when incremental counter numbers (or a duration time) for transmission increase." Only the encryption method about the life activity detection signal 248 with event information is described in section 6.4.3 with reference to FIG. 35, but the same encryption method is adopted for the life activity information 249 with event information.

Similarly to the explanation in section 6.4.3 with reference to FIG. 35, the mind communication provider 211 is notified of first encryption key information for the life activity information 249 with event information and "an initial value key to set to a variable shifting position generator 153 which provides and outputs a variable shifting number in a M-serial cyclic circuit regarding incremental counter numbers for transmitting the life activity detection signal or regarding a cumulative duration time to transmit the life activity detection signal." On the other hand, the mind communication provider 211 is notified, from the encryption key generator, of only first encryption key information for the life activity detection signal 248 with event information, while the mind service distributor 212 is notified, from the encryption key generator, of only first encryption key information for the life activity information 249 with event information. In view of this, every time the incremental counter numbers (or a duration time) exceed a specific number (time), the mind communication provider 211 needs to buy new key information from the encryption key generator so as to decrypt an encrypted life activity detection signal 248 with event information.

Similarly, every time the incremental counter numbers (or a duration time) exceed a specific number (time), the mind service distributor 212 needs to buy new key information from the encryption key generator so as to decrypt encrypted life activity information 249 with event information.

With the use of this mechanism, the encryption key generator can monitor a frequency of usage per each life detecting division 218 shown in FIG. 44, sequentially. Thus, with the combination of the "key to be supplied first" and the "key to be required when incremental counter numbers (or a duration time) for transmission increase," prevention of invasion of privacy and protection of personal information can be performed more firmly.

10.3) Other Abuse Prevention Methods

In order that various applications (NEI) using the measurement technique of biosis activity are used in a right manner while preventing abuses, it is desirable to perform "publication of the purpose of use."

With the use of the method in section 10.1, the encryption key generator can grasp a frequency of use per application. At the time of buying "a key to be required when incremental counter numbers (or a duration time) for transmission increase" from the encryption key generator, an object of the application should be self-reported by a buyer. Then, the object of the application and its frequency of use which the encryption key generator could know are posted on the Web, so that anyone can see the object and frequency of use. Thus, unauthorized use can be easily found from this Web page by people around the world. If an unfavorable application is performed, a request to prohibit the use is sent to a corresponding mind communication provider 211 or mind service distributor 212.

Thus, it is eagerly desired that this applied embodiment (NEI) be used for good purposes.

11) Other Applied Embodiments Regarding Detection/Control of Life Activity 11.1) Other Life Activity Phenomena of which Contracted and Relaxed States of Skeletal Muscle are to be Detected/Controlled As examples of dynamical life activities occurring in a life object, chapters 1 to 5 mainly dealt with methods for detecting an action potential state and a signal transmission state of the nervous system. However, the present exemplary embodiment is not limited to them, and as shown in section 6.1 and Table 6, every "detection, measurement, or control of dynamical life activities in a life object by a non-contact method" will be included in the present exemplary embodiment or the applied embodiments. In the explanation of section 6.1.1 with reference to Table 6 and the explanation of section 6.5.4 with reference to FIGS. 41 and 42, the detection of a signal transmission state to the neuromuscular junction (an activation of the neuromuscular junction 5) is used for the detection of contraction and relaxation states of a skeletal muscle. As an applied embodiment of the above exemplary embodiment, chapter 11 explains a method for directly detecting an actual contraction state and an actual relaxation state of a skeletal muscle, and a principle thereof. Further, a method for controlling contraction/relaxation of a skeletal muscle by use of the detection principle is also explained herein.

According to B. Alberts et. al.: Molecular Biology of the Cell, 4th Edi. (Garland Science, 2002) Chap. 16, a process of contraction of a skeletal muscle is mainly constituted by the following two steps:

a] control to enable contraction of the skeletal muscle by release of calcium ions into a muscle cell; and b] contraction of the skeletal muscle by migration of Myosin to actin filaments in the muscle cell.

Meanwhile, the "signal transmission to the neuromuscular junction (the activation of the neuromuscular junction 5)" explained in sections 6.1.1 and 6.5.4 occurs as a front step right before the above step [a].

In the contraction step of the skeletal muscle in [b], "deformation of Myosin," "attachment of a Myosin head to actin filaments," "restoration of a Myosinshape in a contact state," and "detachment of the Myosin head from the actin filaments" are repeated. Here, the "deformation of Myosin" occurs by using hydrolysis of ATP (Adenosine triphosphate). That is, a part of the Myosin includes a specific enzyme called Myosin ATPase, and when ATP in which three phosphoryls are connected in series bonds thereto, one neighboring water molecule is incorporated therein and one of the phosphoryls is removed from the bond.

Thus, the contraction of the skeletal muscle requires "attachment of a Myosin head to actin filaments." However, in relaxation of the skeletal muscle, Tropomyosin occupies this bonding site, and obstructs the "attachment of a Myosin head to actin filaments." Meanwhile, when the "signal transmission to the neuromuscular junction (the activation of the neuromuscular junction 5)" explained in sections 6.1.1 and 6.5.4 occurs, a large quantity of calcium ions flow into this site as the step [a]. When the calcium ion thus flowing in at this time bonds to Troponin, Tropomyosin connected to the Troponin is displaced, and the "attachment of a Myosin head to actin filaments" is enabled. When this calcium ion bonds to the Troponin, it is estimated that an ionic bond is formed between a residue of Aspartate included in the Troponin or a carboxyl group constituting a part of a residue of Glutamate, and the calcium ion $Ca^{2+}$.

11.2) Basic Thought Regarding Biocatalyst Action by Enzyme

The following section 11.3 will explain a mechanism for ATP hydrolysis by Myosin ATPase, but before that, this section explains a quantum-chemical thought regarding biocatalyst action by enzyme.

FIG. 57 (*a*) shows an electron cloud density distribution of a bonding orbital while an atom A and an atom B are covalently-bonded. According to the electrostatic theorem of Hellmann-Feynman (see Y Harada: *Ryoushi kagaku* (Quantum Chemistry) vol. 2 (Shyoukabou, 2007) p. 55), a force to work on one atomic nucleus A in a molecule is expressed by a sum of coulomb attraction from an electron probability (electron cloud density) constituting the bonding orbital and coulomb repulsion from another atomic nucleus B. That is, the electron cloud density distributed between the atomic nuclei A and B and an electrostatic attraction between the atomic nuclei A and B having positive electric charge work to form a bond between the atomic nuclei A and B.

FIG. 57(*b*) shows an electron cloud density of a bonding orbital when a quaternized amino group —$NH_3^+$ included in a residue of Lysine is hydrogen-bonded to the atomic nucleus A. Since a nitrogen atom in the quaternized amino group has positive electric charge, an electron cloud located around the atomic nucleus A is affected by an electrostatic attraction and is unevenly distributed on a side of the quaternized amino group. As shown in FIG. 15(*b*), the molecular orbital at this time reaches around a nitrogen atomic nucleus. As a result, the electron cloud density distributed between the atomic nuclei A and B decreases. This decreases a bonding strength between the atomic nuclei A and B, thereby resulting in that a distance between the atomic nuclei A and B is expanded due to electrostatic repulsion between the atomic nuclei A and B.

FIG. 57(*c*) shows an electron cloud density distribution of a bonding orbital in a case where the atomic nucleus B comes toward an atom C relatively charged with positive electricity, as a result of the expansion of the distance between the atomic nuclei A and B. At this time, the electron cloud located around the atomic nucleus B is unevenly distributed on a side of the atom C due to an electrostatic attraction. When the amount of uneven distribution becomes large and causes an area where the electron cloud density becomes "0" between the atomic nuclei A and B, the bonding between the atomic nuclei A and B is cleaved due to the electrostatic repulsion between the atomic nuclei A and B. The molecular orbital at this time is an antibonding orbital to the atomic nuclei A and B (Y. Harada: *Ryoushi kagaku* (Quantum Chemistry) vol. 1 (Shyoukabou, 2007), p. 263 and p. 290).

11.3) Movement Mechanism of Myosin ATPase

A partial molecular structure where ATP bonds to an active site having a function of Myosin ATPase in Myosin is described on p. 15850 in I. Rayment: Journal of Biological Chemistry vol. 271 (1996), and an extract of its principal part is shown in FIG. 58. In FIG. 58, a bold solid line indicates a covalent bond, a bold wavy line indicates an ionic bond, and a vertical line made up of lateral continuous lines indicates a hydrogen bond. Further, an arrow of a fine solid line indicates a biased direction of an electron probability distribution of a bonding orbital (an electron cloud density distribution). Here, ATP has a molecular structure in which three phosphoryls are connected to adenosine in series, but in FIG. 58, a state where one phosphoryl is connected to the adenosine is collectively described as AMP (Adenosine monophosphate). It is said that a magnesium ion $Mg^{2+}$ plays an important part in hydrolysis of ATP, and a water molecule activated by the action of the magnesium ion $Mg^{2+}$ directly works on a bonding site between two phosphoryls to cleave the bonding. Further, an active site having a function of Myosin ATPase in Myosin includes Lysine Lys185 and Asparagine Asn235. Here, the number in FIG. 58 indicates a sequential identification number of amino acid in Myosin, which is a protein.

When ATP bonds to the active site having a function of Myosin ATPase, oxygen atoms $O5^-$ and $O2$ therein are hydrogen-bonded to a part of a residue of Lysine Lys185 and a part of a residue of Asparagine Asn235. Further, a hydrogen atom H1 in a water molecule around ATP is hydrogen-bonded to an oxygen atom O2 in ATP. On the other hand, a magnesium ion $Mg^{2+}$ forms a weak ionic bond to an oxygen atom O1 in the water molecule, thereby activating the water molecule.

In addition, it is also considered that the magnesium ion $Mg^{2+}$ also forms a weak ionic bond to an oxygen atom O9 in another water molecule, as well as forming weak ionic bonds to two oxygen atoms $O3^-$ and $O8^-$ in ATP. It is said that in a water environment in a life object (about pH 7), ATP is charged with negative electricity, and a γ phosphoryl and a β phosphoryl therein correspond to two negative electric charges and one negative electric charge, respectively.

In FIG. 58, for the convenience of explanation, it is assumed that $O3^-$, $O5^-$ and $O8^-$ are each charged with one negative electric charge. When a residue of Lysine Lys185 and a divalent magnesium ion $Mg^{2+}$, which are charged with positive electric charge in the waters environment in a life object (about pH 7), bond to them, an electrically neutralized state is formed as a whole. When each molecule is placed three-dimensionally to form various bonds as such, an electron existence probability (a density distribution of an electron cloud) around the oxygen atom $O5^-$ in ATP makes a movement α toward a nitrogen atom $N1^+$ charged with positive electricity, via a hydrogen atom H2 in the residue of Lysine Lys185, as has been described in FIG. 57(b). Then, in order to make up for the decrease of the electron cloud density around the oxygen atom O5−, a part of the electron probability of a bonding orbital between a phosphorus atom P1 and an oxygen atom O2 moves in a direction β.

On the other hand, since the oxygen atom O2 bonding two phosphoryls in ATP forms is hydrogen-bonded to a hydrogen atom H6 in a residue of Asparagine Asn235, a part of the electron cloud density distribution located around the oxygen atom O2 slightly moves toward a nitrogen atom N2 via the hydrogen atom H6 as shown by an arrow γ. Further, in order to make up for an overwhelming lack of the electron cloud density around the magnesium ion $Mg^{2+}$ having two positive electric charges, the electron cloud density distribution makes a movement δ from the vicinity of the oxygen atom O2 via a phosphorus atom P2 and an oxygen atom O8−.

As a result, the electron cloud density around the oxygen atom O2 largely decreases, but since this oxygen atom O2 forms a hydrogen bond to a hydrogen atom H1 in the water molecule, the decrease of the electron cloud density is prevented by use of this hydrogen bonding path. More specifically, the electron probability of a bonding orbital between the oxygen atom O1 and the hydrogen atom H1 in the water molecule decreases as shown by an arrow ε, and the electron existence probability of the hydrogen bond increases. The electrons thus increased work as a bonding orbital between the hydrogen atom H1 and the oxygen atom O2, thereby forming a covalent bond between the hydrogen atom H1 and the oxygen atom O2. Further, the magnesium ion $Mg^{2+}$ draws a peripheral electron cloud density toward its circumference, so that the electron cloud flows in a direction of an arrow ζ.

As a result of this, the electron existence probability of the bonding orbital between the oxygen atom O1 and the hydrogen atom H1 in the water molecule decreases and the covalent bond is changed into a hydrogen bond. In accordance with this change, a distance between the oxygen atom O1 and the hydrogen atom H1 is broadened, but the description about the distance change is omitted in FIG. 58. When the bias of the electron cloud density occurs in the directions shown by the arrows ε and ζ as such, the electron cloud density around the oxygen atom O1 largely decreases, and the water molecule is activated. This causes the oxygen atom O1 to take the electron cloud density around the phosphorus atom P1 adjacent to the oxygen atom O1 so as to make up for the depressed electron cloud density around the oxygen atom O1 (η).

This results in that the electron cloud density increases between the phosphorus atom P1 and the oxygen atom O1, and the electron existence probability works as a bonding orbital between the phosphorus atom P1 and the oxygen atom O1. This forms a covalent bond between the phosphorus atom P1 and the oxygen atom O1. On the other hand, the magnesium ion $Mg^{2+}$ draws a peripheral electron cloud density thereof toward its circumference, so that the electron cloud further flows in a direction shown by an arrow θ. Then, the electron cloud density moves in the directions shown by the arrows β, γ, δ, η, and θ, which largely reduces the electron existence probability of the bonding orbital between the phosphorus atom P1 and the oxygen atom O2. When an area having an electron existence probability of "0" occurs between the phosphorus atom P1 and the oxygen atom O2 as shown in FIG. 57(c) as a result thereof, the bonding orbital between the phosphorus atom P1 and the oxygen atom O2 changes into an antibonding orbital and the bonding between the phosphorus atom P1 and the oxygen atom O2 is cleaved.

When the hydrolysis mechanism of ATP is summarized, the following things can be said as shown in FIG. 58 (b).

The covalent bond between the oxygen atom O1 and the hydrogen atom H1 in the water molecule changes into a hydrogen bond, and the hydrogen bond between the oxygen atom O2 and the hydrogen atom H1 in ATP changes into a covalent bond.

In FIG. 58(b), a γ phosphoryl and a β phosphoryl having a phosphorus atom P1 and a phosphorus atom P2 in a center each have a hydroxyl group —OH just after hydrolysis of the ATP in an area where a bond between the phosphorus atom P1 and the oxygen atom O2 changes into a bond between the phosphorus atom P1 and the oxygen atom O1, but a bond between OH is cleaved immediately in the water environment (pH 7) in the body.

The hydrolysis reaction of ATP has a large feature that "a γ phosphoryl (an oxygen atom O5 therein)/a β phosphoryl (oxygen atoms O2 and O6 therein) are respectively hydrogen-bonded to a residue of Lysine Lys185/a residue of Asparagine Asn235" over the reaction.

11.4) Characteristics of Detection/Control of Life Activity

Section 11.4 relates to an appropriate wavelength range of an electromagnetic wave (light) to be used at the time of optically detecting/measuring or controlling contracted and relaxed states of a skeletal muscle and performs examination from a wide viewpoint. The appropriate wavelength range at the time of detecting or measuring an action potential state of a neuron has been already explained in section 4.7. This section first discusses the explanation in section 4.7 more specifically, and then discusses a suitable wavelength range of an electromagnetic wave (light) to be used for the detection/measurement or control by a non-contact method with respect to more general dynamical activities occurring "in a life object," as well as the action potential state of a neuron and the contracted and relaxed states of a skeletal muscle. Subsequently, based on general results of the consideration, an appropriate wavelength range of an electromagnetic wave (light) to be used at the time of detecting or controlling the contracted and relaxed states of a skeletal muscle is discussed.

The present exemplary embodiment or its applied embodiment has a large feature in that:

[1] detection/measurement or control is performed on dynamical life activities occurring "in a life object." A more specific feature thereof is such that: in order to embody the detection/measurement or control,

[2] detection/measurement or control is performed by use of a transition of a vibration mode according to an interaction of an external electromagnetic field (an electromagnetic wave) with a vibration mode which occurs during an activity in the life object or when the activity changes and which is caused by two or more specific atoms in a molecule at that time.

Further, near infrared light is suitable for the electromagnetic wave which can pass through the "life object," and particularly, has a feature that:

[3] a transition between vibration modes which a hydrogen atom (forming a hydrogen bond) involves is easy to interact with near infrared light. This is because a hydrogen atom is the most lightweight among other atoms and therefore is easy to oscillate at high speed (at high frequencies) (in view of classical physics). Accordingly, in an exemplary embodiment or its applied embodiment having the feature [3], absorption changes of near infrared light at a shorter wavelength (high frequency) which is less absorbed by water molecules can be easily detected/measured, which allows detection/measurement or control of life activity in a relatively deep area in the life object.

With regard to the wavelengths which meet the above features in the present exemplary embodiment or the applied embodiment, the following first discusses [1] a range in which detection/measurement or control can be easily performed "in a life object." Visible light does not pass through a human skin and therefore an inside of the human body cannot be observed. In general, visible light having a wavelength of 0.8 µm or less can hardly pass through the life object. In the meantime, when a palm is held against sunlight while fingers are closed, red light can be seen from the gap between the fingers. From such a phenomenon, it can be understood that light having a wevelength longer than red light passes through a life object to some extent. More specifically, it is demonstrated by experiments that light having a wavelength of 0.84 µm or more passes through skin on a life-object surface to enter the life object easily. On the other hand, as has been described in section 4.7, since infrared light having a wavelength of more than 2.5 µm is easily absorbed by water molecules in a life object (as excitation energy of a symmetrically telescopic vibration, an anti-symmetrically telescopic vibration, and a rotation of water molecules), it is difficult to transmit electromagnetic waves therethrough due to light attenuation. As has been described in section 4.7, water molecules occupy 70% (by weight) of chemical compounds constituting an animal cell, so that a wavelength light beam with a little light attenuation due to absorption by water molecules can pass through a life object. Accordingly, in a case where detection/measurement or control of life activity is performed using an electromagnetic wave which "passes through a life object," it is desirable to use near infrared light having a wavelength in a range from 0.84 µm (or 0.875 µm) to 2.5 µm.

The following discusses [1] a range in which detection/measurement or control can be easily performed "in a life object," more specifically. As has been already described in section 4.7, there are absorption bands corresponding to combinations of a water molecule around center wavelengths of 1.91 µm and 1.43 µm. Further, there is another absorption band around a center wavelength of 0.97 µm, though light absorption is small. Here, the following discusses in detail near infrared absorption spectra of water which is shown in FIG. 2.1.1 on page 12 and FIG. 4.6.1 on page 180 of Yukihiro Ozaki/Satoshi Kawata: Kinsekigai bunkouhou (Gakkai Shuppan Center, 1996), which is referred to for the above absorption bands. As a result, it is found that wavelength ranges indicative of half values of absorbances at the largest absorption wavelengths of 0.97 µm, 1.43 µm, and 1.91 µm are given in ranges from 0.943 to 1.028 µm, from 1.394 to 1.523 µm, and from 1.894 to 2.061 µm, as shown in FIG. 56. That is, light absorption by water is large in these wavelength regions. Accordingly, in the wavelength ranges from 0.84 µm to 2.5 µm, a wavelength region except for the above ranges corresponds to a region where the light absorption by water is small. That is, in the present exemplary embodiment or the applied embodiment, when light absorption is considered to be small in the absorption band around a center wavelength of 0.97 µm (there is little influence of the light absorption), it is desirable to use, for detection/measurement or control of life activity, electromagnetic waves including an electromagnetic wave having a wavelength within any of a first applicable wavelength range I from 2.061 µm to 2.5 µm, a second applicable wavelength range II from 1.523 µm to 1.894 µm, and a third applicable wavelength range III from 0.84 µm to 1.394 µm, as shown in FIG. 56. In the meantime, in a case where the influence (light absorption) by an oxygen concentration indicator in a living tissue is desired to be removed at the time of detection or control of life activity (see section 4.7), the third applicable wavelength range III will be from 0.875 µm to 1.394 µm. By setting the third applicable wavelength range III as such, even if the oxygen concentration indicator exists in the middle of a detection light path, the detection light is not absorbed, so that the S/N ratio of a life activity detection signal can be secured. Further, in order to prevent light absorption in the absorption band having a center wavelength of 0.97 µm, it is desirable to use electromagnetic waves including an electromagnetic wave having a wavelength within any of a fourth applicable wavelength range IV from 1.028 µm to 1.394 µm and a fifth applicable wavelength range V from 0.84 µm to 0.943 µm (or from 0.875 µm to 0.943 µm) in addition to the above ranges.

Naturally, the desirable wavelength range of the electromagnetic wave for the detection/measurement or control of life activity is applied to the detection or measurement of an action potential state of a neuron explained in section 4.7. Subsequently, in regard to a result of the above consideration,

[2] the detection or measurement of an action potential state of a neuron is discussed in consideration of the feature of the present exemplary embodiment or the applied embodiment that detection/measurement or control is performed by use of an interaction of an external electromagnetic field with a transition between vibration modes occurring between two or more specific atoms in a molecule during activity in a life object or when the activity changes. At the time of detection/measurement of an action potential state of a neuron, a using wavelength corresponding to the 1st overtone for transition between anti-symmetrically telescopic vibration modes mainly caused by C—H—Cl⁻ is in a range from 2.05 to 2.48 µm, according to section 4.7. However, this wavelength range overlaps with the wavelength region of 2.05 to 2.061 µm where water absorbs light greatly. Accordingly, it is desired that the electromagnetic waves corresponding to the 1st overtone and used for the detection/measurement include an electromagnetic wavelength within a wavelength range of 2.061 to 2.48 µm so that the above overlapping range can be avoided. In the meantime, in a case where the light absorption by water in the absorption band having a center wavelength of 0.97 µm causes any problem, it is desirable that the electromagnetic waves corresponding to the 3rd overtone of the transition between anti-symmetrically telescopic vibration modes and used for the detection/measurement include an electromagnetic wavelength within a wavelength range of 0.840 to 1.37 µm according to section 4.7. Further, in order to remove the influence by the oxygen concentration indicator as described above, it is desirable that the electromagnetic waves corresponding to the 3rd overtone and used for the detection/measurement include an electromagnetic wavelength within a wavelength range of 0.875 to 1.37 µm. However, in order to avoid the influence of light absorption by water in the absorption band having a center wavelength of 0.97 µm so as to obtain highly accurate detection/measurement, it is preferable to use electromagnetic waves including an electromagnetic wave having a wavelength in either range from 0.840 µm to 0.943 µm (or 0.875 µm to 0.943 µm) or from 1.028 µm to 1.37 µm for the detection/measurement of an action potential state of a neuron.

In consideration of the feature of [1] detection/measurement or control in a life object and the feature of [2] interaction of a transition between vibration modes with an external electromagnetic field (an electromagnetic wave) as well, the following describes a case of performing detection/measure or control of contracted and relaxed states of a skeletal muscle. As has been described in section 11.1, a contraction/relaxation motion of a skeletal muscle is constituted by two steps:

a] control to enable contraction of the skeletal muscle by release of calcium ions into a muscle cell; and
b] contractile function of the skeletal muscle.

Accordingly, the detection/measurement or control can be performed on each of the two steps, independently.

Initially explained is a detection/measurement method or a control method related to the step [a]. As described in section 11.1, in the step (a), it is expected that an ionic bond between a carboxyl group and a calcium ion $Ca^{2+}$ occurs. In this case, as described in section 3.5, it is considered that a relative light absorbance of the absorption band corresponding to a symmetrically telescopic vibration mode of a single carboxyl group largely decreases. Accordingly, in this exemplary embodiment, the change (rapid decrease) of the relative light absorbance of the absorption band corresponding to the symmetrically telescopic vibration mode of the carboxyl group is detected so as to detect/measure whether or not the skeletal muscle is in a contractable state,
or alternatively, excitation light in a vibration mode is projected to increase an energy level of the symmetrically telescopic vibration mode of the carboxyl group, so that a bond of a calcium ion $Ca^{2+}$ to the carboxyl group is prevented and the contraction/relaxation action of the skeletal muscle is controlled. The symmetrically telescopic vibration mode of the carboxyl group is generally a ground state (a vibration state in which the energy level is the lowest). When it is illuminated with excitation light corresponding to the nth overtone, the energy level of the symmetrically telescopic vibration mode of the carboxyl group rises. In a case where a vibration of the carboxyl group is small (the energy level is low), a calcium ion $Ca^{2+}$ easily bonds to the carboxyl group. On the other hand, in a case where the energy level of the vibration mode rises, even if the calcium ion $Ca^{2+}$ bond thereto temporarily, it is highly probable that the calcium ion $Ca^{2+}$ is thrown off (separated) due to the high energy. That is, by illumination with excitation light corresponding to the nth overtone, the calcium ion $Ca^{2+}$ is hard to bond to the carboxyl group, so that contraction control of the skeletal muscle is obstructed and a relaxed state of the skeletal muscle continues.

Since section 3.5 only shows a wavenumber value of a reference tone exciting the symmetrically telescopic vibration mode of the carboxyl group, the following explains a wavelength corresponding to excitation light of the nth overtone. The following explanation is not limited to the control of contraction/relaxation of the skeletal muscle, but can be applied commonly to every exemplary embodiment or applied embodiment described in section 11.4, in which [2] detection/measurement or control is performed by use of a transition of a vibration mode according to an interaction of an external electromagnetic field (an electromagnetic wave) with a vibration mode which occurs during activity in the life object or when the activity changes and which is caused by two or more specific atoms in a molecule at that time.

Initially, by use of the following formula (A 38) as described in section 4.5:

Formula 38

$$\varepsilon_m \cong \underline{\varepsilon_m} + <\underline{m} \bigg| \kappa_3 x^3 + \kappa_4 x^4 \bigg| \underline{m}> = \frac{2\kappa_2}{\beta}\left(m + \frac{1}{2}\right) + \frac{3\kappa^2}{4\beta^2}(2m^2 + 2m + 1),$$  (A·38)

a necessary amount $h\nu_m$ of energy at the time when an energy level $\varepsilon_0$ is shifted to $\varepsilon_m$ is expressed by:

Formula 60

$$h\nu_m = \varepsilon_m - \varepsilon_0 = \frac{2\kappa^2}{\beta}m + \frac{3\kappa_4}{2\beta^2}(m^2 + m).$$  (A·60)

Accordingly, from formula (A 60), where frequencies of the reference tone, the 1st overtone, and the 2nd overtone are assumed $\nu_1$, $\nu_2$ and $\nu_3$, the following relations are established:

Formula 61

$$\frac{2\kappa_2}{\beta h} = 2\nu_2 - \nu_3 = 2\nu_1 - \frac{\nu_3}{3};$$  (A·61)

and

Formula 62

$$\frac{3\kappa_4}{2\beta^2 h} = \frac{\nu_3}{3} - \frac{\nu_2}{2} = \frac{\nu_3}{6} - \frac{\nu_1}{\nu_2}.$$  (A·62)

With the use of formulae (A 60) to (A 62) thus obtained, a value of a wavelength $\lambda m$ (a frequency $\nu_m$) of a (m−1)th overtone can be estimated from the frequencies $\nu_1$, $\nu_2$, and $\nu_3$ of the reference tone, the 1st overtone, and the 2nd overtone based on the anharmonic vibration.

Based on the reference documents, wavelengths $\lambda m$ of the reference tone and the (m−1)th overtones estimated by calculation using formulae (A 60) to (A 62) are shown in Table 7. Among the values shown in Table 7, a value to which (1) is attached is referred from Yukihiro Ozaki/Satoshi Kawata: Kinsekigai bunkouhou (Gakkai Shuppan Center, 1996) P. 218 to P. 219. On the other hand, a value to which (2) is attached is obtained by combining the calculation result in section 3.5 with a reference from R. M. Silverstein and F. X. Webster: Spectrometric Identification of Organic Compounds 6th Edit. (John Wiley & Sons, Inc., 1998) Chapter 3, Section 3.6. Further, a wavelength of the (m−1)th overtone of a symmetrically telescopic vibration of an ionic carboxylic acid group —$COO^-$ is calculated by extrapolation of a calculated value of a vibration of C=O of carboxylic acid —COOH by use of a value of the wavelength of the reference tone.

TABLE 7

| | Reference tone (μm) | 1st overtone (μm) | 2nd overtone (μm) | 3rd overtone (μm) | 4th overtone (μm) |
|---|---|---|---|---|---|
| Intermolecular hydrogen bonding in primary amide —CONH$_2$ | 3.19-3.21 (calculation result) | 1.60-1.62 Reference (1) | 1.07-1.09 Reference (1) | 0.81-0.83 (calculation result) | 0.65-0.67 (calculation result) |
| Vibration of hydrogen bonding part in secondary amide —CONH$^-$ | 3.02-3.32 (calculation result) | 1.53-1.67 Reference (1) | 1.04-1.12 Reference (1) | 0.79-0.85 (calculation result) | 0.64-0.68 (calculation result) |
| Vibration between C=O of carboxylic acid —COOH | 5.68 Reference (2) | 2.84-2.86 (calculation result) | 1.89-1.92 Reference (1) | 1.42-1.45 (calculation result) | 1.13-1.17 (calculation result) |
| Symmetrically telescopic vibration of ionic carboxylic acid group —COO$^-$ | 6.25-6.37 Reference (2) | 3.12-3.21 (calculation result) | 2.08-2.15 (calculation result) | 1.56-1.63 (calculation result) | 1.24-1.31 (calculation result) |
| Intermolecular hydrogen bonding in associated —OH alcohol | 2.90-3.25 (calculation result) | 1.50-1.60 Reference (1) | 1.04-1.05 Reference (1) | 0.80-0.77 (calculation result) | 0.67-0.61 (calculation result) |

Most carboxyl groups are in a state of an ionic carboxylic acid group —COO$^-$ in a water environment (pH=around 7) in a life object. Accordingly, the excitation light of the nth overtone with respect to a symmetrically telescopic vibration mode of the carboxyl group in the present exemplary embodiment basically corresponds to a row of "Symmetrically telescopic vibration of ionic carboxylic acid group —COO$^-$" in Table 7. However, even under this water environment, there is a probability that some carboxyl groups keep a state of a carboxylic acid —COOH, and a calcium ion Ca$^{2+}$ bonds to this C=O site. Accordingly, in a] control to enable contraction of the skeletal muscle by release of calcium ions into a muscle cell, in the present exemplary embodiment, both wavelengths are combined and assumed as follows:

a wavelength range corresponding to the 2nd overtone is assumed 1.89 to 2.15 μm, a wavelength range corresponding to the 3rd overtone is assumed 1.42 to 1.63 μm, and a wavelength range corresponding to the 4th overtone is assumed 1.13 to 1.31 μm.

Further, similarly to section 4.7, measurement errors to these values are expected by about 10%. In view of this, respective lower limits of the above ranges are 1.89×(1−0.05)=1.80, 1.42×(1−0.05)=1.35, and 1.13×(1−0.05)=1.07. Similarly, respective upper limits thereof are 2.15×(1+0.05)=2.26, 1.63×(1+0.05)=1.71, and 1.31×(1+0.05)=1.38. Thus, the wavelength ranges including measurement errors of ±5% are as follows:

the wavelength corresponding to the 2nd overtone is assumed 1.80 to 2.26 μm, the wavelength corresponding to the 3rd overtone is assumed 1.35 to 1.71 μm, and the wavelength range corresponding to the 4th overtone is assumed 1.07 to 1.38 μm.

In consideration of overlapping parts, it is concluded that "a wavelength range suitable for detection/measurement or control is in a range from 1.07 to 1.71 μm and in a range from 1.80 μm to 2.26 μm." Further, by excluding, from this range, the wavelength range in which light is largely absorbed by water molecules, as shown in FIG. 56, the wavelength range suitable for [a] detection/measurement or control to a bond between Ca$^+$ and a carboxyl group —COO$^-$ is 1.07 to 1.39 μm, 1.52 to 1.71 μm, and 2.06 to 2.26 μm. This wavelength range is shown in FIG. 56.

In a case where a life object is illuminated with electromagnetic waves including an electromagnetic wave having a wavelength in the range explained as above, in the present exemplary embodiment or the applied embodiment, measurement/control is performed as follows:

A signal related to a life activity is detected by an absorption amount or an absorption change of the electromagnetic wave having a wavelength in the above range in a life object, and the detection signal is processed to measure a life activity state; and An illumination amount of the electromagnetic wave having a wavelength in the above range is increased in the life object (temporarily) so as to control the life activity. That is, a light amount of the electromagnetic wave projected to the body for detection of life activity is very small, so that a ratio of carboxyl groups in which a vibration mode is excited in a skeletal muscle is small and the life activity itself is not affected. However, when the light amount of the electromagnetic wave thus projected is increased, most of the carboxyl groups in the skeletal muscle are excited to cause vibrations, thereby resulting in that bonding of calcium ions Ca$^{2+}$ thereto is obstructed and contraction of the skeletal muscle becomes impossible.

Further, in the present exemplary embodiment or the applied embodiment, detection/measurement and control related to life activity may be performed at the same time. In this case, while an illumination amount of the electromagnetic wave having a wavelength in the above range is decreased to detect/measure a life activity and check an active state thereof, the control of life activity is performed (by increasing the illuminating light amount sometimes).

Next will be explained a feature of an activity at a molecular level to be used for detection/measurement or control in the present exemplary embodiment or the applied embodiment, that is,

[3] a case where the transition between vibration modes which a hydrogen atom (forming a hydrogen bond) involves (which has been already explained in this section) is used.

As shown in FIG. 58, in a hydrolysis reaction of ATP in a skeletal muscle, hydrogen bonds to a part of a residue of Lysine Lys185 and a part of a residue of Asparagine Asn235 are formed. In order to cause a hydrolysis reaction stably by a neutralization effect of local charges, "a hydrogen bond between a residue of amino acid having positive electric charge and ATP having negative electric charge" is required. Therefore, in the hydrolysis of ATP, hydrogen bonds to residues of Lysine Lys185 are also formed in other areas in addition to the skeletal muscle very often. That is, as described in section 11.3, since ATP has negative electric charge in the water environment of pH 7, local bonds to a magnesium ion $Mg^{2+}$ and a residue of amino acid having positive electric charge is necessary for electrical neutralization. A residue of amino acid having positive electric charge is included in only the residue of Arginine except for the residue of Lysine Lys185, and in either case, a hydrogen atom is placed outside the positively charged part. Accordingly, in an electrically neutralized state, it is highly probable that a hydrogen bond is formed between this hydrogen atom and an oxygen atom in the ATP. Further, since the hydrogen atom itself, which is involved with this hydrogen bond, is more lightweight than other atoms, the use of this transition between vibration modes makes it easy to perform detection/measurement or control of life activity in a relatively deep region in a life object, as described earlier.

Only small part of a residue of Lysine and a residue of Arginine is hydrogen-bonded to a water molecule (an oxygen atom thereof), but an absorption band occurring in ATP hydrolysis and an absorption band deriving from the hydrogen bond to the water molecule have different values of center wavelengths for the following reason. FIG. 59($a$) shows a case where a part of the residue of Lysine Lys185 is hydrogen-bonded to an oxygen atom in ATP, and FIG. 59($b$) shows a case where a part of the residue of Lysine Lys185 is hydrogen-bonded to an oxygen atom in a water molecule. When a distance between a hydrogen atom H2 involved with hydrogen bonding and an oxygen atom O5 or O10 becomes smaller than an optimal value, the water molecule is fixed not lightly and therefore relative arrangements between the oxygen atom O10 and hydrogen atoms H9/H10 do not change. In contrast, when the distance between the hydrogen atom H2 and the oxygen atom O5 becomes smaller than the optimal value, distortion occurs in ATP and intramolecular energy in ATP and the whole Lysine Lys185 forming a hydrogen bond increases, as shown in FIG. 59($b$).

As a result, an increasing amount of the energy of the whole molecule at the time when the distance between the hydrogen atom H2 and the oxygen atom O5/O10 becomes smaller than the optimal value is larger in the case of hydrogen bonding to a part in ATP than in the case of hydrogen bonding to a water molecule.

FIG. 60 shows an influence to an anharmonic vibration potential property due to a difference in a molecular structure involved with a hydrogen bond. A distance between two atoms forming an electric dipole moment, indicated by a lateral axis in FIG. 60, represents a distance between the hydrogen atom H2 in the residue of Lysine Lys185 and the oxygen atom O5/O10 of a hydrogen-bonding partner in the example of FIG. 59. The property of FIG. 59($a$) corresponds to an alternating long and short dash line in FIG. 60, while the property of FIG. 59($b$) corresponds to a broken line in FIG. 60. It is considered that a potential property in a direction in which two hydrogen-bonded atoms are distanced away from each other (a direction in which the distance between the hydrogen atom H2 and the oxygen atom O5/O10 becomes larger than the optimal value) is not affected by a molecular structure involved with the hydrogen bond that much. On the other hand, when the two hydrogen-bonded atoms come closer (the distance between the hydrogen atom H2 and the oxygen atom O5/O10 becomes smaller than the optimal magnitude), distortion occurs in a molecular structure in ATP in a direction in which the distance between the two atoms increases as shown in FIG. 59($a$), thereby resulting in that a difference value of total energy increases (which is indicated by the property of the dash line of FIG. 60).

Further, as the difference value of total energy increases when the two hydrogen-bonded atoms come closer, coefficient values of $\kappa 2$ and $\kappa 4$ both increase as shown in FIG. 60. Consequently, as shown in formula (A 60), the frequency of the absorption band increases (the wavelength decreases). For this reason, depending on whether a hydrogen-bonding partner to which a part of the residue of Lysine Lys185 is hydrogen-bonded is ATP or a water molecule, the wavelength of the absorption band varies. Further, as shown in the explanation above, depending on a difference in a residue of amino acid involved with a hydrogen bond (e.g., whether the residue of amino acid is a residue of Lysine Lys185, a residue of Arginine, or a residue of Asparagine Asn235), a wavelength value of the absorption band varies.

In this way, the present exemplary embodiment or the applied embodiment has such an effect that a difference of molecules involved with bonding is estimated from a wavelength value of the absorption band which varies (temporarily) during life activities, so that a difference between detailed life activities (internal reactions) can be identified. Further, this feature and effect are not limited to the contraction/relaxation in a skeletal muscle and hydrogen bonding, but also applicable to any life activities (internal reactions) accompanied with (temporal) variations in a vibration mode of a specific atom. Further, when this wavelength selectivity by the molecular difference involved with bonding is used for life activity control to be explained in chapter 12, it is possible to perform control according to the difference of an appropriate wavelength so that other life activities are less affected. This yields such an effect that side effects caused unnecessarily due to the life activity control can be reduced.

On the other hand, from a combination of the explanations in chapters 4 and 5, when an anharmonic vibration potential property changes as shown in FIG. 60, a distribution characteristic of electrons located around a hydrogen atom involved with a hydrogen bond changes. In view of this, the detection or measurement of any life activities (internal reactions) accompanied with (temporal) variations in a vibration mode of a specific atom may be performed by use of not only the difference in the wavelength value of the absorption band, but also the difference in the chemical shift value at the time of Nuclear Magnetic Resonance (see chapter 5).

A detailed correspondence between a wavelength value of the absorption band corresponding to hydrogen bonding occurring in a life activity (internal reaction) and a combination of molecules involved with the hydrogen bond requires data filing of theoretical calculation and experimental values. In the present specification, instead of explaining strict values, an outline of the wavelength range of the absorption band which takes into account measurement errors and differences of detection values caused due to a measurement environment is explained. The transition between vibration modes corresponding to hydrogen bonding occurring in hydrolysis of ATP structurally has a characteristic close to the row of "Intermolecular hydrogen bonding of primary amide —$CONH_2$" in Table 7. The hydrogen bonding in the ATP hydrolysis corresponding to the contraction of a skeletal muscle is related to a residue of Lysine Lys185 and a residue of Asparagine Asn235 (FIG. 58), but a variation of the center wavelength of the absorption band depending on the difference of the residue of amino acid is considered to be relatively small. The wavelength ranges of respective absorption bands are explained below together. As described in section 4.7, when a variation range considering the difference in a detection value caused by measurement errors or measurement environments is estimated as ±15%, the variation ranges are as follows: 1.60×(1−0.15)=1.36, 1.62×(1+0.15)=1.86, 1.07×(1−0.15)=0.91, and 1.09×(1+0.15)=1.25. Accordingly, when the values are summarized, the following ranges can be obtained:

a wavelength range of an absorption band corresponding to the 1st overtone is from 1.36 µm to 1.86 µm; and a wavelength range of an absorption band corresponding to the 2nd overtone is from 0.91 µm to 1.25 µm.

With respect to the ranges thus obtained, remaining ranges obtained by excluding the wavelength ranges greatly absorbed by the water molecule shown in FIG. 56 are as follows:

the wavelength range of the absorption band corresponding to the 2nd overtone is from 1.03 µm to 1.25 µm; and the wavelength range of the absorption band corresponding to the 1st overtone is from 1.52 µm to 1.86 µm, as shown in FIG. 56.

However, the ranges show only a detection range of the nth overtone to the last. Further, an absorption band corresponding to combinations is also included in the near-infrared region. In view of this, when the wavelength range to detect combinations is also taken into account, the first, second, third, fourth, and fifth wavelength ranges I to V with less absorption by water shown in FIG. 56 can be taken as target ranges. Alternatively, if an absorption amount in the absorption band for the combinations is large and is not affected by the absorption by water very much, a desirable wavelength range will be in a range from 0.84 µm (or 0.875 µm) to 2.50 µm as shown in section 4.7. Further, similarly to the above as for the hydrolysis of ATP, the following can be performed:

Detection of a signal related to a life activity based on an absorption amount or an absorption change of the electromagnetic wave having a wavelength in the above range in a life object, and measurement of a life activity state by processing the detection signal; and Control of the life activity by increasing (temporarily) an illumination amount of the electromagnetic wave having a wavelength in the above range in the life object (note that detection/measurement and control may be performed in parallel). That is, in order to contract a skeletal muscle, oxygen atoms O2, O6, and O5⁻ in ATP are hydrogen-bonded to a part of a residue of Lysine Lys185 and a part of a residue of Asparagine Asn235 just before a hydrolysis reaction of ATP (FIG. 58). At this time, a high-intensity electromagnetic wave is projected so that vibration modes of most of the hydrogen atoms H6, H5, and H2 related to hydrogen bonding are excited. This causes the hydrogen atoms H6, H5 and H2 to vibrate in an excited state, thereby cleaving the hydrogen bonds by the energy. This causes ATP not to have a molecular arrangement in which hydrolysis can be performed as shown in FIG. 58, thereby resulting in that the hydrolysis reaction of ATP is obstructed, so that the skeletal muscle does not contract and its relaxed state continues.

The above explanation mainly deals with detection/measurement or control for contraction/relaxation of a skeletal muscle as an example, but the present exemplary embodiment is also applicable to detection/measurement or control for any activities in a life object related to the "hydrolysis of ATP" as an applied embodiment. For example, the detection/measurement or control by the aforementioned method is applicable to an ion pump function to pump a specific ion out of a cell to the outside or carbon fixation during photosynthesis as an operation using the hydrolysis of ATP. Further, according to B. Alberts et. al.: Molecular Biology of the Cell, 4th Edi. (Garland Science, 2002) Chap. 16, motor protein is used for substance transport in a cell including substance transport in a neuronal axon, but the hydrolysis of ATP is also used for movement of this motor protein. Accordingly, the detection/measurement or control by the aforementioned method is applicable to this substance transport in a cell as one example of life activities.

11.5) Features of Detection Method of Life Activity

This section explains characteristics of a life activity detection signal obtained by using a hydrolysis reaction of ATP for muscular contraction detection and a measurement method related to it. However, the present exemplary embodiment is not limited to the above, and a phenomenon of a] control to enable contraction of a skeletal muscle by release of calcium ions into a muscle cell, as described in the above section, may be used for detection of muscle. Initially, as premise for the detection of life activity, a muscle portion is illuminated with an electromagnetic wave (light) including a center wavelength of the absorption band which occurs when a part of a residue of Lysine Lys185 is hydrogen-bonded to an oxygen atom in ATP, as described in the previous section (section 11.4), so as to detect an absorbing state of the electromagnetic wave (light). FIG. 61 shows a difference in absorption change of an electromagnetic wave (light) before initiation of a muscular contraction activity 511 and during a muscular contraction activity 512. Before initiation of the muscular contraction activity 511, no hydrogen bonding occurs between a part of a residue of Lysine Lys185 and an oxygen atom in ATP, so that an absorption band corresponding to that is not caused and a light absorption amount at a center wavelength thereof is small. After that, during the muscular contraction activity 512, a hydrolysis reaction of ATP occurs asynchronously, so that an absorption amount of the electromagnetic wave fluctuates greatly along a detection time. That is, a very large number of Myosins exist in a muscle cell, and timings to cause the hydrolysis reaction of ATP are different between individual Myosins. At the moment when many Myosins cause the hydrolysis reaction of ATP at the same time, the absorption amount of the electromagnetic wave (light) increases, but on the other hand, at the moment when only a few Myosins cause the hydrolysis reaction of ATP, the absorption amount of the electromagnetic wave (light) decreases. Accordingly, in the present exemplary embodiment, as for the detection signal characteristic shown in FIG. 61, muscle contractile activity is evaluated based on an amplitude value 513 of the absorption change amount of the electromagnetic wave (light). Alternatively, an amount of muscle contractile activity may be evaluated using a maximum value of the absorption change amount of the electromagnetic wave (light) within a specific time.

In the present exemplary embodiment, a "contraction state of facial muscles of a human" is detected so as to measure an emotional reaction of an examinee as described in section 6.5.4, as a method for measuring a life activity by detecting the "muscular contractile activity" as a detection subject of life activity. J. H. Warfel: The Extremities 6th edition (Lea & Febiger, 1993) describes a relationship between contraction of an expression muscle on a face and an expression, and an extract therefrom is shown in FIG. 62. When a person is surprised, an epicranius 501 contracts, and when a person feels pain, a corrugator 502 contracts. This corresponds to phenomena that the eyebrows are raised when a person is surprised and that the forehead is wrinkled when a person feels pain. Further, cheeks rise with the smile, which indicates a state where a zygomaticus 503 contracts when smiling. On the other hand, when a person feels sorrow, a depressor anguli oris 505 contracts, so that the mouth stretches and the outside of the mouth turns down. In the meantime, when a person wants to say something or to express feelings such as dissatisfaction, the person sometimes shoots out the lips. When a person wants to represent facial expression, an orbicularis oris 504 contracts. On the other hand, when a person is expressionless, a depressor labii inferioris 506 tends to contract. When a person has some doubt and shows disdain, a mentalis 507 contracts and a center of the mouth turns down.

A relationship between a location of a mimetic muscle which contracts on a face and a facial expression suggests that "what emotional reaction is expressed can be found according to which mimetic muscle contracts." The present exemplary embodiment has such a feature that an emotional reaction or a feeling of an examinee is measured in real time to find which muscle contracts and how strong the contraction is by use of this phenomenon. There has been conventionally known a technique in which a feeling of the examinee is estimated from geometric information such as a placement, a shape, or a time dependent variation of constituent parts (eyes and a mouth) on the face. However, this method has such a problem that an original facial structure of the examinee and a facial angle in measurement largely affect the measurement, so that measurement accuracy is poor and the measurement takes time. In contrast, in this exemplary embodiment, since the emotional reaction or the feeling is measured according to a location or strength of a mimetic muscle to contract, highly accurate measurement can be performed instantly. Further, since the measurement is a non-contact method, the measurement can be advantageously performed on the examinee in a natural state without imposing a burden on the examinee.

Further, not only the present exemplary embodiment can perform measurement in a non-contact manner, but also the present exemplary embodiment has such a device that the measurement can be performed stably even if the examinee moves around freely. In a case where the examinee moves around freely during the measurement, a position 522 of a detection subject of life activity (that is, the examinee) may move toward a corner of a detectable range 521 in the detecting section for life activity in some cases, as shown in FIG. 63, for example. In such a case, the present exemplary embodiment utilizes a signal obtained from the position monitoring section 46 regarding a detected point for life activity so as to detect a life activity. As has been already described in section 6.1.3, the present exemplary embodiment has a large feature that the second detection is performed based on the first detection. The "first detection" as used herein indicates "position detection of a detected point for life activity" as defined in section 6.1.3, and the "position monitoring section 46 regarding a detected point for life activity" shown in FIG. 22, for example, performs the detection. Further, the "second detection" indicates "detection of life activity" and the "detecting section 47 for life activity" shown in FIG. 22, for example, performs the detection.

In the meantime, the present exemplary embodiment also has such a feature that in order to attain the feature, an operation check (S101) of the detecting section 101 for life activity and the position monitoring section 46 regarding a detected point for life activity is performed in advance, as shown in FIG. 64 or 65, and when at least either one of position detection (the first detection) of a detected point for life activity and detection of life activity (the second detection) is not performable (S102), such a process is performed that a life activity detection signal 106 (see FIG. 31, 32, or 35) is not output (S103).

For example, as shown in FIG. 63, if the position 522 of the detection subject of life activity (for example, the examinee) is within the detectable range 521 in the detecting section for life activity, the detection of life activity (the second detection) can be performed. However, if the position 522 of the detection subject of life activity (for example, the examinee) is out of the detectable range 521 in the detecting section for life activity, the detection of life activity (the second detection) cannot be performed. Further, as shown in FIGS. 31 and 32, reflection light obtained by illuminating the detection subject of life activity (e.g., the examinee) with the illuminating light 115 for life activity detection is detected, but if light is blocked on a part of the optical path, the detection of life activity (the second detection) cannot be performed. Similarly, a case where position detection by the position monitoring section 46 regarding a detected point for life activity shown in S102 of FIG. 64 or 65 cannot be performed corresponds to a case where the detection subject of life activity (e.g., the examinee) moves outside the range where the position detection by the position monitoring section 46 regarding a detected point for life activity is performable or a case where light is blocked on a part of the detection light path.

Further, as described above, in a case where at least either of the first and second detections is not performable, a specific value such as "0" may be output, for example, as shown in S103 of FIG. 64 or 65, instead of stopping the output of the life activity detection signal 106. At the same time, the user may be notified of the state where the detection of life activity is not performable, by means of a "screen display" or "audio" (S103).

On the other hand, section 6.1.3 describes that a position of a measurement subject in three dimensions is calculated by position detection of a detected point for life activity (the first detection) and a signal of detection (the second detection) related to the life activity is obtained from the calculated position in a life object. This specific content thereof will be explained, more specifically. The meaning of "based on the first detection" in the above feature is that:

a position in a depth direction of the detected point 30 for life activity is detected based on the position detection (the first detection) of the detected point for life activity. This corresponds to the step of S104 in FIG. 64 or 65 (detection by the position monitoring section 46 regarding a detected point for life activity). The principle of "trigonometry" is used as a specific method thereof as described in section 6.2.2 with reference to FIG. 22. Subsequently, based on "positional information in the depth direction of the detected point 30 for life activity" obtained as a result of the detection in S104 (corresponding to the distance 44 surface points of an area where the detecting section for life activity is disposed in FIG. 22), the objective lens 31 (FIG. 23 or 24) provided in the detecting section 101 for life activity is displaced in the optical axial direction so as to be moved to a position optimum for detection of life activity. This corresponds to controlling of an operation of the detecting section 101 for life activity as described in S105. In the meantime, the camera lens 42 is also provided in the position monitoring section 46 regarding a detected point for life activity as shown in FIG. 22, and the camera lens 42 is optimized in accordance with the position in the depth direction of the detected point 30 for life activity obtained in S104. As a result, a clear imaging pattern of the life-object surface 41 is obtained on the two-dimensional photodetector 43 provided in the position monitoring section 46 regarding a detected point for life activity. Thus, only after the clear imaging pattern is obtained in the position monitoring section 46 regarding a detected point for life activity, an efficient life activity detection signal 106 specialized in the measurement of life activity (described later) is obtained.

The explanation with reference to FIG. 62 has described that "when a location of a muscle to contract in mimetic muscles is found, it is easy to find a corresponding emotional reaction." That is, all life activity detection signals indicative of muscular contraction amounts over the region in the detectable range 521 in the detecting section for life activity as shown in FIG. 63 are not output, but "a location of a muscle related to the emotional reaction" (or expression) is extracted from the detectable range 521 in the detecting section for life activity and only a contraction state of the muscle is output as the life activity detection signal 106 (FIG. 31, 32, or 35). This makes it easy to perform interpretation using the life activity detection signal 106 (that is, life activity measurement). Accordingly, the present exemplary embodiment has a large feature in that:

a life activity detection signal 106 is output based on position detection (the first detection) of a detected point for life activity. Then, if a relationship between the position 522 of the detection subject of life activity (a relative position of the detected point 30 for life activity in FIG. 23, 24, or 26 to the position monitoring section 46 regarding a detected point for life activity shown in FIG. 22) and the life activity detection signal 106 is examined, it can be easily determined whether or not this feature is performed. That is, even in a case where the examinee keeping the same feeling (emotion) moves, if the life activity detection signal 106 is output continuously and stably, it can be determined that a position of a specific muscle is followed and a contraction state of the muscle is output as the life activity detection signal 106, based on the position detection (the first detection) of the detected points for life activity (the feature is performed). On the other hand, in a case where light is blocked on a part of the detection light path of the position monitoring section 46 regarding a detected point for life activity, and even after a while (in consideration of a buffer process in the life activity detection signal 106), a reliable life activity detection signal 106 is still kept output, it is estimated that the feature is not performed.

Before "a location of a muscle related to an emotional reaction (or expression)" is extracted from the detectable range 521 in the detecting section for life activity, it is necessary to extract a position 522 of a detection subject of life activity in the detectable range 521 in the detecting section for life activity in the position monitoring section 46 regarding a detected point for life activity. This position extraction process uses, for example, a "face recognition technique" and a "facial angle extraction technique" used in digital cameras or the like. In this face recognition technique, positions of eyes, a mouth, a nose, and ears having shapes peculiar to a human face are extracted by a pattern matching so as to find a "place thought to be a face." After the "place thought to be a face" is found as such, positions of eyes, a mouth, a nose, and ears in the place are searched, and a facial angle is estimated.

Here, "positions of various mimetic muscles related to an emotional reaction (expression)" can be deduced from the positions of the eyes and the mouth as shown in FIG. 62. An operation to deduce the "positions of various mimetic muscles related to the emotional reaction (or expressiveness)" from the imaging pattern in two dimensions on the two-dimensional photodetector 43 corresponds to the method for detecting a position in two dimensions on a planer orientation of the detected point 30 for life activity by the position monitoring section 46 regarding a detected point for life activity, in step 106 described in FIG. 64 or 65. Meanwhile, this section 11.5 explains the detection of contracted states of various mimetic muscles as exemplary detection of life activity. However, the exemplary embodiment shown in FIG. 64 or 65 is not limited to that, and is applicable to detection or measurement of any life activities, for example, extraction of a place where a neuron fires an action potential as described in chapter 4, extraction of a position of an activated cell based on a phosphorylation activity as will be described later in chapter 13, and the like.

There are two methods as a method for leading a detection result obtained in step 106 in FIG. 64 or 65 to a life activity detection signal 106. First of all, in the present exemplary embodiment shown in FIG. 64, a detection location in the detecting section 101 for life activity is controlled based on the detection result of step 106 (S107). In this step, the control is performed so as to obtain a life activity detection signal only from the "positions of various mimetic muscles related to an emotional reaction (expression)" in the detectable range 521 in the detecting section for life activity. That is, locations corresponding to the "positions of various mimetic muscles related to an emotional reaction (expression)" obtained in step 106 are set as light transmission sections 56 in the two-dimensional liquid crystal shutter of FIGS. 24 and 25 (see section 6.3.1).

As a result, in the longitudinal one-dimensional alignment photo detecting cell 55 in FIG. 24, only a life activity detection signal 106 associated with muscular contraction (an ATP hydrolysis reaction) of a corresponding mimetic muscle is obtained. Then, the life activity detection signal 106 (FIG. 31, 32, or 34) obtained here is output as it is (S108). In this exemplary embodiment, since the extracting method of the life activity detection signal 106 is very simple, it is advantageously possible to manufacture the detecting section 101 for life activity at low cost and to obtain a highly precise detection signal.

On the other hand, in the applied embodiment shown in FIG. 65, life activities are detected in the whole detection region (all regions in the detectable range 521 in the detecting section for life activity shown in FIG. 63) in the detecting section 101 for life activity, as shown in S111. Further, in this case, as the detecting section for life activity, the method explained in section 6.3.2 with reference to FIG. 26 to FIG. 28 is used. In the signal processing operation section 143 of the rear part shown in FIG. 34 in the rear part 86 of the life activity detection circuit, a necessary detection signal is extracted from the life activity detection signals obtained in S111 by use of detection information of S106 (S112), and is output as a necessary life activity detection signal 106 (see FIG. 31 or 32) (S113). In a case where this method is adopted, contraction information of other face muscles except the "mimetic muscles related to the emotional reaction (or expression)" illustrated in FIG. 62 is also obtained as a detection signal, thereby making it possible to perform advanced signal processing with the use of those detection signals in the signal processing operation section 143 of the rear part in FIG. 34. Accordingly, with the use of the method shown in this applied embodiment, it is possible to more highly precisely measure life activities.

The above exemplary embodiment in which a location of a mimetic muscle contracting on a face and its contraction amount are detected to measure an emotional reaction (or emotional movement) of an examinee can be applied to prevention of depression, or early detection or diagnosis thereof. The following explains this applied embodiment. Most people do not laugh when feeling depressed, and the number of active expressions tends to decrease. Accordingly, as described above with reference to FIG. 62, when even a physically unimpaired person feels depressed, it is estimated that the number of contractions of the zygomaticus 503 and the orbicularis oris 504 decreases. When the person feels further depressed or feels sad triggered by the depression, it is considered that the frequency of slight contraction of the depressor anguli oris 505 increases. When the depression further progresses, the person laughs less and grows expressionless. In this case, it is very likely that the zygomaticus 503 and the orbicularis oris 504 are relaxed while the depressor labii inferioris 506 is kept strained. In view of this, by detecting a location of a mimetic muscle to contract and an amount of the contraction, how deep the depressed feeling is at that point can be estimated (measured). Further, the frequency of a depressed feeling through time (e.g., how long the depressed feeling continues or how often the depressed feeling occurs in a day or week) or a time dependent variation of the occurrence frequency of the depressed feeling (whether or not the person forget the feeling and gets well soon, or whether or not the depressed state progresses as time passes) will also be a problem. As such, 1] if the progress of the depression of the examinee can be measured over time, it will be useful for early detection or medical examination of the depression.

In addition to that, the use of this applied embodiment enables

2] prevention of the depression according to mental inclination of the examinee.

That is, people who are apt to think relatively seriously and sober people tend to develop depression more easily. Accordingly, by monitoring a facial expression and grasping mental inclination of the examinee, precautionary measures to depression can be performed according to the mental inclination of the examinee. Concrete methods are explained below. As described above, a location of a mimetic muscle contracting on a face and its contraction amount are detected, and how deep the depressed feeling of the examinee is (progress in view of depression) at that point is expressed with a value. Then, if the measurement can be performed continuously over time by means of the life detecting division 218 described in section 7.2.2.3 with reference to FIG. 44, a time dependent variation of the level of the depressed feeling thus expressed with a value is examined. This allows easy judgment on which level the examinee is at, for example, "healthy," "feeling blue," "caution needed for mental health," "brief depression (=continuous examination required)," "treatment required," or "very serious," and timely treatment by a psychiatrist is enabled.

Conventionally, such an attempt has been made that oxygen analyzing in blood with a brain wave or near infrared light is used for diagnosis of depression. However, it is necessary that a measuring apparatus be made contact with a patient in the above method, thereby causing such a problem that a large burden is imposed on a patient and continuous measurement for a long period is difficult. In contrast, this applied embodiment is measurement in a completely non-contact manner, so that continuous measurement for a long period can be performed easily without imposing a burden on the examinee.

The following describes prophylaxis and a diagnosis method for depression by use of the life detecting division 218 explained in chapter 7 with reference to FIG. 44.

<Method in which Life Detecting Division is Provided in Consulting Room of Psychiatrist>

This is a method to utilize the life detecting division 218 as a diagnosis device and corresponds to the packaged device as described in section 7.1. When an ambulatory patient sits down before this life activity control device, a progression level of depression appears in the form of a numerical value sequentially. By use of this value, a psychiatrist can grasp therapeutic effects numerically.

<Method in which Life Detecting Division is Provided Around Body of Patient and Time Dependent Change of Feeling of Patient is Grasped Through Time>

Assume a case where the life detecting division 218 is provided on a desk or adjacent to a television or a personal computer as described in section 7.2.2.3. In this applied embodiment, the life detecting division 218 can be provided in a non-contact manner to an examinee. Further, in a case where the method explained with reference to FIG. 64 or 65 is used, even if the examinee moves, the movement can be followed automatically. Accordingly, this makes it possible to grab a change of the feeling of the patient for an extended period through time. Then, as described in section 7.2 with reference to FIG. 44, a life activity detection signal 248 or life activity information 249 obtained by the life detecting division 218 is transferred to a psychiatrist or an administrator of a company via the network in real time. This allows the psychiatrist or the administrator of the company to perform early preventive treatment or early detection to depression.

If such early detection to depression is enabled based on the above technique, a corresponding early treatment is also performable. Further, an applied embodiment which will be described in section 13.2 can contribute to this treatment of depression.

12] Control Method of Life Activity

This exemplary embodiment has a feature in that:

[1] an inside of a life object is illuminated with an electromagnetic wave from its outside;

[2] a state in the life object is locally changed; and

[3] a life activity is controlled in a non-contact manner.

The following describes a configuration of a life activity control device for performing the control, a basic principle used for the control of life activity, and the like.

12.1) Outline of Basic Control Method of Life Activity

FIG. 66 shows an example of the life activity control device to be used in the present exemplary embodiment. The life activity control device to be used in the present exemplary embodiment has the following features:

An electromagnetic wave having a relatively high intensity is projected to an inside of a life object from its outside so as to be used as control light;

An electromagnetic wave having a wavelength in a range of not less than 0.84 µm but not more than 2.5 µm is used as the control light;

The control light is condensed on a specific location in the life object;

The control of life activity and the detection of life activity may be performed in parallel The control is performed after an active state is detected at the location to be controlled in the life object, or the control is performed while the detection is performed; and A specific voltage from the exterior can be applied at the same time as irradiation of the control light.

In the measuring method of life activity in the present exemplary embodiment, it is necessary to set a location to be a control object in a life object at first. A part 600 of an organism to be detected/controlled, which is taken as the control object, is assumed the head of an examinee in FIG. 66 for convenience sake, and the present exemplary embodiment takes, as an example, an action potential control in a neuron. However, the present exemplary embodiment is not limited to that, and any location in the life object including a hand, a foot, and a waist may be taken as the part 600 of an organism to be detected/controlled, and the organism herein may be plants, bacteria, and microorganisms besides animals.

This life activity control device is provided with a position detecting monitor section 432 of a detected point for life activity to monitor the location of the part 600 of an organism to be detected/controlled. This position detecting monitor section 432 of the detected point for life activity performs monitoring according to the method explained in section 6.2 with reference to FIGS. 20 and 22. Further, in a case where the examinee is an animal, it may move slightly during detection or control. In case of such slight movement, the objective lens 31 is moved in three axial directions to follow the detected point 30 for life activity.

More specifically, when the part 600 of an organism to be detected/controlled moves after the position detecting monitor section 432 of the detected point for life activity initially sets a position of the detected point 30 for life activity, the position detecting monitor section 432 of detected point for life activity automatically detects a displacement amount thereof, and the objective lens 31 is moved by an operation of an objective lens driving circuit 605 according to the displacement amount thus detected, thereby mechanically correcting the displacement amount. In the exemplary embodiment shown in FIG. 66, a position detecting light source 431 of the detected point for life activity is provided as a different member from a light source for light (electromagnetic wave) to be used for detection or control of life activity, and projects light to the same location as the detected point 30 for life activity where the detection or control of life activity is performed or to its neighboring region (a slightly wide region including the detected point 30 for life activity). Alternatively, the position detection of a detected point for life activity may be performed using the same light source as the light source to be used for the detection or control of life activity.

An electromagnetic wave (light) 608 for detection/control of life activity emitted from a light emitting component 111 is converted into parallel light by a collimating lens 606, and then condensed by the objective lens 31 on a detected point 30 for life activity in the part 600 of an organism to be detected/controlled. By condensing the electromagnetic wave (light) 608 for detection/control of life activity as such, the following effects are yielded: (1) a life activity only at a local specific location in a life object can be controlled; and (2) the energy of the electromagnetic wave (light) 608 for detection/control of life activity can be used effectively.

FIG. 66 shows a configuration having only one light emitting component 111, but alternatively, a plurality of light emitting components 111 may be provided. If the electromagnetic wave (light) 608 for detection/control of life activity emitted from the plurality of emitting components 111 is passed through the same objective lens 31, light can be condensed at a plurality of spots in the part 600 of an organism to be detected/controlled at the same time, so that life activities in a plurality of different detected points 30 for life activity can be controlled at the same time. Further, by independently controlling respective light emissions from the plurality of light emitting components 111, respective timings of the control of life activity in a plurality of different detected points 30 for life activity can be changed, independently.

Further, the detecting section 101 for life activity is provided in the life activity control device shown in FIG. 66, and detection of life activity can be performed in parallel with the control of life activity. This yields the following effects of the present exemplary embodiment: (1) the control of life activity can be performed after checking a necessity of the control at the detected point 30 for life activity by detecting a life activity state thereof, so that efficiency of the control of life activity increases; and (2) the detection of life activity can be performed while the life activity is controlled, so that effects of the control of life activity can be checked in real time and effectiveness of the control of life activity is increased. Note that the detecting section 101 for life activity in FIG. 66 uses the principle explained in section 6.3 with reference to FIGS. 23 to 28 and has the configuration explained in section 6.4 with reference to FIGS. 31 to 35.

Meanwhile, in the life activity control device shown in FIG. 66, a single light source (the light emitting section 111) is used for the detection and the control of life activity. This yields the following effects: (1) the number of necessary components can be reduced, so that downsizing and cost reduction of the life activity control device can be achieved; and (2) it is not necessary to align the optical systems (optical adjustment) separately for the detection and the control of life activity and assembling of the life activity control device is simplified, so that cost reduction and high reliability of the life activity control device can be achieved. In the case of this method, the light amount of the electromagnetic wave (light) emitted from the light emitting component 111 is changed through time, so as to switch between the detection and the control to the life activity through time. That is, the light amount of the electromagnetic wave (light) emitted from the light emitting component 111 is reduced at the time of the detection of life activity, and in the meantime, the light amount of the electromagnetic wave (light) emitted from the light emitting component 111 is increased at the time of the control of life activity performed intermittently. The changing of the light emission amount at this time is controlled by a modulation signal generator 118 based on an instruction from a control section 603. Then, a light emitting component driver 114 changes the amount of a current to be supplied to the light emitting component 111 in accordance with an output signal from this modulation signal generator 118.

Alternatively, different light sources may be provided for the detection and the control of life activity. In that case, there is such an advantage that (1) the control and the detection of life activity can be performed at the same time zone, so that accuracy of the detection of life activity is improved and the effectiveness of the control of life activity is more improved. As shown in FIG. 56, appropriate wavelengths for the detection and the control of life activity are separated in a plurality of regions (ranges), in general. Accordingly, in a case where different light sources are used for the detection and the control of life activity, it is desirable to select light sources for emitting respective electromagnetic waves (light) having wavelengths included in different wavelength ranges (regions) from each other.

Further, the life activity control device shown in FIG. 66 has feature in that irradiation of the electromagnetic wave (light) 608 for detection/control of life activity to the detected point 30 for life activity and application of a specific voltage from the outside can be performed at the same time. When the application of a specific voltage is performed at the same time as such, the control of life activity can be performed more effectively. Here, a control section 603 performs a synchronous control of a timing to increase a light emission amount of the light emitting component 111 and a timing to apply a specific voltage at the time of the control of life activity. That is, when a command signal is output from the control section 603, the modulation signal generator 604 operates a power supply 602 for high voltage and high frequency generation so as to generate a high voltage temporarily. This high voltage is applied to electrode terminals (plates) 601-1 and 601-2, so that a strong electric field occurs between the electrode terminal (plate) 601-1 and the electrode terminal (plate) 601-2. An effect of this strong electric field occurring between the electrode terminal (plate) 601-1 and the electrode terminal (plate) 601-2 is similar to AED (Automated External Defibrillator) used for heart resuscitation.

Meanwhile, an arrangement of the two electrode terminals (plates) 601-1 and 601-2 is fixed in the life activity control device shown in FIG. 66, and the part 600 of an organism to be detected/controlled (the head or the like of the examinee) is to be inserted therebetween. However, the arrangement is not limited to that, and the electrode terminal (plate) 601-1 and the electrode terminal (plate) 601-2 may be directly attached (or temporarily adhere) to a surface of the part 600 of an organism to be detected/controlled (the head or the like of the examinee).

Further, FIG. 67 shows an applied embodiment of the life activity control device shown in FIG. 66. FIG. 67 has a feature in that an electromagnetic wave 608 for detection/control of life activity is led to an optical waveguide 609, so that an inside of a life object is illuminated with the electromagnetic wave 608 for detection/control of life activity like an endoscope and a catheter. Further, in this case, a signal obtained from the position detecting monitor section 432 of a detected point for life activity is transmitted to an optical waveguide driving circuit 610 so as to control a position of the objective lens 31 provided at a tip of the optical waveguide 609. As shown in FIG. 67, when the optical waveguide 609 is used, the control of life activity can be performed even at a location deep in an organism to be a detection/control object by illuminating the location with the electromagnetic wave 608 for detection/control of life activity, thereby drastically improving a controllable range.

Further, the present exemplary embodiment is not limited to the configuration, and the light emitting component driver 114, the light emitting component 111, and the detecting section 101 for life activity may be housed in one small capsule. In this case, the capsule is introduced into a body in such a manner that an examinee shallows the capsule, for example, and a position of the capsule is controlled from the outside by wirelessly communicating with a control section provided outside the body. In the applied embodiment in FIG. 67, the examinee has a burden at the time of introducing the optical waveguide 609 into the body. In contrast, if the capsule is used, not only the burden on the examinee can be largely reduced, but also the electromagnetic wave 608 for detection/control of life activity can be continuously projected for a long time, so that the efficiency of the control of life activity (e.g., treatment efficiency) can be largely improved.

12.2) Outline of Basic Principle Used for Control of Life Activity

First explained is a basic principle used for the control of life activity by using the life activity control device shown in FIG. 66 or the applied embodiment shown in FIG. 67.

A basic principle to be common in all of the present exemplary embodiment and applied embodiments has a large feature in that:

A] an electromagnetic wave related to a specific life activity is projected to control the life activity. Here, the wording "related to a specific life activity" indicates "an absorption band related to the specific life activity" occurring in a life object, and in the present exemplary embodiment or the applied embodiment, the life activity is controlled by illuminating an inside of the life object with an electromagnetic wave (light) including a wavelength of the absorption band. Further, the "absorption band" as used herein indicates an absorption band occurring when the specific life activity occurs inside the life object, and relates to a vibration (or excitation of a vibration mode) of a specific atom at the time of the specific life activity. Then, the life activity is controlled by a combination of the above feature [A] and any one or more of the following features.

B] A temperature of a particular region in the life object is locally increased so as to promote a vital reaction including internal catalysis.

A reaction velocity of the vital reaction including internal catalysis tends to improve according to the increase of an environmental temperature.

A conventional therapeutic method of warming or cooling a whole body and conventional medication expanding in the whole body may cause side effects, because a undesirable vital reaction is also promoted at the same time while a desirable vital reaction is promoted. In contrast, in this exemplary embodiment/applied embodiment, the electromagnetic wave (light) 608 for detection/control of life activity is condensed, and therefore "a temperature of only a very narrow region is locally increased." This hardly promotes undesirable vital reactions, thereby yielding such an effect that side effects hardly occur.

In this method, in order to locally increase the temperature of a particular region, it is most efficient that "water molecules are vibrated." In view of this, as a wavelength of the illuminating light when this method is used, it is desirable to select "a wavelength easily absorbed by water molecules." That is, as shown in FIG. 56, desirable wavelengths in this case are as follows:

a range of not less than 0.943 µm but not more than 1.028 µm;

a range of not less than 1.394 µm but not more than 1.523 µm; and a range of not less than 1.894 µm but not more than 2.061 µm.

Not only water molecules are caused to absorb heat as described above, but also "heat may be absorbed by a site causing a specific life activity, selectively," as will be explained later in section 13.2.

C] A specific vital reaction including internal catalysis is obstructed, so that the life activity is controlled.

The case where "contraction motion of a skeletal muscle is obstructed to maintain a relaxed state of the skeletal muscle" as described in section 11.4 is an example using this feature.

D] A temporary intermolecular bond occurring in a life object is obstructed to block a chemical signal transmission pathway.

More specifically, a temporary bond between a ligand of a signal transmitter and a receptor is obstructed to block a chemical signal transmission pathway in the life object.

As a specific example, the following explains a method for "relieving a pollen disease" by the control of life activity.

When pollen attaches to a mucosal bleeding cell of the nose, histamine, which is a ligand, is released from the mucosal bleeding cell, and the histamine thus released bonds to a histamine receptor in another cell surface, which develops various symptoms of the pollen disease. Here, it is considered that a hydrogen bond is formed between N—H . . . O when the histamine bonds to the histamine receptor. In view of this, as described in section 11.4, by projecting light exciting a vibration mode occurring at the time of forming the hydrogen bond (more specifically, by providing, in a face mask, a light-emitting diode which emits light having a wavelength of this excitation light), the bond between the histamine and the histamine receptor is obstructed, thereby relieving the pollen disease.

As another applied embodiment, there is such a method in which Acetylcholine, which is one of ligands, is prevented from bonding to choline-esterase having an inhibitory effect to the Acetylcholine by use of the principle explained in chapter 4, thereby improving an effect of the Acetylcholine in the body.

E] One of reactions antagonistic to each other in a life object (two reactions to work in an opposite direction to each other) is obstructed or promoted.

A method which uses this feature mainly will be explained in chapter 13.

F] A property of a molecular structure constituting a life object is changed.

The "property" to be changed as used herein indicates a change of any of the following properties:

F1) the intensity of the molecular structure; F2) the shape of the molecular structure; and F3) a local configuration (including destruction) of the molecular structure.

In regard to "F2) the shape of the molecular structure," the catalysis of an enzyme is switched between an active state and an inactive state by changing a tertiary structure of the enzyme by illumination of a specific wavelength light beam.

Further, an example of "F3) a local configuration (including destruction) of the molecular structure" is as follows: after a connection of an internal neural network is grasped by the method explained in section 9.3 with reference to FIGS. 52 and 53, the electromagnetic wave (light) 608 for detection/control of life activity is condensed on a part of an axon forming an unnecessary neural circuit, so that the axon can be burned out by heat generated as above.

The fMRI device conventionally used for the detection of life activity is very expensive, and it is difficult to perform detection/measurement easily. In contrast, a device necessary to "A] vibrate (or excite a vibration mode of) a specific atom in a life object by illumination of an electromagnetic wave (light)" can be manufactured at very low cost as shown in FIG. 66, and therefore anyone can easily perform detection/measurement and control of life activity. Particularly, the present exemplary embodiment or the applied embodiment has such a technical significance that not only "a life activity only at a local specific location in a life object can be controlled with a high spatial resolution by condensing the electromagnetic wave (light) 608 for detection/control of life activity on the location," but also "only a specific life activity can be controlled selectively" by use of selectivity of a wavelength of the electromagnetic wave (light) to be projected. Particularly, as described in section 11.4, since a difference in a wavelength value of an absorption band occurring (temporarily) in a life activity causes a difference in a molecule involved with bonding (occurring temporarily) at the time when a reaction is caused in the life object (it occurs temporarily), the selectivity of a wavelength to a life activity to be a control object is very high. Accordingly, there is little influence to other life activities, thereby yielding such an effect that side effects due to the control are hardly caused.

In regard to this technical significance, the following explains an example of controlling "F3) a local configuration (including destruction) of the molecular structure." According to B. Alberts et. al.: Molecular Biology of the Cell, 4th Edi. (Garland Science, 2002) Chap. 5 and 17, a DNA ligase acts in gene transcription, and active chromosome movement occurs in mitosis. It is considered that in the movement of this DNA ligase and the chromosome movement, the hydrolysis reaction of ATP as described in section 11.3 occurs, and light absorption at a wavelength explained in section 11.4 is caused at this time. Particularly, the DNA ligase movement and the chromosome movement actively occur in a cancer cell, and therefore, the light (electromagnetic wave) having a center wavelength of the absorption band corresponding to the ATP hydrolysis is absorbed particularly abundantly, in comparison with other cells. Accordingly, when the light (electromagnetic wave) having this wavelength is strongly projected, only the cancer cell absorbs this light (electromagnetic wave) particularly abundantly in comparison with neighboring normal cells, so that only the cancer cell is selectively hot and broken. Here, if the body is illuminated with strong light (electromagnetic wave), the skeletal muscle contracting might be broken in particular. However, the life activity control device shown in FIG. 66 can illuminate only a local area with a very high spatial resolution, and therefore, has no danger to break an unnecessary site by mistake. A method in which this method is used in combination with drug administration will be described later in section 13.2.

In the meantime, as a specific method for controlling a life activity by changing "F1) the intensity of the molecular structure," the next chapter deals with gating control of a voltage-gated ion channel.

12.3) Molecular Structure of Ion Channel and Gating Control Method

It is said that the voltage-gated $Na^+$ ion channels 11 shown in FIG. 2 exist in the neuron cell body 1 in FIG. 1, and many of them are distributed near the root of the axon 2 in the neuron cell body 1, in particular. Section 1.2 uses a plain analogy to explain a function of the voltage-gated $Na^+$ ion channel 11, and therefore the view in FIG. 2 does not necessarily indicate an actual configuration of the voltage-gated $Na^+$ ion channel 11. In B. Hille: Ion Channels of Excitable Membranes 3rd Edition (Sinauer Associates, Inc., 2001) p. 110, Plate 7, a model of the voltage-gated ion channel is described, and a simplified conformation of an extract of the model is shown in FIG. 68(a). Here, the "cover (gate)" and the "positively charged part" of the voltage-gated $Na^+$ ion channel 11 explained in section 1.2 with reference to FIG. 2 correspond to a gate 615 and a charged part 616 in FIG. 68(a), respectively.

Meanwhile, as shown in FIG. 68(a), an ion channel is embedded in a cell membrane 613 which separates an inside layer 612 facing the cytoplasm in a neuron and an outside layer 611 of the cell membrane located outside the neuron. This ion channel is made from a protein constituted by amino acids connected to each other. As shown in FIG. 68(b), in the protein, an atomic arrangement constituted by two carbon atoms C and one nitrogen atom is repeated to form a principal chain 623 of the amino acid. Particularly, a hydrogen bonding part 621 is formed between an oxygen atom double-bonded to a carbon atom C on one principal chain 623 of the amino acid and a hydrogen atom covalently bonded to a nitrogen atom on an adjacent principal chain 623 of the amino acid, which may result in that a part of the protein has an α helix conformation in which the principal chain 623 of the amino acid has a spiral tertiary structure.

Here, a residue of amino acid is expressed with "R" in FIG. 68 (b). In FIGS. 68(a), (c), and (d), a part in the protein which has this α helix conformation is expressed with a shape of a "cylinder," and respective cylindrical parts are expressed with α, β, γ, and δ. In the meantime, the bonding strength of one hydrogen bonding part 621 itself is not so strong, but there are many hydrogen bonding parts 621 in the α helix conformation, so that the overall bonding strength becomes strong. Accordingly, a cylindrical part having an α helix conformation has a very strong mechanical strength (bending stress).

As shown in FIG. 68(a), ends of the cylindrical parts α and β are closed during a resting term, so that a gate 615 is closed. Even during this resting term, ions having positive electric charge is going to enter the inside layer 612 facing the cytoplasm, because [1] the outside layer 611 of the cell membrane is much higher in ion concentration than the inside layer 612 facing the cytoplasm, and [2] there occurs a potential gradient (an arrow in wavy line) in the cell membrane 613. However, the mechanical strengths of the cylindrical parts α and β prevent incoming forces of the positive ions. Further, inside each of the cylindrical parts γ and δ respectively connected to the cylindrical parts α and β, a residue having "positive electric charge" is bonded to a residue 622 of amino acid, thereby forming a charged part 616. This residue having positive electric charge is presumably a residue of Lysine or a residue of Arginine. Since an amount of positive electric charges in a residue of Histidine is very small in a water environment (about pH 7) in a life object, it is not assumed that the residue of Histidine contributes to that.

Further, during the resting term, due to an electrostatic force from an electric field occurring by the potential gradient indicated by the arrow in wavy line in the cell membrane 613, this charged part 616 moves to a location closest to the inside layer 612 facing the cytoplasm most. The movement of the charged part 616 causes the cylindrical parts γ and δ to be twisted, so that a space of a crack 614 is expanded. It is considered that an expanding force of this crack 614 reaches the cylindrical parts α and β and works as a force closing the gate 615. Here, a state in which positive electric charges gather on a surface of the outside layer 611 of the cell membrane 613 and negative electric charges gather on the inside layer 612 facing the cytoplasm, thereby causing a potential gradient called a "polarized state."

On the other hand, when a depolarized state is caused as shown in FIG. 68(c) and the potential gradient decreases, a force to bring the charged part 616 closer to the inside layer 612 facing the cytoplasm by the electrostatic force weakens. This weakens a twisting force of the cylindrical parts γ and δ, so that the charged part 616 is brought back to a regular position and the space in the crack 614 is shortened. Accordingly, the cylindrical parts α and β open the gate 615 in conjunction with each other. When the gate 615 is opened, Na$^+$ ions flow into the inside layer 612 facing the cytoplasm from the outside layer 611 of the cell membrane and a "neuronal action potential" or "impulse propagation along axon fiber" occurs. The explanation so far has been known conventionally.

In this regard, this exemplary embodiment has a feature in that during the resting term, "this ion channel is illuminated with electromagnetic waves (light) including an electromagnetic wave (light) having a specific wavelength, so that the mechanical strengths of the cylindrical parts α and β are changed so as to control opening and closing of the gate 615." As described in section 12.2, the present exemplary embodiment has the following effects: [1] since the life activity control device is inexpensive, anyone can easily perform detection/measurement and control of life activity; [2] because of a high spatial resolution, adverse effects hardly occur in places other than a target part to be a controlled; and [3] because of selectivity of wavelength, adverse effects hardly occur in other life activities.

As described above, the mechanical strengths of the cylindrical parts α and β, which are indispensable to surely perform the opening and closing of the gate 615, are maintained by the bonding strength of the hydrogen bond shown in FIG. 68(b). The present exemplary embodiment has a feature in that an electromagnetic wave (light) exciting a vibration mode occurring in this hydrogen bond of C=O . . . H—N is projected. Due to a very high vibrational energy of the excited state, in the hydrogen bonding part 621 in the excited state, [1] a hydrogen bonding strength is largely weakened, or [2] a phenomenon that the hydrogen bond is cleaved occurs. As a result, the mechanical strengths of the cylindrical parts α and β largely decrease and the incoming force of positive ions toward the inside layer 612 facing the cytoplasm cannot be restrained, thereby resulting in that the gate 615 is opened as shown in FIG. 68(d).

The explanation so far dealt with a method in which a neuronal action potential is accelerated only by illumination of an electromagnetic field (light) without a combination of an external electric field. As another applied embodiment, the neuronal action potential and the impulse propagation along an axon fiber can be controlled finely with higher accuracy by support of the external electric field application to be used together with the illumination of the electromagnetic field (light). That is, the gate 615 of the ion channel is closed in a polarized state of FIG. 68(a), while the gate 615 of the ion channel is opened in a depolarized state of FIG. 68 (c). In this regard, a specific ion channel is set to be in an intermediate state between the polarization and the depolarization (a field strength caused just before the gate 615 is opened) by applying a strong electric field thereto from the outside. Accordingly, in an ion channel in this intermediate state, its gate 615 is opened due to slight changes in the mechanical strengths (deterioration of strength) of the cylindrical parts α and β.

A method to give a strong electric field from the outside is such that a high voltage is temporarily applied between the electrode terminals (plates) 601-1 and 601-2 by driving the power supply 602 for high voltage and high frequency generation in the life activity control device shown in FIG. 66. Since a light amount of an electromagnetic field (light) to be projected can be largely decreased by the support of the external electric field application, not only occurrences of side effects caused due to the control of life activity can be further reduced, but also a destruction risk of ion channels due to the illumination of a strong electromagnetic field (light) can be reduced. This yields such an effect that the support of the external electric field application can largely improve safety during the control of life activity.

12.4) Characteristic of Control of Life Activity

A wavelength suitable for the electromagnetic field (light) to be projected for neuronal action potential control by opening and closing of the gate 615 of the ion channel or impulse propagation along axon fiber control will be explained below. As described in section 12.3, it is necessary to excite a vibration mode caused in the hydrogen bond of C=O . . . H—N, in this case. The excitation of the vibration mode of this type has a feature relatively near to the row of the "Vibration of hydrogen bonding part of secondary amide —CONH—" in Table 7. Thus, as shown in section 4.7 or 11.4, when a variation range considering the difference in a detection value caused by measurement errors or measurement environments is estimated as ±15%, the variation ranges are as follows:

$$1.53 \times (1-0.15) = 1.30, 1.67 \times (1+0.15) = 1.92, \text{ and}$$

$$1.04 \times (1-0.15) = 0.88, 1.12 \times (1+0.15) = 1.29.$$

Accordingly, when these values are summarized, the following ranges can be obtained:

a wavelength range of an absorption band corresponding to the 1st overtone is from 1.30 to 1.92 µm; and a wavelength range of an absorption band corresponding to the 2nd overtone is from 0.88 µm to 1.29 µm.

With respect to the ranges thus obtained, remaining ranges obtained by excluding the wavelength ranges greatly absorbed by the water molecule shown in FIG. 56 are as follows:

the wavelength range of an absorption band corresponding to the 2nd overtone is from 0.88 µm to 0.94 µm and 1.03 µm to 1.29 µm.

the wavelength range of an absorption band corresponding to the 1st overtone is from 1.52 µm to 1.89 µm, as shown in FIG. 56.

However, the ranges show only a detection range of the nth overtone to the last. An absorption band corresponding to the combinations is also included in the near-infrared region. In view of this, when the wavelength range to detect combinations is also taken into account, the first, second, third, fourth, and fifth wavelength ranges I to V with less absorption by water shown in FIG. 56 can be taken as target ranges. Alternatively, if an absorption amount in the absorption band for the combinations is large and is not affected by the absorption by water very much, a desirable wavelength range will be in a range from 0.84 µm (or 0.875 µm) to 2.50 µm as shown in section 4.7.

As a concrete example to control a life activity by decreasing the mechanical strength of an α helix, section 12.3 has described the gating control in the ion channel. Alternatively, a life activity may be controlled by decreasing a mechanical strength of other α helices, as another exemplary embodiment. For example, as described in section 11.1, Myosin is included in a skeletal muscle. An α helix is included in a tertiary structure of this Myosin so as to secure a mechanical strength at the time the skeletal muscle contracts. In view of this, when the skeletal muscle contracts, the skeletal muscle may be illuminated with light having a wavelength within the above range to decrease the mechanical strength of the α helix, so that a muscular contractive force is weakened.

12.5) Suppression Control of Neuronal Action Potential

Section 12.3 has described the method in which an action potential is accelerated only by opening the gate 615 of the voltage-gated Na$^+$ ion channel in a depolarized state. On the other hand, this section explains a control method in which a neuronal action potential is restrained. As described in section 1.3, when a transmitter substance is released in a synaptic cleft, a gate of a ligand-gated Na$^+$ ion channel is opened and a depolarization potential 22 is attained. This causes a cover (gate) of a voltage-gated Na+ ion channel 11 to open, thereby causing an action potential phenomenon.

The transmitter substance which accelerates the action potential as such is called an excitatory transmitter substance, which corresponds to Glutamic acid or Acetylcholine as specific substances. On the other hand, a transmitter substance which suppresses the action potential is called an inhibitory transmitter substance, which corresponds to γ-aminobutyric acid and Glycine. Further, an ion channel which receives this inhibitory transmitter substance corresponds to a ligand-gated Cl$^-$ ion channel, and when γ-aminobutyric acid or Glycine bonds to this, a gate thereof which allows chlorine ions Cl$^-$ to pass therethrough is opened. When the Cl$^-$ ions flow into the inside layer 612 facing the cytoplasm, a hyperpolarization state in which the potential gradient in the cell membrane 613 increases occurs. Since the potential gradient in the cell membrane 613 increases in this hyperpolarization state, the gate 615 of the voltage-gated Na$^+$ ion channel is difficult to open.

Accordingly, this applied embodiment has a large feature in that (in a state where no inhibitory transmitter substance is released) only the ligand-gated Cl$^-$ ion channel is illuminated with an electromagnetic wave (light) including a specific wavelength to open the gate for Cl$^-$ ions and form a hyperpolarization state, thereby suppressing a neuronal action potential.

The ligand-gated Cl$^-$ ion channel has a conformation largely different from the conformation of the voltage-gated Na$^+$ ion channel 11 explained in section 12.3. However, for the purpose of simplification of the explanation, only an image of an operating principle of this applied embodiment is explained with reference to FIG. 68. An image of a basic motion of the ligand-gated Cl$^-$ ion channel is as follows. That is, when inhibitory transmitter substances bond to parts of the cylindrical parts γ and δ facing the outside layer 611 of the cell membrane, the arrangement of the cylindrical parts α and β is changed triggered by the changes in the conformations of the cylindrical parts γ and δ, and the gate 615 is opened. Accordingly, in conventional techniques, if no inhibitory transmitter substance bonds thereto, the gate 615 is not opened and Cl$^-$ ions do not inflow therein.

On the other hand, in this applied embodiment, the gate 615 can be opened without any bonding of the inhibitory transmitter substance. That is, in this applied embodiment, when only the ligand-gated Cl$^-$ ion channel is illuminated with an electromagnetic wave (light) including a specific wavelength, the mechanical strengths of the cylindrical parts α to δ decrease as described in section 12.3 with reference to FIG. 68(b). As a result, as shown in FIG. 68(d), Cl$^-$ ions can flow into the inside layer 612 facing the cytoplasm by use of an inflow pressure of the Cl$^-$ ions.

Here, as shown in FIG. 66, in the life activity control device realizing this applied embodiment, since the electromagnetic wave 608 for detection/control of life activity can be condensed, by use of the objective lens 31, on one detected point 30 for life activity in the part 600 of an organism to be detected/controlled, only the ligand-gated Cl$^-$ ion channel can be illuminated with the electromagnetic wave (light) including a specific wavelength (the electromagnetic wave 608 for detection/control of life activity). The life activity control device shown in FIG. 66 has a high spatial resolution as such, and therefore, high control accuracy to control only the ligand-gated Cl$^-$ ion channel and high reliability can be secured.

Meanwhile, in this applied embodiment, an identification operation of a location of the ligand-gated Cl$^-$ ion channel is required before control. For the identification operation, preliminary operation of detection of life activity is performed before the control. The identification operation of the location of the ligand-gated Cl$^-$ ion channel to be performed in advance in this applied embodiment is performed by either of the following operations:

(1) search for a neuron to release an inhibitory transmitter substance from a neuron formation; and
(2) search for a signal transmission pathway in a neuronal network to search for the location of the ligand-gated Cl— ion channel.

First of all, a preliminary searching method related to (1) is explained. The aforementioned excitatory transmitter substance is often released mainly from a pyramidal cell (a neuron which has a relatively large cytoplasm and has a pyramid shape), while the inhibitory transmitter substance is often released from a stellate cell (a neuron which has a relatively small cytoplasm and in which a dendrite extends in a relatively uniform radical manner), such as a granule cell. Accordingly, a suppressor cell to be a signal source is searched by use of the position detecting monitor section 432 of the detected point for life activity as shown in FIG. 66 and a state in which an axon extends therefrom is traced, so that the location of the ligand-gated Cl⁻ ion channel can be searched.

Next explained is a preliminary searching method related to (2). Initially, under a specific consciousness condition of an examinee, a signal transmission pathway in a neural transmission network is searched by the method explained in section 9.3.1 with reference to FIGS. 52 and 53, and a position of a numerous bouton (synaptic knob) which restrainingly works as consciousness is extracted. Then, it is assumed that a large number of ligand-gated Cl⁻ ion channels are distributed over at a position of the corresponding numerous bouton (synaptic knob).

This applied embodiment can be applied to dementia measures for elderly people. The pyramidal cell is large in cytoplasm size, and is easy to live under a relatively terrible environment. In contrast, the stellate cell such as a granule cell is relatively small in cytoplasm size, and is easy to perish under a terrible environment. Therefore, a dementia disorder such as rudeness is easy to be developed when people reach an advanced age. Another applied embodiment of this has a feature in that "a stellate cell is activated to live longer by stimulating a ligand-gated Cl⁻ ion channel, thereby suppressing progression of dementia."

According to Teiichi Furuichi: Noukagaku 5 Bunshi, saibou, sinapusu karamiru nou (University of Tokyo Press, 2008) p. 215, FIG. 7.7, when a receptor side such as the ligand-gated Cl⁻ ion channel is activated (performs a specific operation), a transmitter substance (such as eCB (endocannabinoid)) is transmitted from a postsynaptic cell of the reception side (such as a stellate cell) in an opposite direction toward a presynaptic cell. Then, triggered by the reception of this transmitter substance in the opposite direction, the stellate cell is activated to live longer. Thus, according to this another applied embodiment, the gate of the ligand-gated Cl⁻ ion channel is opened frequently by the above method, thereby activating the stellate cell so as to live longer. This yields such an effect that the progression of dementia is suppressed.

13] Detection and Control of Intracellular Life Activity 13.1) General View of Intracellular Life Activity In regard to the detection, measurement, or control method to dynamical life activities in a life object by a non-contact method, chapters 1 to 5, 11, and 12 have mainly explained about detection/measurement and control of an activity of a whole cell or activities in a local area constituted by a plurality of cells. Chapter 13 will explain about detection/measurement and control to a life activity in one cell.

Based on a diagram of an intracellular signal transmission pathway described in B. Alberts et. al.: Molecular Biology of the Cell, 4th Edi. (Garland Science, 2002) Chap. 15, FIGS. 15 to 16, FIG. 69 shows an explanatory view of a state of an intracellular life activity chain within one cell, focusing on signal transmission. A signal transmission pathway in an actual cell is very complicated, but this view is largely simplified for explanation. On a surface of one cell (on a cell membrane 613), various receptors A701 and B702 for receiving signal transmitters transmitting signals from the outside are located. Depending on to which receptor (either of the receptor A701 and the receptor B702) a signal transmitter from the outside bonds to, a different intracellular signal transmission cascade A703/B704 occurs in the cell. A tip of the intracellular signal transmission cascade A often leads to a phosphorylation cascade 711, which indicates a reaction chain to phosphorylate a macromolecule (mainly a protein) existing in a cell.

However, in some cases, a bond of a signal transmitter from the outside to the receptor A701 may directly lead to the phosphorylation process cascade 711. In the meantime, a dephosphorylation process 712, which takes a phosphoryl from a phosphorylated macromolecule (mainly a protein), also exists in the cell, and as a result, this dephosphorylation process 712 may cause an inhibitory action 713 to the phosphorylation process cascade 711 mentioned above. Here, besides a case where the dephosphorylation process 712 occurs spontaneously, the dephosphorylation process 712 may be activated due to an occurrence of an intracellular signal transmission cascade B704. Due to the occurrence of this phosphorylation process cascade 711, secretion of a new signal transmitter to the outside of the cell, apoptosis which means cell division/cell death, or exhibition 723 of a specific cellular function of changing a cell shape may be caused in some cases. Further, as another process different from that, the phosphorylation process cascade 711 may cause transcription from a gene in the cell, which is a gene expression 721, to a messenger ribonucleic acid (mRNA). Then, a protein synthesis 722 is generated by information translation from the mRNA thus transcribed, so that an exhibition 723 of a specific cellular function may be caused as a result of this.

In either of the processes, the phosphorylation process cascade 711 often causes the exhibition 723 of a specific cellular function, and there is a relative correlation between activation of an intercellular activity and the frequency of the "phosphorylation process." In view of this, there is such a thought that the frequency of an intracellular phosphorylation process is considered as one index to attain an intracellular activation. Section 13.1 has given an outline of a chain of a life activity in one cell, which has been well known, but the following explains the present exemplary embodiment including more specific contents thereof.

13.2) Thought of Detection Method and Control Method for Contradicting Life Activities As described in section 12.2, the large feature of the control method of life activity in the present exemplary embodiment is:

A] an electromagnetic wave related to a specific life activity is projected to control the life activity.

A method to apply this basic feature to detection and control of intracellular life activity is such that:

electromagnetic waves including an electromagnetic wave having a specific wavelength is projected and some activities in a life activity chain in a life object are detected; and electromagnetic waves including an electromagnetic wave having a specific wavelength is projected and some activity levels or efficiency in a chain reaction of a life activity chain in a life object is changed to control an intracellular life activity.

A target portion to be detected or controlled in the present exemplary embodiment or its applied embodiment is explained more specifically with reference to FIG. 69. First of all, there is a method to detect or control some reaction of the intracellular signal transmission cascade A703/B704.

Further, as will be described later in sections 13.4 and 13.6, an activation state of a corresponding cell can be evaluated (digitized) by detecting some phosphorylation process of the phosphorylation process cascade 711. Further, the efficiency of the phosphorylation process can be changed using an electromagnetic wave (light) including the same wavelength. That is, in the present exemplary embodiment, the efficiency of the phosphorylation process is reduced by a method to be described later in section 13.6 so as to obstruct activation of an intracellular activity. On the other hand, as will be described later in sections 13.5 and 13.6, an activation suppression level in a cell can be also evaluated (digitalized) by detecting the frequency of the dephosphorylation process 712. Further, if an electromagnetic wave (light) including a specific wavelength is projected to decrease the efficiency of the dephosphorylation process 712 and thereby suppress the inhibitory action 713 of the phosphorylation process cascade 711, it is also possible to activate the phosphorylation process cascade 711 and thereby promote activation of an intracellular activity.

As a detection or control object of the other reactions, some reaction of protein synthesis (translation of mRNA) 722 may be detected or controlled. As described in B. Alberts et. al.: Molecular Biology of the Cell, 4th Edi. (Garland Science, 2002) Chap. 6, FIGS. 15 to 16, at an end of the mRNA formed by transcription of genetic information due to the reaction of gene expression 721 in FIG. 69, a "cap" constituted by 7-Methylguanosine nucleotide having positive electric charges is formed. Then, a small subunit of a ribosome bonding to a transfer ribonucleic acid and an initiation factorsoid detects this cap position and the protein synthesis (translation of mRNA) 722 starts.

It is expected that, in order to detect a start position of the protein synthesis (translation of mRNA) 722, a methyl group in the cap is temporarily hydrogen-bonded to the small subunit side. It is expected that a hydrogen bond configuration at this time is —N(CH$_3$)$_3$O$^-$OC—, which is obtained by substituting a Cl$^-$ portion of the hydrogen bonding part —N(CH$_3$)$_3$Cl$^-$ as described in section 3.2 for a carboxyl group, and thus is a unique hydrogen bond configuration. In view of this, for the reason explained in section 11.4, a peculiar absorption band corresponding to the unique hydrogen bond configuration is caused. Accordingly, by detecting a change of an absorption amount of an electromagnetic wave (light) at a wavelength in the peculiar absorption band, a start reaction of the protein synthesis (translation of mRNA) 722 can be detected. Further, it is expected that, upon illumination of light having a wavelength corresponding to excitation light of a vibration mode of a constituent atom (mainly a hydrogen atom) corresponding to this unique hydrogen bond configuration, the detection of a start position of the protein synthesis (translation of mRNA) 722 is obstructed by photoexcitation. Accordingly, the protein synthesis 722 (translation of mRNA) can be controlled to stop while the illumination of the excitation light continues.

With reference to FIG. 69, the above has described how the receptor A701/B702 receives a signal transmitter which transmits a signal from the outside. Among the signal transmitters which transmit a signal from the outside, a signal transmitter which is small in size and highly hydrophobic, such as steroid hormone, thyroid hormone, retin, and vitamin D, is scattered in the cell membrane 613 to go into the cell, thereby directly affecting the intracellular life activity shown in FIG. 69. However, most of the signal transmitters are hydrophilic, and therefore are blocked off by the cell membrane 613 and cannot go into the cell, directly.

Accordingly, in the case of a drug administration for the purpose of a treatment which is one of the conventional controls of life activity, a most part of an administered medicinal substance cannot pass through the cell membrane 613 and directly go into the cell, but works on the receptor A701/B702 to accelerate/suppress the intracellular life activity. Therefore, there is not only a limitation in the control of life activity in most medical therapies, but also a large risk to generate side effects as a result of causing unexpected life activities.

In contrast, in the present exemplary embodiment or the applied embodiment, an electromagnetic wave (light) (such as near infrared light) not only can pass through the cell membrane 613 and directly go into the cell, but also can work on or detect a specific life activity by use of the selectivity of wavelength. In view of this, the present exemplary embodiment or the applied embodiment yields such an effect that control efficiency of life activity is improved in comparison with the conventional medical therapies.

Further, in this exemplary embodiment, a life activity state can be detected in real time and fed back to control (that is, a life activity can be controlled while an effect of the control of the life activity is checked in real time). As a result, the control efficiency is increased by using the detection of life activity together.

However, the applied embodiment thereof is not limited to the control of life activity only by the illumination of an electromagnetic wave including a specific wavelength, but a drug administration may be used together so as to improve the effect of the control of life activity and improve its safety. The following explains this applied embodiment. In recent years, the use of a molecular target drug has achieved an effect for cancer therapy. There is a receptor tyrosine kinase, which is one of receptors called "enzyme-linked receptor," which is one type of the aforementioned receptor A701. When a growth factor or the like of a signal transmitter which transmits a signal from the outside bonds to this receptor, autophosphorylation corresponding to the start process of the phosphorylation process cascade 711 occurs. As a result, a cell proliferation function, which is one form of the exhibition 723 of a specific cellular function is accelerated.

It is said that at the same time, a reaction of the phosphorylation process cascade 711 is activated, which leads to an activation of an intranuclear transcription factor, thereby promoting actions such as proliferation/invasion/metastasis of a cancer cell. Further, the aforementioned molecular target drug bonds to this receptor tyrosine kinase, and obstructs the activity of the phosphorylation process cascade 711. Further, in a case where monoclonal antibodies are used as this molecular target drug, the molecular target drug has such effects of automatically recognizing this cancer cell and performing phagocytosis on this cancer cell. However, this molecular target drug cannot directly go into a cell, as described above, so that there is no other way except working on the receptor tyrosine kinase existing on a cell membrane surface. Of course, this receptor tyrosine kinase does not exist just to "make a cancer cell." Therefore, if the activity of the receptor tyrosine kinase is obstructed, unnecessary side effects are caused as well. In order to solve such present problems, if this applied embodiment is used together, it is possible to "make the molecular target drug work on only the cancer cell." In this case, the autophosphorylation process of the receptor tyrosine kinase may be detected similarly to the molecular target drug, so as to be used for the "identification of the cancer cell".

At this time, as will be described later in sections 13.4 and 13.6, a unique absorption band occurring during the phosphorylation process is detected. On the other hand, instead of detecting the location of this phosphorylation process, "the hydrolysis reaction of ATP activated particularly in a cancer cell may be used for the identification of the cancer cell," as described in sections 11.3, 11.4, and 12.2. In either of the above methods to be used for the identification of the cancer cell, the cancer cell particularly absorbs a wavelength light beam corresponding to its life activity, as described in section 12.2. As a result, only the cancer cell selectively becomes hot in comparison with neighboring normal cells. There is such a feature that most vital reactions including antibody responses are activated according to an increase in temperature in a surrounding environment.

Therefore, if an antibody response (fressreflex) of the aforementioned molecular target drug is accelerated in a hot environment, the molecular target drug will intensively work on the cancer cell which becomes hot. In view of this, with the use of this applied embodiment together with the molecular target drug, the molecular target drug can be caused to work on the cancer cell selectively, which not only can improve therapeutic effects, but also can provide a safe therapeutic method in which side effects are reduced because an administration amount of the molecular target drug can be reduced.

In addition to that, the combination of this applied embodiment and the medical therapy also promises an effect for the treatment of depression. For the treatment of depression, SSRI having a work mechanism to obstruct reuptake of Serotonin is used. However, SSRI has delayed-acting, and therefore, it is difficult to explain its effect only by an inhibition mechanism of reuptake of Serotonin.

On the other hand, in view of the measure in FIG. 69, if it is considered that some sort of gene expression 721 or protein synthesis 722 is promoted triggered by bonding of Serotonin to the receptor A701 and thereby advances a long-term intraneuronal activation, the delayed-acting of SSRI can be explained. Accordingly, when SSRI is administered to a melancholiac, bonding persistency between Serotonin and a Serotonin receptor A701 is maintained, and an intracellular signal transmission cascade A703 and a phosphorylation process cascade 711 according to it are continued for a long period. However, in a case of only a drug (SSRI) administration, a dephosphorylation process 712 occurs in parallel and works as an inhibitory action 713 to the phosphorylation process cascade 711. In view of this, it is presumed that an intraneuronal activation only by SSRI has limitations.

In order to solve this problem, in this applied embodiment, the electromagnetic wave 608 for detection/control of life activity (FIG. 66) which obstructs the dephosphorylation process 712 is projected in parallel with the drug (SSRI) administration. The electromagnetic wave 608 for detection/control of life activity projected at this time should include a wavelength light beam which will be described later in sections 13.5 and 13.6. This accordingly obstructs the dephosphorylation process 712 having an inhibitory action 713 to the phosphorylation process cascade 711 and activates the phosphorylation process cascade, so that the intracellular activation is accelerated for a long period. Since the medical treatment to depression can be supported according to this applied embodiment as such, therapeutic effects to the depression are improved.

13.3) Memory and Obliteration Mechanism Models in Pyramidal Cell

A chain path of a life activity in one cell is very complicated in a practical sense, and therefore, FIG. 69 shows it in an extremely simplified manner. Therefore, the explanation may lack concreteness. In view of this, as a specific applied embodiment section 13.3 explains a control method of memory and obliteration in a pyramidal cell. FIG. 70 provides a little more detailed illustration than FIG. 69. However, an actual activity in a life object is much more complicated, and therefore, the explanation even in this section is considerably simplified and roughened.

First of all, the description of Teiichi Furuichi: Noukagaku 5 Bunshi, saibou, sinapusu karamiru nou (University of Tokyo Press, 2008) P. 46, FIG. 3.2, and P. 219 to P. 224, is simplified, and the following explains long-term potentiation and long-term depression mechanisms about memory in a pyramidal cell, which has been known currently. As shown in FIG. 70, there is a synaptic cleft 731 between a presynaptic cell and a postsynaptic cell. In a part of a pyramidal cell which corresponds to the postsynaptic cell and faces the synaptic cleft 731, a spine 735 having a dendrite surface is formed. Various types of receptors exist on this spine as the receptor A701, but FIG. 70 only deals with a metabotropic glutamate (mGluR) receptor 741, an N-methyl-D-aspartate-type ionotropic glutamate (NMDA) receptor 742, and α-amino-3-hydroxy-5-methyl-4-issoxazol propionate (AMPA) receptor 743.

The AMPA receptor 743 is one type of the transmitter-dependent ion channel described in section 12.5, and when Glutamic acid released from the presynaptic cell to the synaptic cleft 731 forms a bond 734 to this, a gate 615 thereof is opened to cause inflow 752 of $Na^+$ ions towards a cytoplasm 612, thereby promoting depolarization in a neuron. Accordingly, it is said that a long-term potentiation of the pyramidal cell about memory is related to an increase of the AMPA receptor 743 in the spine 735, while the long-term depression is related to a decrease of the AMPA receptor 743. On the other hand, when a glutamic acid bond 733 to the MNDA receptor 742 is formed at the same time as the occurrence of the depolarization by the AMPA receptor 743, $Mg^{2+}$ ions which block the inside of the MNDA receptor 742 come off toward the side of the synaptic cleft 731 and the gate 615 is opened, thereby causing inflow 751 of $Ca^{2+}$ ions towards the cytoplasm 612 (in the neuron).

In a case 748 where a concentration of the $Ca^{2+}$ ions to flow is low, activation 761 of Calcineurin occurs to cause dephosphorylation 762 of an inhibiter 1. This consequently causes activation 763 of a protein phosphatase enzyme 1 from a suppressed state, and an uptake reaction 764 of the AMPA receptor from the spine 735 occurs. This uptake reaction 764 of the AMPA receptor from the spine 735 is involved with a long-term obliteration action 772 in the pyramidal cell.

On the other hand, in a case 747 where the concentration of $Ca^{2+}$ ions to flow is high, generation 755 of mRNA is caused by gene expression 754 in a cell nucleus triggered by phosphorylation 753 of CaM-kinase. Here, since Calcineurin originally has a high reaction sensitivity to $Ca^{2+}$ ions, a chain reaction leading to the activation 763 of the protein phosphatase enzyme 1 is caused even by slight inflow 751 of $Ca^{2+}$ ions. However, the frequency of this chain reaction is relatively low. On the other hand, a reaction sensitivity of the phosphorylation 753 of CaM-kinase to $Ca^{2+}$ ions is low, but once the reaction starts, the reaction frequency is high, and therefore, the signal transmission pathway seems to vary depending on the differences 747/748 in the concentration of $Ca^{2+}$ ions.

Subsequently, when a glutamic acid bond 732 to the mGluR receptor 741 is formed, activation 758 of a protein kinase B is caused through a phosphorylation cascade 758, triggered by generation 750 of PI(3, 4, 5)P$_3$. Due to the activation 758 of this protein kinase, translation 756 of mRNA starts, and an AMPA receptor 743 is generated. Then, an insertion 757 of the generated AMPA receptor 743 onto the spine 735 is performed, which contributes to the memory action 771 of the pyramidal cell.

In regard to the well-known mechanism model, in this exemplary embodiment, the electromagnetic wave 608 for detection/control of life activity is locally projected using the life activity control device shown in FIG. 66 and an electric field is applied from the outside (by high-voltage application), so as to perform control for the long-term memory or the long-term obliteration. As a control object 724 in the present exemplary embodiment, the NMDA receptor 742 is subjected to the operation from the outside in common with the mechanism models of the memory action and the obliteration action shown in FIG. 70. In regard to the long-term memory control of the present exemplary embodiment, the activation 761 of Calcineurin is obstructed.

On the other hand, in regard to the long-term obliteration control of the present exemplary embodiment, a phosphorylation process is prevented to stop any of phosphorylation 753 of CaM-kinase, phosphorylation cascade 758, and activation 759 of protein kinase B. At first, a specific long-term memory control method is shown in FIG. 71(a). For the convenience of explanation, the method is shown in order from S81 to S84, but alternatively, S81 to S84 may be performed at the same time. Initially, in a formation process S81 of an external electric field, a high voltage is applied between the electrode terminals (plates) 601-1 and 601-2 by driving the power supply 602 for high voltage and high frequency generation shown in FIG. 66, so as to apply an external electric field to a part 600 of an organism to be detected/controlled (the head or the like of an examinee). This causes the NMDA receptor 74 in FIG. 70 to be in a depolarized state. Subsequently, in an input S82 of memory information, the examinee watches a video, listens to voice, or reads texts, so that information to be memorized is input to the examinee. This operation temporarily activates a part of a neural network in the examinee. As a result, glutamic acid is released in a synaptic cleft 731 related to long-term memory, and the glutamic acid forms a bond 733 to the NMDA receptor 742. In a case where a sufficiently large electric field is applied to the NMDA receptor 74, detachment of $Mg^{2+}$ ions can be caused in all NMDA receptors 74 in the neuron related to the memory information input as above.

However, in some cases, glutamic acid may be released even in paths except the neuron related to the memory at the time of the input S82 of the memory information. In view of this, in this exemplary embodiment, in order to perform the long-term memory control only in a necessary neuron to a minimum, inflow 751 of $Ca^+$ ions is caused only in a specific NMDA receptor 74 by combining the formation of the external electric field and the illumination of the electromagnetic wave 608 for detection/control of life activity. That is, a value of the high voltage to be applied between the electrode terminals (plates) 601-1 and 601-2 is restrained to be low so as not to cause the detachment of $Mg^{2+}$ ions in the NMDA receptor 74 even if the formation S81 of the external electric field and the input S82 of the memory information occur at the same time. While this state is maintained, only an intended neuron to be subjected to the long-term memory control is selectively illuminated with the electromagnetic wave 608 for detection/control of life activity (FIG. 66). As described in section 12.3, 12.4, or 12.5 with reference to FIG. 68(d), it is necessary for the electromagnetic wave 608 for detection/control of life activity to include an electromagnetic wave (near infrared light) having an appropriate wavelength to cause a reduction S83 in the mechanical strength of an α helix in the NMDA receptor 742. As a subsequent step, obstruction S84 to the dephosphorylation path is performed so that the memory control can be stably performed even in a case 748 where the amount of the inflow 751 of $Ca^{2+}$ is small at this time. In the obstruction S84, the electromagnetic wave 608 for detection/control of life activity including a wavelength light beam described later in sections 13.5 and 13.6 is projected to obstruct the activation 761 of Calcineurin shown in FIG. 70.

Here, only one light emitting component 111 is described in the life activity control device shown in the FIG. 66, but the life activity control device corresponding to the present exemplary embodiment has a plurality of light emitting components 111, so that a single detected point 30 for life activity can be illuminated with a plurality of light beams at the same time. Further, since a glutamic acid bond 732 is formed even in the mGluR receptor 741 related to an intended neuron to be subjected to memory control by the above input S82 of the memory information, translation 756 of mRNA related to the AMPA receptor 743 in FIG. 70 is performed. After long-term memory is formed in such a manner, an experiment of confirmation S85 is performed on the examinee. Then, if the long-term memory is not formed, a setting condition is changed, and the operations from S81 to S85 are repeated.

Next will be shown a specific long-term obliteration control method in FIG. 71(b). For the convenience of explanation, the method is shown in order from S91 to S94, but alternatively, S91 to S94 may be performed at the same time. As shown in FIG. 70, it is necessary to cause inflow 751 of $Ca^+$ ions in a pyramidal cell so as to cause an oblivion action 772 in the pyramidal cell. In view of this, in a formation process S91 of an external electric field, which is a first step, a high voltage is applied between the electrode terminals (plates) 601-1 and 601-2 by driving the power supply 602 for high voltage and high frequency generation shown in FIG. 66, so as to apply an external electric field to a part 600 of an organism to be detected/controlled (the head or the like of an examinee). This causes the NMDA receptor 74 in FIG. 70 to be slightly in a depolarized state.

In a subsequent step of recollection S92 of memory information, the examinee recalls a memory which the examinee wants to delete (or forget for a long term) again. Hereby, a neuron on a neural transmission pathway related to the memory which the examinee wants to forget is activated. In a case where the intensity of the external electric field to be applied in the formation process S91 of the external electric field is strong, a sufficiently large depolarization potential will be provided to the NMDA receptor 74. Therefore, if the recollection S92 of memory information is performed in this state, a glutamic acid bond 733 (FIG. 70) is formed in the NMDA receptor 742 in the neuron related to the recollection of memory information in a neuronal information transmission network, thereby resulting in that the inflow 751 of $Ca^{2+}$ ions is caused by the detachment of $Mg^{2+}$ ions in the NMDA receptor 742. If the inflow 751 of $Ca^{2+}$ ions into all pyramidal cells related to the recollection S92 of memory information is caused, a risk of erasing even important memories which the examinee should not forget rises, in particular.

Accordingly, in order to prevent the oblivion control with respect to an unnecessary part (a signal transmission pathway which should not be forgotten), the intensity of the external electric field to be applied in the formation process S91 of the external electric field is set weak, in this applied embodiment. Then, the NMDA receptor 74 is controlled not to be in a largely depolarized state only in this formation process S91 of the external electric field, so that the inflow 751 of $Ca^{2+}$ ions due to the detachment of $Mg^{2+}$ ions in the NMDA receptor 742 is prevented even if the recollection S92 of memory information occurs. In this state, only an intended neuron to be subjected to the long-term obliteration control is selectively illuminated with the electromagnetic wave 608 for detection/control of life activity shown in FIG. 66.

As a result, as described in section 12.3, 12.4, or 12.5 with reference to FIG. 68(*d*), reduction S93 of the mechanical strength of an α helix is performed only on a specific NMDA receptor 742. As such, the inflow 751 of $Ca^{2+}$ ions (FIG. 70) is caused only in a specific neuron. In order to perform the obliteration control even in a case 747 where a concentration of $Ca^{2+}$ ions thus flowed at this time is high, the electromagnetic wave 608 for detection/control of life activity including a wavelength which will be described later in sections 13.4 and 13.6 (FIG. 66) is projected at the same time. This hereby causes the obstruction S94 of a phosphorylation path (any path of the phosphorylation cascade 758, the activation 759 of protein kinase B, and the phosphorylation 753 of CaM-kinase in FIG. 70), and the long-term obliteration control is performed stably.

As described above, the life activity control device (see FIG. 66) to be used in this applied embodiment is provided with two types of light emitting components 111, i.e., a light emitting component 111 of an electromagnetic wave 608 for detection/control of life activity including a wavelength for use in the reduction S93 of the mechanical strength of the α helix in the NMDA receptor 742, and a light emitting component 111 of an electromagnetic wave 608 for detection/control of life activity including a wavelength for use in the obstruction S94 to the phosphorylation path, so that these electromagnetic waves can be condensed on a single detected point 30 for life activity in an overlapping manner. Then, at a stage where a series of the operations from S91 to S94 for the obliteration control are completed, an obliteration state is checked as shown in S95. This operation uses oral examination to the examinee. If the obliteration control is not stably performed at this stage, the control from S91 to S95 is performed again.

Particularly for "students troubled with poor memory," "elderly people who feel a failure of memory," or "people who are bothered by getting stuck with some problems," for example, the technique of "controlling a memory from the outside" may seem to be the good news. Also, a "mental inclination" to tend to interpret anything pessimistically/positively can be expected to have some relevance with selection inclination of a signal transmission pathway in a neural network. Accordingly, the memory control could cause an influence on the mental inclination. It is preferable that this technique be used for treatment and rehabilitation of illness, and it is not preferable that "a physically unimpaired person depend on this technique easily." There is danger to advance the physically unimpaired person to the way to a corruption if he/she excessively depends on this technique routinely. In fact, everyone possesses an "ability to control a memory" which far exceeds this technique. Therefore, the inventor of this technique hopes that everyone utilizes his/her natural abilities rather than depending on this technique. A specific method thereof will be described below with reference to FIG. 70. However, FIG. 70 only extracts a part of the activity of a pyramidal cell. There exists a much more complicated signal transmission pathway in a practical sense. Further, there are various neurons in the brain besides the pyramidal cell, and in view of this, it should be noted that the following methods are merely reference information.

<Method to Reinforce Memory>

To memorize repeatedly

Repetition gradually increases the amounts of AMPA receptors 743 on the spine 735.

To memorize in connected with other contents

Like an association memory technique, memorize intended information to remember together with information related to the information (e.g., ambient environment at the time to memorize the information, factor information of the intended information, a play on words). Due to a conscious stimulation of the related information, Glutamic acid is released to another synaptic cleft 731 in the same neuron to cause depolarization, which may cause $Mg^{2+}$ ions in the NMDA receptor 742 to easily detach therefrom. A method in which intended information to remember is converted into an image and the information is memorized with the image can be expected to yield a similar effect.

To handle information with interest and impression

By taking an interest or being impressed, Glutamic acid is released to another synaptic cleft 731 in the same neuron to cause partial depolarization, and its depolarization potential is propagated. As a result, a membrane potential around the NMDA receptor 742 related to the intended information to remember nears the depolarization potential, which may cause $Mg^{2+}$ ions in the NMDA receptor 742 to easily detach therefrom.

To concentrate to memorize/Not to try to remember unwillingly

When an "attention is distracted" at the moment of remembering, a decrease 748 of the inflow 751 of $Ca^{2+}$ ions occurs, which may cause a danger that the oblivion action 772 may work conversely. Further, when the "attention is directed to a feeling of repulsion" by having the feeling of repulsion with respect to the memory operation itself (by trying to remember unwillingly), the oblivion action 772 may work.

To do something different only after checking a memorized content once to be retained If an attention is distracted just after starting some action, an object of the action may be forgotten in some cases. This is presumably because "a neural circuit for being conscious of an object of an action" is switched to "a neural circuit for controlling an action" and the oblivion action 772 works on the consciousness of the object of the action. A little time to "check a memorized content once" causes an increase 747 of the inflow 751 of $Ca^{2+}$ ions, and the memory action 771 works.

Not to distract the attention even when a memorized content is recalled

A state at the time when information memorized in the past is recalled is important. When another piece of information pops out at the moment when a memorized content is recalled, an intraneuronal signal transmission circuit is switched into another one, which causes the decrease 748 of the inflow 751 of $Ca^{2+}$ ions. This situation may accordingly cause the oblivion action 772 to work, which may become a trigger to forget the content, adversely. In view of this, when the memorized content is recalled, "the memory thus recalled should be checked," so that the memory action 771 is reinforced, and the oblivion action 772 is hard to occur.
<Method for Deleting a Memory Desired to be Forgotten>

To distract the attention on purpose at the moment when a memory desired to be forgotten comes into the head A method to distract the attention may be, for example: "to think about other things strongly," "to start irrelevant actions," or "to watch or listen to irrelevant information (to watch TV)." If a neural circuit is switched instantly before the increase 747 of the inflow 751 of $Ca^{2+}$ ions, the oblivion action 772 works.

Not to direct the attention to a memory desired to be forgotten when it comes into the head A consciousness to pay attention to a memory desired to be forgotten or to try to "forcibly forget" the memory works as the memory action 771.

13.4) Reaction Process of Phosphoenzyme (Kinase)

On explaining a center wavelength of an absorption band originally occurring in a process to cause an intracellular phosphorylation process which is in one form of the life activity, a mechanism model of the phosphorylation process is described first with reference to FIG. 72. There are various phosphoenzymes (kinase) which work as catalysis in the phosphorylation process in a cell, and they have slightly different mechanisms of the phosphorylation process. Here, a mechanism model of a phosphorylation process of PKA (Protein Kinase A) is described as a typical example, and common characteristics will be extracted therefrom for different phosphoenzymes (kinase). A part of a conformation of PKA and a part of phosphorylation actions described in J. A. Adams: Chemical Reviews vol. 101 (2001) p. 2274-p. 2282 are extracted, and a further simplified view thereof is shown in FIG. 72. When the hydrolysis reaction of ATP as described in section 11.3 with reference to FIG. 58 is compared with the phosphorylation process, they are in common in that:

a bond between a γ phosphoryl and a β phosphoryl is cleaved after the reaction. However, they are basically different in that:

the γ phosphoryl after the reaction bonds to a part of an activated water molecule in the hydrolysis reaction of ATP, whereas the γ phosphoryl bonds to a part of an activated hydroxyl group on a substrate in the phosphorylation process.

Further, a magnesium ion $Mg^{2+}$ relates to the activation of the water molecule in the hydrolysis reaction of ATP, whereas a carboxyl group in the phosphoenzyme (kinase) constituted by proteins is involved with the activation of the hydroxyl group in the phosphorylation process. More specifically, an oxygen atom O12- in a carboxyl group which is a part of a residue of Aspartate Asp166 in FIG. 72(b) is hydrogen-bonded to a hydrogen atom H1 in a hydroxyl group belonging to a part of the substrate. Meanwhile, in comparison with the mechanism model of the hydrolysis reaction of ATP, it seems that "the activation of the hydroxyl group" is essential for stabilization of the phosphorylation process. Accordingly, even in phosphorylation processes by most of the other kinases (phosphoenzymes) except PKA, it is estimated that a hydroxyl group to be phosphorylated is activated in advance, in connection with a carboxyl group. Accordingly, in the present exemplary embodiment or the applied embodiment, as will be described later in section 13.6, an absorption band corresponding to a hydrogen bond between a hydroxyl group and a carboxyl group, which absorption band occurs temporarily in a phosphorylation process, is used for detection/measurement or control of a life activity (the phosphorylation process in this case).

Further, a common characteristic between the hydrolysis reaction of ATP and the phosphorylation process is that "a magnesium ion $Mg^{2+}$ and a residue of Lysine relate to the reaction." In a water environment (about pH 7) in a life object, a γ phosphoryl in an ATP state (having a phosphorus atom P1 in its center) has a negative electric charge of "−2" and a β phosphoryl (having a phosphorus atom P2 in its center) has a negative electric charge of "−1." Accordingly, in order to stabilize the phosphorylation process, "electric neutralization by a metal ion or a residue of amino acid having positive electric charge" is required.

In the meantime, as described in section 11.3, it is said that among three types of amino acids which can have positive electric charge, Histidine has a very small amount of positive electric charge in a water environment (about pH 7) in a life object. Accordingly, it is very likely that a residue of Lysine or a residue of Arginine is involved with the phosphorylation process. In a case where they are involved with this reaction, it is highly likely that a part of the residue of Lysine or the residue of Arginine (a hydrogen atom placed at an outermost side) is hydrogen-bonded to an oxygen atom in ATP. In view of this, in the present exemplary embodiment or the applied embodiment, an absorption band occurring due to the hydrogen bonding between a part of the residue of Lysine/residue of Arginine and the oxygen atom in ATP can be also used for detection/measurement or control of a life activity (the phosphorylation process in this case). In the phosphorylation process according to PKA shown in FIG. 72, in particular, an oxygen atom $O4^-$ in the γ phosphoryl is hydrogen bonded to a hydrogen atom H2 in the residue of Lysine Lys168.

A large feature of the phosphorylation process as compared to the hydrolysis reaction of ATP is that "a magnesium ion $Mg^{2+}$ does not activate a water molecule." If an activated water molecule exists around ATP, a γ phosphoryl just detached from the bonding to a β phosphoryl bonds to this water molecule, and there will be no bond binding to a hydroxyl group of a part of the substrate. In the meantime, a magnesium ion $Mg^{2+}$ tends to interact with four atoms (relatively charged negatively) around it underwater. Accordingly, if four atoms except constituent atoms of the water molecule are arranged around the magnesium ion $Mg1^{2+}$, the magnesium ion $Mg1^{2+}$ cannot activate the water molecule. In view of this, in the mechanism model of the phosphorylation process shown in FIG. 72, the magnesium ion $Mg1^{2+}$ interacts with two oxygen atoms $O3^-$ and $O8^-$ belonging to a γ/β phosphoryl arranged around the magnesium ion $Mg1^{2+}$ and two oxygen atoms $O9^-$ and O10 belonging a residue of Aspartate Asp184.

As shown in FIG. 72(a), when ATP bonds to an active site in PKA, it is considered that an oxygen atom $O4^-$ in the γ phosphoryl (having a phosphorus atom P1 in its center) of ATP is hydrogen-bonded to a hydrogen atom H2 in a residue of Lysine Lys168. As explained in section 4.6.3 with reference to FIG. 15, an electron existence probability (electron cloud) moves between atoms involved with a hydrogen bond via a hydrogen atom located midway. That is, in the example of FIG. 72(a), since a nitrogen atom $N1^+$ in the residue of Lysine Lys168 is charged with positive electricity, an electron existence probability (electron cloud) around an oxygen atom $O4^-$ moves in a direction α via an intermediate hydrogen atom H2. As a result, in order to make up for a decrease in the electron existence probability (electron cloud) in a peripheral area, the oxygen atom O4⁻ takes an electron existence probability (electron cloud) from around a phosphorus atom P1 as shown by β.

On the other hand, since the magnesium ion $Mg1^{2+}$ "has a positive electric charge of +2" (=an electron existence probability is overwhelmingly insufficient in its periphery), an electron existence probability (electron cloud) of a bonding orbital between the phosphorus atom P1 and an oxygen atom O2 drifts toward a direction of the magnesium ion $Mg1^{2+}$ (γ and δ) via oxygen atoms O3⁻ and O8⁻ forming an ionic bond. However, only by this movement of the electron cloud, a considerable amount of the electron existence probability (electron cloud) of the bonding orbital between the phosphorus atom P1 and the oxygen atom O2 still remains, and therefore, the phosphoryl bond between γ and β is not cleaved. In view of this, in order to promote the phosphorylation process (cleavage of the phosphoryl bonding between γ and β), PKA further uses a magnesium ion $Mg2^{2+}$.

Meanwhile, the magnesium ion $Mg2^{2+}$ interacts with not only an oxygen atom O5 in the γ phosphoryl and an oxygen atom O1 of a residue of Asparagine Asn171 shown in FIG. 72, but also an oxygen atom O9⁻ in a residue of Aspartate Asp184 and an oxygen atom in a residue of an α phosphoryl, which has not been explained here. This magnesium ion $Mg2^{2+}$ takes an electron existence probability (electron cloud) of a bonding orbital between the phosphorus atom P1 and the oxygen atom O2 via the oxygen atom O5, as shown by ε. As a result, the electron existence probability of the bonding orbital between the phosphorus atom P1 and the oxygen atom O2 changes from a state in FIG. 57(a) to a state in FIG. 57(b), so that a distance between the phosphorus atom P1 and the oxygen atom O2 is broadened. Then, as shown in FIG. 72, the γ phosphoryl nears a substrate 780 to be phosphorylated.

On the other hand, as described above, the hydrogen atom H1 in the hydroxyl group of the substrate 780 is hydrogen-bonded to the oxygen atom O12⁻ in Aspartate Asp166 in advance. In the meantime, since the oxygen atom O12⁻ in Aspartate Asp166 is charged with negative electricity in the water environment (about pH 7) in the life object (a surplus electron cloud density is located around the oxygen atom O12⁻), the surplus electron cloud moves toward a side of the oxygen atom O11 via the hydrogen atom H1 involved with the hydrogen bond, as shown by ζ.

As a result, the hydroxyl group in the substrate 780 is "activated" and the surplus electron cloud is located around this oxygen atom O11. On the other hand, as described above, since the electron existence probability (electron cloud) largely decreases around the phosphorus atom P1, the surplus electron cloud located around this oxygen atom O11 is drawn toward the phosphorus atom P1 (in a direction η). This electron existence probability works as a bonding orbital between the oxygen atom O1 and the phosphorus atom P1, and a phosphorylation process which causes the γ phosphoryl to bond to the substrate 780 occurs. Further, triggered by this, the electron existence probability existing between the phosphorus atom P1 and the oxygen atom O2 changes from the state in FIG. 57(b) into an antibonding orbital as shown in FIG. 57(c), the bonding between the γ phosphoryl and the β phosphoryl is cleaved.

A series of steps in the above phosphorylation process can be summarized as shown in FIG. 72(c). That is, from the viewpoint of the phosphorus atom P1, a bond binding to the oxygen atom O2 moves to a bond at a side of the substrate 780 (an oxygen atom O11 therein). On the other hand, from the viewpoint of the hydrogen atom H1 in the hydroxyl group of the substrate 780, a covalent bond to the oxygen atom 11 which has constituted a hydroxyl group together with the hydrogen atom H1 is changed to a hydrogen bond to the oxygen atom O12⁻ of the residue of Aspartate Asp166.

When the phosphorylation process of PKA occurs, it is found from FIG. 72 that a "O11-H1-O12⁻ hydrogen bond" formed between the oxygen atom O12⁻ in Aspartate Asp166 and the hydroxyl group at the side of the substrate 780 and a "N1⁺-H2-O4⁻ hydrogen bond" formed between a part of the residue of Lysine Lys168 and the oxygen atom O4⁻ in the γ phosphoryl occur temporarily. Accordingly, by detecting absorption changes in light (electromagnetic wave) at respective center wavelengths of absorption bands occurring at the time when the respective hydrogen bonds occur, it is possible to estimate what kind of life activity (phosphorylation process) occurs. The present exemplary embodiment is not limited to the phosphorylation process of PKA, and life activities in other cells (or related to a whole cell) are also detectable. For example, as another configuration of the phosphorylation process which is different from PKA, there is an activation of $Ca^{2+}$/calmodulin-dependent protein kinase. That is, when a $Ca^{2+}$ ion flows into a cell, calmodulin bonding to the $Ca^{2+}$ ion bonds to the $Ca^{2+}$/calmodulin-dependent protein kinase (hereinafter, referred to as CaM-kinase), in response to the intracellular signal transfer cascade A703 in FIG. 69.

In the meantime, this CaM-kinase has an autophosphorylation effect and phosphorylates the CaM-kinase itself to be activated. This autophosphorylation process corresponds to an initial stage of the phosphorylation process cascade 711 in FIG. 69. At a subsequent stage of the phosphorylation process cascade 711, this activated CaM-kinase phosphorylates a gene regulatory protein such as CREB (Cyclic AMP response element binding protein). Then, this gene regulatory protein thus activated by phosphorylation works to start gene expression 721 in FIG. 69.

In the meantime, it is said that the calmodulin is closely related with Troponin C described in section 11.1. It is said that when a $Ca^{2+}$ ion bonds to the calmodulin, an ionic bond is formed between a residue of Glutamate in this calmodulin and a residue of Aspartate. Accordingly, from the content explained in section 11.1 and [a] of section 11.4, it is expected that when a $Ca^{2+}$ ion bonds to calmodulin, a change (rapid decrease) of relative light absorbance of an absorption band corresponding to the symmetrically telescopic vibration mode of the carboxyl group occurs. On the other hand, as described in the first half of this chapter, since the activation of a hydroxyl group in the substrate is essential for the phosphorylation process, an occurrence of an absorption band corresponding to a hydrogen bond between a hydroxyl group and a carboxyl group is also detected. Accordingly, in a case where [1] absorption in light (electromagnetic wave) at a wavelength of the absorption band corresponding to the hydrogen bond between a hydroxyl group and a carboxyl group increases, and [2] absorption in light (electromagnetic wave) at a wavelength of the absorption band corresponding to the symmetrically telescopic vibration mode of the carboxyl group decreases, an occurrence of the life activity related to the "calmodulin→CaM-kinase" is detected.

13.5) Reaction Process of Calcineurin

As shown in FIG. 70, it is said that the activation 761 of Calcineurin is involved with the oblivion action 772 in the pyramidal cell. Section 13.5 describes a wavelength range that can be detected as a center wavelength of an absorption band newly occurring during the activation 761 of Calcineurin. F. Rusnak and P. Merts: Physiol. Rev. vol. 80 (2000) p. 1483-p. 1521 describes a conformation of Calcineurin and a mechanism model of a dephosphorylation process in an active site thereof. Here, it is shown that in the dephosphorylation process, a residue of Arginine, which is a part of Calcineurin, is hydrogen-bonded to an oxygen atom included in a phosphoryl. On the other hand, as described in section 11.4, the value of the center wavelength of the corresponding absorption band varies depending on whether a hydrogen-bonding partner to an oxygen atom included in the phosphoryl is a residue of Lysine or a residue of Arginine. In view of this, in a case where the value of the center wavelength of the absorption band occurring during the life activity is detected, if a hydrogen bond to the residue of Arginine is detected, the oblivion action 772 due to the activation 761 of Calcineurin may be caused.

13.6) Characteristics of Detection and Control of Intracellular Life Activity

As shown in FIG. 72, when a phosphoenzyme (kinase) is activated to cause a phosphorylation process, it is estimated that a hydroxyl group of the substrate 780 is hydrogen bonded to a carboxyl group. In the meantime, this "O11-H1-O12$^-$ hydrogen bond" is "a hydrogen bond between oxygen atoms across a hydrogen atom," which is locally similar to a structure of the hydrogen bond between water molecules. However, while molecules forming the hydrogen bond between the water molecules are water molecules, molecules forming the hydrogen bond in the phosphorylation process are different from them (i.e., a hydroxyl group and a carboxyl group). In view of this, as explained in section 11.4 with reference to 59 and 60, an absorption band corresponding to the phosphorylation process occurs in a wave range different from that for the hydrogen bond between water molecules. This absorption band resembles an absorption band occurring at the time when "intermolecular hydrogen bonding in associated —OH alcohol" in Table 7 has occurred. As described in sections 4.7 and 11.4, when a variation range considering the difference in a detection value caused by measurement errors or measurement environments is estimated as ±15%, the variation ranges are as follows: 1.04×(1−0.15)=0.88, 1.05×(1+0.15)=1.21, 1.50×(1−0.15)=1.28, and 1.60×(1+0.15)=1.84, that is, a wavelength range of an absorption band corresponding to the 2nd overtone is from 0.88 μm to 1.21 μm, and a wavelength range of an absorption band corresponding to the 1st overtone is from 1.28 μm to 1.84 μm.

With respect to the ranges thus obtained, remaining ranges obtained by excluding the wavelength ranges greatly absorbed by the water molecule shown in FIG. 56 are as follows:

the wavelength range of an absorption band corresponding to the 2nd overtone is from 0.88 μm to 0.94 μm and 1.03 μm to 1.21 μm; and the wavelength range of an absorption band corresponding to the 2nd overtone is from 1.28 μm to 1.39 μm and 1.52 μm to 1.84 μm.

A difference between 1.21 μm and 1.28 μm is very small, so that these ranges can be connected as one wavelength range. In view of this, as shown in FIG. 56, a wavelength range of an absorption band which can be detected when a hydroxyl group is hydrogen-bonded to a carboxyl group is as follows:

a range from 0.88 μm to 0.94 μm, a range from 1.03 μm to 1.39 μm, and a range from 1.52 μm to 1.84 μm.

However, the ranges show only a detection range of the nth overtone to the last. Further, an absorption band corresponding to combinations is also included in the near-infrared region. In view of this, when the wavelength range to detect the combinations is also taken into account, the first, second, third, fourth, and fifth wavelength ranges I to V with less absorption by water shown in FIG. 56 can be taken as target ranges. Alternatively, if an absorption amount in the absorption band for the combinations is large and is not affected by the absorption by water very much, a desirable wavelength range will be in a range from 0.84 μm (or 0.875 μm) to 2.50 μm as shown in section 4.7.

On the other hand, in the phosphorylation process related to PKA, a "N1$^+$-H2-O4$^-$ hydrogen bond" temporarily occurs between an oxygen atom in the γ phosphoryl and a part of the residue of Lysine, as explained in section 13.4. This type of hydrogen bond resembles a vibration mode of the "intermolecular hydrogen bonding of primary amide —CONH$_2$" in Table 7. Accordingly, similarly to the explanation in section 11.4, a range where a center wavelength of an absorption band occurring in this case is detected will be as follows:

a wavelength range of an absorption band corresponding to the 2nd overtone is from 1.03 μm to 1.25 μm; and a wavelength range of an absorption band corresponding to the 1st overtone is from 1.52 μm to 1.86 μm.

However, when a center wavelength of an absorption band corresponding to combinations is also taken into account, a desirable wavelength range will be in a range from 0.84 μm (or 0.875 μm) to 2.50 μm as shown in section 4.7.

On the other hand, it is suggested that when a dephosphorylation process due to Calcineurin occurs, a hydrogen bond is formed between an oxygen atom in a phosphoryl and a part of a residue of Arginine. As described in section 11.4 with reference to FIGS. 59 and 60, the value of a center wavelength of an absorption band to occur varies depending on whether a hydrogen-bonding partner is a residue of Lysine or a residue of Arginine. However, when a "range where a center wavelength of an absorption band can be detected" is taken into account, their ranges are substantially identical with each other, and correspond to a vibration mode of the "intermolecular hydrogen bonding of primary amide —CONH$_2$" in Table 7. In view of this, similarly to the above, the range where the center wavelength of the absorption band to occur at the time when the dephosphorylation process due to Calcineurin occurs can be detected is as follows:

a wavelength range of an absorption band corresponding to the 2nd overtone is from 1.03 μm to 1.25 μm; and a wavelength range of an absorption band corresponding to the 1st overtone is from 1.52 μm to 1.86 μm.

However, when a center wavelength of an absorption band corresponding to combinations is also taken into account, a desirable wavelength range will be in a range from 0.84 μm (0.875 μm) to 2.50 μm.

A technical subject of the present exemplary embodiment or the applied embodiment is to perform "detection or measurement of life activity by means of illumination of an electromagnetic wave including a predetermined wavelength." In view of this, the present exemplary embodiment or the applied embodiment is not limited to the detection of an absorption change of an electromagnetic wave related to an absorption band occurring in response to a life activity, and other methods may be usable. As another applied embodiment, for example, the life activity may be detected or measured by use of fMRI. That is, in response to a phosphorylation process, a hydroxyl group of the substrate 780 is hydrogen-bonded to a carboxyl group, thereby temporarily forming an "O11-H1-O12$^-$ hydrogen bond." An electron existence probability (an electron cloud density) around a hydrogen atom H1 at a center of this bond at this time is different from an electron existence probability around a hydrogen atom of a hydrogen bond formed between water molecules.

In the meantime, since the electronic existence probability around the hydrogen atom H1 has a magnetic shielding effect with respect to the external magnetic field in the Nuclear Magnetic Resonance (see chapter 5), a unique "chemical shift value" corresponding to the phosphorylation process is detected. Further, when a dephosphorylation process occurs, a maximum absorption occurs at a unique chemical shift value, similarly. By measuring an absorption change at this unique chemical shift value thus detected, the phosphorylation process or the dephosphorylation process can be detected or measured.

The explanation of section 13.2 with reference to FIG. 69 shows a method in which some activity of the phosphorylation process cascade 711 is obstructed by illumination of an electromagnetic wave (light) to decrease the efficiency of the phosphorylation process, or a method in which the efficiency of the dephosphorylation process 712 is decreased to activate the phosphorylation process cascade 711. Further, as a specific example thereof, section 13.3 has described a method to promote the memory action 771 or the oblivion action 772 in a pyramidal cell by similar control. Here, a more detailed mechanism about the control method in the present exemplary embodiment or the applied embodiment is described as below.

In order to stably cause a process such as the phosphorylation process cascade 711 in FIG. 69, or the phosphorylation cascade 758 or the phosphorylation 753 of CaM-kinase in FIG. 70, the "activation of a hydroxyl group in the substrate 780" is essential as described in section 13.4. Further, the activation requires hydrogen bonding between the hydroxyl group and a carboxyl group. Even if a slight amount of an electromagnetic wave (light) is projected to detect an "absorption band occurring at the time when the hydroxyl group is hydrogen-bonded to the carboxyl group," the phosphorylation process is hardly affected. However, if a large amount of an electromagnetic wave (light) corresponding to the above absorption band and included in the aforementioned wavelength ranges:

a range from 0.88 µm (or 0.875 µm) to 0.94 µm;
a range from 1.03 µm to 1.39 µm; and
a range from 1.52 µm to 1.84 µm, are projected, all vibration modes in hydrogen bonds between hydroxyl groups and carboxyl groups are activated. Since the vibration modes in this excited state have high energy, most of the hydrogen bonds are cleaved triggered by that. As a result, the "activation of the hydroxyl group in the substrate 780" is obstructed, so that the efficiency of the phosphorylation process can be largely decreased. In view of this, by illumination of a large amount of the electromagnetic wave (light) having a wavelength corresponding to the absorption band occurring when the hydroxyl group is hydrogen-bonded to the carboxyl group, the phosphorylation process cascade 711 (FIG. 69) is obstructed, so that the activity level of a cell can be decreased, or the memory action 771 (FIG. 70) is obstructed, so that the oblivion action 772 can be accelerated.

Meanwhile, in the present exemplary embodiment or the applied embodiment, the catalytic efficiency of Calcineurin of a dephosphorylation enzyme can be decreased. As described previously, when a dephosphorylation process due to Calsineurin occurs, it is suggested that a hydrogen bond is formed between an oxygen atom in a phosphoryl and a part of a residue of Arginine. Even if a small amount of an electromagnetic wave (light) is projected to detect presence of an absorption band associated with the hydrogen bond with which the residue of Arginine is involved, life activities are hardly affected.

However, if a large amount of an electromagnetic wave (light) having a center wavelength of an absorption band corresponding to the hydrogen bond with which the residue of Arginine is involved and included in the following wavelength ranges:

a wavelength range from 1.03 µm to 1.25 µm, or
a wavelength range from 1.52 µm to 1.86 µm, most of the vibration modes in hydrogen bonds with which residues of Arginine are involved are changed into an excited state. Further, since the energy of the excited state is high, most of the hydrogen bonds with which residues of Arginine are involved are cleaved, and the dephosphorylation process due to Calsineurin is obstructed. As a result, when a large amount of the electromagnetic wave (light) including the above wavelength is projected, the following control can be performed: the dephosphorylation process 712 (FIG. 69) is obstructed, so that the phosphorylation process cascade 711 is accelerated to activate a cell; or the oblivion action 772 (FIG. 70) is obstructed, so that the memory action 771 is accelerated.

The above exemplary embodiment has explained a detection/measurement method or a control method of life activity by taking, as an example, the phosphorylation process and the dephosphorylation process with respect to intracellular life activities. However, the present exemplary embodiment or the applied embodiment is not limited to that, and is applicable to other detection/measurement methods and control methods of life activity performed using an electromagnetic wave (light) corresponding to an absorption band associated with an intracellular or extracellular life activity.

REFERENCE SIGNS LIST

1 . . . Neuron cell body,
2 . . . Axon,
3 . . . Numerous bouton (Synaptic knob),
4 . . . Signal detection area (Ending) of sensory neuron,
5 . . . Neuromuscular junction,
6 . . . Muscle cell,
7 . . . Central nervous system layer (Cerebral cortex layer),
8 . . . Nervous relay pathway layer (including thalamus, cerebellum, and reticular formation),
9 . . . Reflex pathway layer (Spinal reflex pathway layer),
11 . . . Voltage-gated $Na^+$ ion channel,
12 . . . Myelin sheath,
13 . . . Extracellular fluid,
14 . . . Axoplasm,
15 . . . Node of Ranvier,
16 . . . Signal transmission direction in axon,
17 . . . Pyramidal cell body,
18 . . . Stellate cell body,
19 . . . Glial cell,
20 . . . Membrane potential,
21 . . . Resting membrane potential,
22 . . . Depolarization potential,
23 . . . Action potential,
24 . . . Term of nerve impulse,
25 . . . During rest,
26 . . . Membrane potential changing of neuron,
27 . . . Potential changing of muscle fiber membrane,
28 . . . Capillary,
29 . . . Transmission path of oxygen molecule, 30 . . . Detected point for life activity,
31 . . . Objective lens,
32 . . . Detection lens,
33 . . . Optical path of detection light,
34 . . . Reflecting mirrors (galvanometer mirror),
35 . . . Pinhole,
36 . . . Photodetector,
37 . . . Grating,
38 . . . Photo detecting cell,
40 . . . Marked position on life-object surface,
41 . . . Life-object surface,
42 . . . Camera lens,
43 . . . Two-dimensional photodetector,
44 . . . Distance from surface points of an area where the detecting section for life activity is disposed,
45 . . . Surface points of an area where the detecting section for life activity is disposed,
46 . . . Position monitoring section regarding detected point for life activity,
47 . . . Reflection light amount of light having wavelength of 780 nm,
48 . . . Reflection light amount of light having wavelength of 830 nm,
51 . . . Two-dimensional liquid crystal shutter,
52 . . . Condensing lens,
53 . . . Grating for light distribution,
54 . . . Lateral one-dimensional alignment photo detecting cell,
55 . . . Longitudinal one-dimensional alignment photo detecting cell,
56 . . . Light transmission section in two-dimensional liquid crystal shutter,
57 . . . Imaging lens,
58 . . . Life activity detection signal,
60 . . . Color filter,
62 . . . Detection signal line output from front part of detecting circuit,
63 . . . Lenticular lenses,
71 . . . Two-dimensionally arranged cell array for detecting changes of Nuclear Magnetic Resonance property,
72 . . . Coil for magnetic field preparation,
73 . . . (Superconducting) magnet,
74 . . . Excitation coil,
75 . . . Part of organism to be detected (head or the like of examinee),
80 . . . One detection cell for detecting changes of Nuclear Magnetic Resonance property,
81 . . . Power line and ground line,
82 . . . Transmission line of system clock+time stamp signal,
83 . . . Output line for life activity detection signal,
84 . . . Detecting coil,
85 . . . Front part of life activity detection circuit,
86 . . . Rear part of life activity detection circuit,
87 . . . Electromagnetic wave detecting cell (Photo detecting cell or Detecting coil),
101 . . . Detecting section for life activity,
102 . . . Light emitting section,
103 . . . Signal detecting section,
104 . . . System clock and modulation signal generating section,
105 . . . Transmitting section of life activity detection signal,
106 . . . Life activity detection signal,
111 . . . Light emitting component,
112 . . . Light modulator,
113 . . . Light modulator driver,
114 . . . Light emitting component driver,
115 . . . Illuminating light for life activity detection,
116 . . . Dichroic band pass filter or color filter,
117 . . . System clock generator,
118 . . . Modulation signal generator,
121 . . . Photo detecting section of life activity,
122 . . . Life activity detection circuit,
131 . . . Preamp,
132 . . . Band-pass filter,
133 . . . Modulating signal component extraction section (synchronous detection section),
134 . . . A/D converter,
135 . . . Memory section in front part,
136 . . . Signal processing operation section of front part,
137 . . . Signal transfer section to rear part,
141 . . . Signal transfer section to front part,
142 . . . Memory section in rear part,
143 . . . Signal processing operation section of rear part,
144 . . . Signal transfer section to transmitting section of life activity detection signal,
151 . . . Counter which generates incremental counter numbers for transmitting the life activity detection signal or describes a cumulative duration time to transmit the life activity detection signal,
152 . . . Variable key generator which provides variable keys depending on incremental counter numbers for transmitting the life activity detection signal or on a cumulative duration time to transmit the life activity detection signal,
153 . . . Variable shifting position generator which provides and outputs a variable shifting number in a M-serial cyclic circuit regarding incremental counter numbers for transmitting the life activity detection signal or regarding a cumulative duration time to transmit the life activity detection signal,
154 . . . Encrypter,
155 . . . Signal transfer section to life activity detection circuit,
156 . . . Memory section in transmitting section of life activity detection signal,
157 . . . Internet protocol forming section which sets the IP address,
158 . . . Network control section,
161 . . . Life activity detected area,
162 . . . Life activity level,
163 . . . Detection time,
171 . . . Evaluation factor,
172 . . . Equivalent level,
173 . . . Event,
178 . . . Content of process or operation to be performed,
201 . . . Internet layer,
202 . . . Mind connection layer,
211 . . . Mind communication provider,
212 . . . Mind service distributor,
213 . . . User,
216 . . . User-side drive system,
217 . . . User-side control system,
218 . . . Life detecting division,
220 . . . Life detecting section,
221 . . . Detection section of event information B,
222 . . . Signal/information multiplexing section,
223 . . . Internet network control section,
224 . . . Extraction section of event information A,
225 . . . Display screen control section,
226 . . . User input section,
227 . . . Interpretation section of life activity,
228 . . . Data base storage area,
229 . . . Maintenance processing section of mind connection layer, 230 . . . Technical support handling section to mind service distributor,
231 . . . Charging/profit-sharing processing section,
232 . . . Screen display/change setting section,
233 . . . Remote operation section to drive system,
234 . . . Direct-service content determination section,
241 . . . Detection of life activity,
242 . . . Event information B,
243 . . . Event information A,
244 . . . Service to be provided,
245 . . . Specific information provision (including information provision service),
247 . . . Direct service (mail/dispatch, and the like),
248 . . . Life activity detection signal with event information,
249 . . . Life activity information with event information,
250 . . . Display screen to user,
251 . . . Remote control to drive system,
252 . . . Payment for tolls,
253 . . . Profit sharing,
254 . . . User input information without detection signal,
301 . . . Detection condition datagram,
302 . . . Event datagram,
303 . . . Detection signal datagram relating to detection wavelength λ,
304 . . . Life activity datagram,
305 . . . Interpretation condition datagram,
310 . . . Interpretation condition packet,
311 . . . Detection condition packet,
312 . . . Event packet,
313 . . . Detection signal packet,
314 . . . Life activity information packet,
315 . . . Internet header,
316 . . . Detection condition data fragment,
317 . . . Event data fragment,
318 . . . Detection signal data fragment,
319 . . . Interpretation condition data fragment,
320 . . . life activity information fragment,
326 . . . Location information of each detected point,
327 . . . Life activity distribution map at time T1,
328 . . . Life activity distribution map at time T2,
331 . . . Service type information,
332 . . . Corresponding datagram identification,
333 . . . Various control of fragment,
334 . . . Fragment offset,
335 . . . Source address,
336 . . . Destination address,
337 . . . Option type (Type=68),
338 . . . Identification of life detecting section or inherent address information for life detecting section,
339 . . . Timestamp,
341 . . . Event source address information (URL of display screen or the like)
342 . . . Number information of events occurring in detection term,
343 . . . API command set in display screen,
346 . . . Event category,
347 . . . Event continuation time,
348 . . . Event content,
351 . . . User identification, Detected person identification, or Detected object (member) identification,
352 . . . Detection start time which is described in the form of year, month, day, hour, minute, second, and sub-second,
353 . . . Basic frequency of timestamp,
354 . . . Measuring items,
355 . . . Detection method,
356 . . . Detection signal category,
357 . . . Location information of detected area and Location rule of detected points,
358 . . . Detecting resolution of detected area,
359 . . . Expressed bit number of quantized detection signal,
360 . . . Sampling frequency of detection signal or sampling interval,
361 . . . Number information of wave-lengths used for detection,
362 . . . Accumulated number information of detection signal sending,
363 . . . Version number of interpretation soft,
364 . . . Data base version number or last modified time of data base used for interpretation,
371 . . . Number information of measuring items,
372 . . . Number information of evaluation factors included in measuring item A,
373 . . . Evaluation factor list relating to measuring item A,
374 . . . Number information of evaluation factors included in measuring item B,
375 . . . evaluation factor list relating to measuring item B,
377 . . . Equivalent level values of evaluation factors included in measuring item A measured at time T1,
378 . . . Equivalent level values of evaluation factors included in measuring item A measured at time T2,
401 . . . Reflection light amount change,
411 . . . Postcentral cerebral cortex,
412 . . . Thalamus,
413 . . . Spinal cord,
414 . . . Vertebral body (anterioris),
415 . . . Lamina (posterior),
416 . . . Spinal cord gray matter,
421 . . . X-axis,
422 . . . Y-axis,
423 . . . Z-axis,
424 . . . Light source for detecting wavelength of 780 nm,
425 . . . Color filter passing light having wavelength of 780 nm,
426 . . . Photodetector for light having wavelength of 780 nm,
427 . . . Light source for detecting wavelength of 830 nm,
428 . . . Color filter passing light having wavelength of 830 nm,
429 . . . Photodetector for light having wavelength of 830 nm,
431 . . . Position detecting light source for detected point for life activity,
432 . . . Position detecting monitor section of detected point for life activity,
433 . . . Beam splitter,
434 . . . Photosynthesis element having color filter characteristic,
437 . . . Quarter wave length plate,
438 . . . Polarized light separation element,
439 . . . Light for monitoring,
440 . . . Term of detection of life activity,
441 . . . Inherent information expressing term of detecting section for life activity,
451 . . . Synchronous signal,
452 . . . ID information for manufacturer identification of detecting section for life activity,
453 . . . Individual identification (production number) of detecting sections for life activity,
454 . . . Manufacturer related information set by manufacturer,
501 . . . Epicranius [surprise],
502 . . . Corrugator [pain],
503 . . . Zygomaticus [laughter], 504 . . . Orbicularis oris [expression]
505 . . . Depressor anguli oris (chin deltoid muscle)[sorrow],
506 . . . Depressor muscles of lower lip (*musculus* quadratus labii inferioris)[amimia],
507 . . . Mentalis [doubt and despite],
511 . . . Before initiation of muscular contraction activity
512 . . . During muscular contraction activity,
513 . . . Amplitude value,
521 . . . Detectable range in detecting section for life activity,
522 . . . Position of life activity object,
600 . . . Part of organism to be detected/controlled (head or the like of examinee),
601 . . . Electrode terminal (plate),
602 . . . Power supply for high voltage and high frequency generation,
603 . . . Control section,
604 . . . Modulation signal generator,
605 . . . Objective lens driving circuit,
606 . . . Collimating lens,
607 . . . Beam splitter,
608 . . . Electromagnetic wave for detection/control of life activity,
609 . . . Optical waveguide,
610 . . . Optical waveguide driving circuit,
611 . . . Outside layer of cell membrane,
612 . . . Inside layer facing cytoplasm,
613 . . . Cell membrane,
614 . . . Crack,
615 . . . Gate,
616 . . . Charged part,
621 . . . Hydrogen bonding part,
622 . . . Residue of amino acid,
623 . . . Principal chain of amino acid,
701 . . . Receptor A,
702 . . . Receptor B,
703 . . . Intracellular signal transmission cascade A,
704 . . . Intracellular signal transmission cascade B,
711 . . . Phosphorylation process cascade,
712 . . . Dephosphorylation process,
713 . . . Inhibitory action,
721 . . . Gene expression (transfer to messenger ribonucleic acid (mRNA)),
722 . . . Protein synthesis (translation of messenger ribonucleic acid (mRNA)),
723 . . . Exhibition of specific cellular function,
724 . . . Control object,
731 . . . Synaptic cleft,
732 . . . Glutamic acid bond,
733 . . . Glutamic acid bond,
734 . . . Glutamic acid bond,
735 . . . Spine,
741 . . . Metabotropic glutamate (mGluR) receptor,
742 . . . N-methyl-D-aspartate-type ionotropic glutamate (NMDA) receptor,
743 . . . A-amino-3-hydroxy-5-methyl-4-issoxazol propionate (AMPA) receptor,
747 . . . In case of high $Ca^+$ ion concentration,
748 . . . In case of low $Ca^+$ ion concentration,
750 . . . Generation of $PI(3, 4, 5)P_3$,
751 . . . Inflow of $Ca^+$ ions,
752 . . . Inflow of $Na^+$ ions,
753 . . . Phosphorylation of CaM-kinase,
754 . . . Gene expression in cell nucleus,
755 . . . Generation of messenger ribonucleic acid (mRNA),
756 . . . Translation of messenger ribonucleic acid (mRNA),
757 . . . Insertion of α-amino-3-hydroxy-5-methyl-4-issoxazol propionate (AMPA) receptor,
758 . . . Phosphorylation cascade,
759 . . . Activation of protein kinase B,
761 . . . Activation of Calcineurin,
762 . . . Dephosphorylation of inhibiter 1,
763 . . . Activation of protein phosphatase enzyme 1,
764 . . . Uptake of a-amino-3-hydroxy-5-methyl-4-issoxazol propionate (AMPA) receptor,
771 . . . Memory action,
772 . . . Obliteration action,
780 . . . Substrate.

What is claimed is:

1. A non-invasive method applied to a life object, comprising:
   irradiating the life object with a first electromagnetic wave having a prescribed wavelength, the prescribed wavelength being included in a range from 1.028 μm to 2.50 μm;
   setting a position of a detected area, which can be moved and is monitored in a depth direction below a surface of the life object;
   detecting a signal relating to a second electromagnetic wave, the second electromagnetic wave having a wavelength same as the prescribed wavelength, and the second electromagnetic wave being obtained from the detected area; and
   detecting muscular activity in the life object based on the detected signal, the muscular activity relating to at least one of muscle contraction and relaxation.

2. The method according to claim 1, wherein the position of the detected area is optically monitored with a third electromagnetic wave obtained from the life object, and
   the third electromagnetic wave has a wavelength same as the prescribed wavelength.

3. The method according to claim 1, wherein the position of the detected area is monitored using trigonometry.

4. The method according to claim 1, further comprising: measuring neural activity in vivo.

5. The method according to claim 1, further comprising: controlling life activity in the life object.

6. The method according to claim 1, further comprising: transmitting information related to the detected signal.

7. The method according to claim 1, further comprising: providing a service based on the detected signal.

8. The method according to claim 2, wherein the position of the detected area is positionally controlled by a moving mechanism based on the position monitored in the depth direction below the surface of the life object.

9. A non-invasive method applied to a life object, comprising:
   irradiating the life object with a first electromagnetic wave having a prescribed wavelength, the prescribed wavelength being included in a range from 1.028 μm to 2.50 μm;
   setting a position of a detected area, which can be moved and is monitored in a depth direction below a surface of the life object;
   detecting a signal relating to a second electromagnetic wave, the second electromagnetic wave having a wavelength same as the prescribed wavelength, and the second electromagnetic wave being obtained from the detected area; and
   detecting cellular activity in the life object based on the detected signal.

10. The method according to claim 9, wherein the position of the detected area is optically monitored with a third electromagnetic wave obtained from the life object, and the third electromagnetic wave has a wavelength same as the prescribed wavelength.

11. The method according to claim 9, further comprising: controlling life activity in the life object.

12. The method according to claim 9, further comprising: transmitting information related to the detected signal.

13. The method according to claim 9, further comprising: providing service based on the detected signal.

14. The method according to claim 10, wherein the position of the detected area is positionally controlled by a moving mechanism based on the position monitored in the depth direction below the surface of the life object.

15. The method according to claim 14, wherein the detected area is located outside of capillaries.

16. The method according to claim 10, wherein the position of the detected area is monitored using trigonometry.

17. An apparatus for detecting muscular activity in a life object, comprising:
  a light emitter for non-invasively emitting a first electromagnetic wave having a prescribed wavelength, the prescribed wavelength being included in a range from 1.028 μm to 2.50 μm; and
  a detecting section configured to non-invasively detect a signal relating to a second electromagnetic wave, the second electromagnetic wave having a wavelength same as the prescribed wavelength, the second electromagnetic wave being obtained from a detected area, a position of the detected area being movable and monitored in a depth direction below a surface of the life object, and the detecting section further configured to detect the muscular activity in the life object based on the detected signal, the muscular activity relating to at least one of muscle contraction and relaxation.

18. The apparatus according to claim 17, wherein the detecting section is configured to have a sensitivity of the prescribed wavelength included in the range from 1.028 μm to 2.50 μm to detect the signal.

19. An apparatus for detecting cellular activity in a life object, comprising:
  a light emitter for non-invasively emitting a first electromagnetic wave having a prescribed wavelength, the prescribed wavelength being included in a range from 1.028 μm to 2.50 μm; and
  a detecting section configured to non-invasively detect a signal relating to a second electromagnetic wave, the second electromagnetic wave having a wavelength same as the prescribed wavelength, the second electromagnetic wave being obtained from a detected area, a position of the detected area being movable and monitored in a depth direction below a surface of the life object, and the detecting section further configured to detect the cellular activity in the life object based on the detected signal.

20. The apparatus according to claim 19, wherein the detecting section is configured to have a sensitivity of the prescribed wavelength included in the range from 1.028 μm to 2.50 μm to detect the signal.

21. The apparatus according to claim 20, further comprising:
  a position monitor section configured to optically monitor the position of the detected area based on a third electromagnetic wave obtained from the life object, the third electromagnetic wave have a wavelength same as the prescribed wavelength.

22. The apparatus according to claim 21, wherein the position of the detected area is monitored using trigonometry.

23. The apparatus according to claim 21, further comprising:
  a moving mechanism configured to correct the position of the detected area in the depth direction below the surface of the life object, and
  the moving mechanism is configured to positionally control the position of the detected area based on an output from the position monitor in the depth direction below the surface of the life object.

24. The apparatus according to claim 23, wherein the detected area is located outside of capillaries.

* * * * *